United States Patent
Hawryluk et al.

(10) Patent No.: US 11,505,548 B2
(45) Date of Patent: Nov. 22, 2022

(54) HETEROCYCLIC COMPOUNDS AND THEIR USE FOR TREATMENT OF HELMINTHIC INFECTIONS AND DISEASES

(71) Applicants: Celgene Corporation, Summit, NJ (US); Zoetis LLC, Kalamazoo, MI (US)

(72) Inventors: Natalie Hawryluk, San Diego, CA (US); Stacie S. Canan, La Jolla, CA (US); Kevin R. Condroski, Lafayette, CO (US); Graham Kyne, Kalamazoo, MI (US); Matthew Bedore, Portage, MI (US); Sanjay Menon, Kalamazoo, MI (US)

(73) Assignees: CELGENE CORPORATION, Summit, NJ (US); ZOETIS LLC, Kalamazoo, MI (US)

( * ) Notice: Subject to any disclaimer, the term of this patent is extended or adjusted under 35 U.S.C. 154(b) by 104 days.

(21) Appl. No.: 16/858,410

(22) Filed: Apr. 24, 2020

(65) Prior Publication Data
US 2020/0339559 A1 Oct. 29, 2020

Related U.S. Application Data

(60) Provisional application No. 62/839,552, filed on Apr. 26, 2019.

(51) Int. Cl.
| | | |
|---|---|---|
| C07D 417/14 | (2006.01) |
| A61P 33/10 | (2006.01) |
| C07D 413/14 | (2006.01) |
| C07D 471/04 | (2006.01) |
| A61K 31/165 | (2006.01) |
| A61K 31/732 | (2006.01) |

(52) U.S. Cl.
CPC ........... *C07D 417/14* (2013.01); *A61P 33/10* (2018.01); *C07D 413/14* (2013.01); *C07D 471/04* (2013.01); *A61K 31/165* (2013.01); *A61K 31/732* (2013.01)

(58) Field of Classification Search
CPC .................................................. C07D 417/14
See application file for complete search history.

(56) References Cited

U.S. PATENT DOCUMENTS 6,387,388 B1   5/2002   Misselbrook et al.

FOREIGN PATENT DOCUMENTS

| | | | |
|---|---|---|---|
| EP | 0276432 A2 | 8/1988 |
| EP | 0675133 A1 | 10/1995 |
| WO | WO 1995/005368 A1 | 2/1995 |
| WO | WO 00/09500 A2 | 2/2000 |
| WO | WO 2008/126933 A2 | 10/2008 |
| WO | WO-2011156610 A2 * | 12/2011 | ........... C07D 411/14 |

OTHER PUBLICATIONS

International Search Report issued for PCT/US2020/029805 dated Jun. 8, 2020.
Auerlio et al., "From sphingosine kinase to dihydroceramide desaturase: a structure-activity relationship (SAR) study of the enzyme inhibitory and anticancer activity of 4-((4-(4-chlorophenyl)thiazol-2-yl)amino)phenol (SKI-II)," *J. Med. Chem.*, 59(3):965-984 (2016).
Huang et al., "A positron emission tomography radioligand for the in vivo labeling of metabotropic glutamate 1 receptor: (3-ethyl-2-[11C]methyl-6-quinolinyl)(cis-4-methoxycyclohexyl)methanone," *J. Med. Chem.*, 48(16):5096-5099 (2015).
Karadjian et al., "Migratory phase of litomosoides sigmodontis filarial infective larvae is associated with pathology and transient increase of S100A9 expressing neutrophils in the lung," *PLoS Negl. Trop. Dis.*, 11(5):e0005596 (2017).
Osei-Atweneboana et al., "Phenotypic evidence of emerging ivermectin resistance in onchocerca volvulus," *PLoS Negl. Trop. Dis.*, 5(3):e998 (2011).
Van Dijken et al., "Acylhydrazones as widely tunable photoswitches," *J. Am. Chem. Soc.*, 137(47):14982-14991 (2015).
Wang et al., "Synthesis of 5-amino and 3,5-diamino substituted 1,2,4-thiadiazoles by $I_2$-mediated oxidative N—S bond formation," *J. Org. Chem.*, 82:5898-5903 (2017).
Wilen et al., "Strategies in optical resolutions," Tetrahedron, 33:2725-2736 (1977).
Wilen, Tables of Resolving Agents and Optical Resolutions, (E.L. Eliel, Ed.), University of Notre Dame Press, Notre Dame, IN, p. 268 (1972).
Ziewer et al., "Immunization with L. *Sigmodontis* microfilariae reduces peripheral microfilaraemia after challenge infection by inhibition of filarial embryogenesis," *PLoS Negi. Trop. Dis.*, 6:e1558 (2012).

* cited by examiner

*Primary Examiner* — John S Kenyon
(74) *Attorney, Agent, or Firm* — Jones Day

(57) ABSTRACT

Provided herein are Heterocyclic compounds of formula I:

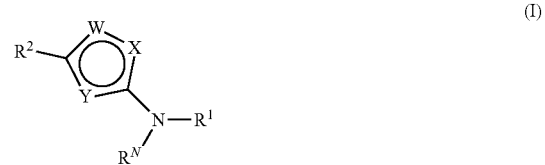

and pharmaceutically acceptable salts, tautomers, isotopologues, or stereoisomers thereof, wherein W, X, Y, $R^1$, $R^2$, and $R^N$ are as defined herein, compositions comprising an effective amount of a Heterocyclic Compound, and methods for treating or preventing animal and human filarial worm infections and diseases.

23 Claims, No Drawings

HETEROCYCLIC COMPOUNDS AND THEIR USE FOR TREATMENT OF HELMINTHIC INFECTIONS AND DISEASES

CROSS REFERENCE TO RELATED APPLICATIONS

This application claims the benefit of U.S. Provisional Application No. 62/839,552 filed Apr. 26, 2019 the disclosure of which is incorporated herein by reference in its entirety.

FIELD

Disclosed herein are compounds and methods for the prevention and/or treatment of helminthic infections and diseases caused by helminthic infection. Also provided herein are such compounds for use in such methods. Also disclosed herein are pharmaceutical compositions comprising such compounds for use in such methods of preventing or treating helminthic infection and/or diseases associated with helminthic infection.

BACKGROUND

There are several types of parasitic worms (helminths), with the most common worldwide the intestinal nematodes or soil-transmitted helminths (STH), schistosomes (parasites of schistosomiasis) and filarial worms, which cause lymphatic filariasis (LF) and onchocerciasis. Filariasis is a parasitic disease that is caused by thread-like filarial nematodes or roundworms. Filariasis is a vector-borne disease that is transmitted via insect bites. Infective larvae of the nematodes can be introduced into the human body via bites of blood sucking insects like mosquitoes or flies. Filariasis can also affect domestic animals like dogs. In dogs, dirofilariasis which is also called heartworm disease, is caused by nematodes called *Dirofilaria immitis* and *Dirofilaria repens*. Dirofilariasis is considered endemic in 49 states of the United States. The vectors as well are blood sucking insects like mosquitoes.

The major causes of human filariasis are the filarial nematodes *Wuchereria bancrofti*, *Brugia malayi*, *Brugia timori*, *Onchocerca volvulus* and *Mansonella* species that have human hosts. The nematodes *Wuchereria bancrofti*, *Brugia malayi* and *Onchocerca volvulus* are responsible for most of the debilitating filarial infections in more than 80 developing countries of the tropics and sub-tropics where 1.1 billion are at risk of infection and about 150 million are infected. All three species are a source of severe pathologies that result in high morbidity and increased mortality. The infection can cause severe morbidity in up to 50% of those infected with the nematodes.

*W. bancrofti* and *B. malayi* infections can develop into lymphatic filariasis, often seen as hydrocoele in men and/or lymphoedema and in extreme cases elephantiasis. *O. volvulus* infections can develop into severe dermatitis and/or onchocerciasis, the visual impairment giving the latter disease its common name River Blindness. Community directed mass drug administration programs are designed to control these infections and eliminate them as a public health problem.

Current efforts aim to eliminate these parasitic nematodes through the use of drugs like diethylcarbamazine, ivermectin, and albendazole that kill the larvae, but not the adult worms. The antihelmintic drug diethylcarbamazine is used to combat lymphatic filariasis in countries without co-endemic *O. volvulus* infections, i.e. outside of Africa. Ivermectin is used to combat onchocerciasis. The greatest efficacy of both drugs is against the first stage larvae found in the blood stream or in the dermis. Since the worms can live up to 14 years and are fecund for most of their lifespan, populations in endemic regions must be treated with high coverage (at least 65%) for many years to break transmission of the disease to uninfected persons.

Two of the major constraints of treatment of filarial diseases are (i) the absence of a macrofilaricidal drug (or for onchocerciasis, one which permanently sterilizes the worm) and (ii) the risk of worms developing drug-resistance. For example, currently available treatments for onchocerciasis include ivermectin, which kills worm larvae, but has little or no activity against adult *Onchocerca volvulus* parasites. Thus, infected patients must be retreated with ivermectin for several years until the adult worms die naturally. In addition, there are also potential signs of resistance to ivermectin within the parasite in a few areas. Osei-Atweneboana M Y, et al., Phenotypic Evidence of Emerging Ivermectin Resistance in *Onchocerca volvulus*, *PLoS Negl Trop Dis* 5(3): e998 (2011). In addition, there is a danger in treating patients co-infected with both (i) *Wuchereria bancrofti*, *Brugia malayi*, *Brugia timori*, and/or *Onchocerca volvulus*; and (ii) *Loa loa* with ivermectin. In such co-infected patients, ivermectin treatment can cause severe reactions, including encephalopathy, leading to coma or even death.

Heartworm infection, caused by the endoparasite *Dirofilaria immitis* (*D. immitis*), can be a severe and life-threatening disease in animals such as dogs and cats. Heartworm has a complicated life cycle involving several life stages before they mature into adults that will eventually infect the pulmonary artery of the host animal. Heartworm transmission also requires the mosquito to act as an intermediate host to complete this life cycle. For example, the beginning of the heartworm life cycle and transmission process involves a mosquito biting a previously infected dog and ingesting blood containing heartworm microfilariae (larva stage 1). Within the mosquito, the microfilariae will molt into infective larva stage 3 (L3) worms over a two week period. Once the mosquito bites another dog, infective L3 worms will move through the bite wound to enter the host and migrate into the tissues where they will begin molting into larva stage 4 (L4) worms, usually within 1 to 3 days post infection. Subsequently, L4 worms will continue their migration through tissues and molt into sexually immature or "adolescent" adults (larva stage 5, immature adult), approximately 50-70 days post infection. Sexually mature worms will eventually migrate to the heart and lungs of the dog, as early as 70 days post infection. Approximately 6-7 months post infection *D. immitis* adults reach maturity and sexually reproduce in the pulmonary artery leading to microfilaria (MF) production and circulation in the blood of the dog, thus completing the heartworm life cycle.

The most commonly used heartworm preventatives are the macrocyclic lactones (MLs) such as ivermectin, moxidectin and selamectin. These agents are administered on a monthly basis whereby they kill *D. immitis* L3 and L4 worms acquired by the host within the previous 30 days. Their primary action is to disrupt the heartworm life cycle by killing L3 and L4 worms thus preventing adult formation and subsequent disease. While very effective at preventing heartworm disease, owners are advised to test dogs for existing heartworm infections (i.e. heartworm positive dogs) prior to starting treatment with MLs due to their potential to kill circulating microfilariae. A rapid decrease in the numbers of microfilariae in the blood can lead to hypersensitivity-type reactions and circulatory shock (e.g. anaphylaxis), presumably due to dead or dying microfilariae. These potential adverse effects can be life-threatening to the dog and as such are presented as caution statements on many ML product labels. Therefore, the discovery of a novel heartworm preventative that would selectively target L3 and L4 stage worms versus microfilariae would offer a potential safety advantage. By not killing circulating microfilariae in heartworm positive dogs, a targeted treatment would prevent the adverse effects known to occur with other heartworm preventatives that lack *D. immitis* stage selectivity.

Thus, alternative, and more effective, treatments for filarial worm diseases are needed.

Citation or identification of any reference in this application is not to be construed as an admission that the reference is prior art to the present application.

SUMMARY

Provided herein are Heterocyclic Compounds of formula (I):

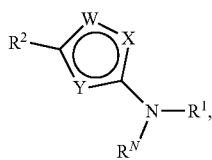

(I)

and pharmaceutically acceptable salts, tautomers, isotopologues, and stereoisomers thereof, wherein W, X, Y, $R^1$, $R^2$, and $R^N$ are as defined herein.

Also provided herein are Heterocyclic Compounds of formula (II):

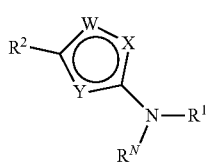

(II)

and pharmaceutically acceptable salts, tautomers, isotopologues, and stereoisomers thereof, wherein W, X, Y, $R^1$, $R^2$, and $R^N$ are as defined herein.

In one aspect, provided herein are Heterocyclic Compounds as described in the instant disclosure, such as, for example, a Heterocyclic Compound of formula (I), formula (Ia), formula (Ib), formula (Ic), formula (II), or formula (IIa), or a compound from Table 1.

In one aspect, provided herein are pharmaceutical compositions comprising an effective amount of a Heterocyclic Compound, as described herein, and a pharmaceutically acceptable carrier, excipient or vehicle. In some embodiments the pharmaceutical composition is suitable for oral, parenteral, mucosal, transdermal or topical administration.

In one aspect, provided herein are methods of treating a subject infected with a helminth. In another aspect, provided herein are uses of Heterocyclic Compounds for treating or preventing helminthic infections, comprising administering to a subject affected by helminthic infections an effective amount of a Heterocyclic Compound as described herein. In one aspect the helminthic infection is a filarial infection.

In one aspect, provided herein are methods of treating a subject infected with a filarial worm. In another aspect, provided herein are uses of Heterocyclic Compounds for treating or preventing filarial infections, comprising administering to a subject affected by filarial infections an effective amount of a Heterocyclic Compound as described herein.

In certain embodiments, the methods described herein includes administering a therapeutically effective amount of a compound of formula (I), formula (Ia), formula (Ib), formula (Ic), formula (II), formula (IIa), or a compound from Table 1, or a pharmaceutically acceptable salt, tautomer, isotopologue, or stereoisomer thereof, to the subject.

The compounds of the present invention are useful for the treatment of helminthic diseases where the helminths are categorized as cestodes (tapeworms), nematodes (roundworms) and trematodes (flatworms or flukes). Non-limiting examples of filarial nematodes within the Onchocercidae Family include the genus *Brugia* spp. (i.e., *B. malayi, B. pahangi, B. timori,* and the like), *Wuchereria* spp. (i.e., *W. bancrofti,* and the like), *Dirofilaria* spp. (*D. immitis, D. repens, D. ursi, D. tenuis, D. spectans, D. lutrae,* and the like), *Dipetalonema* spp. (i.e., *D. reconditum, D. repens,* and the like), *Onchocerca* spp. (i.e., *O. gibsoni, O. gutturosa, O. volvulus,* and the like), *Elaeophora* spp. (*E. bohmi, E. elaphi, E. poeli, E. sagitta, E. schneideri,* and the like), *Mansonella* spp. (i.e., *M. ozzardi, M. perstans,* and the like), and *Loa* spp. (i.e., *L. loa*). In certain embodiments, the filarial worm is *Onchocerca volvulus*. In certain embodiments, the filarial worm is *Wuchereria bancrofti*. In certain embodiments, the filarial worm is *Brugia malayi*. In certain embodiments, the filarial worm is *Brugia timori*. In certain embodiments, the filarial worm is *Mansonella*. In certain embodiments, the filarial worm is *Dirofilaria immitis*. In some embodiments, the nematode is *Haemonchus contortus*.

In one aspect, provided herein are uses of Heterocyclic Compounds for treating or preventing helminthic infections, comprising administering to a subject affected by helminthic infection an effective amount of a Heterocyclic Compound as described herein. In another aspect, provided herein are uses of Heterocyclic Compounds for treating or preventing filarial worm infections, wherein the methods comprise administering to a subject affected by filarial worm infections an effective amount of a Heterocyclic Compound as described herein.

In one aspect, provided herein is a Heterocyclic Compound for use as a medicament. In a particular embodiment, provided herein is the Heterocyclic Compound for use in a method for the treatment or prevention of a helminthic infection, the method comprising administering to a subject an effective amount of the Heterocyclic Compound. In a particular embodiment, provided herein is the Heterocyclic Compound for use in a method for the treatment or prevention of a filarial worm infection, the method comprising administering to a subject an effective amount of the Heterocyclic Compound.

In another aspect provided herein are methods for preparing Heterocyclic Compounds as described herein.

The present embodiments can be understood more fully by reference to the detailed description and examples, which are intended to exemplify non-limiting embodiments.

DETAILED DESCRIPTION

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein and unless otherwise specified, an "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. An "alkenyl" group is an alkyl group that contains one or more carbon-carbon double bonds. An "alkynyl" group is an alkyl group that contains one or more carbon-carbon triple bonds. Examples of unsaturated alkyl groups include, but are not limited to, vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_2$CH$_3$), among others. An alkyl group can be substituted or unsubstituted. When the alkyl groups described herein are said to be "substituted," they may be substituted with any substituent or substituents as those found in the exemplary compounds and embodiments disclosed herein, as well as halogen; hydroxy; alkoxy; cycloalkyloxy, aryloxy, heterocyclyloxy, heteroaryloxy, heterocycloalkyoxy, cycloalkylalkyloxy, aralkyloxy, heterocyclylalkyloxy, heteroarylalkyloxy, heterocycloalkyalkyloxy; oxo (═O); amino, alkylamino, cycloalkylamino, arylamino, heterocyclylamino, heteroarylamino, heterocycloalkylamino; imino; imido; amidino; guanidino; enamino; acylamino; sulfonylamino; urea, nitrourea; oxime; hydroxylamino; alkoxyamino; aralkoxyamino; hydrazino; hydrazido; hydrazono; azido; nitro; thio (—SH), alkylthio; ═S; sulfinyl; sulfonyl; aminosulfonyl; phosphonate; phosphinyl; acyl; formyl; carboxy; ester; carbamate; amido; cyano; isocyanato; isothiocyanato; cyanato; thiocyanato; or —B(OH)$_2$.

As used herein and unless otherwise specified, a "cycloalkyl" group is a saturated, or partially saturated cyclic alkyl group of from 3 to 10 carbon atoms having a single cyclic ring or multiple condensed or bridged rings which can be optionally substituted. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

As used herein and unless otherwise specified, an "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryl groups include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

As used herein and unless otherwise specified, a "heteroaryl" group is an aromatic ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indol-2-onyl), isoindolin-1-onyl, azaindolyl, pyrrolopyridyl (e.g., 1H-pyrrolo[2,3-b]pyridyl), indazolyl, benzimidazolyl (e.g., 1H-benzo[d]imidazolyl), azabenzimidazolyl, imidazopyridyl (e.g., 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl, 3,4-dihydroisoquinolin-1(2H)-onyl, tetrahydroquinolinyl, quinoxalinyl, and quinazolinyl groups. A heteroaryl group can be substituted or unsubstituted.

As used herein and unless otherwise specified, a "heterocyclyl" is an aromatic ring system (also referred to as heteroaryl) or non-aromatic cycloalkyl (also referred to as heterocycloalkyl) in which one to four of the ring carbon atoms are independently replaced with a heteroatom. Suitable heteroatoms include oxygen, sulfur and nitrogen. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocyclyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-onyl or imidazolidin-2,4-dionyl) groups. The phrase heterocyclyl includes fused ring species, including those comprising fused aromatic and non-aromatic groups, such as, for example, 1- and 2-aminotetraline, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, oxetanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, 1,4-dioxaspiro[4.5]decanyl, homopiperazinyl, quinuclidyl, indolyl (e.g., indol-2-onyl), isoindolin-1-onyl, indolinyl, isoindolyl, isoindolinyl, azaindolyl, pyrrolopyridyl (e.g, 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (e.g., benzo[d]oxazolyl), benzothiazolyl, benzothiadiazolyl, benzo[1,3]dioxolyl, pyrazolopyridyl (e.g., 1H-pyrazolo[3,4-b]pyridyl, 1H-pyrazolo[4,3-b]pyridyl), azabenzimidazolyl, imidazopyridyl (e.g., 1H-imidazo[4,5-b]pyridyl), triazolopyridyl, isoxazolopyridyl, purinyl, xanthinyl, adeninyl, guaninyl, quinolinyl, isoquinolinyl, 3,4-dihydroisoquinolin-1(2H)-onyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative non-aromatic heterocyclyl groups do not include fused ring species that comprise a fused aromatic group. Examples of non-aromatic heterocyclyl groups include aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

As used herein and unless otherwise specified, a "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopropylmethyl, cyclobutylmethyl, cyclopentylmethyl, cyclohexylmethyl, cyclopropylethyl, cyclobutylethyl, cyclopentylethyl, cyclohexylethyl, cyclopentylpropyl, cyclohexylpropyl and the like.

As used herein and unless otherwise specified, an "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and aralkyl groups wherein the aryl group is fused to a cycloalkyl group such as indan-4-yl ethyl.

As used herein and unless otherwise specified, a "heterocyclylalkyl" group is a radical of the formula: -alkyl-heterocyclyl, wherein alkyl and heterocyclyl are defined above. A "heteroarylalkyl" group is a radical of the formula: -alkyl-heteroaryl, wherein alkyl and heteroaryl are defined above. A "heterocycloalkylalkyl" group is a radical of the formula: -alkyl-heterocycloalkyl, wherein alkyl and heterocycloalkyl are defined above. Substituted heterocyclylalkyl groups may be substituted at the alkyl, the heterocyclyl, or both the alkyl and the heterocyclyl portions of the group. Representative heterocyclylalkyl groups include but are not limited to morpholin-4-yl ethyl, morpholin-4-yl propyl, furan-2-yl methyl, furan-3-yl methyl, pyridin-3-yl methyl, tetrahydrofuran-2-yl ethyl, and indol-2-yl propyl.

As used herein and unless otherwise specified, a "halogen" is fluorine, chlorine, bromine or iodine.

As used herein and unless otherwise specified, a "hydroxyalkyl" group is an alkyl group as described above substituted with one or more hydroxy groups.

As used herein and unless otherwise specified, an "alkoxy" group is —O-(alkyl), wherein alkyl is defined above. An "alkylthio" group is —S-(alkyl), wherein alkyl is defined above.

As used herein and unless otherwise specified, an "alkoxyalkyl" group is -(alkyl)-O-(alkyl), wherein alkyl is defined above.

As used herein and unless otherwise specified, a "cycloalkyloxy" group is —O-(cycloalkyl), wherein cycloalkyl is defined above.

As used herein and unless otherwise specified, an "aryloxy" group is —O-(aryl), wherein aryl is defined above.

As used herein and unless otherwise specified, a "heterocyclyloxy" group is —O-(heterocyclyl), wherein heterocyclyl is defined above. A "heteroaryloxy" group is —O-(heteroaryl), wherein heteroaryl is defined above. A "heterocycloalkyloxy" group is —O-(heterocycloalkyl), wherein heterocycloalkyl is defined above.

As used herein and unless otherwise specified, an "amino" group is a radical of the formula: —NH$_2$, —NH(R$^{\#}$), or —N(R$^{\#}$)$_2$, wherein each R$^{\#}$ is independently an alkyl, cycloalkyl, cycloalkylalkyl, aryl, aralkyl, heterocyclyl (e.g., heteroaryl or heterocycloalkyl), or heterocyclylalkyl (e.g., heteroarylalkyl or heterocycloalkylalkyl) group defined above, each of which is independently substituted or unsubstituted.

In one embodiment, an "amino" group is an "alkylamino" group, which is a radical of the formula: —NH-alkyl or —N(alkyl)$_2$, wherein each alkyl is independently defined above. The term "cycloalkylamino", "arylamino", "heterocyclylamino", "heteroarylamino", "heterocycloalkylamino", or the like, mirrors the above description for "alkylamino" where the term "alkyl" is replaced with "cycloalkyl", "aryl", "heterocyclyl", "heteroaryl", "heterocycloalkyl", or the like, respectively.

As used herein and unless otherwise specified, a "carboxy" group is a radical of the formula: —C(O)OH.

As used herein and unless otherwise specified, an "acyl" group is a radical of the formula: —C(O)(R#) or —C(O)H, wherein R# is defined above. A "formyl" group is a radical of the formula: —C(O)H.

As used herein and unless otherwise specified, an "amido" group is a radical of the formula: —C(O)—NH$_2$, —C(O)—NH(R#), —C(O)—N(R#)$_2$, —NH—C(O)H, —NH—C(O)—(R#), —N(R#)—C(O)H, or —N(R#)—C(O)—(R#), wherein each R# is independently defined above.

In one embodiment, an "amido" group is an "aminocarbonyl" group, which is a radical of the formula: —C(O)—NH$_2$, —C(O)—NH(R#), —C(O)—N(R#)$_2$, wherein each R# is independently defined above.

In one embodiment, an "amido" group is an "acylamino" group, which is a radical of the formula: —NH—C(O)H, —NH—C(O)—(R#), —N(R#)—C(O)H, or —N(R#)—C(O)—(R#), wherein each R# is independently defined above.

As used herein and unless otherwise specified, a "sulfonylamino" group is a radical of the formula: —NHSO$_2$(R#) or —N(R#)SO$_2$(R#), wherein each R# is defined above.

As used herein and unless otherwise specified, an "ester" group is a radical of the formula: —C(O)—O—(R#) or —O—C(O)—(R#), wherein R# is defined above.

In one embodiment, an "ester" group is an "alkoxycarbonyl" group, which is a radical of the formula: —C(O)—O-(alkyl), wherein alkyl is defined above. The term "cycloalkyloxycarbonyl", "aryloxycarbonyl", "heterocyclyloxycarbonyl", "heteroaryloxycarbonyl", "heterocycloalkyloxycarbonyl", or the like, mirrors the above description for "alkoxycarbonyl" where the term "alkoxy" is replaced with "cycloalkyloxy", "aryloxy", "heterocyclyloxy", "heteroaryloxy", "heterocycloalkyloxy", or the like, respectively.

As used herein and unless otherwise specified, a "carbamate" group is a radical of the formula: —O—C(O)—NH$_2$, —O—C(O)—NH(R#), —O—C(O)—N(R#)$_2$, —NH—C(O)—O—(R#), or —N(R#)—C(O)—O—(R#), wherein each R# is independently defined above.

As used herein and unless otherwise specified, a "urea" group is a radical of the formula: —NH(CO)NH$_2$, —NHC(O)NH(R#), —NHC(O)N(R#)$_2$, —N(R#)C(O)NH$_2$, —N(R#)C(O)NH(R#), or —N(R#)C(O)N(R#)$_2$, wherein each R# is independently defined above.

As used herein and unless otherwise specified, a "sulfinyl" group is a radical of the formula: —S(O)R#, wherein R# is defined above.

As used herein and unless otherwise specified, a "sulfonyl" group is a radical of the formula: —S(O)$_2$R#, wherein R# is defined above.

As used herein and unless otherwise specified, an "aminosulfonyl" group is a radical of the formula: —SO$_2$NH$_2$, —SO$_2$NH(R#), or —SO$_2$N(R#)$_2$, wherein each R# is independently defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen; alkyl, alkenyl, alkynyl, cycloalkyl, aryl, heterocyclyl, heteroaryl, heterocycloalky, cycloalkylalkyl, aralkyl, heterocyclylalkyl, heteroarylalkyl, heterocycloalkylalkyl, optionally further substituted; hydroxy; alkoxy; cycloalkyloxy, aryloxy, heterocyclyloxy, heteroaryloxy, heterocycloalkyoxy, cycloalkylalkyloxy, aralkyloxy, heterocyclylalkyloxy, heteroarylalkyloxy, heterocycloalkyalkyloxy; oxo (═O); oxide (e.g., a nitrogen atom substituted with an oxide is called N-oxide); amino, alkylamino, cycloalkylamino, arylamino, heterocyclylamino, heteroarylamino, heterocycloalkylamino; imino; imido; amidino; guanidino; enamino; acylamino; sulfonylamino; urea, nitrourea; oxime; hydroxylamino; alkoxyamino; aralkoxyamino; hydrazino; hydrazido; hydrazono; azido; nitro; thio (—SH), alkylthio; ═S; sulfinyl; sulfonyl; aminosulfonyl; phosphonate; phosphinyl; acyl; formyl; carboxy; ester; carbamate; amido; cyano; isocyanato; isothiocyanato; cyanato; thiocyanato; or —B(OH)$_2$.

As used herein, the term "Heterocyclic Compound" includes compounds of formula (I), formula (Ia), formula (Ib), formula (Ic), formula (II), formula (IIa), and Table 1 as well as to further embodiments of compounds of formula (I), formula (Ia), formula (Ib), formula (Ic), formula (II), formula (IIa), and Table 1 provided herein. For example, the term "Heterocyclic Compound" includes deuterated compounds of formula (I), formula (Ia), formula (Ib), formula (Ic), formula (II), formula (IIa), and Table 1. In one embodiment, a "Heterocyclic Compound" is a compound set forth in Table 1. In certain embodiments, the term "Heterocyclic Compound" includes pharmaceutically acceptable salts, tautomers, isotopologues, and/or stereoisomers of the Heterocyclic Compounds provided herein.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I), formula (Ia), formula (Ib), formula (Ic), and Table 1, include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "stereoisomer" or "stereomerically pure" means one stereoisomer of a Heterocyclic Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Heterocyclic Compounds can have chiral centers and can occur as racemates, individual enantiomers or diastereomers, and mixtures thereof. All such isomeric forms are included within the embodiments disclosed herein, including mixtures thereof.

The use of stereomerically pure forms of such Heterocyclic Compounds, as well as the use of mixtures of those forms, are encompassed by the embodiments disclosed herein. For example, mixtures comprising equal or unequal amounts of the enantiomers of a particular Heterocyclic Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Heterocyclic Compounds can include E and Z isomers, or a mixture thereof, and cis and trans isomers or a mixture thereof. In certain embodiments, the Heterocyclic Compounds are isolated as either the E or Z isomer. In other embodiments, the Heterocyclic Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

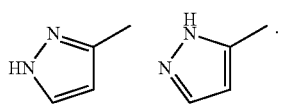

As readily understood by one skilled in the art, a wide variety of functional groups and other structures may exhibit tautomerism and all tautomers of compounds of formula (I), formula (Ia), formula (Ib), formula (Ic), formula (II), formula (IIa), and Table 1 are within the scope of the present invention.

It should also be noted the Heterocyclic Compounds can contain unnatural proportions of atomic isotopes at least one of the atoms. For example, the compounds may be radiolabeled with radioactive isotopes, such as for example tritium ($^{3}$H), iodine-125 ($^{125}$I), sulfur-35 ($^{35}$S), or carbon-14 ($^{14}$C), or may be isotopically enriched, such as with carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the Heterocyclic Compounds as described herein, whether radioactive or not, are intended to be encompassed within the scope of the embodiments provided herein. In some embodiments, there are provided isotopologues of the Heterocyclic Compounds, for example, the isotopologues are carbon-13, or nitrogen-15 enriched Heterocyclic Compounds. As used herein, "deuterated", means a compound wherein at least one hydrogen (H) has been replaced by deuterium (indicated by D or $^{2}$H), that is, the compound is enriched in deuterium in at least one position.

It should be noted that if there is a discrepancy between a depicted structure and a name for that structure, the depicted structure is to be accorded more weight.

As used herein, "inhibit" and "inhibition" mean that a specified response of a designated activity (e.g., worm motility) is comparatively decreased in the presence of a Heterocyclic Compound. Inhibition of worm motility, for example motility of *Onchocerca volvulus*, *Brugia malayi* and/or *Brugia timori*, can be determined by the assays described herein.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder, disorder or condition is a helminthic infection.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder, disorder or condition is a helminthic infection.

The term "effective amount" in connection with a Heterocyclic Compound means an amount capable of treating or preventing a disorder, disease or condition, or symptoms thereof, disclosed herein. In one embodiment, the disorder, disorder or condition is a helminthic infection.

The term "subject" or "patient" includes humans and other primates as well as domesticated and semi-domesticated animals including, but not limited to, poultry, honeybees, cows, sheep, cattle, goats, pigs, horses, dogs, cats, rabbits, rats, mice and the like. The term "poultry" encompasses all types of domestic fowl, including, but not limited to chickens, turkey, ducks, geese, the ratite group of birds and game birds. In certain embodiments, the subject is a human. In certain embodiments, the subject is a dog. In certain embodiments, the subject is a cat. In certain embodiments, the subject is a livestock. In certain embodiments, the subject is a cow. In certain embodiments, the subject is a sheep. In another embodiment, the subject is a goat.

The term "combination" or administration "in combination" includes administration as a mixture, simultaneous administration using separate formulations, and consecutive administration in any order.

The term "helminthic infections" or "helminth infection" as used herein refers to infections that are caused by parasitic worms. An infection caused by a helminth, known as "helminthiasis" (plural "helminthiases"), is any macroparasitic disease of humans and other animals in which a part of the body is infected with parasitic worms, known as helminths. There are numerous species of these parasites, which are broadly classified into tapeworms, flukes, and roundworms.

The term "filariasis" as used herein refers to helminth infections that are caused by filarial nematodes. Non-limiting examples of filarial nematodes within the Onchocercidae family include the genus *Brugia* spp. (i.e., *B. malayi, B. pahangi, B. timori*, and the like), *Wuchereria* spp. (i.e., *W. bancrofti*, and the like), *Dirofilaria* spp. (*D. immitis, D. repens, D. ursi, D. tenuis, D. spectans, D. lutrae*, and the like), *Dipetalonema* spp. (i.e., *D. reconditum, D. repens*, and the like), *Onchocerca* spp. (i.e., *O. gibsoni, O. gutturosa, O. volvulus*, and the like), *Elaeophora* spp. (*E. bohmi, E. elaphi, E. poeli, E. sagitta, E. schneideri*, and the like), *Mansonella* spp. (i.e., *M. ozzardi, M. perstans*, and the like), and *Loa* spp. (i.e., *L. loa*). An infection is the colonization of a host organism by parasite species. Infections with human filarial nematodes can cause lymphatic filariasis or onchocerciasis. The term "lymphatic filariasis" refers to an infection with the nematodes *Wuchereria bancrofti, Brugia malayi* or *Brugia timori*. The term "onchocerciasis" refers to an infection with the nematode *Onchocerca volvulus*. Lymphatic filariasis may cause hydrocoele, lymphoedema, and elephantiasis. Onchocerciasis may cause skin inflammation and blindness, so called River Blindness. In dogs, an infection with nematode species called *Dirofilaria immitis* or *Dirofilaria repens* causes dirofilariasis. In sheep and goats and infection with a nematoide species called *Haemonchus contortus* causes haemonchosis.

The term "worm" or "nematode" as used interchangeably herein refers to all life stages of the organism, such as an egg, an unfertilized egg, a fertilized egg, a larva or juvenile worm, a larva in any one of four larval stages (L1, L2, L3, L4), a worm in sexually immature stage (stage L5), a worm in mature stage, a worm in fully mature stage, an adult worm, a worm in pre-parasitic stage, or a worm in parasitic stage.

The term "microfilaria" or "mf" as used herein refers to an early stage in the life cycle of certain parasitic nematodes. Microfilaria is considered to be the first larva stage also referred to as L1. The terms "microfilaria," "mf," or "L1" are used alternatively and/or interchangeably.

The term "macrofilaria" as used herein refers to the adult stage in the life cycle of certain parasitic nematodes.

Unless otherwise defined, the technical and scientific terms used herein have the same meaning as commonly understood by one of ordinary skill in the art to which this application belongs.

Surprisingly, it was found that the compounds disclosed herein are effective in the treatment of helminthic infections, for example, filarial infections. In vitro and in vivo results demonstrated that the compounds disclosed herein are effective against filarial nematodes. In some embodiments, the compounds disclosed herein surprisingly presented distinct activity between parasitic nematodes in adult and juvenile stage. In some such embodiments, the compounds disclosed herein are selectively effective against adult filarial nematodes (also referred to as macrofilaricidal activity). In other embodiments, the compounds disclosed herein are selectively effective against the juvenile stage filarial nematodes (also referred to as microfilaricidal activity). Therefore, the compounds disclosed herein have the potential to be potent anti-filarial drugs.

Compounds

Provided herein are Heterocyclic Compounds having the following formula (I):

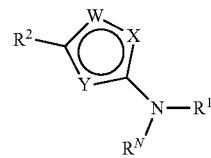

(I)

and pharmaceutically acceptable salts, tautomers, isotopologues, and stereoisomers thereof, wherein:

W is N or NR;
X is N, NR, O, or S;
Y is N, NR, O, or S;
$R^1$ is 2-pyridyl, 3-pyridyl, pyrazinyl, or pyrimidyl, each unsubstituted or substituted with one or more substituents independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —$NR_2$, —COOR, —$OR^3$, —$SO_2NR_2$, —$SO_2$ (substituted or unsubstituted heterocyclyl), —N(R)CO($R^4$), —CON($R^5$)$_2$, and substituted or unsubstituted $C_{6-10}$ aryl;

$R^2$ is

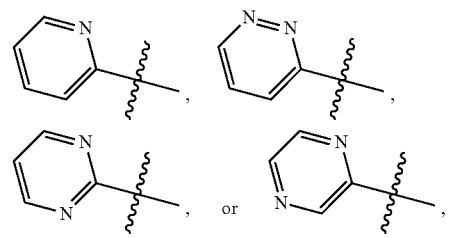

each unsubstituted or substituted with one or more substituents Z, wherein Z is independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —NR(substituted or unsubstituted $C_{3-7}$ cycloalkyl), —N(R)COR, —COOR, —$SO_2(C_{1-3}$ alkyl), —$SO_2NR_2$, —$SO_2$(substituted or unsubstituted heterocyclyl), —$OR^6$, and —CON($R^7$)$_2$; or two Z together with the carbons to which they are attached form a substituted or unsubstituted 5-6 membered heterocyclyl or substituted or unsubstituted $C_{5-6}$ heteroaryl;

Each $R^3$ is independently selected from substituted or unsubstituted $C_{1-5}$ alkyl, or substituted or unsubstituted 3-6 membered heterocyclyl;

Each $R^4$ is independently selected from substituted or unsubstituted $C_{1-5}$ alkyl, or substituted or unsubstituted $C_{3-6}$ cycloalkyl;

Each $R^5$ is independently selected from H, substituted or unsubstituted $C_{1-5}$ alkyl, substituted or unsubstituted $C_{3-6}$ cycloalkyl, and substituted or unsubstituted ($C_{1-3}$ alkyl)($C_{3-6}$ cycloalkyl), or two $R^5$ and the nitrogen to which they are attached form a substituted or unsubstituted 3 to 6 membered heterocyclyl;

Each $R^6$ is independently selected from substituted or unsubstituted $C_{1-5}$ alkyl, substituted or unsubstituted $C_{3-6}$ cycloalkyl, —($C_{1-3}$ alkyl)(substituted or unsubstituted $C_{3-6}$ cycloalkyl), or substituted or unsubstituted 3-8 membered heterocyclyl;

Each $R^7$ is independently selected from H, and substituted or unsubstituted $C_{1-5}$ alkyl, or two $R^7$ and the nitrogen to which they are attached form a substituted or unsubstituted 3 to 6 membered heterocyclyl.

$R^N$ is H, or substituted or unsubstituted $C_{1-5}$ alkyl; and each R is independently selected from H and substituted or unsubstituted $C_{1-4}$ alkyl;

provided $R^1$ and $R^2$ are not both unsubstituted.

In one embodiment, the compound is a compound of formula (Ia)

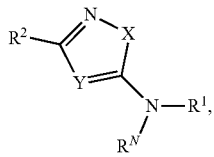

(Ia)

and pharmaceutically acceptable salts, tautomers, isotopologues, and stereoisomers thereof. In some such embodiments, the compound is a compound of formula (Ia), wherein X is NR, O, or S, and Y is N. In other such embodiments, the compound is a compound of formula (Ia), wherein X is O or S, and Y is N.

In other embodiments, the compound is a compound of formula (Ib)

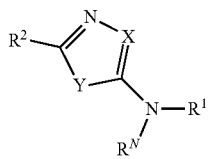

(Ib)

and pharmaceutically acceptable salts, tautomers, isotopologues, and stereoisomers thereof. In some such embodiments, the compound is a compound of formula (Ib), wherein X is N, and Y is NR, O, or S. In other such embodiments, the compound is a compound of formula (Ib), wherein X is N, and Y is O or S.

In still other embodiments, the compound is a compound of formula (Ic)

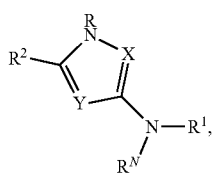

(Ic)

and pharmaceutically acceptable salts, tautomers, isotopologues, and stereoisomers thereof. In some such embodiments, the compound is a compound of formula (Ic) wherein X is N and Y is N.

Provided herein are Heterocyclic Compounds having the following formula (II):

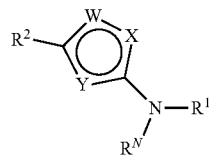

(II)

and pharmaceutically acceptable salts, tautomers, isotopologues, and stereoisomers thereof, wherein:

W is N, NR, or S;
X is N, NR, O, or S;
Y is N, NR, O, or S;
$R^1$ is 2-pyridyl, 3-pyridyl, pyrazinyl, or pyrimidyl, each unsubstituted or substituted with one or more substituents independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —$NR_2$, —COOR, —$OR^3$, —$SO_2NR_2$, —$SO_2$(substituted or unsubstituted heterocyclyl), —N(R)CO($R^4$), —CON($R^5$)$_2$, and substituted or unsubstituted $C_{6-10}$ aryl;
$R^2$ is

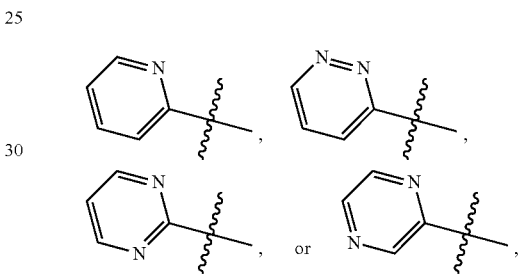

each unsubstituted or substituted with one or more substituents Z, wherein Z is independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —NR(substituted or unsubstituted $C_{3-7}$ cycloalkyl), —N(R)COR, —COOR, —$SO_2(C_{1-3}$ alkyl), —$SO_2NR_2$, —$SO_2$(substituted or unsubstituted heterocyclyl), —$OR^6$, and —CON($R^7$)$_2$; or two Z together with the carbons to which they are attached form a substituted or unsubstituted 5-6 membered heterocyclyl or substituted or unsubstituted $C_{5-6}$ heteroaryl;

Each $R^3$ is independently selected from substituted or unsubstituted $C_{1-5}$ alkyl, or substituted or unsubstituted 3-6 membered heterocyclyl;

Each $R^4$ is independently selected from substituted or unsubstituted $C_{1-5}$ alkyl, or substituted or unsubstituted $C_{3-6}$ cycloalkyl;

Each $R^5$ is independently selected from H, substituted or unsubstituted $C_{1-5}$ alkyl, substituted or unsubstituted $C_{3-6}$ cycloalkyl, and substituted or unsubstituted ($C_1$-3 alkyl)($C_{3-6}$ cycloalkyl), or two $R^5$ and the nitrogen to which they are attached form a substituted or unsubstituted 3 to 6 membered heterocyclyl;

Each $R^6$ is independently selected from substituted or unsubstituted $C_{1-5}$ alkyl, substituted or unsubstituted $C_{3-6}$ cycloalkyl, —($C_{1-3}$ alkyl)(substituted or unsubstituted $C_{3-6}$ cycloalkyl), or substituted or unsubstituted 3-8 membered heterocyclyl;

Each $R^7$ is independently selected from H, and substituted or unsubstituted $C_{1-5}$ alkyl, or two $R^7$ and the nitrogen to which they are attached form a substituted or unsubstituted 3 to 6 membered heterocyclyl.

$R^N$ is H, or substituted or unsubstituted $C_{1-5}$ alkyl; and each R is independently selected from H and substituted or unsubstituted $C_{1-4}$ alkyl;

provided $R^1$ and $R^2$ are not both unsubstituted.

In other embodiments, the compound is a compound of formula (IIa)

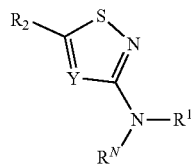

(IIa)

and pharmaceutically acceptable salts, tautomers, isotopologues, and stereoisomers thereof. In some such embodiments, the compound is a compound of formula (IIa) wherein Y is N.

In some embodiments of compounds of formula (I), (Ia), (Ib), (Ic), (II) and (IIa), $R^1$ is substituted with one or more substituents independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, substituted or unsubstituted $C_{6-10}$ aryl, —$NR_2$, —COOR, —$OR^3$, —$SO_2NR_2$, —$SO_2$(substituted or unsubstituted heterocyclyl), —N(R)CO($R^4$), and —CON($R^5$)$_2$. In some such embodiments, $R^1$ is substituted with one or more substituents independently selected from Cl, F, Br, CN, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CH_2F$, —$CHF_2$, —$CF_3$; substituted or unsubstituted cycloalkyl selected from cyclopropyl, cyclobutyl, and cyclopentyl; substituted or unsubstituted heterocyclyl selected from pyrrolidyl, pyrrolidinonyl, piperidyl, piperazinyl, and morpholinyl; substituted or unsubstituted phenyl; —$NH_2$, —$NHCH_3$, —N($CH_3$)$_2$, —COOH, —$COOCH_3$, —$OR^3$, —$SO_2N(CH_3)_2$; —$SO_2$(aziridinyl), —NHCO($R^4$), —N($CH_3$)CO($R^4$), —N($CH_2CH_3$)CO($R^4$), —N($CH_2CH_2CH_3$)CO($R^4$), —N($CH_2CH(CH_3)_2$)CO($R^4$), and —CON($R^5$)$_2$. In some such embodiments, $R^3$ is —$CH_3$, —$CH_2CH_3$, —$CH_2CH_2CH_3$, —$CH(CH_3)_2$, cyclohexyl, tetrahydrofuranyl, tetrahydropyranyl, piperidyl, or 1-$CH_3$-piperidyl. In other such embodiments, $R^3$ is —$CH_3$, —$CH(CH_3)_2$, cyclohexyl, tetrahydropyranyl, piperidyl, or 1-$CH_3$-piperidyl. In yet other such embodiments, $R^4$ is selected from —$CH_3$, —$CH_2CH_3$, —$CH_2CH_2CH_3$, —$CH(CH_3)_2$; substituted or unsubstituted cycloalkyl selected from cyclopropyl, cyclobutyl, cyclopentyl and cyclohexyl. For example, $R^4$ is selected from —$CH_3$, —$CH_2CH(CH_3)_2$, cyclopropyl, cyclobutyl, or cyclopentyl. In other embodiments, each $R^5$ is independently selected from H, —$CH_3$, —$CH_2CH_3$, —$CH_2CH_2CH_3$, —$CH(CH_3)_2$; substituted or unsubstituted cycloalkyl selected from cyclopropyl, cyclobutyl, cyclopentyl and cyclohexyl; substituted or unsubstituted -(alkyl)-(cycloalkyl) selected from —$CH_2$-cyclopropyl, —$CH_2$-cyclobutyl, and —$CH_2$-cyclopentyl; or two $R^5$ and the nitrogen to which they are attached form a pyrrolidyl. In some other such embodiments, each $R^5$ is independently selected from H, —$CH_3$, cyclopropyl, cyclobutyl, cyclobutyl substituted with one or more F, and —$CH_2$-cyclopropyl; or two $R^5$ and the nitrogen to which they are attached form a pyrrolidyl.

Also provided are compounds of formula (I), (Ia), (Ib), (Ic), (II) and (IIa), wherein $R^1$ is 2-pyridyl, 3-pyridyl or pyrazinyl. In some embodiments of compounds of formula (I), (Ia), (Ib), (Ic), (II) and (IIa), $R^1$ is 2-pyridyl, unsubstituted or substituted with one or more substituents independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, substituted or unsubstituted aryl, —$NR_2$, —COOR, —$OR^3$, —$SO_2NR_2$, —$SO_2$(substituted or unsubstituted heterocyclyl), —N(R)CO($R^4$), and —CON($R^5$)$_2$. In some embodiments of compounds of formula (I), (Ia), (Ib), (Ic), (II) and (IIa), $R^1$ is 2-pyridyl, substituted with one or more substituents independently selected from Cl, F, Br, CN, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$C(CH_3)_3$, —$CH_2F$, —$CHF_2$, —$CF_3$; substituted or unsubstituted cycloalkyl selected from cyclopropyl, cyclobutyl, and cyclopentyl; substituted or unsubstituted heterocyclyl selected from pyrrolidyl, pyrrolidinonyl, piperidyl, piperazinyl, and morpholinyl; substituted or unsubstituted phenyl; —$NH_2$, —$NHCH_3$, —N($CH_3$)$_2$, —COOH, —$COOCH_3$, —$OR^3$, —$SO_2N(CH_3)_2$; —$SO_2$(aziridinyl), —NHCO($R^4$), —N($CH_3$)CO($R^4$), —N($CH_2CH_3$)CO($R^4$), —N($CH_2CH_2CH_3$)CO($R^4$), —N($CH_2CH(CH_3)_2$)CO($R^4$), and —CON($R^5$)$_2$. In still other embodiments of compounds of formula (I), (Ia), (Ib), (Ic), (II) and (IIa), $R^1$ is 2-pyridyl, unsubstituted or substituted with one or more substituents independently selected from F; CN; —$CH_3$, —$CH(CH_3)_2$, —$C(CH_3)_3$, —$CHF_2$, —$CF_3$; cyclopropyl, cyclopentyl; pyrrolidyl, pyrrolidinonyl, piperidyl, 1-methyl-piperidyl, piperazinyl, piperazinyl substituted with —$COCH_3$ or —($COCH_2CF_3$), morpholinyl; phenyl; —$NHCH_3$, —N($CH_3$)$_2$; —COOMe; —$OCH_3$, —$OCH(CH_3)_2$, —O-(cyclohexyl), —O-piperidyl, —O-tetrahydropyranyl, —O-(1-methyl-piperidyl); —$SO_2N(CH_3)_2$; —$SO_2$ (aziridinyl), —$NHCOCH_3$, —N($CH_3$)$COCH_3$, —N($CH(CH_3)_2$)$COCH_3$, —N($CH_3$)CO($CH(CH_3)_2$), —N($CH_3$)CO(cyclopropyl), —N($CH_3$)CO(cyclobutyl), —N($CH_3$)CO(cyclopentyl); —$CONH_2$, —$CONHCH_3$, —CON($CH_3$)$_2$, —CON($CH_3$)cyclopropyl, —CONH(difluorocyclobutyl), —CON($CH_3$)(difluorocyclobutyl), —CONH($CH_2$-cyclopropyl), and —CO(pyrrolidyl).

In another aspect, also provided are compounds of formula (Ia), wherein X is S and Y is N, and $R^1$ is 2-pyridyl, unsubstituted or substituted with one or more substituents independently selected from F; CN; —$CH_3$, —$CH(CH_3)_2$, —$C(CH_3)_3$, —$CHF_2$, —$CF_3$; cyclopropyl, cyclopentyl; pyrrolidyl, pyrrolidinonyl, piperidyl, 1-methyl-piperidyl, piperazinyl, piperazinyl substituted with $COCH_3$ or ($COCH_2CF_3$), morpholinyl; phenyl; —$NHCH_3$, —N($CH_3$)$_2$; —COOMe; —$OCH_3$, —$OCH(CH_3)_2$, —O-piperidyl, —O-tetrahydropyranyl, —O-(1-methyl-piperidyl); —$SO_2N(CH_3)_2$; —$SO_2$(aziridinyl), —$NHCOCH_3$, —N($CH_3$)$COCH_3$, —N($CH(CH_3)_2$)$COCH_3$, —N($CH_3$)CO($CH(CH_3)_2$), —N($CH_3$)CO(cyclopropyl), —N($CH_3$)CO(cyclobutyl), —N($CH_3$)CO(cyclopentyl); —$CONH_2$, —$CONHCH_3$, —CON($CH_3$)$_2$, —CON($CH_3$)cyclopropyl, —CONH(difluorocyclobutyl), —CON($CH_3$)(difluorocyclobutyl), —CONH($CH_2$-cyclopropyl), and —CO(pyrrolidyl).

In another aspect, also provided are compounds of formula (Ib), wherein X is N and Y is S, and $R^1$ is 2-pyridyl, substituted with one or more substituents independently selected from —$CH_3$, —$CH(CH_3)_2$, —$CF_3$, phenyl, —$OCH_3$, and —$O(CH(CH_3)_2)$.

In still another aspect, provided are compounds of formula (Ia), wherein X is O and Y is N, and $R^1$ is 2-pyridyl, unsubstituted or substituted with one or more substituents independently selected from —CH$_3$, —CF$_3$, pyrrolidyl, phenyl, —N(CH$_3$)$_2$, —OCH$_2$CH$_3$, —O(CH(CH$_3$)$_2$), —O-tetrahydropyranyl, —N(CH$_3$)COCH$_3$, and —N(CH$_3$)CO(cyclopropyl).

In another aspect, provided are compounds of formula (Ib), wherein X is N and Y is O, and R$^1$ is 2-pyridyl, unsubstituted or substituted with one or more substituents independently selected from —CH$_3$, —CH(CH$_3$)$_2$, —CF$_3$, phenyl, —N(CH$_3$)$_2$, —OCH$_3$, —O(CH(CH$_3$)$_2$), and —O-(cyclohexyl).

In still another aspect, provided are compounds of formula (Ia), wherein X is NH and Y is N, and R$^1$ is 2-pyridyl, unsubstituted or substituted with one or more substituents independently selected from —CH$_3$, —CF$_3$, and —N(CH$_3$)$_2$.

In yet another aspect, provided are compounds of formula (Ib), wherein X is N and Y is NH, and R$^1$ is 2-pyridyl, unsubstituted or substituted with one or more substituents independently selected from —CH$_3$, phenyl, —O(CH(CH$_3$)$_2$), and —O-(cyclohexyl).

Also provided are compounds of formula (Ib), wherein X is N and Y is S, and R$^1$ is 2-pyridyl, unsubstituted or substituted with —O-(cyclohexyl).

Also provided are compounds of formula (Ib), wherein X is N and Y is N, and R$^1$ is 3-pyridyl, unsubstituted or substituted with one or more substituents independently selected from —CF$_3$ and —N(CH$_3$)COCH$_3$.

Also provided are compounds of formula (Ic), wherein R is —CH$_3$, X is N and Y is N, and R$^1$ is 2-pyridyl, unsubstituted or substituted with one or more substituents independently selected from —CH$_3$, —CH(CH$_3$)$_2$, —CF$_3$, —O(CH(CH$_3$)$_2$), and —O-(cyclohexyl).

Also provided are compounds of formula (Ic), wherein R is H, X is N and Y is N, and R$^1$ is 2-pyridyl, unsubstituted or substituted with one or more substituents independently selected from —CF$_3$ and —N(CH$_3$)COCH$_3$.

Also provided are compounds of formula (Ic), wherein R is —CH$_3$, X is N and Y is N, and R$^1$ is 2-pyridyl, unsubstituted or substituted with one or more substituents independently selected from —OCH(CH$_3$)$_2$ and —O-(cyclohexyl).

In another aspect, provided are compounds of formula (IIa), wherein Y is N and R$^1$ is 2-pyridyl, unsubstituted or substituted with one or more substituents independently selected from CH$_3$, —CF$_3$ and —N(CH$_3$)COCH$_3$.

In another aspect, also provided are compounds of formula (I), wherein R$^1$ is 3-pyridyl, substituted with one or more substituents independently selected from —CF$_3$ and —N(CH$_3$)COCH$_3$. In yet another aspect, also provided are compounds of formula (I), wherein R$^1$ is pyrazinyl, substituted with —CH$_3$, —N(CH$_3$)$_2$, —NH(CH$_3$), or —N(CH$_3$)COCH$_3$. In still another aspect, also provided are compounds of formula (I), wherein R$^1$ is unsubstituted pyrimidyl.

In some embodiments of compounds of formula (I), (Ia), (Ib), (Ic), (II), and (IIa), R$^2$ is substituted with one or more substituents Z, wherein Z is independently selected from halogen, CN, substituted or unsubstituted C$_{1-4}$ alkyl, substituted or unsubstituted C$_{3-7}$ cycloalkyl, substituted or unsubstituted 3-6 membered heterocyclyl, —NR(substituted or unsubstituted C$_{3-7}$ cycloalkyl), —N(R)COR, —COOR, —SO$_2$(C$_{1-3}$ alkyl), —SO$_2$NR$_2$, —SO$_2$(substituted or unsubstituted heterocyclyl), —OR$^6$, and —CON(R$^7$)$_2$ or two Z together with the carbons to which they are attached form a substituted or unsubstituted 5-6 membered heterocyclyl or substituted or unsubstituted C$_{5-6}$ heteroaryl. In some such embodiments, R$^2$ is substituted with one or more substituents independently selected from Cl, F, Br, CN, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —C(CH$_3$)$_3$, —CH$_2$F, —CHF$_2$, —CF$_3$; substituted or unsubstituted cycloalkyl selected from cyclopropyl, cyclobutyl, and cyclopentyl; substituted or unsubstituted heterocyclyl selected from piperidyl, piperazinyl, morpholinyl and thiomorpholinyl; —NH(bicyclo[1.1.1]pentyl), —N(CH$_3$)(bicyclo[1.1.1] pentyl); —NHCO(CH$_3$), —N(CH$_3$)CO(CH$_3$), —NHCO (CH$_2$CH$_3$), —N(CH$_3$)CO(CH$_2$CH$_3$); —COOH, —COOCH$_3$; —SO$_2$CH$_3$, —SO$_2$CH$_2$CH$_3$; —SO$_2$NHCH$_3$, —SO$_2$N(CH$_3$)$_2$; —SO$_2$(aziridinyl), —SO$_2$(piperidyl), —SO$_2$(1-methyl-aziridinyl), —SO$_2$(1-methyl-piperidyl), —SO$_2$(1-cyclopropyl-piperidyl), —OR$^6$, and —CON(R$^7$)$_2$.

In some such embodiments, R$^6$ is selected from —CH$_3$, —CH$_2$CH$_3$, —CH$_2$CH$_2$CH$_3$, —CH(CH$_3$)CH$_3$, —CH(CH$_3$)$_2$, —CH$_2$CH$_2$CH$_2$CH$_3$, —CH(CH$_3$)CH$_2$CH$_3$, —C(CH$_3$)$_3$, —CH$_2$F, —CHF$_2$, —CF$_3$, —CH$_2$CH$_2$F, —CH$_2$CHF$_2$, —CH$_2$CF$_3$, cyclopropyl, cyclobutyl, cyclopentyl, cyclohexyl, difluorocyclobutyl, difluorocyclopentyl, —CH$_2$-cyclopropyl, —CH$_2$-cyclobutyl, oxetanyl, piperidyl, fluoropiperidyl, -(1-methyl-piperidyl), -(1-isopropyl-piperidyl), -(1-isopropyl-fluoropiperidyl), -(1-isopropyl-difluoropiperidyl), -(1-cyclopropyl-piperidyl), -(1-cyclobutyl-piperidyl), -(1-cyclopentyl-piperidyl), -(1-cyclopropyl-fluoropiperidyl), -(1-cyclopropyl-difluoropiperidyl), -(1-CH$_2$-cyclopropyl-piperidyl), -(1-acetyl-piperidyl), -(1-(COCH(CH$_3$)$_2$)-piperidyl), tetrahydrofuranyl, tetrahydropyranyl, -(2-methyl-2-azaspiro[3.3]heptyl), -(2-cyclopropyl-2-azaspiro[3.3]heptyl), and -(6-methyl-6-azaspiro[3.4]octyl). In some other such embodiments, R$^6$ is selected from —CH$_3$, —CH(CH$_3$)$_2$, —C(CH$_3$)$_3$, —CH(CH$_3$)CH$_2$CH$_3$, —CHF$_2$, —CF$_3$, —CH$_2$CF$_3$, cyclopropyl, cyclohexyl, difluorocyclobutyl, —CH$_2$-cyclopropyl, oxetanyl, piperidyl, -(1-methyl-piperidyl), -(1-isopropyl-difluoropiperidyl), -(1-cyclopentyl-piperidyl), -(1-cyclopropyl-fluoropiperidyl), -(1-cyclopropyl-difluoropiperidyl), -(1-CH$_2$-cyclopropyl-piperidyl), -(1-acetyl-piperidyl), -(1-(COCH(CH$_3$)$_2$)-piperidyl), tetrahydropyranyl, -(2-methyl-2-azaspiro[3.3]heptyl), -(2-cyclopropyl-2-azaspiro[3.3] heptyl), and -(6-methyl-6-azaspiro[3.4]octyl). In yet other such embodiments, each R$^7$ is independently selected from H, —CH$_3$, —CH$_2$CH$_3$, —CH$_2$F, —CHF$_2$, —CF$_3$, —CH$_2$CH$_2$F, —CH$_2$CHF$_2$, and —CH$_2$CF$_3$, or two R$^7$ and the nitrogen to which they are attached form a heterocycle selected from unsubstituted or substituted pyrrolidyl, piperidyl, piperazinyl, or morpholinyl. In still other embodiments, each R$^7$ is independently selected from H, —CH$_3$, and —CH$_2$CF$_3$, or two R$^7$ and the nitrogen to which they are attached form a pyrrolidyl, 1-methyl-piperazinyl, or morpholinyl. In some such embodiments, R$^N$ is H, or substituted or unsubstituted C$_{1-5}$ alkyl. In some such embodiments, R$^N$ is —H, —CH$_3$, —CH$_2$CH$_3$, or —CH(CH$_3$)$_2$.

Also provided are compounds of formula (I), (Ia), (Ib), (Ic), (II), or (IIa), wherein R$^2$ is 2-pyridyl, substituted with one or more substituents Z, wherein Z is independently selected from halogen, CN, substituted or unsubstituted C$_{1-4}$ alkyl, substituted or unsubstituted C$_{3-7}$ cycloalkyl, substituted or unsubstituted 3-6 membered heterocyclyl, —NR (substituted or unsubstituted C$_{3-7}$ cycloalkyl), —N(R)COR, —COOR, —SO$_2$(C$_{1-3}$ alkyl), —SO$_2$NR$_2$, —SO$_2$(substituted or unsubstituted heterocyclyl), —OR$^6$, and —CON (R$^7$)$_2$, or two Z together with the carbons to which they are attached form a substituted or unsubstituted 5-6 membered heterocyclyl or substituted or unsubstituted C$_{5-6}$ heteroaryl.

Also provided are compounds of formula (I), (Ia), (Ib), (Ic)

(II), or (IIa), wherein $R^2$ is 2-pyridyl, substituted with one or more substituents independently selected from Cl, F, Br, CN, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$C(CH_3)_3$, —$CH_2F$, —$CHF_2$, —$CF_3$; substituted or unsubstituted cycloalkyl selected from cyclopropyl, cyclobutyl, and cyclopentyl; substituted or unsubstituted heterocyclyl selected from piperidyl, piperazinyl, morpholinyl and thiomorpholinyl; —NH(bicyclo[1.1.1]pentyl), —N($CH_3$)(bicyclo[1.1.1]pentyl); —NHCO($CH_3$), —N($CH_3$)CO($CH_3$), —NHCO($CH_2CH_3$), —N($CH_3$)CO($CH_2CH_3$); —COOH, —COOCH$_3$; —SO$_2$CH$_3$, —SO$_2$CH$_2$CH$_3$; —SO$_2$NHCH$_3$, —SO$_2$N(CH$_3$)$_2$; —SO$_2$(aziridinyl), —SO$_2$(piperidyl), —SO$_2$(1-methyl-aziridinyl), —SO$_2$(1-methyl-piperidyl), —SO$_2$(1-cyclopropyl-piperidyl), —OR$^6$, and —CON($R^7$)$_2$. Also provided are compounds of formula (I), (Ia), (Ib), (Ic), (II), or (IIa), wherein $R^2$ is 2-pyridyl, substituted with one or more substituents independently selected from F, CN, —CH$_3$, —CH(CH$_3$)$_2$, —CHF$_2$, —CF$_3$; -cyclopropyl; -(1-methyl-piperidyl), -(1-methyl-piperazinyl), thiomorpholinyl 1,1-dioxidyl; —NH(bicyclo[1.1.1]pentyl); —NHCO(CH$_3$), —N(CH$_3$)CO(CH$_3$); —COOCH$_3$; —SO$_2$CH$_3$; —SO$_2$N(CH$_3$)$_2$; —SO$_2$(1-methyl-aziridinyl), —SO$_2$(1-methyl-piperidyl), —SO$_2$(1-cyclopropyl-piperidyl); —OCH$_3$, —OCH(CH$_3$)$_2$, —OC(CH$_3$)$_3$, —OCH(CH$_3$)CH$_2$CH$_3$, —OCHF$_2$, —OCF$_3$, —OCH$_2$CF$_3$, —O-cyclopropyl, —O-cyclohexyl, —O-difluorocyclobutyl, —O—(CH$_2$-cyclopropyl), —O-oxetanyl, —O-piperidyl, —O-(1-methyl-piperidyl), —O-(1-isopropyl-difluoropiperidyl), —O-(1-cyclopentyl-piperidyl), —O-(1-cyclopropyl-fluoropiperidyl), —O-(1-cyclopropyl-difluoropiperidyl), —O-(1-CH$_2$-cyclopropyl-piperidyl), —O-(1-acetyl-piperidyl), —O-(1-(COCH(CH$_3$)$_2$)-piperidyl), —O-tetrahydropyranyl, —O-(2-methyl-2-azaspiro[3.3]heptyl), —O-(2-cyclopropyl-2-azaspiro[3.3]heptyl), —O-(6-methyl-6-azaspiro[3.4]octyl); —CONH$_2$, —CON(CH$_3$)$_2$, —CONHCH$_2$CF$_3$, —CO(pyrrolidyl), —CO(1-methyl-piperazinyl), and —CO(morpholinyl).

In another aspect, provided are compounds of formula (Ia), wherein X is S and Y is N, and $R^2$ is 2-pyridyl, unsubstituted or substituted with one or more substituents independently selected from F, CN, —CH$_3$, —CH(CH$_3$)$_2$, —CHF$_2$, —CF$_3$; cyclopropyl; -(1-methyl-piperidyl), -(1-methyl-piperazinyl), thiomorpholinyl 1,1-dioxidyl; —NH(bicyclo[1.1.1]pentyl); —NHCO(CH$_3$), —N(CH$_3$)CO(CH$_3$); —COOCH$_3$; —SO$_2$CH$_3$; —SO$_2$N(CH$_3$)$_2$; —SO$_2$(1-methyl-aziridinyl), —SO$_2$(1-methyl-piperidyl), —SO$_2$(1-cyclopropyl-piperidyl); —OCH$_3$, —OCH(CH$_3$)$_2$, —OCH(CH$_3$)CH$_2$CH$_3$, —OCF$_3$, —OCH$_2$CF$_3$, —O-cyclopropyl, —O-cyclohexyl, 0-difluorocyclobutyl, —O—(CH$_2$-cyclopropyl), —O-oxetanyl, —O-piperidyl, —O-(1-methyl-piperidyl), —O-(1-isopropyl-difluoropiperidyl), —O-(1-cyclopentyl-piperidyl), —O-(1-cyclopropyl-fluoropiperidyl), —O-(1-cyclopropyl-difluoropiperidyl), —O-(1-CH$_2$-cyclopropyl-piperidyl), —O-(1-acetyl-piperidyl), —O-(1-(COCH(CH$_3$)$_2$)-piperidyl), —O-tetrahydropyranyl, —O-(2-methyl-2-azaspiro[3.3]heptyl), —O-(2-cyclopropyl-2-azaspiro[3.3]heptyl), —O-(6-methyl-6-azaspiro[3.4]octyl); —CONH$_2$, —CON(CH$_3$)$_2$, —CONHCH$_2$CF$_3$, —CO(pyrrolidyl), —CO(1-methyl-piperazinyl), and —CO(morpholinyl).

In yet another aspect, provided are compounds of formula (Ib), wherein X is N and Y is S, and $R^2$ is 2-pyridyl, unsubstituted or substituted with one or more substituents independently selected from —CH$_3$, —OCH$_3$, —OCH(CH$_3$)$_2$, —O-cyclohexyl, —O-(1-methyl-piperidyl), and —O-tetrahydropyranyl.

In still another aspect, provided are compounds of formula (Ia), wherein X is O and Y is N, and $R^2$ is 2-pyridyl, unsubstituted or substituted with one or more substituents independently selected from F, —CH$_3$, —OCH$_3$, —OCH(CH$_3$)$_2$, —O-oxetanyl, —O-cyclohexyl, —O-(1-methyl-piperidyl), —O-tetrahydropyranyl, and —CON(CH$_3$)$_2$.

In another aspect, provided are compounds of formula (Ib), wherein X is N and Y is O, and $R^2$ is 2-pyridyl, unsubstituted or substituted with one or more substituents independently selected from —CH$_3$, —CH(CH$_3$)$_2$, —CF$_3$, —OCH$_3$, —OCH(CH$_3$)$_2$, —O-cyclohexyl, and —O-tetrahydropyranyl.

In another aspect, provided are compounds of formula (Ia), wherein X is NH and Y is N, and $R^2$ is 2-pyridyl, unsubstituted or substituted with one or more substituents independently selected from —OCH(CH$_3$)$_2$, and —O-(1-methyl-piperidyl).

In another aspect, also provided are compounds of formula (Ib), wherein X is N and Y is NH, and $R^2$ is 2-pyridyl, unsubstituted or substituted with one or more substituents independently selected from —CH$_3$, —OCH$_3$, and —O-tetrahydropyranyl.

In another aspect, provided are compounds of formula (Ic), wherein R is —CH$_3$, X is N and Y is N, and $R^2$ is 2-pyridyl, unsubstituted or substituted with one or more substituents independently selected from —OCH(CH$_3$)$_2$, and —O-cyclopropyl.

In another aspect, provided are compounds of formula (IIa), wherein Y is N and $R^2$ is 2-pyridyl, unsubstituted or substituted with one or more substituents independently selected from —CH$_3$, —O(C(CH$_3$)$_3$, and —O-tetrahydropyranyl.

In still another aspect, provided are compounds of formula (I), (Ia), (Ib), (Ic), (II), or (IIa), wherein $R^2$ is pyridazinyl, substituted with —OCH(CH$_3$)$_2$. In another aspect, provided are compounds of formula (I), (Ia), (Ib), (Ic), (II), or (Ia), wherein $R^2$ is pyrazinyl, substituted with —OCH$_3$, —OCH(CH$_3$)$_2$, or —OCH$_2$CH(CH$_3$)$_2$. In still another aspect, provided are compounds of formula (I), (Ia), (Ib), (Ic), (II), or (IIa), wherein $R^2$ is pyrimidyl, substituted with —OCH(CH$_3$)$_2$ or —O-(1-methyl-piperidyl).

Also provided are compounds of formula (I), (Ia), (Ib), (Ic), (II), or (IIa), wherein $R^2$ is 2-pyridyl substituted with two substituents Z, wherein the two Z together with the carbons to which they are attached form a substituted or unsubstituted 5-membered heterocyclyl. In some such embodiments, the two Z together with the carbons to which they are attached form a substituted or unsubstituted dihydropyrolyl or dihydrofuryl.

Also provided are compounds of formula (I), (Ia), (Ib), (Ic), (II), or (IIa), wherein $R^2$ is 2-pyridyl substituted with two substituents Z, wherein the two Z together with the carbons to which they are attached form a substituted or unsubstituted $C_{5-6}$ heteroaryl. In some other embodiments, $R^2$ is a substituted or unsubstituted 6,7-dihydro-5H-pyrrolo[3,4-b]pyridyl; 2,3-dihydro-1H-pyrrolo[2,3-c]pyridyl; 2,3-dihydro-1H-pyrrolo[3,4-c]pyridyl; 2-oxo-2,3-dihydro-1H-pyrrolo[2,3-c]pyridyl; 1H-pyrrolo[2,3-c]pyridyl; or 2,3-dihydrofuro[2,3-c]pyridyl. In some such embodiments, $R^2$ is substituted with one or more substituents selected from —CH$_3$, —CH(CH$_3$)$_2$, —CH$_2$-cyclopropyl, and —COCH$_3$.

Also provided are compounds of formula (I), (Ia), (Ib), (Ic), (II), or (IIa), wherein $R^2$ is

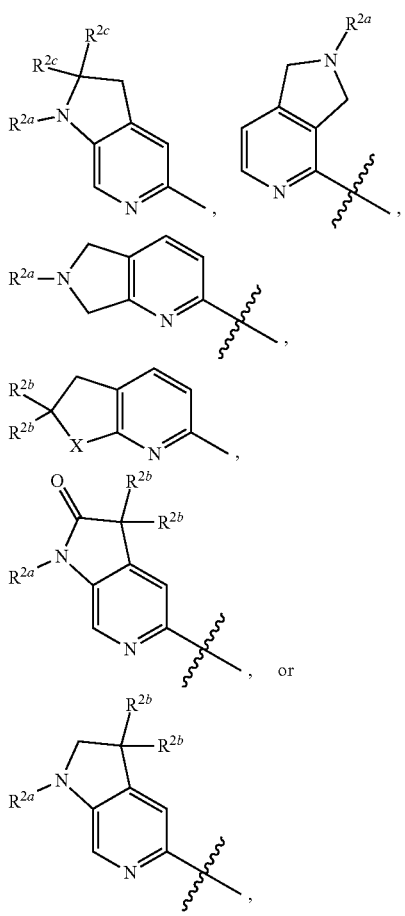

wherein $R^{2a}$ is H, —CH$_3$, —CH(CH$_3$)$_2$, —CH$_2$cyclopropyl, or —COCH$_3$, $R^{2b}$ is —CH$_3$, $R^{2c}$ is H or —CH$_3$ and X is O or NR. In some such embodiments, R is independently H, or —CH$_3$.

In some embodiments of compounds of formula (I), (Ia), (Ib), (Ic), (II), or (IIa) $R^N$ is —H, —CH$_3$, —CH$_2$CH$_3$, or —CH(CH$_3$)$_2$. In other embodiments of compounds of formula (I), (Ia), (Ib), (Ic), (II), or (IIa), each R is independently H, or —CH$_3$.

In some embodiments of compounds of formula (I), (Ia), (Ib), (Ic), (II), or (IIa), $R^1$ is 2-pyridyl, 3-pyridyl or pyrazinyl, wherein $R^1$ is unsubstituted or substituted with one or more substituents independently selected from halogen, CN, substituted or unsubstituted C$_{1-4}$ alkyl, substituted or unsubstituted C$_{3-7}$ cycloalkyl, substituted or unsubstituted 3-6 membered heterocyclyl, substituted or unsubstituted aryl, —NR$_2$, —COOR, —OR$^3$, —SO$_2$NR$_2$, —SO$_2$(substituted or unsubstituted heterocyclyl), —N(R)CO(R$^4$), and —CON(R$^5$)$_2$; and $R^2$ is 2-pyridyl, pyridazinyl, pyrazinyl or pyrimidyl, wherein $R^2$ is substituted with one or more substituents Z, wherein Z is independently selected from halogen, CN, substituted or unsubstituted C$_{1-4}$ alkyl, substituted or unsubstituted C$_{3-7}$ cycloalkyl, substituted or unsubstituted 3-6 membered heterocyclyl, —NR(substituted or unsubstituted C$_{3-7}$ cycloalkyl), —N(R)COR, —COOR, —SO$_2$(C$_{1-3}$ alkyl), —SO$_2$NR$_2$, —SO$_2$(substituted or unsubstituted heterocyclyl), —OR$^6$, and —CON(R$^7$)$_2$. In some such embodiments, $R^N$ is H, or substituted or unsubstituted C$_{1-5}$ alkyl. In some such embodiments, $R^1$ is unsubstituted or substituted with one or more substituents independently selected from F; CN; —CH$_3$, —CH(CH$_3$)$_2$, —C(CH$_3$)$_3$, —CHF$_2$, —CF$_3$; cyclopropyl, cyclopentyl; pyrrolidyl, pyrrolidinonyl, piperidyl, 1-methyl-piperidyl, piperazinyl, piperazinyl substituted with —COCH$_3$ or —(COCH$_2$CF$_3$), morpholinyl; phenyl; —NHCH$_3$, —N(CH$_3$)$_2$; —COOMe; —OCH$_3$, —OCH(CH$_3$)$_2$, —O— piperidyl, —O-tetrahydropyranyl, —O-(1-methyl-piperidyl); —SO$_2$N(CH$_3$)$_2$; —SO$_2$(aziridinyl), —NHCOCH$_3$, —N(CH$_3$)COCH$_3$, —N(CH(CH$_3$)$_2$)COCH$_3$, —N(CH$_3$)CO(CH(CH$_3$)$_2$), —N(CH$_3$)CO(cyclopropyl), —N(CH$_3$)CO(cyclobutyl), —N(CH$_3$)CO(cyclopentyl); —CONH$_2$, —CONHCH$_3$, —CON(CH$_3$)$_2$, —CON(CH$_3$)cyclopropyl, —CONH(difluorocyclobutyl), —CON(CH$_3$)(difluorocyclobutyl), —CONH(CH$_2$-cyclopropyl), and —CO(pyrrolidyl); and $R^2$ is substituted with one or more substituents independently selected from F, CN, —CH$_3$, —CH(CH$_3$)$_2$, —CHF$_2$, —CF$_3$; -cyclopropyl; -(1-methyl-piperidyl), -(1-methyl-piperazinyl), thiomorpholinyl 1,1-dioxidyl; —NH(bicyclo[1.1.1]pentyl); —NHCO(CH$_3$), —N(CH$_3$)CO(CH$_3$); —COOCH$_3$; —SO$_2$CH$_3$; —SO$_2$N(CH$_3$)$_2$; —SO$_2$(1-methyl-aziridinyl), —SO$_2$(1-methyl-piperidyl), —SO$_2$(1-cyclopropyl-piperidyl); —OCH$_3$, —OCH(CH$_3$)$_2$, —OCH(CH$_3$)CH$_2$CH$_3$, —OCHF$_2$, —OCF$_3$, —OCH$_2$CF$_3$, —O-cyclopropyl, —O-cyclohexyl, —O-difluorocyclobutyl, —O—(CH$_2$-cyclopropyl), —O-oxetanyl, —O-piperidyl, —O-(1-methyl-piperidyl), —O-(1-isopropyl-difluoropiperidyl), —O-(1-cyclopentyl-piperidyl), —O-(1-cyclopropyl-fluoropiperidyl), —O-(1-cyclopropyl-difluoropiperidyl), —O-(1-CH$_2$-cyclopropyl-piperidyl), —O-(1-acetyl-piperidyl), —O-(1-(COCH(CH$_3$)$_2$)-piperidyl), —O-tetrahydropyranyl, —O-(2-methyl-2-azaspiro[3.3]heptyl), —O-(2-cyclopropyl-2-azaspiro[3.3]heptyl), —O-(6-methyl-6-azaspiro[3.4]octyl); —CONH$_2$, —CON(CH$_3$)$_2$, —CONHCH$_2$CF$_3$, —CO(pyrrolidyl), —CO(1-methyl-piperazinyl), and —CO(morpholinyl). In some such embodiments, $R^N$ is —H, —CH$_3$, —CH$_2$CH$_3$, or —CH(CH$_3$)$_2$. In some embodiments of compounds of formula (I), (Ia), (Ib), (Ic), (II), or (IIa), $R^1$ is 2-pyridyl, substituted with one or more substituents independently selected from —CH$_3$, —CF$_3$, —C(CH$_3$)$_3$, pyrrolidyl, pyrrolidinonyl, —N(CH$_3$)CO(CH$_3$), —N(CH$_3$)CO(cyclopropyl), —SO$_2$N(CH$_3$)$_2$ and —SO$_2$(aziridinyl); and $R^2$ is 2-pyridyl, substituted with one or more substituents selected from —CF$_3$, —OCH(CH$_3$)$_2$, and —OC(CH$_3$)$_3$; or $R^2$ is 2,3-dihydro-1H-pyrrolo[2,3-c]pyridine, substituted with —CH$_3$, or —CH(CH$_3$)$_2$. In some such embodiments, $R^N$ is —H.

In some embodiments of compounds of formula (I), (Ia), (Ib), (Ic), (II), or (IIa), $R^1$ is pyrazinyl, substituted with one or more substituents selected from NHCH$_3$ and N(CH$_3$)COCH$_3$; and $R^2$ is 1H-pyrrolo[2,3-c]pyridine, substituted with —CH(CH$_3$)$_2$.

In some embodiments of compounds of formula (I), (Ia), (Ib), (Ic), (II), or (IIa), $R^1$ is 2-pyridyl substituted with one or more substituents independently selected from —CF$_3$, —N(CH$_3$)COCH$_3$ and —CON(CH$_3$)$_2$; and $R^2$ is 2-oxo-2,3-dihydro-1H-pyrrolo[2,3-c]pyridine, substituted with —CH$_3$.

Further embodiments provided herein include combinations of at least one of the particular embodiments set forth above.

Representative compounds of formula (I), formula (Ia), formula (Ib), formula (Ic), formula (II), and formula (IIa) are set forth in Table 1.

Each of the compounds in Table 1 was tested in one or more of the in vitro parasite motility assays and was found to have activity therein.

Methods for Making Compounds

The Heterocyclic Compounds of formula (I), (Ia), (Ib), (Ic), (II), or (IIa), and Table 1, can be made using conventional organic syntheses and commercially available starting materials. By way of example and not limitation, Heterocyclic Compounds of formula (I), (Ia), (Ib), (Ic), (II), or (IIa), and Table 1, can be prepared as outlined in Scheme 1, shown below, as well as in the examples set forth herein. It should be noted that one skilled in the art would know how to modify the procedures set forth in the illustrative schemes and examples to arrive at the desired products.

to about 25° C. Compounds of formula (Ia) wherein $R^N$ is substituted or unsubstituted $C_{1-5}$ alkyl, are obtained by the combination of imidamides (B) and carbamothioate (D') in a solvent, such as DMSO, in the presence of base, such as potassium tert-butoxide, at temperatures ranging from about 0 to about 25° C. Subsequent alkylation of the latter compound with $R^N$—I, in a solvent, such as DMF, in the presence of a base, such as potassium carbonate, at room Scheme 1

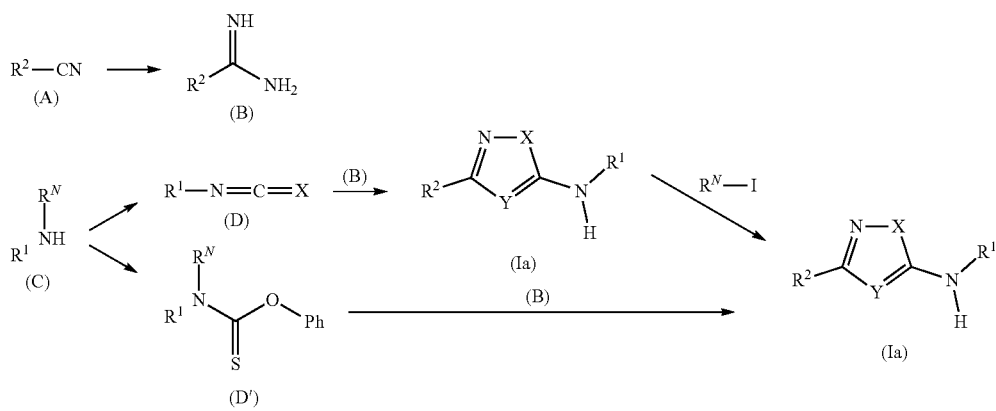

As shown in Scheme 1, compounds of formula (Ia) wherein X is S and Y is N, and $R^1$, $R^2$ and $R^N$ are as defined herein, can be prepared starting from an appropriately derivatized imidamide (B) and isothiocyanates (D) (wherein X is S) or carbamothioate (D'). Imidamides (B) are commercially available or may be prepared according to known methods (see for example, J. Med. Chem. (2016), 59, 965-984). Treatment of appropriately substituted nitriles (A) with $NH_4Cl$ in the presence of a base, such as sodium methoxide, in a solvent, such as MeOH, and heating at temperatures ranging from about 15 to about 70° C. provides imidamides (B). Isothiocyanates (D) are commercially available or may be prepared according to known methods (see for example, J. Org. Chem. (2017), 82, 5898-5903). Reaction of appropriately substituted amines (C) wherein $R^N$ is H, with thiophosgene, optionally in the presence of a base, such as DIPEA, in a solvent, such as DCM, at temperatures ranging from about −5 to about 20° C. provides isothiocyanates (D). Compounds of formula (Ia) wherein $R^N$ is H, are obtained by the combination of imidamides (B) and isothiocyanates (D) in a solvent, such as DCM or acetone, in the presence of a base, such as TEA, and heating at temperatures ranging from about 15 to about 70° C., and subsequent cyclization with I2 and oxidation with hydrogen peroxide in a solvent, such as EtOH, at temperatures ranging from about 0 to about 25° C. or cyclization by treatment with diisopropyl azodiformate in a solvent, such as THF, at temperatures ranging from about 0 to about 25° C. Amines (C) wherein $R^N$ is substituted or unsubstituted $C_{1-5}$ alkyl are commercially available or may be prepared by alkylation of amine (C) wherein $R^N$ is H with $R^N$—I, in a solvent, such as THF, in the presence of a base, such as n-BuLi, at temperatures ranging from about 0 to about 25° C. Carbamothioate (D') may be prepared by reaction of appropriately substituted amines (C), wherein $R^N$ is substituted or unsubstituted $C_{1-5}$ alkyl, with O-phenyl carbonochloridothioate in a solvent, such as THF, in the presence of a base, such as potassium carbonate, at temperatures ranging from about 0 temperature, provided the compounds of formula (Ia), wherein X is S and Y is N, and $R^N$ is substituted or unsubstituted $C_{1-5}$ alkyl.

Scheme 2

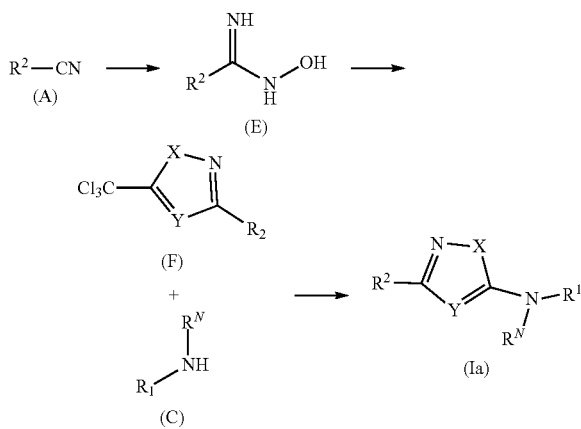

Alternatively, as shown in Scheme 2, compounds of formula (Ia) wherein X is O, Y is N and $R^1$, $R^2$ and $R^N$ are as defined herein, can be prepared starting from an appropriately derivatized trichloromethyl-oxadiazole (F) and amine (C). Trichloromethyl-oxadiazole (F) can be prepared from appropriately substituted N-hydroxyimidamides (E), which are commercially available or may be prepared according to known methods. For example treatment of appropriately substituted nitriles (A) with hydroxylamine hydrochloride in the presence of a base, such as TEA, in a solvent, such as EtOH, and heating at temperatures of about 70° C., provides the N-hydroxyimidamides (E). Treatment of N-hydroxyimidamides (E) with 2,2,2-trichloroacetic anhydride in a solvent, such as toluene, at a temperature of about 110° C., provides trichloromethyl-oxadiazoles (F). SN-aryl substitution reaction of trichloromethyl-oxadiazole (F) with $R^1NH_2$ (C) in in the presence of a base, such as NaH, in a solvent, such as THF, and heating at temperatures ranging from about 0 to about 25° C., provides compounds of formula (Ia), wherein X is O, and Y is N.

Scheme 3

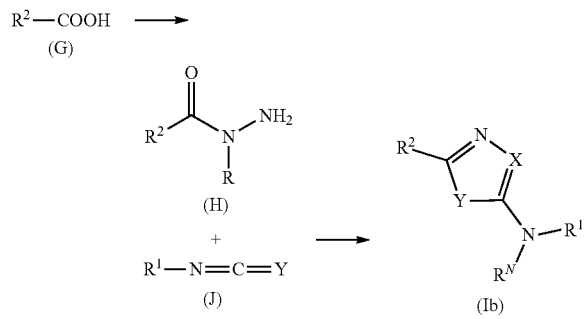

As shown in Scheme 3, compounds of formula (Ib) wherein X is N, Y is S or O, R is H, and $R^1$, $R^2$ and $R^N$ are as defined herein, can be prepared starting from an appropriately derivatized hydrazide (H) and isothiocyanates (J), wherein Y is S. Hydrazides (H) and isothiocyanates (J) are commercially available or may be prepared according to known methods (see, for example, *J. American Chemical Society* (2015), 137(47), 14982-14991) and those described herein. Esterification of appropriately substituted carboxylic acids (G), for example by treatment with $SOCl_2$ in a solvent, such as MeOH, and heating at temperatures ranging from about 10 to about 70° C., provides the ester derivative, which is subsequently transformed to hydrazide (H), wherein R is H, by treatment with hydrazine hydrate in a solvent, such as MeOH, and heating at temperatures ranging from room temperature to about 80° C. Compounds of formula (Ib), wherein X is N, Y is S and $R^N$ is H, are obtained by reaction of the derivatized hydrazides (H) and isothiocyanates (J) in a solvent, such as DCM, and heating at temperatures of about 30° C., followed by treatment with an acid, for example, p-toluenesulfonic acid, in a solvent, such as toluene, and heating at elevated temperatures, such as at about 100° C. Compounds of formula (Ib), wherein X is N, Y is O and $R^N$ is H, are obtained by reaction of the derivatized hydrazides (H) and isothiocyanates (J) in a solvent, such as DCM, and heating at temperatures of about 30° C., followed by cyclization with either 1-ethyl-3-(3-dimethylaminopropyl)carbodiimide in a solvent, such as DMSO, and heating at temperatures of about 60° C., or by cyclization with 2-iodylbenzoic acid in the presence of base, such as trimethylamine, at temperatures of about 0° C.

Scheme 4

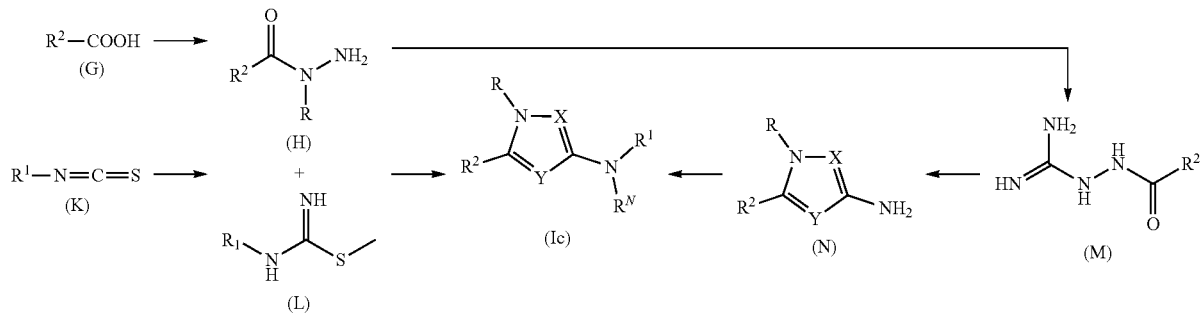

As shown in Scheme 4, compounds of formula (Ic), wherein X and Y are N, $R^N$ is H or substituted or unsubstituted $C_{1-4}$ alkyl, and R, $R^1$, $R^2$ are as defined herein, can be prepared starting from an appropriately derivatized hydrazide (H) and carbamimidothioate (L). Hydrazides (H) are commercially available or when R is H, may be prepared according to known methods, as described above. Hydrazides (H), wherein R is substituted or unsubstituted $C_{1-4}$ alkyl, may be prepared by treatment of appropriately substituted carboxylic acids (G) with appropriately N-substituted tert-butyl aminocarbamate in a solvent, such as DCM, in the presence of a base, such as DIPEA, and coupling reagents, such as hydroxybenzotriazole and 1-ethyl-3-(3-dimethylaminopropyl)carbodiimide hydrochloride, at temperatures ranging from about 0 to about 25° C. Carbamimidothioate (L) are commercially available or may be prepared according to known methods from appropriately substituted isothiocyanates (K). Treatment of isothiocyanates (K) with ammonium hydroxide in a solvent, such as DCM, at ambient temperature provides the thiourea derivative, which upon alkylation with iodomethane in a solvent, such as ACN, and heating at temperatures ranging from room temperature to about 40° C., provides carbamimidothioate (L). Treatment of hydrazide (H) and carbamimidothioate (L) in the presence of a base, such a pyridine or NaOH, and heating at temperatures ranging from about 100 to about 160° C., provides compounds of formula (Ic), wherein X and Y are N, and $R^N$ is H. Alternatively, compounds of formula (Ic), wherein X and Y are N, and $R^N$ is H, can be obtained by SN-aryl substitution reaction with triazole (N). Treatment of the appropriately substituted hydrazide (H) with methylisothiourea in the presence of an acid, such as sulfuric acid, in a solvent, such as $H_2O$, and heating at temperatures up to about 100° C., provides hydrazinecarboximidamide (M). Upon subsequent treatment with a base, such as pyridine or NaOH, and heating at temperatures ranging from about 100 to about 160° C. provides the triazole derivative (N). Triazole derivative (N) is further elaborated by SN-aryl substitution with $R^1$-Hal, wherein Hal is halogen, for example F, in the presence of a base, such as NaH, in a solvent, such as DMF, and heating at temperatures ranging from about 0 to about 25° C., to provide compounds of formula (Ic), wherein X and Y are N, and $R^N$ is H.

Scheme 5

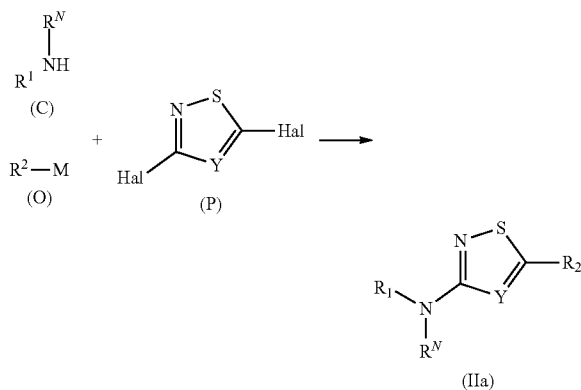

As shown in Scheme 5, compounds of formula (IIa) wherein Y is N, and $R^1$, $R^2$ and $R^N$ are as defined herein, can be prepared via two cross coupling reactions with a 3,5-dihalogenated-1,2,4-thiadiazole (P), wherein Hal is halogen, appropriately substituted amine (C) and organometallic compound (O). 3,5-Dihalogenated-1,2,4-thiadiazole (P) is commercially available. Organometallic compound (O) are commercially available or may be prepared by known methods (see for example, J. Med. Chem. (2015) 48(16), 5096-5099). Treatment of 3,5-dihalogenated-1,2,4-thiadiazole (P), wherein Hal is either Cl or Br, with appropriately substituted organometallic compound (O) in the presence of a metal catalyst and ligand, such as $Pd(PPh_3)_4$ and copper(I) thiophene-2-carboxylate, in a solvent, such as 1,4-dioxane at temperatures ranging from about 0 to about 20° C. followed by subsequent treatment with amine (C) in the presence of metal catalyst and ligand, such as $Pd_2(dba)_3$ and Xantphos and in a solvent, such as 1,4-dioxane at temperatures ranging from about 20 to about 110° C. provides compounds of formula (IIa) wherein Y is N.

In one aspect, provided herein are methods for preparing a Heterocyclic Compound of formula (Ia):

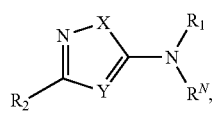

(Ia)

wherein X is S, Y is N, and $R^N$ is substituted or unsubstituted $C_{1-5}$ alkyl, the methods comprising contacting a Heterocyclic Compound of formula (Ia)

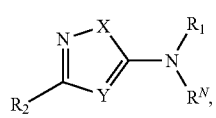

(Ia)

wherein $R^N$ is H,
with $R^N$—I, wherein $R^N$ is substituted or unsubstituted $C_{1-5}$ alkyl, in a solvent, in the presence of a base, under conditions suitable to provide a Heterocyclic Compound of formula (Ia); wherein X is S;
Y is N;
$R^N$ is substituted or unsubstituted $C_{1-5}$ alkyl;
$R^1$ is 2-pyridyl, 3-pyridyl, pyrazinyl, or pyrimidyl, each unsubstituted or substituted with one or more substituents independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —$NR_2$, —COOR, —$OR^3$, —$N(R)CO(R^4)$, —$CON(R^5)_2$, and substituted or unsubstituted $C_{6-10}$ aryl;
$R^2$ is

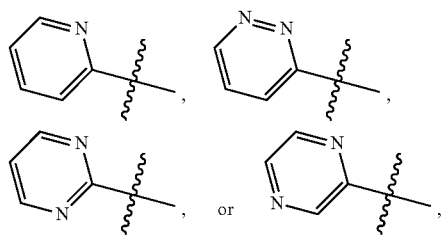

each unsubstituted or substituted with one or more substituents Z, wherein Z is independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —NR(substituted or unsubstituted $C_{3-7}$ cycloalkyl), —N(R)COR, —COOR, —$SO_2(C_{1-3}$ alkyl), —$SO_2NR_2$, —$SO_2$(substituted or unsubstituted heterocyclyl), —$OR^6$, and —$CON(R^7)_2$; or two Z together with the carbons to which they are attached form a substituted or unsubstituted 5-6 membered heterocyclyl;

Each $R^3$ is independently selected from substituted or unsubstituted $C_{1-5}$ alkyl, or substituted or unsubstituted 3-6 membered heterocyclyl;

Each $R^4$ is independently selected from substituted or unsubstituted $C_{1-5}$ alkyl, or substituted or unsubstituted $C_{3-6}$ cycloalkyl;

Each $R^5$ is independently selected from H, substituted or unsubstituted $C_{1-5}$ alkyl, substituted or unsubstituted $C_{3-6}$ cycloalkyl, and substituted or unsubstituted ($C_{1-3}$ alkyl)($C_{3-6}$ cycloalkyl), or two $R^5$ and the nitrogen to which they are attached for a substituted or unsubstituted 3 to 6 membered heterocyclyl;

Each $R^6$ is independently selected from substituted or unsubstituted $C_{1-5}$ alkyl, substituted or unsubstituted $C_{3-6}$ cycloalkyl, —($C_{1-3}$ alkyl)(substituted or unsubstituted $C_{3-6}$ cycloalkyl), or substituted or unsubstituted 3-8 membered heterocyclyl;

Each $R^7$ is independently selected from H, and substituted or unsubstituted $C_{1-5}$ alkyl, or two $R^5$ and the nitrogen to which they are attached for a substituted or unsubstituted 3 to 6 membered heterocyclyl; and each R is independently selected from H and substituted or unsubstituted $C_{1-4}$ alkyl;

provided $R^1$ and $R^2$ are not both unsubstituted.

In some such embodiments, the solvent is DMF. In some embodiments, the base is potassium carbonate. In some embodiments, the contacting is performed at room temperature.

In some embodiments, the methods further comprise preparing a Heterocyclic Compound of formula (Ia):

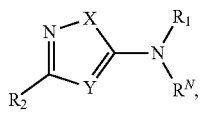

(Ia)

wherein X is S, Y is N, and $R^N$ is H,
the methods comprising:
a) contacting a compound of formula (B):

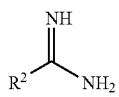

(B)

with $R^1$—NCX, wherein X is S, in a first solvent, optionally in the presence of a base;
b) contacting the product of step a) with I2 and hydrogen peroxide, in a second solvent; under conditions suitable to provide a Heterocyclic Compound of formula (Ia), wherein $R^N$ is H.

In some embodiments, the base is TEA. In some embodiments, the first solvent is DCM, acetone, or a mixture thereof. In some embodiments, the contacting in step (a) is performed at a temperature ranging from about 15 to about 70° C.

In some embodiments, the second solvent is EtOH. In some embodiments, the contacting in step (b) is performed at a temperature ranging from about 0 to about 25° C.

In some other embodiments, the methods further comprise preparing a Heterocyclic Compound of formula (Ia):

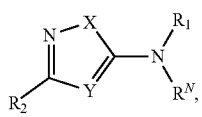

(Ia)

wherein X is S, Y is N, and $R^N$ is H, the methods comprising:
a) contacting a compound of formula (B):

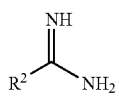

(B)

with $R^1$—NCX, wherein X is S, in a first solvent, optionally in the presence of a base;
b) contacting the product of step a) with diisopropyl azodiformate, in a second solvent, under conditions suitable to provide a Heterocyclic Compound of formula (Ia), wherein $R^N$ is H.

In some embodiments, the base is TEA. In some embodiments, the first solvent is DCM, acetone, or a mixture thereof. In some embodiments, the contacting in step (a) is performed at a temperature ranging from about 15 to about 70° C.

In some embodiments, the second solvent is THF. In some embodiments, the contacting in step (b) is performed at a temperature ranging from about 0 to about 25° C.

In some embodiments, the methods further comprise preparing a compound of formula (B):

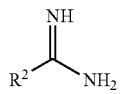

(B)

the method comprising contacting $R^2$—CN with $NH_4Cl$ in the presence of a base, in a solvent, under conditions suitable to provide a compound of formula (B).

In one embodiment, the base is sodium methoxide. In one embodiment, the solvent is MeOH. In some embodiments, the contacting is performed at a temperature ranging from 15 to 70° C.

In some embodiments, the methods further comprise preparing a compound of formula (D):

(D)

wherein X is S, the method comprising contacting $R^1NH_2$ with thiophosgene, optionally in the presence of a base, in a solvent, under conditions suitable to provide a compound of formula (D) wherein X is S.

In one embodiment, the base is DIPEA. In one embodiment, the solvent is DCM. In some embodiments, the contacting is performed at a temperature ranging from −5 to 20° C.

In another aspect, provided herein are methods for preparing a Heterocyclic Compound of formula (Ia):

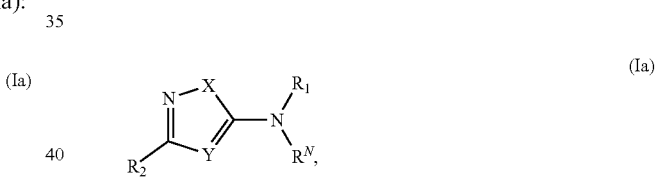

(Ia)

wherein X is O, and Y is N,
the methods comprising contacting a compound of formula (F)

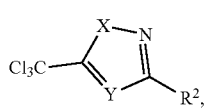

(F)

with $NHR^1R^N$, in a solvent, in the presence of a base, under conditions suitable to provide a Heterocyclic Compound of formula (Ia); wherein
X is O;
Y is N;
$R^1$ is 2-pyridyl, 3-pyridyl, pyrazinyl, or pyrimidyl, each unsubstituted or substituted with one or more substituents independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —$NR_2$, —COOR, —$OR^3$, —$N(R)CO(R^4)$, —$CON(R^5)_2$, and substituted or unsubstituted $C_{6-10}$ aryl;

$R^2$ is

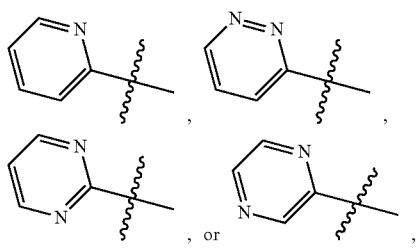, or each unsubstituted or substituted with one or more substituents Z, wherein Z is independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —NR(substituted or unsubstituted $C_{3-7}$ cycloalkyl), —N(R)COR, —COOR, —SO$_2$(C$_{1-3}$ alkyl), —SO$_2$NR$_2$, —SO$_2$(substituted or unsubstituted heterocyclyl), —OR$^6$, and —CON(R$^7$)$_2$; or two Z together with the carbons to which they are attached form a substituted or unsubstituted 5-6 membered heterocyclyl;

Each $R^3$ is independently selected from substituted or unsubstituted $C_{1-5}$ alkyl, or substituted or unsubstituted 3-6 membered heterocyclyl;

Each $R^4$ is independently selected from substituted or unsubstituted $C_{1-5}$ alkyl, or substituted or unsubstituted $C_{3-6}$ cycloalkyl;

Each $R^5$ is independently selected from H, substituted or unsubstituted $C_{1-5}$ alkyl, substituted or unsubstituted $C_{3-6}$ cycloalkyl, and substituted or unsubstituted (C$_{1-3}$ alkyl)(C$_{3-6}$ cycloalkyl), or two $R^5$ and the nitrogen to which they are attached for a substituted or unsubstituted 3 to 6 membered heterocyclyl;

Each $R^6$ is independently selected from substituted or unsubstituted $C_{1-5}$ alkyl, substituted or unsubstituted $C_{3-6}$ cycloalkyl, —(C$_{1-3}$ alkyl)(substituted or unsubstituted $C_{3-6}$ cycloalkyl), or substituted or unsubstituted 3-8 membered heterocyclyl;

Each $R^7$ is independently selected from H, and substituted or unsubstituted $C_{1-5}$ alkyl, or two $R^5$ and the nitrogen to which they are attached for a substituted or unsubstituted 3 to 6 membered heterocyclyl;

$R^N$ is H, or substituted or unsubstituted $C_{1-5}$ alkyl; and each R is independently selected from H and substituted or unsubstituted $C_{1-4}$ alkyl;

provided $R^1$ and $R^2$ are not both unsubstituted.

In some such embodiments, the solvent is THF. In some embodiments, the base is NaH. In some embodiments, the contacting is performed at temperatures ranging from about 0 to about 25° C.

In some embodiments, the methods further comprise preparing a compound of formula (F)

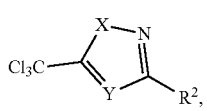 (F)

the methods comprising contacting N-hydroxyimidamides of formula (E)

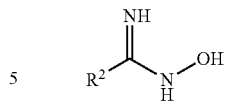 (E)

with 2,2,2-trichloroacetic anhydride in a solvent, under conditions suitable to provide a a compound of formula (F). In one embodiment, the solvent is toluene. In another embodiment, the contacting is performed at a temperature of about 110° C.

In some embodiments, the methods further comprise preparing a compound of formula (E)

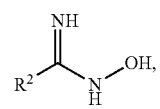 (E)

the methods comprising contacting $R^2$CN with hydroxylamine hydrochloride in the presence of a base, such as TEA, in a solvent, and heating at temperatures of about 70° C., under conditions suitable to provide a a compound of formula (E).

In one embodiment, the base is TEA. In one embodiment, the solvent is EtOH. In another embodiment, the contacting is performed at a temperature of about 70° C.

In one aspect, also provided herein are methods for preparing a Heterocyclic Compound of formula (Ib):

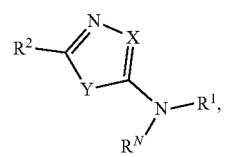 (Ib)

wherein X is N, Y is O, and $R^N$ is H,
the methods comprising contacting a compound of formula (H)

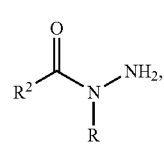 (H)

with a compound of formula (J)

$R^1$—N=C=Y (J)

wherein Y is S, in a solvent, at a first temperature, followed by cyclization with 2-iodylbenzoic acid in the presence of a base, at a second temperature, under conditions suitable to provide a Heterocyclic Compound of formula (Ib); wherein
X is N;
Y is O;
$R^N$ is H;
$R^1$ is 2-pyridyl, 3-pyridyl, pyrazinyl, or pyrimidyl, each unsubstituted or substituted with one or more substituents independently selected from halogen, CN, substituted or unsubstituted C$_{1-4}$ alkyl, substituted or unsubstituted C$_{3-7}$ cycloalkyl, substituted or unsubstituted 3-6 membered heterocyclyl, —NR$_2$, —COOR, —OR$^3$, —N(R)CO(R$^4$), —CON(R$^5$)$_2$, and substituted or unsubstituted C$_{6-10}$ aryl;

R$^2$ is

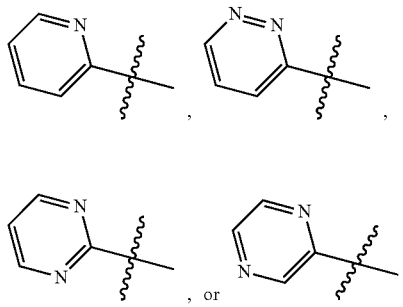

each unsubstituted or substituted with one or more substituents Z, wherein Z is independently selected from halogen, CN, substituted or unsubstituted C$_{1-4}$ alkyl, substituted or unsubstituted C$_{3-7}$ cycloalkyl, substituted or unsubstituted 3-6 membered heterocyclyl, —NR(substituted or unsubstituted C$_{3-7}$ cycloalkyl), —N(R)COR, —COOR, —SO$_2$(C$_{1-3}$ alkyl), —SO$_2$NR$_2$, —SO$_2$(substituted or unsubstituted heterocyclyl), —OR$^6$, and —CON(R$^7$)$_2$; or two Z together with the carbons to which they are attached form a substituted or unsubstituted 5-6 membered heterocyclyl;

Each R$^3$ is independently selected from substituted or unsubstituted C$_{1-5}$ alkyl, or substituted or unsubstituted 3-6 membered heterocyclyl;

Each R$^4$ is independently selected from substituted or unsubstituted C$_{1-5}$ alkyl, or substituted or unsubstituted C$_{3-6}$ cycloalkyl;

Each R$^5$ is independently selected from H, substituted or unsubstituted C$_{1-5}$ alkyl, substituted or unsubstituted C$_{3-6}$ cycloalkyl, and substituted or unsubstituted (C$_{1-3}$ alkyl)(C$_{3-6}$ cycloalkyl), or two R$^5$ and the nitrogen to which they are attached for a substituted or unsubstituted 3 to 6 membered heterocyclyl;

Each R$^6$ is independently selected from substituted or unsubstituted C$_{1-5}$ alkyl, substituted or unsubstituted C$_{3-6}$ cycloalkyl, —(C$_{1-3}$ alkyl)(substituted or unsubstituted C$_{3-6}$ cycloalkyl), or substituted or unsubstituted 3-8 membered heterocyclyl;

Each R$^7$ is independently selected from H, and substituted or unsubstituted C$_{1-5}$ alkyl, or two R$^5$ and the nitrogen to which they are attached for a substituted or unsubstituted 3 to 6 membered heterocyclyl; and each R is independently selected from H and substituted or unsubstituted C$_{1-4}$ alkyl;

provided R$^1$ and R$^2$ are not both unsubstituted.

In some such embodiments, the solvent is DCM. In some embodiments, the contacting is performed at a temperature of about 30° C. In some embodiments, the base is potassium carbonate. In some embodiments, the second temperature is about 0° C.

In one aspect, also provided herein are methods for preparing a Heterocyclic Compound of formula (Ib):

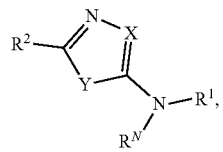

wherein X is N, Y is O, and R$^N$ is H, the methods comprising contacting a compound of formula (H)

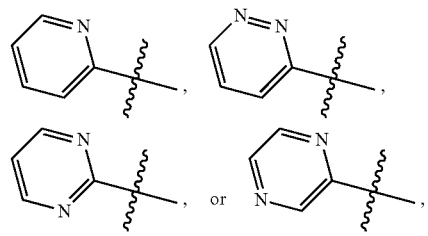

with a compound of formula (J)

$$R^1-N=C=Y \qquad (J)$$

wherein Y is S, in a solvent, at a first temperature, followed by cyclization with 1-ethyl-3-(3-dimethylaminopropyl)carbodiimide in a second solvent, at a second temperature, under conditions suitable to provide a Heterocyclic Compound of formula (Ib); wherein X is N;
Y is O;
R$^N$ is H;
R$^1$ is 2-pyridyl, 3-pyridyl, pyrazinyl, or pyrimidyl, each unsubstituted or substituted with one or more substituents independently selected from halogen, CN, substituted or unsubstituted C$_{1-4}$ alkyl, substituted or unsubstituted C$_{3-7}$ cycloalkyl, substituted or unsubstituted 3-6 membered heterocyclyl, —NR$_2$, —COOR, —OR$^3$, —N(R)CO(R$^4$), —CON(R$^5$)$_2$, and substituted or unsubstituted C$_{6-10}$ aryl;

R$^2$ is

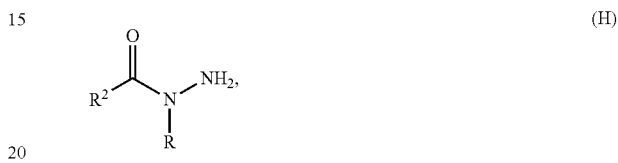

each unsubstituted or substituted with one or more substituents Z, wherein Z is independently selected from halogen, CN, substituted or unsubstituted C$_{1-4}$ alkyl, substituted or unsubstituted C$_{3-7}$ cycloalkyl, substituted or unsubstituted 3-6 membered heterocyclyl, —NR(substituted or unsubstituted C$_{3-7}$ cycloalkyl), —N(R)COR, —COOR, —SO$_2$(C$_{1-3}$ alkyl), —SO$_2$NR$_2$, —SO$_2$(substituted or unsubstituted heterocyclyl), —OR$^6$, and —CON(R$^7$)$_2$; or two Z together with the carbons to which they are attached form a substituted or unsubstituted 5-6 membered heterocyclyl;

Each R$^3$ is independently selected from substituted or unsubstituted C$_{1-5}$ alkyl, or substituted or unsubstituted 3-6 membered heterocyclyl;

Each R⁴ is independently selected from substituted or unsubstituted $C_{1-5}$ alkyl, or substituted or unsubstituted $C_{3-6}$ cycloalkyl;

Each R⁵ is independently selected from H, substituted or unsubstituted $C_{1-5}$ alkyl, substituted or unsubstituted $C_{3-6}$ cycloalkyl, and substituted or unsubstituted ($C_{1-3}$ alkyl)($C_{3-6}$ cycloalkyl), or two R⁵ and the nitrogen to which they are attached for a substituted or unsubstituted 3 to 6 membered heterocyclyl;

Each R⁶ is independently selected from substituted or unsubstituted $C_{1-5}$ alkyl, substituted or unsubstituted $C_{3-6}$ cycloalkyl, —($C_{1-3}$ alkyl)(substituted or unsubstituted $C_{3-6}$ cycloalkyl), or substituted or unsubstituted 3-8 membered heterocyclyl;

Each R⁷ is independently selected from H, and substituted or unsubstituted $C_{1-5}$ alkyl, or two R⁵ and the nitrogen to which they are attached for a substituted or unsubstituted 3 to 6 membered heterocyclyl; and each R is independently selected from H and substituted or unsubstituted $C_{1-4}$ alkyl;

provided R¹ and R² are not both unsubstituted.

In some such embodiments, the solvent is DCM. In some embodiments, the contacting is performed at a temperature of about 30° C. In some embodiments, the second solvent is DMSO. In some embodiments, the second temperature is about 60° C.

In some embodiments, the methods further comprise preparing a compound of formula (Ib):

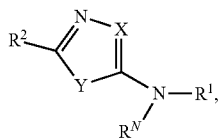
(Ib)

wherein X is N, Y is S, and $R^N$ is H, the methods comprising:

a) contacting a compound of formula (H)

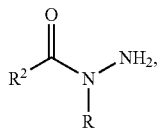
(H)

with a compound of formula (J)

R¹—N=C=Y    (J)

wherein Y is S, in a first solvent;

b) contacting the product of step a) with an acid, in a second solvent, under conditions suitable to provide a Heterocyclic Compound of formula (Ib), wherein X is N, Y is S, and $R^N$ is H.

In some embodiments, the first solvent is DCM. In some embodiments, the contacting in step (a) is performed at a temperature ranging of about 30° C.

In some embodiments, the second solvent is toluene. In some embodiments the acid is p-toluenesulfonic acid. In some embodiments, the contacting in step (b) is performed at elevated temperature. In one embodiment, the contacting in step (b) is performed at a temperature of about 100° C.

In some embodiments, the methods further comprise preparing a compound of formula (H):

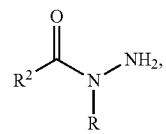
(H)

wherein R is H, the methods comprising:

a) contacting R²COOH with SOCl₂, in a first solvent; and b) contacting the product of step a) with hydrazine hydrate, in a second solvent under conditions suitable to provide a compound of formula (H), wherein R is H.

In some embodiments, the first solvent is MeOH. In one embodiment, the contacting in step a) is performed at a temperature ranging from about 10 to about 70° C.

In some embodiments, the second solvent is MeOH. In one embodiment, the contacting in step b) is performed at a temperature ranging from room temperature to about 80° C.

In one aspect, provided herein are methods for preparing a Heterocyclic Compound of formula (Ic):

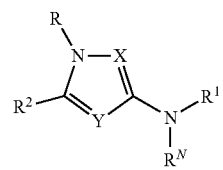
(Ic)

wherein X and Y are N, $R^N$ is H, the methods comprising contacting a compound of formula (H):

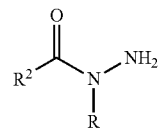
(H)

with a compound of formula (L):

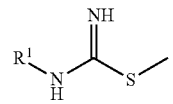
(L)

in a solvent, in the presence of a base, under conditions suitable to provide a Heterocyclic Compound of formula (Ic), wherein X is N;

Y is N;

$R^N$ is H;

R¹ is 2-pyridyl, 3-pyridyl, pyrazinyl, or pyrimidyl, each unsubstituted or substituted with one or more substituents independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —NR₂, —COOR, —OR³, —N(R)CO(R⁴), —CON(R⁵)₂, and substituted or unsubstituted $C_{6-10}$ aryl;

$R^2$ is

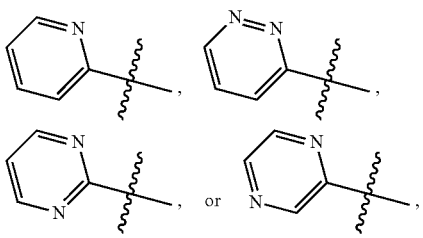

each unsubstituted or substituted with one or more substituents Z, wherein Z is independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —NR(substituted or unsubstituted $C_{3-7}$ cycloalkyl), —N(R)COR, —COOR, —SO$_2$($C_{1-3}$ alkyl), —SO$_2$NR$_2$, —SO$_2$(substituted or unsubstituted heterocyclyl), —OR$^6$, and —CON(R$^7$)$_2$; or two Z together with the carbons to which they are attached form a substituted or unsubstituted 5-6 membered heterocyclyl;

Each $R^3$ is independently selected from substituted or unsubstituted $C_{1-5}$ alkyl, or substituted or unsubstituted 3-6 membered heterocyclyl;

Each $R^4$ is independently selected from substituted or unsubstituted $C_{1-5}$ alkyl, or substituted or unsubstituted $C_{3-6}$ cycloalkyl;

Each $R^5$ is independently selected from H, substituted or unsubstituted $C_{1-5}$ alkyl, substituted or unsubstituted $C_{3-6}$ cycloalkyl, and substituted or unsubstituted ($C_{1-3}$ alkyl)($C_{3-6}$ cycloalkyl), or two $R^5$ and the nitrogen to which they are attached for a substituted or unsubstituted 3 to 6 membered heterocyclyl;

Each $R^6$ is independently selected from substituted or unsubstituted $C_{1-5}$ alkyl, substituted or unsubstituted $C_{3-6}$ cycloalkyl, —($C_{1-3}$ alkyl)(substituted or unsubstituted $C_{3-6}$ cycloalkyl), or substituted or unsubstituted 3-8 membered heterocyclyl;

Each $R^7$ is independently selected from H, and substituted or unsubstituted $C_{1-5}$ alkyl, or two $R^5$ and the nitrogen to which they are attached for a substituted or unsubstituted 3 to 6 membered heterocyclyl; and each R is independently selected from H and substituted or unsubstituted $C_{1-4}$ alkyl;

provided $R^1$ and $R^2$ are not both unsubstituted.

In some embodiments, the base is pyridine or NaOH. In some embodiments, the contacting is performed at a temperature ranging from about 100 to about 160° C.

In some embodiments, the methods further comprise preparing a compound of formula (D):

(L)

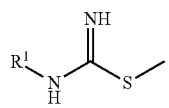

the methods comprising:
a) contacting R$^1$—NCS with ammonium hydroxide in a first solvent; and
b) contacting the product of step a) with iodomethane, in a second solvent, under conditions suitable to provide a compound of formula (L).

In some embodiments, the first solvent is DCM. In one embodiment, the contacting in step a) is performed at room temperature.

In some embodiments, the second solvent is MeCN. In one embodiment, the contacting in step b) is performed at a temperature ranging from room temperature to about 40° C.

In one aspect, provided herein are methods for preparing a Heterocyclic Compound of formula (Ic):

(Ic)

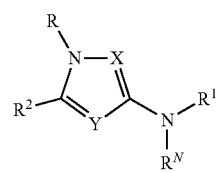

X and Y are N, and $R^N$ is H,
the methods comprising contacting a compound of formula (N):

(N)

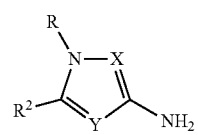

with $R^1$-Hal, wherein Hal is F, in the presence of a base, in a solvent, under conditions suitable to provide a Heterocyclic Compound of formula (Ic), wherein
X is N;
Y is N;
$R^N$ is H;
$R^1$ is 2-pyridyl, 3-pyridyl, pyrazinyl, or pyrimidyl, each unsubstituted or substituted with one or more substituents independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —NR$_2$, —COOR, —OR$^3$, —N(R)CO(R$^4$), —CON(R$^5$)$_2$ and substituted or unsubstituted $C_{6-10}$ aryl;
$R^2$ is

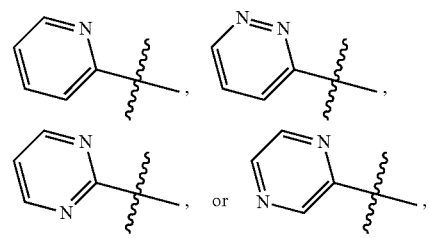

each unsubstituted or substituted with one or more substituents Z, wherein Z is independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —NR(substituted or unsubstituted $C_{3-7}$ cycloalkyl), —N(R)COR, —COOR, —SO$_2$($C_{1-3}$ alkyl), —SO$_2$NR$_2$, —SO$_2$(substituted or unsubstituted heterocyclyl), —OR$^6$, and —CON(R$^7$)$_2$; or two Z together with the carbons to which they are attached form a substituted or unsubstituted 5-6 membered heterocyclyl;

Each R³ is independently selected from substituted or unsubstituted $C_{1-5}$ alkyl, or substituted or unsubstituted 3-6 membered heterocyclyl;

Each R⁴ is independently selected from substituted or unsubstituted $C_{1-5}$ alkyl, or substituted or unsubstituted $C_{3-6}$ cycloalkyl;

Each R⁵ is independently selected from H, substituted or unsubstituted $C_{1-5}$ alkyl, substituted or unsubstituted $C_{3-6}$ cycloalkyl, and substituted or unsubstituted ($C_{1-3}$ alkyl)($C_{3-6}$ cycloalkyl), or two R⁵ and the nitrogen to which they are attached for a substituted or unsubstituted 3 to 6 membered heterocyclyl;

Each R⁶ is independently selected from substituted or unsubstituted $C_{1-5}$ alkyl, substituted or unsubstituted $C_{3-6}$ cycloalkyl, —($C_{1-3}$ alkyl)(substituted or unsubstituted $C_{3-6}$ cycloalkyl), or substituted or unsubstituted 3-8 membered heterocyclyl;

Each R⁷ is independently selected from H, and substituted or unsubstituted $C_{1-5}$ alkyl, or two R⁵ and the nitrogen to which they are attached for a substituted or unsubstituted 3 to 6 membered heterocyclyl; and each R is independently selected from H and substituted or unsubstituted $C_{1-4}$ alkyl;

provided R¹ and R² are not both unsubstituted.

In some embodiments, the base is NaH. In some embodiments, the solvent is DMF. In some embodiments, the contacting is performed at a temperature ranging from about 0 to about 25° C.

In some other embodiments, the methods further comprise preparing a Heterocyclic Compound of formula (IIa):

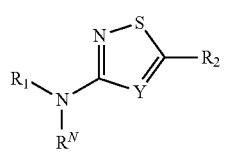

(IIa)

Y is N, and $R^N$ is H, the methods comprising contacting a compound of formula (P):

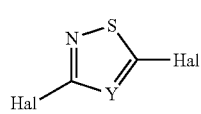

(P)

with $NHR^1R^N$, in a solvent, in the presence of a metal catalyst and ligand, in a solvent, under conditions suitable to provide a Heterocyclic Compound of formula (IIa), wherein Y is N;

$R^N$ is H;

R¹ is 2-pyridyl, 3-pyridyl, pyrazinyl, or pyrimidyl, each unsubstituted or substituted with one or more substituents independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —NR₂, —COOR, —OR³, —N(R)CO(R⁴), —CON(R⁵)₂, and substituted or unsubstituted $C_{6-10}$ aryl;

R² is

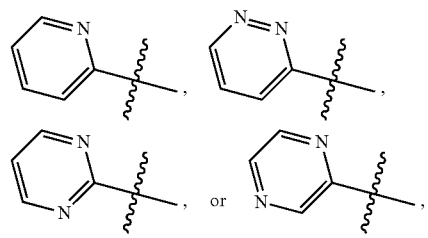

each unsubstituted or substituted with one or more substituents Z, wherein Z is independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —NR(substituted or unsubstituted $C_{3-7}$ cycloalkyl), —N(R)COR, —COOR, —SO₂($C_{1-3}$ alkyl), —SO₂NR₂, —SO₂(substituted or unsubstituted heterocyclyl), —OR⁶, and —CON(R⁷)₂; or two Z together with the carbons to which they are attached form a substituted or unsubstituted 5-6 membered heterocyclyl;

Each R³ is independently selected from substituted or unsubstituted $C_{1-5}$ alkyl, or substituted or unsubstituted 3-6 membered heterocyclyl;

Each R⁴ is independently selected from substituted or unsubstituted $C_{1-5}$ alkyl, or substituted or unsubstituted $C_{3-6}$ cycloalkyl;

Each R⁵ is independently selected from H, substituted or unsubstituted $C_{1-5}$ alkyl, substituted or unsubstituted $C_{3-6}$ cycloalkyl, and substituted or unsubstituted ($C_{1-3}$ alkyl)($C_{3-6}$ cycloalkyl), or two R⁵ and the nitrogen to which they are attached for a substituted or unsubstituted 3 to 6 membered heterocyclyl;

Each R⁶ is independently selected from substituted or unsubstituted $C_{1-5}$ alkyl, substituted or unsubstituted $C_{3-6}$ cycloalkyl, —($C_{1-3}$ alkyl)(substituted or unsubstituted $C_{3-6}$ cycloalkyl), or substituted or unsubstituted 3-8 membered heterocyclyl;

Each R⁷ is independently selected from H, and substituted or unsubstituted $C_{1-5}$ alkyl, or two R⁵ and the nitrogen to which they are attached for a substituted or unsubstituted 3 to 6 membered heterocyclyl; and each R is independently selected from H and substituted or unsubstituted $C_{1-4}$ alkyl;

provided R¹ and R² are not both unsubstituted.

In some such embodiments, the solvent is 1,4-dioxane. In some embodiments, the catalyst and ligand is Pd(PPh₃)₄ and copper(I) thiophene-2-carboxylate. In some embodiments the second catalyst and ligand is Pd₂(dba)₃ and Xantphos. In some embodiments, the contacting is performed at temperatures ranging from about 10 to about 110° C.

In some embodiments, the methods further comprise preparing a compound of formula (N):

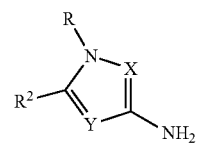

(N)

the methods comprising contacting a compound of formula (M):

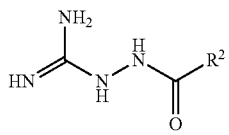
(M)

with a base, in a solvent, under conditions suitable to provide a compound of formula (N).

In some embodiments, the base is pyridine or NaOH. In some embodiments, the solvent is $H_2O$. In some embodiments, the contacting is performed at a temperature ranging from about 100 to about 160° C.

In some embodiments, the methods further comprise preparing a compound of formula (M):

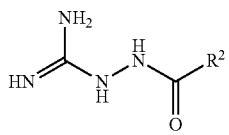
(M)

the methods comprising contacting a compound of formula (H):

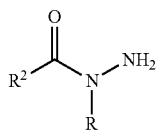
(H)

with methylisothiourea in presence of an acid, in a solvent, under conditions suitable to provide a compound of formula (M).

In some embodiments, the acid is sulfuric acid. In some embodiments, the solvent is $H_2O$. In some embodiments, the contacting is performed at a temperature ranging from room temperature to about 100° C.

In some embodiments, the methods further comprise preparing a compound of formula (H)

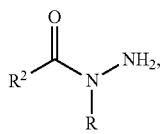
(H)

wherein R is substituted or unsubstituted $C_{1-4}$ alkyl, the methods comprising contacting $R^2COOH$ with

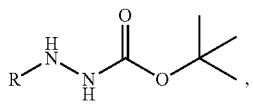

in a solvent, in the presence of a base and a coupling reagent, under conditions suitable to provide a compound of formula (H), wherein R is substituted or unsubstituted $C_{1-4}$ alkyl.

In one embodiment, the solvent is DCM. In another embodiment, the base is DIPEA. In other embodiments, the coupling agent is hydroxybenzotriazole and 1-ethyl-3-(3-dimethylaminopropyl)carbodiimide hydrochloride. In some embodiments, the contacting is performed at a temperature from about 0 to about 25° C.

Methods of Use

The Heterocyclic Compounds, including compounds of formula (I), (Ia), (Ib), (Ic), (II), (IIa), and Table 1 have utility as pharmaceuticals to treat, prevent or improve conditions in animals and humans. The Heterocyclic Compounds provided herein have utility for use in the treatment or prevention of all diseases, disorders or conditions disclosed herein.

In one aspect, provided herein is a method of treating a disease caused by a helminthic infection. In certain embodiments, a compound as described herein is used in human medical therapy, particularly in the treatment of helminthic infection. In certain embodiments, a compound as provided herein is used in animal medical therapy, particularly in the treatment of helminthic infections. In certain embodiments, the method includes administering a therapeutically effective amount of a compound as described to a subject having a disease caused by a helminthic infection.

In one aspect, provided herein is a method of treating a disease caused by a filarial worm infection. In certain embodiments, a compound as described herein is used in human medical therapy, particularly in the treatment of filarial worm infection. In certain embodiments, a compound as provided herein is used in animal medical therapy, particularly in the treatment of filarial worm infections. In certain embodiments, the method includes administering a therapeutically effective amount of a compound as described to a subject having a disease caused by a filarial worm infection.

In one embodiment, provided herein is a method for the treatment or prevention of helminthic infections and diseases, the methods comprising administering to a subject an effective amount of a Heterocyclic Compound, or a pharmaceutically acceptable salt, tautomer, isotopologue, or stereoisomer thereof. In some such embodiments, the helminthic infection is a filarial worm infection.

In one aspect, provided herein is a method of treating a disease caused by helminthic infection. In certain embodiments, a Heterocyclic Compound, or a pharmaceutically acceptable salt, tautomer, isotopologue, or stereoisomer thereof, is used in human medical therapy, particularly in the treatment of helminthic infections. In certain embodiments, a Heterocyclic Compound, or a pharmaceutically acceptable salt, tautomer, isotopologue, or stereoisomer thereof, is used in animal medical therapy, particularly in the treatment of helminthic infections. In certain embodiments, the method includes administering a therapeutically effective amount of a Heterocyclic Compound, or a pharmaceutically acceptable salt, tautomer, isotopologue, or stereoisomer thereof, to a subject having a disease caused by helminthic infection.

In one embodiment, provided herein is a method for the treatment or prevention of filarial worm infections and diseases, the methods comprising administering to a subject an effective amount of a Heterocyclic Compound, or a pharmaceutically acceptable salt, tautomer, isotopologue, or stereoisomer thereof.

In one aspect, provided herein is a method of treating a disease caused by a filarial worm infection. In certain embodiments, a Heterocyclic Compound, or a pharmaceutically acceptable salt, tautomer, isotopologue, or stereoisomer thereof, is used in human medical therapy, particularly in the treatment of a filarial worm infections. In certain embodiments, a Heterocyclic Compound, or a pharmaceutically acceptable salt, tautomer, isotopologue, or stereoisomer thereof, is used in animal medical therapy, particularly in the treatment of of a filarial worm infection. In certain embodiments, the method includes administering a therapeutically effective amount of a Heterocyclic Compound, or a pharmaceutically acceptable salt, tautomer, isotopologue, or stereoisomer thereof, to a subject having a disease caused by a filarial worm infection.

In another aspect, also provided is a method of preventing a disease caused by helminthic infection. In certain embodiments, a Heterocyclic Compound, or a pharmaceutically acceptable salt, tautomer, isotopologue, or stereoisomer thereof, is used in human medical therapy, particularly in the prevention of helminthic infection. In certain embodiments, a Heterocyclic Compound, or a pharmaceutically acceptable salt, tautomer, isotopologue, or stereoisomer thereof, is used in animal medical therapy, particularly in the prevention of helminthic infection. In certain embodiments, the method includes administering a therapeutically effective amount of a Heterocyclic Compound, or a pharmaceutically acceptable salt, tautomer, isotopologue, or stereoisomer thereof, to a subject to prevent a disease caused by helminthic infection.

In another aspect, also provided is a method of preventing a disease caused by a filarial worm infection. In certain embodiments, a Heterocyclic Compound, or a pharmaceutically acceptable salt, tautomer, isotopologue, or stereoisomer thereof, is used in human medical therapy, particularly in the prevention of a filarial worm infection. In certain embodiments, a Heterocyclic Compound, or a pharmaceutically acceptable salt, tautomer, isotopologue, or stereoisomer thereof, is used in animal medical therapy, particularly in the prevention of a filarial worm infection. In certain embodiments, the method includes administering a therapeutically effective amount of a Heterocyclic Compound, or a pharmaceutically acceptable salt, tautomer, isotopologue, or stereoisomer thereof, to a subject to prevent a disease caused by a filarial worm infection.

In another aspect, provided herein is a method of treating or preventing a parasitic disease. In certain embodiments, the parasitic disease is associated with a worm. In certain embodiments, the parasitic disease is caused by a worm. In certain embodiments, the parasitic worm is categorized as cestode (tapeworm), nematode (roundworm) and trematode (flatworm or fluke). In certain embodiments, the parasitic disease is associated with a helminth. In certain embodiments, the parasitic disease is associated with a nematode. In certain embodiments, the nematode is *Wuchereria bancrofti*. In certain embodiments, the nematode is *Brugia malayi*. In certain embodiments, the nematode is *Brugia timori*. In certain embodiments, the nematode is *Onchocerca volvulus*. In certain embodiments, the nematode is *Dirofilaria immitis*. In some embodiments, the nematode is *Haemonchus contortus*. In certain embodiments, the nematode is *Ascaris lumbricoides*. In certain embodiments, the nematode is *Necator americanus*. In still another embodiments, the nematode is *Ancylostoma duodenale*. In yet other embodiments, the nematode is *Trichuris trichiura*. In certain embodiments, the parasitic disease is associated with a trematode. In certain embodiments, the parasitic disease is associated with *Schistosoma*. In certain embodiments, the parasitic disease is associated with *Schistosoma mansoni*. In certain embodiments, the parasitic disease is enterobiasis, oxyuriasis, ascariasis, ancylostomiasis, necatoriasis, dracunculiasis, filariasis, onchocerciasis, schistosomiasis, or trichuriasis. In certain embodiments, the parasitic disease is schistosomiasis. In certain embodiments, the parasitic disease is urinary schistosomiasis. In certain embodiments, the parasitic disease is intestinal schistosomiasis. In certain embodiments, the parasitic disease is Asian intestinal schistosomiasis. In certain embodiments, the parasitic disease is visceral schistosomiasis. In certain embodiments, the parasitic disease is acute schistosomiasis. In certain embodiments, the parasitic disease is lymphatic filariasis. In certain embodiments, the parasitic disease is bancroftian filariasis. In certain embodiments, the parasitic disease is subcutaneous filariasis. In certain embodiments, the parasitic disease is serious cavity filariasis. In certain embodiments, the parasitic disease is elephantiasis. In certain embodiments, the parasitic disease is elephantiasis tropica. In certain embodiments, the parasitic disease is onchocerciasis. In certain embodiments, the dirofilariasis is dirofilariasis in dogs. In some embodiments, the dirofilariasis is caused by *Dirofilaria immitis* or *Dirofilaria repens*. In certain embodiments, the parasitic disease is haemonchosis. In certain embodiments, the haemonchosis is haemonchosis in sheep and goats. In some embodiments, the haemonchosis is caused by *Haemonchus contortus*.

In certain aspects, the present methods comprise a step of administering a Heterocyclic Compound, or a pharmaceutically acceptable salt, tautomer, isotopologue, or stereoisomer thereof, to a subject. In certain embodiments, the methods comprise administering a Heterocyclic Compound, or a pharmaceutically acceptable salt, tautomer, isotopologue, or stereoisomer thereof, to a subject for no more than fourteen (14) days. In certain embodiments, the methods comprise administering a Heterocyclic Compound, or a pharmaceutically acceptable salt, tautomer, isotopologue, or stereoisomer thereof, to a subject for no more than seven (7) days. In certain embodiments, the subject is in need of treatment for an helminthic infection. In certain embodiments, the subject is in need of treatment for a filarial infection. In certain embodiments, the subject has an helminthic infection. In certain embodiments, the subject is at risk for having an helminthic infection. In certain embodiments, the subject has a filarial infection. In certain embodiments, the subject is at risk for having a filarial infection. In certain embodiments, the subject is a pediatric subject. In certain embodiments, the subject is less than nine (9) years of age. In certain embodiments, the subject is less than eight (8) years of age. In certain embodiments, the subject is a pregnant woman. In certain embodiments, the subject is a post-partum woman. In certain embodiments, the subject is a woman of childbearing potential. In certain embodiments, the subject is an individual attempting to conceive a child. In certain embodiments, the subject is a domestic animal. In certain embodiments, the subject is a dog.

The compounds disclosed herein exhibit potency against helminths, and, therefore, have the potential to kill and/or inhibit the growth, molt, or motility of such helminths. The compounds disclosed herein exhibit potency against filarial worms, and, therefore, have the potential to kill and/or inhibit the molt, or motility of such filarial worms. Thus, in one aspect provided is a method of killing a filarial worm, comprising: contacting the filarial worm with a Heterocyclic Compound, or a pharmaceutically acceptable salt, tautomer, isotopologue, or stereoisomer thereof, in an amount effective to kill the filarial worm. In another aspect, provided herein is a method of inhibiting growth or molt of a filarial worm, comprising: contacting the filarial worm with a Heterocyclic Compound, or a pharmaceutically acceptable salt, tautomer, isotopologue, or stereoisomer thereof, in an amount effective to inhibit growth or molt of the filarial worm. In another aspect, provided herein is a method of inhibiting motility of a filarial worm, comprising: contacting the filarial worm with a Heterocyclic Compound, or a pharmaceutically acceptable salt, tautomer, isotopologue, or stereoisomer thereof, in an amount effective to inhibit motility of the filarial worm. In certain embodiments, the worm is an egg. In certain embodiments, the egg is an unfertilized egg. In certain embodiments, the egg is fertilized egg. In certain embodiments, the worm is a larva. In certain embodiments, the worm is in a larval or juvenile stage. In certain embodiments, the worm is a larva in any one of four larval stages (L1, L2, L3, L4). In certain embodiments, the worm is a larva of stage L1 or microfilaria. In certain embodiments, microfilaria is a larva of stage L1. In certain embodiments, the worm is a larva of stage L2. In certain embodiments, the worm is a larva of stage L3. In certain embodiments, the worm is a larva of stage L4. In certain embodiments the worm is in sexually immature stage (stage L5). In certain embodiments, the worm is mature. In certain embodiments, the worm is fully mature. In certain embodiments, the worm is in adult stage. In certain embodiments, the worm is in pre-parasitic stage. In certain embodiments, the worm is in parasitic stage. In certain embodiments, the worm is contacted with a Heterocyclic Compound, or a pharmaceutically acceptable salt, tautomer, isotopologue, or stereoisomer thereof, inside a subject. In certain embodiments, the worm is contacted with a Heterocyclic Compound, or a pharmaceutically acceptable salt, tautomer, isotopologue, or stereoisomer thereof, outside a subject.

As discussed herein, compounds provided herein are useful for treating and preventing certain diseases and disorders in humans and animals. In certain embodiments, a Heterocyclic Compound, or a pharmaceutically acceptable salt, tautomer, isotopologue, or stereoisomer thereof, is used to treat a disease caused by helminthic infection. In certain embodiments, a Heterocyclic Compound, or a pharmaceutically acceptable salt, tautomer, isotopologue, or stereoisomer thereof, is used to treat a disease caused by parasitic worm infection, including, but not limited to, heartworm disease, ascariasis, trichuriasis, schistosomiasis, haemonchosis, onchocerciasis, and lymphatic filariasis. In certain embodiments, treatment or prevention of such diseases and disorders can be effected by administering a Heterocyclic Compound, or a pharmaceutically acceptable salt, tautomer, isotopologue, or stereoisomer thereof, either alone or in combination with another active agent as part of a combination therapy. The term "combination" as in the phrase "in combination with another active agent" includes co-administration of a first agent and a second agent, which for example may be dissolved or intermixed in the same pharmaceutically acceptable carrier, or administration of a first agent, followed by the second agent, or administration of the second agent, followed by the first agent. The present methods and compositions, therefore, include methods of combination therapeutic treatment and combination pharmaceutical compositions. The term "combination therapy" refers to the administration of two or more therapeutic substances, such as a compound described herein and another drug (e.g., an antihelminthic agent such as ivermectin, albendazole, flubendazole, diethylcarbamazine, or emodepside). The other drug(s) may be administered concomitant with, prior to, or following the administration of the macrolide antibiotic.

In one embodiment, provided is a method for the treatment or prevention of helminthic infections and diseases, the methods comprising administering to a subject an effective amount of a Heterocyclic Compound, or a pharmaceutically acceptable salt, tautomer, isotopologue, or stereoisomer thereof, in combination with one or more antihelminthic agent. In some such embodiments, the helminthic infection is a filarial worm infection. In one embodiment, the treatment of helminthic infections comprises administration of an antihelminthic agent such as benzimidazoles, for example, flubendazole, albendazole, mebendazole, thiabendazole, fenbendazole, or triclabendazole. In one embodiment, the treatment of helminthic infections comprises administration of one or more antihelminthic agents, for example, ivermectin, abamectin, diethylcarbamazine (DEC), suramin, pyrantel pamoate, levamisole, niclosamide, nitazoxanide, oxyclozanide, praziquantel, emodepside, monepantel, derquantel, oxfendazole, or pelletierine sulphate. In one embodiment, the antihelminthic agent is invermectin, moxidectin or selamectin. In certain embodiments, a Heterocyclic Compound, or a pharmaceutically acceptable salt, tautomer, isotopologue, or stereoisomer thereof, is used to treat helminthic infections in combination with one or more antihelminthic agents. In some embodiments, the antihelminthic agent is a benzimidazole, for example, flubendazole, albendazole, mebendazole, thiabendazole, fenbendazole, or triclabendazole. In some embodiments, the antihelminthic agent is one or more of ivermectin, abamectin, diethylcarbamazine (DEC), suramin, pyrantel pamoate, levamisole, niclosamide, nitazoxanide, oxyclozanide, praziquantel, emodepside, monepantel, derquantel, oxfendazole, or pelletierine sulphate. In one embodiment, the antihelminthic agent is invermectin, moxidectin or selamectin. In certain embodiments, a Heterocyclic Compound, or a pharmaceutically acceptable salt, tautomer, isotopologue, or stereoisomer thereof, is used in a method of treatment or prevention of filarial worm infections and diseases, the method comprising administering to a subject an effective amount of a Heterocyclic Compound, or a pharmaceutically acceptable salt, tautomer, isotopologue, or stereoisomer thereof in combination with one or more antihelminthic agents. In some such embodiments, the antihelminthic agent is selected from flubendazole, albendazole, mebendazole, thiabendazole, fenbendazole, triclabendazole, ivermectin, abamectin, diethylcarbamazine (DEC), suramin, pyrantel pamoate, levamisole, niclosamide, nitazoxanide, oxyclozanide, praziquantel, emodepside, monepantel, derquantel, oxfendazole, or pelletierine sulphate. In one embodiment, the antihelminthic agent is invermectin, moxidectin or selamectin. In one embodiment, the antihelminthic agent is a *Wolbachia* targeting agent. In one embodiment, the *Wolbachia* targeting agent is doxycycline.

Pharmaceutical Compositions and Routes of Administration

Provided herein are pharmaceutical compositions comprising an effective amount of a Heterocyclic Compound, as described herein, and a pharmaceutically acceptable carrier, excipient or vehicle. The Heterocyclic Compounds can be administered to a subject enterally (for example, orally, rectally), topically, or parenterally (for example, intravenously, intramuscularly, subcutaneously), in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrrolidone or aluminum stearate), a dispersing agent (e.g., hydroxypropylmethylcellulose), a diluent (e.g., water), a cosolvent (e.g., propylene glocyl/glycofurol), a buffer, a copolymer (e.g., poly(lactic-co-glycolic acid, i.e PLGA), and base wax (e.g., cocoa butter, white petrolatum or polyethylene glycol). The effective amount of the Heterocyclic Compound in the pharmaceutical composition may be at a level that will exercise the desired effect; for example, about 0.005 mg/kg of a subject's body weight to about 20 mg/kg of a subject's body weight in unit dosage for both oral and parenteral administration.

The dose of a Heterocyclic Compound to be administered to a subject is rather widely variable and can be subject to the judgment of a health-care practitioner. In general, the Heterocyclic Compound can be administered one to four times a day in a dose of about 0.5 mg/kg of a subject's body weight to about 20 mg/kg of a subject's body weight in a subject, but the above dosage may be properly varied depending on the age, body weight and medical condition of the subject and the type of administration. In one embodiment, the dose is about 0.1 mg/kg of a subject's body weight to about 3 mg/kg of a subject's body weight, about 0.5 mg/kg of a subject's body weight to about 2 mg/kg of a subject's body weight, about 1 mg/kg of a subject's body weight to about 2 mg/kg of a subject's body weight or about 1.5 mg/kg of a subject's body weight to about 2 mg/kg of a subject's body weight. In one embodiment, the dose is about 1 mg/kg of a subject's body weight to about 3 mg/kg of a subject's body weight. In one embodiment, the dose is about 0.5 mg/kg of a subject's body weight to about 1 mg/kg of a subject's body weight. In one embodiment, the dose is about 1 mg/kg of a subject's body weight to about 2 mg/kg of a subject's body weight. In one embodiment, the dose is about 1.5, 1.6, 1.7, 1.8, 1.9, 2.0, 2.1, 2.2, 2.3, 2.4, 2.5, 2.6, 2.7, 2.8, 2.9, 3.0 mg/kg of a subject's body weight. In one embodiment, one dose is given per day. In any given case, the amount of the Heterocyclic Compound administered will depend on such factors as the solubility of the active component, the formulation used and the route of administration. In one embodiment, application of a topical concentration provides intracellular exposures or concentrations of about 0.01-10 µM.

In another embodiment, provided herein are methods for the treatment or prevention of a disease or disorder comprising the administration of about 1 mg/day to about 1200 mg/day of a Heterocyclic Compound to a subject affected by helmintics infections. In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of a Heterocyclic Compound to a subject affected by helmintics infections. In one embodiment, the methods for the treatment of a disease or disorder comprise the administration of about 0.375 mg/day to about 750 mg/day of a Heterocyclic Compound to a subject affected by helmintics infections. In one embodiment, the methods for the treatment of a disease or disorder comprise the administration of about 0.75 mg/day to about 375 mg/day of a Heterocyclic Compound to a subject affected by helmintics infections. In one embodiment, the methods for the treatment of a disease or disorder comprise the administration of about 3.75 mg/day to about 75 mg/day of a Heterocyclic Compound to a subject affected by helmintics infections. In one embodiment, the methods for the treatment of a disease or disorder comprise the administration of about 7.5 mg/day to about 55 mg/day of a Heterocyclic Compound to a subject affected by helmintics infections. In one embodiment, the methods for the treatment of a disease or disorder comprise the administration of about 18 mg/day to about 37 mg/day of a Heterocyclic Compound to a subject affected by helmintics infections.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of a Heterocyclic Compound. In one embodiment, the unit dosage formulations comprises between about 1 mg and 200 mg of a Heterocyclic Compound. In one embodiment, the unit dosage formulations comprises between about 35 mg and about 1400 mg of a Heterocyclic Compound. In one embodiment, the unit dosage formulations comprises between about 125 mg and about 1000 mg of a Heterocyclic Compound. In one embodiment, the unit dosage formulations comprises between about 250 mg and about 1000 mg of a Heterocyclic Compound. In one embodiment, the unit dosage formulations comprises between about 500 mg and about 1000 mg of a Heterocyclic Compound.

In a particular embodiment, provided herein are unit dosage formulations comprising about 100 mg or 400 mg of a Heterocyclic Compound.

In another embodiment, provided herein are unit dosage formulations that comprise 1 mg, 5 mg, 10 mg, 15 mg, 20 mg, 30 mg, 35 mg, 40 mg, 50 mg, 70 mg, 100 mg, 125 mg, 130, mg, 140 mg, 175 mg, 200 mg, 250 mg, 280 mg, 350 mg, 500 mg, 560 mg, 700 mg, 750 mg, 1000 mg or 1400 mg of a Heterocyclic Compound. In one embodiment, the unit dosage formulations comprise 1 mg of a Heterocyclic Compound. In one embodiment, the unit dosage formulations comprise 5 mg of a Heterocyclic Compound. In one embodiment, the unit dosage formulations comprise 10 mg of a Heterocyclic Compound. In one embodiment, the unit dosage formulations comprise 15 mg of a Heterocyclic Compound. In one embodiment, the unit dosage formulations comprise 20 mg of a Heterocyclic Compound. In one embodiment, the unit dosage formulations comprise 25 mg of a Heterocyclic Compound. In one embodiment, the unit dosage formulations comprise 30 mg of a Heterocyclic Compound. In one embodiment, the unit dosage formulations comprise 35 mg of a Heterocyclic Compound. In one embodiment, the unit dosage formulations comprise 40 mg of a Heterocyclic Compound. In one embodiment, the unit dosage formulations comprise 50 mg of a Heterocyclic Compound. In one embodiment, the unit dosage formulations comprise 70 mg of a Heterocyclic Compound. In one embodiment, the unit dosage formulations comprise 100 mg of a Heterocyclic Compound. In one embodiment, the unit dosage formulations comprise 125 mg of a Heterocyclic Compound. In one embodiment, the unit dosage formulations comprise 130 mg of a Heterocyclic Compound. In one embodiment, the unit dosage formulations comprise 140 mg of a Heterocyclic Compound. In one embodiment the unit dosage formulations comprise 175 mg of a Heterocyclic Compound. In one embodiment, the unit dosage formulations comprise 200 mg of a Heterocyclic Compound. In one embodiment, the unit dosage formulations comprise 250 mg of a Heterocyclic Compound. In one embodiment, the unit dosage formulations comprise 280 mg of a Heterocyclic Compound. In one embodiment, the unit dosage formulations comprise 350 mg of a Heterocyclic Compound. In one embodiment, the unit dosage formulations comprise 500 mg of a Heterocyclic Compound. In one embodiment, the unit dosage formulations comprise 560 mg of a Heterocyclic Compound. In one embodiment, the unit dosage formulations comprise 700 mg of a Heterocyclic Compound. In one embodiment, the unit dosage formulations comprise 750 mg of a Heterocyclic Compound. In one embodiment, the unit dosage formulations comprise 1000 mg of a Heterocyclic Compound. In one embodiment, the unit dosage formulations comprise 1400 mg of a Heterocyclic Compound.

A Heterocyclic Compound can be administered once, twice, three, four or more times daily. In a particular embodiment, doses of 600 mg or less are administered as a once daily dose and doses of more than 600 mg are administered twice daily in an amount equal to one half of the total daily dose.

A Heterocyclic Compound can be administered orally for reasons of convenience. In one embodiment, when administered orally, a Heterocyclic Compound is administered with a meal and water. In another embodiment, the Heterocyclic Compound is dispersed in water or juice (e.g., apple juice or orange juice) and administered orally as a suspension.

The Heterocyclic Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin, or by local ocular (i.e., subconjunctival, intravitreal, retrobulbar, intracameral). The mode of administration is left to the discretion of the health-care practitioner, and can depend in-part upon the site of the medical condition.

In one embodiment, provided herein are capsules containing a Heterocyclic Compound without an additional carrier, excipient or vehicle.

In another embodiment, provided herein are compositions comprising an effective amount of a Heterocyclic Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories, suspensions, gels, intra-ruminal devices (e.g., for prolonged prophylaxis or controlled release), implants, topical pour-ons, transdermal delivery gels, spot-ons, implants (including devices, gels, liquids (e.g., PLGA), and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a Heterocyclic Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Heterocyclic Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Heterocyclic Compound can be delayed or prolonged by proper formulation. For example, a slowly soluble pellet of the Heterocyclic Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Heterocyclic Compound in oily or emulsified vehicles, or adding amounts of PLGA, that allow it to disperse slowly in the serum.

EXAMPLES

The following Examples are presented by way of illustration, not limitation. Compounds are named using the automatic name generating tool provided in Chemdraw Ultra 13.0 (Cambridgesoft), which generates systematic names for chemical structures, with support for the Cahn- Ingold-Prelog rules for stereochemistry. One skilled in the art can modify the procedures set forth in the illustrative examples to arrive at the desired products.

Abbreviations used:

| | |
|---|---|
| Ac₂O | Acetic anhydride |
| BINAP | (2,2'-Bis(diphenylphosphino)-1,1'-binaphthyl) |
| nBuLi | n-Butyl lithium |
| DCM | Dichloromethane |
| DIPEA | Diisopropylethylamine |
| DMF | N,N-Dimethylformamide |
| DMSO | Dimethylsulfoxide |
| EDCI | N-(3-Dimethylaminopropyl)-N'-ethylcarbodiimide hydrochloride |
| ESI | Electrospray ionization |
| EtOAc | Ethyl acetate |
| EtOH | Ethanol |
| H₂O | Water |
| HATU | O-(7-Azabenzotriazol-1-yl)-N,N,N',N'-tetramethyluronium hexafluorophosphate |
| HEPES | (4-(2-Hydroxyethyl)-1-piperazineethanesulfonic acid) |
| HPLC | High performance liquid chromatography |
| LCMS | Liquid chromatography mass spectrometry |
| m-CPBA | meta-Chloroperoxybenzoic acid |
| MeCN or ACN | Acetonitrile |
| MeOH | Methanol |
| MS | Mass spectrometry |
| MTBE | Methyl tertiary butyl ether |
| NaH | Sodium hydride |
| NBS | N-Bromosuccinimide |
| NH₄Cl | Ammonium chloride |
| NMR | Nuclear magnetic resonance |
| Pd/C | Palladium (0) on carbon |
| Pd(PPh₃)₂Cl₂ | Bis(triphenylphosphine)palladium (II) dichloride |
| Pd(PPh₃)₄ | Tetrakis(triphenylphosphine)palladium (0) |
| Pd₂(dba)₃ | Tris(dibenzylideneacetone)dipalladium (0) |
| TEA | Triethylamine |
| THF | Tetrahydrofuran |
| TLC | Thin layer chromatography |
| UPLC | Ultra Performance Liquid Chromatography |
| UHPLC | Ultra High Performance Liquid Chromatography |
| Xantphos | 4,5-Bis(diphenylphosphino)-9,9-dimethylxanthene |

Compound Synthesis

Example 1: 3-(4-Isopropylpyridin-2-yl)-N-(4-(trifluoromethyl)pyridin-2-yl)-1,2,4-thiadiazol-5-amine

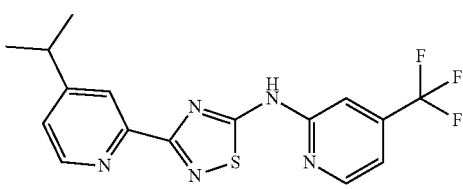 [SMILES: CC(C)c1ccnc(-c2nsc(Nc3cc(C(F)(F)F)ccn3)n2)c1]

4-(Prop-1-en-2-yl)picolinonitrile

To a mixture of 4-bromopicolinonitrile (12.0 g, 65.5 mmol) in DMSO (100 mL) was added potassium carbonate (19.9 g, 144 mmol), Pd(dppf)C₁₂ (4.80 g, 6.56 mmol) and potassium trifluoro(prop-1-en-2-yl)borate (10.6 g, 72.1 mmol). The mixture was degassed with nitrogen for 3 times. The mixture was stirred at 100° C. for 8 h. The mixture was poured into H₂O and extracted with EtOAc. The organic layers were concentrated to give the crude product, which was purified by silica gel chromatography to give 4-isopropenylpyridine-2-carbonitrile (5.00 g, 34.6 mmol, 52.89% yield).

4-(Prop-1-en-2-yl)picolinimidamide

To a mixture of 4-(prop-1-en-2-yl)picolinonitrile (3.30 g, 22.8 mmol) in MeOH (30 mL) was added sodium methoxide (618 mg, 11.4 mmol). The reaction mixture was then stirred at 25° C. for 10 h. NH₄Cl (2.08 g, 38.9 mmol) was added to the mixture and the mixture was then stirred at 75° C. for another 3 h. The mixture was concentrated to remove MeOH and the residue was diluted with EtOH (50 mL). The mixture was warmed to 70° C. and stirred at this temperature for 0.5 h. Then the mixture was filtered and the filtrate was concentrated to remove EtOH to give the crude product, which was diluted with ACN (150 mL) and H₂O (30 mL). OH-type resin (10 g) was added to the mixture and filtered, and the filtrate was concentrated and lyophilized to give 4-(prop-1-en-2-yl)picolinimidamide (5.40 g, crude).

4-Isopropylpicolinimidamide

To a mixture of 4-isopropenylpyridine-2-carboxamidine (5.30 g, 32.8 mmol) in MeOH (60 mL) was added palladium/C (0.5 g, 32.8 mmol, 10% purity). The suspension was degassed under vacuum and purged with hydrogen several times. The mixture was stirred under hydrogen (15 psi) at 20° C. for 2 h. The solution was filtered and the filtrate was concentrated in vacuum to give crude product 4-isopropylpicolinimidamide (5 g, crude).

4-Isopropyl-N-((4-(trifluoromethyl)pyridin-2-yl)carbamothioyl)picolinimidamide

To a mixture of 4-isopropylpicolinimidamide (0.70 g, 4.29 mmol) and 2-isothiocyanato-4-(trifluoromethyl)pyridine (875 mg, 4.29 mmol) in acetone (10 mL) and DCM (10 mL) was added TEA (867 mg, 8.58 mmol) under nitrogen. The reaction was stirred at 20° C. for 1 h. The mixture was poured into H₂O (40 mL) and extracted with DCM. The combined organic phases were washed with H₂O, dried with anhydrous sodium sulfate, filtered, and concentrated in vacuum to give 4-isopropyl-N-((4-(trifluoromethyl)pyridin-2-yl)carbamothioyl) picolinimidamide (1.58 g, crude).

3-(4-Isopropylpyridin-2-yl)-N-(4-(trifluoromethyl)pyridin-2-yl)-1,2,4-thiadiazol-5-amine To a mixture of 4-isopropyl-N-((4-(trifluoromethyl)pyridin-2-yl)carbamothioyl) picolinimidamide (1.58 g, 4.30 mmol) in EtOH (15 mL) was added iodine (218 mg, 860.12 μmol) and hydrogen peroxide (975 mg, 8.60 mmol, 30% purity). The mixture was stirred at 20° C. for 0.5 h. The mixture was poured into saturated sodium sulfite (30 mL) and extracted with EtOAc. The combined organic phases were washed with H₂O, dried with anhydrous sodium sulfate, filtered, and concentrated in vacuum. The product was isolated and purified via standard methods to give 3-(4-isopropylpyridin-2-yl)-N-(4-(trifluoromethyl)pyridin-2-yl)-1,2,4-thiadiazol-5-amine (267.09 mg, 720 μmol, 16.7% yield, 97.72% purity). LCMS (ESI): m/z 366.1 [M+1]⁺.

Example 2: 3-(4-Cyclopropylpyridin-2-yl)-N-(3-(trifluoromethyl)pyridin-2-yl)-1,2,4-thiadiazol-5-amine

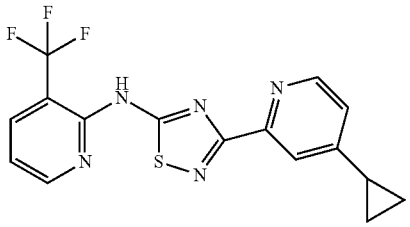 [SMILES: FC(F)(F)c1cccnc1Nc1nc(-c2cc(C3CC3)ccn2)ns1]

4-Cyclopropylpicolinonitrile

To a mixture of 4-bromopicolinonitrile (11.18 g, 61.0 mmol), cyclopropylboronic acid (5.25 g, 61.0 mmol) and potassium carbonate (16.89 g, 122.0 mmol) in dioxane (400 mL) was added Pd(dppf)Cl$_2$ (2.24 g, 3.05 mmol) under nitrogen. The mixture was stirred at 100° C. for 5 h. The mixture was concentrated to remove dioxane and the residue was diluted with H$_2$O. The aqueous phase was extracted with EtOAc. The combined organic phases were dried with anhydrous sodium sulfate, filtered, and concentrated to give crude product which was purified by silica gel chromatography to give 4-cyclopropylpicolinonitrile (8.3 g, 50.0 mmol, 81.8% yield, 86.9% purity).

4-Cyclopropylpicolinimidamide

To a mixture of 4-cyclopropylpicolinonitrile (5.00 g, 34.6 mmol) in MeOH (50 mL) was added sodium methoxide (936 mg, 17.3 mmol). The reaction mixture was then stirred at 25° C. for 15 h. NH$_4$Cl (3.15 g, 58.9 mmol) was added to the mixture and the mixture was then stirred at 75° C. for another 3 h. The mixture was concentrated to remove MeOH and then diluted with EtOH. The mixture was warmed to 70° C. and stirred for 0.5 h. Then the mixture was filtered and the filtrate was concentrated to remove EtOH to afford the crude product. The crude product was then diluted with ACN and H$_2$O. OH-type resin (10 g) was added to the mixture and the mixture was stirred at 25° C. for 0.5 h. Then the mixture was filtered and the filtrate was concentrated and lyophilized to give 4-cyclopropylpicolinimidamide (5.1 g, crude).

2-Isothiocyanato-3-(trifluoromethyl)pyridine

To a mixture of thiophosgene (3.55 g, 30.8 mmol) in DCM (50 mL) was added a solution of 3-(trifluoromethyl)pyridin-2-amine (5 g, 30.8 mmol) in DCM (150 mL) under nitrogen. The mixture was stirred at 0° C. for 1 h. The mixture was poured into saturated sodium bicarbonate and extracted with DCM. The combined organic phases were washed with H$_2$O, dried with anhydrous sodium sulfate, filtered, and concentrated in vacuum. The residue was purified by silica gel chromatography to give 2-isothiocyanato-3-(trifluoromethyl)pyridine (3.50 g, 17.1 mmol, 55.5% yield).

4-Cyclopropyl-N-((3-(trifluoromethyl)pyridin-2-yl)carbamothioyl)picolinimidamide To a mixture of 4-cyclopropylpicolinimidamide (1.00 g, 6.20 mmol) and 2-isothiocyanato-3-(trifluoromethyl)pyridine (1.27 g, 6.20 mmol) in acetone (2 mL) and DCM (2 mL) was added TEA (1.26 g, 12.4 mmol) under nitrogen. The reaction was stirred at 20° C. for 1 h. The mixture was poured into H$_2$O and extracted with DCM. The combined organic phases were washed with H$_2$O, dried with anhydrous sodium sulfate, filtered, and concentrated in vacuum to give 4-cyclopropyl-N-((3-(trifluoromethyl)pyridin-2-yl)carbamothioyl) picolinimidamide (1 g, crude).

3-(4-Cyclopropylpyridin-2-yl)-N-(3-(trifluoromethyl)pyridin-2-yl)-1,2,4-thiadiazol-5-amine To a mixture of 4-cyclopropyl-N-((3-(trifluoromethyl)pyridin-2-yl)carbamothioyl)picolinimidamide (1.20 g, 3.28 mmol) in EtOH (15 mL) was added iodine (166 mg, 656 µmol) and hydrogen peroxide (223 mg, 6.57 mmol). The mixture was stirred at 20° C. for 0.5 h. The mixture was poured into saturated sodium sulfite and extracted with EtOAc. The product was isolated and purified via standard methods to give 3-(4-cyclopropylpyridin-2-yl)-N-(3-(trifluoromethyl)pyridin-2-yl)-1,2,4-thiadiazol-5-amine (397.62 mg, 1.08 mmol, 32.9% yield, 99% purity). LCMS (ESI): m/z 364.0 [M+1]$^+$.

Example 3: N-(3-Methylpyridin-2-yl)-3-(5-(methylsulfonyl)pyridin-2-yl)-1,2,4-thiadiazol-5-amine

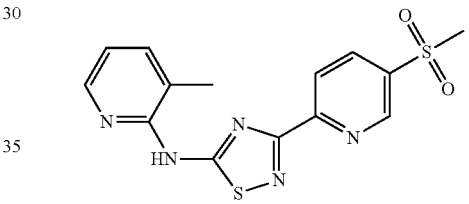

5-(Methylthio)picolinonitrile

To a mixture of 5-fluoropicolinonitrile (10 g, 81.9 mmol) in DMF (150 mL) was added sodium methanethiolate (6.89 g, 98.3 mmol) at 0° C. The mixture was stirred at 0° C. for 0.5 h and then warmed to 20° C. The mixture was stirred at 20° C. for 2 h. The mixture was poured into saturated NH$_4$Cl (2 L) and then extracted with EtOAc. The organic layers were concentrated to give 5-(methylthio)-picolinonitrile (8.5 g, 51.0 mmol, 62.27% yield, 90.12% purity) and used without further purification.

5-(Methylthio)picolinimidamide

To a mixture of 5-(methylthio)picolinonitrile (4.00 g, 26.6 mmol) in MeOH (50 mL) was added sodium methoxide (475.0 mg, 8.80 mmol) and the mixture was stirred at 20° C. for 10 h. NH$_4$Cl (3.13 g, 58.6 mmol) was added. The mixture was heated to 70° C. and stirred for 10 h. The mixture concentrated under reduce pressure to remove MeOH. The residue was dissolved in EtOH (100 mL) and the mixture was stirred at 70° C. for 1 h. The mixture is filtered and the filtrate was concentrated. The residue was then triturated by DCM (100 mL). The product was collected as a solid by filtration. The solid was dissolved in ACN (100 mL) and H$_2$O (20 mL). Amberlyst A 26 (3.50 g) was added and the mixture was stirred at 20° C. for 15 min. The mixture was filtered and the filtrate was concentrated and then diluted with toluene. The mixture was concentrated to give 5-methylsulfanylpyridine-2-carboxamidine (3.5 g, 20.9 mmol, 78.6% yield).

N-(3-Methylpyridin-2-yl)-3-(5-(methylthio)pyridin-2-yl)-1,2,4-thiadiazol-5-amine To a mixture of 5-(methylthio)picolinimidamide (2.00 g, 11.9 mmol) in DCM (50 mL), acetone (50 mL) and DMF (50 mL) were added TEA (6.05 g, 59.8 mmol) and 2-isothiocyanato-3-methylpyridine (2.69 g, 17.9 mmol). The mixture was stirred at 20° C. for 10 h. The mixture was concentrated. The residue was purified by prep-HPLC to give N-(3-methylpyridin-2-yl)-3-(5-(methylthio)pyridin-2-yl)-1,2,4-thiadiazol-5-amine (450 mg, 718.0 μmol, 6.00% yield).

N-(3-Methylpyridin-2-yl)-3-(5-(methylsulfonyl)pyridin-2-yl)-1,2,4-thiadiazol-5-amine To a mixture of N-(3-methylpyridin-2-yl)-3-(5-(methylthio)pyridin-2-yl)-1,2,4-thiadiazol-5-amine (230 mg, 729.0 μmol) in DMF (10 mL) was added 2-chlorobenzoperoxoic acid (370.0 mg, 1.8 mmol, 85% purity). The mixture was stirred at 0° C. for 1 h. The reaction was quenched with saturated sodium sulfite (6 mL) then poured into H$_2$O (100 mL). The product was isolated and purified via standard methods to give N-(3-methylpyridin-2-yl)-3-(5-(methylsulfonyl)pyridin-2-yl)-1,2,4-thiadiazol-5-amine (208.3 mg, 302.2 μmol, 41.12% yield). LCMS (ESI): m/z 348.1 [M+1]$^+$.

Example 4: N-(3-Cyclopropylpyridin-2-yl)-3-(5-isopropoxypyridin-2-yl)-1,2,4-thiadiazol-5-amine

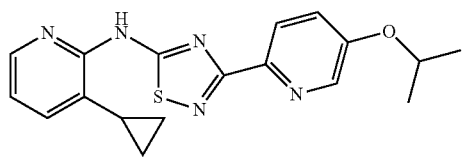 [SMILES: CC(C)Oc1ccc(-c2nsc(Nc3ncccc3C3CC3)n2)nc1]

3-Cyclopropylpyridin-2-amine

To a mixture of 3-bromopyridin-2-amine (5 g, 28.9 mmol), cyclopropylboronic acid (3.23 g, 37.5 mmol) and potassium carbonate (13.9 g, 101 mmol) in dioxane (30 mL) and H$_2$O (3 mL) was added Pd(dppf)Cl$_2$(4.23 g, 5.78 mmol) under nitrogen. The reaction was stirred at 100° C. under nitrogen for 2 h. The mixture was poured into H$_2$O and extracted with EtOAc. The combined organic phases were washed with brine, dried with anhydrous sodium sulfate, filtered, and concentrated in vacuum to give crude product which was purified by silica gel chromatography to give 3-cyclopropylpyridin-2-amine (2.5 g, 18.0 mmol, 62.6% yield, 97.1% purity).

3-Cyclopropyl-2-isothiocyanatopyridine

To a mixture of thiophosgene (3.21 g, 27.9 mmol) in DCM (10 mL) was added 3-cyclopropylpyridin-2-amine (2.5 g, 18.6 mmol) at 0° C. Then the mixture was stirred at 20° C. for 0.5 h. The reaction mixture was washed by saturated sodium bicarbonate, the organic phase was dried by anhydrous sodium sulfate, and then concentrated under reduced pressure to give red oil. The red oil was purified by silica gel chromatography to give 3-cyclopropyl-2-isothiocyanatopyridine (1.3 g, 6.79 mmol, 36.4% yield, 92% purity).

N-((3-Cyclopropylpyridin-2-yl)carbamothioyl)-5-isopropoxypicolinimidamide

To a mixture of 3-cyclopropyl-2-isothiocyanatopyridine (1.2 g, 6.81 mmol) and TEA (1.38 g, 13.6 mmol) in DCM (10 mL) and acetone (10 mL) was added 5-isopropoxypyridine-2-carboxamidine (1.22 g, 6.81 mmol) under nitrogen. The reaction was stirred at 20° C. for 2 h. The solution was poured into H$_2$O and the aqueous phase was extracted with DCM. The combined organic phases were washed with H$_2$O, dried with anhydrous sodium sulfate, filtered, and concentrated in vacuum to give N-((3-cyclopropylpyridin-2-yl)carbamothioyl)-5-isopropoxypicolinimidamide (1.8 g, 3.04 mmol, 44.6% yield, 60% purity).

N-(3-Cyclopropylpyridin-2-yl)-3-(5-isopropoxypyridin-2-yl)-1,2,4-thiadiazol-5-amine To a mixture of N-((3-cyclopropylpyridin-2-yl)carbamothioyl)-5-isopropoxypicolinimidamide (1.8 g, 3.04 mmol) in EtOH (10 mL) was added a solution of iodine (154 mg, 607 μmol) in EtOH (2 mL) and hydrogen peroxide (688 mg, 6.08 mmol 30% purity) under nitrogen. The mixture was stirred at 20° C. for 2 h. The mixture was poured into saturated sodium sulphite (50 ml) and extracted with DCM. The product was isolated and purified via standard methods to give N-(3-cyclopropylpyridin-2-yl)-3-(5-isopropoxypyridin-2-yl)-1,2,4-thiadiazol-5-amine (153.37 mg, 385 μmol, 13.7% yield, 97.9% purity, HCl). LCMS (ESI): m/z 354.1 [M+1]$^+$.

Example 5: N$^2$-(3-(5-Cyclopropoxypyridin-2-yl)-1,2,4-thiadiazol-5-yl)-N$^3$,N$^3$-dimethylpyridine-2,3-diamine

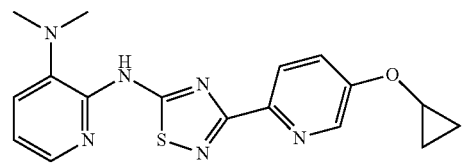 [SMILES: CN(C)c1cccnc1Nc1nc(-c2ccc(OC3CC3)cn2)ns1]

N,N-Dimethyl-2-nitropyridin-3-amine

To a mixture of 3-fluoro-2-nitropyridine (30 g, 211.0 mmol) and potassium carbonate (116.7 g, 8445 mmol) in ACN (500 mL) was added dimethylamine hydrochloride (25.8 g, 317.0 mmol). The reaction mixture was stirred at 20° C. for 2 h. The mixture was concentrated to remove ACN and then diluted with H$_2$O and EtOAc. The aqueous phase was extracted with EtOAc. The combined organic phases were dried with anhydrous sodium sulfate, filtered, and concentrated to give N,N-dimethyl-2-nitropyridin-3-amine (34 g, 201.0 mmol, 95.18% yield, 98.8% purity).

N$^3$,N$^3$-Dimethylpyridine-2,3-diamine

To a mixture of N,N-dimethyl-2-nitropyridin-3-amine (30 g, 180 mmol) in MeOH (200 mL) and glycol dimethyl ether (200 mL) was added Pd/C (3 g, 180 mmol, 10% purity) under N₂. The reaction was degassed under N₂ and purged with H₂ 3 times. The reaction mixture was then stirred at 30° C. under H₂ (50 psi) for 5 h. The solution was filtered, concentrated and purified by silica gel chromatography to give $N^3$,$N^3$-dimethylpyridine-2,3-diamine (24 g, 169.5 mmol, 94.46% yield, 96.9% purity).

2-Isothiocyanato-N,N-dimethylpyridin-3-amine

To mixture of thiophosgene (7.54 g, 65.6 mmol) in DCM (50 mL) was added $N^3$,$N^3$-dimethylpyridine-2,3-diamine (3 g, 21.9 mmol) at 0° C. under N₂. The mixture was stirred at 20° C. for 3 h. The mixture was poured into saturated sodium bicarbonate and extracted with DCM. The combined organic phases were washed with saturated sodium bicarbonate, dried with anhydrous sodium sulfate, filtered and concentrated in vacuum to give 2-isothiocyanato-N,N-dimethylpyridin-3-amine (2.3 g, crude).

$N^2$-(3-(5-Cyclopropoxypyridin-2-yl)-1,2,4-thiadiazol-5-yl)-$N^3$,$N^3$-dimethylpyridine-2,3-diamine To a mixture of 2-isothiocyanato-N,N-dimethylpyridin-3-amine (1.01 g, 5.64 mmol and DIPEA (1.46 g, 11.29 mmol) in DCM (20 mL) and acetone (20 mL) was added 5-cyclopropoxypicolinimidamide (1 g, 5.64 mmol) under N₂. The mixture was stirred at 20° C. for 10 h. The mixture was poured into H₂O and extracted with DCM. The product was isolated and purified via standard methods to give $N^2$-[3-[5-(cyclopropoxy)-2-pyridyl]-1,2,4-thiadiazol-5-yl]-$N^3$,$N^3$-dimethyl-pyridine-2,3-diamine; HCl salt (277 mg, 0.709 mmol, 12.56% yield, 100% purity).

Example 6: 3-(5-(Cyclopropylmethoxy)pyridin-2-yl)-N-(3-methylpyridin-2-yl)-1,2,4-thiadiazol-5-amine

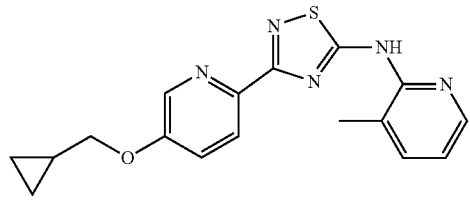 [SMILES: Cc1cccnc1Nc1nc(-c2ccc(OCC3CC3)cn2)ns1]

5-(Cyclopropylmethoxy)picolinonitrile

To a mixture of cyclopropylmethanol (6.26 g, 86.8 mmol) in DMF (300 mL) was added NaH (3.60 g, 90.1 mmol, 60% purity) at 0° C. and stirred 1 h. 5-fluoropicolinonitrile (10 g, 81.9 mmol) was added at 0° C. and stirred for 1 h. Then the mixture was stirred at 20° C. for 1 h. The mixture was poured into saturated NH₄Cl. The aqueous phase was extracted with EtOAc. The combined organic layers were concentrated to give 5-(cyclopropylmethoxy)picolinonitrile (10.20 g, 55.6 mmol, 67.91% yield, 94.99% purity) which was used directly to next step.

5-(Cyclopropylmethoxy)picolinimidamide

To a mixture of 5-(cyclopropylmethoxy)picolinonitrile (9.00 g, 51.7 mmol) in MeOH (100 mL) was added sodium methoxide (976.90 mg, 18.1 mmol). The mixture was heated to 70° C. and stirred at 20° C. for 10 h. NH₄Cl (6.36 g, 118.8 mmol) was added and the mixture was stirred at 70° C. for 10 h. The solvent was concentrated under reduced pressure to remove MeOH. The residue was dissolved in EtOH (100 mL) and heated to 70° C. for 1 h. The mixture was filtered at 70° C. The filtrate was concentrated. The residue was then triturated with DCM and then filtered. The solid was dissolved in ACN and H₂O. Amberlyst A 26 (4.00 g) was added and the mixture was stirred at 20° C. for 15 min. The mixture was filtered and the filtrate was concentrated and then toluene (50 mL) was added. The mixture was concentrated to give 5-(cyclopropylmethoxy)picolinimidamide (3.61 g, 18.9 mmol, 36.54% yield, 100% purity).

3-(5-(Cyclopropylmethoxy)pyridin-2-yl)-N-(3-methylpyridin-2-yl)-1,2,4-thiadiazol-5-amine To a mixture of 5-(cyclopropylmethoxy)picolinimidamide (3.50 g, 18.3 mmol) and TEA (5.56 g, 54.9 mmol) in DCM (80 mL) and acetone (80 mL) was added a solution of 2-isothiocyanato-3-methylpyridine (4.12 g, 27.5 mmol) in DCM (50 mL). The mixture was stirred at 20° C. for 10 h. The product was isolated and purified via standard methods to give 3-(5-(cyclopropylmethoxy)pyridin-2-yl)-N-(3-methylpyridin-2-yl)-1,2,4-thiadiazol-5-amine; HCl salt (214 mg, 556 mmol, 3.0% yield, 97.8% purity). LCMS (ESI): m/z 340.1 [M+1]⁺.

Example 7: 3-(5-((2-Cyclopropyl-2-azaspiro[3.3]heptan-6-yl)oxy)pyridin-2-yl)-N-(3-methylpyridin-2-yl)-1,2,4-thiadiazol-5-amine

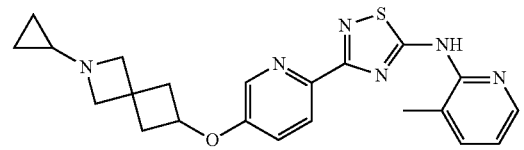 [SMILES: Cc1cccnc1Nc1nc(-c2ccc(OC3CC4(C3)CN(C3CC3)C4)cn2)ns1]

5-((2-Cyclopropyl-2-azaspiro[3.3]heptan-6-yl)oxy)picolinonitrile

To a mixture of 5-(2-azaspiro[3.3]heptan-6-yloxy)picolinonitrile (1.57 g, 7.29 mmol) in MeOH (20 mL) and acetic acid (10 mL) was added (1-ethoxycyclopropoxy)trimethylsilane (6.36 g, 36.5 mmol). The reaction mixture was stirred at 20° C. for 30 min. Then sodium cyanoborohydride (1.38 g, 21.9 mmol) was added to the mixture and the mixture was then stirred at 80° C. for another 2 h. The mixture was concentrated under vacuum to give the residue. The residue was diluted with H₂O and the pH was adjusted to 7 with ammonium hydroxide (25%). The mixture was purified by C+ reverse column to give 5-((2-cyclopropyl-2-azaspiro[3.3]heptan-6-yl)oxy)picolinonitrile (850 mg, 3.11 mmol, 42.63% yield, 93.4% purity).

5-((2-Cyclopropyl-2-azaspiro[3.3]heptan-6-yl)oxy)picolinimidamide

To a mixture of 5-((2-cyclopropyl-2-azaspiro[3.3]heptan-6-yl)oxy)picolinonitrile (400 mg, 1.57 mmol) in MeOH (4 mL) was added sodium methoxide (42.3 mg, 783.0 μmol) and the reaction mixture was then stirred at 25° C. for 15 h.

NH$_4$Cl (126.0 mg, 2.35 mmol) was added to the mixture and the mixture was then stirred at 75° C. for another 12 h. The mixture was concentrated to remove MeOH and then diluted with EtOH (10 mL). The mixture was warmed to 70° C. and stirred at this temperature for 0.5 h. Then the mixture was filtered and the filtrate was concentrated to give 520 mg crude product (HCl salt), which was then diluted with ACN and H$_2$O. OH-type resin (CAS: 39339-85-0, 1 g) was added to the mixture. The mixture was filtered and the filtrate was then lyophilized to give 5-((2-cyclopropyl-2-azaspiro[3.3] heptan-6-yl)oxy)picolinimidamide (350 mg, crude).

5-((2-Cyclopropyl-2-azaspiro[3.3]heptan-6-yl)oxy)-N-((3-methylpyridin-2-yl)carbamothioyl)picolinimidamide To a mixture of 5-((2-cyclopropyl-2-azaspiro[3.3]heptan-6-yl)oxy)picolinimidamide (350 mg, 1.29 mmol) and TEA (260.0 mg, 2.57 mmol) in DCM (5 mL) was added a solution of 2-isothiocyanato-3-methyl-pyridine (193.0 mg, 1.29 mmol) in DCM (1 mL). The mixture was then stirred at 25° C. for 2 h. The mixture was quenched with saturated sodium sulfite and then extracted with EtOAc. The combined organic phases were dried with anhydrous sodium sulfate, filtered and concentrated to give 5-((2-cyclopropyl-2-azaspiro[3.3]heptan-6-yl)oxy)-N-((3-methylpyridin-2-yl) carbamothioyl)picolinimidamide (660 mg, crude) which was used in the next step directly.

3-(5-((2-Cyclopropyl-2-azaspiro[3.3]heptan-6-yl) oxy)pyridin-2-yl)-N-(3-methyl pyridin-2-yl)-1,2,4-thiadiazol-5-amine To a mixture of 5-((2-cyclopropyl-2-azaspiro[3.3]heptan-6-yl)oxy)-N-((3-methyl-pyridin-2-yl)carbamothioyl)picolinimidamide (660 mg, 1.56 mmol) in EtOH (10 mL) was added iodine (79.3 mg, 312.0 μmol) and hydrogen peroxide (354.0 mg, 3.12 mmol, 30% purity). The reaction mixture was then stirred at 25° C. for 1.5 h. The product was isolated and purified via standard methods to give 3-[5-[(2-cyclopropyl-2-azaspiro[3.3]heptan-6-yl]oxy]-2-pyridyl]-N-(3-methyl-2-pyridyl)-1,2,4-thiadiazol-5-amine (83.45 mg, 0.179 mmol, 11.45% yield, 100% purity). LCMS (ESI): m/z 421.2 [M+1]$^+$.

Example 8: 3-(5-((1-Cyclopropyl-3,3-difluoropiperidin-4-yl)oxy)pyridin-2-yl)-N-(3-isopropyl pyridin-2-yl)-1,2,4-thiadiazol-5-amine

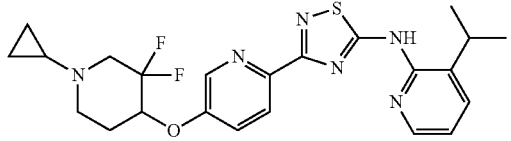 [SMILES: CC(C)c1cccnc1Nc1nc(-c2ccc(OC3CCN(C4CC4)CC3(F)F)cn2)ns1]

tert-Butyl 4-((6-cyanopyridin-3-yl)oxy)-3,3-difluoropiperidine-1-carboxylate

To a mixture of NaH (786 mg, 19.7 mmol, 60% purity) in DMF (80 mL) was added tert-butyl 3,3-difluoro-4-hydroxypiperidine-1-carboxylate (3.89 g, 16.4 mmol) at 0° C. and the mixture was warmed up to 15° C. stirring for 0.5 h. Then the mixture was re-cooled to 0° C. and 5-fluoropicolinonitrile (2.00 g, 16.4 mmol) was added in portions. The resulting mixture was stirred at 0° C. for 0.5 h. The mixture was poured into saturated aqueous NH$_4$Cl (150 mL) and extracted with EtOAc. The organic phase was washed with H$_2$O and brine, dried over sodium sulfate, and filtered. The filtrate was concentrated under vacuum to give tert-butyl 4-((6-cyanopyridin-3-yl)oxy)-3,3-difluoropiperidine-1-carboxylate (5.50 g, crude) which was used directly without purification.

5-((3,3-Difluoropiperidin-4-yl)oxy)picolinonitrile

To a mixture of tert-butyl 4-((6-cyanopyridin-3-yl)oxy)-3,3-difluoropiperidine-1-carboxylate (5.50 g, 16.2 mmol) in DCM (50 mL) was added trifluoroacetic acid (15.4 g, 135 mmol, 10 mL) dropwise at 0° C. and the mixture was stirred at 15° C. for 2 h. The mixture was concentrated under vacuum to give 5-((3,3-difluoropiperidin-4-yl)oxy)picolinonitrile (3.88 g, crude) which was neutralized with TEA in MeOH (40 mL) to pH=~8 and used directly in the next step without purification.

5-((1-Cyclopropyl-3,3-difluoropiperidin-4-yl)oxy) picolinonitrile

To a mixture of 5-((3,3-difluoropiperidin-4-yl)oxy)picolinonitrile (3.88 g, 16.2 mmol) in MeOH (40 mL) and acetic acid (20 mL) was added (1-ethoxycyclopropoxy)trimethylsilane (14.1 g, 81.1 mmol, 16.3 mL) at 15° C. and the mixture was stirred at 15° C. for 0.5 h. Sodium cyanoborohydride (3.06 g, 48.7 mmol) was added to the mixture at 15° C. and the resulting mixture was stirred at 80° C. for 2 h. The mixture was concentrated under vacuum to give the residue. The residue was diluted with saturated sodium carbonate under stirring and the resulting mixture was extracted with EtOAc. The organic phase was washed with brine, dried over sodium sulfate, and filtered. The filtrate was concentrated under vacuum to give the crude product. The crude product was purified by silica gel column chromatography (9%-25% EtOAc in petroleum ether) to give 5-((1-cyclopropyl-3,3-difluoropiperidin-4-yl)oxy)picolinonitrile (4.50 g, 12.9 mmol, 79.7% yield, 80.2% purity).

5-((1-Cyclopropyl-3,3-difluoropiperidin-4-yl)oxy) picolinimidamide

To a solution of 5-((1-cyclopropyl-3,3-difluoropiperidin-4-yl)oxy)picolinonitrile (1.50 g, 4.31 mmol) in MeOH (30 mL) was added sodium methoxide (116 mg, 2.15 mmol) at 15° C. and the mixture was stirred at 15° C. for 14 h. NH$_4$Cl (461 mg, 8.61 mmol) was added to the reaction mixture at 15° C. The mixture was stirred at 70° C. for another 2 h. The mixture was concentrated under vacuum to give a residue. The residue was diluted with EtOH (60 mL) and the mixture was stirred at 25° C. for 0.5 h. The mixture was filtered and the filtrate was concentrated under vacuum to give a solid which was triturated with EtOAc (50 mL) at 15° C. for 0.5 h. The resulting mixture was filtered and the solid was collected, dried under vacuum to give 5-((1-cyclopropyl-3, 3-difluoropiperidin-4-yl)oxy)picolinimidamide (1.28 g, crude) as hydrochloride salt. The hydrochloride salt was dissolved in H$_2$O (60 mL) and Amberlyst A 26 was added under stirring in portions until the pH of the solution was adjusted to 8 and stirred for 2 h at 15° C. The mixture was filtered and washed with H$_2$O (20 mL), and the filtrate was lyophilized for three days to give 5-((1-cyclopropyl-3,3-difluoropiperidin-4-yl)oxy)picolinimidamide (0.960 g, 1.65 mmol, 38.3% yield, 50.9% purity).

5-((1-Cyclopropyl-3,3-difluoropiperidin-4-yl)oxy)-N-((3-isopropylpyridin-2-yl) carbamothioyl)picolinimidamide To the mixture of 5-((1-cyclopropyl-3,3-difluoropiperidin-4-yl)oxy)picolinimidamide (0.480 g, 825 μmol) and TEA (167 mg, 1.65 mmol) in DCM (10 mL) and acetone (10 mL) was added 3-isopropyl-2-isothiocyanatopyridine (273 mg, 1.24 mmol) at 15° C. under nitrogen atmosphere and the mixture was stirred at 15° C. for 2 h. The mixture was diluted with DCM and washed with $H_2O$. The organic phase was concentrated under vacuum to give 5-((1-cyclopropyl-3,3-difluoropiperidin-4-yl)oxy)-N-((3-isopropylpyridin-2-yl)carbamo-thioyl)picolinimidamide (0.740 g, crude), which was used in the next step without purification.

3-(5-((1-Cyclopropyl-3,3-difluoropiperidin-4-yl) oxy)pyridin-2-yl)-N-(3-isopropyl pyridin-2-yl)-1,2,4-thiadiazol-5-amine To a mixture of 5-((1-cyclopropyl-3,3-difluoropiperidin-4-yl)oxy)-N-((3-isopropylpyridin-2-yl)carbamothioyl)picolinimidamide (0.730 g, 1.54 mmol) in EtOH (20 mL) was added hydrogen peroxide (349 mg, 3.08 mmol, 30% purity) and a solution of iodine (78.1 mg, 308 μmol) in EtOH (2 mL). The mixture was stirred at 15° C. for 2 h. The product was isolated and purified via standard methods to give 3-(5-((1-cyclopropyl-3,3-difluoropiperidin-4-yl)oxy)pyridin-2-yl)-N-(3-isopropylpyridin-2-yl)-1,2,4-thiadiazol-5-amine (206.99 mg, 0.438 mmol, 28.5% yield, 100% purity). LCMS (ESI): m/z 473.3 [M+1].

Example 9: N-(5-Cyclopentylpyridin-2-yl)-3-(5-methoxypyridin-2-yl)-1,2,4-thiadiazol-5-amine

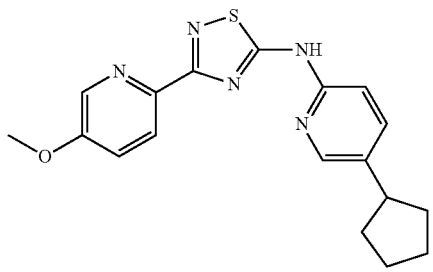 [SMILES: COc1ccc(-c2nsc(Nc3ccc(C4CCCC4)cn3)n2)nc1]

5-(Cyclopent-1-en-1-yl)-2-nitropyridine

To a mixture of 5-bromo-2-nitro-pyridine (2.5 g, 12.32 mmol), 2-(cyclopenten-1-yl)-4,4,5,5-tetramethyl-1,3,2-dioxaborolane (3.0 g, 15.39 mmol), sodium carbonate (2.61 g, 24.6 mmol) in dioxane (30 mL) and H2O (1.00 mL) was added tetrakis (triphenylphosphine) palladium (427.1 mg, 0.369 mmol). The mixture was degassed and refilled with $N_2$. The mixture was stirred at 80° C. for 6 h. To the mixture was added another bath of 2-(cyclopenten-1-yl)-4,4,5,5-tetramethyl-1,3,2-dioxaborolane (956.1 mg, 4.93 mmol) and tetrakis (triphenylphosphine) palladium (142.4 mg, 0.123 mmol). The mixture was degassed and refilled with $N_2$ and stirred at 80° C. for an additional 3 h. Dichloro (1,1'-bis (diphenylphosphanyl)ferrocene) palladium(II) (180.29 mg, 0.246 mmol) was added, the mixture was degassed and refilled with $N_2$ and stirred at 90° C. for an additional 6 h. The mixture was diluted with EtOAc and filtered. The filtrate was concentrated and the residue purified by silica gel chromatography to give 5-(cyclopenten-1-yl)-2-nitropyridine (1.60 g, 8.41 mmol, 68% yield).

5-Cyclopentylpyridin-2-amine

To a mixture of 5-(cyclopenten-1-yl)-2-nitro-pyridine (1.6 g, 8.41 mmol) in 2,2,2-trifluoroethanol (20 mL) was added Pd/C (2.0 g). The mixture was degassed and refilled with $H_2$ (15 psi) and stirred at 30° C. for 2 h. The mixture was stirred at 40° C. for 1 h. Then diluted with EtOAc, filtered and the filtrate concentrated. The residue was purified by silica gel chromatography to give 5-cyclopentylpyridin-2-amine (900 mg, 5.55 mmol, 66% yield).

5-Cyclopentyl-2-isothiocyanatopyridine

To a mixture of di(imidazol-1-yl)methanethione (549 mg, 3.08 mmol) in DMF (10 mL) was added a solution of 5-cyclopentylpyridin-2-amine (500 mg, 3.08 mmol) in DMF (10 mL). The mixture was stirred at 10° C. for 1 h. 5-Cyclopentyl-2-isothiocyanato-pyridine (629 mg, crude) in DMF (20 mL) was used in the next step directly.

N-((5-Cyclopentylpyridin-2-yl)carbamothioyl)-5-methoxypicolinimidamide

To a mixture of 5-cyclopentyl-2-isothiocyanato-pyridine (629 mg, 3.1 mmol) in DMF (20 mL) was added 5-methoxypyridine-2-carboxamidine (512 mg, 3.4 mmol) and DIPEA (2 g, 15.4 mmol, 2.7 mL). The mixture was stirred at 30° C. for 4 h. The mixture was diluted with $H_2O$. The resultant mixture was extracted with EtOAc and the combined organic layers were washed with saturated brine, dried over anhydrous sodium sulfate, filtered, and concentrated to give 1-(5-cyclopentyl-2-pyridyl)-3-(5-methoxypyridine-2-carboximidoyl)thiourea (1.1 g, crude), which was used in the next step directly.

N-(5-Cyclopentylpyridin-2-yl)-3-(5-methoxypyridin-2-yl)-1,2,4-thiadiazol-5-amine To a solution of 1-(5-cyclopentyl-2-pyridyl)-3-(5-methoxypyridine-2-carboximidoyl)thiourea (1.1 g, 3.1 mmol) in EtOH (20 mL) were added hydrogen peroxide (702 mg, 6.2 mmol, 0.6 mL, 30% purity) and a solution of iodine (157 mg, 0.619 mmol) in EtOH (5 mL). The mixture was stirred at 15° C. for 1 h. The product was isolated and purified via standard methods to give N-(5-cyclopentyl-2-pyridyl)-3-(5-methoxy-2-pyridyl)-1,2,4-thiadiazol-5-amine (576.40 mg, 1.61 mmol, 52% yield, 99% purity). LCMS (ESI): m/z 354.1 [M+1]⁺.

Example 10: 3-(4-Isopropylpyridin-2-yl)-N-(3-(trifluoromethyl)pyridin-2-yl)-1,2,4-thiadiazol-5-amine

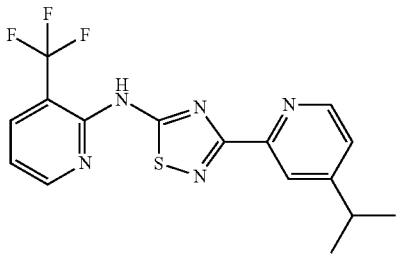 [SMILES: CC(C)c1ccnc(-c2nsc(Nc3ncccc3C(F)(F)F)n2)c1]

4-(Prop-1-en-2-yl)picolinonitrile

To a mixture of 4-bromopicolinonitrile (2.00 g, 10.9 mmol) and potassium trifluoro(prop-1-en-2-yl)borate (3.23 g, 21.9 mmol) in 1,4-dioxane (20 mL) and H$_2$O (2 mL) was added potassium carbonate (943 mg, 6.82 mmol) and dichloro(1,1'-bis(diphenylphosphanyl)ferrocene)palladium (II) chloroform complex (800 mg, 1.09 mmol) under nitrogen. The mixture was stirred at 80° C. for 4 h. The mixture was poured into H$_2$O (100 mL). The aqueous phase was extracted with EtOAc. The combined organic phases were washed with brine, dried over anhydrous sodium sulfate, filtered, and concentrated in vacuo. The residue was purified by silica gel chromatography to give 4-(prop-1-en-2-yl) picolinonitrile (1.44 g, 9.99 mmol, 91.3% yield).

4-(Prop-1-en-2-yl)picolinimidamide Hydrochloride

To a mixture of 4-(prop-1-en-2-yl)picolinonitrile (1.65 g, 11.4 mmol) in MeOH (15 mL) was added sodium methanolate (185 mg, 3.43 mmol). The mixture was stirred at 30° C. for 16 h under nitrogen. NH$_4$Cl (796 mg, 14.9 mmol) was added into the above mixture. The mixture was stirred at 70° C. for 3 h. The mixture was concentrated in vacuo and the residue was diluted with EtOH (80 mL). The mixture was refluxed at 80° C. for 15 min. The mixture was filtered and the filter cake was triturated with DCM (30 mL), then dried in vacuo to give 4-(prop-1-en-2-yl)picolinimidamide hydrochloride (1.70 g, 8.60 mmol, 75% yield).

4-Isopropylpicolinimidamide Hydrochloride

To a solution of 4-(prop-1-en-2-yl)picolinimidamide hydrochloride (1.60 g, 8.09 mmol) in 2,2,2-trifluoroethanol (80 mL) was added Pd/C (480 mg). The mixture was stirred at 20° C. for 2.5 h under hydrogen balloon (15 psi). The mixture was filtered through celite and the filtrate concentrated in vacuo to give 4-isopropylpicolinimidamide hydrochloride (1.60 g, 8.01 mmol, 99.1% yield).

4-Isopropylpicolinimidamide

To a solution of 4-isopropylpicolinimidamide hydrochloride (1.80 g, 9.01 mmol) in ACN (75 mL) and H$_2$O (15 mL) was added Amberlyst A 26. The pH of the mixture was adjusted to about 10-11. The mixture was stirred at 20° C. for 4 h. The reaction mixture was filtered and the filtrate was concentrated in vacuo followed by lyophilization to give 4-isopropylpicolinimidamide (1.40 g, 8.49 mmol, 94% yield, 99% purity).

4-Isopropyl-N-((3-(trifluoromethyl)pyridin-2-yl)carbamothioyl)picolinimidamide To a solution of 4-isopropylpyridine-2-carboxamidine (500 mg, 3.03 mmol) in DCM (5 mL) and acetone (5 mL) were added TEA (3.07 g, 30.30 mmol) and 2-isothiocyanato-3-(trifluoromethyl)pyridine (635 mg, 3.03 mmol). The mixture was stirred at 15° C. for 1 h. The mixture was concentrated and the residue poured into H$_2$O. The aqueous phase was extracted with EtOAc and the combined organic phases dried over anhydrous sodium sulfate, filtered, and concentrated under vacuum. The crude product 4-isopropyl-N-((3-(trifluoromethyl)pyridin-2-yl)carbamothioyl)picolinimidamide (1.00 g, 1.90 mmol, 62.6% yield, 69.7% purity) was used into the next step without further purification.

3-(4-Isopropylpyridin-2-yl)-N-(3-(trifluoromethyl)pyridin-2-yl)-1,2,4-thiadiazol-5-amine To a solution of 4-isopropyl-N-((3-(trifluoromethyl)pyridin-2-yl)carbamothioyl) picolinimidamide (1.00 g, 1.90 mmol) in EtOH (20 mL) were added iodine (96 mg, 0.379 mmol) and hydrogen peroxide (129 mg, 3.79 mmol). The mixture was stirred at 15° C. for 1 h under N$_2$. The mixture was diluted with H$_2$O (30 mL) and saturated aqueous sodium sulfite (0.5 mL). The mixture was stirred at 0° C. for another 0.5 h and checked by potassium iodide-starch test paper to see whether hydrogen peroxide was destroyed. The aqueous phase was extracted with EtOAc. The product was isolated and purified via standard methods to give 3-(4-isopropyl-2-pyridyl)-N-[3-(trifluoromethyl)-2-pyridyl]-1,2,4-thiadiazol-5-amine (373.04 mg, 0.975 mmol, 51.3% yield, 95.5% purity).

Example 11: 3-(5-Isopropoxypyridin-2-yl)-N-(5-isopropyl-3-(trifluoromethyl)pyridin-2-yl)-1,2,4-thiadiazol-5-amine

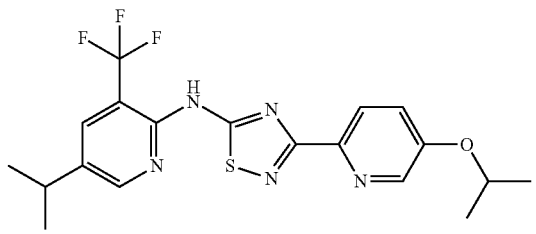 [SMILES: CC(C)Oc1ccc(-c2nsc(Nc3ncc(C(C)C)cc3C(F)(F)F)n2)nc1]

5-Bromo-3-(trifluoromethyl)pyridin-2-amine

To a mixture of 3-(trifluoromethyl)pyridin-2-amine (25 g, 154.21 mmol) in THF (250 mL) was added N-bromosuccinimide (27.45 g, 154.21 mmol) in portions at 0° C. Then the mixture was stirred at 15° C. for 1.5 h. The reaction mixture was concentrated under reduced pressure to give a crude product. The crude product was purified by column chromatography to give 5-bromo-3-(trifluoromethyl)pyridin-2-amine (34.1 g, 141.49 mmol, 91.75% yield).

5-(Prop-1-en-2-yl)-3-(trifluoromethyl)pyridin-2-amine

To a mixture of 5-bromo-3-(trifluoromethyl)pyridin-2-amine (34.1 g, 141.49 mmol), potassium trifluoro(prop-1- en-2-yl)borate (31.41 g, 212.23 mmol), potassium carbonate (39.11 g, 282.98 mmol) in dioxane (500 mL) and H$_2$O (50 mL) was added [1,1-bis(diphenylphosphino)ferrocene]-dichloropalladium (2.07 g, 2.83 mmol) under nitrogen. The mixture was stirred at 80° C. for 5 h. The mixture was filtered and the filtrate was concentrated and purified by column chromatography to give 5-isopropenyl-3-(trifluoromethyl)pyridin-2-amine (26.9 g, 133.05 mmol, 94.04% yield).

5-Isopropyl-3-(trifluoromethyl)pyridin-2-amine

To the mixture 5-isopropenyl-3-(trifluoromethyl)pyridin-2-amine (26.9 g, 133.05 mmol) in MeOH (150 mL) was added dry Pd/C (1.5 g, 10% purity) and wet hydroxide Pd/C (1.5 g, 20% purity) under nitrogen. The mixture was degassed under vacuum and purged with hydrogen several times. The mixture was stirred under hydrogen (15 psi) at 20° C. for 16 h. The mixture was filtered and the filtrate was concentrated to give 5-isopropyl-3-(trifluoromethyl)pyridin-2-amine (26.7 g, 130.76 mmol, 98.28% yield).

5-Isopropyl-2-isothiocyanato-3-(trifluoromethyl)pyridine

To a mixture of thiocarbonyl dichloride (5.07 g, 44.08 mmol, 3.38 mL) in DCM (50 mL) was added a solution of 5-isopropyl-3-(trifluoromethyl)pyridin-2-amine (6 g, 29.38 mmol) in DCM (10 mL) at 0° C. under nitrogen. The mixture was stirred at 0° C. for 1 h. The reaction mixture was quenched with saturated sodium bicarbonate (70 mL) at 0° C. The organic phase was separated and dried over anhydrous sodium sulfate, filtered and concentrated under reduced pressure to give a residue. The residue was purified by column chromatography to give 5-isopropyl-2-isothiocyanato-3-(trifluoromethyl)pyridine (5.5 g, 21.22 mmol, 72.21% yield, 95% purity).

5-Isopropoxy-N-((5-isopropyl-3-(trifluoromethyl)pyridin-2-yl)carbamothioyl) picolinimidamide To the mixture 5-isopropoxypyridine-2-carboxamidine (363.89 mg, 2.03 mmol) and 5-isopropyl-2-isothiocyanato-3-(trifluoromethyl)pyridine (0.5 g, 2.03 mmol) in DCM (20 mL) and acetone (20 mL) was added TEA (616.38 mg, 6.09 mmol, 0.85 mL). The mixture was stirred at 20° C. for 1 h. and concentrated at reduced pressure to give a residue. H2O and saturated sodium carbonate were added to the residue and the mixture was extracted with EtOAc. The combined organic phases were dried over anhydrous sodium sulfate, filtered and concentrated at reduced pressure to give 5-isopropoxy-N-((5-isopropyl-3-(trifluoromethyl)pyridin-2-yl)carbamothioyl)picolinimidamide (484 mg, 1.02 mmol, 50.42% yield, 90% purity).

3-(5-Isopropoxypyridin-2-yl)-N-(5-isopropyl-3-(trifluoromethyl)pyridin-2-yl)-1,2,4-thiadiazol-5-amine To the mixture of 5-isopropoxy-N-((5-isopropyl-3-(trifluoromethyl)pyridin-2-yl)carbamothioyl)picolinimidamide (484 mg, 1.02 mmol, 90% purity) and hydrogen peroxide (348.20 mg, 3.07 mmol, 0.30 mL, 30% purity) in EtOH (20 mL) was added iodine (51.97 mg, 0.21 mmol) at 0° C. The mixture was stirred at 20° C. for 0.5 h. The reaction mixture was quenched with saturated sodium sulfite (10 mL) at 0° C. The resulting mixture was concentrated to give a residue. The product was isolated and purified via standard methods to give 3-(5-isopropoxy-2-pyridyl)-N-[5-isopropyl-3-(trifluoromethyl)-2-pyridyl]-1,2,4-thiadiazol-5-amine (290.48 mg, 679.12 µmol, 66.33% yield); LCMS (ESI): m/z 424.2 [M+1]$^+$.

Example 12: 5-(5-Isopropoxypyridin-2-yl)-N-(3-methylpyridin-2-yl)-1,3,4-thiadiazol-2-amine

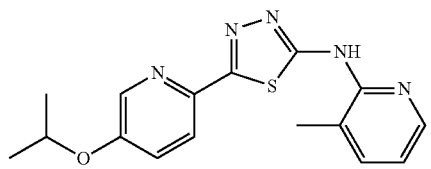 [SMILES: Cc1cccnc1Nc1nnc(-c2ccc(OC(C)C)cn2)s1]

5-Isopropoxypicolinohydrazide

To a solution of methyl 5-isopropoxypicolinate (600 mg, 3.07 mmol) in MeOH (6 mL) was added hydrazine hydrate (230 mg, 4.60 mmol). The mixture was stirred at 70° C. for 5 h. The mixture was concentrated to give 5-isopropoxypicolinohydrazide (600 mg, 2.83 mmol, 92% yield, 92% purity).

2-(5-Isopropoxypicolinoyl)-N-(3-methylpyridin-2-yl)hydrazinecarbothioamide

To a solution of 5-isopropoxypicolinohydrazide (500 mg, 2.36 mmol) in DCM (20 mL) was added 2-isothiocyanato-3-methylpyridine (532 mg, 3.54 mmol). The mixture was stirred at 30° C. for 19 h. The mixture was concentrated. The residue was purified by prep-HPLC to give 2-(5-isopropoxypicolinoyl)-N-(3-methylpyridin-2-yl)hydrazinecarbothioamide (130 mg, 0.376 mmol, 15.95% yield).

5-(5-Isopropoxypyridin-2-yl)-N-(3-methylpyridin-2-yl)-1,3,4-thiadiazol-2-amine

To a solution of 2-(5-isopropoxypicolinoyl)-N-(3-methylpyridin-2-yl)hydrazinecarbothioamide (160 mg, 0.463 mmol) in toluene (5 mL) was added p-toluenesulfonic acid (80 mg, 0.463 mmol). The mixture was stirred at 100° C. for 4 h. The mixture was concentrated. The product was isolated and purified via standard methods to give 5-(5-isopropoxypyridin-2-yl)-N-(3-methylpyridin-2-yl)-1,3,4-thiadiazol-2-amine (89.15 mg, 0.237 mmol, 51% yield, 99.1% purity). LCMS (ESI): m/z 328.2 [M+1]$^+$.

Example 13: 5-(5-(((1-methylpiperidin-4-yl)oxy)pyridin-2-yl)-N-(3-methylpyridin-2-yl)-1,3,4-thiadiazol-2-amine

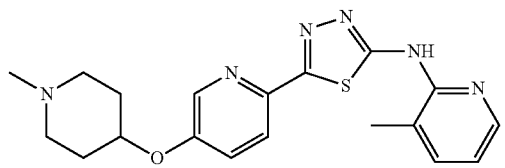 [SMILES: Cc1cccnc1Nc1nnc(-c2ccc(OC3CCN(C)CC3)cn2)s1]

2-(5-((1-Methylpiperidin-4-yl)oxy)picolinoyl)-N-(3-methylpyridin-2-yl)hydrazinecarbothioamide To a solution of 5-((1-methylpiperidin-4-yl)oxy)picolinohydrazide (500 mg, 1.98 mmol) in DCM (20 mL) was added 2-isothiocyanato-3-methylpyridine (496 mg, 2.97 mmol). The mixture was stirred at 30° C. for 19 h. The mixture was concentrated. The residue was diluted with MeOH (5 mL). The solid was collected and dried in vacuo to give 150 mg of product. The filtrate was purified by prep-HPLC. Two parts of products were combined and the solution was dried by lyophilization to give 2-(5-((1-methylpiperidin-4-yl)oxy)picolinoyl)-N-(3-methylpyridin-2-yl)hydrazinecarbothioamide (300 mg, 0.749 mmol, 38% yield).

5-(5-((1-Methylpiperidin-4-yl)oxy)pyridin-2-yl)-N-(3-methylpyridin-2-yl)-1,3,4-thiadiazol-2-amine To a solution of 2-(5-((1-methylpiperidin-4-yl)oxy)picolinoyl)-N-(3-methylpyridin-2-yl)hydrazinecarbothioamide (300 mg, 0.749 mmol) in toluene (20 mL) was added p-toluenesulfonic acid (129 mg, 0.749 mmol). The mixture was stirred at 100° C. for 6 h. The mixture was concentrated. The residue was diluted with saturated sodium carbonate and H$_2$O. The aqueous phase was extracted with EtOAc. The combined organic phase was dried over anhydrous sodium sulfate, filtered, and concentrated under vacuum to give the crude product. The product was isolated and purified via standard methods to give 5-(5-((1-methylpiperidin-4-yl)oxy)pyridin-2-yl)-N-(3-methylpyridin-2-yl)-1,3,4-thiadiazol-2-amine (93.60 mg, 0.237 mmol, 32% yield, 96.8% purity). LCMS (ESI): m/z 383.1 [M+1]$^+$.

Example 14: N$^2$-(3-(5-isopropoxypyridin-2-yl)-1,2,4-thiadiazol-5-yl)-N$^3$,N$^3$-dimethylpyridine-2,3-diamine

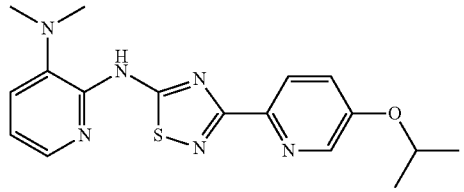 [SMILES: CC(C)Oc1ccc(-c2nsc(Nc3ncccc3N(C)C)n2)nc1]

N-((3-(Dimethylamino)pyridin-2-yl)carbamothioyl)-5-isopropoxypicolinimid amide To a solution of 5-isopropoxypyridine-2-carboxamidine (500 mg, 2.79 mmol) in DCM (10 mL), acetone (10 mL) and TEA (2.82 g, 27.90 mmol) was added 2-isothiocyanato-N,N-dimethyl-pyridin-3-amine (500 mg, 2.79 mmol) under N$_2$. The mixture was stirred at 15° C. for 2 h under N$_2$. The mixture was concentrated. The residue was poured into H$_2$O (50 mL). The aqueous phase was extracted with EtOAc. The combined organic phases were dried over anhydrous sodium sulfate, filtered, and concentrated under vacuum to give N-((3-(dimethylamino)pyridin-2-yl)carbamothioyl)-5-isopropoxypicolinimid amide (1.10 g, crude).

N$^2$-(3-(5-Isopropoxypyridin-2-yl)-1,2,4-thiadiazol-5-yl)-N$^3$,N$^3$-dimethylpyridine-2,3-diamine To a solution of N-((3-(dimethylamino)pyridin-2-yl)carbamothioyl)-5-isopropoxypicolinimid amide (1.10 g, 3.08 mmol) in EtOH (10 mL) was added iodine (156 mg, 0.616 mmol) and hydrogen peroxide (698 mg, 6.16 mmol, 30% purity) under N$_2$. The mixture was stirred at 15° C. for 1 h under N$_2$. The residue was diluted with H$_2$O and saturated aqueous sodium sulfite. The mixture was stirred at 0° C. for another 0.5 h, the reaction was checked by potassium iodide-starch test paper to see whether hydrogen peroxide was destroyed. The aqueous phase was extracted with EtOAc. The product was isolated and purified via standard methods to give N$^2$-(3-(5-isopropoxypyridin-2-yl)-1,2,4-thiadiazol-5-yl)-N$^3$,N$^3$-dimethylpyridine-2,3-diamine (174.56 mg, 0.469 mmol, 15% yield, 95.8% purity). LCMS (ESI): m/z 357.1 [M+1]$^+$.

Example 15: (4-Methylpiperazin-1-yl)(6-(5-((3-methylpyridin-2-yl)amino)-1,2,4-thiadiazol-3-yl)pyridin-3-yl)methanone

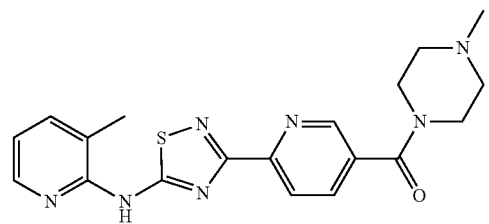 [SMILES: Cc1cccnc1Nc1nc(-c2ccc(C(=O)N3CCN(C)CC3)cn2)ns1]

Methyl 6-carbamimidoylnicotinate Hydrochloride

To a solution of methyl 6-cyanonicotinate (3.00 g, 18.5 mmol) in MeOH (45 mL) was added sodium methoxide (200 mg, 3.70 mmol). The mixture was stirred at 30° C. for 16 h. NH$_4$Cl (1.19 g, 22.2 mmol) was added, the mixture was stirred at 70° C. for 4 h. The hot solution was filtered. The filtrate was concentrated to give a white solid. The white solid was triturated with hot EtOH (30 mL). The mixture was filtered and the filtrated was concentrated to give the crude product. The crude product was triturated with DCM (30 mL) to give methyl 6-carbamimidoylnicotinate hydrochloride (2.30 g, 10.5 mmol, 57% yield, 98% purity).

Methyl 6-carbamimidoylnicotinate

To a solution of 6-carbamimidoylnicotinate hydrochloride (1.80 g, 8.35 mmol) in MeOH (30 mL) was added Amberlyst A 26 (5.00 g) to adjust the pH to 10-11. The mixture was stirred at 15° C. for 3 h. The reaction mixture was filtered and concentrated. The residue was diluted with H$_2$O (20 mL) and dried by lyophilization to give 6-carbamimidoylnicotinate (900 mg, 4.87 mmol, 58% yield, 97% purity).

Methyl 6-(N-((3-methylpyridin-2-yl)carbamothioyl)carbamimidoyl)nicotinate

To a solution of 2-isothiocyanato-3-methylpyridine (1.00 g, 6.66 mmol) in DCM (30 mL) and acetone (30 mL) were added methyl 6-carbamimidoylnicotinate (1.19 g, 6.66 mmol) and TEA (6.74 g, 66.60 mmol). The mixture was stirred at 15° C. for 16 h. The residue was diluted with H$_2$O and the aqueous phase was extracted with EtOAc. The combined organic phases were dried over anhydrous sodium sulfate, filtered, and concentrated under vacuum to give methyl 6-(N-((3-methylpyridin-2-yl)carbamothioyl)carbamimidoyl)nicotinate (2.50 g, crude).

Methyl 6-(5-((3-methylpyridin-2-yl)amino)-1,2,4-thiadiazol-3-yl)nicotinate

To a solution of methyl 6-(N-((3-methylpyridin-2-yl)carbamothioyl)carbamimidoyl)nicotinate (2.50 g, 7.59 mmol) in EtOH (100 mL) were added iodine (385 mg, 1.52 mmol) and hydrogen peroxide (1.72 g, 15.2 mmol, 30% purity). The mixture was stirred at 15° C. for 1 h. The mixture was cooled to 0° C. and quenched with saturated sodium sulfite (50 mL). The mixture was concentrated and the residue was diluted with H$_2$O. The aqueous phase was extracted with EtOAc. The combined organic phases were dried over anhydrous sodium sulfate, filtered, and concentrated under vacuum to give the crude product. The crude product was triturated with ACN (20 mL) to give 650 mg of product with 94% purity. The filtrate was concentrated and the residue was purified by silica gel chromatography followed by prep-HPLC to give 150 mg of product. Two parts of products were combined to give methyl 6-(5-((3-methylpyridin-2-yl)amino)-1,2,4-thiadiazol-3-yl)nicotinate (800 mg, 2.44 mmol, 32% yield).

6-(5-((3-Methylpyridin-2-yl)amino)-1,2,4-thiadiazol-3-yl)nicotinic Acid

To a solution of methyl 6-(5-((3-methylpyridin-2-yl)amino)-1,2,4-thiadiazol-3-yl)nicotinate (650 mg, 1.87 mmol) in THE (60 mL) and H$_2$O (10 mL) was added lithium hydroxide (785 mg, 18.70 mmol) at 0° C. The mixture was stirred at 15° C. for 2 h. The mixture was concentrated to remove the THF. The aqueous phase was adjusted to pH of approximately 5 with 2 N HCl and solid was formed. The mixture was filtered, the solid was collected, and dried under vacuum to give 6-[5-[(3-methyl-2-pyridyl)amino]-1,2,4-thiadiazol-3-yl]pyridine-3-carboxylic acid (500 mg, 1.44 mmol, 77% yield, 90% purity).

(4-Methylpiperazin-1-yl)(6-(5-((3-methylpyridin-2-yl)amino)-1,2,4-thiadiazol-3-yl)pyridin-3-yl)methanone To a solution of 6-(5-((3-methylpyridin-2-yl)amino)-1,2,4-thiadiazol-3-yl)nicotinic acid (150 mg, 0.431 mmol), 1-methylpiperazine (86 mg, 0.861 mmol) and DIPEA (167 mg, 1.29 mmol) in DMF (3 mL) was added HATU (327 mg, 0.862 mmol) at 0° C. The mixture was stirred at 30° C. for 5 h. The product was isolated and purified via standard methods to give (4-methylpiperazin-1-yl)-[6-[5-[(3-methyl-2-pyridyl)amino]-1,2,4-thiadiazol-3-yl]-3-pyridyl]methanone (121.27 mg, 0.269 mmol, 63% yield, 98.0% purity). LCMS (ESI): m/z 396.1 [M+1]$^+$.

Example 16: 3-(5-Methoxypyridin-2-yl)-N-(5-((tetrahydro-2H-pyran-4-yl)oxy)pyridin-2-yl)-1,2,4-thiadiazol-5-amine

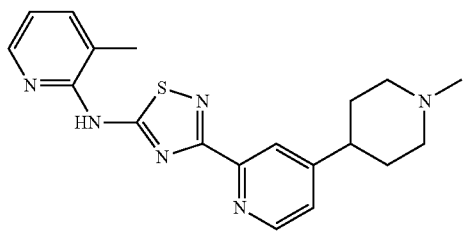 [SMILES: Cc1cccnc1Nc1nc(-c2cc(C3CCN(C)CC3)ccn2)ns1]

1'-Methyl-1',2',3',6'-tetrahydro-[4,4'-bipyridine]-2-carbonitrile

To a mixture of 4-bromopicolinonitrile (1 g, 5.46 mmol) and 1-methyl-4-(4,4,5,5-tetramethyl-1,3,2-dioxaborolan-2-yl)-1,2,3,6-tetrahydropyridine (1.46 g, 6.55 mmol) in H$_2$O (16 mL) and dioxane (80 mL) were added sodium carbonate (1.45 g, 13.7 mmol) and palladium triphenylphosphine (316 mg, 0.273 mmol) under nitrogen. The mixture was stirred at 80° C. for 16 h. The mixture was poured into H$_2$O. The aqueous phase was extracted with EtOAc. The combined organic phases were washed with brine, dried over anhydrous sodium sulfate, filtered, and concentrated in vacuo. The residue was purified by silica gel chromatography to give 1'-methyl-1',2',3',6'-tetrahydro-[4,4'-bipyridine]-2-carbonitrile (1.8 g, 9.03 mmol, 83% yield).

1'-Methyl-1',2',3',6'-tetrahydro-[4,4'-bipyridine]-2-carboximidamide hydrochloride To a solution of 1'-methyl-1',2',3',6'-tetrahydro-[4,4'-bipyridine]-2-carbonitrile (1.30 g, 6.52 mmol) in MeOH (65 mL) was added sodium methanolate (106 mg, 1.96 mmol). The mixture was stirred at 25° C. for 16 h under nitrogen. NH$_4$Cl (698 mg, 13.0 mmol) was added into the above mixture. The mixture was stirred at 70° C. for 4 h. The mixture was concentrated in vacuo and the residue was triturated with DCM. The mixture was filtered and the filter cake was dried in vacuo to give 1'-methyl-1',2',3',6'-tetrahydro-[4,4'-bipyridine]-2-carboximidamide; HCl salt (1.5 g, crude).

4-(1-Methylpiperidin-4-yl)picolinimidamide

To a solution of 1'-methyl-1',2',3',6'-tetrahydro-[4,4'-bipyridine]-2-carboximidamide hydrochloride (1.90 g, 7.52 mmol) in MeOH (50 mL) was added Pd/C (190 mg, 15% purity). The mixture was stirred at 50° C. for 6 h under hydrogen balloon (15 psi). The mixture was filtered though celite and the filtrate was concentrated in vacuo to give 4-(1-methylpiperidin-4-yl)picolinimidamide hydrochloride (1.25 g, crude). The obtained compound in MeOH (50 mL) was adjusted to pH about 10 by addition of Amberlyst A 26. The mixture was stirred at 25° C. for 3 h. The reaction mixture was filtered and the filtrate was concentrated to give 4-(1-methylpiperidin-4-yl)picolinimidamide (1.25 g, crude), which was used directly in the next step.

4-(1-Methylpiperidin-4-yl)-N-((3-methylpyridin-2-yl)carbamothioyl) picolinimidamide To a mixture of 4-(1-methylpiperidin-4-yl)picolinimidamide (917 mg, 4.20 mmol) and TEA (4.25 g, 42.0 mmol) in acetone (15 mL) and DCM (15 mL) was added 2-isothiocyanato-3-methylpyridine (757 mg, 5.04 mmol). The mixture was stirred at 25° C. for 16 h under nitrogen. The mixture was concentrated in vacuo. The residue was diluted with H$_2$O (70 mL). The aqueous phase was extracted with EtOAc. The combined organic phases were washed with brine, dried over anhydrous sodium sulfate, filtered, and concentrated in vacuo to get the crude product. The crude product was purified by prep-TLC to give a mixture of 4-(1-methylpiperidin-4-yl)-N-((3-methylpyridin-2-yl)carbamothioyl) picolinimidamide and 3-(4-(1-methylpiperidin-4-yl)pyridin-2-yl)-N-(3-methylpyridin-2-yl)-1,2,4-thiadiazol-5-amine (590 mg, 0.442 mmol, 21% yield, 55% purity).

3-(5-Methoxypyridin-2-yl)-N-(5-((tetrahydro-2H-pyran-4-yl)oxy)pyridin-2-yl)-1,2,4-thiadiazol-5-amine To a solution of 5-methoxy-N-((5-((tetrahydro-2H-pyran-4-yl)oxy)pyridin-2 yl)carbamothioyl) picolinimidamide and 3-(5-methoxypyridin-2-yl)-N-(5-((tetrahydro-2H-pyran-4-yl)oxy)pyridin-2-yl)-1,2,4-thiadiazol-5-amine (490 mg, 0.367 mmol) in EtOH (25 mL) were added hydrogen peroxide (83.1 mg, 0.733 mmol, 30% purity) and iodine (18.6 mg, 0.073 mmol). The mixture was stirred at 25° C. for 3 h. The residue was diluted with H₂O (50 mL) and saturated aqueous sodium sulfite (10 mL). The mixture was stirred at 25° C. for another 0.5 h. The aqueous phase was extracted with EtOAc. The product was isolated and purified via standard methods to give 3-(4-(1-methylpiperidin-4-yl)pyridin-2-yl)-N-(3-methylpyridin-2-yl)-1,2,4-thiadiazol-5-amine (277.82 mg, 0.645 mmol, 88% yield, 95.7% purity). LCMS (ESI): m/z 367.1 [M+1]⁺.

Example 17: 3-(5-Methoxypyridin-2-yl)-N-(5-((tetrahydro-2H-pyran-4-yl)oxy)pyridin-2-yl)-1,2,4-thiadiazol-5-amine

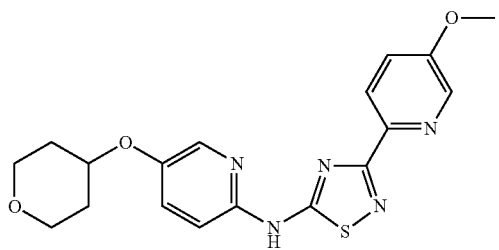 [SMILES: COc1ccc(-c2nsc(Nc3ccc(OC4CCOCC4)cn3)n2)nc1]

2-Chloro-5-((tetrahydro-2H-pyran-4-yl)oxy)pyridine

To a mixture of 6-chloropyridin-3-ol (2.00 g, 15.4 mmol) and tetrahydro-2H-pyran-4-ol (3.15 g, 30.88 mmol) in THF (60 mL) was added PPh₃ (8.10 g, 30.9 mmol) at 0° C. under nitrogen. Then diisopropyl azodicarboxylate (6.24 g, 30.9 mmol) was added into the above solution drop-wise at 0° C. The mixture was stirred at 25° C. for 20 h. The mixture was concentrated under reduced pressure. The residue was purified by column to give 2-chloro-5-((tetrahydro-2H-pyran-4-yl)oxy)pyridine (1.60 g, 7.49 mmol, 49% yield).

N-(2,4-Dimethoxybenzyl)-5-((tetrahydro-2H-pyran-4-yl)oxy)pyridin-2-amine

To a mixture of 2-chloro-5-((tetrahydro-2H-pyran-4-yl)oxy)pyridine (750 mg, 3.51 mmol), (2,4-dimethoxyphenyl)methanamine (1.17 g, 7.02 mmol), dicyclohexyl(2',6'-dimethoxy-[1,1'-biphenyl]-2-yl)phosphine (288 mg, 0.702 mmol) and sodium 2-methylpropan-2-olate (675 mg, 7.02 mmol) in toluene (70 mL) was added palladium (II) acetate (79 mg, 0.351 mmol) under nitrogen. The mixture was stirred at 100° C. for 16 h. The mixture was poured into H₂O (80 mL). The aqueous phase was extracted with EtOAc. The combined organic phases were washed with brine, dried over anhydrous sodium sulfate, filtered, and concentrated in vacuo. The residue was purified by column to give N-(2,4-dimethoxybenzyl)-5-((tetrahydro-2H-pyran-4-yl)oxy)pyridin-2-amine (1.63 g, 4.21 mmol, 60% yield, 89% purity).

5-((Tetrahydro-2H-pyran-4-yl)oxy)pyridin-2-amine

To a mixture of N-(2,4-dimethoxybenzyl)-5-((tetrahydro-2H-pyran-4-yl)oxy)pyridin-2-amine (1.43 g, 4.15 mmol) in DCM (2 mL) was added trifluoroacetic acid (3.08 g, 2 mL) dropwise at 0° C. The mixture was stirred at 25° C. for 1 h. The mixture was concentrated in vacuo. The residue was adjusted with saturated sodium bicarbonate (15 mL) to pH 8-9 and diluted with DCM (15 mL). Precipitate was formed. The mixture was filtered and the filter cake was washed with DCM. The organic phase was separated and the aqueous phase was extracted with DCM. The combined organic phases were washed with brine, dried over anhydrous sodium sulfate, filtered, and concentrated in vacuo. The residue was purified by column to give 5-((tetrahydro-2H-pyran-4-yl)oxy)pyridin-2-amine (800 mg, crude).

2-Isothiocyanato-5-((tetrahydro-2H-pyran-4-yl)oxy)pyridine

To a solution of di(1H-imidazol-1-yl)methanethione (433 mg, 2.43 mmol) in DMF (10 mL) was added a mixture of 5-((tetrahydro-2H-pyran-4-yl)oxy)pyridin-2-amine (430 mg, 2.21 mmol) in DMF (5 mL) drop-wise. The mixture was stirred at 25° C. for 3 h. 2-Isothiocyanato-5-((tetrahydro-2H-pyran-4-yl)oxy)pyridine (512 mg, 2.17 mmol, 98.19% yield) in DMF (15 mL) was obtained and used in the next step without purification.

5-Methoxy-N-((5-((tetrahydro-2H-pyran-4-yl)oxy)pyridin-2-yl)carbamothioyl)picolinimidamide To a mixture of 2-isothiocyanato-5-((tetrahydro-2H-pyran-4-yl)oxy)pyridine (520 mg, 2.20 mmol) in DMF (15 mL) were added 5-methoxypicolinimidamide (399 mg, 2.64 mmol) and DIPEA (1.42 g, 11.0 mmol). The mixture was stirred at 40° C. for 16 h. The mixture was poured into H₂O (30 mL). The aqueous phase was extracted with EtOAc. The combined organic phases were washed with H₂O. The combined aqueous phases were extracted with EtOAc. The combined organic phases were washed with brine, dried over anhydrous sodium sulfate, filtered, and concentrated in vacuo to give a mixture of 5-methoxy-N-((5-((tetrahydro-2H-pyran-4-yl)oxy)pyridin-2-yl)carbamothioyl)picolinimidamide and 3-(5-methoxypyridin-2-yl)-N-(5-((tetrahydro-2H-pyran-4-yl)oxy)pyridin-2-yl)-1,2,4-thiadiazol-5-amine (816 mg, crude).

3-(5-Methoxypyridin-2-yl)-N-(5-((tetrahydro-2H-pyran-4-yl)oxy)pyridin-2-yl)-1,2,4-thiadiazol-5-amine To a mixture of 5-methoxy-N-((5-((tetrahydro-2H-pyran-4-yl)oxy)pyridin-2-yl)carbamothioyl) picolinimidamide and 3-(5-methoxypyridin-2-yl)-N-(5-((tetrahydro-2H-pyran-4-yl)oxy)pyridin-2-yl)-1,2,4-thiadiazol-5-amine (766 mg, crude) in EtOH (50 mL) was added hydrogen peroxide (449 mg, 3.96 mmol) and iodine (101 mg, 0.396 mmol). The mixture was stirred at 25° C. for 3 h. The product was isolated and purified via standard methods to give 3-(5-methoxypyridin-2-yl)-N-(5-((tetrahydro-2H-pyran-4-yl)oxy)pyridin-2-yl)-1,2,4-thiadiazol-5-amine (357.45 mg, 0.916 mmol, 46% yield, 98.8% purity). LCMS (ESI): m/z 386.1 [M+1]⁺.

Example 18: N-(6-(5-((3-Methylpyridin-2-yl)amino)-1,2,4-thiadiazol-3-yl)pyridin-3-yl)acetamide

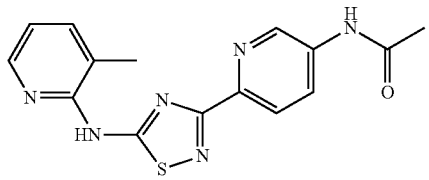 [SMILES: CC(=O)Nc1ccc(-c2nsc(Nc3ncccc3C)n2)nc1]

N-(6-Cyanopyridin-3-yl)acetamide

To a solution of 5-aminopicolinonitrile (1.00 g, 8.39 mmol) and TEA (2.55 g, 25.2 mmol) in DCM (50 mL) was added acetyl chloride (1.32 g, 16.8 mmol) at 0° C. The mixture was stirred at 20° C. for 16 h. The mixture was diluted with 100 mL of DCM and washed with brine. The organic phase was dried over anhydrous sodium sulfate, filtered, and concentrated under vacuum. The residue was purified by flash column to give the crude product. The crude product was purified by prep-TLC to give N-(6-cyanopyridin-3-yl)acetamide (400 mg, crude).

N-(6-Carbamimidoylpyridin-3-yl)acetamide Hydrochloride

To a solution of N-(6-cyanopyridin-3-yl)acetamide (400 mg, 2.48 mmol) in MeOH (10 mL) was added sodium methoxide (40 mg, 0.744 mmol). The mixture was stirred at 40° C. for 16 h. $NH_4Cl$ (172 mg, 3.22 mmol) was added to the mixture, and the mixture was stirred at 70° C. for 4 h. The mixture was concentrated, and the residue was diluted with 20 mL of EtOH, the resulting mixture was refluxed for 0.5 h. The mixture was filtered and the filtrate was concentrated. The residue was triturated with DCM (20 mL) to give N-(6-carbamimidoylpyridin-3-yl)acetamide hydrochloride (500 mg, crude).

N-(6-Carbamimidoylpyridin-3-yl)acetamide

To a solution of N-(6-carbamimidoylpyridin-3-yl)acetamide hydrochloride (400 mg, 1.86 mmol) in MeOH (20 mL) was added Amberlyst A 26 (2.5 g). The mixture was stirred at 25° C. for 2 h. The reaction mixture was filtered and the filtrate was concentrated to give N-(6-carbamimidoylpyridin-3-yl)acetamide (280 mg, crude).

N-(6-(N-((3-methylpyridin-2-yl)carbamothioyl)carbamimidoyl)pyridin-3-yl) acetamide To a solution of N-(6-carbamimidoylpyridin-3-yl)acetamide (280 mg, 1.57 mmol) and 2-isothiocyanato-3-methylpyridine (354 mg, 2.36 mmol) in DCM (15 mL) and acetone (15 mL) was added TEA (794 mg, 7.85 mmol). The mixture was stirred at 25° C. for 3 h. The mixture was concentrated. The residue was diluted with 30 mL of $H_2O$, the aqueous phase was extracted with EtOAc. The combined organic phases were dried over anhydrous sodium sulfate, filtered, and concentrated under vacuum. The residue was purified by prep-TLC to give N-(6-(N-((3-methylpyridin-2-yl)carbamothioyl)carbamimidoyl)pyridin-3-yl) acetamide (200 mg, crude).

N-(6-(5-((3-Methylpyridin-2-yl)amino)-1,2,4-thiadiazol-3-yl)pyridin-3-yl) acetamide To a solution of N-(6-(N-((3-methylpyridin-2-yl)carbamothioyl)carbamimidoyl) pyridin-3-yl)acetamide (200 mg, 0.609 mmol) in THF (10 mL) was added diisopropyl azodiformate (184 mg, 0.914 mmol). The mixture was stirred at 25° C. for 2 h. The product was isolated and purified via standard methods to give N-[6-[5-[(3-methyl-2-pyridyl)amino]-1,2,4-thiadiazol-3-yl]-3-pyridyl]acetamide (50.72 mg, 0.148 mmol, 24% yield, 95.5% purity). LCMS (ESI): m/z 327.1 $[M+1]^+$.

Example 19: 3-(5-Isopropoxypyridin-2-yl)-N-(3-methylpyridin-2-yl)-1,2,4-thiadiazol-5-amine

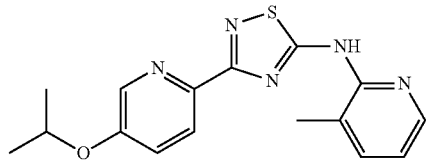 [SMILES: Cc1cccnc1Nc1nc(-c2ccc(OC(C)C)cn2)ns1]

5-Isopropoxypicolinonitrile

To a solution of propan-2-ol (1.18 g, 19.7 mmol, 1.49 mL) in N,N-dimethylformamide (40 mL) was added NaH (983 mg, 24.6 mmol, 60% purity) at 0° C. under nitrogen. The mixture was stirred at 25° C. for 30 min. Then 5-fluoropicolinonitrile (2.00 g, 16.4 mmol) was added to the reaction mixture at 0° C. under nitrogen. The mixture was stirred at 25° C. for 4 h. The mixture was poured into cold $H_2O$. The aqueous phase was extracted with EtOAc. The organic layers were washed with brine, dried over sodium sulfate, filtered, and concentrated to give a residue. The residue was purified by silica gel chromatography to give 5-isopropoxypicolinonitrile (2.10 g, crude).

5-Isopropoxypicolinimidamide

To a solution of 5-isopropoxypicolinonitrile (500 mg, 3.08 mmol) in MeOH (25 mL) was added sodium methanolate (16.6 mg, 308 μmol). The mixture was stirred at 25° C. for 8 h. $NH_4Cl$ (330 mg, 6.16 mmol) was added to the mixture and refluxed at 70° C. for 4 h. The mixture was concentrated under reduced pressure to give a residue. The residue was triturated with DCM (30 mL). The mixture was filtered, and the filter cake was dried to remove the solvent to give 5-isopropoxypicolinimidamide hydrochloride (800 mg, crude).

2-Isothiocyanato-3-methylpyridine

To a solution of thiophosgene (5.32 g, 46.2 mmol) in DCM (80 mL) was added a solution of 3-methylpyridin-2-amine (5 g, 46.2 mmol) in DCM (50 mL) at −5° C. under nitrogen atmosphere. The mixture was stirred at 25° C. for 3 h. Saturated sodium bicarbonate was added to the mixture. The mixture was extracted with DCM. The combined organic layers were dried over sodium sulfate, filtered, and concentrated under reduced pressure to give a residue. The residue was purified by silica gel column chromatography to give 2-isothiocyanato-3-methylpyridine (1.00 g, 6.66 mmol, 14% yield).

5-Isopropoxy-N-((3-methylpyridin-2-yl)carbamothioyl)picolinimidamide

To a solution of 2-isothiocyanato-3-methylpyridine (557 mg, 3.71 mmol) and TEA (3.75 g, 37.1 mmol, 5.14 mL) in DCM (15 mL) and acetone (15 mL) was added 5-isopropoxypicolinimidamide hydrochloride (800 mg, 3.71 mmol). The mixture was stirred at 25° C. for 20 h. The reaction mixture was concentrated under reduced pressure, diluted with H$_2$O, and extracted with EtOAc. The combined organic layers were washed with brine, dried over sodium sulfate, filtered, and concentrated under reduced pressure to give 5-isopropoxy-N-((3-methylpyridin-2-yl)carbamothioyl) picolinimidamide (350 mg, crude).

3-(5-Isopropoxypyridin-2-yl)-N-(3-methylpyridin-2-yl)-1,2,4-thiadiazol-5-amine To a solution of 5-isopropoxy-N-((3-methylpyridin-2-yl)carbamothioyl)picolinimidamide (350 mg, 1.06 mmol) in THF (10 mL) was added diisopropyl azodiformate (279 mg, 1.38 mmol). The mixture was stirred at 25° C. for 20 h. The product was isolated and purified via standard methods to give 3-(5-isopropoxypyridin-2-yl)-N-(3-methylpyridin-2-yl)-1,2,4-thiadiazol-5-amine (126 mg, 0.385 mmol, 36% yield, 99.3% purity). LCMS (ESI): m/z 328.2 [M+1]$^+$.

Example 20: N,N-Dimethyl-6-(5-((3-methylpyridin-2-yl)amino)-1,2,4-thiadiazol-3-yl) nicotinamide

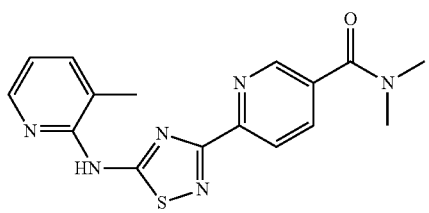 [SMILES: Cc1cccnc1Nc1nc(-c2ccc(C(=O)N(C)C)cn2)ns1]

6-Cyano-N,N-dimethylnicotinamide

To a solution of 6-cyanonicotinic acid (1.00 g, 6.75 mmol), N-methylmethanamine hydrochloride (605 mg, 7.43 mmol) and DIPEA (2.62 g, 20.3 mmol) in DCM (50 mL) was added HATU (3.08 g, 8.10 mmol) at 0° C. The mixture was stirred at 20° C. for 16 h. The mixture was concentrated and purified by flash column to give 6-cyano-N,N-dimethylnicotinamide (1.00 g, crude).

6-Carbamimidoyl-N,N-dimethylnicotinamide hydrochloride

To a solution of 6-cyano-N,N-dimethylnicotinamide (500 mg, 2.85 mmol) in MeOH (10 mL) was added sodium methoxide (31 mg, 0.571 mmol). The mixture was stirred at 20° C. for 16 h. NH$_4$Cl (183 mg, 3.42 mmol) was added to the solution, and the mixture was stirred at 70° C. for 4 h. The mixture was concentrated and triturated with DCM (20 mL) to give 6-carbamimidoyl-N,N-dimethylnicotinamide hydrochloride (500 mg, crude).

N,N-Dimethyl-6-(N-((3-methylpyridin-2-yl)carbamothioyl)carbamimidoyl)-nicotinamide To a solution of 2-isothiocyanato-3-methylpyridine (300 mg, 2.00 mmol) and TEA (2.02 g, 20.0 mmol) in DCM (20 mL) and acetone (20 mL) was added 6-carbamimidoyl-N,N-dimethylnicotinamide hydrochloride (457 mg, 2.00 mmol). The mixture was stirred at 20° C. for 16 h. The mixture was concentrated and purified by prep-TLC to give N,N-dimethyl-6-(N-((3-methylpyridin-2-yl)carbamothioyl)carbamimidoyl)nicotinamide (300 mg, crude).

N,N-Dimethyl-6-(5-((3-methylpyridin-2-yl)amino)-1,2,4-thiadiazol-3-yl) nicotinamide To a solution of N,N-dimethyl-6-(N-((3-methylpyridin-2-yl)carbamothioyl) carbamimidoyl)nicotinamide (300 mg, 0.876 mmol) in THF (15 mL) was added diisopropyl azodiformate (177 mg, 0.876 mmol). The mixture was stirred at 20° C. for 2 h. The mixture was concentrated. The product was isolated and purified via standard methods to give N,N-dimethyl-6-(5-((3-methylpyridin-2-yl)amino)-1,2,4-thiadiazol-3-yl)nicotinamide (158.80 mg, 0.462 mmol, 52% yield, 99% purity). LCMS (ESI): m/z 341.1 [M+1]$^+$.

Example 21: N$^3$-methyl-N$^2$-(3-(4-methylpyridin-2-yl)-1,2,4-thiadiazol-5-yl)pyridine-2,3-diamine

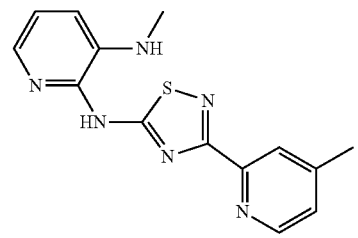 [SMILES: CNc1cccnc1Nc1nc(-c2cc(C)ccn2)ns1]

tert-butyl-(2-Nitropyridin-3-yl)carbamate

To a solution of 2-nitropyridin-3-amine (2.00 g, 14.4 mmol) in TH (30 mL) was added 1,1,1-trimethyl-n-(trimethylsilyl)-silanamin sodium (1 M, 21.6 mL) at 0° C. The mixture was stirred at 20° C. for 1 h. Then di-tert-butyl dicarbonate (3.45 g, 15.8 mmol) in THF (20 mL) was added at 0° C. The mixture was stirred at 25° C. for 16 h. The mixture was poured into cold H$_2$O. The aqueous phase was extracted with EtOAc. The combined organic phases were washed with brine, dried over anhydrous sodium sulfate, filtered, and concentrated under vacuum. The residue was purified by silica gel chromatography to give tert-butyl (2-nitropyridin-3-yl) carbamate (2.00 g, 8.36 mmol, 58% yield).

tert-butyl-methyl-(2-nitropyridin-3-yl)carbamate

To a solution of tert-butyl (2-nitropyridin-3-yl) carbamate (2.00 g, 8.36 mmol) in DMF (30 mL) was added NaH (501 mg, 12.5 mmol, 60% purity) at 0° C. The mixture was stirred at 25° C. for 0.5 h. Iodomethane (1.54 g, 10.9 mmol) was added at 0° C., the mixture was stirred at 25° C. for 2 h. The residue was poured into cold H$_2$O. The aqueous phase was extracted with EtOAc (300 mL). The organic phase was washed with brine, dried over anhydrous sodium sulfate, filtered, and concentrated under vacuum. The residue was purified by silica gel chromatography to give tert-butyl methyl-(2-nitropyridin-3-yl)carbamate (1.80 g, crude).

tert-butyl-(2-aminopyridin-3-yl)(methyl)carbamate

To a solution of tert-butyl methyl-(2-nitropyridin-3-yl) carbamate (1.80 g, 7.11 mmol) in MeOH (40 mL) was added wet Pd/C (300 mg). The mixture was stirred at 25° C. for 1 h under H₂ (15 psi). The reaction mixture was filtered and the filtrate was concentrated to give tert-butyl (2-aminopyridin-3-yl)-(methyl)-carbamate (1.40 g, 6.27 mmol, 88% yield).

tert-butyl-(2-isothiocyanatopyridin-3-yl)(methyl) carbamate

To a solution of thiocarbonyl dichloride (1.03 g, 8.96 mmol) in DCM (20 mL) was added a mixture of tert-butyl (2-aminopyridin-3-yl)(methyl)carbamate (1.00 g, 4.48 mmol) in DCM (20 mL) at −5° C. The mixture was stirred at 25° C. for 2 h. The mixture was diluted with 50 mL of DCM. The organic phase was washed with sodium bicarbonate, dried over anhydrous sodium sulfate, filtered, and concentrated under vacuum. The residue was purified by silica gel chromatography to give tert-butyl (2-isothiocyanatopyridin-3-yl)-(methyl)carbamate (700 mg, crude).

tert-butyl-(2-(3-(imino(4-methylpyridin-2-yl)methyl) thioureido)pyridin-3-yl)(methyl)carbamate To a solution of tert-butyl (2-isothiocyanatopyridin-3-yl)-(methyl)-carbamate (400 mg, 1.51 mmol) and TEA (1.53 g, 15.1 mmol) in DCM (20 mL) and acetone (20 mL) was added 4-methylpicolinimidamide hydrochloride (259 mg, 1.51 mmol). The mixture was stirred at 25° C. for 16 h. The mixture was concentrated and the residue was diluted with 30 mL of H₂O. The aqueous phase was extracted with DCM. The combined organic phases were dried over anhydrous sodium sulfate, filtered, and concentrated under vacuum. The residue was purified by prep-TLC to give tert-butyl (2-(3-(imino-(4-methylpyridin-2-yl)methyl)-thioureido) pyridin-3-yl)(methyl)carbamate (400 mg, crude).

tert-butyl-methyl-(2-((3-(4-methylpyridin-2-yl)-1,2, 4-thiadiazol-5-yl)amino)pyridin-3-yl)carbamate To a solution of tert-butyl (2-(3-(imino-(4-methylpyridin-2-yl)methyl)thioureido)pyridin-3-yl)(methyl) carbamate (400 mg, 0.999 mmol) in THF (2 mL) was added diisopropyl azodiformate (202 mg, 0.999 mmol). The mixture was stirred at 25° C. for 2 h. The mixture was diluted with 100 mL of EtOAc. The organic phase was washed with brine, dried over anhydrous sodium sulfate, filtered, and concentrated under vacuum to give tert-butyl methyl(2-((3-(4-methylpyridin-2-yl)-1,2,4-thiadiazol-5-yl)amino)pyridin-3-yl)carbamate (500 mg, crude).

N³-methyl-N²-(3-(4-methylpyridin-2-yl)-1,2,4-thiadiazol-5-yl)pyridine-2,3-diamine To a solution of tert-butyl methyl-(2-((3-(4-methylpyridin-2-yl)-1,2,4-thiadiazol-5-yl)amino)pyridin-3-yl)carbamate (400 mg, 1.00 mmol) in DCM (6 mL) was added trifluoroacetic acid (3 mL) at 0° C. The mixture was stirred at 25° C. for 2 h and concentrated at 25° C. The product was isolated and purified via standard methods to give N³-methyl-N²-(3-(4-methylpyridin-2-yl)-1,2,4-thiadiazol-5-yl)pyridine-2,3-diamine trifluoroacetate (50.10 mg, 0.116 mmol, 12% yield, 95.1% purity). LCMS (ESI): m/z 299.3 [M+1]⁺.

Example 22: N-(3-Methoxypyridin-2-yl)-3-(4-methylpyridin-2-yl)-1,2,4-thiadiazol-5-amine

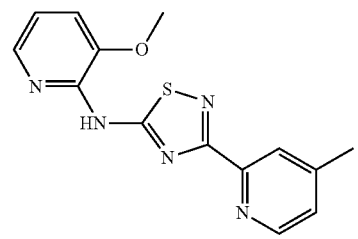 [SMILES: COc1cccnc1Nc1nc(-c2cc(C)ccn2)ns1]

2-Iothiocyanato-3-methoxypyridine

To a solution of thiocarbonyl dichloride (1.11 g, 9.66 mmol) in DCM (10 mL) was added a solution of 3-methoxypyridin-2-amine (600 mg, 4.83 mmol) in DCM (5 mL) dropwise at −5° C. under N₂. The mixture was stirred at 25° C. for 3 h under N₂. Saturated sodium bicarbonate solution was added to the mixture, the aqueous phase was extracted with DCM. The combined organic layers were dried over sodium sulfate, filtered, and concentrated under reduced pressure to give a residue. The residue was purified by silica gel chromatography to give 2-isothiocyanato-3-methoxypyridine (160 mg, 0.97 mmol, 20% yield).

N-((3-Methoxypyridin-2-yl)carbamothioyl)-4-methylpicolinimidamide

To a solution of 2-isothiocyanato-3-methoxy-pyridine (160 mg, 0.963 mmol) in DCM (15 mL) and acetone (15 mL) was added TEA (2.19 g, 21.64 mmol) and 4-methylpyridine-2-carboxamidine hydrochloride (215 mg, 1.25 mmol). The mixture was stirred at 25° C. for 16 h. The reaction mixture was quenched with H₂O (30 mL). The aqueous phase was extracted with EtOAc. The combined organic layers were dried over anhydrous sodium sulfate, filtered, and concentrated under reduce pressure to give a residue. The residue was purified by prep-TLC (SiO₂, petroleum ether/EtOAc=1/1) to give N-((3-methoxypyridin-2-yl) carbamothioyl)-4-methylpicolinimidamide (180 mg, crude).

N-(3-Methoxypyridin-2-yl)-3-(4-methylpyridin-2-yl)-1,2,4-thiadiazol-5-amine

To a solution of N-((3-methoxypyridin-2-yl) carbamothioyl)-4-methyl picolinimidamide (180 mg, 0.597 mmol) in THF (10 mL) was added diisopropyl azodiformate (121 mg, 0.597 mmol). The mixture was stirred at 25° C. for 2 h. The product was isolated and purified via standard methods to give N-(3-methoxy-2-pyridyl)-3-(4-methyl-2-pyridyl)-1,2,4-thiadiazol-5-amine (49.8 mg, 0.165 mmol, 27% yield, 99% purity). LCMS (ESI): m/z 300.1 [M+1]⁺.

Example 23: N-(3-Fluoropyridin-2-yl)-3-(4-methylpyridin-2-yl)-1,2,4-thiadiazol-5-amine

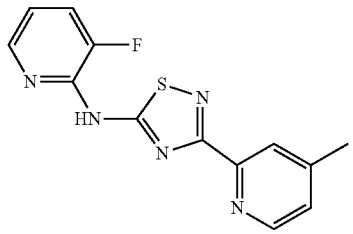 [SMILES: Cc1ccnc(-c2nsc(Nc3ncccc3F)n2)c1]

3-Fluoro-2-isothiocyanatopyridine

To a solution of 3-fluoropyridin-2-amine (2.00 g, 17.8 mmol) in DCM (40 mL) was added DIPEA (4.61 g, 35.7 mmol) at 25° C. Thiophosgene (2.05 g, 17.8 mmol) was added slowly into the reaction mixture at 0° C. The reaction mixture was stirred at 25° C. for 16 h. The reaction mixture was concentrated under reduced pressure to give a residue. The residue was purified by silica gel chromatography to give 3-fluoro-2-isothiocyanatopyridine (340 mg, crude).

4-Methylpicolinimidamide Hydrochloride

To a solution of 4-methylpicolinonitrile (1.00 g, 8.46 mmol) in MeOH (20 mL) was added sodium methanolate (46 mg, 0.846 mmol). The mixture was stirred at 25° C. for 20 h. $NH_4Cl$ (498 mg, 9.31 mmol) was added to the mixture. The mixture was stirred at 70° C. for 4 h. The mixture was concentrated under reduced pressure to give a residue. The residue was refluxed for 30 min in EtOH (30 mL). The hot solution was filtered and the cake washed with EtOH. The filtrate was evaporated in vacuo to give 4-methylpicolinimidamide hydrochloride (1.30 g, crude).

N-((3-Fluoropyridin-2-yl)carbamothioyl)-4-methylpicolinimidamide

To a solution of 4-methylpicolinimidamide hydrochloride (379 mg, 2.21 mmol) and TEA (670 mg, 6.62 mmol) in DCM (10 mL) and acetone (10 mL) was added 3-fluoro-2-isothiocyanatopyridine (340 mg, 2.21 mmol). The mixture was stirred at 25° C. for 20 h. The reaction mixture was concentrated under reduced pressure to give a residue. The residue was diluted with $H_2O$ and extracted with EtOAc. The combined organic layers were washed with brine, dried over sodium sulfate, filtered, and concentrated under reduced pressure to give a residue. The residue was purified by silica gel chromatography to give N-((3-fluoropyridin-2-yl)carbamothioyl)-4-methylpicolinimidamide (200 mg, crude).

N-(3-Fluoropyridin-2-yl)-3-(4-methylpyridin-2-yl)-1,2,4-thiadiazol-5-amine

To a solution of 1-(3-fluoro-2-pyridyl)-3-(4-methylpyridine-2-carboximidoyl)thiourea (100 mg, 346 µmol) in THF (8 mL) was added diisopropyl azodiformate (60 mg, 0.297 mmol). The mixture was stirred at 25° C. for 20 h. The product was isolated and purified via standard methods to give N-(3-fluoro-2-pyridyl)-3-(4-methyl-2-pyridyl)-1,2,4-thiadiazol-5-amine (35.47 mg, 0.104 mmol, 30% yield, 98.5% purity). LCMS (ESI): m/z 288.1 $[M+1]^+$.

Example 24: N-(3-(5-Isopropoxypyridin-2-yl)-1H-1,2,4-triazol-5-yl)-3-methylpyridin-2-amine

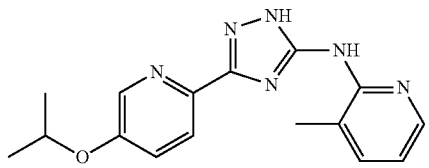

1-(3-Methylpyridin-2-yl)thiourea

To a solution of 2-isothiocyanato-3-methyl-pyridine (1.50 g, 8.99 mmol) in DCM (15 mL) was added ammonium hydroxide (3.78 g, 26.9 mmol, 25% purity). The mixture was stirred at 30° C. for 1 h. The mixture was concentrated in vacuo. The residue was diluted with $H_2O$ and the aqueous phase was extracted with DCM. The combined organic phases were dried over anhydrous sodium sulfate, filtered, and concentrated under vacuum to give 1-(3-methylpyridin-2-yl)thiourea (1.00 g, 4.73 mmol, 52.6% yield, 79.1% purity).

Methyl (3-methylpyridin-2-yl)carbamimidothioate

To a solution of 1-(3-methylpyridin-2-yl)thiourea (1.10 g, 5.20 mmol) in ACN (10 mL) was added iodomethane (960 mg, 6.76 mmol). The mixture was stirred at 40° C. for 16 h. The mixture was concentrated. The residue was diluted with $H_2O$, and the aqueous phase was adjusted to pH of 8 with saturated sodium bicarbonate. The aqueous phase was extracted with EtOAc and the combined organic phases were dried over anhydrous sodium sulfate, filtered, and concentrated under vacuum. The residue was purified by column chromatography to give methyl (3-methylpyridin-2-yl) carbamimidothioate (450 mg, 2.13 mmol, 41% yield, 85.7% purity).

N-(3-(5-Isopropoxypyridin-2-yl)-1H-1,2,4-triazol-5-yl)-3-methylpyridin-2-amine

To a solution of methyl (3-methylpyridin-2-yl)carbamimidothioate (250 mg, 1.38 mmol) in pyridine (5 mL) was added 5-isopropoxypyridine-2-carbohydrazide (269 mg, 1.38 mmol). The mixture was stirred at 120° C. for 16 h. The product was isolated and purified via standard methods to give N-(3-(5-isopropoxy pyridin-2-yl)-1H-1,2,4-triazol-5-yl)-3-methylpyridin-2-amine (127.08 mg, 0.400 mmol, 29% yield, 98.8% purity). LCMS (ESI): m/z 311.3 $[M+1]^+$.

Example 25: 3-Methyl-N-(3-(5-((1-methylpiperidin-4-yl)oxy)pyridin-2-yl)-1H-1,2,4-triazol-5-yl) pyridin-2-amine

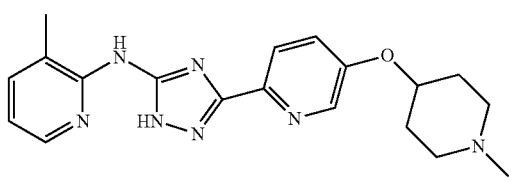 [SMILES: Cc1cccnc1Nc1nc(-c2ccc(OC3CCN(C)CC3)cn2)n[nH]1]

5-((1-Methylpiperidin-4-yl)oxy)picolinic Acid

To a solution of 5-((1-methylpiperidin-4-yl)oxy)picolinonitrile (4.70 g, 21.6 mmol) in EtOH (80 mL) and H₂O (20 mL) was added sodium hydroxide (6.06 g, 151.41 mmol). The mixture was stirred at 80° C. for 16 h. The mixture was concentrated and the residue was diluted with 50 mL of H₂O. The aqueous phase was adjusted to pH of 6 with 6 N HCl and the aqueous phase was concentrated to give a white solid. The solid was triturated with MeOH (100 mL). The filtrate was concentrated to give 5-((1-methylpiperidin-4-yl)oxy)picolinic acid (10.0 g, crude).

Methyl 5-((1-methylpiperidin-4-yl)oxy)picolinate

To a solution of 5-((1-methylpiperidin-4-yl)oxy)picolinic acid (10.0 g, 42.3 mmol) in MeOH (100 mL) was added thionyl chloride (15.1 g, 127 mmol) at 10° C. The mixture was stirred at 70° C. for 3 h. The mixture was concentrated and the residue was diluted with 50 mL of H₂O. The aqueous phase was adjusted to pH of 8 with saturated sodium bicarbonate and extracted with EtOAc. The combined organic phases were dried over anhydrous sodium sulfate, filtered, and concentrated in vacuum to give methyl 5-((1-methylpiperidin-4-yl)oxy)picolinate (500 mg, 1.97 mmol, 5% yield, 98.4% purity).

5-((1-Methylpiperidin-4-yl)oxy)picolinohydrazide

To a solution of methyl methyl 5-((1-methylpiperidin-4-yl)oxy)picolinate (500 mg, 2.00 mmol) in MeOH (5 mL) was added hydrazine hydrate (150 mg, 3.00 mmol). The mixture was stirred at 70° C. for 3 h. Hydrazine hydrate (100 mg, 2.00 mmol) was added to the above mixture. The mixture was stirred at 70° C. for 1 h. The reaction was concentrated in vacuo to give 5-((1-methylpiperidin-4-yl)oxy)picolinohydrazide (500 mg, 2.00 mmol, 99.8% yield).

3-Methyl-N-(3-(5-((1-methylpiperidin-4-yl)oxy)pyridin-2-yl)-1H-1,2,4-triazol-5-yl)pyridin-2-amine To a solution of 2-methyl-N-(3-methyl-2-pyridyl)isothiourea (270 mg, 1.27 mmol) in pyridine (5 mL) was added 5-[(1-methyl-4-piperidyl)oxy]pyridine-2-carbohydrazide (317 mg, 1.27 mmol). The mixture was stirred at 120° C. for 16 h. The product was isolated and purified via standard methods to give 3-methyl-N-(3-(5-((1-methylpiperidin-4-yl)oxy)pyridin-2-yl)-1H-1,2,4-triazol-5-yl)pyridin-2-amine (53.73 mg, 0.125 mmol, 10% yield, 95.6% purity). LCMS (ESI): m/z 366.1 [M+1]⁺.

Example 26: N-(3-(5-Isopropoxypyridin-2-yl)-1H-1,2,4-triazol-5-yl)-3-(trifluoromethyl) pyridine-2-amine

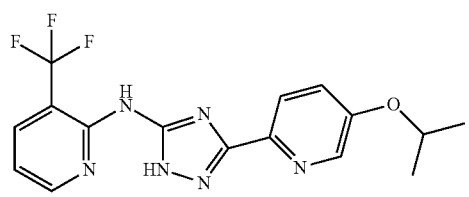 [SMILES: CC(C)Oc1ccc(-c2n[nH]c(Nc3ncccc3C(F)(F)F)n2)nc1]

Methyl 5-hydroxypicolinate

To a mixture of 5-hydroxypicolinic acid (16.00 g, 115 mmol) and DMF (84 mg, 1.15 mmol) in MeOH (150 mL) was added thionyl chloride (41.05 g, 345.06 mmol) at 10° C. The mixture was stirred at 80° C. for 4 h. Thionyl chloride (6.84 g, 57.51 mmol) was added to the above mixture and stirred at 80° C. for 2 h. The mixture was concentrated and the residue was diluted with H₂O. The aqueous phase was adjusted to pH of 8 with saturated sodium bicarbonate. A solid formed, the solid was collected and dried in vacuo to give methyl 5-hydroxypicolinate (12.80 g, 83.6 mmol, 73% yield).

Methyl 5-isopropoxypicolinate

To a mixture of methyl 5-hydroxypicolinate (6.00 g, 39.2 mmol) in DMF (20 mL) and ACN (100 mL) were added potassium carbonate (16.25 g, 117.54 mmol) and 2-bromopropane (14.46 g, 117.54 mmol). The mixture was stirred at 80° C. for 16 h under N₂. The mixture was diluted with ACN (100 mL). The mixture was filtered and the filtrate was concentrated to give methyl 5-isopropoxypicolinate (7.10 g, 36.4 mmol, 93% yield).

5-Isopropoxypicolinohydrazide

To a solution of methyl 5-isopropoxypicolinate (9.00 g, 46.1 mmol) in MeOH (60 mL) was added hydrazine hydrate (3.53 g, 69.2 mmol, 98% purity). The mixture was stirred 70° C. at for 1 h. The reaction was concentrated in vacuo to give 5-isopropoxypicolinohydrazide (9.00 g, 45.5 mmol, 99% yield, 98.7% purity).

2-(5-Isopropoxypicolinoyl)hydrazinecarboximidamide

The mixture of 5-isopropoxypicolinohydrazide (8.00 g, 40.5 mmol) and 2-methylisothiourea; sulfuric acid (11.3 g, 40.5 mmol) in H₂O (80 mL) was stirred at 100° C. for 16 h. The mixture was concentrated to give a solid. The solid was triturated with EtOH (30 mL) to give 2-(5-isopropoxypicolinoyl)hydrazinecarboximidamide (9.60 g, 38.2 mmol, 94% yield, 94.4% purity).

3-(5-isopropoxypyridin-2-yl)-1H-1,2,4-triazol-5-amine

To a solution of sodium hydroxide (3.06 g, 76.4 mmol) in H₂O (96 mL) was added 2-(5-isopropoxypicolinoyl)-hydrazinecarboximidamide (9.60 g, 38.20 mmol). The mixture was stirred at 100° C. for 6 h. and then neutralized with hydrogen chloride (6 N) to a pH of 6-7. The mixture was filtered and the filter cake was washed with EtOH (0.5 mL) to give 3-(5-isopropoxypyridin-2-yl)-1H-1,2,4-triazol-5-amine (5.60 g, 25.3 mmol, 66% yield, 99.0% purity).

3-(5-Isopropoxypyridin-2-yl)-1-((2-(trimethylsilyl)ethoxy)methyl)-1H-1,2,4-triazol-5-amine To a solution of 3-(5-isopropoxypyridin-2-yl)-1H-1,2,4-triazol-5-amine (500 mg, 2.28 mmol) in DMF (20 mL) was added NaH (228 mg, 5.70 mmol, 60% purity) at 0° C. under N₂. The mixture was stirred at 10° C. for 1 h. (2-(Chloromethoxy)ethyl)trimethylsilane (380 mg, 2.28 mmol) was then added at −20° C. The mixture was stirred at 0° C. for 1 h. The mixture was quenched with H₂O and the resultant mixture was extracted with EtOAc and the combined organic phases were dried over sodium sulfate, filtered, and concentrated under reduced pressure to give a residue (1.0 g). The residue (0.8 g) was purified by prep-HPLC to give 3-(5-isopropoxypyridin-2-yl)-1-((2-(trimethylsilyl)ethoxy)methyl)-1H-1,2,4-triazol-5-amine (90 mg, 0.260 mmol, 11% yield).

N-(3-(5-Isopropoxypyridin-2-yl)-1-((2-(trimethylsilyl)ethoxy)methyl)-1H-1,2,4-triazol-5-yl)-3-(trifluoromethyl)pyridin-2-amine To a solution of 3-(5-isopropoxypyridin-2-yl)-1-((2-(trimethylsilyl)ethoxy)methyl)-1H-1,2,4-triazol-5-amine in DMF (2 mL) was added NaH (41 mg, 1.03 mmol, 60% purity) at 0° C. The mixture was stirred at 25° C. for 0.5 h. Then a solution of 2-fluoro-3-(trifluoromethyl)pyridine (51 mg, 0.31 mmol) in DMF (1 mL) was added at 0° C. The mixture was stirred at 25° C. for 2 h and the residue was poured into cold $H_2O$. The aqueous phase was extracted with EtOAc. The combined organic phases were washed with brine, dried over anhydrous sodium sulfate, filtered, and concentrated under vacuum to give N-(3-(5-isopropoxypyridin-2-yl)-1-((2-(trimethylsilyl)ethoxy)methyl)-1H-1,2,4-triazol-5-yl)-3-(trifluoromethyl)pyridin-2-amine (130 mg, crude).

N-(3-(5-Isopropoxypyridin-2-yl)-1H-1,2,4-triazol-5-yl)-3-(trifluoromethyl) pyridine-2-amine To a solution of N-(3-(5-isopropoxypyridin-2-yl)-1-((2-(trimethylsilyl)ethoxy) methyl)-1H-1,2,4-triazol-5-yl)-3-(trifluoromethyl)pyridin-2-amine (130 mg, 0.260 mmol) in EtOAc (3 mL) was added HCl/EtOAc (4 M, 6.6 mL). The mixture was stirred at 25° C. for 1 h. The product was isolated and purified via standard methods to give N-(3-(5-isopropoxypyridin-2-yl)-1H-1,2,4-triazol-5-yl)-3-(trifluoromethyl)pyridine-2-amine (59.45 mg, 0.161 mmol, 61% yield, 98.7% purity). LCMS (ESI): m/z 365.1 $[M+1]^+$.

Example 27: 3-(3-Fluoropyridin-2-yl)-N-(4-(trifluoromethyl)pyridin-2-yl)-1,2,4-oxadiazol-5 amine

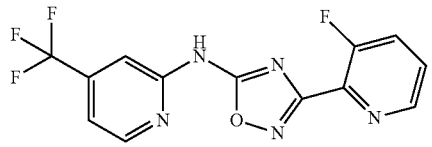 [SMILES: Fc1cccnc1-c1noc(Nc2cc(C(F)(F)F)ccn2)n1]

3-Fluoro-N-hydroxypicolinimidamide

To a solution of 3-fluoropicolinonitrile (1.0 g, 8.19 mmol) in EtOH (20 mL) were added hydroxylamine hydrochloride (1.14 g, 16.4 mmol) and TEA (1.66 g, 16.4 mmol, 2.27 mL). The mixture was stirred at 70° C. for 16 h. The mixture was concentrated under reduced pressure to give a residue. The residue was diluted with EtOAc (60 mL) and washed with $H_2O$ (10 mL). The aqueous phase was extracted with EtOAc. The combined organic layers were dried over anhydrous sodium sulfate, filtered, and concentrated to give 3-fluoro-N-hydroxypicolinimidamide (1.20 g, crude).

3-(3-Fluoropyridin-2-yl)-5-(trichloromethyl)-1,2,4-oxadiazole

To a solution of 3-fluoro-N-hydroxypicolinimidamide (1.20 g, 7.74 mmol) in toluene (50 mL) was added 2,2,2-trichloroacetic anhydride (4.78 g, 15.5 mmol). The mixture was stirred at 110° C. for 4 h. The mixture was concentrated under reduced pressure to give a residue. The residue was diluted with EtOAc (60 mL), washed with sodium bicarbonate (20 mL). The aqueous phase was extracted with EtOAc. The combined organic layers were dried over anhydrous sodium sulfate, filtered, and concentrated to give a crude product. The crude product was purified by silica gel chromatography to give 3-(3-fluoropyridin-2-yl)-5-(trichloromethyl)-1,2,4-oxadiazole (1.70 g, 5.84 mmol, 75% yield, 97% purity).

3-(3-Fluoropyridin-2-yl)-N-(4-(trifluoromethyl)pyridin-2-yl)-1,2,4-oxadiazol-5-amine To a solution of 4-(trifluoromethyl)pyridin-2-amine (460 mg, 2.83 mmol) in THF (20 mL) was added NaH (211 mg, 60% purity) slowly at 0° C. The mixture was stirred at 25° C. for 0.5 h under nitrogen. Then a solution of 3-(3-fluoropyridin-2-yl)-5-(trichloromethyl)-1,2,4-oxadiazole (1.0 g, 3.54 mmol) in THF (8 mL) was added to the reaction mixture at 0° C. The reaction mixture was stirred at 25° C. for 2 h under nitrogen. The product was isolated and purified via standard methods to give 3-(3-fluoropyridin-2-yl)-N-(4-(trifluoromethyl)pyridin-2-yl)-1,2,4-oxadiazol-5-amine (132.72 mg, 0.406 mmol, 12% yield, 99.45% purity). LCMS (ESI): m/z 326.1 $[M+1]^+$.

Example 28: 3-(3-Methylpyridin-2-yl)-N-(5-(pyrrolidin-1-yl)pyridin-2-yl)-1,2,4-oxadiazol-5-amine

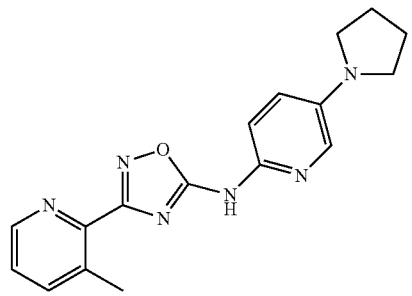 [SMILES: Cc1cccnc1-c1noc(Nc2ccc(N3CCCC3)cn2)n1]

N-Hydroxy-3-methylpicolinimidamide

To a solution of 3-methylpyridine-2-carbonitrile (1.00 g, 8.46 mmol) and TEA (1.71 g, 16.92 mmol) in EtOH (15 mL) was added $NH_2OH \cdot HCl$ (559 mg, 16.92 mmol). The mixture was stirred at 80° C. for 16 h. The reaction mixture was concentrated under reduced pressure to give a residue. The residue was diluted with $H_2O$ (20 mL) and the aqueous layer was extracted with EtOAc. The combined organic layers were dried over anhydrous sodium sulfate, filtered, and concentrated under reduced pressure to give N-hydroxy-3-methyl-pyridine-2-carboxamidine (1.20 g, 7.86 mmol, 93% yield, 99% purity).

3-(3-Methylpyridin-2-yl)-5-(trichloromethyl)-1,2,4-oxadiazole

To a solution of N-hydroxy-3-methyl-pyridine-2-carboxamidine (1.20 g, 7.94 mmol) in toluene (30 mL) was added trichloroacetic anhydride (4.90 g, 15.88 mmol). The mixture was stirred at 110° C. for 3 h under $N_2$. The reaction mixture was concentrated under reduced pressure to give a residue. The residue was diluted with H₂O and extracted with EtOAc. The combined organic phases were washed with saturated sodium bicarbonate, dried over anhydrous sodium sulfate, filtered, and concentrated under reduced pressure to give a residue. The residue was purified by column chromatography to give 3-(3-methyl-2-pyridyl)-5-(trichloromethyl)-1,2,4-oxadiazole (2.10 g, 7.22 mmol, 91% yield, 95.8% purity).

2-Nitro-5-(pyrrolidin-1-yl)pyridine

A solution of 5-bromo-2-nitro-pyridine (500 mg, 2.46 mmol) and pyrrolidine (8.76 g, 123.16 mmol) were combined in a microwave tube. The sealed tube was heated at 120° C. for 1 h under microwave. The residue was poured into H₂O. The aqueous phase was extracted with EtOAc. The organic phase was dried over anhydrous sodium sulfate, filtered, and concentrated under vacuum. The residue was triturated with petroleum ether:EtOAc (1:1, 40 mL) and filtered, and the filter cake was dried to give 2-nitro-5-pyrrolidin-1-yl-pyridine (2.80 g, 13.8 mmol, 56% yield, 95.1% purity).

5-(Pyrrolidin-1-yl)pyridin-2-amine

To a solution of 2-nitro-5-pyrrolidin-1-yl-pyridine (2.80 g, 14.49 mmol) in MeOH (30 mL) was added Pd/C (560 mg, 10% purity). The suspension was degassed under vacuum and purged with H₂ several times. The mixture was stirred under H₂ (15 psi) at 25° C. for 2 h. The reaction mixture was filtered and the filtrate was concentrated. The residue was dried by lyophilization to give 5-pyrrolidin-1-ylpyridin-2-amine (1.70 g, 8.56 mmol, 59% yield, 82.2% purity).

3-(3-Methylpyridin-2-yl)-N-(5-(pyrrolidin-1-yl)pyridin-2-yl)-1,2,4-oxadiazol-5-amine To a solution of 5-pyrrolidin-1-ylpyridin-2-amine (293 mg, 1.80 mmol) in THF (10 mL) was added n-BuLi (2.5 M, 0.72 mL) at −70° C. under N₂. The mixture was stirred at −70° C. for 1 h. A solution of 3-(3-methyl-2-pyridyl)-5-(trichloromethyl)-1,2,4-oxadiazole (500 mg, 1.80 mmol) in THF (5 mL) was added into above mixture. The reaction was stirred at −20° C. for 2 h. The product was isolated and purified via standard methods to give 3-(3-methyl-2-pyridyl)-N-(5-pyrrolidin-1-yl-2-pyridyl)-1,2,4-oxadiazol-5-amine (139.78 mg, 0.430 mmol, 24% yield, 99.1% purity). LCMS (ESI): m/z 323.3 [M+1]⁺

Example 29: 3-(5-Methoxypyridin-2-yl)-N-(4-((tetrahydro-2H-pyran-4-yl)oxy)pyridin-2-yl)-1,2,4-oxadiazol-5-amine

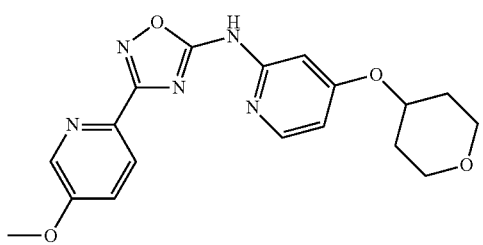 [SMILES: COc1ccc(-c2noc(Nc3cc(OC4CCOCC4)ccn3)n2)nc1]

5-Methoxypicolinonitrile

To a mixture of 5-hydroxypicolinonitrile (1.00 g, 8.33 mmol) and potassium carbonate (2.30 g, 16.7 mmol) in DMF (15 mL) was added iodomethane (1.77 g, 12.5 mmol) at 25° C. The mixture was stirred at 25° C. for 24 h. The mixture was poured into H₂O and the aqueous phase was extracted with EtOAc. The combined organic phases were washed with brine, dried over anhydrous sodium sulfate, filtered, and concentrated under vacuum to give a residue. The residue was purified by silica gel chromatography to give 5-methoxypicolinonitrile (750 mg, 5.54 mmol, 66% yield, 99% purity).

N-Hydroxy-5-methoxypicolinimidamide

To a solution of 5-methoxypicolinonitrile (750 mg, 5.54 mmol) in EtOH (15 mL) were added NH₂OH.HCl (769 mg, 11.1 mmol) and TEA (1.12 g, 11.1 mmol). The mixture was stirred at 70° C. for 4 h. The mixture was concentrated under reduced pressure to give a residue. The residue was diluted with EtOAc (30 mL). The organic layer was washed with H₂O (30 mL). The aqueous phase was extracted with EtOAc (30 mL). The combined organic layers were dried over anhydrous sodium sulfate, filtered, and concentrated to give N-hydroxy-5-methoxypicolinimidamide (900 mg, 5.38 mmol, 97% yield, 99% purity).

3-(5-Methoxypyridin-2-yl)-5-(trichloromethyl)-1,2,4-oxadiazole

To a solution of N-hydroxy-5-methoxypicolinimidamide (900 mg, 5.38 mmol) in toluene (30 mL) was added trichloroacetic anhydride (3.32 g, 10.8 mmol). The mixture was stirred at 110° C. for 3 h. The mixture was concentrated under reduce pressure to give a residue. The residue was diluted with EtOAc (50 mL). The organic layer was washed with sodium bicarbonate (20 mL). The aqueous phase was extracted with EtOAc. The combined organic layers were wash with brine, dried over anhydrous sodium sulfate, filtered, and concentrated to give a residue. The residue was purified by silica gel chromatography to give 3-(5-methoxypyridin-2-yl)-5-(trichloromethyl)-1,2,4-oxadiazole (1.50 g, 5.01 mmol, 93% yield, 98% purity).

3-(5-Methoxypyridin-2-yl)-N-(4-((tetrahydro-2H-pyran-4-yl)oxy)pyridin-2-yl)-1,2,4-oxadiazol-5-amine To a solution of 4-((tetrahydro-2H-pyran-4-yl)oxy)pyridin-2-amine (396 mg, 2.04 mmol) in THF (15 mL) was added NaH (73 mg, 3.06 mmol) slowly at 0° C. The mixture was stirred at 25° C. for 0.5 h under N₂. Then a solution of 3-(5-methoxypyridin-2-yl)-5-(trichloromethyl)-1,2,4-oxadiazole (600 mg, 2.04 mmol) in THF (5 mL) was added to the reaction mixture. The reaction mixture was stirred at 25° C. for 12 h under N₂. The product was isolated and purified via standard methods to give 3-(5-methoxypyridin-2-yl)-N-(4-((tetrahydro-2H-pyran-4-yl)oxy)pyridin-2-yl)-1,2,4-oxadiazol-5-amine (74.27 mg, 0.198 mmol, 10% yield, 98.4% purity). LCMS (ESI): m/z 370.2 [M+1]⁺.

Example 30: N,N-dimethyl-6-(5-((3-methylpyridin-2-yl)amino)-1,2,4-oxadiazol-3-yl)nicotinamide

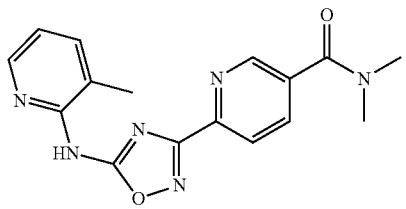 [SMILES: Cc1cccnc1Nc1nc(-c2ccc(C(=O)N(C)C)cn2)no1]

6-cyano-N,N-dimethylnicotinamide

To a solution of 6-cyanonicotinic acid (400 mg, 2.70 mmol), N-methylmethanamine (264 mg, 3.24 mmol, HCl) and DIPEA (1.05 g, 8.10 mmol) in DCM (20 mL) was added HATU (1.23 g, 3.24 mmol) at 0° C. The mixture was stirred at 25° C. for 3 h. The mixture was concentrated. The residue was purified by prep-TLC to give 6-cyano-N,N-dimethylnicotinamide (400 mg, crude). $^1$H NMR (400 MHz, CDCl3) δ 8.76 (dd, J1=2.0, J2=0.8 Hz, 1H), 7.91 (dd, J1=8.0, J2=2.0 Hz, 1H), 7.77 (dd, J1=8.0, J2=0.8 Hz, 1H), 3.15 (s, 3H), 3.01 (s, 3H).

6-(N-Hydroxycarbamimidoyl)-N,N-dimethylnicotinamide

To a solution of 6-cyano-N,N-dimethylnicotinamide (600 mg, 3.42 mmol) and TEA (692 mg, 6.84 mmol) in EtOH (20 mL) was added NH$_2$OH.HCl (475 mg, 6.84 mmol). The mixture was stirred at 80° C. for 16 h. The mixture was concentrated. The residue was diluted with 150 mL of EtOAc and 50 mL of H$_2$O. The organic phase was separated and dried over anhydrous sodium sulfate, filtered, and concentrated under vacuum to give 6-(N-hydroxycarbamimidoyl)-N,N-dimethylnicotinamide (650 mg, crude).

N,N-Dimethyl-6-(5-(trichloromethyl)-1,2,4-oxadiazol-3-yl)nicotinamide

To a solution of 6-(N-hydroxycarbamimidoyl)-N,N-dimethylnicotinamide (650 mg, 3.12 mmol) in toluene (30 mL) was added trichloroacetic anhydride (1.93 g, 6.24 mmol). The mixture was stirred at 110° C. for 16 h. The mixture was concentrated under vacuum. The residue was purified by silica gel to give N,N-dimethyl-6-(5-(trichloromethyl)-1,2,4-oxadiazol-3-yl)nicotinamide (700 mg, 2.04 mmol, 65% yield, 97.6% purity).

N,N-Dimethyl-6-(5-((3-methylpyridin-2-yl)amino)-1,2,4-oxadiazol-3-yl)nicotinamide To a solution of 3-methylpyridin-2-amine (116 mg, 1.07 mmol) in THF (10 mL) was added NaH (54 mg, 1.34 mmol, 60% purity). The mixture was stirred at 25° C. for 0.5 h. Then N,N-dimethyl-6-(5-(trichloromethyl)-1,2,4-oxadiazol-3-yl)nicotinamide (300 mg, 0.894 mmol) in THF (5 mL) was added. The mixture was stirred at 25° C. for 2.5 h. The product was isolated and purified via standard methods to give N,N-dimethyl-6-(5-((3-methylpyridin-2-yl)amino)-1,2,4-oxadiazol-3-yl)nicotinamide (53.80 mg, 0.166 mmol, 19% yield, 99.9% purity). LCMS (ESI): m/z 325.2 [M+1]$^+$.

Example 31: 3-(5-Isopropoxypyrazin-2-yl)-N-(3-methylpyridine-2-yl)-1,2,4-thiadiazol-5-amine

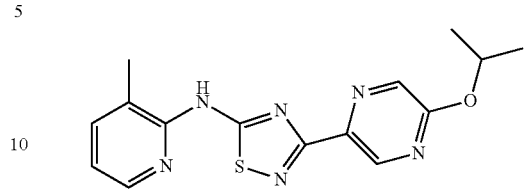

5-Isopropoxypyrazine-2-carbonitrile

To a mixture of propan-2-ol (3.23 g, 53.75 mmol) in DMF (40 mL) was added sodium hydrogen (2.15 g, 53.75 mmol, 60% purity) in portions at 0° C. under nitrogen. The mixture was stirred at 25° C. for 30 min, then 5-chloropyrazine-2-carbonitrile (5 g, 35.83 mmol) was added and the mixture was stirred at 25° C. for 3 h. The mixture was poured into H$_2$O (100 mL) and extracted with EtOAc. The combined organic phases were washed with brine, dried over sodium sulfate, filtered and concentrated at reduced pressure to give a residue. The residue was purified by silica gel chromatography to give 5-isopropoxypyrazine-2-carbonitrile (3.8 g, 23.29 mmol, 64.99% yield).

5-Isopropoxypyrazine-2-carboximidamide

Sodium (141 mg, 6.13 mmol) was added into MeOH (20 mL). To the mixture 5-isopropoxypyrazine-2-carbonitrile (2 g, 12.26 mmol) was added and the mixture was stirred at 25° C. for 2 h. NH$_4$Cl (983 mg, 18.38 mmol) was added and the mixture was stirred at 70° C. for 1.5 h. The hot mixture was filtered and the filtrate was concentrated to give a residue. The residue was triturated with Petroleum ether:EtOAc (10:1, 50 mL) to give the crude product as hydrochloride salt. The product was isolated and purified by standard methods to give 5-isopropoxypyrazine-2-carboxamidine (1.8 g, 9.99 mmol, 81.49% yield). LCMS (ESI): m/z 329.1 [M+1]$^+$.

Example 32: 3-(5-Cyclopropoxy-3-(trifluoromethyl)pyridin-2-yl)-n-(3-methylpyridin-2-yl)-1,2,4-thiadiazol-5-amine

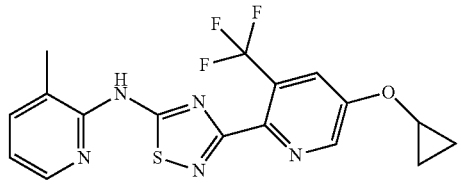 [SMILES: Cc1cccnc1Nc1nc(-c2ncc(OC3CC3)cc2C(F)(F)F)ns1]

5-Chloro-3-(trifluoromethyl)picolinonitrile

To a mixture of 5-amino-3-(trifluoromethyl)picolinonitrile (1.8 g, 9.62 mmol) and cuprous chloride (1.43 g, 14.4 mmol) in hydrochloric acid (30 mL) was stirred at 0° C. for 0.5 h. Then a solution of sodium nitrite (730.0 mg, 10.6 mmol) in H$_2$O (30 mL) was added drop wise to the mixture and the mixture was stirred at 0° C. for another 0.5 h. The mixture was extracted with EtOAc. The combined organic phases were dried with anhydrous sodium sulphate, filtered and concentrated to give 5-chloro-3-(trifluoromethyl)picolinonitrile (1.9 g, 8.55 mmol, 88.93% yield).

5-Cyclopropoxy-3-(trifluoromethyl)picolinonitrile

To a mixture of NaH (376.0 mg, 9.41 mmol, 60% purity) in DMF (30 mL) was added a solution of cyclopropanol (497.0 mg, 8.55 mmol) in DMF (5 mL) at −20° C. under $N_2$. The reaction mixture was stirred at −20° C. for 0.5 h and then a solution of 5-chloro-3-(trifluoromethyl)picolinonitrile (1.9 g, 8.55 mmol) in DMF (5 mL) was added to the mixture. The mixture was then stirred at this temperature for another 20 min. The mixture was quenched by cold saturated $NH_4Cl$ solution (150 mL). The aqueous phase was extracted with EtOAc. The combined organic phases were then washed with saturated brine, dried with anhydrous sodium sulfate, filtered and concentrated to give crude yellow oil which was purified by silica gel chromatography to give 5-cyclopropoxy-3-(trifluoromethyl)picolinonitrile (1.85 g, 6.41 mmol, 74.87% yield).

5-Cyclopropoxy-3-(trifluoromethyl)picolinimidamide

To a mixture of 5-cyclopropoxy-3-(trifluoromethyl)picolinonitrile (840 mg, 3.68 mmol) in MeOH (30 mL) was added sodium methoxide (99.44 mg, 1.84 mmol), the mixture was stirred at 25° C. for 3 h. $NH_4Cl$ (295.0 mg, 5.52 mmol) was then added to the mixture and the mixture was then stirred at 75° C. for another 2 h. and was concentrated to remove MeOH and then dissolved with EtOH (5 mL). The mixture was heated at 70° C. for 0.5 h and then filtered. The filtrate was concentrated to give a solid which was triturated by EtOAc (5 mL) to give 500 mg product. The solid was combined with another batch and then purified by Cis reverse column (0%-100% ACN in $H_2O$ (0.5% HCl) to give a solution of pure product in ACN and $H_2O$). OH-type resin was added to the mixture and the mixture was filtered and lyophilized to give 5-cyclopropoxy-3-(trifluoromethyl)picolinimidamide (240 mg, 919.0 μmol, 24.97% yield).

5-Cyclopropoxy-N-((3-methylpyridin-2-yl)carbamothioyl)-3-(trifluoromethyl)picolinimidamide To a mixture of 5-cyclopropoxy-3-(trifluoromethyl)picolinimidamide (550 mg, 2.24 mmol) and TEA (454.0 mg, 4.49 mmol) in DCM (1 mL) was added 2-isothiocyanato-3-methylpyridine (337.0 mg, 2.24 mmol). The mixture was then stirred at 25° C. for 1 h. and was concentrated to give a solid. The solid was triturated with MTBE (20 mL) to give 5-cyclopropoxy-N-((3-methylpyridin-2-yl)carbamothioyl)-3-(trifluoromethyl)picolinimidamide (550 mg, 1.26 mmol, 56.29% yield).

3-(5-Cyclopropoxy-3-(trifluoromethyl)pyridin-2-yl)-N-(3-methylpyridin-2-yl)-1,2,4-thiadiazol-5-amine To a mixture of 5-cyclopropoxy-N-((3-methylpyridin-2-yl)carbamothioyl)-3-(trifluoromethyl)picolinimidamide (500 mg, 1.26 mmol) in EtOH (20 mL) and DCM (20 mL) was added hydrogen peroxide (287.0 mg, 2.53 mmol, 30% purity) and iodine (64.2 mg, 253.0 μmol). The reaction mixture was then stirred at 25° C. for 2 h and was concentrated to give a solid which was triturated with methyl tertiary butyl ether (10 mL) and EtOAc (1 mL) to give a solid. The solid was triturated with ACN (2 mL) to give 3-(5-cyclopropoxy-3-(trifluoromethyl)pyridin-2-yl)-N-(3-methylpyridin-2-yl)-1,2,4-thiadiazol-5-amine (167.66 mg, 422.28 μmol, 33.39% yield). LCMS (ESI): m/z 394.0 [M+1]$^+$.

5-Isopropoxy-N-((3-methylpyridin-2-yl)carbamothioyl)pyrazine-2-carboximidamide

To a mixture of 5-isopropoxypyrazine-2-carboxamidine (240 mg, 1.33 mmol) and 2-isothiocyanato-3-methylpyridine (0.3 g, 1.88 mmol) in DCM (10 mL) and acetone (10 mL) was added TEA (404 mg, 4.00 mmol). The mixture was stirred at 25° C. for 5 h under nitrogen and was concentrated at reduced pressure to give a residue. Saturated sodium carbonate was added into the residue and the mixture was extracted with EtOAc. The combined organic phases were dried over sodium sulfate, filtered and concentrated at reduced pressure to give 5-isopropoxy-N-((3-methylpyridin-2-yl)carbamothioyl)pyrazine-2-carboximidamide (0.5 g, crude).

3-(5-Isopropoxypyrazin-2-yl)-N-(3-methylpyridin-2-yl)-1,2,4-thiadiazol-5-amine

To a mixture of 5-isopropoxy-N-((3-methylpyridin-2-yl)carbamothioyl)pyrazine-2-carboximidamide (0.5 g) and hydrogen peroxide (343 mg, 3.03 mmol, 30% purity) in EtOH (20 mL) was added iodine (7.68 mg, 0.03 mmol). The mixture was stirred at 25° C. for 1 h. The mixture was quenched with saturated sodium sulfite (5 mL) at 0° C. Then the mixture was diluted with $H_2O$ and extracted with EtOAc. The combined organic phases were washed with brine, dried over sodium sulfate, filtered and concentrated at reduced pressure to give a residue. The product was isolated and purified by standard methods to give 3-(5-isopropoxypyrazin-2-yl)-N-(3-methyl-2-pyridyl)-1,2,4-thiadiazol-5-amine (160.14 mg, 0.447 mmol). LCMS (ESI): m/z 329.1 [M+1]$^+$.

Example 33: $N^3,N^3$-Dimethyl-$N^2$-(3-(5-((1-methylazetidin-3-yl)sulfonyl)pyridin-2-yl)-1,2,4-thiadiazol-5-yl)pyridine-2,3-diamine

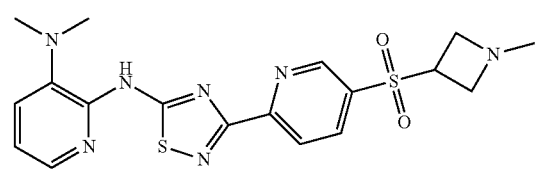 [SMILES: CN1CC(S(=O)(=O)c2ccc(-c3nsc(Nc4ncccc4N(C)C)n3)nc2)C1]

tert-Butyl 3-(acetylthio)azetidine-1-carboxylate

To a mixture of tert-butyl 3-iodoazetidine-1-carboxylate (20 g, 70.64 mmol) in DMF (400 mL) was added potassium ethanethioate (16.14 g, 141.29 mmol). The mixture was stirred at 70° C. for 16 h under nitrogen. The mixture was poured into $H_2O$ and the resulting mixture was extracted with EtOAc. The combined organic phases were washed with brine, dried over sodium sulfate, filtered and concentrated at reduced pressure to give a residue. The residue was purified by silica gel chromatography to give tert-butyl 3-acetylsulfanylazetidine-1-carboxylate (12 g, 51.88 mmol, 73.44% yield).

tert-Butyl 3-mercaptoazetidine-1-carboxylate

Sodium (2.39 g, 103.76 mmol) was added into MeOH (50 mL) in portions and the mixture was stirred at 25° C. for 30 min. Then this mixture was added into tert-butyl 3-acetylsulfanylazetidine-1-carboxylate (12 g, 51.88 mmol) which was dissolved in MeOH (50 mL) slowly at 0° C. The mixture was stirred at 25° C. for 4 h and was concentrated at reduced pressure to give a residue. The residue was diluted with $H_2O$ and adjusted pH to about 7 with 6 M HCl acid. The resulting mixture was extracted with DCM. The combined organic phases were washed with brine, dried over sodium sulfate, filtered and concentrated at reduced pressure to give a residue. The residue was purified by silica gel chromatography to give tert-butyl 3-mercaptoazetidine-1-carboxylate (8 g, 42.27 mmol, 81.47% yield).

tert-Butyl 3-((6-cyanopyridin-3-yl)thio)azetidine-1-carboxylate

To a mixture of tert-butyl 3-mercaptoazetidine-1-carboxylate (8 g, 42.27 mmol) in DMF (50 mL) was added NaH (2.03 g, 50.72 mmol, 60% purity) in portions at 0° C. under nitrogen. The mixture was stirred at 25° C. for 30 min, then 5-fluoropyridine-2-carbonitrile (5.16 g, 42.27 mmol) in DMF (10 mL) was added slowly and the mixture was stirred at 25° C. for 2 h. The mixture was diluted with $H_2O$ (500 mL) and the mixture was extracted with EtOAc. The combined organic phases were washed with brine, dried over sodium sulfate, filtered and concentrated at reduced pressure to give a residue. The residue was purified by silica gel chromatography to give tert-butyl 3-((6-cyanopyridin-3-yl)thio)azetidine-1-carboxylate (7 g, crude).

tert-Butyl 3-((6-cyanopyridin-3-yl)sulfonyl)azetidine-1-carboxylate

To a mixture of tert-butyl 3-[(6-cyano-3-pyridyl)sulfanyl]azetidine-1-carboxylate (3 g) in DCM (30 mL) was added m-chlorine perbenzoic acid (5.55 g, 25.73 mmol, 80% purity) which was dissolved with DCM (50 mL) slowly at 25° C. under nitrogen. The mixture was stirred at 25° C. for 2 h. The mixture was quenched with saturated sodium sulfite (30 mL). The mixture was separated and the organic phase was washed with saturated sodium carbonate, brine, dried over sodium sulfate, filtered and concentrated at reduced pressure to give a residue. The residue was purified by silica gel chromatography to give tert-butyl 3-((6-cyanopyridin-3-yl)sulfonyl) azetidine-1-carboxylate (2.8 g, 8.66 mmol).

5-(Azetidin-3-ylsulfonyl)picolinonitrile

To a mixture of tert-butyl 3-((6-cyanopyridin-3-yl)sulfonyl) azetidine-1-carboxylate (2.8 g, 8.66 mmol) in DCM (30 mL) was added trifluoroacetic acid (9.24 g, 81.04 mmol) slowly at 0° C. under nitrogen. The mixture was stirred at 0° C. for 1 h. The reaction mixture was purified by silica gel chromatography; TLC to give 5-(azetidin-3-ylsulfonyl)picolinonitrile trifluoroacetic acid (2.3 g, 6.82 mmol, 78.76% yield).

5-((1-Methylazetidin-3-yl)sulfonyl)picolinonitrile

To a mixture of 5-(azetidin-3-ylsulfonyl)picolinonitrile trifluroacetic acid (2.3 g, 6.82 mmol) in MeOH (10 mL) was added TEA (828.06 mg, 8.18 mmol). The mixture was stirred at 25° C. for 30 min, then formaldehyde (5.53 g, 68.19 mmol) and acetic acid (122.86 mg, 2.05 mmol) were added and the mixture was stirred at 25° C. for 2 h. Then sodium cyanoborohydride (1.29 g, 20.46 mmol) was added in portions at 0° C. and the mixture was stirred at 25° C. for 14 h. The mixture was adjusted pH to about 7 with saturated sodium bicarbonate. The resulting mixture was concentrated at reduced pressure to give a residue which was diluted with saturated sodium carbonate and extracted with DCM. The combined organic phases were dried over sodium sulfate, filtered and concentrated at reduced pressure to give a residue. The residue was purified by silica gel chromatography to give 5-((1-methylazetidin-3-yl)sulfonyl)picolinonitrile (0.6 g).

5-((1-Methylazetidin-3-yl)sulfonyl)picolinonitrile

Sodium (29.07 mg, 1.26 mmol) was added into MeOH (10 mL) and this mixture was stirred at 25° C. for 0.5 h. 5-((1-Methylazetidin-3-yl)sulfonyl)picolinonitrile (0.6 g, 2.53 mmol) was added into the mixture and the mixture was stirred at 25° C. for 2 h. $NH_4Cl$ (202.89 mg, 3.79 mmol) was added and the mixture was stirred at 70° C. for 1 hour. The hot mixture was filtered and the filtrate was concentrated at reduced pressure to give 5-(1-methylazetidin-3-yl)sulfonylpyridine-2-carboxamidine hydrochloride (0.9 g, crude).

N-((3-(Dimethylamino)pyridin-2-yl)carbamothioyl)-5-((1-methylazetidin-3-yl) sulfonyl)picolinimidamide To a mixture of 5-(1-methylazetidin-3-yl)sulfonylpyridine-2-carboxamidine hydrochloride (0.8 g) and 2-isothiocyanato-N,N-dimethylpyridin-3-amine (563.86 mg, 3.15 mmol) in DCM (15 mL) and acetone (15 mL) was added TEA (954.97 mg, 9.44 mmol). The mixture was stirred at 25° C. for 2 h under nitrogen. The mixture (combined with another batch) was concentrated at reduced pressure to give a residue. The residue was diluted with saturated sodium bicarbonate and the resulting mixture was extracted with EtOAc. The combined organic phases were washed with brine, dried over sodium sulfate, filtered and concentrated at reduced pressure to give N-((3-(dimethylamino)pyridin-2-yl)carbamothioyl)-5-((1-methylazetidin-3-yl) sulfonyl)picolinimidamide (1 g, crude).

$N^3,N^3$-Dimethyl-$N^2$-(3-(5-((1-methylazetidin-3-yl)sulfonyl)pyridin-2-yl)-1,2,4-thiadiazol-5-yl)pyridine-2,3-diamine To a mixture of N-((3-(dimethylamino)pyridin-2-yl)carbamothioyl)-5-((1-methylazetidin-3-yl) sulfonyl)picolinimidamide (1 g, crude) and hydrogen peroxide (523 mg, 4.61 mmol) in EtOH (20 mL) was added iodine (117 mg, 0.461 mmol) in portions. The mixture was stirred at 25° C. for 1 h. The mixture was quenched with saturated sodium sulfite (5 mL) at 0° C. and the resulting mixture was concentrated at reduced pressure to give a residue. The product was isolated and purified by standard methods to give $N^3,N^3$-dimethyl-$N^2$-(3-(5-((1-methylazetidin-3-yl) sulfonyl)pyridin-2-yl)-1,2,4-thiadiazol-5-yl)pyridine-2,3-diamine formic acid (290.8 mg, 0.597 mmol, 98% purity). LCMS (ESI): m/z 432.1 $[M+1]^+$

Example 34: N-(3,3-difluorocyclobutyl)-6-((3-(5-isopropoxypyridin-2-yl)-1,2,4-thiadiazol-5-yl)amino)-5-isopropylnicotinamide

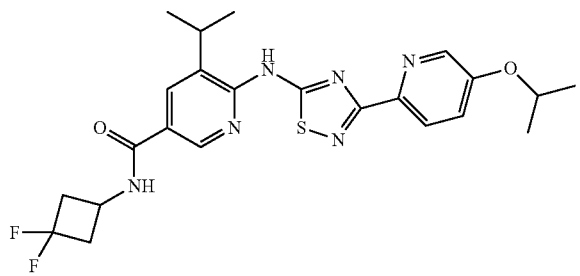 [SMILES: CC(C)Oc1ccc(-c2nsc(Nc3ncc(C(=O)NC4CC(F)(F)C4)cc3C(C)C)n2)nc1]

Methyl 6-amino-5-bromonicotinate

To a mixture of methyl 6-aminonicotinate (15 g, 98.59 mmol, 1 eq) in TH (300 mL) was added N-bromobutanimide (18.42 g, 103.52 mmol) in portions at 0° C. The mixture was stirred at 25° C. for 2 h. The reaction mixture was concentrated under vacuum. The residue was purified by silica gel chromatography to give methyl 6-amino-5-bromonicotinate (19 g, 79.77 mmol, 80.91% yield).

Methyl 6-amino-5-(prop-1-en-2-yl)nicotinate

To a mixture of methyl 6-amino-5-bromonicotinate (10 g, 43.28 mmol) and potassium; trifluoro(isopropenyl)boranuide (9.61 g, 64.92 mmol) in dioxane (150 mL) and H$_2$O (30 mL) were added [1,1'-bis(diphenylphosphino)ferrocene]dichloropalladium(II) (1.58 g, 2.16 mmol) and sodium carbonate (9.17 g, 86.56 mmol) under nitrogen. The mixture was stirred at 80° C. for 12 h under nitrogen. The reaction mixture was concentrated under vacuum and the residue was diluted with H$_2$O. The aqueous phase was extracted with EtOAc and the combined organic phases were dried with anhydrous sodium sulfate, filtered and concentrated in vacuum. The residue was purified by silica gel chromatography to give methyl 6-amino-5-(prop-1-en-2-yl)nicotinate (6.3 g, 30.48 mmol, 70.43% yield).

Methyl 6-amino-5-isopropylnicotinate

To a mixture of methyl 6-amino-5-(prop-1-en-2-yl)nicotinate (6.3 g, 30.48 mmol) in MeOH (90 mL) were added Pd/C (0.3 g, 10%) and hydroxide Pd/C (0.3 g, 20%). The mixture was stirred at 20° C. for 3 h under hydrogen (15 psi). The mixture was filtered and the filtrate was concentrated under vacuum to give methyl 6-amino-5-isopropylnicotinate (3.3 g, 15.80 mmol, 51.84% yield).

Methyl 5-isopropyl-6-isothiocyanatonicotinate

To a mixture of thiophosgene (1.98 g, 17.24 mmol, 1.32 mL) in DCM (40 mL) was added a solution of methyl 6-amino-5-isopropylnicotinate (1.8 g, 8.62 mmol) in DCM (20 mL) dropwise at 0° C. The mixture was stirred at 0° C. for 1 h. The mixture was quenched with saturated sodium bicarbonate. The organic phase was dried with anhydrous sodium sulfate, filtered and concentrated in vacuum. The residue was purified by silica gel chromatography to give methyl 5-isopropyl-6-isothiocyanatonicotinate (1.8 g, 7.62 mmol, 88.39% yield).

Methyl-6-(3-(imino(5-isopropoxypyridin-2-yl)methyl)thioureido)-5-isopropylnicotinate To a mixture of methyl 5-isopropyl-6-isothiocyanatonicotinate (0.9 g, 3.81 mmol) and 5-isopropoxypicolinimidamide (682.62 mg, 3.81 mmol) in DCM (20 mL) and acetone (20 mL) was added TEA (1.93 g, 19.04 mmol). The mixture was stirred at 20° C. for 3 h under nitrogen and was concentrated under vacuum to give methyl 6-(3-(imino(5-isopropoxypyridin-2-yl)methyl)thioureido)-5-isopropylnicotinate (1.6 g, crude).

Methyl-6-((3-(5-isopropoxypyridin-2-yl)-1,2,4-thiadiazol-5-yl)amino)-5-isopropylnicotinate To a mixture of methyl 6-(3-(imino(5-isopropoxypyridin-2-yl)methyl)thioureido)-5-isopropylnicotinate (1.6 g, crude) in EtOH (30 mL) were added iodine (195.47 mg, 0.770 mmol) and hydrogen peroxide (873.20 mg, 7.70 mmol, 30% purity) at 0° C. The mixture was stirred at 20° C. for 1 h. The mixture was quenched with saturated sodium sulfite (20 mL) at 0° C. and concentrated. The residue was diluted with H$_2$O and extracted with EtOAc. The combined organic phases were dried with anhydrous sodium sulfate, filtered and concentrated. The residue was purified by silica gel chromatography to give methyl-6-((3-(5-isopropoxypyridin-2-yl)-1,2,4-thiadiazol-5-yl)amino)-5-isopropylnicotinate (1.2 g, 2.41 mmol, 62.55% yield).

6-((3-(5-Isopropoxypyridin-2-yl)-1,2,4-thiadiazol-5-yl)amino)-5-isopropylnicotinic Acid To a mixture of methyl 6-((3-(5-isopropoxypyridin-2-yl)-1,2,4-thiadiazol-5-yl)amino)-5-isopropylnicotinate (1.2 g, 2.41 mmol) in MeOH (20 mL) was added a solution of lithium hydroxide (1.01 g, 24.09 mmol) in H$_2$O (10 mL). The mixture was stirred at 20° C. for 22 h and 50° C. for 12 h. and was concentrated under vacuum. The aqueous phase was adjusted to pH of 5 with 6 N HCl. The resulting suspension was filtered and the filter cake was dried by lyophilization to give 6-((3-(5-isopropoxypyridin-2-yl)-1,2,4-thiadiazol-5-yl)amino)-5-isopropylnicotinic acid (0.9 g, 2.25 mmol, 93.53% yield).

N-(3,3-difluorocyclobutyl)-6-((3-(5-isopropoxypyridin-2-yl)-1,2,4-thiadiazol-5-yl)amino)-5-isopropylnicotinamide To a mixture of 6-((3-(5-isopropoxypyridin-2-yl)-1,2,4-thiadiazol-5-yl)amino)-5-isopropylnicotinic acid (500 mg, 1.25 mmol) and 3,3-difluorocyclobutanamine (215.63 mg, 1.50 mmol, HCl) in DMF (10 mL) were added HATU (713.88 mg, 1.88 mmol) and DIPEA (485.31 mg, 3.76 mmol). The mixture was stirred at 20° C. for 4 h. The mixture was diluted with 100 mL of EtOAc. The organic phase was washed with brine, dried with anhydrous sodium sulfate, filtered and concentrated in vacuum. The product was isolated and purified by standard methods to give N-(3,3-difluorocyclobutyl)-6-((3-(5-isopropoxypyridin-2-yl)-1,2,4-thiadiazol-5-yl)amino)-5-isopropylnicotinamide (228.0 mg, 0.467 mmol, 37.28% yield). LCMS (ESI): m/z 489.3 [M+1]$^+$.

Example 35: N²-(3-(5-Isopropoxy-4-(trifluoromethyl)pyridin-2-yl)-1,2,4-thiadiazol-5-yl)-N³,N³-dimethylpyridine-2,3-diamine

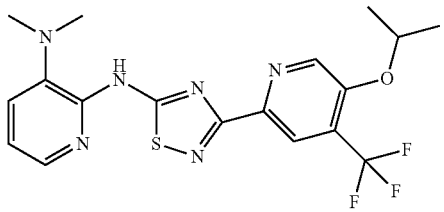 [SMILES: CC(C)Oc1cnc(-c2nsc(Nc3ncccc3N(C)C)n2)cc1C(F)(F)F]

Methyl 5-chloro-4-(trifluoromethyl)picolinate

To a mixture of 2,5-dichloro-4-(trifluoromethyl)pyridine (5 g, 23.15 mmol) in MeOH (100 mL) were added bis(diphenylphosphino)ferrocene]dichloropalladium (846.93 mg, 1.16 mmol) and TEA (7.03 g, 69.45 mmol, 9.67 mL) under nitrogen. The mixture was stirred at 60° C. for 3 h under carbon monoxide (50 psi). The mixture was filtered and the filtrate was concentrated. The residue was purified by silica gel chromatography to give methyl 5-chloro-4-(trifluoromethyl)picolinate (4.5 g, 18.78 mmol, 81.14% yield).

5-Chloro-4-(trifluoromethyl)picolinamide

To a mixture of methyl 5-chloro-4-(trifluoromethyl)picolinate (4.5 g, 17.78 mmol) in MeOH (100 mL) was added ammonia/MeOH (29 M, 45.34 mL) at 0° C. The mixture was stirred at 15° C. for 16 h. and was concentrated to give 5-chloro-4-(trifluoromethyl)picolinamide (4 g, 17.81 mmol, 94.83% yield).

5-Chloro-4-(trifluoromethyl)picolinonitrile

To a mixture of 5-chloro-4-(trifluoromethyl)picolinamide (4 g, 17.81 mmol) and TEA (9.01 g, 148.06 mmol) in DCM (200 mL) was added trifluoroacetic anhydride (18.66 g, 88.84 mmol) at 0° C. The mixture was stirred at 25° C. for 3 h. The mixture was poured into cold $H_2O$. The organic phase was separated and the aqueous phase was extracted with DCM. The combined organic phases were concentrated under vacuum. The residue was purified by silica gel chromatography to give 5-chloro-4-(trifluoromethyl)picolinonitrile (3.6 g, 17.43 mmol, 97.85% yield).

5-Isopropoxy-4-(trifluoromethyl)picolinonitrile

To a mixture of NaH (1.74 g, 43.57 mmol, 60% purity) in DMF (40 mL) was added propan-2-ol (2.09 g, 34.86 mmol) at −20° C. under nitrogen. The mixture was stirred at −10° C. for 0.5 h under nitrogen. Then 5-chloro-4-(trifluoromethyl)picolinonitrile (3.6 g, 17.43 mmol) in DMF (10 mL) was added into the above mixture at −20° C. The mixture was stirred at −20° C. for 1 h. The mixture was poured into cold saturated $NH_4Cl$ slowly. The mixture was diluted with 300 mL of EtOAc. The organic phase was washed with brine. The organic phase was dried over anhydrous sodium sulfate, filtered and concentrated under vacuum. The residue was purified by silica gel chromatography to give 5-isopropoxy-4-(trifluoromethyl)picolinonitrile (3 g, 12.38 mmol, 71.04% yield).

5-Isopropoxy-4-(trifluoromethyl)picolinimidamide hydrochloride

Sodium (25 mg, 1.09 mmol) was added into MeOH (10 mL). To the mixture was added 5-isopropoxy-4-(trifluoromethyl)picolinonitrile (0.5 g, 2.17 mmol). The mixture was stirred at 15° C. for 3 h. $NH_4Cl$ (174.28 mg, 3.26 mmol) was added. The mixture was stirred at 70° C. for 2 h. The hot mixture was filtered and the filtrate was concentrated to give a residue. The residue was triturated with petroleum ether: EtOAc (2:1, 15 mL) to give 5-isopropoxy-4-(trifluoromethyl)picolinimidamide hydrochloride (0.6 g, crude).

N-((3-(Dimethylamino)pyridin-2-yl)carbamothioyl)-5-isopropoxy-4-(trifluoromethyl)picolinimidamide To a mixture of 2-isothiocyanato-N,N-dimethylpyridin-3-amine (0.38 g, 2.12 mmol) and 5-isopropoxy-4-(trifluoromethyl)picolinimidamide hydrochloride (601 mg, crude) in DCM (15 mL) and acetone (15 mL) was added TEA (2.15 g, 21.20 mmol, 2.95 mL). The mixture was stirred at 15° C. for 16 h under nitrogen and was concentrated and the residue was poured into $H_2O$. The aqueous phase was extracted with EtOAc. The combined organic phases were dried over anhydrous sodium sulfate, filtered and concentrated under vacuum to give N-((3-(dimethylamino)pyridin-2-yl) carbamothioyl)-5-isopropoxy-4-(trifluoromethyl)picolinimidamide (1 g, 1.34 mmol, 63.05% yield).

N²-(3-(5-Isopropoxy-4-(trifluoromethyl)pyridin-2-yl)-1,2,4-thiadiazol-5-yl)-N³,N³-dimethylpyridine-2,3-diamine To a mixture of N-((3-(dimethylamino)pyridin-2-yl)carbamothioyl)-5-isopropoxy-4-trifluoromethyl)picolinimidamide (1 g, 1.34 mmol, 57% purity) in EtOH (20 mL) were added iodine (67.85 mg, 0.267 mmol) and hydrogen peroxide (454.57 mg, 4.01 mmol, 30% purity) at 0° C. The mixture was stirred at 15° C. for 0.5 h and then quenched with saturated sodium sulfite. The mixture was concentrated to remove the organic solvent. The product was isolated and purified by standard methods to give N²-(3-(5-isopropoxy-4-(trifluoromethyl)pyridin-2-yl)-1,2,4-thiadiazol-5-yl)-N³,N³-dimethylpyridine-2,3-diamine (431.76 mg, 1.01 mmol, 75.93% yield). LCMS (ESI) m/z 425.1 [m+1]⁺.

Example 36: N-(2-((3-(5-Isopropoxypyridin-2-yl)-1,2,4-thiadiazol-5-yl)amino)pyridin-3-yl)-N-methylacetamide

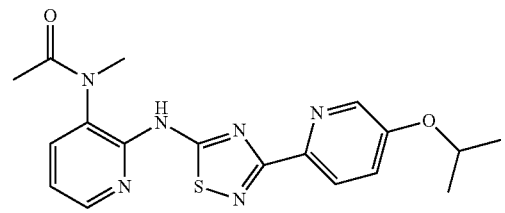 [SMILES: CC(=O)N(C)c1cccnc1Nc1nc(-c2ccc(OC(C)C)cn2)ns1]

tert-Butyl(2-(3-(imino(5-isopropoxypyridin-2-yl)methyl)thioureido)pyridin-3-yl)(methyl)carbamate To a mixture of tert-butyl (2-isothiocyanatopyridin-3-yl)(methyl)carbamate (0.4 g, 1.42 mmol) and 5-isopropoxypicolinimidamide (254 mg, 1.42 mmol) in DCM (10 mL) and acetone (10 mL) was added TEA (430 mg, 4.25 mmol). The mixture was stirred at 15° C. for 2 h and was concentrated at reduced pressure to give a residue. The residue was diluted with saturated sodium bicarbonate and the resulting mixture was extracted with EtOAc. The combined organic phases were washed with brine, dried over sodium sulfate, filtered and concentrated at reduced pressure to give tert-butyl (2-(3-(imino(5-isopropoxypyridin-2-yl)methyl)thioureido)pyridin-3-yl)(methyl)carbamate (0.7 g, crude).

tert-Butyl(2-((3-(5-isopropoxypyridin-2-yl)-1,2,4-thiadiazol-5-yl)amino)pyridine-3-yl)(methyl)carbamate To a mixture of tert-butyl (2-(3-(imino(5-isopropoxypyridin-2-yl)methyl)thioureido)pyridin-3-yl)(methyl)carbamate (0.7 g, crude) and hydrogen peroxide (357 mg, 3.15 mmol, 30% purity) in EtOH (10 mL) was added iodine (79.93 mg, 0.315 mmol) in portions. The mixture was stirred at 15° C. for 0.5 h. The mixture was quenched with saturated sodium sulfite at 0° C. and the resulting mixture was concentrated at reduced pressure to give a residue. The mixture was diluted with H2O and the resulting mixture was extracted with DCM. The combined organic phases were washed with brine, dried over sodium sulfate, filtered and concentrated at reduced pressure to give a residue. The residue was purified by silica gel chromatography to give tert-butyl (2-((3-(5-isopropoxypyridin-2-yl)-1,2,4-thiadiazol-5-yl)amino)pyridin-3-yl)(methyl)carbamate (0.4 g, 0.777 mmol, 49.37% yield, 86% purity).

N2-(3-(5-Isopropoxypyridin-2-yl)-1,2,4-thiadiazol-5-yl)-N3-methylpyridine-2,3-diamine hydrochloride To a mixture of tert-butyl (2-((3-(5-isopropoxypyridin-2-yl)-1,2,4-thiadiazol-5-yl)amino)pyridin-3-yl)(methyl)carbamate (0.4 g, 0.777 mmol, 86% purity) in EtOAc (15 mL) was added hydrochloride/EtOAc (4 M, 19.43 mL) at 0° C. The mixture was stirred at 20° C. for 3 h. The mixture was concentrated to give N2-(3-(5-isopropoxypyridin-2-yl)-1,2,4-thiadiazol-5-yl)-N3-methylpyridine-2,3-diamine hydrochloride (0.3 g, 0.673 mmol, 86.58% yield, 85% purity).

N-(2-((3-(5-Isopropoxypyridin-2-yl)-1,2,4-thiadiazol-5-yl)amino)pyridin-3-yl)-N-methylacetamide To a mixture of N2-(3-(5-isopropoxypyridin-2-yl)-1,2,4-thiadiazol-5-yl)-N3-methylpyridine-2,3-diamine hydrochloride (200 mg, 0.449 mmol) in ACN (20 mL) were added TEA (454 mg, 4.49 mmol) and $Ac_2O$ (59.55 mg, 0.583 mmol). The mixture was stirred at 30° C. for 16 h and was concentrated. The product was isolated and purified by standard methods to give N-(2-((3-(5-isopropoxypyridin-2-yl)-1,2,4-thiadiazol-5-yl)amino)pyridin-3-yl)-N-methylacetamide (183.19 mg, 0.468 mmol, 69.59% yield, 98.3% purity). LCMS (ESI) m/z 385.2 $[M+1]^+$.

Example 37: 2-((3-(5-Isopropoxypyridin-2-yl)-1,2,4-thiadiazol-5-yl)amino)nicotinamide

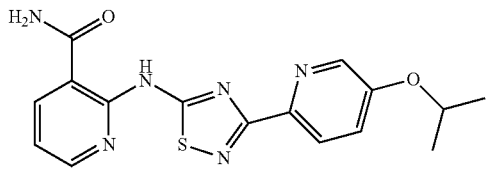 [SMILES: CC(C)Oc1ccc(-c2nsc(Nc3ncccc3C(N)=O)n2)nc1]

Methyl 2-isothiocyanatonicotinate

To a mixture of thiophosgene (11.34 g, 98.59 mmol, 7.56 mL) in DCM (50 mL) was added methyl 2-aminonicotinate (5 g, 32.86 mmol) which was dissolved with DCM (50 mL) slowly at 0° C. The mixture was stirred at 0° C. for 2 h. The mixture was quenched with saturated sodium bicarbonate slowly at 0° C. and the resulting mixture was separated. The organic phase was dried over sodium sulfate, filtered and concentrated at reduced pressure to give a residue. The residue was purified by silica gel chromatography; TLC to give methyl 2-isothiocyanatonicotinate (4.5 g, 23.17 mmol, 70.51% yield).

Methyl 2-(3-(imino(5-isopropoxypyridin-2-yl)methyl)thioureido)nicotinate

To the mixture methyl 2-isothiocyanatonicotinate (1 g, 5.15 mmol) and 5-isopropoxypicolinimidamide (922.81 mg, 5.15 mmol) in DCM (10 mL) and acetone (10 mL) was added TEA (1.56 g, 15.45 mmol, 2.15 mL). The mixture was stirred at 20° C. for 4 h. The reaction was concentrated to give a residue. The residue was diluted with $H_2O$ and extracted EtOAc. The combined organic layers were dried over anhydrous sodium sulfate, filtered and concentrated under reduced pressure to give methyl 2-(3-(imino(5-isopropoxypyridin-2-yl)methyl)thioureido)nicotinate (1.88 g, crude).

Methyl 2-((3-(5-isopropoxypyridin-2-yl)-1,2,4-thiadiazol-5-yl)amino)nicotinate

To the mixture of methyl 2-(3-(imino(5-isopropoxypyridin-2-yl)methyl)-thioureido)nicotinate (1.88 g, crude) and hydrogen peroxide (1.54 g, 13.58 mmol, 1.31 mL, 30% purity) in EtOH (50 mL) was added iodine (230 mg, 0.91 mmol) at 0° C. The mixture was stirred at 20° C. for 1.5 h. The reaction mixture was quenched with saturated sodium sulfite at 0° C. and the residue was diluted with $H_2O$ and extracted with DCM. The combined organic layers were washed with brine, dried over anhydrous sodium sulfate, filtered and concentrated under reduced pressure to give methyl 2-((3-(5-isopropoxy-pyridin-2-yl)-1,2,4-thiadiazol-5-yl)amino)nicotinate (0.6 g, crude).

2-((3-(5-Isopropoxypyridin-2-yl)-1,2,4-thiadiazol-5-yl)amino)nicotinamide

To a mixture of methyl 2-((3-(5-isopropoxypyridin-2-yl)-1,2,4-thiadiazol-5-yl)amino)nicotinate (0.6 g, crude) in MeOH (15 mL) was added ammonia/MeOH (24.5 M, 15 mL) at 0° C. The mixture was stirred at 15° C. for 16 h. The reaction was stirred at 50° C. for an additional 2 h. To the mixture was added ammonia/MeOH (20 M, 15 mL). The mixture was stirred at 50° C. for another 2 h and was concentrated. The product was isolated and purified by standard methods to give 2-((3-(5-isopropoxypyridin-2-yl)-1,2,4-thiadiazol-5-yl)amino)nicotinamide (333.04 mg, 0.89 mmol, 54.95% yield, 95% purity). LCMS (ESI): m/z 357.3 $[M+1]^+$.

Example 38: 2-((3-(5-Isopropoxy-4-(trifluoromethyl)pyridin-2-yl)-1,2,4-thiadiazol-5-yl)amino)-N,N-dimethylnicotinamide

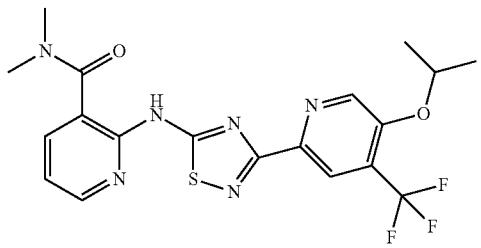 [SMILES: CC(C)Oc1cnc(-c2nsc(Nc3ncccc3C(=O)N(C)C)n2)cc1C(F)(F)F]

Methyl 5-chloro-4-(trifluoromethyl)picolinate

To a mixture of 2,5-dichloro-4-(trifluoromethyl)pyridine (5 g, 23.15 mmol) in MeOH (100 mL) were added Bis(diphenylphosphino)ferrocene]dichloropalladium (846.93 mg, 1.16 mmol), BINAP (360.36 mg, 0.579 mmol) and TEA (7.03 g, 69.45 mmol, 9.67 mL) under nitrogen. The mixture was stirred at 60° C. for 3 h under carbon monoxide (50 psi). The mixture was filtered and the filtrate was concentrated. The residue was purified by silica gel chromatography to give methyl 5-chloro-4-(trifluoromethyl)picolinate (5.0 g, 20.87 mmol, 90.15% yield).

5-Chloro-4-(trifluoromethyl)picolinamide

To a mixture of methyl 5-chloro-4-(trifluoromethyl)picolinate (5.0 g, 20.87 mmol) in MeOH (50 mL) was added ammonia/MeOH (10 M, 62.61 mL) at 0° C. The mixture was stirred at 25° C. for 16 h. and was concentrated to give 5-chloro-4-(trifluoromethyl)picolinamide (4.5 g, 20.04 mmol, 96.02% yield).

5-Chloro-4-(trifluoromethyl)picolinonitrile

To a mixture of 5-chloro-4-(trifluoromethyl)picolinamide (4.5 g, 20.04 mmol) and TEA (10.14 g, 100.19 mmol) in DCM (100 mL) was added trifluoroacetic anhydride (12.63 g, 60.12 mmol) at 0° C. The mixture was stirred at 25° C. for 2 h. The mixture was poured into cold $H_2O$. The organic phase was separated and the aqueous phase was extracted with DCM. The combined organic phases were concentrated under vacuum. The residue was purified by silica gel chromatography to give 5-chloro-4-(trifluoromethyl)picolinonitrile (3.8 g, 18.4 mmol, 91.81% yield).

5-Isopropoxy-4-(Trifluoromethyl)picolinonitrile

To a mixture of NaH (1.84 g, 45.99 mmol, 60% purity) in DMF (40 mL) was added propan-2-ol (2.21 g, 36.79 mmol) at −20° C. under nitrogen. The mixture was stirred at −10° C. for 0.5 h under nitrogen. Then 5-chloro-4-(trifluoromethyl)picolinonitrile (3.8 g, 18.4 mmol) in DMF (10 mL) was added into the above mixture at −20° C. The mixture was stirred at −20° C. for 1 h. The mixture was poured into cold saturated $NH_4Cl$ slowly. The mixture was diluted with EtOAc. The organic phase was washed with brine and dried over anhydrous sodium sulfate, filtered and concentrated under vacuum. The residue was purified by silica gel chromatography to give crude product. The crude product was purified by reverse MPLC (ACN/$H_2O$, formic acid) to give 5-isopropoxy-4-(trifluoromethyl)picolinonitrile (0.4 g, 1.74 mmol, 9.46% yield). The residue was purified by prep-HPLC (column: Phenomenex Synergi Max-RP 250*50 mm*10 μm; mobile phase: [$H_2O$ (0.225% FA)-ACN]; B %: 30%-60%, 32 MIN, 60% min) to give 5-isopropoxy-4-(trifluoromethyl)picolinonitrile (0.8 g, 3.48 mmol).

5-Isopropoxy-4-(trifluoromethyl)picolinimidamide Hydrochloride

Sodium (20 mg, 0.869 mmol) was added into MeOH (5 mL). To the mixture was added 5-isopropoxy-4-(trifluoromethyl)picolinonitrile (0.4 g, 1.74 mmol). The mixture was stirred at 25° C. for 2 h. $NH_4Cl$ (139 mg, 2.61 mmol) was added and the mixture was stirred at 70° C. for 2 h. The hot mixture was filtered and the filtrate was concentrated to give a residue. The residue was triturated with petroleum ether: EtOAc (2:1, 30 mL) to give 5-isopropoxy-4-(trifluoromethyl)picolinimidamide hydrochloride (0.5 g, 1.73 mmol, 99.4% yield).

Methyl-2-(3-(imino(5-isopropoxy-4-(trifluoromethyl)pyridin-2-yl)methyl)thioureido)nicotinate To a mixture of 5-isopropoxy-4-(trifluoromethyl)picolinimidamide hydrochloride (0.5 g, 1.73 mmol) and methyl 2-isothiocyanatonicotinate (436 mg, 2.25 mmol) in DCM (30 mL) and acetone (30 mL) was added TEA (873.93 mg, 8.64 mmol). The mixture was stirred at 25° C. for 18 h under nitrogen and was concentrated under vacuum to give methyl 2-(3-(imino(5-isopropoxy-4-(trifluoromethyl)pyridin-2-yl)methyl)thioureido) nicotinate (0.8 g, crude).

Methyl-2-((3-(5-isopropoxy-4-(trifluoromethyl)pyridin-2-yl)-1,2,4-thiadiazol-5-yl)amino)nicotinate To a mixture of methyl 2-(3-(imino(5-isopropoxy-4-(trifluoromethyl)pyridin-2-yl)methyl)thioureido)nicotinate (0.8 g, crude) in EtOH (15 mL) was added a solution of iodine (9.20 mg, 0.036 mmol) in EtOH (5 mL) and hydrogen peroxide (410.97 mg, 3.62 mmol, 30% purity) at 0° C. The mixture was stirred at 25° C. for 2 h. The mixture was quenched by addition of saturated sodium sulfite aqueous (50 mL) at 0° C. The mixture was concentrated under vacuum and the aqueous phase was extracted with DCM. The combined organic phases were washed with brine, dried with anhydrous sodium sulfate, filtered and concentrated in vacuum to give methyl 2-((3-(5-isopropoxy-4-(trifluoromethyl)pyridin-2-yl)-1,2,4-thiadiazol-5-yl)amino)nicotinate (1 g, crude).

2-((3-(5-Isopropoxy-4-(trifluoromethyl)pyridin-2-yl)-1,2,4-thiadiazol-5-yl)amino)nicotinic Acid To a mixture of methyl 2-((3-(5-isopropoxy-4-(trifluoromethyl)pyridin-2-yl)-1,2,4-thiadiazol-5-yl)amino)nicotinate (1 g, crude) in MeOH (30 mL) was added a solution of lithium hydrate (955.00 mg, 22.76 mmol) in $H_2O$ (10 mL). The mixture was stirred at 25° C. for 20 h. and was concentrated to remove the EtOH. The resulting mixture was adjusted to pH of 4 with 6N HCl. The suspension was filtered and the filter cake was collected and dried under vacuum to give 2-((3-(5-isopropoxy-4-(trifluoromethyl)pyridin-2-yl)-1,2,4-thiadiazol-5-yl)amino)nicotinic acid (0.9 g, crude).

2-((3-(5-Isopropoxy-4-(trifluoromethyl)pyridin-2-yl)-1,2,4-thiadiazol-5-yl)amino)-N,N-dimethylnicotinamide To a mixture of 2-((3-(5-isopropoxy-4-(trifluoromethyl)pyridin-2-yl)-1,2,4-thiadiazol-5-yl)amino)nicotinic acid (0.9 g, crude) and dimethylamine hydrochloride (517.58 mg, 6.35 mmol) in DMF (20 mL) were added DIPEA (1.37 g, 10.58 mmol, 1.84 mL) and HATU (965.36 mg, 2.54 mmol) at 0° C. The mixture was stirred at 25° C. for 19 h. The mixture was diluted with EtOAc. The organic phase was washed with brine, dried with anhydrous sodium sulfate, filtered and concentrated in vacuum. The products was isolated and purified by standard methods to give 2-((3-(5-isopropoxy-4-(trifluoromethyl)pyridin-2-yl)-1,2,4-thiadiazol-5-yl)amino)-N,N-dimethylnicotinamide (95.25 mg, 0.202 mmol, 9.55% yield). LCMS (ESI) m/z 453.3[M+1]$^+$.

Example 39: N-(5-(Difluoromethyl)-2-((3-(5-isopropoxypyridin-2-yl)-1,2,4-thiadiazol-5-yl)amino)pyridin-3-yl)-N-methylacetamide

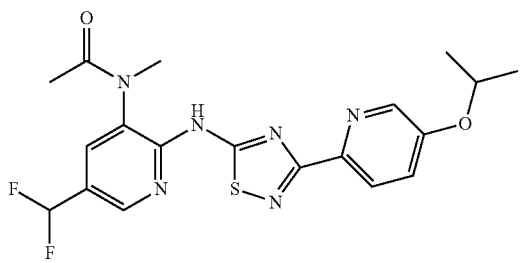 [SMILES: CC(=O)N(C)c1cc(C(F)F)cnc1Nc1nc(-c2ccc(OC(C)C)cn2)ns1]

tert-Butyl (2-aminopyridin-3-yl)(methyl)carbamate

To a mixture of tert-butyl methyl(2-nitropyridin-3-yl)carbamate (41.5 g, 163.87 mmol) in MeOH (600 mL) were added palladium hydroxide/carbon (2 g, 20% purity) and Pd/C (2 g, 10% purity) under nitrogen. The mixture was stirred at 20° C. for 16 h under hydrogen (15 psi). The mixture was filtered and the filtrate was concentrated under vacuum to give tert-butyl (2-aminopyridin-3-yl)(methyl)carbamate (32 g, 143.32 mmol, 87.46% yield).

tert-Butyl (2-amino-5-bromopyridin-3-yl)(methyl)carbamate

To a mixture of tert-butyl (2-aminopyridin-3-yl)(methyl)carbamate (12 g, 53.75 mmol) in THF (120 mL) was added NBS (10.04 g, 56.43 mmol) in portions at 0° C., the mixture was stirred at 20° C. for 1 h. The mixture was concentrated under vacuum to give a residue. The residue was purified by silica gel column chromatography to give tert-butyl (2-amino-5-bromopyridin-3-yl)(methyl)carbamate (12.8 g, 40.24 mmol, 74.88% yield, 95% purity).

tert-Butyl (2-amino-5-formylpyridin-3-yl)(methyl)carbamate

To a mixture of tert-butyl (2-amino-5-bromopyridin-3-yl)(methyl)carbamate (10.5 g, 34.75 mmol) in THF (100 mL) was added n-BuLi (2.5 M, 50.04 mL) at −70° C. under nitrogen. The mixture was stirred at −70° C. for 0.5 h. Then DMF (7.62 g, 104.25 mmol) was added at −70° C. The mixture was stirred at −70° C. for 1 h. The mixture was poured into saturated NH$_4$Cl and the aqueous phase was extracted with EtOAc. The combined organic phases were washed with brine, dried with anhydrous sodium sulfate, filtered and concentrated in vacuum. The residue was purified by flash silica gel chromatography to give tert-butyl (2-amino-5-formylpyridin-3-yl)(methyl)carbamate (4.7 g, 18.70 mmol, 53.83% yield).

tert-Butyl (2-amino-5-(difluoromethyl)pyridin-3-yl)(methyl)carbamate

To a mixture of tert-butyl (2-amino-5-formylpyridin-3-yl)(methyl)carbamate (4.2 g, 16.71 mmol) in DCM (120 mL) was added diethylaminosulphur trifluoride (5.39 g, 33.43 mmol) at 0° C. The mixture was stirred at 10° C. for 2 h. The reaction was quenched carefully with saturated sodium bicarbonate at 0° C. The organic phase was separated and the aqueous phase was extracted with DCM. The combined organic phases were dried with anhydrous sodium sulfate, filtered and concentrated in vacuum. The residue was purified by silica gel chromatography to give a solid. The solid was triturated with EtOAc. The filter cake was discarded and the filtrate was concentrated under vacuum to give crude product. The crude product was purified by prep-HPLC (column: Phenomenex Synergi Max-RP 250*50 mm*10 μm; mobile phase: [H$_2$O (0.225% FA)-ACN]; B %: 15%-40%, 19 min) followed by lyophilization to give tert-butyl (2-amino-5-(difluoromethyl)pyridin-3-yl)(methyl)carbamate (0.8 g, 2.93 mmol, 17.53% yield).

tert-Butyl-(5-(difluoromethyl)-2-isothiocyanatopyridin-3-yl)(methyl)carbamate To a mixture of thiophosgene (673.20 mg, 5.85 mmol) in DCM (10 mL) was added a solution of tert-butyl (2-amino-5-formylpyridin-3-yl)(methyl)carbamate (0.8 g, 2.93 mmol) in DCM (10 mL). The mixture was stirred at 0° C. for 2 h. The mixture was quenched with H$_2$O and saturated sodium bicarbonate. The organic phase was separated and aqueous phase was extracted with DCM and the combined organic phases were concentrated in vacuum. The residue was purified by silica gel chromatography to give tert-butyl (5-(difluoromethyl)-2-isothiocyanatopyridin-3-yl)(methyl)carbamate (0.75 g, 2.38 mmol, 81.25% yield).

tert-Butyl-(5-(difluoromethyl)-2-(3-(imino(5-isopropoxypyridin-2-yl)methyl)thioureido)pyridin-3-yl)(methyl)carbamate To a mixture of tert-butyl (5-(difluoromethyl)-2-isothiocyanatopyridin-3-yl)(methyl)carbamate (0.35 g, 1.11 mmol, 1 eq) and 5-isopropoxypicolinimidamide (198.92 mg, 1.11 mmol) in DCM (10 mL) and acetone (10 mL) was added TEA (561.56 mg, 5.55 mmol). The mixture was stirred at 30° C. for 16 h under nitrogen and was concentrated under vacuum to give tert-butyl-(5-(difluoromethyl)-2-(3-(imino(5-isopropoxypyridin-2-yl)methyl)thioureido)pyridin-3-yl)(methyl)carbamate (0.55 g, crude).

tert-Butyl-(5-(difluoromethyl)-2-((3-(5-isopropoxypyridin-2-yl)-1,2,4-thiadiazol-5-yl)amino)pyridin-3-yl)(methyl)carbamate To a mixture of tert-butyl (5-(difluoromethyl)-2-(3-(imino(5-isopropoxypyridin-2-yl)methyl)thioureido)pyridin-3-yl)(methyl)carbamate (0.55 g, crude) in EtOH (10 mL) were added iodine (56.45 mg, 0.222 mmol) and hydrogen peroxide (252.19 mg, 2.22 mmol, 30% purity) at 0° C. The mixture was stirred at 15° C. for 1 h. The mixture was quenched with saturated sodium sulfite (20 mL) at 0° C. and was concentrated to remove the organic solvent. The aqueous phase was diluted with H$_2$O and extracted with EtOAc. The combined organic phases were dried with anhydrous sodium sulfate, filtered and concentrated. The residue was purified by silica gel chromatography to give tert-butyl (5-(difluoromethyl)-2-((3-(5-isopropoxypyridin-2-yl)-1,2,4-thiadiazol-5-yl)amino)pyridin-3-yl)(methyl)carbamate (0.47 g, 0.954 mmol, 85.80% yield).

5-(Difluoromethyl)-N$^2$-(3-(5-isopropoxypyridin-2-yl)-1,2,4-thiadiazol-5-yl)-N$^3$-methylpyridine-2,3-diamine hydrochloride To a mixture of tert-butyl (5-(difluoromethyl)-2-((3-(5-isopropoxypyridin-2-yl)-1,2,4-thiadiazol-5-yl)amino)pyridin-3-yl)(methyl)carbamate (0.47 g, 0.954 mmol) in EtOAc (5 mL) was added hydrochloride/EtOAc (4 M, 5 mL) at 0° C. The mixture was stirred at 15° C. for 3 h. The mixture was concentrated under vacuum to give 5-(difluoromethyl)-N$^2$-(3-(5-isopropoxypyridin-2-yl)-1,2,4-thiadiazol-5-yl)-N$^3$-methylpyridine-2,3-diamine hydrochloride (0.4 g, crude).

N-(5-(Difluoromethyl)-2-((3-(5-isopropoxypyridin-2-yl)-1,2,4-thiadiazol-5-yl)amino)pyridin-3-yl)-N-methylacetamide To a mixture of 5-(difluoromethyl)-N$^2$-(3-(5-isopropoxypyridin-2-yl)-1,2,4-thiadiazol-5-yl)-N$^3$-methylpyridine-2,3-diamine hydrochloride (0.4 g, crude) in ACN (15 mL) were added TEA (471.87 mg, 4.66 mmol) and Ac$_2$O (123.78 mg, 1.21 mmol). The mixture was stirred at 30° C. for 5 h. The mixture was stirred at 30° C. for 16 h and was concentrated under vacuum. The product was isolated and purified by standard methods to give N-(5-(difluoromethyl)-2-((3-(5-isopropoxypyridin-2-yl)-1,2,4-thiadiazol-5-yl)amino)pyridin-3-yl)-N-methylacetamide (219.91 mg, 0.506 mmol, 54.22% yield). LCMS (ESI): m/z 435.1 [M+1]$^+$.

Example 40: 2-((3-(4-(Difluoromethyl)-5-isopropoxypyridin-2-yl)-1,2,4-thiadiazol-5-yl)amino)-N,N-dimethylnicotinamide

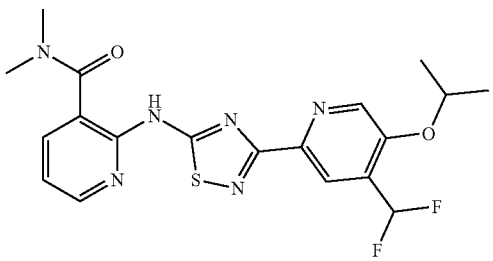 [SMILES: CC(C)Oc1cnc(-c2nsc(Nc3ncccc3C(=O)N(C)C)n2)cc1C(F)F]

2-Bromo-5-fluoroisonicotinaldehyde

To a mixture of 2-bromo-5-fluoropyridine (23 g, 130.69 mmol) in THF (200 mL) was added lithium diisopropylamide (2 M, 85 mL) at −65° C. slowly, the resulting mixture was stirred at −65° C. for 2 h. Then DMF (19.00 g, 259.94 mmol, 20 mL) in THF (30 mL) was added to the mixture at −65° C. slowly and stirred at −65° C. for 1 h. The reaction mixture was poured into cold H$_2$O and saturated sodium bicarbonate aqueous. The aqueous phase was extracted with EtOAc and the combined organic phases were washed with brine, dried with anhydrous sodium sulfate, filtered and concentrated under vacuum. The residue was purified by silica gel chromatography to give 2-bromo-5-fluoroisonicotinaldehyde (10 g, 49.02 mmol, 37.51% yield) and 2-bromo-5-fluoroisonicotinaldehyde (8 g, crude).

2-Bromo-4-(difluoromethyl)-5-fluoropyridine

To a mixture of 2-bromo-5-fluoroisonicotinaldehyde (8 g, crude) in DCM (150 mL) was added N-ethyl-N-(trifluorosulfanyl)ethanamine (11.38 g, 70.59 mmol, 9.33 mL) dropwise at −20° C. slowly, then the mixture was warmed to 25° C. and stirred for 3 h. The mixture was poured into saturated sodium bicarbonate aqueous and stirred for 5 min. The aqueous phase was extracted with DCM. The combined organic phases were washed with brine, dried with anhydrous sodium sulfate, filtered and concentrated in vacuum. The residue was purified by silica gel chromatography to give 2-bromo-4-(difluoromethyl)-5-fluoropyridine (5.4 g, 23.89 mmol, 60.93% yield).

4-(Difluoromethyl)-5-fluoropicolinonitrile

To a mixture of 2-bromo-4-(difluoromethyl)-5-fluoropyridine (5.4 g, 23.89 mmol), zinc cyanide (5.61 g, 47.79 mmol) and zinc (312.49 mg, 4.78 mmol) in DMF (50 mL) was added tetrakis (triphenylphosphine) palladium (2.76 g, 2.39 mmol) under nitrogen, then the mixture was stirred at 120° C. for 6 h. The mixture was filtered with a pad of celite and the filtrate was poured into EtOAc and brine. The aqueous phase was extracted with EtOAc. The combined organic phases were washed with brine, dried with anhydrous sodium sulfate, filtered and concentrated under vacuum. The residue was purified by silica gel chromatography to give 4-(difluoromethyl)-5-fluoropicolinonitrile (3 g, 17.43 mmol, 72.95% yield).

4-(Difluoromethyl)-5-isopropoxypicolinonitrile

To a mixture of propan-2-ol (1.05 g, 17.43 mmol) in DMF (30 mL) was added NaH (1.39 g, 34.86 mmol, 60% purity) at 0° C., then the mixture was stirred at 25° C. for 0.5 h. Then 4-(difluoromethyl)-5-fluoropicolinonitrile (3 g, 17.43 mmol) was added in portions at 0° C., the resulting mixture was stirred at 25° C. for 2 h. The mixture was poured into saturated NH$_4$Cl aqueous (200 mL). The aqueous phase was extracted with EtOAc. The combined organic phases were washed with brine, dried with anhydrous sodium sulfate, filtered and concentrated under vacuum. The residue was purified by silica gel chromatography to give 4-(difluoromethyl)-5-isopropoxypicolinonitrile (1.7 g, 8.01 mmol, 45.96% yield).

4-(Difluoromethyl)-5-isopropoxypicolinimidamide

To a mixture of 4-(difluoromethyl)-5-isopropoxypicolinonitrile (1.7 g, 8.01 mmol) in MeOH (10 mL) was added a solution of sodium (55.25 mg, 2.40 mmol) in MeOH (3 mL) and stirred until solid sodium disappeared. The resulting mixture was stirred at 25° C. for 3 h.

To the mixture was added NH$_4$Cl (557.11 mg, 10.41 mmol), then heated to 70° C. and stirred for 2 h. The hot mixture was filtered and the filtrate was concentrated under vacuum. The crude product was triturated with MTBE (30 mL) and stirred for 0.5 h. The suspension was filtered and the filtered cake was freed by Amberlyst A 26 in H₂O (20 ml) and ACN (20 mL) until pH was greater than 12. Then the mixture was filtered with a pad of celite. The filtrate was concentrated to remove ACN and dried by lyophilization to give 4-(difluoromethyl)-5-isopropoxypicolinimidamide (1.8 g, 7.85 mmol, 98.02% yield).

2-Amino-N,N-dimethylnicotinamide

To a mixture of 2-aminonicotinic acid (5 g, 36.20 mmol), HATU (18.5 g, 48.65 mmol) and DIPEA (22.26 g, 172.23 mmol, 30 mL) in DMF (50 mL) was added dimethylamine (8.5 g, 104.24 mmol, 9.55 mL, HCl) at 0° C., the mixture was stirred at 25° C. for 3 h. The mixture was stirred at 25° C. for 13 h and was concentrated to give a residue. The residue was purified by silica gel column chromatography to give 2-amino-N,N-dimethylnicotinamide (3 g, 18.16 mmol, 50.17% yield).

2-Isothiocyanato-N,N-dimethylnicotinamide

To a mixture of thiophosgene (4.18 g, 36.32 mmol, 2.78 mL) in DCM (20 mL) was added a solution of 2-amino-N,N-dimethylnicotinamide (3 g, 18.16 mmol) in DCM (30 mL) at 0° C., the mixture was stirred at 0° C. under nitrogen for 2 h. The mixture was poured into saturated sodium bicarbonate, the aqueous phase was extracted with DCM, the combined organic phases were concentrated under vacuum to give a mixture. The mixture was purified by silica gel column chromatography to give 2-isothiocyanato-N,N-dimethylnicotinamide (3 g, 14.48 mmol, 79.71% yield).

2-(3-((4-(Difluoromethyl)-5-isopropoxypyridin-2-yl) (imino)methyl)thioureido)-2-isothiocyanato-N,N-dimethylnicotinamide-N,N-dimethylnicotinamide To a mixture of 4-(difluoromethyl)-5-isopropoxypicolinimidamide (0.5 g, 2.18 mmol) and 2-isothiocyanato-N,N-dimethylnicotinamide (452.07 mg, 2.18 mmol) in DCM (10 mL) and acetone (10 mL) was added TEA (1.10 g, 10.91 mmol, 1.52 mL), then the mixture was stirred at 25° C. for 16 h and was concentrated under vacuum to give 2-(3-((4-(difluoromethyl)-5-isopropoxypyridin-2-yl)(imino)methyl) thioureido)-N,N-dimethylnicotinamide (1 g, crude).

2-((3-(4-(Difluoromethyl)-5-isopropoxypyridin-2-yl)-1,2,4-thiadiazol-5-yl)-amino)-N,N-dimethylnicotinamide To a mixture of 2-(3-((4-(difluoromethyl)-5-isopropoxypyridin-2-yl)(imino)methyl)thioureido)-N,N-dimethylnicotinamide (1 g, crude) in EtOH (10 mL) was added hydrogen peroxide (519.53 mg, 4.58 mmol, 30% purity) and a solution of iodine (116.30 mg, 458.21 μmol) in EtOH (3 mL), then the mixture was stirred at 25° C. for 2 h. The mixture was quenched by addition of saturated sodium sulfite aqueous at 0° C., then concentrated under vacuum. The aqueous phase was extracted with DCM. The combined organic phases were washed with brine, dried with anhydrous sodium sulfate, filtered and concentrated under vacuum. The product was isolated and purified by standard methods to give 2-((3-(4-(difluoromethyl)-5-isopropoxypyridin-2-yl)-1,2,4-thiadiazol-5-yl)amino)-N,N-dimethylnicotinamide (342.28 mg, 0.788 mmol, 34.39% yield). LCMS (ESI): m/z 435.3 [M+1]⁺.

Example 41:5-Isopropoxy-N,N-dimethyl-2-(5-((3-methylpyridin-2-yl)amino)-1,2,4-thiadiazol-3-yl) isonicotinamide

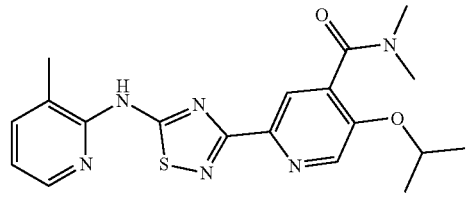 [SMILES: Cc1cccnc1Nc1nc(-c2cc(C(=O)N(C)C)c(OC(C)C)cn2)ns1]

2-Bromo-5-isopropoxy-N,N-dimethylisonicotinamide

To a mixture of 2-bromo-5-isopropoxyisonicotinic acid (2 g, 7.69 mmol) and oxalyl chloride (2.17 g, 17.14 mmol, 1.50 mL) in DCM (30 mL) was added DMF (9.50 mg, 0.129 mmol, 0.01 mL) at 25° C. The mixture was stirred at 25° C. for 1 h and was concentrated under vacuum to give a residue. To a mixture of the residue in DCM (30 mL) was added TEA (2.33 g, 23.07 mmol, 3.21 mL) and dimethylamine hydrochloride (0.8 g, 9.81 mmol, 0.898 mL) at 0° C., the mixture was stirred at 25° C. for 1 h and was concentrated under vacuum to give a residue. The residue was purified by silica gel column chromatography to give 2-bromo-5-isopropoxy-N,N-dimethylisonicotinamide (2.1 g, crude).

2-Cyano-5-isopropoxy-N,N-dimethylisonicotinamide

To a mixture of 2-bromo-5-isopropoxy-N,N-dimethylisonicotinamide (2 g, crude), zinc cyanide (1.64 g, 13.93 mmol) and zinc (90.00 mg, 1.38 mmol) in DMF (30 mL) was added tetrakis(triphenylphosphine)palladium (1.61 g, 1.39 mmol), the mixture was stirred at 120° C. for 14 h under nitrogen. The mixture was filtered through a pad of celite and the filtrate was poured into H₂O. The mixture was extracted with EtOAc. The combined organic phases were washed with brine, and concentrated under vacuum to give a residue. The residue was purified by prep-HPLC (column: Phenomenex Synergi Max-RP 250*50 mm*10 μm; mobile phase: [H₂O (0.225% FA)-ACN]; B %: 25ACN %-55ACN %, 28 min, 60% min) and followed by lyophilization to give 2-cyano-5-isopropoxy-N,N-dimethylisonicotinamide (0.8 g, 3.43 mmol, 49.24% yield).

2-Carbamimidoyl-5-isopropoxy-N,N-dimethylisonicotinamide

A mixture of sodium (47 mg, 2.04 mmol) in MeOH (10 mL) was stirred at 25° C. for 10 min. To the mixture was added 2-cyano-5-isopropoxy-N,N-dimethylisonicotinamide (0.8 g, 3.43 mmol) at 25° C., the mixture was stirred at 40° C. for 4 h. Then to the mixture was added NH₄Cl (0.29 g, 5.42 mmol), the mixture was stirred at 70° C. for 1.5 h and was concentrated under vacuum to give a residue. The residue was triturated with MTBE (20 mL), the precipitate was collected by filtration and dried under high vacuum to give 2-carbamimidoyl-5-isopropoxy-N,N-dimethylisonicotinamide hydrochloride (0.98 g, 3.42 mmol, 99.65% yield).

5-Isopropoxy-N,N-dimethyl-2-(N-((3-methylpyridin-2-yl)carbamothioyl)carbamimidoyl)isonicotinamide To a mixture of 2-carbamimidoyl-5-isopropoxy-N,N-dimethylisonicotinamide (0.3 g, 1.05 mmol) and 2-isothiocyanato-3-methylpyridine (0.19 g, 1.14 mmol) in acetone (30 mL) and DCM (30 mL) was added TEA (1.06 g, 10.46 mmol, 1.46 mL). The mixture was stirred at 25° C. for 3 h. To the mixture was added 2-isothiocyanato-3-methylpyridine (0.08 g, 0.53 mmol) and TEA (1.06 g, 10.46 mmol, 1.46 mL). Then the mixture was stirred at 25° C. for 12 h. The mixture was then stirred at 40° C. for 6 h and concentrated under vacuum to give a crude product. The crude product was used directly in the next step. 5-isopropoxy-N,N-dimethyl-2-(N-((3-methyl-pyridin-2-yl)carbamothioyl)carbamimidoyl)isonicotinamide (0.7 g, crude).

5-Isopropoxy-N,N-dimethyl-2-(5-((3-methylpyridin-2-yl)amino)-1,2,4-thiadiazol-3-yl)isonicotinamide To a mixture of 5-isopropoxy-N,N-dimethyl-2-(N-((3-methyl-pyridin-2-yl)carb-amothioyl)carbamimidoyl)isonicotinamide (0.7 g, 1.75 mmol) in EtOH (40 mL) was added iodine (88.00 mg, 346.72 μmol) and hydrogen peroxide (413.00 mg, 3.64 mmol, 0.35 mL, 30% purity) at 0° C. The mixture was stirred at 25° C. for 40 min. The mixture was quenched with saturate sodium sulfite and concentrated under vacuum to give an aqueous phase. The aqueous phase was extracted with DCM. The combined organic phases were concentrated under vacuum to give a residue. The product was isolated and purified by standard methods to give 5-isopropoxy-N,N-dimethyl-2-(5-((3-methylpyridin-2-yl)amino)-1,2,4-thiadiazol-3-yl)isonicotinamide (134.84 mg, 335.68 μmol, 19.21% yield, 99.2% purity). LCMS (ESI): m/z 427.3 [M+1]+.

Example 42:1-(4-(6-((3-(5-Cyclopropoxypyridin-2-yl)-1,2,4-thiadiazol-5-yl)amino)pyridin-3-yl)piperazin-1-yl)-3,3,3-trifluoropropan-1-one and 1-(4-(6-((3-(5-Cyclopropoxypyridin-2-yl)-1,2,4-thiadiazol-5-yl)amino)pyridin-3-yl)piperazin-1-yl)ethanone)

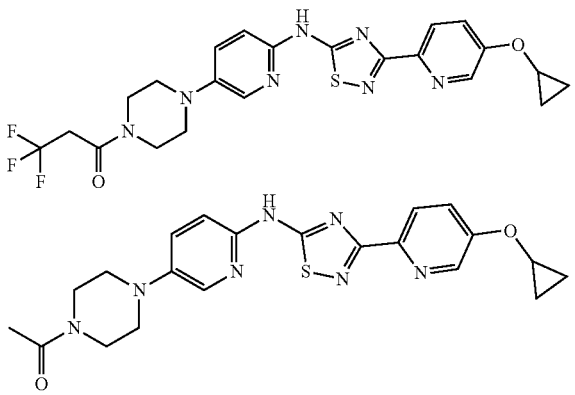

tert-Butyl 4-(6-nitropyridin-3-yl)piperazine-1-carboxylate

To a mixture of 5-chloro-2-nitropyridine (12.7 g, 80.10 mmol) and tert-butyl piperazine-1-carboxylate (14.92 g, 80.10 mmol) in DMSO (120 mL) was added cesium fluoride (14.60 g, 96.13 mmol). The reaction mixture was stirred at 80° C. for 16 h. The reaction mixture was diluted with H₂O and extracted with EtOAc. The combined organic layers were washed with brine, dried over sodium sulfate, filtered and concentrated under reduced pressure to give a residue. The residue was triturated with petroleum ether and EtOAc and filtered to afford a solid. The solid was purified by column chromatography to give tert-butyl 4-(6-nitropyridin-3-yl)piperazine-1-carboxylate (10.2 g, 24.15 mmol, 30.15% yield).

tert-Butyl 4-(6-aminopyridin-3-yl)piperazine-1-carboxylate

Two batches: To a mixture of tert-butyl 4-(6-nitropyridin-3-yl)piperazine-1-carboxylate (5 g, 11.84 mmol) in MeOH (200 mL) was added Pd/C (1 g, 10% purity). The mixture was degassed under vacuum and purged with hydrogen several times. The mixture was stirred under hydrogen (15 Psi) at 25° C. for 0.5 h. The reaction mixture was filtered and the filter was concentrated under reduced pressure to give a residue. The residue was purified by column chromatography to give tert-butyl 4-(5-aminopyridin-2-yl)piperazine-1-carboxylate (1.5 g, 5.28 mmol, 22.31% yield, 98% purity) as solid and tert-butyl 4-(6-aminopyridin-3-yl)piperazine-1-carboxylate (5.8 g, 20.42 mmol, 86.25% yield) was obtained.

tert-Butyl 4-(6-isothiocyanatopyridin-3-yl)piperazine-1-carboxylate

To a mixture of di(imidazol-1-yl)methanethione (2.45 g, 13.73 mmol) in DMF (15 mL) was added a solution of tert-butyl 4-(6-aminopyridin-3-yl)piperazine-1-carboxylate (3 g, 10.56 mmol) in DMF (15 mL). The mixture was stirred at 25° C. for 0.5 h. The crude product tert-butyl 4-(6-isothiocyanatopyridin-3-yl)piperazine-1-carboxylate (3.38 g, crude) in DMF (30 mL) as a solution was used in the next step.

tert-Butyl-4-(6-(3-((5-cyclopropoxypyridin-2-yl)(imino)methyl)thioureido)pyridin-3-yl)piperazine-1-carboxylate To a mixture of tert-butyl 4-(6-isothiocyanatopyridin-3-yl)piperazine-1-carboxylate (3.35 g) in DMF (30 mL) were added diisopropylethylamine (4.05 g, 31.32 mmol) and 5-(cyclopropoxy)pyridine-2-carboxamidine (1.85 g, 10.44 mmol). The mixture was stirred at 25° C. for 1 h. The reaction mixture was poured into H₂O and diluted with EtOAc. The mixture was extracted with EtOAc and the combined organic layers were dried over anhydrous sodium sulfate, filtered and concentrated under vacuum to give tert-butyl 4-(6-(3-((5-cyclopropoxypyridin-2-yl)(imino)methyl)thioureido)pyridin-3-yl)piperazine-1-carboxylate (5.2 g, crude).

tert-Butyl-4-(6-((3-(5-cyclopropoxypyridin-2-yl)-1,2,4-thiadiazol-5-yl)amino) pyridin-3-yl)piperazine-1-carboxylate To a mixture of tert-butyl 4-(6-(3-((5-cyclopropoxypyridin-2-yl)(imino)methyl)thioureido)pyridin-3-yl)piperazine-1-carboxylate (5.2 g) in EtOH (70 mL) was added a solution of iodine (530 mg, 2.09 mmol) in EtOH (10 mL) and hydrogen peroxide (2.37 g, 20.91 mmol, 2.01 mL, 30% purity) under nitrogen. The mixture was stirred at 25° C. for 2 h. The mixture was cooled and poured into saturated sodium sulphite (100 ml). The mixture was triturated with H₂O, filtered and the filter cake dissolved in MeOH and DCM and was concentrated under vacuum. The residue was triturated with ACN (50 mL) and filtered to give tert-butyl 4-(6-((3-(5-cyclopropoxypyridin-2-yl)-1,2,4-thiadiazol-5-yl)amino)pyridin-3-yl)piperazine-1-carboxylate (3.8 g, crude).

3-(5-Cyclopropoxypyridin-2-yl)-N-(5-(piperazin-1-yl)pyridin-2-yl)-1,2,4-thiadiazol-5-amine To a mixture of tert-butyl 4-(6-((3-(5-cyclopropoxypyridin-2-yl)-1,2,4-thiadiazol-5-yl) amino)pyridin-3-yl)piperazine-1-carboxylate (1 g) in DCM (5 mL) was added hydrochloride/dioxane (4 M, 20 mL). The mixture was stirred at 25° C. for 1 h and concentrated to give 3-(5-cyclopropoxypyridin-2-yl)-N-(5-(piperazin-1-yl)pyridin-2-yl)-1,2,4-thiadiazol-5-amine (1 g, crude, HCl). 500 mg of 3-(5-cyclopropoxypyridin-2-yl)-N-(5-(piperazin-1-yl)pyridin-2-yl)-1,2,4-thiadiazol-5-amine as the free amine was recovered in next acid amine coupling.

1-(4-(6-((3-(5-Cyclopropoxypyridin-2-yl)-1,2,4-thiadiazol-5-yl)amino)pyridin-3-yl)piperazin-1-yl)-3,3,3-trifluoropropan-1-one and 1-(4-(6-((3-(5-cyclopropoxypyridin-2-yl)-1,2,4-thiadiazol-5-yl)amino)pyridin-3-yl)piperazin-1-yl)ethanone To a mixture of 3-(5-cyclopropoxypyridin-2-yl)-N-(5-(piperazin-1-yl)pyridin-2-yl)-1,2,4-thiadiazol-5-amine (500 mg, 1.26 mmol), 3,3,3-trifluoropropanoic acid (243 mg, 1.90 mmol) and DIPEA (490 mg, 3.79 mmol) in DMF (50 mL) was added HATU (721 mg, 1.90 mmol) at 0° C. The mixture was stirred at 45° C. for 16 h. The mixture was filtered and the filtrate concentrated to give a residue. The products were isolated and purified by standard methods to give 1-(4-(6-((3-(5-cyclopropoxypyridin-2-yl)-1,2,4-thiadiazol-5-yl)amino)pyridin-3-yl)piperazin-1-yl)-3,3,3-trifluoropropan-1-one (157.96 mg, 0.308 mmol, 24.34% yield); LCMS (ESI) m/z 506.1 [M+1]+ and 1-(4-(6-((3-(5-cyclopropoxypyridin-2-yl)-1,2,4-thiadiazol-5-yl)amino)pyridin-3-yl)piperazin-1-yl)ethanone (32.64 mg, 0.0724 mmol, 5.72% yield, 97% purity); LCMS (ESI) m/z 438.1 [M+1]+.

Example 43: 1-(2-((3-(5-Isopropoxypyridin-2-yl)-1,2,4-thiadiazol-5-yl)amino)pyridin-3-yl)pyrrolidin-2-one

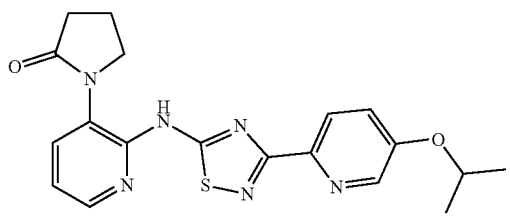 [SMILES: CC(C)Oc1ccc(-c2nsc(Nc3ncccc3N3CCCC3=O)n2)nc1]

1-(2-Nitropyridin-3-yl)pyrrolidin-2-one

A mixture of palladium acetate (1 g, 4.45 mmol) and (5-diphenylphosphanyl-9,9-dimethyl-xanthen-4-yl)-diphenyl-phosphane (2.61 g, 4.51 mmol) in toluene (130 mL) was stirred at 15° C. for 15 min under nitrogen. To the mixture were added 3-bromo-2-nitropyridine (4.5 g, 22.17 mmol), pyrrolidin-2-one (2.25 g, 26.44 mmol, 2.03 mL), copper iodide (846.00 mg, 4.44 mmol) and cesium carbonate (10.80 g, 33.15 mmol), and the mixture was stirred at 75° C. for 4 h under nitrogen. The reaction mixture was cooled to room temperature. The reaction mixture was filtered and the filtrate was concentrated to give a residue. The residue was purified by silica gel column chromatography to give 1-(2-nitropyridin-3-yl)pyrrolidin-2-one (4.5 g, crude).

1-(2-Aminopyridin-3-yl)pyrrolidin-2-one

To a mixture of 1-(2-nitropyridin-3-yl)pyrrolidin-2-one (2.5 g, crude) in trifluoroethanol (50 mL) were added Pd/C (0.5 g, 10% purity) and palladium hydroxide/carbon (0.5 g, 20% purity) under nitrogen. The reaction mixture was degassed under vacuum and purged with hydrogen for 3 times. The reaction mixture was stirred at 60° C. under hydrogen (15 psi) for 3 h. The reaction mixture was filtered and the filtrate was concentrated to afford a crude product. The crude product was purified by silica gel column chromatography to give 1-(2-aminopyridin-3-yl)pyrrolidin-2-one (2.6 g, 10.42 mmol).

1-(2-Isothiocyanatopyridin-3-yl)pyrrolidin-2-one

To a mixture of thiocarbonyl dichloride (1.50 g, 13.05 mmol, 1 mL) in DCM (10 mL) was added a solution of 1-(2-amino-3-pyridyl)pyrrolidin-2-one (1.5 g, 6.01 mmol) in DCM (5 mL) dropwise at 0° C. The mixture was stirred at 0° C. for 1 h. To the mixture was added saturated sodium bicarbonate aqueous and the mixture was separated layers. The aqueous phase was extracted with DCM. The combined organic phases were concentrated under vacuum to give a residue. The residue was purified by silica gel column chromatography to give 1-(2-isothiocyanatopyridin-3-yl)pyrrolidin-2-one (1.2 g, 5.47 mmol, 91.06% yield).

5-Isopropoxy-N-((3-(2-oxopyrrolidin-1-yl)pyridin-2-yl)carbamothioyl)picolinimidamide To a mixture of 1-(2-isothiocyanatopyridin-3-yl)pyrrolidin-2-one (0.35 g, 1.60 mmol) and 5-isopropoxypicolinimidamide (0.29 g, 1.62 mmol) in DCM (7 mL) and acetone (7 mL) was added TEA (1.11 mL, 7.96 mmol). The mixture was stirred at 25° C. for 3 h. To the mixture was added saturated sodium hydrogen bicarbonate, the mixture was was extracted with DCM. The combined organic phases were concentrated to give 5-isopropoxy-N-((3-(2-oxopyrrolidin-1-yl)pyridin-2-yl)carbamothioyl)picolinimidamide (0.63 g, crude).

1-(2-((3-(5-Isopropoxypyridin-2-yl)-1,2,4-thiadiazol-5-yl)amino)pyridin-3-yl)pyrrolidin-2-one To a mixture of 5-isopropoxy-N-((3-(2-oxopyrrolidin-1-yl)pyridin-2-yl) carbamothioyl)picolinimidamide (0.63 g, crude) in EtOH (10 mL) was added a solution of iodine (0.05 g, 0.197 mmol) in EtOH (5 mL) and hydrogen peroxide (0.34 mL, 54 mmol, 30% purity) at 0° C. Then the mixture was stirred at 25° C. for 1 h. To the mixture was added saturated sodium sulfite, the mixture was extracted with DCM, then the combined organic phases were concentrated to give a crude product. The product was isolated and purified by standard methods to give 1-(2-((3-(5-isopropoxypyridin-2-yl)-1,2,4-thiadiazol-5-yl)amino) pyridin- 3-yl)pyrrolidin-2-one (284.3 mg, 0.716 mmol, 99.9% purity). LCMS (ESI): m/z 397.2 [M+1]+.

Example 44: $N^3,N^3$-Dimethyl-$N^2$-(3-(2-methyl-2,3-dihydro-1H-pyrrolo[3,4-c]pyridin-4-yl)-1,2,4-thiadiazol-5-yl)pyridine-2,3-diamine

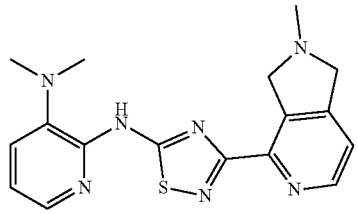 [SMILES: CN1Cc2ccnc(-c3nsc(Nc4ncccc4N(C)C)n3)c2C1]

tert-Butyl-1H-pyrrolo[3,4-c]pyridine-2(3H)-carboxylate

To a mixture of 2,3-dihydro-1H-pyrrolo[3,4-c]pyridine hydrochloride (4 g, 25.54 mmol) and TEA (7.75 g, 76.62 mmol) in DCM (120 mL) was added Boc-anhydride (6.69 g, 30.65 mmol) at 0° C. The mixture was stirred at 10° C. for 3 h and concentrated under vacuum. The residue was purified by silica gel chromatography to give tert-butyl 1H-pyrrolo[3,4-c]pyridine-2(3H)-carboxylate (3.4 g, 15.44 mmol, 60.44% yield).

2-(tert-Butoxycarbonyl)-2,3-dihydro-1H-pyrrolo[3,4-c]pyridine 5-oxide

To a mixture of tert-butyl 1H-pyrrolo[3,4-c]pyridine-2(3H)-carboxylate (3.40 g, 15.44 mmol) in DCM (100 mL) was added m-CPBA (4.00 g, 18.52 mmol, 80% purity) at 0° C. The mixture was stirred at 15° C. for 2 h and concentrated under vacuum. The residue was purified by silica gel chromatography to give 2-(tert-butoxycarbonyl)-2,3-dihydro-1H-pyrrolo[3,4-c]pyridine 5-oxide (3.5 g, 12.44 mmol, 80.62% yield, 84% purity).

tert-Butyl 4-cyano-1H-pyrrolo[3,4-c]pyridine-2(3H)-carboxylate

To a mixture of 2-(tert-butoxycarbonyl)-2,3-dihydro-1H-pyrrolo[3,4-c]pyridine 5-oxide (3.5 g, 12.44 mmol) and trimethylsilyl cyanide (6.17 g, 62.20 mmol) in DCM (100 mL) was added dimethylcarbamic chloride (6.69 g, 62.20 mmol, 5.72 mL). The mixture was stirred at 10° C. for 16 h. The reaction mixture was poured into 100 mL 10% potassium carbonate $H_2O$ solution. The aqueous phase was extracted with DCM. The combined organic phases were dried with anhydrous sodium sulfate, filtered and concentrated in vacuum. The residue was purified by silica gel chromatography to give tert-butyl 4-cyano-1H-pyrrolo[3,4-c]pyridine-2(3H)-carboxylate (2.7 g, 11.01 mmol, 88.49% yield).

tert-Butyl-4-carbamimidoyl-1H-pyrrolo[3,4-c]pyridine-2(3H)-carboxylate hydrochloride Sodium (140.60 mg, 6.12 mmol) was added into MeOH (30 mL). To the mixture was added tert-butyl 4-cyano-1H-pyrrolo[3,4-c]pyridine-2(3H)-carboxylate (3 g, 12.23 mmol). The mixture was stirred at 15° C. for 3 h. Ammonia chloride (981.36 mg, 18.35 mmol) was added. The mixture was stirred at 70° C. for 2 h and was concentrated under vacuum. The residue was diluted with EtOH and the mixture was stirred at 70° C. for 10 min. The mixture was filtered and the filtrate was concentrated to give a solid. The solid was triturated with DCM (30 mL) and the filtrate was concentrated to give tert-butyl 4-carbamimidoyl-1H-pyrrolo[3,4-c]pyridine-2(3H)-carboxylate hydrochloride (3 g, crude).

tert-Butyl-4-(N-((3-(dimethylamino)pyridin-2-yl)carbamothioyl)carbamimidoyl)-1H-pyrrolo[3,4-c]pyridine-2(3H)-carboxylate To a mixture of 2-isothiocyanato-N,N-dimethylpyridin-3-amine (1.2 g, 6.69 mmol) and tert-butyl 4-carbamimidoyl-1H-pyrrolo[3,4-c]pyridine-2(3H)-carboxylate hydrochloride (2.00 g, 6.69 mmol) in DCM (30 mL) and acetone (30 mL) was added TEA (6.77 g, 66.95 mmol). The mixture was stirred at 15° C. for 3 h under nitrogen and concentrated under vacuum. The residue was poured into $H_2O$. The aqueous phase was extracted with EtOAc and the combined organic phases were dried over anhydrous sodium sulfate, filtered and concentrated under vacuum to give tert-butyl 4-(N-((3-(dimethylamino)pyridin-2-yl)carbamothioyl)carbamimidoyl)-1H-pyrrolo[3,4-c]pyridine-2(3H)-carboxylate (4 g, 5.98 mmol, 89.31% yield, 66% purity).

tert-Butyl-4-(5-((3-(dimethylamino)pyridin-2-yl)amino)-1,2,4-thiadiazol-3-yl)-1H-pyrrolo[3,4-c]pyridine-2(3H)-carboxylate To a mixture of tert-butyl-4-(N-((3-(dimethylamino)pyridin-2-yl)carbamothioyl)carbamimidoyl)-1H-pyrrolo[3,4-c]pyridine-2(3H)-carboxylate (4 g, 5.98 mmol, 66% purity) in EtOH (60 mL) were added iodine (303.50 mg, 1.20 mmol) and hydrogen peroxide (2.03 g, 17.94 mmol, 1.72 mL, 30% purity) at 0° C. The mixture was stirred at 15° C. for 0.5 h. The mixture was quenched with saturated sodium sulfite at 0° C. The mixture was concentrated to remove the organic solvent. The aqueous phase was diluted with $H_2O$ and extracted with EtOAc. The combined organic phases were dried with anhydrous sodium sulfate, filtered and concentrated. The residue was purified by silica gel chromatography to give tert-butyl 4-(5-((3-(dimethylamino)pyridin-2-yl)amino)-1,2,4-thiadiazol-3-yl)-1H-pyrrolo[3,4-c]pyridine-2(3H)-carboxylate (2.6 g, 4.91 mmol, 82.12% yield, 83% purity).

$N^2$-(3-(2,3-Dihydro-1H-pyrrolo[3,4-c]pyridin-4-yl)-1,2,4-thiadiazol-5-yl)-$N^3,N^3$-dimethylpyridine-2,3-diamine trifluoroacetic Acid To a mixture of tert-butyl 4-(5-((3-(dimethylamino)pyridin-2-yl)amino)-1,2,4-thiadiazol-3-yl)-1H-pyrrolo[3,4-c]pyridine-2(3H)-carboxylate (1 g, 1.89 mmol) in DCM (10 mL) was added trifluoroacetic acid (3.23 g, 28.33 mmol, 2.10 mL) at 0° C. The mixture was stirred at 20° C. for 2 h and was concentrated under vacuum to give $N^2$-(3-(2,3-Dihydro-1H-pyrrolo[3,4-c]pyridin-4-yl)-1,2,4-thiadiazol-5-yl)-$N^3,N^3$-dimethylpyridine-2,3-diamine trifluoroacetic acid (1.1 g, crude).

$N^3,N^3$-Dimethyl-$N^2$-(3-(2-methyl-2,3-dihydro-1H-pyrrolo[3,4-c]pyridin-4-yl)-1,2,4-thiadiazol-5-yl)pyridine-2,3-diamine To a mixture of $N^2$-(3-(2,3-dihydro-1H-pyrrolo[3,4-c]pyridin-4-yl)-1,2,4-thiadiazol-5-yl)-$N^3,N^3$-dimethylpyridine-2,3-diamine trifluoroacetic acid (1.1 g, 2.43 mmol) in MeOH (20 mL) was added TEA (490.95 mg, 4.85 mmol) at 0° C. The mixture was stirred at 0° C. for 0.1 h. Then formaldehyde (984.32 mg, 12.13 mmol), acetic acid (437.04 mg, 7.28 mmol) and sodium cyanoborohydride (457.34 mg, 7.28 mmol) were added at 0° C. The mixture was stirred at 20° C. for 1 h and was concentrated in reduced pressure. The residue was poured into H$_2$O and saturated sodium bicarbonate. The aqueous phase was extracted with EtOAc. The combined organic phases were dried with anhydrous sodium sulfate, filtered and concentrated in vacuum. The product was isolated and purified by standard methods to give N$^3$,N$^3$-dimethyl-N$^2$-(3-(2-methyl-2,3-dihydro-1H-pyrrolo[3,4-c]pyridin-4-yl)-1,2,4-thiadiazol-5-yl)pyridine-2,3-diamine formic acid (394.61 mg, 0.959 mmol, 39.54% yield). LCMS (ESI) m/z 354.3 [M+1]$^+$.

Example 45: N-Methyl-N-(2-((3-(1-methyl-2,3-dihydro-1H-pyrrolo[2,3-c]pyridin-5-yl)-1,2,4-thiadiazol-5-yl)amino)pyridin-3-yl)acetamide

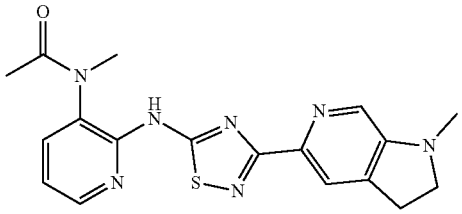 [SMILES: CC(=O)N(C)c1cccnc1Nc1nc(-c2cc3c(cn2)N(C)CC3)ns1]

tert-Butyl 1H-pyrrolo[2,3-c]pyridine-1-carboxylate

To a mixture of 1H-pyrrolo[2,3-c]pyridine (50 g, 423.24 mmol), DMAP (2.59 g, 21.16 mmol) and TEA (85.66 g, 746.48 mmol) in DCM (500 mL) was added Boc-anhydride (96.99 g, 444.4 mmol) was added dropwise at 0° C. The mixture was stirred at 25° C. for 3 h and was concentrated under vacuum. The residue was purified by silica gel chromatography to give tert-butyl 1H-pyrrolo[2,3-c]pyridine-1-carboxylate (90 g, 412.37 mmol, 97.43% yield).

tert-Butyl 2,3-dihydro-1H-pyrrolo[2,3-c]pyridine-1-carboxylate

To a mixture of tert-butyl 1H-pyrrolo[2,3-c]pyridine-1-carboxylate (90 g, 412.37 mmol) in MeOH (1000 mL) were added Pd/C (5 g, 10% purity) and palladium hydroxide/carbon (5 g, 20% purity) under nitrogen. The mixture was stirred at 25° C. for 6 h under hydrogen (50 psi). The mixture was filtered and the filtrate was concentrated under vacuum. The residue was purified by silica gel chromatography to give tert-butyl 2,3-dihydro-1H-pyrrolo[2,3-c]pyridine-1-carboxylate (86 g, 390.44 mmol, 94.68% yield).

1-(tert-Butoxycarbonyl)-2,3-dihydro-1H-pyrrolo[2,3-c]pyridine 6-oxide

Two batches: To a mixture of tert-butyl 2,3-dihydro-1H-pyrrolo[2,3-c]pyridine-1-carboxylate (43 g, 195.2 mmol) in DCM (400 mL) was added m-CPBA (46.32 g, 214.74 mmol, 80% purity) at 0° C. The mixture was stirred at 0° C. for 2 h. And was concentrated under vacuum at 25° C. The mixture was purified by silica gel chromatography to tert-butyl 6-oxido-2,3-dihydropyrrolo[2,3-c]pyridin-6-ium-1-carboxylate (42 g, 177.77 mmol, 45.53% yield, 100% purity). The crude product was purified by silica gel chromatography to give tert-butyl 6-oxido-2,3-dihydropyrrolo[2,3-c]pyridin-6-ium-1-carboxylate (43 g, 180.18 mmol, 46.15% yield).

tert-Butyl-7-cyano-2,3-dihydro-1H-pyrrolo[2,3-c]pyridine-1-carboxylate and tert-butyl 5-cyano-2,3-dihydro-1H-pyrrolo[2,3-c]pyridine-1-carboxylate To a mixture of 1-(tert-butoxycarbonyl)-2,3-dihydro-1H-pyrrolo[2,3-c]pyridine 6-oxide (43 g, 180.18 mmol) in DCM (650 mL) was added N,N-dimethylcarbamoyl chloride (58.13 g, 540.53 mmol) dropwise at 0° C. Then trimethylsilyl cyanide (53.62 g, 540.53 mmol) was added dropwise at 0° C. The mixture was stirred at 25° C. for 16 h. The reaction mixture was poured into 400 mL of 20% potassium carbonate H$_2$O solution. The organic phase was separated and the aqueous phase was extracted with DCM. The combined organic phases were washed with brine, dried with anhydrous sodium sulfate, filtered and concentrated in vacuum. The residue was purified by silica gel chromatography to give tert-butyl 5-cyano-2,3-dihydro-1H-pyrrolo[2,3-c]pyridine-1-carboxylate (16 g, 65.2 mmol, 18.1% yield) and a mixture of tert-butyl 7-cyano-2,3-dihydro-1H-pyrrolo[2,3-c]pyridine-1-carboxylate and tert-butyl 5-cyano-2,3-dihydro-1H-pyrrolo[2,3-c]pyridine-1-carboxylate (78 g, crude). The mixture of tert-butyl 7-cyano-2,3-dihydro-1H-pyrrolo[2,3-c]pyridine-1-carboxylate and tert-butyl 5-cyano-2,3-dihydro-1H-pyrrolo[2,3-c]pyridine-1-carboxylate (78 g, crude) was purified by reverse MPLC (MeCN/H$_2$O, formic acid). The eluent was concentrated to remove ACN and the aqueous phase was extracted with EtOAc. The combined organic phases were dried with anhydrous sodium sulfate, filtered and concentrated in vacuum to give tert-butyl 7-cyano-2,3-dihydro-1H-pyrrolo[2,3-c]pyridine-1-carboxylate (42 g, 171.24 mmol) and tert-butyl 5-cyano-2,3-dihydro-1H-pyrrolo[2,3-c]pyridine-1-carboxylate (11 g, 44.85 mmol).

2,3-Dihydro-1H-pyrrolo[2,3-c]pyridine-5-carbonitrile

To a mixture of tert-butyl 5-cyano-2,3-dihydro-1H-pyrrolo[2,3-c]pyridine-1-carboxylate (10 g, 40.77 mmol) in DCM (80 mL) was added trifluoroacetic acid (80 mL) at 0° C. The mixture was stirred at 0° C. for 2 h and was concentrated under vacuum at 25° C. The residue was diluted with DCM and cold saturated sodium bicarbonate. The organic phase was separated and the aqueous phase was extracted with DCM. The combined organic phases were dried with anhydrous sodium sulfate, filtered and concentrated in vacuum to give 2,3-dihydro-1H-pyrrolo[2,3-c]pyridine-5-carbonitrile (7 g, crude).

1-Methyl-2,3-dihydro-1H-pyrrolo[2,3-c]pyridine-5-carbonitrile

To a mixture of 2,3-dihydro-1H-pyrrolo[2,3-c]pyridine-5-carbonitrile (7 g, crude), acetic acid (2.90 g, 48.22 mmol) and formaldehyde (19.57 g, 241.11 mmol, 17.95 mL, 37%) in MeOH (150 mL) was added sodium cyanoborohydride (6.06 g, 96.44 mmol) at 0° C. The mixture was stirred at 25° C. for 16 h and was concentrated under vacuum. The residue was poured into cold saturated sodium bicarbonate and the aqueous phase was extracted with DCM. The combined organic phases were dried with anhydrous sodium, filtered and concentrated in vacuum. The residue was purified by silica gel chromatography to give 3.5 g of product and 3 g of crude product. 3 g of crude product was purified by reverse MPLC (1/1000, FA) to give 0.8 of product. Two batches products were combined to give 1-methyl-2,3-dihydro-1H-pyrrolo[2,3-c]pyridine-5-carbonitrile (4.3 g, 27.01 mmol, 56.05% yield, 100% purity).

1-Methyl-2,3-dihydro-1H-pyrrolo[2,3-c]pyridine-5-carboximidamide Hydrochloride

To the mixture of 1-methyl-2,3-dihydro-1H-pyrrolo[2,3-c]pyridine-5-carbonitrile (4.3 g, 27.01 mmol) in MeOH (60 mL) was added sodium methoxide (729.65 mg, 13.51 mmol) (freshly prepared). The mixture was stirred at 30° C. for 16 h. NH$_4$Cl (2.17 g, 40.52 mmol) was added. The mixture was stirred at 70° C. for 1 h. and was concentrated under vacuum. The residue was diluted with 150 mL of EtOH and stirred at 80° C. for 0.5 h. The mixture was filtered and the filtrate was concentrated to give a solid. The solid was triturated with MTBE (100 mL) and filtered. The filter cake was collected dried to give 1-methyl-2,3-dihydropyrrolo[2,3-c]pyridine-5-carboxamidine hydrochloride (4 g, 18.81 mmol, 69.64% yield). The filtrate was concentrated to give 1-methyl-2,3-dihydropyrrolo[2,3-c]pyridine-5-carbonitrile (1 g, crude).

tert-Butyl-(2-(3-(Imino(1-methyl-2,3-dihydro-1H-pyrrolo[2,3-c]pyridin-5-yl)methyl)thioureido)pyridin-3-yl)(methyl)carbamate To a 1-methyl-2,3-dihydro-1H-pyrrolo[2,3-c]pyridine-5-carboximidamide hydrochloride (3 g, 14.11 mmol) and tert-butyl (2-isothiocyanatopyridin-3-yl)(methyl)carbamate (3.74 g, 14.11 mmol) in DMF (100 mL) was added triethylamine (7.14 g, 70.53 mmol, 9.82 mL, 5 eq). The mixture was stirred at 30° C. for 16 h under nitrogen. The mixture was poured into H$_2$O and the aqueous phase was extracted with EtOAc. The combined organic phases were washed with brine, dried with anhydrous sodium sulfate, filtered and concentrated in vacuum to give tert-butyl (2-(3-(imino(1-methyl-2,3-dihydro-1H-pyrrolo[2,3-c]pyridin-5-yl)methyl)thioureido)pyridin-3-yl)(methyl)carbamate (6 g, crude).

tert-Butyl Methyl(2-((3-(1-methyl-2,3-dihydro-1H-pyrrolo[2,3-c]pyridin-5-yl)-1,2,4-thiadiazol-5-yl)amino)pyridin-3-yl)carbamate To a mixture of tert-butyl (2-(3-(imino(1-methyl-2,3-dihydro-1H-pyrrolo[2,3-c]pyridin-5-yl)methyl)thioureido)pyridin-3-yl)(methyl)carbamate (6.5 g, crude) in EtOH (100 mL) were added iodine (747.26 mg, 2.94 mmol) and hydrogen peroxide (3.34 g, 29.44 mmol, 30% purity) at 0° C. The mixture was stirred at 20° C. for 1 h. The mixture was quenched with saturated sodium sulfite at 0° C. and was concentrated to remove the organic solvent. The aqueous phase was diluted with H$_2$O and extracted with DCM. The combined organic phases were dried with anhydrous sodium sulfate, filtered and concentrated. The residue was purified by silica gel chromatography to give 2.7 g of crude product. The crude product was triturated with 20 mL of MeOH to give tert-butyl methyl(2-((3-(1-methyl-2,3-dihydro-1H-pyrrolo[2,3-c]pyridin-5-yl)-1,2,4-thiadiazol-5-yl)amino)pyridin-3-yl)carbamate (2.1 g, 4.78 mmol, 32.46% yield).

N$^3$-Methyl-N$^2$-(3-(1-methyl-2,3-dihydro-1H-pyrrolo[2,3-c]pyridin-5-yl)-1,2,4-thiadiazol-5-yl)pyridine-2,3-diamine To a mixture of tert-butyl methyl(2-((3-(1-methyl-2,3-dihydro-1H-pyrrolo[2,3-c]pyridin-5-yl)-1,2,4-thiadiazol-5-yl)amino)pyridin-3-yl)carbamate (2.10 g, 4.78 mmol) in EtOAc (50 mL) was added hydrochloride/EtOAc (4 M, 50 mL) at 0° C. The mixture was stirred at 30° C. for 0.5 h and was concentrated under vacuum to give N$^3$-methyl-N$^2$-(3-(1-methyl-2,3-dihydro-1H-pyrrolo[2,3-c]pyridin-5-yl)-1,2,4-thiadiazol-5-yl)pyridine-2,3-diamine hydrochloride (1.8 g, crude).

N-Methyl-N-(2-((3-(1-methyl-2,3-dihydro-1H-pyrrolo[2,3-c]pyridin-5-yl)-1,2,4-thiadiazol-5-yl)amino) pyridin-3-yl)acetamide To a mixture of N$^3$-methyl-N$^2$-(3-(1-methyl-2,3-dihydro-1H-pyrrolo[2,3-c]pyridin-5-yl)-1,2,4-thiadiazol-5-yl)pyridine-2,3-diamine hydrochloride (1.8 g, 4.79 mmol) and Ac$_2$O (733.32 mg, 7.18 mmol) in ACN (40 mL) was added TEA (2.42 g, 23.94 mmol, 3.33 mL). The mixture was stirred at 45° C. for 16 h and was concentrated under vacuum. The product was isolated and purified by standard methods to give N-methyl-N-(2-((3-(1-methyl-2,3-dihydro-1H-pyrrolo[2,3-c]pyridin-5-yl)-1,2,4-thiadiazol-5-yl) amino)pyridin-3-yl)acetamide formic acid (808.16 mg, 1.88 mmol, 39.28% yield) and N$^3$-methyl-N$^2$-(3-(1-methyl-2,3-dihydro-1H-pyrrolo[2,3-c]pyridin-5-yl)-1,2,4-thiadiazol-5-yl)pyridine-2,3-diamine (2 g, crude). LCMS (ESI): m/z 382.2 [M+1]$^+$.

Example 46: N-(2-((3-(2,2-Dimethyl-2,3-dihydrofuro[2,3-c]pyridin-5-yl)-1,2,4-thiadiazol-5-yl)amino) pyridin-3-yl)-N-methylacetamide

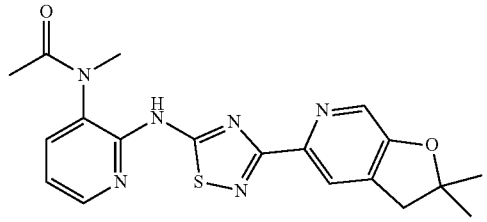 [SMILES: CC(=O)N(C)c1cccnc1Nc1nc(-c2cc3c(cn2)OC(C)(C)C3)ns1]

1-(3-Bromopyridin-4-yl)-2-methylpropan-2-ol

In two batches, LDA (2 M, 87.20 mL) was added to a mixture of 3-bromo-4-methyl-pyridine (25 g, 145.33 mmol, 16.13 mL) in THF (250 mL) at 0° C., the mixture was stirred at 0° C. for 1 h.

To the mixture was added acetone (16.88 g, 290.66 mmol, 21.37 mL) at 0° C. in one portion, the mixture was stirred at 20° C. for 3 h. The 2 batches mixture were combined and quenched with saturated NH$_4$Cl, the aqueous phase was extracted with EtOAc. The combined organic phases were concentrated under vacuum to give a residue. The residue was purified by silica gel column chromatography to give 1-(3-bromopyridin-4-yl)-2-methylpropan-2-ol (39 g, 169.49 mmol, 58.31% yield).

2,2-Dimethyl-2,3-dihydrofuro[2,3-c]pyridine

To a mixture of 1-(3-bromopyridin-4-yl)-2-methylpropan-2-ol (39 g, 169.49 mmol), cesium carbonate (110.45 g, 338.98 mmol) in toluene (350 mL) was added cuprous iodide (3.23 g, 16.95 mmol) and 8-hydroxyquinoline (3.69 g, 25.42 mmol). The mixture was stirred at 120° C. for 24 h under nitrogen. The mixture was filtered through a pad of celite and silica gel, the filtrate was concentrated under vacuum to give a residue. The residue was purified by silica gel column chromatography to give 2,2-dimethyl-2,3-dihydrofuro[2,3-c]pyridine (18 g, 120.65 mmol, 71.19% yield).

2,2-Dimethyl-2,3-dihydrofuro[2,3-c]pyridine 6-oxide

To a mixture of 2,2-dimethyl-2,3-dihydrofuro[2,3-c]pyridine (18 g, 120.65 mmol) in DCM (150 mL) was added m-CPBA (26.23 g, 121.59 mmol, 80% purity) at 0° C., the mixture was stirred at 20° C. for 4 h. The mixture was purified directly, without work-up. The mixture was purified by silica gel column chromatography to give 2,2-dimethyl-2,3-dihydrofuro[2,3-c]pyridine 6-oxide (18 g, 108.97 mmol, 90.31% yield).

2,2-Dimethyl-2,3-dihydrofuro[2,3-c]pyridine-5-carbonitrile

To a mixture of 2,2-dimethyl-2,3-dihydrofuro[2,3-c]pyridine 6-oxide (18 g, 108.97 mmol) in DCM (150 mL) were added trimethylsilyl cyanide (32.43 g, 326.90 mmol, 40.90 mL) and N,N-dimethylcarbamoyl chloride (35.15 g, 326.90 mmol, 30.05 mL), the mixture was warmed to 20° C. under 2 h and stirred at 20° C. for 12 h. The mixture was poured into saturated sodium bicarbonate, the aqueous phase was extracted with DCM, and the combined organic phases were concentrated under vacuum to give a residue. The residue was purified by silica gel column chromatography to give 2,2-dimethyl-2,3-dihydrofuro[2,3-c]pyridine-5-carbonitrile (1.6 g, 9.18 mmol, 8.43% yield) and 2,2-dimethyl-3H-furo[2,3-c]pyridine-7-carbonitrile (15 g, 86.11 mmol, 79.02% yield).

2,2-Dimethyl-2,3-dihydrofuro[2,3-c]pyridine-5-carboximidamide

To a mixture of 2,2-dimethyl-2,3-dihydrofuro[2,3-c]pyridine-5-carbonitrile (1.8 g, 10.33 mmol) in MeOH (10 mL) was added sodium methoxide (167.47 mg, 3.10 mmol). The mixture was stirred at 20° C. for 14 h. To the mixture was added sodium methoxide (111.65 mg, 2.07 mmol). The mixture was stirred at 30° C. for 2 h. To the mixture was added NH$_4$Cl (829.09 mg, 15.50 mmol). The mixture was stirred at 70° C. for 1 h and was concentrated under vacuum to give a residue. The residue was triturated with MTBE (60 mL), the filter cake was collected. To a mixture of the filter cake in ACN:H$_2$O (2:1, 100 mL) was added Amberlyst A-26 (2 g), the mixture was stirred at 20° C. for 30 min, the mixture was filtered and the filtrate was dried by lyophilization to give 2,2-dimethyl-2,3-dihydrofuro[2,3-c]pyridine-5-carboximidamide (1.8 g, 7.91 mmol, 76.51% yield).

tert-Butyl(2-(3-((2,2-dimethyl-2,3-dihydrofuro[2,3-c]pyridin-5-yl)(imino)methyl) thioureido)pyridin-3-yl)(methyl)carbamate To a mixture of tert-butyl (2-isothiocyanatopyridin-3-yl)(methyl)carbamate (0.5 g, 1.88 mmol) and 2,2-dimethyl-2,3-dihydrofuro[2,3-c]pyridine-5-carboximidamide (360 mg, 1.88 mmol) in acetone (30 mL) and DCM (30 mL) was added TEA (953.43 mg, 9.42 mmol, 1.31 mL). The mixture was stirred at 30° C. for 2 h under nitrogen and was concentrated under vacuum to give tert-butyl (2-(3-((2,2-dimethyl-2,3-dihydrofuro[2,3-c]pyridin-5-yl)(imino)methyl)thioureido)pyridin-3-yl)(methyl)carbamate (0.86 g, crude).

tert-Butyl-(2-((3-(2,2-dimethyl-2,3-dihydrofuro[2,3-c]pyridin-5-yl)-1,2,4-thiadiazol-5-yl)amino)pyridin-3-yl)(methyl)carbamate To a mixture of tert-butyl (2-(3-((2,2-dimethyl-2,3-dihydrofuro[2,3-c]pyridin-5-yl)(imino)methyl)thioureido)pyridin-3-yl)(methyl)carbamate (0.86 g, crude) in EtOH (30 mL) were added iodine (95.62 mg, 0.376 mmol) and hydrogen peroxide (427 mg, 3.77 mmol, 30% purity) at 0° C. The mixture was stirred at 20° C. for 1 h. The mixture was quenched with saturated sodium sulfite at 0° C. and was concentrated. The aqueous phase was diluted with H$_2$O and extracted with EtOAc. The combined organic phases were dried with anhydrous sodium sulfate, filtered and concentrated. The residue was purified by silica gel chromatography to give tert-butyl (2-((3-(2,2-dimethyl-2,3-dihydrofuro[2,3-c]pyridin-5-yl)-1,2,4-thiadiazol-5-yl) amino)pyridin-3-yl)(methyl)carbamate (0.55 g, 1.21 mmol, 64.24% yield).

$N^2$-(3-(2,2-Dimethyl-2,3-dihydrofuro[2,3-c]pyridin-5-yl)-1,2,4-thiadiazol-5-yl)-$N^3$-methylpyridine-2,3-diamine hydrochloride To a mixture of tert-butyl (2-((3-(2,2-dimethyl-2,3-dihydrofuro[2,3-c]pyridin-5-yl)-1,2,4-thiadiazol-5-yl)amino) pyridin-3-yl)(methyl)carbamate (0.55 g, 1.21 mmol) in EtOAc (5 mL) was added hydrochloride/EtOAc (4 M, 10 mL) The mixture was stirred at 20° C. for 1 h and was concentrated under vacuum to give $N^2$-(3-(2,2-dimethyl-2,3-dihydrofuro[2,3-c]pyridin-5-yl)-1,2,4-thiadiazol-5-yl)-$N^3$-methylpyridine-2,3-diamine hydrochloride (0.47 g, crude).

N-(2-((3-(2,2-Dimethyl-2,3-dihydrofuro[2,3-c]pyridin-5-yl)-1,2,4-thiadiazol-5-yl)amino)pyridin-3-yl)-N-methylacetamide To a mixture of $N^2$-(3-(2,2-dimethyl-2,3-dihydrofuro[2,3-c]pyridin-5-yl)-1,2,4-thiadiazol-5-yl)-$N^3$-methylpyridine-2,3-diamine hydrochloride (0.47 g, crude) and TEA (608.35 mg, 6.01 mmol) in ACN (20 mL) was added Ac$_2$O (159.57 mg, 1.56 mmol). The mixture was stirred at 30° C. for 16 h and was concentrated under vacuum. The product was isolated and purified by standard methods to give N-[2-[[3-(2,2-dimethyl-3H-furo[2,3-c]pyridin-5-yl)-1,2,4-thiadiazol-5-yl]amino]-3-pyridyl]-N-methylacetamide (182.76 mg, 0.461 mmol, 38.30% yield). LCMS (ESI): m/z 397.2 [M+1]$^+$.

Example 47: 3-(5-Isopropoxypyridin-2-yl)-N-isopropyl-N-(3-methylpyridin-2-yl)-1,2,4-thiadiazol-5-amine

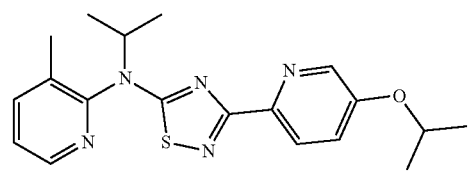 [SMILES: Cc1cccnc1N(c1nc(-c2ccc(OC(C)C)cn2)ns1)C(C)C]

N-Isopropyl-3-methylpyridin-2-amine

To a mixture of 3-methylpyridin-2-amine (3 g, 27.74 mmol) in THF (60 mL) was added butyl lithium (2.5 M, 13.32 mL) slowly at −70° C. under nitrogen. The mixture was stirred at 0° C. for 30 min. Then 2-iodopropane (5.19 g, 30.51 mmol) in THF (5 mL) was added slowly at 0° C. and the mixture was stirred at 25° C. for 16 h. The mixture was stirred at 65° C. for 16 h. The mixture was quenched with saturated NH$_4$Cl at 0° C. and the resulting mixture was extracted with EtOAc. The combined organic phases were washed with brine, dried over sodium sulfate, filtered and concentrated at reduced pressure to give a residue. The residue was purified by silica gel chromatography to give N-isopropyl-3-methyl-pyridin-2-amine (1.3 g, 8.65 mmol, 31.20% yield).

O-Phenyl isopropyl(3-methylpyridin-2-yl)carbamothioate

To a mixture of N-isopropyl-3-methyl-pyridin-2-amine (1.20 g, 7.99 mmol) and potassium carbonate (3.31 g, 23.96 mmol) in THF (20 mL) was added O-phenyl carbonochloridothioate (2.76 g, 15.98 mmol) which was dissolved with THF (5 mL) slowly at 0° C. under nitrogen. The mixture was stirred at 25° C. for 16 h and then filtered and the filtrate was concentrated at reduced pressure to give a residue. The residue was purified by silica gel chromatography to give O-phenyl isopropyl(3-methylpyridin-2-yl)carbamothioate (2.2 g, 7.37 mmol, 92.32% yield, 96% purity).

5-Isopropoxy-N-(isopropyl(3-methylpyridin-2-yl)carbamothioyl) picolinimidamide and O-phenyl isopropyl(3-methylpyridin-2-yl)carbamothioate To a mixture of O-phenyl isopropyl(3-methylpyridin-2-yl)carbamothioate (1.54 g, 5.36 mmol) and 5-isopropoxypicolinimidamide (1.15 g, 6.44 mmol) in anhydrous DMSO (15 mL) was added potassium tert-butoxide (1 M, 6.44 mL) slowly. The mixture was stirred at 25° C. for 16 h. The mixture was poured into H$_2$O and the resulting mixture was extracted with EtOAc. The combined organic phases were washed with brine, dried over sodium sulfate, filtered and concentrated at reduced pressure to give a residue. The residue was purified by silica gel chromatography to give 5-isopropoxy-N-(isopropyl(3-methylpyridin-2-yl)carbamothioyl)picolinimidamide (0.42 g, 1.13 mmol, 21.08% yield) and O-phenyl isopropyl(3-methylpyridin-2-yl)carbamothioate (1 g, 3.49 mmol, 65.10% yield).

3-(5-Isopropoxypyridin-2-yl)-N-isopropyl-N-(3-methylpyridin-2-yl)-1,2,4-thiadiazol-5-amine To a mixture of 5-isopropoxy-N-(isopropyl(3-methylpyridin-2-yl)carbamothioyl) picolinimidamide (0.42 g, 1.13 mmol) and hydrogen peroxide (256 mg, 2.26 mmol, 30% purity) in EtOH (10 mL) was added iodine (57.39 mg, 0.226 mmol). The mixture was stirred at 25° C. for 1 h. The mixture was quenched with saturated sodium sulfite at 0° C. and the resulting mixture was concentrated at reduced pressure to give a residue. The residue was diluted with H$_2$O and the aqueous phase was extracted with EtOAc, the combined organic phases were washed with brine, dried over sodium sulfate, filtered and concentrated at reduced pressure to give a residue. The product was isolated and purified by standard methods to give 3-(5-isopropoxypyridin-2-yl)-N-isopropyl-N-(3-methylpyridin-2-yl)-1,2,4-thiadiazol-5-amine formic acid (254.92 mg, 0.607 mmol, 53.72% yield). LCMS (ESI): m/z 370.1 [M+1]+.

Example 48: 5-(5-Isopropoxypyridin-2-yl)-N-(5-isopropyl-4-(trifluoromethyl)pyridin-2-yl)-1,3,4-oxadiazol-2-amine

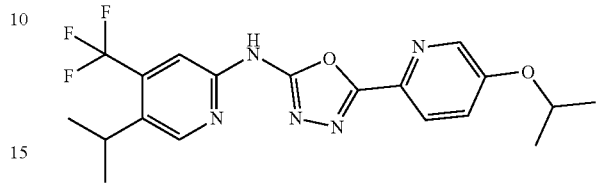

5-(Prop-1-en-2-yl)-4-(trifluoromethyl)pyridin-2-amine

To a mixture of 5-bromo-4-(trifluoromethyl)pyridin-2-amine (20 g, 82.98 mmol), potassium hydride;trifluoro(isopropenyl)boron (18.42 g, 124.48 mmol) and cesium carbonate (54.08 g, 165.97 mmol) in dioxane (500 mL) and H$_2$O (50 mL) was added bis(diphenylphosphino)ferrocene] dichloropalladium (3.04 g, 4.15 mmol) under nitrogen. The mixture was then stirred at 80° C. for 5 h. The mixture was filtered and the filtrate was concentrated to give the aqueous phase. The aqueous phase was extracted with EtOAc. The organic phase was washed with brine, dried with anhydrous sodium sulfate, filtered and concentrated in vacuum. The residue was purified by silica gel chromatography to give 5-(prop-1-en-2-yl)-4-(trifluoromethyl)pyridin-2-amine (13 g, 51.44 mmol, 61.99% yield).

5-Isopropyl-4-(trifluoromethyl)pyridin-2-amine

To a mixture of 5-(prop-1-en-2-yl)-4-(trifluoromethyl) pyridin-2-amine (13 g, 51.44 mmol) in MeOH (180 mL) was added Pd/C (800 mg, 10% purity) and palladium hydroxide (800 mg, 20% purity). The mixture was stirred at 25° C. for 16 h under hydrogen (15 psi). The mixture was filtered and the filtrate was concentrated to give 12 g of crude product as solid. To a mixture of 12 g of crude product in MeOH (150 mL) was added Pd/C (600 mg, 10% purity) and palladium hydroxide (600 mg, 20% purity). The mixture was stirred at 15° C. for 5 h under hydrogen (15 psi) and then for an additional 16 h at 15° C. under hydrogen (15 psi). The mixture was filtered and the filtrate was concentrated to give 12 g of crude product. To a mixture of 5-(prop-1-en-2-yl)-4-(trifluoromethyl)pyridin-2-amine (12 g, crude) in MeOH (100 mL) were added palladium hydroxide (0.4 g, 20% purity) and Pd/C (0.5 g, 10% purity) under nitrogen. The mixture was stirred at 15° C. for 16 h under hydrogen (15 psi). HNMR of a sample showed 10% of double bond remained. The mixture was stirred at 15° C. for 16 h under hydrogen (15 psi). The mixture was filtered and the filtrate was concentrated to give 5-isopropyl-4-(trifluoromethyl) pyridin-2-amine (12 g, 58.77 mmol).

5-Isopropyl-2-isothiocyanato-4-(trifluoromethyl) pyridine

To a mixture of thiophosgene (2.25 g, 19.59 mmol) in DCM (50 mL) was added a mixture of 5-isopropyl-4-(trifluoromethyl)pyridin-2-amine (2 g, 9.79 mmol) in DCM (10 mL) at 0° C. The mixture was stirred at 0° C. for 1 h. The saturated sodium bicarbonate was added to the mixture until pH=8, then resulting mixture was extracted with DCM. The combined organic phases were concentrated. The residue was purified by column chromatography to give 5-isopropyl-2-isothiocyanato-4-(trifluoromethyl)pyridine (0.9 g, 3.65 mmol, 37.31% yield).

2-(5-Isopropoxypicolinoyl)-N-(5-isopropyl-4-(trifluoromethyl)pyridin-2-yl) hydrazinecarbothioamide To a mixture of 5-isopropyl-2-isothiocyanato-4-(trifluoromethyl)pyridine (0.5 g, 2.03 mmol) in DCM (20 mL) was added 5-isopropoxypicolinohydrazide (455.61 mg, 2.03 mmol). The mixture was stirred at 15° C. for 16 h and was concentrated to give 0.9 g of crude product. 0.8 g of crude product was purified by silica gel chromatography to give 2-(5-isopropoxypicolinoyl)-N-(5-isopropyl-4-(trifluoromethyl)pyridin-2-yl)hydrazinecarbothioamide (0.9 g, 1.53 mmol, 75.30% yield, 75% purity).

5-(5-Isopropoxypyridin-2-yl)-N-(5-isopropyl-4-(trifluoromethyl)pyridin-2-yl)-1,3,4-oxadiazol-2-amine To a mixture of 2-(5-isopropoxypicolinoyl)-N-(5-isopropyl-4-(trifluoromethyl)pyridin-2-yl)hydrazinecarbothioamide (0.85 g, 1.44 mmol) in DMSO (20 mL) was added EDCI (553.65 mg, 2.89 mmol). The mixture was stirred at 60° C. for 2 h. The mixture was poured into 100 mL of H$_2$O and diluted with 200 mL of EtOAc. The organic phase was separated and washed with brine, dried with anhydrous sodium sulfate, filtered and concentrated in vacuum. The product was isolated and purified by standard methods to give 5-(5-isopropoxypyridin-2-yl)-N-(5-isopropyl-4-(trifluoromethyl)pyridin-2-yl)-1,3,4-oxadiazol-2-amine (211.6 mg, 0.506 mmol, 35.03% yield). LCMS (ESI) m/z 408.1 [m+1]$^+$.

Example 49: $N^2$-(5-(5-Methoxypyrazin-2-yl)-1,3,4-oxadiazol-2-yl)-$N^3$,$N^3$-dimethylpyridine-2,3-diamine

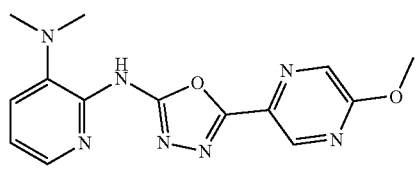 [SMILES: COc1cnc(-c2nnc(Nc3ncccc3N(C)C)o2)cn1]

Methyl 5-isopropoxypyrazine-2-carboxylate

To the mixture of methyl 5-chloropyrazine-2-carboxylate (5 g, 28.97 mmol) and propan-2-ol (1.92 g, 31.87 mmol, 2.44 mL) in DMF (50 mL) was added cesium carbonate (18.88 g, 57.95 mmol). The mixture was stirred at 25° C. for 16 h. To the mixture was added cesium carbonate (18.88 g, 57.95 mmol) and propan-2-ol (2.61 g, 43.46 mmol, 3.33 mL). The mixture was stirred at 30° C. for 24 h. To the mixture was added EtOAc (250 mL), the mixture was filtered. The filtrate was washed with brine, dried with anhydrous sodium sulfate, concentrated under reduce pressure to give a residue. The residue was purified by silica gel chromatography to give methyl 5-isopropoxypyrazine-2-carboxylate (1.65 g, 7.99 mmol, 27.57% yield, 95% purity) and 2.1 g crude product. Then 2.1 g crude product purified by silica gel chromatography to give to give methyl 5-isopropoxypyrazine-2-carboxylate (0.9 g, 4.59 mmol, 15.83% yield).

5-Methoxypyrazine-2-carbohydrazide

A mixture of methyl 5-isopropoxypyrazine-2-carboxylate (1.65 g, 7.99 mmol) and hydrazine hydrate (479.93 mg, 9.59 mmol, 465.95 µL) in MeOH (20 mL) was stirred at 70° C. for 10 h. The reaction mixture was suspended and the suspension filtered to give 5-methoxypyrazine-2-carbohydrazide (0.8 g, 4.76 mmol, 59.55% yield).

N-(3-(Dimethylamino)pyridin-2-yl)-2-(5-methoxypyrazine-2-carbonyl) hydrazinecarbothioamide A mixture of 5-methoxypyrazine-2-carbohydrazide (0.8 g, 4.76 mmol) and 2-isothiocyanato-N,N-dimethyl-pyridin-3-amine (730.83 mg, 4.08 mmol) in DCM (20 mL) was stirred at 20° C. for 16 h. The mixture was suspended and concentrated under reduced pressure to give a residue. Then the residue was triturated with MeOH (20 mL) to give a mixture of 5-methoxypyrazine-2-carbohydrazide and N-(3-(dimethylamino)pyridin-2-yl)-2-(5-methoxypyrazine-2-carbonyl)hydrazinecarbothioamide (1.4 g, crude). A mixture of 5-methoxypyrazine-2-carbohydrazide and N-(3-(dimethylamino)pyridin-2-yl)-2-(5-methoxypyrazine-2-carbonyl)hydrazinecarbothioamide (1.4 g, crude) and 2-isothiocyanato-N,N-dimethylpyridin-3-amine (400 mg, 2.23 mmol) in DCM (40 mL) was stirred at 20° C. for 16 h. The mixture was filtered to give filter cake. N-(3-(dimethylamino)pyridin-2-yl)-2-(5-methoxypyrazine-2-carbonyl)hydrazinecarbothioamide (0.8 g, 2.30 mmol, 88.39% yield) and the filtrate was concentrated to give a crude product. The crude product was purified by column chromatography to give N-(3-(dimethylamino)pyridin-2-yl)-2-(5-methoxypyrazine-2-carbonyl)hydrazinecarbothioamide (0.6 g, 1.73 mmol, 66.37% yield).

$N^2$-(5-(5-Methoxypyrazin-2-yl)-1,3,4-oxadiazol-2-yl)-$N^3$,$N^3$-dimethylpyridine-2,3-diamine A mixture of N-(3-(dimethylamino)pyridin-2-yl)-2-(5-methoxypyrazine-2-carbonyl)hydrazinecarbothioamide (0.7 g, 2.01 mmol) and N-(3-dimethylaminopropyl)-N'-ethylcarbodiimide hydrochloride (772.56 mg, 4.03 mmol) in DMSO (20 mL) was stirred at 60° C. for 2 h. The mixture was diluted with H$_2$O, the resulting mixture was extracted with EtOAc. The combined organic phases were washed with brine, dried with anhydrous sodium sulfate, concentrated under reduce pressure to give the crude product. The product was isolated and purified by standard methods to give $N^2$-(5-(5-methoxypyrazin-2-yl)-1,3,4-oxadiazol-2-yl)-$N^3$,$N^3$-dimethylpyridine-2,3-diamine (179.70 mg, 0.500 mmol, 24.82% yield, formic acid). LCMS (ESI): m/z 314.1 [M+1]$^+$ Example 50: 5-Isopropyl-N-(1-methyl-5-(pyridin-2-yl)-1H-1,2,4-triazol-3-yl)-4-(trifluoromethyl)pyridin-2-amine

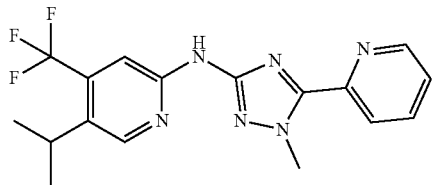 [SMILES: CC(C)c1cnc(Nc2nc(-c3ccccn3)n(C)n2)cc1C(F)(F)F]

5-Isopropyl-2-isothiocyanato-4-(trifluoromethyl) pyridine

To a mixture of thiophosgene (4 g, 35.26 mmol, 2.70 mL) in DCM (100 mL) was added a mixture of 5-isopropyl-4-(trifluoromethyl) pyridin-2-amine (3.6 g, 17.63 mmol) in DCM (30 mL) at 0° C. The mixture was stirred at 0° C. for 2 h. The residue was cooled at 0° C. The mixture was added saturated sodium bicarbonate and the aqueous phase was extracted with DCM. The combined organic layers were dried over sodium sulfate, filtered and concentrated under reduced pressure to give a residue. The residue was purified by silica gel chromatography to give 5-isopropyl-N-(1-methyl-5-(pyridin-2-yl)-1H-1,2,4-triazol-3-yl)-4-(trifluoromethyl)pyridin-2-amine (3 g, 12.18 mmol, 69.10% yield).

5-Isopropyl-N-(1-methyl-5-(pyridin-2-yl)-1H-1,2,4-triazol-3-yl)-4-(trifluoromethyl)pyridin-2-amine To a mixture of 5-isopropyl-2-isothiocyanato-4-(trifluoromethyl)pyridine (2 g, 8.12 mmol) in DCM (20 mL) was added ammonium hydroxide (3.42 g, 24.37 mmol, 3.75 mL, 25% purity). The mixture was stirred at 25° C. for 1 h. The residue was concentrated in vacuum. The mixture was diluted with $H_2O$. The aqueous phase was extracted with EtOAc. The organic phase was dried with anhydrous sodium sulfate and filtered. The filtrate was concentrated under vacuum to give methyl(5-isopropyl-4-(trifluoromethyl)pyridin-2-yl)carbamimidothioate (2 g, crude).

Methyl (5-isopropyl-4-(trifluoromethyl)pyridin-2-yl) carbamimidothioate

To a mixture of [5-isopropyl-4-(trifluoromethyl)-2-pyridyl]thiourea (2 g, crude) in ACN (20 mL) was added iodomethane (1.40 g, 9.86 mmol). The mixture was stirred at 70° C. for 1 h. and was concentrated. The residue was diluted with $H_2O$. The aqueous phase was adjusted to pH=8 with saturated sodium bicarbonate. The aqueous phase was extracted with EtOAc and the combined organic phases were dried over anhydrous sodium sulfate, filtered and concentrated under vacuum. The residue was purified by column chromatography followed by lyophilization to give 1-[5-isopropyl-4-(trifluoromethyl)-2-pyridyl]-2-methyl-isothiourea (2 g, 7.21 mmol).

tert-Butyl 2-methyl-2-picolinoylhydrazinecarboxylate

To a mixture of pyridine-2-carboxylic acid (1.5 g, 12.18 mmol) and tert-butyl N-(methylamino)carbamate (1.78 g, 12.18 mmol) in DCM (60 mL) was added DIPEA (4.72 g, 36.55 mmol, 6.37 mL), hydroxybenzo (1.98 g, 14.62 mmol) and carbodiimide (2.80 g, 14.62 mmol). The mixture was stirred at 25° C. for 3 h. The mixture was diluted with DCM (30 mL), washed with aqueous hydrochloric acid (1 M, 40 mL) and $H_2O$. The organic phase was dried over sodium sulfate and filtered. The filtrate was concentrated under vacuum to give a crude product. The crude product was purified by silica gel chromatography to give tert-butyl N-[methyl(pyridine-2-carbonyl)amino]carbamate (2.2 g, 8.76 mmol, 71.86% yield).

N-Methylpicolinohydrazide hydrochloride

To a mixture of tert-butyl N-[methyl(pyridine-2-carbonyl) amino]carbamate (1 g, 3.98 mmol) in EtOAc (20 mL) was added EtOAc hydrochloric acid (4M, 20 mL). The mixture was stirred at 25° C. for 2 h. The mixture was filtered and the filter cake concentrated to give the crude product. The crude product was triturated with EtOAc (20 mL) to give N-methylpyridine-2-carbohydrazide (580 mg, 3.84 mmol, 96.41% yield).

N-Methylpicolinohydrazide

To a mixture of N-methylpyridine-2-carbohydrazide (1 g, 5.33 mmol, HCl) in MeOH (15 mL) was added Amberlyst A-26 (2 g). The mixture was stirred at 25° C. for 30 min. The mixture was filtered and the filtrate was concentrated. The residue was purified by silica gel chromatography to give N-methylpyridine-2-carbohydrazide (550 mg, 3.64 mmol, 68.27% yield).

5-Isopropyl-N-(1-methyl-5-(pyridin-2-yl)-1H-1,2,4-triazol-3-yl)-4-(trifluoromethyl)pyridin-2-amine To a mixture of 1-[5-isopropyl-4-(trifluoromethyl)-2-pyridyl]-2-methyl-isothiourea (750.47 mg, 2.71 mmol) in pyridine (8 mL) was added N-methylpyridine-2-carbohydrazide (450 mg, 2.98 mmol). The mixture was stirred at 120° C. for 3 h and then at 25° C. for 16 h. The mixture was filtered and the filtrate was concentrated. The product was isolated and purified by standard methods to give 5-isopropyl-N-[1-methyl-5-(2-pyridyl)-1,2,4-triazol-3-yl]-4-(trifluoromethyl)pyridin-2-amine (187.98 mg, 4.467 mmol, 17.25% yield). LCMS (ESI): m/z 363.1 [M+1]$^+$.

Example 51: 2-((3-(4-Isopropoxypyridin-2-yl)-1,2,4-thiadiazol-5-yl)amino)-N,N-dimethylpyridine-3-sulfonamide

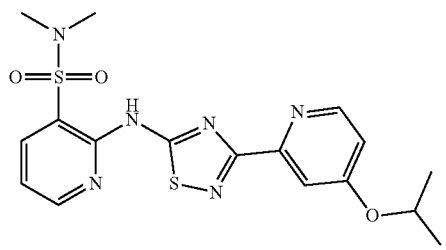 [SMILES: CC(C)Oc1ccnc(-c2nsc(Nc3ncccc3S(=O)(=O)N(C)C)n2)c1]

4-Isopropoxypicolinonitrile

To a solution of propan-2-ol (1.21 g, 20.21 mmol, 1.55 mL) in DMF (10 mL) was added NaH (866.01 mg, 21.65 mmol, 60% purity) at 0° C. The mixture was stirred at 25° C. for 30 min then to the mixture was added 4-chloropicolinonitrile (2 g, 14.43 mmol) in DMF (40 mL) at 0° C. The mixture was stirred at 25° C. for 1 h. The mixture was poured into cold saturated $NH_4Cl$ and then extracted with EtOAc. The combined organic layers were washed with brine, dried with anhydrous sodium sulfate and filtered. The filtrate was concentrated under reduced pressure and the residue was purified by flash silica gel chromatography to give 4-isopropoxypicolinonitrile (1.01 g, 6.23 mmol, 43.14% yield). LCMS (ESI): m/z 163.1 [M+1]$^+$. $^1$H NMR (400 MHz, CDCl$_3$) 8.48 (d, J=5.8 Hz, 1H), 7.17 (d, J=2.4 Hz, 1H), 6.95 (dd, J$_1$=5.8, J$_2$=2.6 Hz, 1H), 4.70-4.63 (m, 1H), 1.40 (d, J=6.1 Hz, 6H).

4-Isopropoxypicolinimidamide

To a solution of 4-isopropoxypicolinonitrile (1.01 g, 6.23 mmol) in MeOH (15 mL) was added sodium (71.58 mg, 3.11 mmol). The mixture was stirred at 25° C. for 12 h. To the mixture was added $NH_4Cl$ (499.66 mg, 9.34 mmol) and the mixture was stirred at 70° C. for 1.5 h. The reaction mixture was concentrated to give a residue which was triturated with MTBE:EtOAc (1:1, 10 mL) for 10 min, filtered and the filter cake was collected and concentrated under reduced pressure to give 4-isopropoxypicolinimidamide (1.4 g, crude, hydrochloride). LCMS (ESI): m/z 180.1 [M+1]$^+$.

N-((3-(N,N-Dimethylsulfamoyl)pyridin-2-yl)carbamothioyl)-4-isopropoxypicolinimidamide To a solution of 4-isopropoxypicolinimidamide (190 mg, crude, hydrochloride) and 2-isothiocyanato-N,N-dimethylpyridine-3-sulfonamide (214.34 mg, 0.88 mmol) in DCM (15 mL) and acetone (15 mL) was added TEA (445.71 mg, 4.40 mmol, 0.6 mL). The mixture was stirred at 25° C. for 12 h. The mixture was concentrated to give N-((3-(N,N-dimethylsulfamoyl)pyridin-2-yl)carbamothioyl)-4-isopropoxypicolinimidamide (372 mg, crude). LCMS (ESI): m/z 423.1 [M+1]$^+$.

2-((3-(4-Isopropoxypyridin-2-yl)-1,2,4-thiadiazol-5-yl)amino)-N,N-dimethylpyridine-3-sulfonamide To a solution of N-((3-(N,N-dimethylsulfamoyl)pyridin-2-yl)carbamothioyl)-4-isopropoxypicolinimidamide (372 mg, crude) in EtOH (10 mL) was added iodine (44.69 mg, 0.17 mmol) and hydrogen peroxide (199.65 mg, 1.76 mmol, 30% purity) at 0° C. The mixture was stirred at 25° C. for 1 h. The mixture was quenched by addition of saturated sodium sulfite at 0° C. and the mixture was concentrated. The aqueous residue was extracted with EtOAc and the combined organic phase was washed with brine, dried with anhydrous sodium sulfate, filtered, and concentrated under vacuum. The residue was purified by prep-HPLC (basic condition; column: Waters Xbridge BEH C18 250*50 mm*10 um; mobile phase: [$H_2O$ (0.04% $NH_3H_2O$+10 mM $NH_4HCO_3$)-ACN]; B %: 45%-75%, 8 min) to give 2-((3-(4-isopropoxypyridin-2-yl)-1,2,4-thiadiazol-5-yl)amino)-N,N-dimethylpyridine-3-sulfonamide (200.82 mg, 0.472 mmol, 53.43% yield, 99% purity). $^1$H NMR (400 MHz, DMSO-$d_6$) 10.67 (br s, 1H), 8.80 (dd, J=1.4, 4.8 Hz, 1H), 8.47 (d, J=5.6 Hz, 1H), 8.28 (dd, J=1.5, 7.8 Hz, 1H), 7.69 (d, J=2.4 Hz, 1H), 7.38 (br dd, J=5.0, 7.5 Hz, 1H), 7.06 (dd, J=2.5, 5.8 Hz, 1H), 4.90-4.81 (m, 1H), 2.80 (s, 6H), 1.33 (d, J=6.0 Hz, 6H). LCMS (ESI): m/z 421.2 [M+1]$^+$.

Example 52: N-(2-((3-(4-Isopropoxypyridin-2-yl)-1,2,4-thiadiazol-5-yl)amino)-5-(trifluoromethyl)pyridin-3-yl)-N-methylacetamide

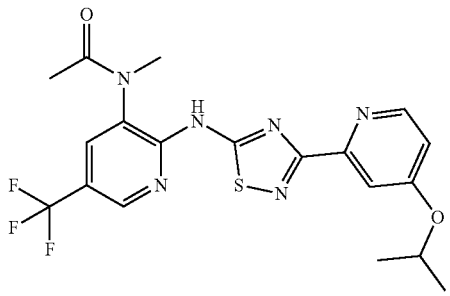 [SMILES: CC(=O)N(C)c1cc(C(F)(F)F)cnc1Nc1nc(-c2cc(OC(C)C)ccn2)ns1]

tert-Butyl (2-(3-(imino(4-isopropoxypyridin-2-yl)methyl)thioureido)-5-(trifluoromethyl)pyridin-3-yl)(methyl)carbamate To a solution of 4-isopropoxypicolinimidamide (241.95 mg, 1.35 mmol) and tert-butyl (2-isothiocyanato-5-(trifluoromethyl)pyridin-3-yl)(methyl)carbamate (0.45 g, 1.35 mmol) in DCM (20 mL) and acetone (20 mL) was added TEA (683.04 mg, 6.75 mmol), then the mixture was stirred at 35° C. for 16 h. The mixture was combined with a previous batch (80 mg, crude) to give tert-butyl (2-(3-(imino(4-isopropoxypyridin-2-yl)methyl)thioureido)-5-(trifluoromethyl)pyridin-3-yl)(methyl)carbamate (770 mg, crude).

tert-Butyl(2-((3-(4-isopropoxypyridin-2-yl)-1,2,4-thiadiazol-5-yl)amino)-5-(trifluoromethyl)pyridin-3-yl)(methyl)carbamate To a solution of tert-butyl (2-(3-(imino(4-isopropoxypyridin-2-yl)methyl)thioureido)-5-(trifluoromethyl)pyridin-3-yl)(methyl)carbamate (770 mg, crude) in EtOH (20 mL) was added iodine (761.43 mg, 3.00 mmol) at 0° C. and the mixture was stirred at 25° C. for 1 h. The mixture was quenched by addition of saturated sodium sulfite at 0° C. The mixture was concentrated and the aqueous residue was extracted with DCM and the combined organic phase was washed with brine, dried with anhydrous sodium sulfate, filtered, and concentrated under vacuum. The residue was purified by silica gel chromatography to give tert-butyl (2-((3-(4-isopropoxypyridin-2-yl)-1,2,4-thiadiazol-5-yl)amino)-5-(trifluoromethyl)pyridin-3-yl)(methyl)carbamate (0.72 g, 1.41 mmol, 94.02% yield).

$N^2$-(3-(4-Isopropoxypyridin-2-yl)-1,2,4-thiadiazol-5-yl)-$N^3$-methyl-5-(trifluoromethyl)pyridine-2,3-diamine To a solution of tert-butyl tert-butyl (2-((3-(4-isopropoxypyridin-2-yl)-1,2,4-thiadiazol-5-yl)amino)-5-(trifluoromethyl)pyridin-3-yl)(methyl)carbamate (0.72 g, 1.41 mmol) in EtOAc (20 mL) was added HCl/EtOAc (4 M, 20 mL) and the mixture was stirred at 20° C. for 1 h. The mixture was concentrated under vacuum to give $N^2$-(3-(4-isopropoxypyridin-2-yl)-1,2,4-thiadiazol-5-yl)-$N^3$-methyl-5-(trifluoromethyl)pyridine-2,3-diamine (0.6 g, 1.34 mmol, 95.2% yield, HCl).

N-(2-((3-(4-Isopropoxypyridin-2-yl)-1,2,4-thiadiazol-5-yl)amino)-5-(trifluoromethyl)pyridin-3-yl)-N-methylacetamide To a solution of $N^2$-(3-(4-isopropoxypyridin-2-yl)-1,2,4-thiadiazol-5-yl)-$N^3$-methyl-5-(trifluoromethyl)pyridine-2,3-diamine (0.45 g, 1.01 mmol, HCl) and TEA (509.49 mg, 5.03 mmol) in DMF (35 mL) was added $Ac_2O$ (154.20 mg, 1.51 mmol) and the mixture was stirred at 35° C. for 16 h. Additional $Ac_2O$ (102.80 mg, 1.01 mmol) was added to the mixture and stirred at 40° C. for 6 h. Temperature was increased to 45° C. for 38 h and then the mixture was concentrated. The residue was purified by prep-HPLC (column: Phenomenex Synergi C18 150*25*10 um; mobile phase: [$H_2O$ (0.1% TFA)-ACN]; B %: 30%-50%, 10 min), followed by lyophilization to give N-(2-((3-(4-isopropoxypyridin-2-yl)-1,2,4-thiadiazol-5-yl)amino)-5-(trifluoromethyl)pyridin-3-yl)-N-methylacetamide (193.68 mg, 0.407 mmol, 40.38% yield, 95% purity). LCMS (ESI): m/z 453.3 [M+1]+.

Example 53: N-(2-((3-(4-Methoxypyridin-2-yl)-1,2,4-thiadiazol-5-yl)amino)-5-(trifluoromethyl)pyridin-3-yl)-N-methylacetamide

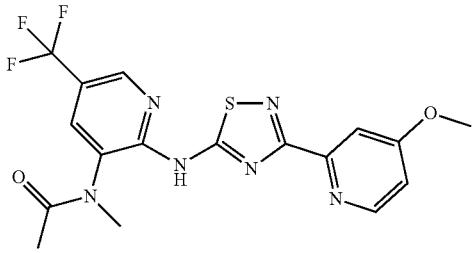 [SMILES: COc1ccnc(-c2nsc(Nc3ncc(C(F)(F)F)cc3N(C)C(C)=O)n2)c1]

4-Methoxypicolinimidamide

To a solution of 4-methoxypicolinonitrile (1 g, 7.46 mmol) in MeOH (15 mL) was added sodium methoxide (120.82 mg, 2.24 mmol) and the mixture was stirred at 30° C. for 4 h. Then NH$_4$Cl (518.41 mg, 9.69 mmol) was added to the mixture and stirred at 75° C. for 2 h. The mixture was concentrated under vacuum and the residue was triturated with EtOAc and stirred for 0.5 h. The suspension was filtered and the filter cake was collected. The filter cake was dissolved with H$_2$O and ACN followed by addition of Amberlyst A-26(OH) (2 g) and the mixture was stirred at 25° C. for 30 min. The mixture was filtered through a pad of celite, concentrated under vacuum and then dried by lyophilization to give 4-methoxypicolinimidamide (1.1 g, 7.28 mmol, 97.61% yield).

tert-Butyl (2-(3-(imino(4-methoxypyridin-2-yl)methyl)thioureido)-5-(trifluoromethyl)pyridin-3-yl)(methyl)carbamate To a solution of 4-methoxypicolinimidamide (226.75 mg, 1.50 mmol) and tert-butyl (2-isothiocyanato-5-(trifluoromethyl)pyridin-3-yl)(methyl)carbamate (0.5 g, 1.50 mmol) in DCM (40 mL) and acetone (40 mL) was added TEA (758.94 mg, 7.50 mmol, 1.04 mL) and the mixture was stirred at 35° C. for 16 h. The mixture was concentrated under vacuum to give tert-butyl (2-(3-(imino(4-methoxypyridin-2-yl)methyl)thioureido)-5-(trifluoromethyl)pyridin-3-yl)(methyl)carbamate (730 mg, crude).

tert-Butyl (2-((3-(4-methoxypyridin-2-yl)-1,2,4-thiadiazol-5-yl)amino)-5-(trifluoromethyl)pyridin-3-yl)(methyl)carbamate To a solution of tert-butyl (2-(3-(imino(4-methoxypyridin-2-yl)methyl)thioureido)-5-(trifluoromethyl)pyridin-3-yl)(methyl)carbamate (730 mg, crude) in EtOH (20 mL) was added iodine (761.43 mg, 3.00 mmol) at 0° C. and the mixture was stirred at 25° C. for 1 h. The mixture was quenched by addition of saturated sodium sulfite at 0° C. and the mixture was concentrated. The aqueous phase was extracted with DCM and the combined organic phases were washed with brine, dried with anhydrous sodium sulfate, filtered, and concentrated in vacuum. The residue was purified by silica gel chromatography to give tert-butyl(2-((3-(4-methoxypyridin-2-yl)-1,2,4-thiadiazol-5-yl)amino)-5-(trifluoromethyl)pyridin-3-yl)(methyl)carbamate (0.5 g, 1.04 mmol).

N$^2$-(3-(4-Methoxypyridin-2-yl)-1,2,4-thiadiazol-5-yl)-N$^3$-methyl-5-(trifluoro methyl)pyridine-2,3-diamine To a solution of tert-butyl (2-((3-(4-methoxypyridin-2-yl)-1,2,4-thiadiazol-5-yl)amino)-5-(trifluoromethyl)pyridin-3-yl)(methyl)carbamate (0.5 g, 1.04 mmol) in EtOAc (20 mL) was added HCl/EtOAc (4 M, 20 mL) and the mixture was stirred at 20° C. for 1 h. The temperature was increased to 50° C. for 0.5 h and then concentrated under vacuum to give N$^2$-(3-(4-methoxypyridin-2-yl)-1,2,4-thiadiazol-5-yl)-N$^3$-methyl-5-(trifluoromethyl)pyridine-2,3-diamine (0.4 g, crude, HCl).

N-(2-((3-(4-Methoxypyridin-2-yl)-1,2,4-thiadiazol-5-yl)amino)-5-(trifluoromethyl)pyridin-3-yl)-N-methylacetamide To a solution of N$^2$-(3-(4-methoxypyridin-2-yl)-1,2,4-thiadiazol-5-yl)-N$^3$-methyl-5-(trifluoromethyl)pyridine-2,3-diamine (0.4 g, crude, HCl) and TEA (96.64 mg, 0.96 mmol) in DMF (30 mL) was added Ac$_2$O (146.25 mg, 1.43 mmol) and the mixture was stirred at 45° C. for 16 h. Additional Ac$_2$O (97.50 mg, 0.96 mmol) was added to the mixture and it was stirred at 45° C. for 16 h. Additional Ac$_2$O (50 mg, 0.5 mmol) was added to the mixture and stirred at 40° C. for 64 h. The mixture was concentrated and the residue was triturated with MeOH. The resulting suspension was filtered and the filter cake was dried by lyophilization to give N-(2-((3-(4-methoxypyridin-2-yl)-1,2,4-thiadiazol-5-yl)amino)-5-(trifluoromethyl)pyridin-3-yl)-N-methylacetamide (166.26 mg, 0.385 mmol, 40.40% yield, 98.5% purity). LCMS (ESI): m/z 425.1 [M+1]$^+$.

Example 54: 2-((3-(5-Isopropoxypyridin-2-yl)-1,2,4-thiadiazol-5-yl)amino)-N,N-dimethylpyridine-3-sulfonamide

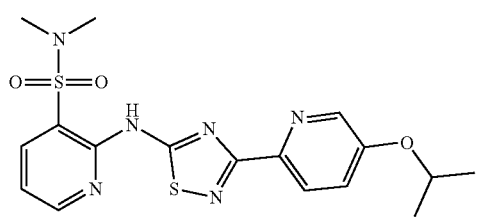 [SMILES: CC(C)Oc1ccc(-c2nsc(Nc3ncccc3S(=O)(=O)N(C)C)n2)nc1]

2-Chloro-N,N-dimethylpyridine-3-sulfonamide

To a solution of 2-chloropyridine-3-sulfonyl chloride (10.2 g, 48.10 mmol) in THF (100 mL) was added dimethylamine (2 M, 24.05 mL) dropwise at 0° C. The mixture was stirred at 15° C. for 2 h. The mixture was poured into ice-H$_2$O and the aqueous phase was extracted with EtOAc. The combined organic phase was washed with brine, dried with anhydrous sodium sulfate, filtered, and concentrated under vacuum. The residue was purified by silica gel chromatography to give 2-chloro-N,N-dimethylpyridine-3-sulfonamide (6.6 g, 29.61 mmol, 61.56% yield, 99% purity).

2-Amino-N,N-dimethylpyridine-3-sulfonamide

This reaction was paralleled for three batches: A mixture of 2-chloro-N,N-dimethylpyridine-3-sulfonamide (2 g, 9.06 mmol, 1 eq) and ammonium hydroxide (19.06 g, 135.95 mmol, 20.94 mL) was stirred at 80° C. for 72 h in a sealed tube. The mixture was filtered and the filter cake was collected and dried under vacuum to give 2-amino-N,N-dimethylpyridine-3-sulfonamide (5 g, 24.85 mmol, 91.38% yield).

2-Isothiocyanato-N,N-dimethylpyridine-3-sulfonamide

To a solution of thiophosgene (2.29 g, 19.88 mmol, 1.52 mL) in DCM (20 mL) was added a solution of 2-amino-N,N-dimethylpyridine-3-sulfonamide (2 g, 9.94 mmol) in DCM (30 mL) and the mixture was stirred at 0° C. for 2 h. The mixture was poured into saturated sodium bicarbonate at 0° C. and the aqueous phase was extracted with DCM. The combined organic phase was concentrated under vacuum and the residue was purified by silica gel chromatography to give 2-isothiocyanato-N,N-dimethylpyridine-3-sulfonamide (1.1 g, 4.52 mmol, 45.48% yield).

N-((3-(N,N-Dimethylsulfamoyl)pyridin-2-yl)carbamothioyl)-5-isopropoxypicolinimidamide To a solution of 2-isothiocyanato-N,N-dimethylpyridine-3-sulfonamide (0.3 g, 1.23 mmol) and 5-isopropoxypicolinimidamide (221 mg, 1.23 mmol) in DCM (20 mL) and acetone (20 mL) was added TEA (124.77 mg, 1.23 mmol) and the mixture was stirred at 35° C. for 16 h. The mixture was combined with another batch (0.2 g, crude) to give N-((3-(N,N-dimethylsulfamoyl)pyridin-2-yl)carbamothioyl)-5-isopropoxypicolinimidamide (0.7 g, crude).

2-((3-(5-Isopropoxypyridin-2-yl)-1,2,4-thiadiazol-5-yl)amino)-N,N-dimethylpyridine-3-sulfonamide To a solution of 1-[3-(dimethylsulfamoyl)-2-pyridyl]-3-(5-isopropoxypyridine-2-carboximidoyl)thiourea (0.7 g, crude) in EtOH (30 mL) was added iodine (84.10 mg, 0.33 mmol) and hydrogen peroxide (375.68 mg, 3.31 mmol, 30% purity) at 0° C. The mixture was stirred at 20° C. for 1 h and then quenched by addition of saturated sodium sulfite at 0° C. The aqueous phase was extracted with DCM and the combined organic phase was dried with anhydrous sodium sulfate, filtered, and concentrated under vacuum. The mixture was triturated with MeOH, the suspension was filtered and the filter cake was dried by lyophilization to give 2-((3-(5-isopropoxypyridin-2-yl)-1,2,4-thiadiazol-5-yl)amino)-N,N-dimethylpyridine-3-sulfonamide (322.18 mg, 0.76 mmol, 45.72% yield, 98.87% purity). LCMS (ESI): m/z 421.2 [M+1]+.

Example 55: N-Methyl-N-(2-((3-(pyridin-2-yl)-1,2,4-thiadiazol-5-yl)amino)-5-(trifluoromethyl)pyridin-3-yl)acetamide

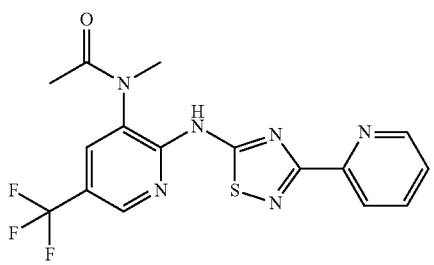 [SMILES: CC(=O)N(C)c1cc(C(F)(F)F)cnc1Nc1nc(-c2ccccn2)ns1]

tert-Butyl (2-azido-5-(trifluoromethyl)pyridin-3-yl)(methyl)carbamate

This reaction was paralleled for two batches: To a solution of sodium azide (9.42 g, 144.83 mmol) (120 mL) was added tert-butyl (2-chloro-5-(trifluoromethyl)pyridin-3-yl)(methyl)carbamate (15 g, 48.28 mmol), and the mixture was stirred at 100° C. for 16 h. The two batches were combined and poured into saturated sodium bicarbonate at 0° C. and stirred for 3 min. The aqueous phase was extracted with EtOAc and the combined organic phase was washed with brine, and concentrated under vacuum to give tert-butyl (2-azido-5-(trifluoromethyl)pyridin-3-yl)(methyl)carbamate (30 g, crude).

tert-Butyl (2-amino-5-(trifluoromethyl)pyridin-3-yl)(methyl)carbamate

To a solution of tert-butyl (2-azido-5-(trifluoromethyl)pyridin-3-yl)(methyl)carbamate (30 g, crude) in MeOH (300 mL) was added Pd/C (3 g, 10% purity) and hydroxide Pd/C (3 g, 20% purity) under nitrogen and the mixture was then stirred at 25° C. for 3 h under hydrogen (15 psi). The mixture was filtered through a pad of celite and to the filtrate was added Pd/C (2 g, 10% purity) and hydroxide Pd/C (2 g, 20% purity), and stirred at 25° C. under hydrogen (15 psi) for 16 h. The mixture was filtered through a pad of Celite, washed with EtOAc, concentrated under vacuum and purified by silica gel chromatography to give tert-butyl (2-amino-5-(trifluoromethyl)pyridin-3-yl)(methyl)carbamate (26 g, 89.26 mmol, 94.40% yield).

tert-Butyl (2-isothiocyanato-5-(trifluoromethyl)pyridin-3-yl)(methyl) carbamate

To a solution of thiophosgene (4.79 g, 41.63 mmol, 3.19 mL) in DCM (20 mL) was added a solution of tert-butyl (2-amino-5-(trifluoromethyl)pyridin-3-yl)(methyl)carbamate (6 g, 20.60 mmol) in DCM (50 mL) dropwise at 0° C. The mixture was stirred at 0° C. for 2 h. poured into saturated sodium bicarbonate at 0° C. and the aqueous phase was extracted with DCM. The combined organic phase was concentrated under vacuum and purified by silica gel chromatography to give tert-butyl (2-isothiocyanato-5-(trifluoromethyl)pyridin-3-yl)(methyl) carbamate (3.2 g, 9.60 mmol, 46.60% yield).

Picolinimidamide

To a solution of picolinonitrile (2 g, 19.21 mmol) in MeOH (15 mL) was added sodium methoxide (518.91 mg, 9.61 mmol) (freshly prepared), the mixture was stirred at 30° C. for 4 h. NH$_4$Cl (1.34 g, 24.97 mmol) was added to the mixture and stirred at 75° C. for 2 h. The mixture was concentrated under vacuum and the residue was triturated with petroleum ether:EtOAc (1:1, 20 mL) and stirred for 0.5 h. The resulting suspension was filtered and the filter cake was collected. The residue was dissolved with H$_2$O and ACN followed by addition of Amberlyst A-26(OH) (2 g) and stirred at 25° C. for 30 min. The mixture was filtered through a pad of celite and the filtrate was concentrated under vacuum and then dried by lyophilization to give picolinimidamide (2.7 g, crude).

tert-Butyl(2-(3-(imino(pyridin-2-yl)methyl)thioureido)-5-(trifluoromethyl)pyridin-3-yl)(methyl)carbamate To a solution of tert-butyl (2-isothiocyanato-5-(trifluoromethyl)pyridin-3-yl)(methyl)carbamate (0.5 g, 1.50 mmol) and picolinimidamide (181.71 mg, crude) in DCM (40 mL) and acetone (40 mL) was added TEA (758.93 mg, 7.50 mmol, 1.04 mL), the mixture was stirred at 35° C. for 16 h. The mixture was concentrated under vacuum to give tert-butyl(2-(3-(imino(pyridin-2-yl)methyl)thioureido)-5-(trifluoromethyl)pyridin-3-yl)(methyl)carbamate (0.86 g, crude).

tert-Butylmethyl(2-((3-(pyridin-2-yl)-1,2,4-thiadiazol-5-yl)amino)-5-(trifluoromethyl)pyridin-3-yl) carbamate To a solution of tert-butyl(2-(3-(imino(pyridin-2-yl)methyl)thioureido)-5-(trifluoromethyl)pyridin-3-yl)(methyl)carbamate (0.86 g, crude) in EtOH (20 mL) was added iodine (960.57 mg, 3.78 mmol) at 0° C. and the mixture was stirred at 25° C. for 1 h. The mixture was quenched by addition of saturated sodium sulfite at 0° C., concentrated and extracted with DCM. The combined organic phase was washed with brine, dried with anhydrous sodium sulfate, filtered and concentrated under vacuum. The residue was purified by silica gel chromatography to give tert-butylmethyl(2-((3-(pyridin-2-yl)-1,2,4-thiadiazol-5-yl)amino)-5-(trifluoromethyl)pyridin-3-yl)carbamate (0.78 g, 1.72 mmol, 91.10% yield).

$N^3$-Methyl-$N^2$-(3-(pyridin-2-yl)-1,2,4-thiadiazol-5-yl)-5-(trifluoromethyl) pyridine-2,3-diamine To a solution of tert-butylmethyl(2-((3-(pyridin-2-yl)-1,2,4-thiadiazol-5-yl)amino)-5-(trifluoromethyl)pyridin-3-yl) carbamate (0.78 g, 1.72 mmol) in EtOAc (20 mL) was added hydrochloric acid/EtOAc (4 M, 20 mL) and the mixture was stirred at 25° C. for 2 h. The mixture was concentrated under vacuum to give $N^3$-methyl-$N^2$-(3-(pyridin-2-yl)-1,2,4-thiadiazol-5-yl)-5-(trifluoromethyl)pyridine-2,3-diamine, HCl salt (0.7 g, crude).

N-Methyl-N-(2-((3-(pyridin-2-yl)-1,2,4-thiadiazol-5-yl)amino)-5-(trifluoromethyl)pyridin-3-yl)acetamide To a solution of $N^3$-methyl-$N^2$-(3-(pyridin-2-yl)-1,2,4-thiadiazol-5-yl)-5-(trifluoromethyl)pyridine-2,3-diamine (0.55 g, crude, HCl salt) and TEA (789.79 mg, 7.80 mmol, 1.09 mL) in DMF (35 mL) was added Ac$_2$O (239.04 mg, 2.34 mmol) and the mixture was stirred at 30° C. for 16 h. Additional Ac$_2$O (79.63 mg, 0.78 mmol) was added to the mixture and stirred at 30° C. for 16 h. The mixture was concentrated and purified by prep-HPLC (column: Phenomenex luna C18 150*40 mm*15 um; mobile phase: [H$_2$O (0.225% FA)-ACN]; B %: 23%-53%, 8.5 min) followed by lyophilization to give N-methyl-N-(2-((3-(pyridin-2-yl)-1,2,4-thiadiazol-5-yl)amino)-5-(trifluoromethyl)pyridin-3-yl)acetamide (172.36 mg, 0.440 mmol, 27.90% yield, 99.6% purity). LCMS (ESI): m/z 395.2 [M+1]+.

Example 56: Isopropyl 2-((3-(5-isopropoxypyridin-2-yl)-1,2,4-thiadiazol-5-yl)amino) nicotinate

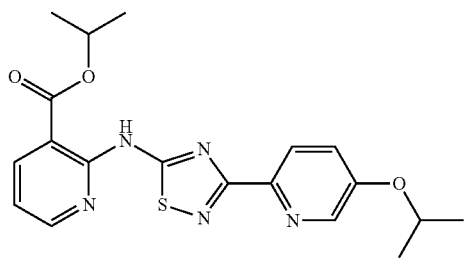 [SMILES: CC(C)OC(=O)c1cccnc1Nc1nc(-c2ccc(OC(C)C)cn2)ns1]

2-((3-(5-Isopropoxypyridin-2-yl)-1,2,4-thiadiazol-5-yl)amino)nicotinic Acid

To a solution of methyl 2-((3-(5-isopropoxypyridin-2-yl)-1,2,4-thiadiazol-5-yl)amino)nicotinate (0.3 g, 0.81 mmol) in MeOH (20 mL) and TH (10 mL) was added lithium hydrate monohydrate (50.84 mg, 1.21 mmol) in H$_2$O (20 mL) and the mixture was stirred at 25° C. for 3 h. The mixture was concentrated under vacuum to remove the volatiles and the residue was adjusted pH to 3-4 with HCl and dried by lyophilization to give 2-((3-(5-isopropoxypyridin-2-yl)-1,2,4-thiadiazol-5-yl)amino)nicotinic acid (370 mg, crude).

Isopropyl 2-((3-(5-isopropoxypyridin-2-yl)-1,2,4-thiadiazol-5-yl)amino) nicotinate To a solution of 2-((3-(5-isopropoxypyridin-2-yl)-1,2,4-thiadiazol-5-yl)amino)nicotinic acid (370 mg, crude) in isopropanol (10 mL) and DMF (0.1 mL) was added thionyl chloride (247.46 mg, 2.08 mmol) and the mixture was stirred at 80° C. for 16 h. Additional thionyl chloride (492.00 mg, 4.14 mmol) was added to the mixture and stirred at 80° C. for 48 h. Additional thionyl chloride (0.5 mL) along with a drop of DMF were added to the mixture and stirred at 80° C. for 16 h. The mixture was concentrated under vacuum and the residue was purified by prep-HPLC (column Waters Xbridge C18 150*50 mm*10 um; mobile phase: [H$_2$O (0.05% ammonia hydroxide v/v)-ACN]; B %: 50%-80%, 11.5 min), followed by lyophilization to give isopropyl 2-((3-(5-isopropoxypyridin-2-yl)-1,2,4-thiadiazol-5-yl) amino) nicotinate (104.65 mg, 0.262 mmol, 25.16% yield, 99.9% purity). LCMS (ESI): m/z 400.2 [M+1]+.

Example 57: (2-((3-(5-Isopropoxypyridin-2-yl)-1,2,4-thiadiazol-5-yl)amino)-5-(trifluoro methyl)pyridin-3-yl)(pyrrolidin-1-yl)methanone

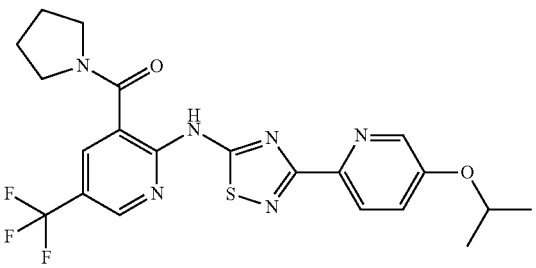 [SMILES: CC(C)Oc1ccc(-c2nsc(Nc3ncc(C(F)(F)F)cc3C(=O)N3CCCC3)n2)nc1]

3-Bromo-5-(trifluoromethyl)pyridin-2-amine

To a solution of 5-(trifluoromethyl)pyridin-2-amine (10 g, 61.69 mmol) in THE (100 mL) was added NBS (11.53 g, 64.77 mmol) portionwise at 0° C. and the mixture was stirred at 20° C. for 1 h. The mixture was concentrated under vacuum and purified by silica gel column chromatography to give 3-bromo-5-(trifluoromethyl)pyridin-2-amine (14 g, 58.09 mmol, 94.17% yield).

Methyl 2-amino-5-(trifluoromethyl)nicotinate

To a solution of 3-bromo-5-(trifluoromethyl)pyridin-2-amine (14 g, 58.09 mmol), (±)-2,2'-bis(diphenylphosphino)-1,1'-binaphthalene (904.26 mg, 1.45 mmol) and TEA (17.63 g, 174.27 mmol, 24.26 mL) in MeOH (140 mL) was added

[1,1'-bis(diphenylphosphino)ferrocene]dichloropalladium (II) (2.13 g, 2.90 mmol). The mixture was de-gassed with nitrogen 3 times and stirred at 70° C. under carbon monoxide (50 psi) for 16 h. The mixture was filtered through a pad of celite and the filtrate was concentrated under vacuum. The residue was purified by silica gel chromatography to give methyl 2-amino-5-(trifluoromethyl)pyridine-3-carboxylate (12 g, 52.33 mmol, 90.08% yield, 96% purity).

2-Amino-5-(trifluoromethyl) Nicotinic Acid

To a solution of methyl 2-amino-5-(trifluoromethyl)pyridine-3-carboxylate (4 g, 18.17 mmol) in MeOH (40 mL) was added a solution of lithium hydroxide monohydrate (1.14 g, 27.25 mmol) in $H_2O$ (10 mL). The mixture was stirred at 25° C. for 5 h, concentrated to remove the volatiles and the residue was adjusted pH to 5-6 with hydrochloric acid and dried by lyophilization to give 2-amino-5-(trifluoromethyl) pyridine-3-carboxylic acid (5.5 g, crude).

(2-Amino-5-(trifluoromethyl)pyridin-3-yl)(pyrrolidin-1-yl)methanone

To a mixture of 2-amino-5-(trifluoromethyl)pyridine-3-carboxylic acid (5.5 g, crude) and pyrrolidine (3.80 g, 53.37 mmol, 4.45 mL) in DMF (50 mL) was added HATU (13.19 g, 34.69 mmol) and diisopropylethylamine (13.79 g, 106.73 mmol, 18.59 mL) at 0° C. and the mixture was stirred at 25° C. for 22 h. To the mixture was added $H_2O$ and EtOAc. The aqueous phase was extracted with EtOAc and the combined organic phase was washed with brine, concentrated under vacuum, and purified by silica gel column chromatography to give [2-amino-5-(trifluoromethyl)-3-pyridyl]-pyrrolidin-1-yl-methanone (5.4 g, 20.83 mmol, 78.07% yield).

(2-Isothiocyanato-5-(trifluoromethyl)pyridin-3-yl)(pyrrolidin-1-yl)methanone

To a solution of thiocarbonyl dichloride (1.77 g, 15.43 mmol, 1.18 mL) in DCM (20 mL) was added a solution of [2-amino-5-(trifluoromethyl)-3-pyridyl]-pyrrolidin-1-yl-methanone (2 g, 7.72 mmol) in DCM (30 mL) dropwise at 0° C., and the mixture was stirred at 0° C. for 2 h. The mixture was poured into saturated sodium bicarbonate and the aqueous phase was extracted with DCM. The combined organic phase was concentrated under vacuum and purified by silica gel column chromatography to give [2-isothiocyanato-5-(trifluoromethyl)-3-pyridyl]-pyrrolidin-1-yl-methanone (0.86 g, 2.71 mmol, 35.15% yield, 95% purity).

5-Isopropoxy-N-((3-(pyrrolidine-1-carbonyl)-5-(trifluoromethyl)pyridin-2-yl)carbamothioyl)picolinimidamide To a solution of [2-isothiocyanato-5-(trifluoromethyl)-3-pyridyl]-pyrrolidin-1-yl-methanone (0.86 g, 2.71 mmol) and 5-isopropoxypyridine-2-carboxamidine (511.56 mg, 2.85 mmol) in DCM (50 mL) and acetone (50 mL) was added TEA (1.44 g, 14.23 mmol, 1.99 mL) and the mixture was stirred at 30° C. for 16 h. The mixture was concentrated under vacuum to give 1-(5-isopropoxypyridine-2-carboximidoyl)-3-[3-(pyrrolidine-1-carbonyl)-5-(trifluoromethyl)-2-pyridyl]thiourea (1.37 g, crude).

(2-((3-(5-Isopropoxypyridin-2-yl)-1,2,4-thiadiazol-5-yl)amino)-5-(trifluoro methyl)pyridin-3-yl)(pyrrolidin-1-yl)methanone To a solution of 1-(5-isopropoxypyridine-2-carboximidoyl)-3-[3-(pyrrolidine-1-carbonyl)-5-(trifluoromethyl)-2-pyridyl]thiourea (1.37 g, crude) in EtOH (20 mL) was added iodine (1.45 g, 5.70 mmol) at 0° C. and the mixture was stirred at 25° C. for 1 h. The mixture was quenched by addition of saturated sodium sulfite aqueous at 0° C. and concentrated. The aqueous phase was extracted with DCM and the combined organic phase was washed with brine, dried with anhydrous sodium sulfate, filtered, and concentrated under vacuum. The residue was purified by prep-HPLC (column: Phenomenex Synergi C18 150*25*10 um; mobile phase: [$H_2O$ (0.2% FA)-ACN]; B %: 50%-80%, 11 min) followed by lyophilization to give [2-[[3-(5-isopropoxy-2-pyridyl)-1,2,4-thiadiazol-5-yl]amino]-5-(trifluoromethyl)-3-pyridyl]-pyrrolidin-1-yl-methanone (448.51 mg, 936.41 umol, 32.84% yield, 99.9% purity). LCMS (ESI): m/z 479.1 [M+1]+.

Example 58: N-Methyl-n-(2-((3-(5-(oxetan-3-yloxy)pyridin-2-yl)-1,2,4-thiadiazol-5-yl)amino)-5-(trifluoromethyl)pyridin-3-yl)acetamide

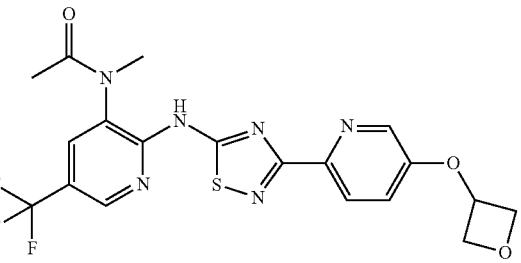

5-(Oxetan-3-yloxy)picolinonitrile

To a solution of NaH (1.97 g, 49.14 mmol, 60% purity) in DMF (25 mL) was added oxetan-3-ol (2.37 g, 31.94 mmol) at 0° C. and the mixture was stirred for 0.5 h. To the mixture was added a solution of 5-fluoropicolinonitrile (3 g, 24.57 mmol) in DMF (15 mL) at 0° C. and stirred at 0° C. for 0.5 h. The reaction mixture was poured into saturated $NH_4Cl$ at 0° C. and the aqueous phase was extracted with EtOAc. The combined organic phase was washed with brine, dried with anhydrous sodium sulfate, filtered, and concentrated under vacuum. The residue was purified by silica gel chromatography to give 5-(oxetan-3-yloxy)picolinonitrile (4 g, 22.71 mmol, 92.41% yield).

5-(Oxetan-3-yloxy)picolinimidamide

To a solution of 5-(oxetan-3-yloxy)picolinonitrile (4 g, 22.71 mmol) in MeOH (30 mL) was added sodium methoxide (613.31 mg, 11.35 mmol, fresh) and the mixture was stirred at 35° C. for 4 h. $NH_4Cl$ (1.58 g, 29.52 mmol) was added to the mixture and stirred at 75° C. for 2 h. The mixture was concentrated under vacuum, triturated with petroleum ether:EtOAc (1:1) and stirred for 0.5 h. The suspension was filtered, and the filter cake was collected and dissolved in $H_2O$ and ACN followed by addition of Amberlyst A-26(OH) (2 g). The mixture was stirred at 25° C. for 0.5 h and filtered through a pad of celite. The filtrate was concentrated under vacuum, then dried by lyophilization to give 5-(oxetan-3-yloxy)picolinimidamide (4.6 g, crude).

tert-Butyl (2-(3-(imino(5-(oxetan-3-yloxy)pyridin-2-yl)methyl)thioureido)-5-(trifluoromethyl)pyridin-3-yl)(methyl)carbamate To a solution of 5-(oxetan-3-yloxy)picolinimidamide (260.83 mg, 1.35 mmol) and tert-butyl (2-isothiocyanato-5-

(trifluoromethyl)pyridin-3-yl)(methyl)carbamate (0.45 g, 1.35 mmol) in DCM (50 mL) and acetone (50 mL) was added TEA (683.04 mg, 6.75 mmol) and the mixture was stirred at 30° C. for 16 h. The mixture was concentrated under vacuum to give tert-butyl (2-(3-(imino(5-(oxetan-3-yloxy)pyridin-2-yl)methyl)thioureido)-5-(trifluoromethyl)pyridin-3-yl)(methyl)carbamate (0.7 g, crude).

tert-Butyl methyl(2-((3-(5-(oxetan-3-yloxy)pyridin-2-yl)-1,2,4-thiadiazol-5-yl) amino)-5-(trifluoromethyl)pyridin-3-yl)carbamate To a solution of tert-butyl (2-(3-(imino(5-(oxetan-3-yloxy)pyridin-2-yl)methyl)thioureido)-5-(trifluoromethyl)pyridin-3-yl)(methyl)carbamate (0.7 g, crude) in EtOH (30 mL) was added hydrogen peroxide (301.47 mg, 2.66 mmol, 30% purity) and iodine (67.49 mg, 0.26 mmol) at 0° C. and the mixture was stirred at 20° C. for 1 h. The mixture was quenched by addition of saturated sodium sulfite aqueous at 0° C. and the aqueous phase was extracted with EtOAc. The combined organic phase was washed with brine, dried with anhydrous sodium sulfate, filtered, and concentrated under vacuum. The residue was purified by silica gel chromatography to give tert-butyl methyl(2-((3-(5-(oxetan-3-yloxy)pyridin-2-yl)-1,2,4-thiadiazol-5-yl)amino)-5-(trifluoromethyl)pyridin-3-yl)carbamate (480 mg, 0.92 mmol, 68.83% yield).

$N^3$-Methyl-$N^2$-(3-(5-(oxetan-3-yloxy)pyridin-2-yl)-1,2,4-thiadiazol-5-yl)-5-(trifluoromethyl)pyridine-2,3-diamine To a solution of tert-butyl methyl(2-((3-(5-(oxetan-3-yloxy)pyridin-2-yl)-1,2,4-thiadiazol-5-yl)amino)-5-(trifluoromethyl)pyridin-3-yl)carbamate (0.48 g, 0.92 mmol) in DCM (20 mL) was added trifluoroacetic acid (7.70 g, 67.53 mmol, 5 mL) at 0° C., then the mixture was stirred at 20° C. for 3 h. The mixture was concentrated under vacuum below 35° C. The residue was diluted with DCM and poured into sodium bicarbonate at 0° C. The aqueous phase was extracted with DCM and the combined organic phase was dried with anhydrous sodium sulfate, filtered, and concentrated under vacuum to give $N^3$-methyl-$N^2$-(3-(5-(oxetan-3-yloxy)pyridin-2-yl)-1,2,4-thiadiazol-5-yl)-5-(trifluoromethyl)pyridine-2,3-diamine (0.4 g, crude).

N-Methyl-N-(2-((3-(5-(oxetan-3-yloxy)pyridin-2-yl)-1,2,4-thiadiazol-5-yl) amino)-5-(trifluoromethyl)pyridin-3-yl)acetamide To a solution of $N^3$-methyl-$N^2$-(3-(5-(oxetan-3-yloxy)pyridin-2-yl)-1,2,4-thiadiazol-5-yl)-5-(trifluoromethyl)pyridine-2,3-diamine (0.4 g, crude) and TEA (476.86 mg, 4.71 mmol) in DMF (35 mL) was added Ac$_2$O (144.33 mg, 1.41 mmol) and the mixture was stirred at 45° C. for 16 h. The mixture was concentrated and the residue was purified by prep-HPLC (column: Phenomenex Synergi C18 150*25*10 um; mobile phase: [H$_2$O (0.2% FA)-ACN]; B %: 32%-62%, 11 min) followed by lyophilization to give N-methyl-N-(2-((3-(5-(oxetan-3-yloxy)pyridin-2-yl)-1,2,4-thiadiazol-5-yl)amino)-5-(trifluoromethyl)pyridin-3-yl)acetamide (168.99 mg, 0.350 mmol, 37.48% yield, 97.5% purity). LCMS (ESI): m/z 467.1 [M+1]$^+$.

Example 59: N-(5-(difluoromethyl)-2-((3-(1-methyl-2,3-dihydro-1H-pyrrolo[2,3-c]pyridin-5-yl)-1,2,4-thiadiazol-5-yl)amino)pyridin-3-yl)-N-methylacetamide

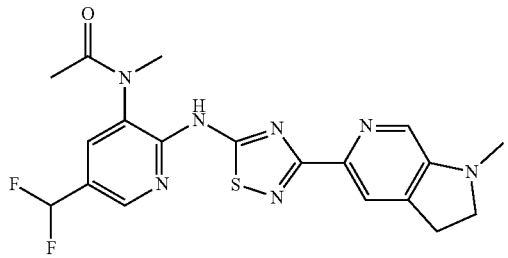 [SMILES: CC(=O)N(C)c1cc(C(F)F)cnc1Nc1nc(-c2cc3c(cn2)N(C)CC3)ns1]

tert-Butyl (5-(difluoromethyl)-2-(3-(imino(5-isopropoxypyridin-2-yl)methyl)thioureido)pyridin-3-yl)(methyl)carbamate To a solution of tert-butyl (5-(difluoromethyl)-2-isothiocyanatopyridin-3-yl)(methyl)carbamate (0.4 g, 1.27 mmol) and 1-methyl-2,3-dihydro-1H-pyrrolo[2,3-c]pyridine-5-carboximidamide (223.53 mg, 1.27 mmol) in DCM (10 mL) and acetone (10 mL) was added TEA (641.79 mg, 6.34 mmol). The mixture was stirred at 30° C. for 16 h under nitrogen. The mixture was concentrated under vacuum to give tert-butyl(5-(difluoromethyl)-2-(3-(imino(1-methyl-2,3-dihydro-1H-pyrrolo[2,3-c]pyridin-5-yl)methyl)thioureido)pyridin-3-yl)(methyl)carbamate (0.62 g, crude).

tert-Butyl (5-(difluoromethyl)-2-((3-(1-methyl-2,3-dihydro-1H-pyrrolo[2,3-c]pyridin-5-yl)-1,2,4-thiadiazol-5-yl)amino)pyridin-3-yl)(methyl)carbamate To a solution of tert-butyl (5-(difluoromethyl)-2-(3-(imino(1-methyl-2,3-dihydro-1H-pyrrolo[2,3-c]pyridin-5-yl)methyl)thioureido)pyridin-3-yl)(methyl)carbamate (0.62 g, crude) in EtOH (10 mL) was added iodine (640.26 mg, 2.52 mmol) at 0° C. The mixture was stirred at 15° C. for 15 min and then quenched with saturated sodium sulfite at 0° C. The mixture was concentrated, the aqueous phase was diluted with H$_2$O and extracted with EtOAc. The combined organic phase was dried with anhydrous sodium sulfate, filtered and concentrated. The residue was purified by flash silica gel chromatography to give tert-butyl (5-(difluoromethyl)-2-((3-(1-methyl-2,3-dihydro-1H-pyrrolo[2,3-c]pyridin-5-yl)-1,2,4-thiadiazol-5-yl)amino)pyridin-3-yl)(methyl)carbamate (0.55 g, 1.06 mmol, 83.73% yield, 94% purity).

5-(Difluoromethyl)-N3-methyl-N2-(3-(1-methyl-2,3-dihydro-1H-pyrrolo[2,3-c]pyridin-5-yl)-1,2,4-thiadiazol-5-yl)pyridine-2,3-diamine hydrochloride To a solution of tert-butyl (5-(difluoromethyl)-2-((3-(1-methyl-2,3-dihydro-1H-pyrrolo[2,3-c]pyridin-5-yl)-1,2,4-thiadiazol-5-yl)amino)pyridin-3-yl)(methyl)carbamate (0.55 g, 1.06 mmol) in EtOAc (5 mL) was added hydrochloride/EtOAc (4 M, 10 mL) at 0° C. The mixture was stirred at 30° C. for 0.5 h and then concentrated under vacuum. 5-(difluoromethyl)-N3-methyl-N2-(3-(1-methyl-2,3-dihydro-1H-pyrrolo[2,3-c]pyridin-5-yl)-1,2,4-thiadiazol-5-yl)pyridine-2,3-diamine, HCl salt (0.45 g, crude).

N-(5-(Difluoromethyl)-2-((3-(1-methyl-2,3-dihydro-1H-pyrrolo[2,3-c]pyridin-5-yl)-1,2,4-thiadiazol-5-yl)amino)pyridin-3-yl)-N-methylacetamide To a solution of 5-(difluoromethyl)-N3-methyl-N2-(3-(1-methyl-2,3-dihydro-1H-pyrrolo[2,3-c]pyridin-5-yl)-1,2,4-thiadiazol-5-yl)pyridine-2,3-diamine (0.45 g, crude, hydrochloride) and Ac₂O (140.23 mg, 1.37 mmol) in ACN (20 mL) was added TEA (534.60 mg, 5.28 mmol). The mixture was stirred at 35° C. for 32 h. The mixture was concentrated under vacuum and the residue was purified by prep-HPLC (column: Phenomenex Luna C18 200*40 mm*10 um; mobile phase: [H₂O (0.225% FA)-ACN]; B %: 5%-35%, 8.5 min) followed by lyophilization to give N-(5-(difluoromethyl)-2-((3-(1-methyl-2,3-dihydro-1H-pyrrolo[2,3-c]pyridin-5-yl)-1,2,4-thiadiazol-5-yl)amino)pyridin-3-yl)-N-methylacetamide (263.37 mg, 0.780 mmol, 54.88% yield, 95% purity). LCMS (ESI): m/z 432.3 [M+1]⁺.

Example 60: N-[2-[[3-(3,3-Dimethyl-2-oxo-1H-pyrrolo[2,3-c]pyridin-5-yl)-1,2,4-thiadiazol-5-yl]amino]-5-(trifluoromethyl)-3-pyridyl]-N-methyl-acetamide

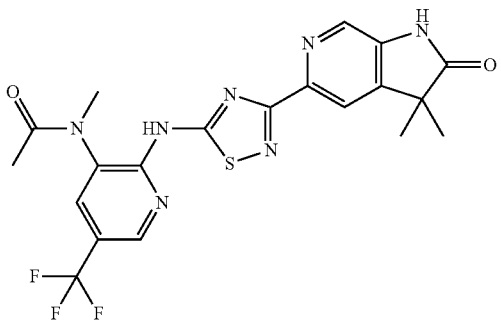 [SMILES: CC(=O)N(C)c1cc(C(F)(F)F)cnc1Nc1nc(-c2cc3c(cn2)NC(=O)C3(C)C)ns1]

3,3-Dimethyl-2-oxo-1H-pyrrolo[2,3-c]pyridine-5-carboxamidine

To a solution of 3,3-dimethyl-2-oxo-1H-pyrrolo[2,3-c]pyridine-5-carbonitrile (500. mg, 2.67 mmol) in MeOH (10 mL) was added a solution of Na (18.43 mg, 0.8000 mmol) in MeOH (3 mL) and the mixture was stirred at 30° C. for 16 h. The mixture was concentrated under vacuum and the residue was triturated with EtOAc and stirred for 0.5 h. The suspension was filtered and the filtrate was concentrated under vacuum to recover 3,3-dimethyl-2-oxo-1H-pyrrolo[2,3-c]pyridine-5-carbonitrile. The filter cake was suspended in H₂O and ACN with OH-type resin and stirred for 0.5 h. The mixture was filtered through a pad of celite and filtrate was dried by lyophilization to give 3,3-dimethyl-2-oxo-1H-pyrrolo[2,3-c]pyridine-5-carboxamidine (50 mg, 0.2448 mmol, 9.2% yield).

3,3-Dimethyl-2-oxo-1H-pyrrolo[2,3-c]pyridine-5-carbonitrile

To a solution of 5-chloro-3,3-dimethyl-1H-pyrrolo[2,3-c]pyridin-2-one (650. mg, 3.31 mmol) in DMA (10 mL) were added zinc cyanide (766.26 mg, 6.61 mmol) and tetrakis[triphenylphosphine]palladium(0) (191. mg, 0.1700 mmol), the mixture was stirred at 120° C. for 16 h under nitrogen. The mixture was filtered through a pad of celite and the filtrate was poured into H₂O. The aqueous phase was extracted with EtOAc and the combined organic phase was washed with brine, dried over anhydrous sodium sulfate, filtered and concentrated under vacuum. The residue was purified by flash silica gel chromatography to give 3,3-dimethyl-2-oxo-1H-pyrrolo[2,3-c]pyridine-5-carbonitrile (180 mg, 0.9615 mmol, 29.1% yield). LCMS (ESI): m/z 188.1 [M+1]+.

tert-Butyl N-[2-isothiocyanato-5-(trifluoromethyl)-3-pyridyl]-N-methyl-carbamate To a solution of thiocarbonyl dichloride (3.66 mL, 48.07 mmol) in DCM (30 mL) was added a solution of tert-butyl N-[2-amino-5-(trifluoromethyl)-3-pyridyl]-N-methyl-carbamate (7.0 g, 24.03 mmol) in DCM (50 mL) at 0° C. and the mixture was stirred at 0° C. for 2 h. The mixture was poured into saturated sodium bicarbonate and the aqueous phase was extracted with DCM. The combined organic phase was concentrated under vacuum and purified by silica gel chromatography to give tert-butyl N-[2-isothiocyanato-5-(trifluoromethyl)-3-pyridyl]-N-methyl-carbamate (3.4 g, 10.2 mmol, 42.4% yield).

tert-Butyl N-[6-[(4-isopropoxypyridine-2-carboximidoyl)carbamothioylamino]-5-(trifluoromethyl)-3-pyridyl]-N-methyl-carbamate To a solution of tert-butyl N-[6-isothiocyanato-5-(trifluoromethyl)-3-pyridyl]-N-methyl-carbamate (500. mg, 1.5 mmol) and 4-isopropoxypyridine-2-carboxamidine (538.52 mg, 3 mmol) in DCM (20 mL) and acetone (20 mL) was added TEA (1.15 mL, 4.5 mmol) and the mixture was stirred at 35° C. for 16 h. The mixture was concentrated under vacuum to give crude tert-butyl N-[6-[(4-isopropoxypyridine-2-carboximidoyl)carbamothioylamino]-5-(trifluoromethyl)-3-pyridyl]-N-methyl-carbamate (770 mg, 1.5023 mmol, 100.15% yield). LCMS (ESI): m/z 512.9 [M+1]+.

N-[2-[[3-(3,3-Dimethyl-2-oxo-1H-pyrrolo[2,3-c]pyridin-5-yl)-1,2,4-thiadiazol-5-yl]amino]-5-(trifluoromethyl)-3-pyridyl]-N-methyl-acetamide To a solution of 3,3-dimethyl-5-[5-[[3-(methylamino)-5-(trifluoromethyl)-2-pyridyl]amino]-1,2,4-thiadiazol-3-yl]-1H-pyrrolo[2,3-c]pyridin-2-one;hydrochloride (160. mg, 0.3400 mmol) and TEA (0.02 mL, 0.3400 mmol) in DMF (5 mL) was added acetyl acetate (103.84 mg, 1.02 mmol) and the mixture was stirred at 30° C. for 16 h. The mixture was concentrated and the residue was resuspended in THF (5 mL). To this was added sodium hydroxide (2 M, 5 mL) and the mixture was stirred at 25° C. for 1 h. The mixture was concentrated under vacuum and purified by prep-HPLC (column: Phenomenex Gemini-NX C18 75*30 mm*3 um; mobile phase: [H₂O (0.1% TFA)-ACN]; B %: 35%-45%, 10 min), then dried by lyophilization to give N-[2-[[3-(3,3-dimethyl-2-oxo-1H-pyrrolo[2,3-c]pyridin-5-yl)-1,2,4-thiadiazol-5-yl]amino]-5-(trifluoromethyl)-3-pyridyl]-N-methyl-acetamide (56.46 mg, 0.1126 mmol, 33.2% yield). LCMS (ESI): m/z 478.1 [M+1]+

Example 61: N-Methyl-N-(5-(trifluoromethyl)-2-((3-(1,3,3-trimethyl-2-oxo-2,3-dihydro-1H-pyrrolo[2,3-c]pyridin-5-yl)-1,2,4-thiadiazol-5-yl)amino)pyridin-3-yl)acetamide

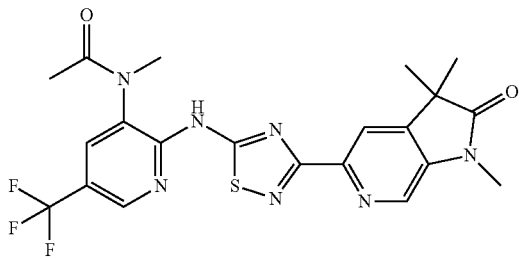 [SMILES: CC(=O)N(C)c1cc(C(F)(F)F)cnc1Nc1nc(-c2cc3c(cn2)N(C)C(=O)C3(C)C)ns1]

tert-Butyl(2-(3-(imino(1,3,3-trimethyl-2-oxo-2,3-dihydro-1H-pyrrolo[2,3-c]pyridin-5-yl)methyl)thioureido)-5-(trifluoromethyl)pyridin-3-yl)(methyl)carbamate To a solution of 1,3,3-trimethyl-2-oxo-2,3-dihydro-1H-pyrrolo[2,3-c]pyridine-5-carboximidamide (530. mg, 2.43 mmol) and tert-butyl (2-isothiocyanato-5-(trifluoromethyl)pyridin-3-yl)(methyl)carbamate (809.42 mg, 2.43 mmol) in DCM (5 mL) and acetone (5 mL) was added TEA (3.1 mL, 12.14 mmol) and the mixture was stirred at 25° C. for 16 h. The mixture was concentrated under vacuum to give tert-butyl (2-(3-(imino(1,3,3-trimethyl-2-oxo-2,3-dihydro-1H-pyrrolo[2,3-c]pyridin-5-yl)methyl)thioureido)-5-(trifluoromethyl)pyridin-3-yl)(methyl)carbamate (1.34 g, crude). LCMS (ESI): m/z 552.1 [M+1]$^+$.

tert-Butyl methyl(5-(trifluoromethyl)-2-((3-(1,3,3-trimethyl-2-oxo-2,3-dihydro-1H-pyrrolo[2,3-c]pyridin-5-yl)-1,2,4-thiadiazol-5-yl)amino)pyridin-3-yl)carbamate To a solution of tert-butyl(2-(3-(imino(1,3,3-trimethyl-2-oxo-2,3-dihydro-1H-pyrrolo[2,3-c]pyridin-5-yl)methyl)thioureido)-5-(trifluoromethyl)pyridin-3-yl)(methyl)carbamate (1.34 g, crude) in EtOH (20 mL) was added iodine (123.32 mg, 0.4900 mmol) and hydrogen peroxide (550.82 mg, 4.86 mmol, 30% purity) at 0° C. The mixture was stirred at 25° C. for 0.5 h, quenched with saturated sodium sulfite aqueous, and the mixture was concentrated under vacuum. The mixture was extracted with EtOAc and the combined organic phase was washed with brine, dried over anhydrous sodium sulfate, filtered and concentrated under vacuum. The residue was purified by flash silica gel chromatography to give tert-butyl methyl(5-(trifluoromethyl)-2-((3-(1,3,3-trimethyl-2-oxo-2,3-dihydro-1H-pyrrolo[2,3-c]pyridin-5-yl)-1,2,4-thiadiazol-5-yl)amino)pyridin-3-yl)carbamate (330 mg, 0.4744 mmol, 19.5% yield). LCLCMS (ESI): m/z 550.0 [M+1]$^+$.

1,3,3-Trimethyl-5-(5-((3-(methylamino)-5-(trifluoromethyl)pyridin-2-yl)amino)-1,2,4-thiadiazol-3-yl)-1H-pyrrolo[2,3-c]pyridin-2(3H)-one To a solution of tert-butyl methyl(5-(trifluoromethyl)-2-((3-(1,3,3-trimethyl-2-oxo-2,3-dihydro-1H-pyrrolo[2,3-c]pyridin-5-yl)-1,2,4-thiadiazol-5-yl)amino)pyridin-3-yl)carbamate (300 mg, 0.5500 mmol) in EtOAc (10 mL) was added hydrochloric acid/EtOAc (10 mL, 40 mmol) and the mixture was stirred at 20° C. for 2 h. The mixture was concentrated under vacuum to give 1,3,3-trimethyl-5-(5-((3-(methylamino)-5-(trifluoromethyl)pyridin-2-yl)amino)-1,2,4-thiadiazol-3-yl)-1H-pyrrolo[2,3-c]pyridin-2(3H)-one; hydrochloride (260 mg, 0.5351 mmol, 98.021% yield).

N-Methyl-N-(5-(trifluoromethyl)-2-((3-(1,3,3-trimethyl-2-oxo-2,3-dihydro-1H-pyrrolo[2,3-c]pyridin-5-yl)-1,2,4-thiadiazol-5-yl)amino)pyridin-3-yl)acetamide To a solution of 1,3,3-trimethyl-5-(5-((3-(methylamino)-5-(trifluoromethyl)pyridin-2-yl)amino)-1,2,4-thiadiazol-3-yl)-1H-pyrrolo[2,3-c]pyridin-2(3H)-one; hydrochloride (260. mg, 0.5400 mmol) and TEA (0.68 mL, 2.68 mmol) in DMF (15 mL) was added acetyl acetate (109.25 mg, 1.07 mmol). The mixture was stirred at 40° C. for 16 h. Additional acetyl acetate (0.05 mL, 0.5400 mmol) was added to the mixture and stirred at 40° C. for 6 h. The mixture was concentrated and the residue was purified by prep-HPLC (column: Unisil 3-100 C18 Ultra 150*50 mm*3 um; mobile phase: [H$_2$O (0.225% FA)-ACN]; B %: 45%-65%, 10 min), then dried by lyophilization to give N-methyl-N-[5-(trifluoromethyl)-2-[[3-(1,3,3-trimethyl-2-oxo-pyrrolo[2,3-c]pyridin-5-yl)-1,2,4-thiadiazol-5-yl]amino]-3-pyridyl]acetamide (106.58 mg, 0.2134 mmol, 39.9% yield). LCMS (ESI): m/z 492.1 [M+1]$^+$.

Example 62: N-Methyl-N-(5-(trifluoromethyl)-2-((3-(1,2,2-trimethyl-2,3-dihydro-1H-pyrrolo[2,3-c]pyridin-5-yl)-1,2,4-thiadiazol-5-yl)amino)pyridin-3-yl)acetamide

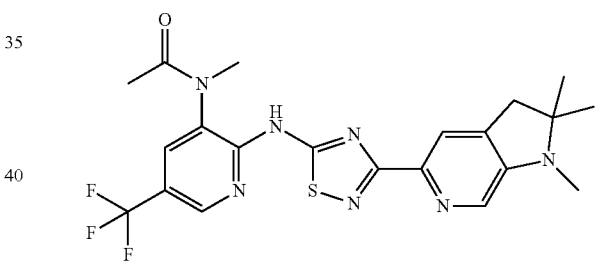

tert-Butyl (2-(3-(imino(1,2,2-trimethyl-2,3-dihydro-1H-pyrrolo[2,3-c]pyridin-5-yl)methyl)thioureido)-5-(trifluoromethyl)pyridin-3-yl)(methyl)carbamate To a mixture of 1,2,2-trimethyl-2,3-dihydro-1H-pyrrolo[2,3-c]pyridine-5-carboximidamide hydrochloride (200. mg, 0.8300 mmol) and tert-butyl (2-isothiocyanato-5-(trifluoromethyl)pyridin-3-yl)(methyl)carbamate (415.4 mg, 1.25 mmol) in DCM (10 mL) and acetone (10 mL) was added TEA (420.35 mg, 4.15 mmol). The mixture was stirred at 25° C. for 6 h under nitrogen and then concentrated under vacuum to give tert-butyl(2-(3-(imino(1,2,2-trimethyl-2,3-dihydro-1H-pyrrolo[2,3-c]pyridin-5-yl)methyl)thioureido)-5-(trifluoromethyl)pyridin-3-yl)(methyl)carbamate (600 mg, crude). LCMS (ESI): m/z 538 [M+1]$^+$.

tert-Butyl methyl(5-(trifluoromethyl)-2-((3-(1,2,2-trimethyl-2,3-dihydro-1H-pyrrolo[2,3-c]pyridin-5-yl)-1,2,4-thiadiazol-5-yl)amino)pyridin-3-yl)carbamate To a mixture of tert-butyl (2-(3-(imino(1,2,2-trimethyl-2,3-dihydro-1H-pyrrolo[2,3-c]pyridin-5-yl)methyl)thioureido)-5-(trifluoromethyl)pyridin-3-yl)(methyl)carbamate (600 mg, crude) in EtOH (20 mL) was added iodine (424.91 mg, 1.67 mmol) at 0° C. The mixture was stirred at 25° C. for 1 h. The mixture was cooled and poured into saturated sodium sulfite. The mixture was concentrated and the aqueous phase was extracted with EtOAc. The combined organic phase was dried over anhydrous sodium sulfate, filtered and concentrated under vacuum. The residue was purified by flash silica gel chromatography to give tert-butyl methyl(5-(trifluoromethyl)-2-((3-(1,2,2-trimethyl-2,3-dihydro-1H-pyrrolo[2,3-c]pyridin-5-yl)-1,2,4-thiadiazol-5-yl)amino)pyridin-3-yl)carbamate (300 mg, 0.5433 mmol, 48.7% yield). LCMS (ESI): 536 [M+1]$^+$.

N3-Methyl-5-(trifluoromethyl)-N2-(3-(1,2,2-trimethyl-2,3-dihydro-1H-pyrrolo[2,3-c]pyridin-5-yl)-1,2,4-thiadiazol-5-yl)pyridine-2,3-diamine hydrochloride To a mixture of tert-butyl methyl(5-(trifluoromethyl)-2-((3-(1,2,2-trimethyl-2,3-dihydro-1H-pyrrolo[2,3-c]pyridin-5-yl)-1,2,4-thiadiazol-5-yl)amino)pyridin-3-yl)carbamate (300. mg, 0.5400 mmol) in EtOAc (4 mL) was added hydrogen chloride/EtOAc (4.07 mL, 16.3 mmol). The mixture was stirred at 25° C. for 1 h. The mixture was concentrated under vacuum to give N$_3$-methyl-5-(trifluoromethyl)-N2-(3-(1,2,2-trimethyl-2,3-dihydro-1H-pyrrolo[2,3-c]pyridin-5-yl)-1,2,4-thiadiazol-5-yl)pyridine-2,3-diamine hydrochloride (250 mg, 0.5297 mmol, 97.499% yield). LCMS (ESI): m/z 436 [M+1]$^+$.

N-Methyl-N-(5-(trifluoromethyl)-2-((3-(1,2,2-trimethyl-2,3-dihydro-1H-pyrrolo[2,3-c]pyridin-5-yl)-1,2,4-thiadiazol-5-yl)amino)pyridin-3-yl)acetamide To a mixture of N3-methyl-5-(trifluoromethyl)-N2-(3-(1,2,2-trimethyl-2,3-dihydro-1H-pyrrolo[2,3-c]pyridin-5-yl)-1,2,4-thiadiazol-5-yl)pyridine-2,3-diamine hydrochloride (250 mg, 0.5300 mmol) and TEA (160.81 mg, 1.59 mmol) in DMF (3 mL) was added acetyl acetate (81.12 mg, 0.7900 mmol). The mixture was stirred at 40° C. for 16 h and then concentrated under vacuum. The residue was purified by prep-HPLC (column: Phenomenex Luna C18 150*25 mm*10 um; mobile phase: [H$_2$O (0.225% FA)-ACN]; B %: 19%-49%, 10 min) followed by lyophilization to give N-methyl-N-(5-(trifluoromethyl)-2-((3-(1,2,2-trimethyl-2,3-dihydro-1H-pyrrolo[2,3-c]pyridin-5-yl)-1,2,4-thiadiazol-5-yl)amino)pyridin-3-yl)acetamide (110.93 mg, 0.2263 mmol, 42.7% yield). LCMS (ESI): m/z 478.2 [M+1]$^+$.

Example 63: 2-((3-(5-Isopropoxypyridin-2-yl)-1,2,4-thiadiazol-5-yl)amino)-N,N-dimethyl-5-(trifluoromethyl)pyridine-3-sulfonamide

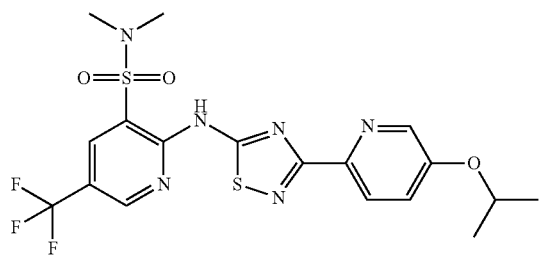 [SMILES: CC(C)Oc1ccc(-c2nsc(Nc3ncc(C(F)(F)F)cc3S(=O)(=O)N(C)C)n2)nc1]

3-Bromo-5-(trifluoromethyl)pyridin-2-amine

To a solution of 5-(trifluoromethyl)pyridin-2-amine (20 g, 123.37 mmol, 1 eq) in ACN (200 mL) was added 1-bromopyrrolidine-2,5-dione (26.35 g, 148.05 mmol) in portions at 0° C. The mixture was stirred at 25° C. for 2 h. The mixture was concentrated under vacuum and the residue was purified by silica gel chromatography to give 3-bromo-5-(trifluoromethyl)pyridin-2-amine (27 g, 107.55 mmol, 87.17% yield, 96% purity).

3-Bromo-2-isothiocyanato-5-(trifluoromethyl)pyridine

To a solution of thiocarbonyl dichloride (9.54 g, 82.98 mmol) in DCM (30 mL) was added a solution of 3-bromo-5-(trifluoromethyl)pyridin-2-amine (10. g, 41.49 mmol) in DCM (50 mL) dropwise at 0° C. and the mixture was stirred at 25° C. for 16 h. The mixture was poured into saturated sodium bicarbonate and the aqueous phase was extracted with DCM. The combined organic phase was concentrated under vacuum and purified by silica gel chromatography to give 3-bromo-2-isothiocyanato-5-(trifluoromethyl)pyridine (3 g, 10.598 mmol, 25.5% yield). LCMS (ESI): m/z 285.2 [M+1]$^+$.

N-((3-Bromo-5-(trifluoromethyl)pyridin-2-yl)carbamothioyl)-5-isopropoxypicolinimidamide To a solution of 3-bromo-2-isothiocyanato-5-(trifluoromethyl)pyridine (1.6 g, 5.65 mmol) and 5-isopropoxypyridine-2-carboxamidine (1.01 g, 5.65 mmol) in DCM (20 mL) and acetone (20 mL) was added TEA (0.79 mL, 5.65 mmol) and the mixture was stirred at 25° C. for 16 h. The mixture was concentrated under vacuum to give crude N-((3-bromo-5-(trifluoromethyl)pyridin-2-yl)carbamothioyl)-5-isopropoxypicolinimidamide (2.6 g, crude).

N-(3-Bromo-5-(trifluoromethyl)pyridin-2-yl)-3-(5-isopropoxypyridin-2-yl)-1,2,4-thiadiazol-5-amine To a solution of crude N-((3-bromo-5-(trifluoromethyl)pyridin-2-yl)carbamothioyl)-5-isopropoxypicolinimidamide (2.6 g, crude) in EtOH (10 mL) was added iodine (175.68 mg, 0.69 mmol) and hydrogen peroxide (784.5 mg, 6.92 mmol, 30% purity) at 0° C. The mixture was stirred at 25° C. for 0.5 h. The mixture was quenched by addition of saturated sodium sulfite aqueous at 0° C. and concentrated under vacuum. The aqueous phase was extracted with EtOAc and the combined organic phase was washed with brine, dried over anhydrous sodium sulfate, filtered and concentrated under vacuum. The residue was purified by flash silica gel chromatography to give N-(3-bromo-5-(trifluoromethyl)pyridin-2-yl)-3-(5-isopropoxypyridin-2-yl)-1,2,4-thiadiazol-5-amine (1 g, 2.1726 mmol, 38.6% yield). LCMS (ESI): m/z 459.9 [M+1]$^+$.

3-(5-Isopropoxypyridin-2-yl)-N-(3-((4-methoxybenzyl)thio)-5-(trifluoromethyl)pyridin-2-yl)-1,2,4-thiadiazol-5-amine To a solution of N-((3-bromo-5-(trifluoromethyl)pyridin-2-yl)carbamothioyl)-5-isopropoxypicolinimidamide (1 g, 2.17 mmol) and (4-methoxyphenyl)methanethiol (502.63 mg, 3.26 mmol) in 1,4-dioxane (10 mL) was added tris(dibenzylideneacetone)dipalladium(0) (99.48 mg, 0.1100 mmol), N-ethyl-N-isopropylpropan-2-amine (561.58 mg, 4.35 mmol) and (5-diphenylphosphinyl-9,9-dimethylxanthen-4-yl)-diphenylphosphine (62.86 mg, 0.1100 mmol). The mixture was de-gassed with nitrogen 3 times and stirred at 100° C. for 16 h under nitrogen. The mixture was filtered through a pad of celite and the filtrate was concentrated under vacuum. The residue was purified by flash silica gel chromatography to give 3-(5-isopropoxypyridin-2-yl)-N-(3-((4-methoxybenzyl)thio)-5-(trifluoromethyl)pyridin-2-yl)-1,2,4-thiadiazol-5-amine (1 g, 1.8741 mmol, 86.3% yield). LCMS (ESI): m/z 534.2 [M+1]+.

2-((3-(5-Isopropoxypyridin-2-yl)-1,2,4-thiadiazol-5-yl)amino)-5-(trifluoromethyl)pyridine-3-sulfonic acid To a solution of 3-(5-isopropoxypyridin-2-yl)-N-(3-((4-methoxybenzyl)thio)-5-(trifluoromethyl)pyridin-2-yl)-1,2,4-thiadiazol-5-amine (900 mg, 1.69 mmol) in a mixture of DCM (10.5 mL), acetic acid (1.5 mL) and H2O (3 mL) was added a solution of 1,3-dichloro-5,5-dimethylhydantoin (660.84 mg, 3.37 mmol) in DCM (5 mL) at 0° C. The mixture was stirred at 0° C. for 2 h and then poured into H2O. The aqueous phase was extracted with DCM and the combined organic phase was dried over anhydrous sodium sulfate, filtered and concentrated under vacuum. The residue was collected to give 2-[[3-(5-isopropoxy-2-pyridyl)-1,2,4-thiadiazol-5-yl]amino]-5-(trifluoromethyl)pyridine-3-sulfonic acid (1 g, crude). LCMS (ESI): m/z 462.0 [M+1]+.

2-((3-(5-Isopropoxypyridin-2-yl)-1,2,4-thiadiazol-5-yl)amino)-5-(trifluoromethyl)pyridine-3-sulfonyl chloride To a solution of 2-((3-(5-isopropoxypyridin-2-yl)-1,2,4-thiadiazol-5-yl)amino)-5-(trifluoromethyl)pyridine-3-sulfonic acid (700. mg, 1.52 mmol) in phosphorus oxychloride (10 mL, 110.28 mmol) was added phosphorus pentachloride (631.8 mg, 3.03 mmol) and the mixture was stirred at 60° C. for 3 h. The mixture was diluted with DCM, poured into saturated sodium bicarbonate aqueous, then adjusted pH to 7-8 with sodium bicarbonate solid at 0° C. The aqueous phase was extracted with DCM and the combined organic phase was washed with brine, dried over anhydrous sodium sulfate, and filtered to give 2-((3-(5-isopropoxypyridin-2-yl)-1,2,4-thiadiazol-5-yl)amino)-5-(trifluoromethyl)pyridine-3-sulfonyl chloride (730 mg, crude).

2-((3-(5-Isopropoxypyridin-2-yl)-1,2,4-thiadiazol-5-yl)amino)-N,N-dimethyl-5-(trifluoromethyl)pyridine-3-sulfonamide To a solution of crude 2-((3-(5-isopropoxypyridin-2-yl)-1,2,4-thiadiazol-5-yl)amino)-5-(trifluoromethyl)pyridine-3-sulfonyl chloride (730. mg, crude) in DCM (50 mL) was added dimethylamine (1.52 mL, 3.04 mmol) (2 M in THF) and the mixture was stirred at 25° C. for 2 h. The mixture was concentrated under vacuum. The residue was triturated with MeOH and DMF at 60° C. for 16 h. The filter cake was dried by lyophilization, then dried by centrifuge. All the mother liquid was combined and purified by prep-HPLC (column: Phenomenex Gemini-NX C18 75*30 mm*3 um; mobile phase: H2O (0.1% TFA)-ACN]; B %: 55%-65%, 10 min), then dried by lyophilization. The two part product was combined and dried by lyophilization to give 2-((3-(5-isopropoxypyridin-2-yl)-1,2,4-thiadiazol-5-yl)amino)-N,N-dimethyl-5-(trifluoromethyl)pyridine-3-sulfonamide (178.38 mg, 0.3619 mmol, 23.788% yield). LCMS (ESI): m/z 489.1 [M+1]+.

Example 64: N,N-Dimethyl-5-(trifluoromethyl)-2-((3-(1,3,3-trimethyl-2,3-dihydro-1H-pyrrolo[2,3-c]pyridin-5-yl)-1,2,4-thiadiazol-5-yl)amino)nicotinamide

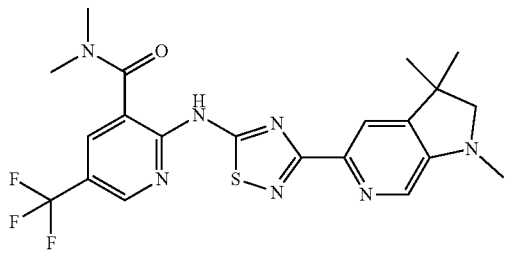 [SMILES: CN(C)C(=O)c1cc(C(F)(F)F)cnc1Nc1nc(-c2cc3c(cn2)N(C)CC3(C)C)ns1]

5-Chloro-1,3,3-trimethyl-1H-pyrrolo[2,3-c]pyridin-2(3H)-one

To a mixture of NaH (3.56 g, 88.98 mmol) in DMF (30 mL) was added a solution of 5-chloro-1H-pyrrolo[2,3-c]pyridin-2(3H)-one (3. g, 17.8 mmol) in DMF (20 mL) at 0° C. The mixture was stirred at 25° C. for 0.5 h then iodomethane (12.63 g, 88.98 mmol) was added at 0° C. The mixture was stirred at 25° C. for 2 h. The mixture was cooled and poured into ice H2O slowly. The aqueous phase was extracted with EtOAc and the combined organic phase was washed with brine, dried over anhydrous sodium sulfate, filtered and concentrated under vacuum. The residue was purified by flash silica gel chromatography to give 5-chloro-1,3,3-trimethyl-1H-pyrrolo[2,3-c]pyridin-2(3H)-one (3.5 g, 16.614 mmol, 93.4% yield).

5-Chloro-1,3,3-trimethyl-2,3-dihydro-1H-pyrrolo[2,3-c]pyridine

To a solution of 5-chloro-1,3,3-trimethyl-1H-pyrrolo[2,3-c]pyridin-2(3H)-one (2. g, 9.49 mmol) in THF (10 mL) was added borane in THF (47.47 mL, 47.47 mmol), the mixture was stirred at 60° C. for 16 h. Then additional borane in THF (18.99 mL, 18.99 mmol) was added to the mixture and stirred at 60° C. for 20 h. The mixture was cooled and poured into cold H2O and the pH was adjusted to 5-6 with hydrochloric acid. The aqueous phase was extracted with EtOAc and the combined organic phase was washed with brine, dried over anhydrous sodium sulfate, filtered and concentrated under vacuum. The residue was purified by flash silica gel chromatography to give 5-chloro-1,3,3-trimethyl-2,3-dihydro-1H-pyrrolo[2,3-c]pyridine (1.3 g, 6.6097 mmol, 69.6% yield). LCMS (ESI): m/z 197.1 [M+1]+.

1,3,3-Trimethyl-2,3-dihydro-1H-pyrrolo[2,3-c]pyridine-5-carbonitrile

To a solution of 5-chloro-1,3,3-trimethyl-2,3-dihydro-1H-pyrrolo[2,3-c]pyridine (1.2 g, 6.1 mmol) in DMF (15 mL) was added tetrakis[triphenylphosphine]palladium(0) (352.52 mg, 0.3100 mmol) and zinc cyanide (1.41 g, 12.2 mmol) and the mixture was stirred at 120° C. for 16 h. The mixture was filtered through a pad of celite and the filtrate was poured into H₂O. The aqueous phase was extracted with EtOAc and the combined organic phase was washed with brine, dried over anhydrous sodium sulfate, filtered and concentrated under vacuum. The residue was purified by flash silica gel chromatography to give 1,3,3-trimethyl-2,3-dihydro-1H-pyrrolo[2,3-c]pyridine-5-carbonitrile (300 mg, 1.6022 mmol, 26.26% yield). LCMS (ESI): m/z 188.1 [M+1]+.

1,3,3-Trimethyl-2,3-dihydro-1H-pyrrolo[2,3-c]pyridine-5-carboximidamide

To a solution of 1,3,3-trimethyl-2,3-dihydro-1H-pyrrolo[2,3-c]pyridine-5-carbonitrile (0.3 g, 1.6 mmol) in MeOH (5 mL) was added a solution of sodium (11.06 mg, 0.4800 mmol) in MeOH (5 mL) and the mixture was stirred at 25° C. for 16 h. Then NH₄Cl (129.78 mg, 2.4 mmol) was added to the mixture and stirred at 75° C. for 2 h. The mixture was concentrated under vacuum and to the residue was added MTBE (10 mL) and stirred at 25° C. for 1 h. The suspension was filtered and to the filter cake in H₂O and ACN was added OH-type resin (1 g). The mixture was stirred for 1 h and filtered through a pad of celite. The filtrate was dried under lyophilization to give 1,3,3-trimethyl-2,3-dihydro-1H-pyrrolo[2,3-c]pyridine-5-carboximidamide (160 mg, 0.7833 mmol, 48.887% yield). LCMS (ESI): m/z 205.1 [M+1]+.

2-(3-(Imino(1,3,3-trimethyl-2,3-dihydro-1H-pyrrolo[2,3-c]pyridin-5-yl) methyl)thioureido)-N,N-dimethyl-5-(trifluoromethyl)nicotinamide To a solution of 1,3,3-trimethyl-2,3-dihydro-1H-pyrrolo[2,3-c]pyridine-5-carboximidamide (90. mg, 0.4400 mmol) and 2-isothiocyanato-N,N-dimethyl-5-(trifluoromethyl)nicotinamide (121.27 mg, 0.4400 mmol) in DCM (5 mL) and acetone (5 mL) was added TEA (0.56 mL, 2.2 mmol) and the mixture was stirred at 25° C. for 1 h under nitrogen. Then 2-isothiocyanato-N,N-dimethyl-5-(trifluoromethyl)nicotinamide (60 mg, 0.22 mmol) was added to the mixture and stirred at 25° C. for 16 h. The mixture was concentrated under vacuum to give 2-(3-(imino(1,3,3-trimethyl-2,3-dihydro-1H-pyrrolo[2,3-c]pyridin-5-yl)methyl)thioureido)-N,N-dimethyl-5-(trifluoromethyl)nicotinamide (210 mg, crude).

N,N-Dimethyl-5-(trifluoromethyl)-2-((3-(1,3,3-trimethyl-2,3-dihydro-1H-pyrrolo[2,3-c]pyridin-5-yl)-1,2,4-thiadiazol-5-yl)amino)nicotinamide To a solution of crude 2-(3-(imino(1,3,3-trimethyl-2,3-dihydro-1H-pyrrolo[2,3-c]pyridin-5-yl)methyl)thioureido)-N,N-dimethyl-5-(trifluoromethyl)nicotinamide (210. mg, crude) in EtOH (10 mL) was added iodine (222.31 mg, 0.8800 mmol) at 0° C. and the mixture was stirred at 25° C. for 1 h. To the mixture was added saturated sodium sulfite at 0° C. and the mixture was concentrated under vacuum. The aqueous phase was extracted with EtOAc and the combined organic phase was washed with brine, dried over anhydrous sodium sulfate, filtered and concentrated under vacuum. The residue was purified by prep-HPLC (column: Unisil 3-100 C18 Ultra 150*50 mm*3 um; mobile phase: [H₂O (0.225% FA)-ACN]; B %: 30%-50%, 10 min), then dried by lyophilization to give N,N-dimethyl-5-(trifluoromethyl)-2-((3-(1,3,3-trimethyl-2,3-dihydro-1H-pyrrolo[2,3-c]pyridin-5-yl)-1,2,4-thiadiazol-5-yl)amino)nicotinamide (47.78 mg, 0.0990 mmol, 22.6% yield, formic acid). LCMS (ESI): m/z 478.2 [M+1]+.

Example 65: N,N-Dimethyl-5-(trifluoromethyl)-2-((3-(1,3,3-trimethyl-2-oxo-2,3-dihydro-1H-pyrrolo[2,3-c]pyridin-5-yl)-1,2,4-thiadiazol-5-yl)amino)nicotinamide

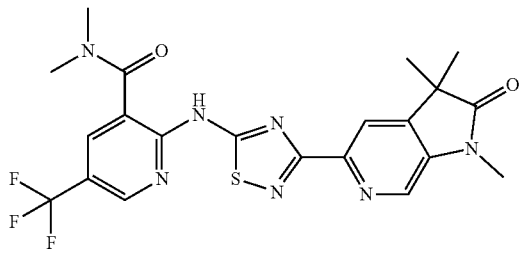 [SMILES: CN(C)C(=O)c1cc(C(F)(F)F)cnc1Nc1nc(-c2cc3c(cn2)N(C)C(=O)C3(C)C)ns1]

1,3,3-Trimethyl-2-oxo-2,3-dihydro-1H-pyrrolo[2,3-c]pyridine-5-carbonitrile

To a solution of 5-chloro-1,3,3-trimethyl-1H-pyrrolo[2,3-c]pyridin-2(3H)-one (2.7 g, 12.82 mmol) and tetrakis[triphenylphosphine]palladium(0) (1.48 g, 1.28 mmol) in DMF (20 mL) was added zinc cyanide (2.97 g, 25.63 mmol) under nitrogen and the mixture was stirred at 120° C. for 16 h. The mixture was filtered through a pad of Celite and the filtrate was poured into H₂O. The aqueous phase was extracted with EtOAc and the combined organic phase was washed with brine, dried over anhydrous sodium sulfate, filtered and concentrated under vacuum. The filter cake was quenched with hydrochloric acid (1 M, 200 mL) and discarded. The residue was purified by flash silica gel chromatography to give 1,3,3-trimethyl-2-oxo-2,3-dihydro-1H-pyrrolo[2,3-c]pyridine-5-carbonitrile (0.3000 g, 1.4909 mmol, 11.6% yield).

1,3,3-Trimethyl-2-oxo-2,3-dihydro-1H-pyrrolo[2,3-c]pyridine-5-carboximidamide To a solution of 1,3,3-trimethyl-2-oxo-2,3-dihydro-H-pyrrolo[2,3-c]pyridine-5-carbonitrile (300. mg, 1.49 mmol) in MeOH (3 mL) was added sodium methoxide (0.04 mL, 0.7500 mmol) and the mixture was stirred at 25° C. for 16 h. Then NH₄Cl (120.76 mg, 2.24 mmol) was added to the mixture and stirred at 75° C. for 2 h. The mixture was concentrated under vacuum and the residue was triturated with MTBE and stirred at 25° C. for 0.5 h. The suspension was filtered and the filter cake was dried under vacuum to give 1,3,3-trimethyl-2-oxo-2,3-dihydro-1H-pyrrolo[2,3-c]pyridine-5-carboximidamide (170 mg, 0.7789 mmol, 52.243% yield). LCMS (ESI): m/z 219.1 [M+1]+.

N,N-Dimethyl-5-(trifluoromethyl)-2-((3-(1,3,3-trimethyl-2-oxo-2,3-dihydro-1H-pyrrolo[2,3-c]pyridin-5-yl)-1,2,4-thiadiazol-5-yl)amino)nicotinamide To a solution of 1,3,3-trimethyl-2-oxo-2,3-dihydro-1H-pyrrolo[2,3-c]pyridine-5-carboximidamide (40 mg, 0.1800 mmol) and 2-isothiocyanato-N,N-dimethyl-5-(trifluoromethyl)nicotinamide (151.33 mg, 0.5500 mmol) in DCM (10 mL) and acetone (10 mL) was added TEA (92.66 mg, 0.9200 mmol), the mixture was stirred at 25° C. for 24 h. The mixture was concentrated under vacuum and purified by prep-HPLC (column: Phenomenex Synergi C18 150*25*10 um; mobile phase: [H₂O (0.225% FA)-ACN]; B %: 35%-

65%, 10 min) followed by lyophilization to give N,N-dimethyl-5-(trifluoromethyl)-2-((3-(1,3,3-trimethyl-2-oxo-2,3-dihydro-1H-pyrrolo[2,3-c]pyridin-5-yl)-1,2,4-thiadiazol-5-yl)amino)nicotinamide (23.74 mg, 0.0475 mmol, 25.9% yield). LCMS (ESI): m/z 492.2 [M+1]⁺.

Example 66: N,N-Dimethyl-5-(trifluoromethyl)-2-((3-(1,2,2-trimethyl-2,3-dihydro-1H-pyrrolo[2,3-c]pyridin-5-yl)-1,2,4-thiadiazol-5-yl)amino)nicotinamide

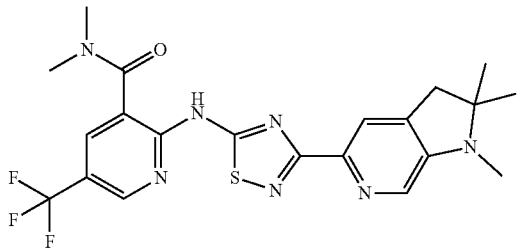 [SMILES: CN(C)C(=O)c1cc(C(F)(F)F)cnc1Nc1nc(-c2cc3c(cn2)N(C)C(C)(C)C3)ns1]

N-(4-(2-Hydroxy-2-methylpropyl)pyridin-3-yl)pivalamide

To a solution of N-(4-methylpyridin-3-yl)pivalamide (7.5 g, 39.01 mmol) in THF (100 mL) was added dropwise n-butyllithium (34.33 mL, 85.82 mmol, 2.5 M in THF) at −70° C. Upon complete addition, the mixture was stirred at 0° C. for 1 hr. Acetone (4.52 g, 78.02 mmol, 5.74 mL) was added dropwise at −70° C. The mixture was stirred at 20° C. for 16 hr, quenched by addition of $H_2O$ at 0° C. and extracted with EtOAc. The combined organic layers were washed with brine, dried over anhydrous sodium sulfate, filtered and concentrated under reduced pressure. The residue was purified by flash silica gel chromatography to give N-(4-(2-hydroxy-2-methylpropyl)pyridin-3-yl)pivalamide (9 g, 35.95 mmol, 75.00% yield). LCMS (ESI): m/z 251.2 [M+1]⁺.

2,2-Dimethyl-2,3-dihydro-1H-pyrrolo[2,3-c]pyridine

A mixture of N-(4-(2-hydroxy-2-methylpropyl)pyridin-3-yl)pivalamide (9 g, 35.95 mmol) and hydrochloric acid (12 M, 30 mL) in $H_2O$ (30 mL) was degassed and purged with nitrogen 3 times and then the mixture was stirred at 80° C. for 36 h under nitrogen. The reaction mixture was concentrated under reduced pressure, purified by prep-HPLC (column: Waters Xbridge BEH C18 250*50 mm*10 um; mobile phase: [$H_2O$ (0.05% ammonia hydroxide v/v)-ACN]; B %: 15%-38%, 20 min) and followed by lyophilization to give 2,2-dimethyl-2,3-dihydro-1H-pyrrolo[2,3-c]pyridine (4 g, 26.99 mmol, 75.07% yield). LCMS (ESI): m/z 149.2 [M+1]⁺.

tert-Butyl 2,2-dimethyl-2,3-dihydro-1H-pyrrolo[2,3-c]pyridine-1-carboxylate

To a solution of 2,2-dimethyl-2,3-dihydro-1H-pyrrolo[2,3-c]pyridine (3.5 g, 23.62 mmol) and 4-(dimethylamino)pyridine (12.98 g, 106.27 mmol) in ACN (10 mL) was added a solution of tert-butoxy carbonyl tert-butyl carbonate (20.62 g, 94.46 mmol, 21.70 mL) in ACN (10 mL). The mixture was stirred at 20° C. for 16 h under nitrogen, concentrated under reduced pressure and purified by flash silica gel chromatography to give tert-butyl 2,2-dimethyl-2,3-dihydro-1H-pyrrolo[2,3-c]pyridine-1-carboxylate (2.1 g, 8.03 mmol, 34.02% yield, 95% purity). LCMS (ESI): m/z 249.0 [M+1]⁺.

1-(tert-Butoxycarbonyl)-2,2-dimethyl-2,3-dihydro-1H-pyrrolo[2,3-c]pyridine 6-oxide To a solution of tert-butyl 2,2-dimethyl-2,3-dihydro-1H-pyrrolo[2,3-c]pyridine-1-carboxylate (1.50 g, 6.03 mmol) in DCM (20 mL) was added m-CPBA (2606.07 mg, 12.09 mmol, 80% purity) and the mixture was stirred at 25° C. for 1 hour. The mixture was concentrated under reduced pressure and purified by silica gel chromatography to give 1-(tert-butoxycarbonyl)-2,2-dimethyl-2,3-dihydro-1H-pyrrolo[2,3-c]pyridine 6-oxide (1.70 g, 5.48 mmol, 96.05% yield). LCMS (ESI): m/z 265.2 [M+1]⁺.

tert-Butyl-5-cyano-2,2-dimethyl-2,3-dihydro-1H-pyrrolo[2,3-c]pyridine-1-carboxylate To a solution of 1-(tert-butoxycarbonyl)-2,2-dimethyl-2,3-dihydro-1H-pyrrolo[2,3-c] pyridine 6-oxide (2.0 g, 7.57 mmol) in ACN (20 mL) was added TEA (2.0 mL, 14.35 mmol) followed by trimethylsilylformonitrile (5.35 g, 52.97 mmol). The mixture was stirred at 80° C. for 16 h and then concentrated under reduced pressure. The residue was purified by column chromatography to give tert-butyl 5-cyano-2,2-dimethyl-2,3-dihydro-1H-pyrrolo[2,3-c]pyridine-1-carboxylate (1.1 g, 4.0244 mmol, 53.18% yield).

2,2-Dimethyl-2,3-dihydro-1H-pyrrolo[2,3-c]pyridine-5-carbonitrile

To a mixture of tert-butyl 5-cyano-2,2-dimethyl-2,3-dihydro-1H-pyrrolo[2,3-c]pyridine-1-carboxylate (1.0 g, 3.66 mmol) in DCM (10 mL) was added trifluoroacetic acid (10 mL, 134.19 mmol) at 0° C. The mixture was stirred at 0° C. for 2 h and concentrated. The residue was poured into cold $H_2O$ and the aqueous phase adjusted to pH 8 with sodium carbonate. The mixture was extracted with EtOAc and the combined organic phase was dried over anhydrous sodium sulfate, filtered and concentrated under vacuum to give 2,2-dimethyl-1,3-dihydropyrrolo[2,3-c]pyridine-5-carbonitrile (700 mg, crude). LCLCMS (ESI): m/z 174 [M+1]⁺.

1,2,2-Trimethyl-2,3-dihydro-1H-pyrrolo[2,3-c]pyridine-5-carbonitrile

To a mixture of 2,2-dimethyl-2,3-dihydro-1H-pyrrolo[2,3-c]pyridine-5-carbonitrile (0.7 g, crude) in DMF (10 mL) was added NaH (0.32 g, 8.08 mmol) at 0° C. The mixture was stirred at 20° C. for 0.5 h. Then iodomethane (0.57 g, 4.04 mmol) was added and the mixture was stirred at 20° C. for 1 h. The mixture was cooled and poured into ice $H_2O$. The aqueous phase was extracted with EtOAc and the combined organic phase was washed with brine, dried over anhydrous sodium sulfate, filtered and concentrated under vacuum. The residue was purified by flash silica gel chromatography to give 1,2,2-trimethyl-2,3-dihydro-1H-pyrrolo[2,3-c]pyridine-5-carbonitrile (500 mg, 2.617 mmol, 64.8% yield).

1,2,2-Trimethyl-2,3-dihydro-1H-pyrrolo[2,3-c]pyridine-5-carboximidamide hydrochloride Sodium (18.43 mg, 0.8000 mmol) was added to MeOH (5 mL) and to this solution was added 1,2,2-trimethyl-2,3- dihydro-1H-pyrrolo[2,3-c]pyridine-5-carbonitrile (500. mg, 2.67 mmol). The mixture was stirred at 30° C. for 16 h. NH₄Cl (185.69 mg, 3.47 mmol) was added and the mixture was stirred at 70° C. for 1 h. The mixture was concentrated and the residue was triturated with petroleum ether:EtOAc (1:1) to give 1,2,2-trimethyl-2,3-dihydro-1H-pyrrolo[2,3-c]pyridine-5-carboximidamide hydrochloride (500 mg, 2.077 mmol, 77.78% yield).

2-(3-(Imino(1,2,2-trimethyl-2,3-dihydro-1H-pyrrolo[2,3-c]pyridin-5-yl)methyl)thioureido)-N,N-dimethyl-5-(trifluoromethyl)nicotinamide To a mixture of 1,2,2-trimethyl-2,3-dihydro-1H-pyrrolo[2,3-c]pyridine-5-carboximidamide hydrochloride (250. mg, 1.04 mmol) and 2-isothiocyanato-N,N-dimethyl-5-(trifluoromethyl)nicotinamide (285.85 mg, 1.04 mmol) in DCM (10 mL) and acetone (10 mL) was added TEA (525.43 mg, 5.19 mmol). The mixture was stirred at 25° C. for 16 h under nitrogen. The mixture was concentrated under vacuum to give N,N-dimethyl-5-(trifluoromethyl)-2-[(1,2,2-trimethyl-3H-pyrrolo[2,3-c]pyridine-5-carboximidoyl)carbamothioylamino]pyridine-3-carboxamide (500 mg, crude).

N,N-Dimethyl-5-(trifluoromethyl)-2-((3-(1,2,2-trimethyl-2,3-dihydro-1H-pyrrolo[2,3-c]pyridin-5-yl)-1,2,4-thiadiazol-5-yl)amino)nicotinamide To a mixture of 2-(3-(imino(1,2,2-trimethyl-2,3-dihydro-1H-pyrrolo[2,3-c]pyridin-5-yl)methyl)thioureido)-N,N-dimethyl-5-(trifluoromethyl)nicotinamide (500 mg, crude) in EtOH (20 mL) was added iodine (396.98 mg, 1.56 mmol) at 0° C. The mixture was stirred at 25° C. for 1 h. The mixture was cooled and poured into saturated sodium sulfite, concentrated and the aqueous phase extracted with EtOAc. The combined organic phase was dried over anhydrous sodium sulfate, filtered and concentrated under vacuum. The residue was purified by prep-HPLC (column: Phenomenex luna C18 150*40 mm*15 um; mobile phase: [H₂O (0.225% FA)-ACN]; B %: 19%-49%, 10 min) to give the crude product. The crude product was purified by prep-HPLC (column: Phenomenex Gemini-NX C18 75*30 mm*3 um; mobile phase: [H₂O (0.1% FA)-ACN]; B %: 32%-42%, 7 min) to give N,N-dimethyl-5-(trifluoromethyl)-2-((3-(1,2,2-trimethyl-2,3-dihydro-1H-pyrrolo[2,3-c]pyridin-5-yl)-1,2,4-thiadiazol-5-yl)amino)nicotinamide (95.36 mg, 0.1945 mmol, 18.654% yield). LCMS(ESI): 478.2 [M+1]⁺.

Example 67: N-(6-((5-(1-Isopropyl-2,3-dihydro-1H-pyrrolo[2,3-c]pyridin-5-yl)-1H-1,2,4-triazol-3-yl)amino)-5-(trifluoromethyl)pyridin-3-yl)-N-methylacetamide

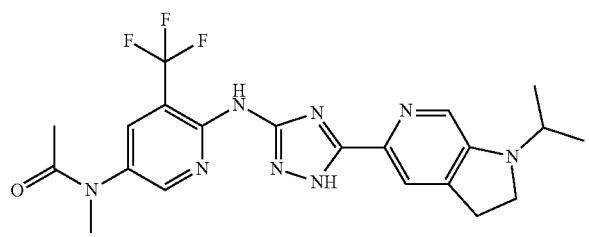 [SMILES: CC(=O)N(C)c1cnc(Nc2n[nH]c(-c3cc4c(cn3)N(C(C)C)CC4)n2)c(C(F)(F)F)c1]

6-Chloro-5-(trifluoromethyl)pyridin-3-amine

To the solution of iron powder (11.71 g, 209.68 mmol) and NH₄Cl (22.43 g, 419.35 mmol) in EtOH (250 mL) and H₂O (25 mL) was added 2-chloro-5-nitro-3-(trifluoromethyl)pyridine (9.5 g, 41.94 mmol). The reaction was stirred at 80° C. for 5 h. The reaction mixture was filtered and concentrated under reduced pressure. The residue was diluted with EtOAc, washed with H₂O, dried over anhydrous sodium sulfate, concentrated under reduced pressure, and purified by silica gel column chromatography to give 6-chloro-5-(trifluoromethyl)pyridin-3-amine (5.41 g, 26.26 mmol, 62.61% yield). LCMS (ESI) m/z 197.0 [M+1]⁺.

tert-Butyl (6-chloro-5-(trifluoromethyl)pyridin-3-yl)carbamate

To a solution of 6-chloro-5-(trifluoromethyl)pyridin-3-amine (5.41 g, 26.26 mmol) and DMAP (320.78 mg, 2.63 mmol) in pyridine (30 mL) was added di-tert-butyl dicarbonate (7.45 g, 34.13 mmol, 7.84 mL) dropwise. The mixture was stirred at 30° C. for 15 h. The reaction mixture was concentrated under reduced pressure and the residue was purified by silica gel column chromatography to give tert-butyl (6-chloro-5-(trifluoromethyl)pyridin-3-yl)carbamate (5.72 g, 18.32 mmol, 69.76% yield, 95% purity).

tert-Butyl (6-chloro-5-(trifluoromethyl)pyridin-3-yl)(methyl)carbamate

To a solution of tert-butyl (6-chloro-5-(trifluoromethyl)pyridin-3-yl)carbamate (10.2 g, 34.38 mmol) in DMF (200 mL) was added NaH (2.06 g, 51.57 mmol, 60% purity) at 0° C. and the mixture was stirred at 0° C. for 0.5 h. Iodomethane (7.32 g, 51.57 mmol, 3.21 mL) was then added to the reaction mixture at 0° C. The resulting mixture was stirred at 30° C. for 2 h under nitrogen atmosphere. The mixture was poured into saturated NH₄Cl solution then extracted with EtOAc. The organic layer was washed with brine, dried over anhydrous sodium sulfate, filtered and concentrated under reduced pressure to give methyl (5-isopropyl-4-(trifluoromethyl)pyridin-2-yl)carbamimidothioate (10 g, 32.19 mmol, 93.61% yield).

tert-Butyl (6-azido-5-(trifluoromethyl)pyridin-3-yl)(methyl)carbamate

To a solution of methyl (5-isopropyl-4-(trifluoromethyl)pyridin-2-yl)carbamimidothioate (450 mg, 1.45 mmol) in DMSO (8 mL) was added sodium azide (282.47 mg, 4.35 mmol) at 25° C. and the mixture was stirred at 100° C. for 12 h under nitrogen atmosphere. The reaction mixture was poured into ice cold saturated sodium bicarbonate and stirred for 3 min. The aqueous phase was extracted with EtOAc and the combined organic phase was concentrated under vacuum to give tert-butyl (6-azido-5-(trifluoromethyl)pyridin-3-yl)(methyl)carbamate (440 mg, crude).

tert-Butyl (6-amino-5-(trifluoromethyl)pyridin-3-yl)(methyl)carbamate

To a mixture of tert-butyl (6-azido-5-(trifluoromethyl)pyridin-3-yl)(methyl)carbamate (420 mg, crude) in MeOH (5 mL) was added Pd/C (100 mg, 0.09 mmol, 10% purity) under nitrogen, then the mixture was degassed and purged with hydrogen 3 times, and the mixture was stirred at 30° C. for 12 h under hydrogen (15 psi) atmosphere. The mixture was filtered, and the filtrate was concentrated under reduced pressure and the residue purified by silica gel column chromatography to give tert-butyl (6-amino-5-(trifluoromethyl)pyridin-3-yl)(methyl)carbamate (200 mg, 51.87% yield).

tert-Butyl (6-isothiocyanato-5-(trifluoromethyl)pyridin-3-yl)(methyl) Carbamate

To a solution of thiophosgene (3.16 g, 27.47 mmol, 2.11 mL) in DCM (20 mL) was added a solution of tert-butyl (6-amino-5-(trifluoromethyl)pyridin-3-yl)(methyl)carbamate (4 g, 13.73 mmol) in DCM (30 mL) dropwise at 0° C., then the mixture was stirred at 0° C. for 2 h. The mixture was poured into saturated sodium bicarbonate at 0° C. The aqueous phase was extracted with DCM and the combined organic phase was concentrated under vacuum. The residue was purified by silica gel chromatography to give tert-butyl (6-isothiocyanato-5-(trifluoromethyl)pyridin-3-yl)(methyl)carbamate (1.3 g, 3.90 mmol, 28.40% yield) and recovered tert-butyl (6-amino-5-(trifluoromethyl)pyridin-3-yl)(methyl)carbamate (2.2 g, 7.55 mmol, 55% yield).

tert-Butyl methyl(6-thioureido-5-(trifluoromethyl)pyridin-3-yl)carbamate

To a solution of tert-butyl (6-isothiocyanato-5-(trifluoromethyl)pyridin-3-yl)(methyl) carbamate (1.3 g, 3.90 mmol) in DCM (10 mL) was added ammonium hydroxide (911.20 mg, 7.80 mmol, 1.00 mL, 30% purity) dropwise at 25° C. and the mixture was stirred at 25° C. for 1 h. The mixture was dried with anhydrous sodium sulfate, filtered and concentrated under vacuum to give tert-butyl methyl(6-thioureido-5-(trifluoromethyl)pyridin-3-yl)carbamate (1.5 g, crude).

tert-Butyl (6-((imino(methylthio)methyl)amino)-5-(trifluoromethyl) pyridin-3-yl)(methyl)carbamate To a solution of tert-butyl methyl(6-thioureido-5-(trifluoromethyl)pyridin-3-yl)carbamate (1.5 g, crude) in ACN (10 mL) was added iodomethane (729.22 mg, 5.14 mmol) and the mixture was stirred at 60° C. for 2 h. The mixture was concentrated under vacuum and purified by flash silica gel chromatography to give tert-butyl (6-((imino(methylthio)methyl)amino)-5-(trifluoromethyl)pyridin-3-yl)(methyl)carbamate (0.42 g, 1.15 mmol, 26.92% yield).

tert-Butyl (6-((5-(1-isopropyl-2,3-dihydro-1H-pyrrolo[2,3-c]pyridin-5-yl)-1H-1,2,4-triazol-3-yl)amino)-5-(trifluoromethyl)pyridin-3-yl)(methyl)carbamate To a solution of tert-butyl(6-((imino(methylthio)methyl)amino)-5-(trifluoromethyl)pyridin-3-yl)(methyl)carbamate (300 mg, 0.82 mmol) and 1-isopropyl-2,3-dihydro-1H-pyrrolo[2,3-c]pyridine-5-carbohydrazide (181.35 mg, 0.82 mmol) in tertiary butanol (3 mL) was added p-toluenesulfonic acid (47 mg, 0.25 mol) and the mixture was stirred at 120° C. for 2 h under microwave irradiation. Additional p-toluenesulfonic acid (31.32 mg, 0.16 mmol) was added to the mixture and stirred at 120° C. for 2 h under microwave irradiation. The mixture was concentrated under vacuum and purified by prep-HPLC (column: Unisil 3-100 C18 Ultra 150*50 mm*3 um; mobile phase: [H$_2$O (0.225% FA)-ACN]; B %: 28%-58%, 10 min) followed by lyophilization to give tert-butyl(6-((5-(1-isopropyl-2,3-dihydro-1H-pyrrolo[2,3-c]pyridin-5-yl)-1H-1,2,4-triazol-3-yl)amino)-5-(trifluoromethyl)pyridin-3-yl)(methyl)carbamate (70 mg, 0.14 mmol, 16.40% yield).

N$^2$-(5-(1-Isopropyl-2,3-dihydro-1H-pyrrolo[2,3-c]pyridin-5-yl)-1H-1,2,4-triazol-3-yl)-N-methyl-3-(trifluoromethyl)pyridine-2,5-diamine To a solution of tert-butyl (6-((5-(1-isopropyl-2,3-dihydro-1H-pyrrolo[2,3-c]pyridin-5-yl)-1H-1,2,4-triazol-3-yl)amino)-5-(trifluoromethyl)pyridin-3-yl)(methyl)carbamate (70 mg, 0.14 mmol) in EtOAc (5 mL) was added hydrochloric acid/EtOAc (4 M, 5 mL) and the mixture was stirred at 25° C. for 2 h. The mixture was concentrated under vacuum to give N$^2$-(5-(1-isopropyl-2,3-dihydro-1H-pyrrolo[2,3-c]pyridin-5-yl)-1H-1,2,4-triazol-3-yl)-N$^5$-methyl-3-(trifluoromethyl)pyridine-2,5-diamine, HCl salt (60 mg, 0.13 mmol, 97.71% yield).

N-(6-((5-(1-Isopropyl-2,3-dihydro-1H-pyrrolo[2,3-c]pyridin-5-yl)-1H-1,2,4-triazol-3-yl)amino)-5-(trifluoromethyl)pyridin-3-yl)-N-methylacetamide To a solution of N$^2$-(5-(1-isopropyl-2,3-dihydro-1H-pyrrolo[2,3-c]pyridin-5-yl)-1H-1,2,4-triazol-3-yl)-N$^5$-methyl-3-(trifluoromethyl)pyridine-2,5-diamine (60 mg, 0.13 mmol, hydrochloric acid salt) and TEA (66.74 mg, 0.66 mmol) in DMF (2 mL) was added Ac$_2$O (40.40 mg, 0.40 mmol) and the mixture was stirred at 40° C. for 19 h. Additional Ac$_2$O (20.20 mg, 0.20 mmol) was added to the mixture and stirred at 40° C. for 4 h followed by a drop of trifluoroacetic acid, then concentrated under vacuum. The residue was resuspended in THF:sodium hydroxide aqueous (6 M) (1:1) and stirred at 25° C. for 2 h, then concentrated under vacuum. The residue was purified by prep-HPLC (column: Phenomenex luna C18 150*25 mm*10 um; mobile phase: [H$_2$O (0.225% FA)-ACN]; B %: 12%-42%, 10 min), then dried by lyophilization to give N-(6-((5-(1-isopropyl-2,3-dihydro-1H-pyrrolo[2,3-c]pyridin-5-yl)-1H-1,2,4-triazol-3-yl)amino)-5-(trifluoromethyl)pyridin-3-yl)-N-methylacetamide (21.89 mg, 0.045 mmol, 34.10% yield, 94.6% purity). $^1$H NMR (400 MHz, DMSO-d$_6$) 9.31-9.21 (m, 1H), 8.37-8.34 (m, 1H), 8.14-8.00 (m, 1H), 7.87-7.77 (m, 2H), 4.05-3.99 (m, 1H), 3.55-3.54 (m, 2H), 3.35 (s, 1H), 3.13-3.12 (m, 4H), 2.20 (s, 0.7H), 1.80 (s, 2.3H), 1.16 (d, J=6.6 Hz, 6H); LCMS (ESI) m/z 461.3 [M+1]$^+$.

Example 68: N-(2-((5-(1-Isopropyl-2,3-dihydro-1H-pyrrolo[2,3-c]pyridin-5-yl)-1H-1,2,4-triazol-3-yl)amino)-5-(trifluoromethyl)pyridin-3-yl)-N-methylacetamide

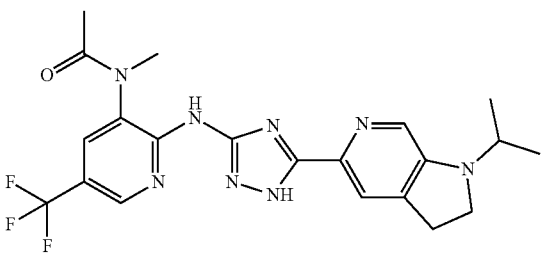 [SMILES: CC(=O)N(C)c1cc(C(F)(F)F)cnc1Nc1n[nH]c(-c2cc3c(cn2)N(C(C)C)CC3)n1]

tert-Butyl N-[2-isothiocyanato-5-(trifluoromethyl)-3-pyridyl]-N-methyl-carbamate To a solution of thiophosgene (3.95 g, 34.33 mmol, 2.63 mL) in DCM (100 mL) was added a solution of tert-butyl (2-amino-5-(trifluoromethyl)pyridin-3-yl)(methyl)carbamate (5.0 g, 17.17 mmol) in DCM (50 mL). The mixture was poured into saturated sodium bicarbonate solution and extracted with DCM. The combined organic layers were dried over sodium sulfate, filtered and concentrated under reduced pressure to give tert-butyl (2-isothiocyanato-5-(trifluoromethyl)pyridin-3-yl)(methyl)carbamate (5.50 g, crude). LCMS (ESI) m/z 334.0 [M+1]$^+$.

tert-Butyl N-[2-(carbamothioylamino)-5-(trifluoromethyl)-3-pyridyl]-N-methyl-carbamate To a solution of tert-butyl (2-isothiocyanato-5-(trifluoromethyl)pyridin-3-yl)(methyl)carbamate (5.5 g, crude) in DCM (50 mL) was added ammonium hydroxide (6.94 g, 49.50 mmol, 7.63 mL, 25% purity). The mixture was stirred at 30° C. for 1 h. The reaction mixture was concentrated under reduced pressure, poured into H$_2$O, extracted with EtOAc and the organic layer washed with brine, dried over sodium sulfate, filtered and concentrated under reduced pressure to give t tert-butyl N-[2-(carbamothioylamino)-5-(trifluoromethyl)-3-pyridyl]-N-methyl-carbamate (5.78 g, crude). LCMS (ESI) m/z 351.1 [M+1]$^+$.

tert-Butyl N-methyl-N-[2-[(methylsulfanylcarbonimidoyl)amino]-5-(trifluoromethyl)-3-pyridyl]carbamate To a solution of tert-butyl N-[2-(carbamothioylamino)-5-(trifluoromethyl)-3-pyridyl]-N-methyl-carbamate (5.78 g, crude) in ACN (50 mL) was added iodomethane (3.51 g, 24.75 mmol, 1.54 mL). The mixture was stirred at 40° C. for 12 h. The mixture was concentrated under vacuum and the residue was diluted with H$_2$O. The aqueous phase was adjusted to pH 8 with saturated sodium bicarbonate. The aqueous phase was extracted with EtOAc and the combined organic phase was dried over anhydrous sodium sulfate, filtered and concentrated under vacuum to give a residue. The residue was purified by silica gel column chromatography to give tert-butyl N-methyl-N-[2-[(methylsulfanylcarbonimidoyl)amino]-5-(trifluoromethyl)-3-pyridyl]carbamate (3.7 g, 10.15 mmol, 61.55% yield). $^1$H NMR (400 MHz, CDCl$_3$) 8.40 (s, 1H), 7.85-7.59 (m, 1H), 7.26 (s, 1H), 3.15 (s, 3H), 2.48 (s, 3H), 1.51 (s, 2H), 1.30 (s, 7H).

tert-Butyl-(2-((5-(1-isopropyl-2,3-dihydro-1H-pyrrolo[2,3-c]pyridin-5-yl)-1H-1,2,4-triazol-3-yl)amino)-5-(trifluoromethyl)pyridin-3-yl)(methyl)carbamate To a solution of tert-butyl N-methyl-N-[2-[(methylsulfanylcarbonimidoyl)amino]-5-(trifluoromethyl)-3-pyridyl]carbamate (827.13 mg, 2.27 mmol) and 1-isopropyl-2,3-dihydro-1H-pyrrolo[2,3-c]pyridine-5-carbohydrazide (500 mg, 2.27 mmol) in n-butyl alcohol (3 mL) was added p-toluenesulfonic acid (195.44 mg, 1.13 mmol). The mixture was stirred at 120° C. for 2 h under microwave irradiation. Then additional p-toluenesulfonic acid (195.44 mg, 1.13 mmol) was added in the mixture and stirred at 120° C. for 2 h under microwave irradiation. The mixture was concentrated under vacuum and the residue was triturated with EtOAc. The suspension was filtered and the filtrate was purified by prep-HPLC (column: Phenomenex luna C18 150*40 mm*15 um; mobile phase: [H$_2$O (0.225% FA)-ACN]; B %: 28%-58%, 9 min), then dried by lyophilization to give tert-butyl(2-((5-(1-isopropyl-2,3-dihydro-1H-pyrrolo[2,3-c]pyridin-5-yl)-1H-1,2,4-triazol-3-yl)amino)-5-(trifluoromethyl)pyridin-3-yl)(methyl)carbamate (242 mg, 0.47 mmol, 20.56% yield).

N$^2$-(5-(1-Isopropyl-2,3-dihydro-1H-pyrrolo[2,3-c]pyridin-5-yl)-1H-1,2,4-triazol-3-yl)-N$^3$-methyl-5-(trifluoromethyl)pyridine-2,3-diamine To a solution of tert-butyl(2-((5-(1-isopropyl-2,3-dihydro-1H-pyrrolo[2,3-c]pyridin-5-yl)-1H-1,2,4-triazol-3-yl)amino)-5-(trifluoromethyl)pyridin-3-yl)(methyl)carbamate (240 mg, 0.46 mol) in EtOAc (10 mL) was added hydrochloric acid/EtOAc (4 M, 10 mL) and the mixture was stirred at 25° C. for 2 h. The mixture was concentrated under vacuum and the residue was triturated with EtOAc and stirred for 1 h. The suspension was filtered and the filter cake was concentrated under vacuum to give N$^2$-(5-(1-isopropyl-2,3-dihydro-1H-pyrrolo[2,3-c]pyridin-5-yl)-1H-1,2,4-triazol-3-yl)-N$^3$-methyl-5-(trifluoromethyl)pyridine-2,3-diamine (200 mg, crude, hydrochloric acid).

N-(2-((5-(1-Isopropyl-2,3-dihydro-1H-pyrrolo[2,3-c]pyridin-5-yl)-1H-1,2,4-triazol-3-yl)amino)-5-(trifluoromethyl)pyridin-3-yl)-N-methylacetamide To a solution of N$^2$-(5-(1-isopropyl-2,3-dihydro-1H-pyrrolo[2,3-c]pyridin-5-yl)-1H-1,2,4-triazol-3-yl)-N$^3$-methyl-5-(trifluoromethyl)pyridine-2,3-diamine (370 mg, 0.88 mmol, hydrochloride) and TEA (447.40 mg, 4.42 mmol, 0.6 mL) in DMF (10 mL) was added Ac$_2$O (270.83 mg, 2.65 mmol, 0.25 mL) and the mixture was stirred at 40° C. for 16 h. The mixture was concentrated under vacuum and the crude product and another batch product (120 mg) were combined and purified by prep-HPLC (column: Waters Xbridge 150*25 mm*5 um; mobile phase: [H$_2$O (0.05% ammonia hydroxide v/v)-ACN]; B %: 31%-60%, 10 min), the eluent was combined with another batch of product and dried by lyophilzation to give N-(2-((5-(1-isopropyl-2,3-dihydro-1H-pyrrolo[2,3-c]pyridin-5-yl)-1H-1,2,4-triazol-3-yl)amino)-5-(trifluoromethyl)pyridin-3-yl)-N-methylacetamide (166.51 mg, 0.358 mmol, 71.55% yield, 99% purity). 1H NMR (400 MHz, DMSO-d6) δ 8.46 (s, 1H), 8.22-7.92 (m, 1H), 7.82 (s, 1H), 7.67 (s, 1H), 3.97-3.94 (m, 1H), 3.48-3.39 (m, 2H), 3.23 (s, 1H), 3.04 (s, 2H), 3.03-2.94 (m, 2H), 2.18 (s, 1H), 1.78 (s, 2H), 1.15 (d, J=6.7 Hz, 6H). LCMS (ESI) m/z 461.3 [M+1]$^+$.

Example 69: N-(6-((3-(5-Isopropoxypyridin-2-yl)-1,2,4-thiadiazol-5-yl)amino)-5-methylpyridin-3-yl)-N-methylacetamide

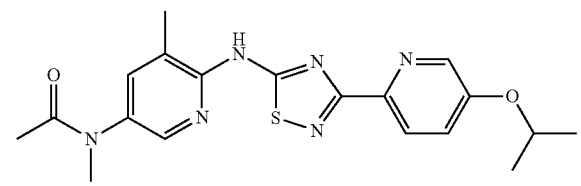 [SMILES: CC(=O)N(C)c1cnc(Nc2nc(-c3ccc(OC(C)C)cn3)ns2)c(C)c1]

tert-Butyl (6-bromo-5-methylpyridin-3-yl)carbamate

This reaction was paralleled for two batches: To a solution of 6-bromo-5-methylpyridin-3-amine (9.5 g, 50.79 mmol) and di-tert-butyl dicarbonate (11.09 g, 50.79 mmol, 11.67 mL) in ACN (120 mL) was added N,N-dimethylpyridin-4-amine (6.21 g, 50.79 mmol) and TEA (10.28 g, 101.58 mmol, 14.14 mL). The mixture was stirred at 80° C. for 12 h. Two batches of parallel reactions were combined. The mixture was concentrated and purified by flash silica gel chromatography to give tert-butyl (6-bromo-5-methylpyridin-3-yl)carbamate (22.3 g, crude).

tert-Butyl (6-bromo-5-methylpyridin-3-yl)(methyl)carbamate

This reaction was paralleled for two batches: To a solution of tert-butyl (6-bromo-5-methylpyridin-3-yl)carbamate (7.75 g, crude) in DMF (100 mL) was added NaH (1.51 g, 37.78 mmol, 60% purity) at 0° C. and the mixture was stirred at 25° C. for 0.5 h. Iodomethane (4.98 g, 35.09 mmol, 2.18 mL) was added at 0° C. and the mixture was stirred at 25° C. for 1 h. Two batches of parallel reactions were combined, and the mixture was diluted with cold saturated $NH_4Cl$ and extracted with EtOAc. The combined organic layers were washed with brine, dried over anhydrous sodium sulfate and filtered. The filtrate was concentrated under reduced pressure and purified by column chromatography to give tert-butyl (6-bromo-5-methylpyridin-3-yl)(methyl)carbamate (20.4 g, crude). LCMS (ESI): m/z 301.0 $[M+1]^+$.

tert-Butyl (6-((ethoxycarbonyl)amino)-5-methylpyridin-3-yl)(methyl)carbamate This reaction was paralleled for two batches: A mixture of tert-butyl (6-bromo-5-methylpyridin-3-yl)(methyl)carbamate (2.5 g, 8.30 mmol), ethyl carbamate (1.85 g, 20.75 mmol), sodium 2-methylpropan-2-olate (2 M, 8.30 mL) in THF (50 mL) and the mixture was degassed and purged with nitrogen 3 times. To this mixture was added [2-(2-aminophenyl)phenyl]-methylsulfonyloxy-palladium;dicyclohexyl-[3,6-dimethoxy-2-(2,4,6-triisopropylphenyl)phenyl]phosphane (376.23 mg, 0.42 mmol) and the mixture was stirred at 100° C. for 12 h under nitrogen atmosphere. The two batches of parallel reactions were combined, diluted with $H_2O$ and extracted with EtOAc. The combined organic layers were washed with brine, dried over anhydrous sodium sulfate and filtered. The filtrate was concentrated under reduced pressure and purified by flash silica gel chromatography to give tert-butyl (6-((ethoxycarbonyl)amino)-5-methylpyridin-3-yl)(methyl)carbamate (3.5 g, crude). LCMS (ESI): m/z 310.1 $[M+1]^+$.

tert-Butyl (6-amino-5-methylpyridin-3-yl)(methyl)carbamate

To a solution of tert-butyl (6-((ethoxycarbonyl)amino)-5-methylpyridin-3-yl)(methyl) carbamate (3.85 g, crude) in EtOH (40 mL) and $H_2O$ (8 mL) was added lithium hydroxide hydrate (2.61 g, 62.23 mmol). The mixture was stirred at 90° C. for 2 h. The mixture was concentrated, $H_2O$ was added to the mixture and the organics were extracted with EtOAc. The combined organic layers were washed with brine, dried over anhydrous sodium sulfate and filtered. The filtrate was concentrated under reduced pressure and purified by flash silica gel chromatography to give tert-butyl (6-amino-5-methylpyridin-3-yl)(methyl)carbamate (1.57 g, 6.62 mmol, 53.16% yield). $^1$H NMR (400 MHz, $CDCl_3$) δ 7.83 (s, 1H), 7.24-7.19 (m, 1H), 4.43-4.27 (m, 2H), 3.20 (s, 3H), 2.13 (s, 3H), 1.44 (s, 9H). LCMS (ESI): m/z 238.1 $[M+1]^+$.

tert-Butyl (6-isothiocyanato-5-methylpyridin-3-yl)(methyl)carbamate

To a solution of thiophosgene (1.99 g, 17.32 mmol, 1.33 mL) in DCM (20 mL) was added tert-butyl (6-amino-5-methylpyridin-3-yl)(methyl)carbamate (1.37 g, 5.77 mmol) in DCM (15 mL) at 0° C. The mixture was stirred at 25° C. for 12 h and then poured into saturated sodium bicarbonate at 0° C. The mixture was extracted with DCM, combined organic layers were concentrated under reduced pressure and purified by column chromatography to give tert-butyl (6-isothiocyanato-5-methylpyridin-3-yl)(methyl)carbamate (1.08 g, crude). LCMS (ESI): m/z 280.1 $[M+1]^+$.

tert-Butyl (6-(3-(imino(5-isopropoxypyridin-2-yl)methyl)thioureido)-5-methylpyridin-3-yl)(methyl)carbamate To a solution of tert-butyl (6-isothiocyanato-5-methylpyridin-3-yl)(methyl)carbamate (857.31 mg, 3.07 mmol) and 5-isopropoxypicolinimidamide (500 mg, 2.79 mmol) in DCM (50 mL) and acetone (50 mL) was added TEA (1.41 g, 13.95 mmol, 1.94 mL). The mixture was stirred at 25° C. for 12 h and concentrated to give tert-butyl (6-(3-(imino(5-isopropoxypyridin-2-yl)methyl) thioureido)-5-methylpyridin-3-yl)(methyl)carbamate (1.28 g, crude). LCMS (ESI): m/z 459.2 $[M+1]^+$.

tert-Butyl (6-((3-(5-isopropoxypyridin-2-yl)-1,2,4-thiadiazol-5-yl)amino)-5-methylpyridin-3-yl)(methyl)carbamate To a solution of tert-butyl (6-(3-(imino(5-isopropoxypyridin-2-yl)methyl) thioureido)-5-methylpyridin-3-yl)(methyl) carbamate (1.28 g, 2.79 mmol) in EtOH (20 mL) was added iodine (141.69 mg, 0.56 mmol) and hydrogen peroxide (632.96 mg, 5.58 mmol, 0.54 mL, 30% purity) at 0° C. The mixture was stirred at 25° C. for 40 min and then quenched by addition of saturated sodium sulfite at 0° C. The mixture was concentrated and the aqueous phase extracted with EtOAc. The combined organic phase was washed with brine, dried with anhydrous sodium sulfate, filtered and concentrated to give the residue under vacuum. The residue was triturated with petroleum ether:EtOAc (10:1, 50 mL) for 10 min, filtered, and the filter cake was collected and concentrated under reduced pressure to give tert-butyl (6-((3-(5-isopropoxypyridin-2-yl)-1,2,4-thiadiazol-5-yl) amino)-5-methylpyridin-3-yl)(methyl)carbamate (855 mg, crude). LCMS (ESI): m/z 457.1 $[M+1]^+$.

$N^2$-(3-(5-Isopropoxypyridin-2-yl)-1,2,4-thiadiazol-5-yl)-$N^5$,3-dimethylpyridine-2,5-diamine To a solution of tert-butyl (6-((3-(5-isopropoxypyridin-2-yl)-1,2,4-thiadiazol-5-yl)amino)-5-methylpyridin-3-yl)(methyl)carbamate (805 mg, crude) in EtOAc (10 mL) was added hydrogen chloride/EtOAc (20 mL, 4 M) and the mixture was stirred at 25° C. for 2 h. The mixture was concentrated to give $N^2$-(3-(5-isopropoxypyridin-2-yl)-1,2,4-thiadiazol-5-yl)-$N^5$,3-dimethylpyridine-2,5-diamine (692 mg, crude, hydrochloride). LCMS (ESI): m/z 357.1 $[M+1]^+$.

N-(6-((3-(5-Isopropoxypyridin-2-yl)-1,2,4-thiadiazol-5-yl)amino)-5-methylpyridin-3-yl)-N-methylacetamide To a solution of N²-(3-(5-isopropoxypyridin-2-yl)-1,2,4-thiadiazol-5-yl)-N⁵,3-dimethylpyridine-2,5-diamine (692 mg, 1.76 mmol, hydrochloride) in DMF (15 mL) was added TEA (891.10 mg, 8.81 mmol, 1.23 mL) and Ac₂O (233.74 mg, 2.29 mmol, 0.21 mL). The mixture was stirred at 40° C. for 12 h. The mixture was concentrated and purified by prep-HPLC (column: Phenomenex Luna PFP(2) 150*21.2 mm 5u; mobile phase: [H₂O (0.2% FA)-ACN]; B %: 30%-60%, 10 min) to give N-(6-((3-(5-isopropoxypyridin-2-yl)-1,2,4-thiadiazol-5-yl)amino)-5-methylpyridin-3-yl)-N-methylacetamide (249.2 mg, 0.621 mmol, 99.3% purity). ¹H NMR (400 MHz-DMSO d₆) δ 11.93 (s, 1H), 8.34-8.33 (m, 2H), 8.17 (d, J=8.8 Hz, 1H), 7.75 (s, 1H), 7.52 (dd, J₁=8.9, J₂=2.9 Hz, 1H), 4.82-4.76 (m, 1H), 3.15 (s, 3H), 2.42 (s, 3H), 1.80 (s, 3H), 1.33 (d, J=6.0 Hz, 6H). LCMS (ESI): m/z 399.1 [M+1]⁺.

Example 70: N-(6-((3-(1-Isopropyl-2,3-dihydro-1H-pyrrolo[2,3-c]pyridin-5-yl)-1,2,4-thiadiazol-5-yl)amino)-5-(trifluoromethyl)pyridin-3-yl)-N-methylacetamide

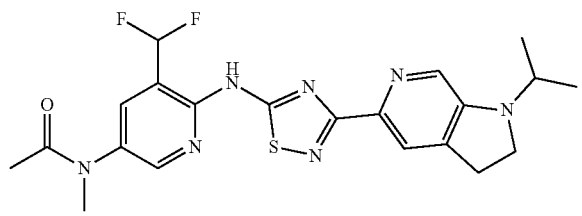 [SMILES: CC(=O)N(C)c1cnc(Nc2nc(-c3cc4c(cn3)N(C(C)C)CC4)ns2)c(C(F)F)c1]

tert-Butyl (6-(3-(imino(1-isopropyl-2,3-dihydro-1H-pyrrolo[2,3-c]pyridin-5-yl)methyl)thioureido)-5-(trifluoromethyl)pyridin-3-yl)(methyl)carbamate To a solution of tert-butyl (6-isothiocyanato-5-(trifluoromethyl)pyridin-3-yl)(methyl) carbamate (452.01 mg, 1.36 mmol) and 1-isopropyl-2,3-dihydro-1H-pyrrolo[2,3-c]pyridine-5-carboximidamide (277 mg, 1.36 mmol) in DCM (20 mL) and acetone (20 mL) was added TEA (686.09 mg, 6.78 mmol, 0.94 mL). The mixture was stirred at 25° C. for 12 h and the mixture was concentrated to give tert-butyl (6-(3-(imino(1-isopropyl-2,3-dihydro-1H-pyrrolo[2,3-c] pyridin-5-yl)methyl)thioureido)-5-(trifluoromethyl)pyridin-3-yl)(methyl)carbamate (729 mg, crude). LCMS (ESI): m/z 538.1 [M+1]⁺.

tert-Butyl (6-((3-(1-isopropyl-2,3-dihydro-1H-pyrrolo[2,3-c]pyridin-5-yl)-1,2,4-thiadiazol-5-yl)amino)-5-(trifluoromethyl)pyridin-3-yl)(methyl)carbamate To a mixture of tert-butyl (6-(3-(imino(1-isopropyl-2,3-dihydro-1H-pyrrolo[2,3-c]pyridin-5-yl)methyl)thioureido)-5-(trifluoromethyl)pyridin-3-yl)(methyl)carbamate (729 mg, crude) in EtOH (15 mL) was added iodine (68.83 mg, 0.27 mmol) and hydrogen peroxide (307.50 mg, 2.71 mmol, 0.26 mL, 30% purity) at 0° C. and the mixture was stirred at 25° C. for 6 min. The mixture was quenched by addition of saturated sodium sulfite at 0° C. and the mixture was concentrated. The aqueous phase was extracted with EtOAc and the combined organic phase was washed with brine, dried with anhydrous sodium sulfate, filtered and concentrated under vacuum to give tert-butyl (6-((3-(1-isopropyl-2,3-dihydro-H-pyrrolo[2,3-c]pyridin-5-yl)-1,2,4-thiadiazol-5-yl)amino)-5-(trifluoromethyl)pyridin-3-yl)(methyl) carbamate (770 mg, crude). LCMS (ESI): m/z 536.1 [M+1]⁺.

N²-(3-(1-Isopropyl-2,3-dihydro-1H-pyrrolo[2,3-c]pyridin-5-yl)-1,2,4-thiadiazol-5-yl)-N-methyl-3-(trifluoromethyl)pyridine-2,5-diamine A mixture of tert-butyl (6-((3-(1-isopropyl-2,3-dihydro-1H-pyrrolo[2,3-c]pyridin-5-yl)-1,2,4-thiadiazol-5-yl)amino)-5-(trifluoromethyl)pyridin-3-yl)(methyl)carbamate (770 mg, crude) in EtOAc (10 mL) was added hydrogen chloride/EtOAc (20 mL, 4 M) and the resulting mixture was stirred at 25° C. for 1.5 h. The reaction mixture was concentrated under vacuum to give N²-(3-(1-isopropyl-2,3-dihydro-1H-pyrrolo[2,3-c]pyridin-5-yl)-1,2,4-thiadiazol-5-yl)-N⁵-methyl-3-(trifluoromethyl)pyridine-2,5-diamine (678 mg, crude, hydrochloride). LCMS (ESI): m/z 436.1 [M+1]⁺.

N-(6-((3-(1-Isopropyl-2,3-dihydro-1H-pyrrolo[2,3-c]pyridin-5-yl)-1,2,4-thiadiazol-5-yl)amino)-5-(trifluoromethyl)pyridin-3-yl)-N-methylacetamide To a mixture of N²-(3-(1-isopropyl-2,3-dihydro-1H-pyrrolo[2,3-c]pyridin-5-yl)-1,2,4-thiadiazol-5-yl)-N⁵-methyl-3-(trifluoromethyl)pyridine-2,5-diamine (678 mg, crude, hydrochloride) in DMF (15 mL) was added Ac₂O (190.67 mg, 1.87 mmol, 0.17 mL) and TEA (726.88 mg, 7.18 mmol, 1 mL) at 25° C. and the mixture was stirred at 40° C. for 12 h. The reaction mixture was filtered and the filtrate was purified by prep-HPLC (column: Phenomenex luna C18 250*50 mm*10 um; mobile phase: [H₂O (0.05% HCl)-ACN]; B %: 5%-35%, 10 min) to give N-(6-((3-(1-isopropyl-2,3-dihydro-1H-pyrrolo[2,3-c]pyridin-5-yl)-1,2,4-thiadiazol-5-yl)amino)-5-(trifluoromethyl)pyridin-3-yl)-N-methylacetamide (168.79 mg, 286.02 µmol, 22.51% yield, 87% purity, hydrochloride). ¹H NMR (400 MHz, DMSO-d₆) δ 8.86-8.77 (m, 1H), 8.42-8.26 (m, 1H), 8.12 (s, 1H), 7.79 (s, 1H), 4.15-4.08 (m, 1H), 3.73-3.69 (m, 2H), 3.41 (s, 0.8H), 3.33-3.29 (m, 2H), 3.19 (s, 2.2H), 2.24 (s, 0.8H), 1.84 (s, 2.2H), 1.18 (d, J=6.5 Hz, 6H). LCMS (ESI): m/z 478.2 [M+1]⁺

Example 71: N-(2-((3-(4-Isopropylpyridin-2-yl)-1,2,4-thiadiazol-5-yl)amino)-5-(trifluoromethyl)pyridin-3-yl)-N-methylacetamide

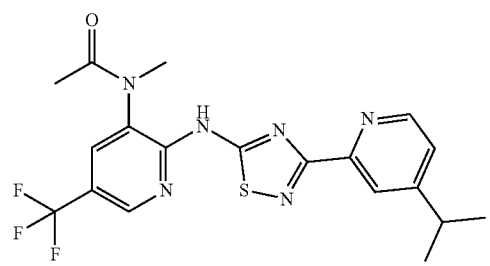 [SMILES: CC(=O)N(C)c1cc(C(F)(F)F)cnc1Nc1nc(-c2cc(C(C)C)ccn2)ns1]

tert-Butyl (2-chloro-5-(trifluoromethyl)pyridin-3-yl) carbamate

This reaction was paralleled for two batches: To a solution of 2-chloro-5-(trifluoromethyl) pyridin-3-amine (15 g, 76.31 mmol) in ACN (200 mL) was added TEA (15.44 g, 152.63 mmol, 21.24 mL) and di-tert-butyl dicarbonate (16.66 g, 76.31 mmol, 17.53 mL) and N,N-dimethylpyridin-4-amine (9.32 g, 76.31 mmol) at 25° C. The mixture was stirred at 80° C. for 12 h. The two batches of mixture was combined and the mixture was concentrated under vacuum and purified by flash silica gel chromatography to give tert-butyl (2-chloro-5-(trifluoromethyl)pyridin-3-yl)carbamate (34.9 g, crude).

tert-Butyl (2-chloro-5-(trifluoromethyl)pyridin-3-yl) (methyl)carbamate

This reaction was paralleled for two batches: To a mixture of tert-butyl (2-chloro-5-(trifluoromethyl)pyridin-3-yl)carbamate (16.9 g, crude) in DMF (200 mL) was added NaH (3.19 g, 79.75 mmol, 60% purity) at 0° C. and the mixture was stirred at 25° C. for 0.5 h. To the mixture was then added methyl iodide (10.51 g, 74.05 mmol, 4.61 mL) at 0° C. and it was stirred at 25° C. for 1 h. The two batches were poured into cold saturated $NH_4Cl$ slowly and the aqueous phase was extracted with EtOAc. The combined organic phase was concentrated and purified by column chromatography to give tert-butyl (2-chloro-5-(trifluoromethyl)pyridin-3-yl) (methyl)carbamate (39.9 g, 64.21 mmol).

tert-Butyl (2-azido-5-(trifluoromethyl)pyridin-3-yl) (methyl)carbamate

This reaction was paralleled for two batches: To a mixture of tert-butyl (2-chloro-5-(trifluoromethyl)pyridin-3-yl) (methyl)carbamate (19.95 g, 64.21 mmol) in DMSO (250 mL) was added sodium azide (12.52 g, 192.63 mmol) at 25° C. and the mixture was stirred at 100° C. for 12 h. The two batches were combined, poured into saturated sodium bicarbonate slowly at 0° C. and stirred for 10 min. The aqueous phase was extracted with EtOAc and the combined organic phase was concentrated under vacuum to give tert-butyl (2-azido-5-(trifluoromethyl)pyridin-3-yl)(methyl)carbamate (50 g, crude).

tert-Butyl (2-amino-5-(trifluoromethyl)pyridin-3-yl) (methyl)carbamate

This reaction was paralleled for two batches: To a mixture of tert-butyl (2-azido-5-(trifluoromethyl)pyridin-3-yl) (methyl)carbamate (25 g, crude) in MeOH (500 mL) was added Pd/C (1.5 g, 10% purity) and hydroxide Pd/C (1.5 g, 20% purity) under nitrogen. The resulting mixture was degassed and purged with hydrogen 3 times, and then the mixture was stirred at 25° C. for 16 h under hydrogen atmosphere (15 psi). The two batches were combined, and the mixture was filtered through a pad of celite, washed with EtOAc, and the filtrate was concentrated under vacuum to give a residue. The residue was purified by flash silica gel chromatography to give tert-butyl N-[2-amino-5-(trifluoromethyl)-3-pyridyl]-N-methyl-carbamate (22.6 g, 77.59 mmol, 49.23% yield). LCMS (ESI): m/z 292.1 $[M+1]^+$.

tert-Butyl (2-isothiocyanato-5-(trifluoromethyl)pyridin-3-yl)(methyl)carbamate This reaction was paralleled for two batches: To a mixture of thiophosgene (3.55 g, 30.90 mmol, 2.37 mL) in DCM (30 mL) was added a solution of tert-butyl (2-amino-5-(trifluoromethyl)pyridin-3-yl)(methyl) carbamate (3 g, 10.30 mmol) in DCM (50 mL) at 0° C. and the mixture was stirred at 25° C. for 12 h. The two batches were combined and then poured into saturated sodium bicarbonate at 0° C. The aqueous layer was extracted with DCM and the combined organic phase was concentrated under vacuum. The residue was purified by column chromatography to give tert-butyl (2-isothiocyanato-5-(trifluoromethyl) pyridin-3-yl)(methyl) carbamate (2.88 g, 8.64 mmol, 41.94% yield).

tert-Butyl (2-(3-(imino(4-isopropylpyridin-2-yl) methyl)thioureido)-5-(trifluoromethyl)pyridin-3-yl) (methyl)carbamate To a mixture of 4-isopropylpicolinimidamide (450 mg, 2.25 mmol, hydrochloride), tert-butyl (2-isothiocyanato-5-(trifluoromethyl)pyridin-3-yl)(methyl) carbamate (751.19 mg, 2.25 mmol) in DCM (20 mL) and acetone (20 mL) was added TEA (1.14 g, 11.27 mmol, 1.57 mL) at 25° C. and the mixture was stirred at 25° C. for 12 h. The mixture was concentrated under vacuum to give tert-butyl (2-(3-(imino (4-isopropylpyridin-2-yl)methyl)thioureido)-5-(trifluoromethyl)pyridin-3-yl)(methyl)carbamate (1.12 g, crude). LCMS (ESI): m/z 497.1 $[M+1]^+$.

tert-Butyl (2-((3-(4-isopropylpyridin-2-yl)-1,2,4-thiadiazol-5-yl)amino)-5-(trifluoromethyl)pyridin-3-yl)(methyl)carbamate To a mixture of tert-butyl (2-(3-(imino(4-isopropylpyridin-2-yl)methyl)thioureido)-5-(trifluoromethyl)pyridin-3-yl)(methyl)carbamate (1.12 g, crude) in EtOH (20 mL) was added iodine (114.50 mg, 0.45 mmol) and hydrogen peroxide (511.48 mg, 4.51 mmol, 0.43 mL, 30% purity) at 0° C. and the mixture was stirred at 25° C. for 45 min. The mixture was quenched by addition of saturated sodium sulfite at 0° C. and concentrated. The aqueous phase was extracted with EtOAc and the combined organic phase was washed with brine, dried with anhydrous sodium sulfate, filtered and concentrated under vacuum to give tert-butyl (2-((3-(4-isopropylpyridin-2-yl)-1,2,4-thiadiazol-5-yl) amino)-5-(trifluoromethyl)pyridin-3-yl)(methyl)carbamate (1.35 g, crude). LCMS (ESI): m/z 495.1 $[M+1]^+$.

$N^2$-(3-(4-Isopropylpyridin-2-yl)-1,2,4-thiadiazol-5-yl)-$N^3$-methyl-5-(trifluoromethyl)pyridine-2,3-diamine To a mixture of tert-butyl (2-((3-(4-isopropylpyridin-2-yl)-1,2,4-thiadiazol-5-yl)amino)-5-(trifluoromethyl)pyridin-3-yl)(methyl)carbamate (1.35 g, crude) in EtOAc (10 mL) was added hydrogen chloride/EtOAc (20 mL, 4M) and the mixture was stirred at 25° C. for 1.5 h. The reaction mixture was concentrated under vacuum to give $N^2$-(3-(4-isopropylpyridin-2-yl)-1,2,4-thiadiazol-5-yl)-$N^3$-methyl-5-(trifluoromethyl)pyridine-2,3-diamine (1.18 g, crude, hydrochloride). LCMS (ESI): m/z 395.1 $[M+1]^+$.

N-(2-((3-(4-Isopropylpyridin-2-yl)-1,2,4-thiadiazol-5-yl)amino)-5-(trifluoromethyl)pyridin-3-yl)-N-methylacetamide To a mixture of $N^2$-(3-(4-isopropylpyridin-2-yl)-1,2,4-thiadiazol-5-yl)-$N^3$-methyl-5-(trifluoromethyl)pyridine-2,3-diamine (1.18 g, crude, hydrochloride) in DMF (20 mL) was added TEA (1.39 g, 13.69 mmol, 1.91 mL) and $Ac_2O$ (335.49 mg, 3.29 mmol, 0.31 mL) at 25° C. and the mixture was stirred at 40° C. for 12 h. The reaction mixture was filtered and the filtrate was purified by prep-HPLC (formic acid condition; column: Phenomenex luna C18 250*50 mm*10 um; mobile phase: [H$_2$O (0.225% FA)-ACN]; B %: 25%-55%, 20 min) to give N-(2-((3-(4-isopropylpyridin-2-yl)-1,2,4-thiadiazol-5-yl)amino)-5-(trifluoromethyl)pyridin-3-yl)-N-methylacetamide (395.21 mg, 0.869 mmol, 29.53% yield, 96% purity). $^1$H NMR (400 MHz, DMSO-d$_6$) 13.14-12.48 (m, 1H), 8.95-8.83 (m, 1H), 8.58 (d, J=5.0 Hz, 1H), 8.39 (s, 0.5H), 8.19 (d, J=2.1 Hz, 0.5H), 8.13-8.12 (m, 1H), 7.39 (dd, J=1.6, 5.0 Hz, 1H), 3.31 (s, 1.6H), 3.10 (s, 1.4H), 3.04-2.97 (m, 1H), 2.23 (s, 1.6H), 1.73 (s, 1.4H), 1.26 (d, J=7.0 Hz, 6H). LCMS (ESI): m/z 437.3 [M+1]$^+$.

Example 72: N-(3-((3-(1-Isopropyl-1H-pyrrolo[2,3-c]pyridin-5-yl)-1,2,4-thiadiazol-5-yl)amino)pyrazin-2-yl)-N-methylacetamide

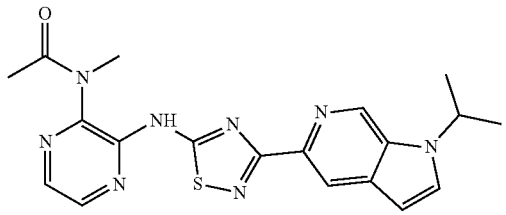 [SMILES: CC(=O)N(C)c1nccnc1Nc1nc(-c2cc3ccn(C(C)C)c3cn2)ns1]

N$^2$-(3-(1-Isopropyl-1H-pyrrolo[2,3-c]pyridin-5-yl)-1,2,4-thiadiazol-5-yl)-N$^3$-methylpyrazine-2,3-diamine To a solution of tert-butyl (3-((3-(1-isopropyl-1H-pyrrolo[2,3-c]pyridin-5-yl)-1,2,4-thiadiazol-5-yl)amino)pyrazin-2-yl)(methyl)carbamate (360 mg, 771.61 μmol) in EtOAc (5 mL) was added hydrogen chloride/EtOAc (10 mL, 4 N). The mixture was stirred at 25° C. for 1.5 h. The mixture was concentrated to give N$^2$-(3-(1-isopropyl-1H-pyrrolo[2,3-c]pyridin-5-yl)-1,2,4-thiadiazol-5-yl)-N$^3$-methylpyrazine-2,3-diamine (310 mg, crude, hydrochloride). LCMS (ESI): m/z 367.1 [M+1]$^+$.

N-(3-((3-(1-Isopropyl-1H-pyrrolo[2,3-c]pyridin-5-yl)-1,2,4-thiadiazol-5-yl)amino)pyrazin-2-yl)-N-methylacetamide To a solution of N$^2$-(3-(1-isopropyl-1H-pyrrolo[2,3-c]pyridin-5-yl)-1,2,4-thiadiazol-5-yl)-N$^3$-methylpyrazine-2,3-diamine (310 mg, 769.41 μmol, hydrochloride) in DMF (10 mL) was added TEA (389.29 mg, 3.85 mmol, 535.47 μL) and Ac$_2$O (102.11 mg, 1.00 mmol, 93.68 μL). The mixture was stirred at 40° C. for 12 h. Additional Ac$_2$O (40 mg) was added and the mixture was stirred at 50° C. for 12 h. The mixture was concentrated and purified by prep-HPLC (FA condition; column: Phenomenex Luna C18 200*40 mm*10 um; mobile phase: [H$_2$O (0.2% FA)-ACN]; B %: 1%-30%, 10 min) followed by prep-HPLC (basic condition; column: Waters Xbridge Prep OBD C18 150*40 mm*10 um; mobile phase: [H$_2$O (0.04% NH3H2O+10 mM NH4HCO3)-ACN]; B %: 35%-60%, 8 min) to give N-[3-[[3-(1-isopropylpyrrolo[2,3-c]pyridin-5-yl)-1,2,4-thiadiazol-5-yl]amino]pyrazin-2-yl]-N-methyl-acetamide (16.32 mg, 39.37 μmol, 5.12% yield, 99% purity). $^1$H NMR (400 MHz, DMSO-d$_6$) 13.02-12.19 (m, 1H), 9.00 (s, 1H), 8.58-8.46 (m, 2H), 8.29-8.18 (m, 1H), 7.83 (s, 1H), 6.67 (d, J=2.9 Hz, 1H), 5.06-4.92 (m, 1H), 3.35 (s, 1.6H), 3.12 (s, 1.3H), 2.27 (s, 1.5H), 1.76 (s, 1.3H), 1.53 (d, J=6.6 Hz, 6H). LCMS (ESI): m/z 409.2 [M+1]$^+$.

Example 73: N$^2$-(3-(1-Isopropyl-1H-pyrrolo[2,3-c]pyridin-5-yl)-1,2,4-thiadiazol-5-yl)-N$^3$-methylpyrazine-2,3-diamine

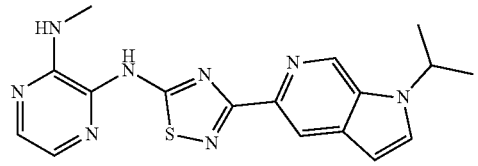 [SMILES: CNc1nccnc1Nc1nc(-c2cc3ccn(C(C)C)c3cn2)ns1]

tert-Butyl (3-(3-(imino(1-isopropyl-2,3-dihydro-1H-pyrrolo[2,3-c]pyridin-5-yl)methyl)thioureido)pyrazin-2-yl)(methyl)carbamate To a mixture of tert-butyl (3-isothiocyanatopyrazin-2-yl)(methyl)carbamate (300 mg, 1.13 mmol) in DCM (20 mL) and acetone (20 mL) was added 1-isopropyl-2,3-dihydro-1H-pyrrolo[2,3-c]pyridine-5-carboximidamide (230.10 mg, 1.13 mmol) and TEA (569.94 mg, 5.63 mmol, 783.96 μL). The reaction mixture was stirred at 20° C. for 12 h and concentrated to give tert-butyl (3-(3-(imino(1-isopropyl-2,3-dihydro-1H-pyrrolo[2,3-c] pyridin-5-yl)methyl)thioureido)pyrazin-2-yl)(methyl)carbamate (600 mg, crude). LCMS (ESI): m/z 471.3 [M+1]$^+$.

tert-Butyl (3-((3-(1-isopropyl-1H-pyrrolo[2,3-c]pyridin-5-yl)-1,2,4-thiadiazol-5-yl)amino)pyrazin-2-yl)(methyl)carbamate To a mixture of tert-butyl (3-(3-(imino(1-isopropyl-2,3-dihydro-1H-pyrrolo[2,3-c]pyridin-5-yl)methyl)thioureido)pyrazin-2-yl)(methyl)carbamate (600 mg, 1.27 mmol) in EtOH (10 mL) was added iodine (64.72 mg, 255.00 μmol) and hydrogen peroxide (289.12 mg, 2.55 mmol, 245.02 μL, 30% purity). The reaction mixture was stirred at 25° C. for 1 h and concentrated to give tert-butyl (3-((3-(1-isopropyl-1H-pyrrolo[2,3-c]pyridin-5-yl)-1,2,4-thiadiazol-5-yl)amino)pyrazin-2-yl)(methyl) carbamate (500 mg, crude). LCMS (ESI): m/z 467.3 [M+1]$^+$.

N$^2$-(3-(1-isopropyl-1H-pyrrolo[2,3-c]pyridin-5-yl)-1,2,4-thiadiazol-5-yl)-N$^3$-methylpyrazine-2,3-diamine To a solution of tert-butyl (3-((3-(1-isopropyl-1H-pyrrolo[2,3-c]pyridin-5-yl)-1,2,4-thiadiazol-5-yl)amino)pyrazin-2-yl)(methyl)carbamate (100 mg, 214.34 μmol) in EtOAc (2 mL) was added hydrogen chloride/EtOAc (4 mL, 4 N). The mixture was stirred at 25° C. for 1.5 h, concentrated and purified by prep-HPLC (HCl condition; column: Phenomenex Luna C18 150*30 mm*5 um; mobile phase: [H$_2$O (0.04% HCl)-ACN]; B %: 25%-50%, 10 min) to give N$^2$-[3-(1-isopropylpyrrolo [2,3-c]pyridin-5-yl)-1,2,4-thiadiazol-5-yl]-N$^3$-methyl-pyrazine-2,3-diamine (35.2 mg, 85.06 μmol, 39.69% yield, 97% purity, hydrochloride). $^1$H NMR (400 MHz, DMSO-d$_6$) 12.41 (br s, 1H), 9.38 (s, 1H), 8.74 (s, 1H), 8.60 (d, J=3.1 Hz, 1H), 7.80 (d, J=3.1 Hz, 1H), 7.67

(d, J=3.1 Hz, 1H), 7.21 (d, J=2.9 Hz, 1H), 5.29-5.23 (m, 1H), 2.97 (s, 3H), 1.56 (d, J=6.7 Hz, 6H). LCMS (ESI): m/z 367.2 [M+1]⁺.

Example 74: N-(2-((3-(1-Isopropyl-2,3-dihydro-1H-pyrrolo[3,2-c]pyridin-6-yl)-1,2,4-thiadiazol-5-yl)amino)-5-(trifluoromethyl)pyridin-3-yl)-N-methylacetamide

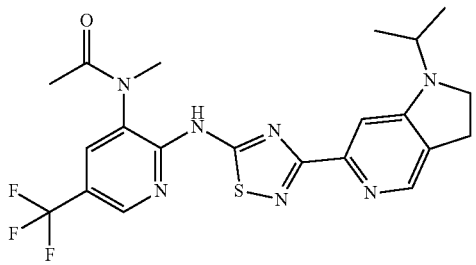 [SMILES: CC(=O)N(C)c1cc(C(F)(F)F)cnc1Nc1nc(-c2cc3c(cn2)CCN3C(C)C)ns1]

tert-Butyl 1H-pyrrolo[3,2-c]pyridine-1-carboxylate

This reaction was paralleled for two batches. To a solution of 1H-pyrrolo[3,2-c]pyridine (15 g, 126.97 mmol) in DCM (150 mL) were added TEA (21.84 g, 215.85 mmol, 30.04 mL) and N,N-dimethylpyridin-4-amine (775.60 mg, 6.35 mmol). To the mixture was added di-tert-butyl dicarbonate (29.10 g, 133.32 mmol, 30.63 mL) at 0° C. and the mixture was stirred at 25° C. for 2 h. The two batches were combined, saturated NH₄Cl aqueous was added, and the mixture was extracted with DCM. The combined organic layers were washed with brine, dried over anhydrous sodium sulfate and filtered. The filtrate was concentrated under reduced pressure and purified by flash silica gel chromatography to give tert-butyl 1H-pyrrolo[3,2-c]pyridine-1-carboxylate (57 g, crude). ¹H NMR (400 MHz, CDCl₃) 8.90 (s, 1H), 8.48 (d, J=5.8 Hz, 1H), 7.99 (d, J=5.3 Hz, 1H), 7.62 (d, J=3.6 Hz, 1H), 6.66 (d, J=3.6 Hz, 1H), 1.70 (s, 9H).

tert-Butyl 2,3-dihydro-1H-pyrrolo[3,2-c]pyridine-1-carboxylate

A mixture of tert-butyl 1H-pyrrolo[3,2-c]pyridine-1-carboxylate (10 g, 45.82 mmol) in MeOH (400 mL) was degassed and purged with nitrogen 3 times, then Pd/C (3 g, 10% purity) and hydroxide Pd/C (3 g, 20% purity) were added. The mixture was stirred at 50° C. for 10 h under hydrogen atmosphere (50 psi). The mixture was filtered and the filtrate was concentrated and purified by flash silica gel chromatography to give tert-butyl 2,3-dihydro-1H-pyrrolo[3,2-c]pyridine-1-carboxylate (18.3 g, crude). ¹H NMR (4000 MHz, CDCl₃) 8.34 (d, J=5.5 Hz, 1H), 8.31 (s, 1H), 7.81-7.34 (m, 1H), 4.01 (t, J=8.8 Hz, 2H), 3.14 (t, J=8.8 Hz, 2H), 1.58 (s, 9H).

1-(tert-Butoxycarbonyl)-2,3-dihydro-1H-pyrrolo[3,2-c]pyridine 5-oxide

To a solution of tert-butyl 2,3-dihydro-1H-pyrrolo[3,2-c]pyridine-1-carboxylate (16 g, 72.64 mmol) in DCM (160 mL) was added m-CPBA (23.50 g, 108.96 mmol, 80% purity) at 0° C. The mixture was stirred at 20° C. for 12 h. The mixture was concentrated DCM and purified by column chromatography to give 1-(tert-butoxycarbonyl)-2,3-dihydro-1H-pyrrolo[3,2-c]pyridine 5-oxide (11.4 g, 48.25 mmol, 66.43% yield). LCMS (ESI): m/z 237.1 [M+1]⁺.

tert-Butyl 6-cyano-2,3-dihydro-1H-pyrrolo[3,2-c]pyridine-1-carboxylate

To a solution of 1-(tert-butoxycarbonyl)-2,3-dihydro-1H-pyrrolo[3,2-c]pyridine 5-oxide (12.9 g, 54.60 mmol) in DCM (130 mL) was added dimethylcarbamic chloride (17.61 g, 163.80 mmol, 15.06 mL) dropwise at 0° C. Trimethylsilanecarbonitrile (16.25 g, 163.80 mmol, 20.49 mL) was then added dropwise at 0° C. and the mixture was stirred at 25° C. for 12 h. To the mixture was added saturated sodium carbonate and it was extracted with DCM. The combined organic layers were washed with brine, dried over anhydrous sodium sulfate and filtered. The filtrate was concentrated and purified to by flash silica gel chromatography to give tert-butyl 6-cyano-2,3-dihydro-1H-pyrrolo[3,2-c]pyridine-1-carboxylate (5.59 g, 22.79 mmol, 41.74% yield).

2,3-Dihydro-1H-pyrrolo[3,2-c]pyridine-6-carbonitrile

To a solution of tert-butyl 6-cyano-2,3-dihydro-1H-pyrrolo[3,2-c]pyridine-1-carboxylate (5.6 g, 22.83 mmol) in DCM (45 mL) was added 2,2,2-trifluoroacetic acid (45 mL) at 0° C. The mixture was stirred at 0° C. for 3 h. The mixture was concentrated DCM and poured into cold saturated sodium bicarbonate. The mixture was extracted with DCM and the combined organic layers were washed with brine, dried over anhydrous sodium sulfate and filtered. The filtrate was concentrated under reduced pressure to give 2,3-dihydro-1H-pyrrolo[3,2-c]pyridine-6-carbonitrile (4.6 g, crude). LCMS (ESI): m/z 146.3 [M+1]⁺.

1-Isopropyl-2,3-dihydro-1H-pyrrolo[3,2-c]pyridine-6-carbonitrile

To a solution of NaH (1.90 g, 47.53 mmol, 60% purity) in DMF (50 mL) was added 2,3-dihydro-1H-pyrrolo[3,2-c]pyridine-6-carbonitrile (4.6 g, 31.69 mmol) at 0° C. and the mixture was stirred at 20° C. for 0.5 h. Then 2-iodopropane (8.08 g, 47.53 mmol, 4.75 mL) was added at 0° C. and the mixture was stirred at 20° C. for 2 h. The mixture was poured into cold saturated NH₄Cl and extracted with EtOAc. The combined organic layers were washed with brine, dried over anhydrous sodium sulfate and filtered. The filtrate was concentrated and purified by flash silica gel chromatography to give crude 1-isopropyl-2,3-dihydro-1H-pyrrolo[3,2-c]pyridine-6-carbonitrile which was re-purified by prep-TLC to give 1-isopropyl-2,3-dihydropyrrolo[3,2-c]pyridine-6-carbonitrile (255 mg, 1.36 mmol, 4.30% yield) crude 1-isopropyl-2,3-dihydro-1H-pyrrolo[3,2-c]pyridine-6-carbonitrile and further re-purified by prep-HPLC (neutral condition; column: Agela DuraShell C18 250*50 mm*10 um; mobile phase: [H₂O (10 mM NH₄HCO₃)-ACN]; B %: 28%-28%, 22 min) to give 1-isopropyl-2,3-dihydro-1H-pyrrolo[3,2-c]pyridine-6-carbonitrile (1.05 g, 5.61 mmol, 52.50% yield). LCMS (ESI): m/z 188.3 [M+1]⁺.

(Z)—N'-Hydroxy-1-isopropyl-2,3-dihydro-1H-pyrrolo[3,2-c]pyridine-6-carboximidamide To a solution of 1-isopropyl-2,3-dihydro-1H-pyrrolo[3,2-c]pyridine-6-carbonitrile (200 mg, 1.07 mmol) in EtOH (10 mL) was added hydroxylamine hydrochloride (85.36 mg, 1.23 mmol) and N-ethyl-N-isopropylpropan-2-amine (158.75 mg, 1.23 mmol, 213.95 µL) at 25° C. The mixture was stirred at 55° C. for 2 h. The mixture was concentrated to give (Z)—N'-hydroxy-1-isopropyl-2,3-dihydro-1H-pyrrolo[3,2-c]pyridine-6-carboximidamide (565 mg, crude). LCMS (ESI): m/z 221.1 [M+1]+.

(Z)—N'Acetoxy-1-isopropyl-2,3-dihydro-1H-pyrrolo[3,2-c]pyridine-6-carboximidamide To a solution of (Z)—N'-hydroxy-1-isopropyl-2,3-dihydro-1H-pyrrolo[3,2-c]pyridine-6-carboximidamide (565 mg, 2.57 mmol) in acetic acid (6 mL) was added $Ac_2O$ (314.23 mg, 3.08 mmol, 288.29 µL). The mixture was stirred at 25° C. for 40 min. The mixture was concentrated, poured into cold saturated sodium bicarbonate, and extracted with EtOAc. The combined organic layers were washed with brine, dried over anhydrous sodium sulfate and filtered. The filtrate was concentrated to give (Z)—N'-acetoxy-1-isopropyl-2,3-dihydro-1H-pyrrolo[3,2-c]pyridine-6-carboximidamide (670 mg, crude). LCMS (ESI): m/z 263.3 [M+1]+.

1-Isopropyl-2,3-dihydro-1H-pyrrolo[3,2-c]pyridine-6-carboximidamide

To the mixture of (Z)—N'-acetoxy-1-isopropyl-2,3-dihydro-1H-pyrrolo[3,2-c]pyridine-6-carboximidamide (670 mg, 2.55 mmol) in EtOH (30 mL) was added Pd/C (350 mg, 10% purity). The mixture was degassed and purged with hydrogen 3 times, then stirred at 40° C. for 40 min under hydrogen atmosphere (15 psi). The mixture was filtered and the filtrate was concentrated to give the crude product. The residue was triturated in EtOAc at 25° C. for 10 min, then the solid was filtered and the filter cake was dried to give 1-isopropyl-2,3-dihydro-1H-pyrrolo[3,2-c]pyridine-6-carboximidamide (520 mg, crude). LCMS (ESI): m/z 205.3 [M+1]+. $^1$H NMR (400 MHz, DMSO-$d_6$) 8.04-7.99 (m, 1H), 7.19 (s, 1H), 3.95-3.88 (m, 1H), 3.58 (t, J=8.9 Hz, 2H), 3.03 (t, J=8.7 Hz, 2H), 1.17 (d, J=6.8 Hz, 6H).

tert-Butyl (2-(3-(imino(1-isopropyl-2,3-dihydro-1H-pyrrolo[3,2-c]pyridin-6-yl)methyl)thioureido)-5-(trifluoromethyl)pyridin-3-yl)(methyl)carbamate This reaction was paralleled for nine batches: To a solution of 1-isopropyl-2,3-dihydro-1H-pyrrolo[3,2-c]pyridine-6-carboximidamide (50 mg, 244.77 µmol) and tert-butyl (2-isothiocyanato-5-(trifluoromethyl)pyridin-3-yl)(methyl)carbamate (81.59 mg, 244.77 µmol) in DCM (4 mL) and acetone (4 mL) was added TEA (123.84 mg, 1.22 mmol, 170.35 µL). The mixture was stirred at 25° C. for 12 h. 9 batches of parallel reactions were combined and concentrated to give tert-butyl (2-(3-(imino(1-isopropyl-2,3-dihydro-1H-pyrrolo[3,2-c] pyridin-6-yl)methyl)thioureido)-5-(trifluoromethyl)pyridin-3-yl)(methyl)carbamate (1.18 g, crude). LCMS (ESI): m/z 538.1 [M+1]+.

tert-Butyl (2-((3-(1-isopropyl-2,3-dihydro-1H-pyrrolo[3,2-c]pyridin-6-yl)-1,2,4-thiadiazol-5-yl)amino)-5-(trifluoromethyl)pyridin-3-yl)(methyl)carbamate This reaction was paralleled for nine batches: To a solution of tert-butyl (2-(3-(imino(1-isopropyl-2,3-dihydro-1H-pyrrolo[3,2-c]pyridin-6-yl)methyl)thioureido)-5-(trifluoromethyl)pyridin-3-yl)(methyl)carbamate (131 mg, 243.68 µmol) in EtOH (3 mL) was added iodine (12.37 mg, 48.74 µmol) and hydrogen peroxide (55.26 mg, 487.35 µmol, 46.83 µL, 30% purity) at 0° C. The mixture was stirred at 25° C. for 7 min. All 9 batches of parallel reactions were combined and quenched by addition of saturated sodium sulfite at 0° C. The mixture was concentrated and the aqueous phase was extracted with EtOAc. The combined organic phase was washed with brine, dried with anhydrous sodium sulfate, filtered and concentrated under vacuum to give tert-butyl (2-((3-(1-isopropyl-2,3-dihydro-1H-pyrrolo [3,2-c]pyridin-6-yl)-1,2,4-thiadiazol-5-yl)amino)-5-(trifluoromethyl)pyridin-3-yl)(methyl)carbamate (1.17 g, crude). LCMS (ESI): m/z 536.1 [M+1]+.

$N^2$-(3-(1-Isopropyl-2,3-dihydro-1H-pyrrolo[3,2-c] pyridin-6-yl)-1,2,4-thiadiazol-5-yl)-$N^3$-methyl-5-(trifluoromethyl)pyridine-2,3-diamine To a solution of tert-butyl (2-((3-(1-isopropyl-2,3-dihydro-1H-pyrrolo[3,2-c]pyridin-6-yl)-1,2,4-thiadiazol-5-yl)amino)-5-(trifluoromethyl)pyridin-3-yl)(methyl)carbamate (1.17 g, 2.18 mmol) in EtOAc (10 mL) was added hydrogen chloride/EtOAc (20 mL, 4 N) at 0° C. The mixture was stirred at 25° C. for 2 h. The mixture was concentrated to give $N^2$-(3-(1-isopropyl-2,3-dihydro-1H-pyrrolo[3,2-c]pyridin-6-yl)-1,2,4-thiadiazol-5-yl)-$N^3$-methyl-5-(trifluoromethyl)pyridine-2,3-diamine (1.03 g, crude, hydrochloride). LCMS (ESI): m/z 436.1 [M+1]+.

N-(2-((3-(1-Isopropyl-2,3-dihydro-1H-pyrrolo[3,2-c] pyridin-6-yl)-1,2,4-thiadiazol-5-yl)amino)-5-(trifluoromethyl)pyridin-3-yl)-N-methylacetamide To a solution of $N^2$-(3-(1-isopropyl-2,3-dihydro-1H-pyrrolo[3,2-c]pyridin-6-yl)-1,2,4-thiadiazol-5-yl)-$N^3$-methyl-5-(trifluoromethyl)pyridine-2,3-diamine (1.03 g, 2.18 mmol, hydrochloride) in DMF (15 mL) was added TEA (1.10 g, 10.91 mmol, 1.52 mL) and $Ac_2O$ (222.81 mg, 2.18 mmol, 204.41 µL). The mixture was stirred at 40° C. for 12 h. Additional $Ac_2O$ (67 mg) was added, then the mixture was stirred at 40° C. for 6 h.

To the mixture was added $Ac_2O$ (45 mg), and the mixture was stirred at 40° C. for 6 h. The mixture was concentrated and purified by prep-HPLC (FA condition; column: Phenomenex luna C18 250*50 mm*10 um; mobile phase: [$H_2O$ (0.225% FA)-ACN]; B %: 15%-45%, 20 min) followed by prep-HPLC (HCl condition; column: Phenomenex Luna C18 150*30 mm*5 um; mobile phase: [$H_2O$ (0.04% HCl)-ACN]; B %: 20%-50%, 10 min) to give N-(2-((3-(1-isopropyl-2,3-dihydro-1H-pyrrolo[3,2-c]pyridin-6-yl)-1,2,4-thiadiazol-5-yl)amino)-5-(trifluoromethyl)pyridin-3-yl)-N-methylacetamide (105.22 mg, 203.19 µmol, 9.31% yield, 98% purity, hydrochloride). $^1$H NMR (400 MHz, DMSO-$d_6$) 13.37 (s, 1H), 13.14 (s, 0.4H), 12.67 (s, 0.5H), 9.02-8.88 (m, 1H), 8.48 (s, 0.5H), 8.28 (d, J=2.1 Hz, 0.5H), 7.92 (s, 1H), 7.32-7.29 (m, 1H), 4.21-4.12 (m, 1H), 3.92 (t, J=8.9 Hz, 2H), 3.32-3.32 (m, 1.7H), 3.17 (t, J=8.9 Hz, 2H), 3.11 (s, 1.3H), 2.24 (s, 1.6H), 1.74 (s, 1.4H), 1.30-1.21 (m, 6H). LCMS (ESI): m/z 478.2 [M+1]+.

Example 75: N-(3-((3-(1-Isopropyl-2,3-dihydro-1H-pyrrolo[2,3-c]pyridin-5-yl)-1,2,4-thiadiazol-5-yl)amino)pyrazin-2-yl)-N-methylacetamide

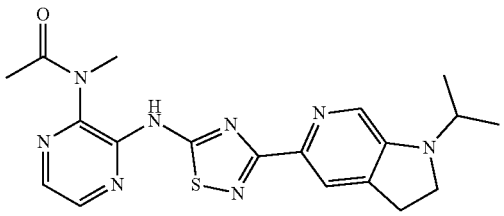 [SMILES: CC(=O)N(C)c1nccnc1Nc1nc(-c2cc3c(cn2)N(C(C)C)CC3)ns1]

tert-Butyl (3-(3-(imino(1-isopropyl-2,3-dihydro-1H-pyrrolo[2,3-c]pyridin-5-yl)methyl)thioureido)pyrazin-2-yl)(methyl)carbamate To a mixture of tert-butyl (3-isothiocyanatopyrazin-2-yl)(methyl)carbamate (300 mg, 1.13 mmol) in DCM (20 mL) and acetone (20 mL) was added 1-isopropyl-2,3-dihydro-1H-pyrrolo[2,3-c]pyridine-5-carboximidamide (230.10 mg, 1.13 mmol) and TEA (569.94 mg, 5.63 mmol, 0.78 mL), then the reaction mixture was stirred at 25° C. for 12 h. The reaction mixture was concentrated to give tert-butyl(3-(3-(imino(1-isopropyl-2,3-dihydro-1H-pyrrolo[2,3-c]pyridin-5-yl)methyl)thioureido)pyrazin-2-yl)(methyl)carbamate (540 mg, crude). LCMS (ESI): m/z 471.2 [M+1]$^+$.

tert-Butyl (3-((3-(1-isopropyl-2,3-dihydro-1H-pyrrolo[2,3-c]pyridin-5-yl)-1,2,4-thiadiazol-5-yl)amino)pyrazin-2-yl)(methyl)carbamate To a mixture of tert-butyl (3-(3-(imino(1-isopropyl-2,3-dihydro-1H-pyrrolo[2,3-c]pyridine-5-yl)methyl)thioureido)pyrazin-2-yl)(methyl)carbamate (540 mg, crude) in EtOH (10 mL) was added iodine (58.25 mg, 0.23 mmol) and hydrogen peroxide (260.21 mg, 2.29 mmol, 0.22 mL, 30% purity) at 0° C. and the reaction mixture was stirred at 25° C. for 10 min. The reaction mixture was quenched with sodium sulfite aqueous and concentrated. The residue was dissolved in EtOAc and washed with H$_2$O. The organic layer was dried over anhydrous sodium sulfate, concentrated, and triturated with MTBE/EtOAc (5:1) at 25° C. for 10 min. The mixture was filtered and the filter cake was dried to give tert-butyl (3-((3-(1-isopropyl-2,3-dihydro-1H-pyrrolo[2,3-c]pyridin-5-yl)-1,2,4-thiadiazol-5-yl)amino)pyrazin-2-yl)(methyl)carbamate (320 mg, 682.92 µmol, 59.51% yield). LCMS (ESI): m/z 469.1 [M+1]$^+$. $^1$H NMR (400 MHz, DMSO-d$_6$) 12.58 (s, 1H), 8.45-8.40 (m, 1H), 8.18 (s, 1H), 7.90 (s, 1H), 7.82 (s, 1H), 3.99-3.96 (m, 1H), 3.45 (t, J=8.7 Hz, 2H), 3.16 (s, 3H), 3.05-3.00 (m, 2H), 1.39-1.24 (m, 9H), 1.15 (d, J=6.6 Hz, 6H).

N$^2$-(3-(1-Isopropyl-2,3-dihydro-1H-pyrrolo[2,3-c]pyridin-5-yl)-1,2,4-thiadiazol-5-yl)-N$^3$-methylpyrazine-2,3-diamine The mixture of tert-butyl (3-((3-(1-isopropyl-2,3-dihydro-1H-pyrrolo[2,3-c]pyridin-5-yl)-1,2,4-thiadiazol-5-yl)amino)pyrazin-2-yl)(methyl)carbamate (320 mg, 682.92 µmol) in EtOAc (5 mL) was added hydrogen chloride/EtOAc (5 mL, 4 M) and stirred at 25° C. for 5 h. The reaction mixture was concentrated to give N$^2$-(3-(1-isopropyl-2,3-dihydro-1H-pyrrolo[2,3-c]pyridin-5-yl)-1,2,4-thiadiazol-5-yl)-N$^3$-methylpyrazine-2,3-diamine (276 mg, crude, hydrochloride). LCMS (ESI): m/z 369.1 [M+1]$^+$.

N-(3-((3-(1-Isopropyl-2,3-dihydro-1H-pyrrolo[2,3-c]pyridin-5-yl)-1,2,4-thiadiazol-5-yl)amino)pyrazin-2-yl)-N-methylacetamide To a mixture of N$^2$-(3-(1-isopropyl-2,3-dihydro-1H-pyrrolo[2,3-c]pyridin-5-yl)-1,2,4-thiadiazol-5-yl)-N-methylpyrazine-2,3-diamine (225 mg, 0.61 mmol) in DMF (8 mL) was added Ac$_2$O (81.04 mg, 0.80 mmol) and TEA (308.96 mg, 3.05 mmol, 0.42 mL) and the mixture was stirred at 50° C. for 32 h. The reaction mixture was filtered and the filtrate was purified by prep-HPLC (base condition, column: Welch Xtimate C18 250*50 mm*10 um; mobile phase: [H$_2$O (0.04% NH$_3$H$_2$O+10 mM NH$_4$HCO$_3$)-ACN]; B %: 25%-45%, 10 min) to give N-(3-((3-(1-isopropyl-2,3-dihydro-1H-pyrrolo[2,3-c]pyridin-5-yl)-1,2,4-thiadiazol-5-yl)amino)pyrazin-2-yl)-N-methylacetamide (20.32 mg, 0.045 mmol, 7.57% yield, 91% purity). $^1$H NMR (400 MHz, DMSO-d$_6$) 13.03-12.18 (m, 1H), 8.59-8.41 (m, 1H), 8.27-8.17 (m, 1H), 7.91 (s, 1H), 7.82 (s, 1H), 4.01-3.92 (m, 1H), 3.45 (t, J=8.7 Hz, 2H), 3.32 (s, 1.7H), 3.09 (s, 1.3H), 3.01 (t, J=8.5 Hz, 2H), 2.25 (s, 1.4H), 1.74 (s, 1.3H), 1.15 (d, J=6.5 Hz, 6H). LCMS (ESI): m/z 411.3 [M+1]$^+$.

Example 76: 1-(2-((3-(5-Isopropoxypyridin-2-yl)-1,2,4-thiadiazol-5-yl)amino)-5-(trifluoromethyl)pyridin-3-yl)pyrrolidin-2-one

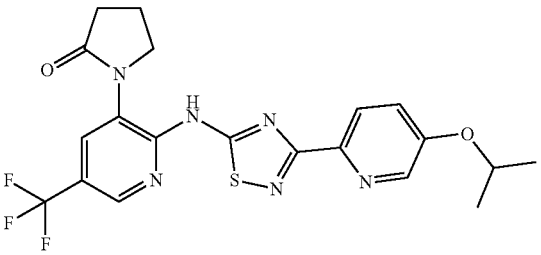 [SMILES: CC(C)Oc1ccc(-c2nsc(Nc3ncc(C(F)(F)F)cc3N3CCCC3=O)n2)nc1]

4-Chloro-N-(2-chloro-5-(trifluoromethyl)pyridin-3-yl)butanamide

To a mixture of 2-chloro-5-(trifluoromethyl)pyridin-3-amine (9.98 g, 50.77 mmol) in DCM (150 mL) was added TEA (10.28 g, 101.55 mmol, 14.13 mL) and 4-chlorobutanoyl chloride (12.89 g, 91.39 mmol, 10.23 mL) at 0° C. The mixture was stirred at 40° C. for 12 h. To the reaction was added TEA (2.57 g, 25.39 mmol, 3.53 mL) and 4-chlorobutanoyl chloride (3.58 g, 25.39 mmol, 2.84 mL) at 25° C. The mixture was stirred at 40° C. for 16 h. The reaction mixture was concentrated and purified by flash silica gel chromatography to give 4-chloro-N-(2-chloro-5-(trifluoromethyl)pyridin-3-yl)butanamide (23 g, crude). LCMS (ESI): m/z 300.9 [M+1]$^+$.

1-(2-Chloro-5-(trifluoromethyl)pyridin-3-yl)pyrrolidin-2-one

Two batches in parallel: To a mixture of 4-chloro-N-(2-chloro-5-(trifluoromethyl)pyridin-3-yl)butanamide (11.4 g, 37.86 mmol) in ACN (250 mL) was added potassium tert-butoxide (8.50 g, 75.72 mmol) at 25° C. and the reaction was stirred at 80° C. for 12 h. The combined reaction mixture was concentrated under reduced pressure and purified by flash silica gel chromatography to give 1-(2-chloro-5-(trifluoromethyl) pyridin-3-yl)pyrrolidin-2-one (5.6 g, 21.16 mmol, 27.95% yield). LCMS (ESI): m/z 264.9 [M+1]$^+$.

1-(2-Amino-5-(trifluoromethyl)pyridin-3-yl)pyrrolidin-2-one

A mixture of 1-(2-chloro-5-(trifluoromethyl)pyridin-3-yl)pyrrolidin-2-one (2.6 g, 9.82 mmol) in ammonium hydroxide (30 mL, 25% purity) and THF (10 mL) was stirred at 100° C. for 16 h. The reaction mixture was concentrated and purified by flash silica gel chromatography to give 1-(2-amino-5-(trifluoromethyl)pyridin-3-yl) pyrrolidin-2-one (1.77 g, 7.22 mmol, 73.47% yield). LCMS (ESI): m/z 246.1 [M+1]$^+$. $^1$H NMR (400 MHz-DMSO-d$_6$) δ 8.23 (d, J=1.1 Hz, 1H), 7.67 (d, J=2.1 Hz, 1H), 6.78 (br s, 2H), 3.58 (t, J=6.9 Hz, 2H), 2.38 (t, J=8.0 Hz, 2H), 2.17-2.09 (m, 2H).

1-(2-Isothiocyanato-5-(trifluoromethyl)pyridin-3-yl)pyrrolidin-2-one

To a solution of thiophosgene (1.13 g, 9.79 mmol, 750.29 μL) in DCM (10 mL) was added a solution of 1-(2-amino-5-(trifluoromethyl)pyridin-3-yl)pyrrolidin-2-one (0.8 g, 3.26 mmol) in DCM (10 mL) at 0° C. The mixture was stirred at 25° C. for 12 h. The mixture was poured into saturated sodium bicarbonate at 0° C. and extracted with DCM. The combined organic phase was concentrated under vacuum and purified by column chromatography to give 1-(2-isothiocyanato-5-(trifluoromethyl)pyridin-3-yl) pyrrolidin-2-one (390 mg, 1.36 mmol, 41.61% yield). LCMS (ESI): m/z 288.0 [M+1]$^+$.

5-Isopropoxy-N-((3-(2-oxopyrrolidin-1-yl)-5-(trifluoromethyl)pyridin-2-yl)carbamothioyl)picolinimidamide To a mixture of 1-(2-isothiocyanato-5-(trifluoromethyl)pyridin-3-yl)pyrrolidin-2-one (195 mg, 678.83 μmol), 5-isopropoxypicolinimidamide (121.66 mg, 678.83 μmol) in DCM (10 mL) and acetone (10 mL) was added TEA (343.45 mg, 3.39 mmol, 472.42 μL) at 25° C. and the mixture was stirred at 25° C. for 12 h. The mixture was concentrated under vacuum to give 5-isopropoxy-N-((3-(2-oxopyrrolidin-1-yl)-5-(trifluoromethyl)pyridin-2-yl)carbamothioyl)picolinimidamide (316 mg, crude). LCMS (ESI): m/z 467.1 [M+1]$^+$.

1-(2-((3-(5-Isopropoxypyridin-2-yl)-1,2,4-thiadiazol-5-yl)amino)-5-(trifluoromethyl)pyridin-3-yl)pyrrolidin-2-one To a mixture of 5-isopropoxy-N-((3-(2-oxopyrrolidin-1-yl)-5-(trifluoromethyl)pyridin-2-yl)carbamothioyl)picolinimidamide (0.567 g, 1.22 mmol) in EtOH (8 mL) was added iodine (61.70 mg, 243.10 μmol) and hydrogen peroxide (275.63 mg, 2.43 mmol, 233.58 μL, 30% purity) at 0° C. and the mixture was stirred at 25° C. for 15 min. The mixture was quenched by addition of saturated sodium sulfite at 0° C. and concentrated. The aqueous phase was extracted with EtOAc and the combined organic phase was washed with brine, dried with anhydrous sodium sulfate, filtered and concentrated under vacuum. The residue was purified by prep-HPLC (FA condition; column: Phenomenex Luna C18 200*40 mm*10 um; mobile phase: [H$_2$O (0.2% FA)-ACN]; B %: 50%-80%, 10 min) to give 1-(2-((3-(5-isopropoxypyridin-2-yl)-1,2,4-thiadiazol-5-yl)amino)-5-(trifluoromethyl)pyridin-3-yl)pyrrolidin-2-one (293.45 mg, 571.81 μmol, 47.04% yield, 99% purity). $^1$H NMR (400 MHz, DMSO-d$_6$) 12.52 (s, 1H), 8.86 (d, J=1.0 Hz, 1H), 8.33 (d, J=2.8 Hz, 1H), 8.28 (d, J=1.9 Hz, 1H), 8.18 (d, J=8.6 Hz, 1H), 7.52 (dd, J=2.9, 8.9 Hz, 1H), 4.83-4.74 (m, 1H), 3.79 (t, J=6.9 Hz, 2H), 2.49-2.43 (m, 2H), 2.22 (q, J=7.5 Hz, 2H), 1.32 (d, J=6.0 Hz, 6H). LCMS (ESI): m/z 465.1 [M+1]$^+$.

Example 77: N-(2-((3-(2-Isopropyl-2,3-dihydro-1H-pyrrolo[3,4-c]pyridin-6-yl)-1,2,4-thiadiazol-5-yl)amino)-5-(trifluoromethyl)pyridin-3-yl)-N-methylacetamide

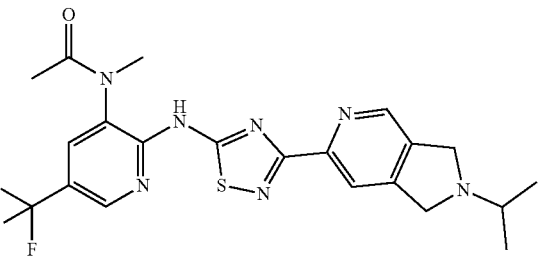

2-Chloro-4,5-bis(chloromethyl)pyridine

To a mixture of (6-chloropyridine-3,4-diyl)dimethanol (3.7 g, 21.31 mmol) in DCM (40 mL) was added sulfurous dichloride (12.68 g, 106.57 mmol, 7.73 mL). The reaction mixture was stirred at 50° C. for 2 h under nitrogen and then concentrated to give 2-chloro-4,5-bis(chloromethyl)pyridine (4.5 g, crude).

6-Chloro-2-isopropyl-2,3-dihydro-1H-pyrrolo[3,4-c]pyridine

To a mixture of 2-chloro-4,5-bis(chloromethyl)pyridine (4.5 g, crude) in DCM (50 mL) was added propan-2-amine (6.32 g, 106.89 mmol, 9.18 mL) at 20° C. and the reaction mixture was stirred at 50° C. for 12 h under nitrogen. The crude product was purified by column chromatography on silica gel to give 6-chloro-2-isopropyl-2,3-dihydro-1H-pyrrolo[3,4-c] pyridine (1.8 g, 9.15 mmol, 42.81% yield). LCMS (ESI): m/z 197.3 [M+1]$^+$.

Methyl 2-isopropyl-2,3-dihydro-1H-pyrrolo[3,4-c]pyridine-6-carboxylate

To a mixture of 6-chloro-2-isopropyl-2,3-dihydro-1H-pyrrolo[3,4-c]pyridine (1.8 g, 9.15 mmol) in MeOH (40 mL) was added TEA (1.85 g, 18.30 mmol, 2.55 mL) and [1,1-bis(diphenylphosphino)ferrocene]dichloropalladium(II) (669.67 mg, 0.92 mmol). The reaction mixture was stirred at 70° C. for 12 h under carbon monoxide (50 psi). The reaction mixture was concentrated and purified by column chromatography on silica gel to give methyl 2-isopropyl-2,3-dihydro-1H-pyrrolo[3,4-c] pyridine-6-carboxylate (1.8 g, 8.17 mmol, 89.29% yield). LCMS (ESI): m/z 221.3 [M+1]$^+$.

2-Isopropyl-2,3-dihydro-1H-pyrrolo[3,4-c]pyridine-6-carboxamide

The mixture of methyl 2-isopropyl-2,3-dihydro-1H-pyrrolo[3,4-c]pyridine-6-carboxylate (2.0 g, 9.08 mmol) in ammonia/methanol (7 M, 20 mL) was stirred at 100° C. for 12 h in a sealed tube. The reaction mixture was concentrated to give 2-isopropyl-2,3-dihydro-1H-pyrrolo[3,4-c] pyridine-6-carboxamide (1.8 g, crude).

2-Isopropyl-2,3-dihydro-1H-pyrrolo[3,4-c]pyridine-6-carbonitrile

A mixture of 2-isopropyl-2,3-dihydro-1H-pyrrolo[3,4-c]pyridine-6-carboxamide (1.7 g, 8.28 mmol) in phosphoryl trichloride (40 mL) was stirred at 90° C. for 2 h. The reaction mixture was concentrated under vacuum and dissolved in EtOAc. The mixture was poured into ice $H_2O$ slowly and solid sodium bicarbonate was added until pH 8 was reached. Organic phases were extracted with EtOAc and the combined organic layers were concentrated and purified by column chromatography to give 2-isopropyl-2,3-dihydro-1H-pyrrolo[3,4-c]pyridine-6-carbonitrile (1.25 g, 6.68 mmol, 80.60% yield). LCMS (ESI): m/z 188.2 [M+1]$^+$. $^1$H NMR (400 MHz, DMSO-$d_6$) 8.64 (s, 1H), 7.96 (s, 1H), 3.95 (d, 4H), 2.80-2.73 (m, 1H), 1.09 (d, J=6.4 Hz, 6H).

2-Isopropyl-2,3-dihydro-1H-pyrrolo[3,4-c]pyridine-6-carboximidamide

To a mixture of 2-isopropyl-2,3-dihydro-1H-pyrrolo[3,4-c]pyridine-6-carbonitrile (1.25 g, 6.68 mmol) in MeOH (20 mL) was added a solution of sodium (76.74 mg, 3.34 mmol) in MeOH (1 mL) at 25° C. and the mixture was stirred at 25° C. for 12 h. To the reaction mixture was added $NH_4Cl$ (535.65 mg, 10.01 mmol) at 25° C. and stirred at 70° C. for 2 h. The reaction mixture was concentrated and triturated with MTBE:EtOAc (10:1, 22 mL) for 10 min. The solution was filtered and the filter cake was collected and concentrated under reduced pressure to give 2-isopropyl-2,3-dihydro-1H-pyrrolo[3,4-c] pyridine-6-carboximidamide (1.49 g, 6.19 mmol, 92.71% yield, hydrochloride). LCMS (ESI): m/z 205.2 [M+1]$^+$.

tert-Butyl (2-(3-(imino(2-isopropyl-2,3-dihydro-1H-pyrrolo[3,4-c]pyridin-6-yl)methyl)thioureido)-5-(trifluoromethyl)pyridin-3-yl)(methyl)carbamate To a mixture of 2-isopropyl-2,3-dihydro-1H-pyrrolo[3,4-c]pyridine-6-carboximidamide (0.5 g, 2.08 mmol, hydrochloride), tert-butyl (2-isothiocyanato-5-(trifluoromethyl) pyridin-3-yl)(methyl)carbamate (692.32 mg, 2.08 mmol) in DCM (10 mL) and acetone (10 mL) was added TEA (1.05 g, 10.38 mmol, 1.45 mL) at 25° C. The mixture was stirred at 25° C. for 12 h and then concentrated under vacuum to give tert-butyl (2-(3-(imino(2-isopropyl-2,3-dihydro-1H-pyrrolo[3,4-c]pyridin-6-yl)methyl)thioureido)-5-(trifluoromethyl)pyridin-3-yl)(methyl)carbamate (1.12 g, crude). LCMS (ESI): m/z 538.2 [M+1]$^+$.

tert-Butyl (2-((3-(2-isopropyl-2,3-dihydro-1H-pyrrolo[3,4-c]pyridin-6-yl)-1,2,4-thiadiazol-5-yl)amino)-5-(trifluoromethyl)pyridin-3-yl)(methyl)carbamate To a mixture of tert-butyl (2-(3-(imino(2-isopropyl-2,3-dihydro-1H-pyrrolo[3,4-c]pyridin-6-yl)methyl)thioureido)-5-(trifluoromethyl)pyridin-3-yl)(methyl)carbamate (1.12 g, crude) in EtOH (16 mL) was added iodine (105.75 mg, 0.42 mmol) and hydrogen peroxide (472.43 mg, 4.17 mmol, 0.4 mL, 30% purity) at 0° C. The mixture was stirred at 25° C. for 15 min and then quenched by addition of saturated sodium sulfite at 0° C. The solution was concentrated under vacuum and triturated with MTBE:EtOAc (3:1, 20 mL) for 10 min. The suspension was filtered, the filter cake dried under vacuum and was suspended in DCM. The suspension was filtered, the filtrate was concentrated under vacuum to give tert-butyl (2-((3-(2-isopropyl-2,3-dihydro-1H-pyrrolo [3,4-c]pyridin-6-yl)-1,2,4-thiadiazol-5-yl)amino)-5-(trifluoromethyl)pyridin-3-yl)(methyl)carbamate (810 mg, 1.51 mmol, 72.59% yield). LCMS (ESI): m/z 536.1 [M+1]$^+$.

$N^2$-(3-(2-Isopropyl-2,3-dihydro-1H-pyrrolo[3,4-c]pyridin-6-yl)-1,2,4-thiadiazol-5-yl)-$N^3$-methyl-5-(trifluoromethyl)pyridine-2,3-diamine A mixture of tert-butyl (2-((3-(2-isopropyl-2,3-dihydro-1H-pyrrolo[3,4-c]pyridin-6-yl)-1,2,4-thiadiazol-5-yl) amino)-5-(trifluoromethyl)pyridin-3-yl)(methyl)carbamate (785 mg, 1.47 mmol) in EtOAc (10 mL) and hydrogen chloride/EtOAc (20 mL, 4 M) was stirred at 25° C. for 2 h. The reaction mixture was concentrated under vacuum to give $N^2$-(3-(2-isopropyl-2,3-dihydro-1H-pyrrolo[3,4-c]pyridin-6-yl)-1,2,4-thiadiazol-5-yl)-$N^3$-methyl-5-(trifluoromethyl)pyridine-2,3-diamine (691 mg, crude, hydrochloride). LCMS (ESI): m/z 436.1 [M+1]$^+$.

N-(2-((3-(2-Isopropyl-2,3-dihydro-1H-pyrrolo[3,4-c]pyridin-6-yl)-1,2,4-thiadiazol-5-yl)amino)-5-(trifluoromethyl)pyridin-3-yl)-N-methylacetamide To a mixture of $N^2$-(3-(2-isopropyl-2,3-dihydro-1H-pyrrolo[3,4-c]pyridin-6-yl)-1,2,4-thiadiazol-5-yl)-$N^3$-methyl-5-(trifluoromethyl)pyridine-2,3-diamine (691 mg, crude, hydrochloride) and $Ac_2O$ (239.16 mg, 2.34 mmol, 0.22 mL) in DMF (15 mL) was added TEA (740.81 mg, 7.32 mmol, 1.02 mL) at 25° C. and then the mixture was stirred at 45° C. for 12 h. Additional $Ac_2O$ (44.84 mg, 0.44 mmol) was added at 25° C. and then stirred at 45° C. for 5 h. The reaction mixture was concentrated under vacuum and purified by prep-HPLC (formic acid condition; column: Phenomenex luna C18 250*80 mm*10 um; mobile phase: [$H_2O$ (0.225% FA)-ACN]; B %: 10%-40%, 20 min) to give a crude product. Then the crude product was re-purified by prep-HPLC (formic acid condition; column: Phenomenex Luna C18 200*40 mm*10 um; mobile phase: [$H_2O$ (0.2% FA)-ACN]; B %: 10%-50%, 10 min) to give a crude product. The crude product was re-purified by prep-HPLC (neutral condition; column: Waters Xbridge BEH C18 100*25 mm*5 um; mobile phase: [$H_2O$ (10 mM NH4HCO3)-ACN]; B %: 55%-85%, 8 min) to give a crude product. Then the crude product was re-purified by prep-HPLC (hydrogen chloride condition; column: Phenomenex Luna C18 150*30 mm*5 um; mobile phase: [$H_2O$ (0.04% HCl)-ACN]; B %: 20%-50%, 10 min) to give N-(2-((3-(2-isopropyl-2,3-dihydro-1H-pyrrolo[3,4-c]pyridin-6-yl)-1,2,4-thiadiazol-5-yl) amino)-5-(trifluoromethyl) pyridin-3-yl)-N-methylacetamide (32.9 mg, 62.73 μmol, 4.30% yield, 98% purity, hydrochloride). $^1$H NMR (400 MHz, DMSO-$d_6$) 13.28-12.60 (m, 1H), 12.19 (br s, 1H), 8.96-8.84 (m, 1H), 8.73 (s, 1H), 8.45-8.18 (m, 2H), 4.93-4.82 (m, 2H), 4.73-4.65 (m, 2H), 3.73-3.68 (m, 1H), 3.30 (s, 1.5H), 3.10 (s, 1.5H), 2.22 (s, 1.5H), 1.73 (s, 1.3H), 1.38 (d, J=6.4 Hz, 6H). LCMS (ESI): m/z 478.2 [M+1]$^+$.

Example 78: N-(3-((3-(5-Isopropoxypyridin-2-yl)-1,2,4-thiadiazol-5-yl)amino)pyrazin-2-yl)-N-methylacetamide

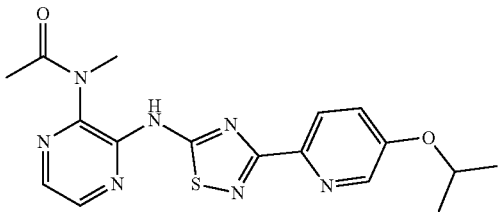 [SMILES: CC(=O)N(C)c1nccnc1Nc1nc(-c2ccc(OC(C)C)cn2)ns1]

tert-Butyl N-tert-butoxycarbonyl-N-(3-chloropyrazin-2-yl)carbamate

To a mixture of 3-chloropyrazin-2-amine (20 g, 154.38 mmol) and di-tert-butyl dicarbonate (67.39 g, 308.77 mmol, 70.94 mL) in DCM (400 mL) was added N,N-dimethylpyridin-4-amine (1.89 g, 15.44 mmol) and then the reaction mixture was stirred at 40° C. for 2 h. The reaction mixture was washed with H$_2$O and extracted with DCM. The combined organic layers were dried over anhydrous sodium sulfate and concentrated to give tert-butyl N-tert-butoxycarbonyl-N-(3-chloropyrazin-2-yl)carbamate (50 g, crude).

tert-Butyl (3-chloropyrazin-2-yl)carbamate

To the mixture of tert-butyl N-tert-butoxycarbonyl-N-(3-chloropyrazin-2-yl)carbamate (50 g, crude) in MeOH (400 mL) was added a solution of sodium hydroxide (11.43 g, 285.74 mmol) in H$_2$O (100 mL) and the reaction mixture was stirred at 20° C. for 1 h. The reaction mixture was concentrated, and the H$_2$O layer was extracted with EtOAc. The combined organic layers were dried over anhydrous sodium sulfate and concentrated to give tert-butyl (3-chloropyrazin-2-yl)carbamate (30 g, crude).

tert-Butyl (3-chloropyrazin-2-yl)(methyl)carbamate

To a solution of tert-butyl (3-chloropyrazin-2-yl)carbamate (20 g, crude) in DMF (200 mL) was added sodium hydride (3.83 g, 95.79 mmol, 60% purity) in portions at 0° C. After addition, the reaction mixture was stirred at 0° C. for 0.5 h, then iodomethane (12.98 g, 91.44 mmol, 5.69 mL) was added at 0° C. The reaction mixture was stirred at 20° C. for 1 h. The reaction mixture was poured into saturated ammonium chloride aqueous and then extracted with EtOAc. The combined organic layers were washed with brine, dried over anhydrous sodium sulfate, filtered and concentrated under reduced pressure to give tert-butyl (3-chloropyrazin-2-yl)(methyl)carbamate (21.22 g, crude). LCMS (ESI): m/z 244.1 [M+1]$^+$.

tert-Butyl (3-azidopyrazin-2-yl)(methyl)carbamate

To a mixture of sodium azide (8.00 g, 123.11 mmol) in DMSO (150 mL) was added tert-butyl (3-chloropyrazin-2-yl)(methyl)carbamate (10 g, crude) and the reaction mixture was stirred at 100° C. for 16 h. To the reaction mixture was added to H$_2$O and the mixture was extracted with EtOAc, the combined organic layers were dried over anhydrous sodium sulfate and concentrated to give tert-butyl (3-azidopyrazin-2-yl)(methyl) carbamate (9.5 g, crude). LCMS (ESI): m/z 251.3 [M+1]$^+$.

tert-Butyl (3-aminopyrazin-2-yl)(methyl)carbamate

To a mixture of tert-butyl (3-azidopyrazin-2-yl)(methyl) carbamate (9.5 g, crude) in MeOH (150 mL) was added Pd/C (1.2 g, 10% purity) and palladium hydroxide/carbon (1.2 g, 8.54 mmol, 20% purity). The reaction mixture was stirred at 20° C. for 12 h under hydrogen atmosphere (15 psi). The reaction mixture was filtered and the filtrate was concentrated and purified by column chromatography to give tert-butyl (3-aminopyrazin-2-yl)(methyl) carbamate (4.3 g, 19.17 mmol, 50.51% yield).

tert-Butyl (3-isothiocyanatopyrazin-2-yl)(methyl)carbamate

A solution of thiocarbonyl dichloride (3.08 g, 26.75 mmol, 2.05 mL) in DCM (50 mL) was cooled to 0° C., then a solution of tert-butyl (3-aminopyrazin-2-yl)(methyl) carbamate (2 g, 8.92 mmol) in DCM (30 mL) was added dropwise to the above mixture at 0° C. After addition, the reaction mixture was stirred at 0° C. for 2 h. The reaction mixture was concentrated and purified by flash column chromatography to give tert-butyl (3-isothiocyanatopyrazin-2-yl) (methyl)carbamate (900 mg, 3.38 mmol, 37.89% yield). LCMS (ESI): m/z 267.3 [M+1]$^+$.

tert-Butyl (3-(3-(imino(5-isopropoxypyridin-2-yl)methyl)thioureido)pyrazin-2-yl)(methyl)carbamate To a mixture of tert-butyl (3-isothiocyanatopyrazin-2-yl) (methyl)carbamate (200 mg, 0.75 mmol) and 5-isopropoxypicolinimidamide (134.59 mg, 0.75 mmol) in DCM (20 mL) and acetone (20 mL) was added TEA (379.96 mg, 3.75 mmol, 0.52 mL) then the reaction mixture was stirred at 20° C. for 3 h. The reaction mixture was concentrated to give tert-butyl (3-(3-(imino(5-isopropoxypyridin-2-yl)methyl)thioureido)pyrazin-2-yl)(methyl) carbamate (340 mg, crude). LCMS (ESI): m/z 446.3 [M+1]$^+$.

tert-Butyl (3-((3-(5-isopropoxypyridin-2-yl)-1,2,4-thiadiazol-5-yl)amino)pyrazin-2-yl)(methyl)carbamate To a mixture of tert-butyl (3-(3-(imino(5-isopropoxypyridin-2-yl)methyl)thioureido) pyrazin-2-yl)(methyl)carbamate (340 mg, crude) in EtOH (10 mL) was added iodine (38.74 mg, 0.15 mmol) and hydrogen peroxide (173.05 mg, 1.53 mmol, 0.15 mL, 30% purity). The reaction mixture was stirred at 20° C. for 0.2 h. The reaction mixture was quenched by saturated sodium sulfite aqueous and concentrated. The residue was extracted with EtOAc and the organic layer was dried over anhydrous sodium sulfate and concentrated to give tert-butyl (3-((3-(5-isopropoxypyridin-2-yl)-1,2,4-thiadiazol-5-yl)amino)pyrazin-2-yl) (methyl) carbamate (300 mg, crude). LCMS (ESI): m/z 444.1 [M+1]$^+$.

N$^2$-(3-(5-Isopropoxypyridin-2-yl)-1,2,4-thiadiazol-5-yl)-N$^3$-methylpyrazine-2,3-diamine The mixture of tert-butyl (3-((3-(5-isopropoxypyridin-2-yl)-1,2,4-thiadiazol-5-yl)amino) pyrazin-2-yl)(methyl)carbamate (300 mg, crude) in hydrogen chloride/EtOAc (4 M, 5 mL) and EtOAc (5 mL) was stirred at 20° C. for 1 h. The reaction mixture was concentrated to give $N^2$-(3-(5-isopropoxypyridin-2-yl)-1,2,4-thiadiazol-5-yl)-$N^3$-methylpyrazine-2,3-diamine (260 mg, crude, hydrochloride salt). LCMS (ESI): m/z 344.2 [M+1]$^+$.

N-(3-((3-(5-Isopropoxypyridin-2-yl)-1,2,4-thiadiazol-5-yl)amino)pyrazin-2-yl)-N-methylacetamide To a mixture of $N^2$-(3-(5-isopropoxypyridin-2-yl)-1,2,4-thiadiazol-5-yl)-$N^3$-methylpyrazine-2,3-diamine (260 mg, crude, hydrochloride) in DMF (5 mL) was added TEA (346.30 mg, 3.42 mmol, 0.47 mL) and Ac$_2$O (90.84 mg, 0.89 mmol) and the reaction mixture was stirred at 45° C. for 12 h. The crude product was purified by prep-HPLC (formic acid condition, Phenomenex Luna C18 100*30 mm*5 um; mobile phase: [H$_2$O (0.2% FA)-ACN]; B %: 30%-45%, 12 min) to give N-(3-((3-(5-isopropoxypyridin-2-yl)-1,2,4-thiadiazol-5-yl)amino)pyrazin-2-yl)-N-methylacetamide (92.34 mg, 0.237 mmol, 35.83% yield, 99% purity). $^1$H NMR (400 MHz, DMSO-d$_6$) 13.13-12.08 (m, 1H), 8.60-8.42 (m, 1H), 8.33 (s, 1H), 8.26-8.14 (m, 2H), 7.52 (d, J=7.0 Hz, 1H), 4.81-4.76 (m, 1H), 3.30 (s, 2.3H), 3.10 (s, 0.7H), 2.26 (s, 1.5H), 1.74 (br s, 1.5H), 1.32 (d, J=5.8 Hz, 6H). LCMS (ESI): m/z 386.1 [M+1]$^+$.

Example 79: 4-Methyl-N-[5-(3-methylpyridin-2-yl)-1,2,4-thiadiazol-3-yl]pyridin-2-amine

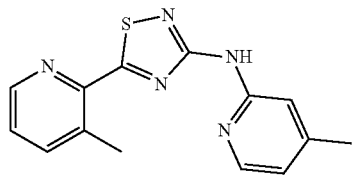 [SMILES: Cc1ccnc(Nc2nsc(-c3ncccc3C)n2)c1]

2-(5-Bromo-1,2,4-thiadiazol-3-yl)-3-methylpyridine

To a stirred solution of 3-bromo-5-chloro-1,2,4-thiadiazole (522 mg, 2.62 mmol) in 1,4-dioxane (25 mL) 3-methyl-2-(tributylstannyl)pyridine (1 g, 2.62 mmol) was added and the reaction mixture was degassed with argon for 10 min. Pd(PPh$_3$)$_4$ (151 mg, 0.13 mmol) was added followed by copper(I) thiophene-2-carboxylate (5 mg, 0.26 mmol) and degassed for an additional 5 min. The resulting mixture was stirred at 25° C. for 16 h. and diluted with EtOAC, H$_2$O and filtered through a short pad of celite. The filtrate was extracted with EtOAc and the combined organic layer was washed with brine, dried over Na$_2$SO$_4$, filtered and concentrated under reduced pressure. The crude compound was purified by column chromatography to afford 2-(4-bromo-1,3-thiazol-2-yl)-3-methylpyridine (170 mg, 25%). LCMS (ESI): m/z 257.8 [M+1]$^+$.

4-Methyl-N-[5-(3-methylpyridin-2-yl)-1,2,4-thiadiazol-3-yl]pyridin-2-amine

To a stirred solution of 2-(4-bromo-1,3-thiazol-2-yl)-3-methylpyridine (150 mg, 0.59 mmol) in 1,4-dioxane (5 mL) 4-methylpyridin-2-amine (126 mg, 1.17 mmol) and Cs$_2$CO$_3$ (384 mg, 1.17 mmol) was added and degassed with argon for 10 min. Xantphos (51 mg, 0.09 mmol) and Pd$_2$(dba)$_3$ (27 mg, 0.03 mmol) were added and the mixture was degassed for an additional 5 min. The resulting mixture was heated to 110° C. for 16 h then cooled, diluted with EtOAc, H$_2$O and filtered through a short pad of celite. The filtrate was extracted with EtOAc and the combined organic layer was washed with brine, dried over Na$_2$SO$_4$, filtered and concentrated under reduced pressure. The crude compound was purified by prep-HPLC to afford 4-methyl-N-[5-(3-methylpyridin-2-yl)-1,2,4-thiadiazol-3-yl]pyridin-2-amine (35 mg, 21%). LCMS (ESI): m/z 283.8 [M+1]$^+$.

Compounds 331-351 in Table 1 can be prepared using analogous methods described herein and those known in the art.

In Vitro Parasite Motility Assays

Parasite Motility Assays.

Adult and microfilariae B. malayi and B. pahangi parasites, harvested from infected jirds, were procured from the NIAID/NIH Filariasis Research Reagent Resource Center (FR3). Adult and microfilariae of L. sigmodontis were procured from TRS labs Inc. (Athens, Ga.). Adult worms were plated in 24-well plates with 2 mL of Advanced RPMI 1640 medium (Invitrogen) supplemented with 25 mM HEPES, 2 mM L-Glutamine (Invitrogen), 100 U/mL Penicillin (Invitrogen), 100 g/mL Streptomycin (Invitrogen), 2.5 g/mL Amphotericin B solution (Invitrogen), and 5% heat inactivated fetal bovine serum and placed in a 37° C. humidified incubator with 5% CO$_2$. After 24 h, adult worms were selected based upon motility as described below. After scoring for motility, 4-6 highly motile worms were selected for each treatment group and were transferred to new plates. Microfilariae were centrifuged at 5000×g for 5 min, and re-suspended in 2 ml of media. Microfilarial density was determined using a hemocytometer and were plated in a 96-well plate at 80 microfilariae/well with 200 μL of complete media. Treatment groups received compounds (0.1% DMSO) at 1 μM and 100 nM with 0.1% DMSO as a vehicle control. Cultures were incubated at 37° C. in a humidified incubator with 5% CO$_2$. Worms were transferred into a new plate containing fresh media and drug every 48 h. Parasite and microfilariae motility were given a score from 0 to 4 with 4, rapid movement and largely coiled; 3, moderated movement and uncoiled; 2, slow movement and uncoiled; 1, twitching movement and uncoiled; 0, no motility (dead). The motility of the worms and microfilariae were evaluated every 24 h and analyzed by a one sided unpaired Student's t-test using Microsoft Excel. Experiments were performed 2-3 times with similar results.

Onchocerciasis: In Vitro Screening Model Onchocerca gutturosa

Parasite and Cell Cultures. Onchocerca gutturosa Adult Male Worms were obtained by dissection from the nuchal ligament connective tissues of naturally infected cattle, from Gambia, W Africa.

The worms were maintained for at least 24 h in culture before use in Eagles Minimum Essential Medium with Earl's Salts (Gibco, UK)+10% heat inactivated new born calf serum (Gibco, UK)+antibiotic cover of 200 units/ml penicillin, 200 μg/ml streptomycin and 0.5 μg/ml amphotericin B (Sigma, UK). Only normally active specimens were used in the test. All cultures and assays were conducted at 37° C. under an atmosphere of 5% CO$_2$ in air.

Drug Sensitivity Assays.

Compound stock solutions were prepared in 100% DMSO unless otherwise indicated and diluted into the medium. Any unused compound stocks were stored at −20° C. Assays were performed in sterile 24-well (2 ml) plates (Falcon, UK).

Worms were then transferred individually to each well of the plate using fine forceps. Worm viability was assessed using 2 parameters:

The measurement of mean worm motility scores on a scale of 0 (immotile) to 10 (maximum) every 24 h, terminating at 120 h, using an Olympus inverted microscope.

The biochemical evaluation of worm viability using MTT/formazan colorimetry. The MTT assay was carried out after the last motility reading (120 h). Single intact worms were placed in each well of a 48-well plate (Falcon, UK) containing 0.5 ml of a solution consisting of 0.5 mg/ml MTT (Sigma UK) in phosphate buffered saline, and then incubated for 30 min at 37° C. The worms were removed, blotted carefully, and individually transferred to separate wells of a 96-well microtiter plate, each containing 200 µl of DMSO to solubilize the formazan. After 1 h the plate was gently agitated to disperse the color evenly and the absorbance value (optical density) of the resulting formazan solution was determined at 490 nm using a multi-well scanning spectrophotometer (Elisa-reader, Dynatech, UK). Inhibition of formazan formation was correlated with worm damage or death.

Primary Screen.

New compounds were usually tested at $1.25 \times 10^{-5}$ M. Also expressed in µg/ml. Test drugs (2 worms/group) were compared to untreated controls (6 worms/group) and a positive control (standard drug, 6 worms/group). The standard used was Immiticide (Merial): this drug produces a reduction in motility of 100%, and mean inhibition of formazan formation of ~85%. The approximate motility $EC_{50}$ for Immiticide was $3 \times 10^{-7}$ M, and for ivermectin was $1 \times 10^{-8}$ M. The readouts are: Motility score (mean % reduction at 120 h) MTT colorimetry (mean inhibition of formazan formation).

A test compound was considered active if there was a 50% or greater reduction in motility score and/or a 50% or greater inhibition of formazan formation compared to untreated controls.

Compounds were classified as moderately active if there was a 50-99% reduction in motility and/or inhibition of formazan, or highly active at 100%/lower concentrations.

Secondary Screen.

All active compounds were re-tested. Serial 1 in 4 drug dilutions was carried out to find activity endpoint and $EC_{50}$ values for motility reduction and inhibition of formazan formation were produced. $EC_{50}$ values were determined using Excel or Origin V7 scientific graphing and data analysis software.

Heartworm Screen Dirofilaria immitis (D. immitis)

Dirofilaria immitis, Microfilaria (DiMF) Assay.

Compounds were dissolved and serially diluted in DMSO. Aliquots were spotted to the empty wells of assay plates. Media and microfilariae of Dirofilaria immitis were added to each well to dilute the test compounds to the desired concentrations. Assay plates were incubated for approximately 72 hours, and the larvae in each well were observed microscopically for drug effect. Microfilariae in each well were assessed subjectively for survival or paralysis, and results were reported as Minimum Effective Dose (MED).

Dirofilaria immitis, L4 Stage (DiL4) Assay.

Compounds were dissolved and serially diluted in DMSO. Aliquots were spotted to the empty wells of assay plates. Media and 4th stage larvae (L4) of Dirofilaria immitis were added to each well to dilute the test compounds to the desired concentrations. Assay plates were incubated for approximately 72 hours, and the larvae in each well were observed microscopically for drug effect. Larvae in each well were assessed subjectively for survival or paralysis, and results were reported as Minimum Effective Dose (MED).

The compounds described herein demonstrated nematocidal activity against either Dirofilaria immitis (Larva stage 4 (DiL4)) and/or Dirofilaria immitis (microfilaria (DiMF)) as determined by reductions in nematode motility either by paralysis or death. Active and selective (DiL4 vs. DiMF potency) example compounds were subsequently evaluated in heartworm positive dog studies to correlate the in vitro selectivity profile with in vivo effects on circulating microfilariae.

Activity of the Heterocyclic Compounds in the parasite motility assays is shown in Table 1.

In Vivo Filariasis Assays

L. sigmodontis In Vivo Assays.

The infection of mice and jirds can be either initiated by the natural route, exposure of mites containing infective third stage larvae (L3) of L. sigmodontis, or via the injection (subcutaneous, intraperitoneal or intravenous) of a known number of L3 larvae (G. Karadjian et al., Migratory phase of Litomosoides sigmodontis filarial infective larvae is associated with pathology and transient increase of S100A9 expressing neutrophils in the lung, PLoS Negl Trop Dis 11, e0005596 (2017)). Upon infection L3 larvae migrate from the site of inoculation within 2-6 days via the lymphatics to the thoracic cavity, where they molt around 10 days post infection (dpi) into 4th stage larvae and around 30 dpi into adult worms. Approximately 56 dpi adult female worms start to release microfilariae that enter the peripheral blood. In BALB/c mice, adult worm burden starts to decline around 70 dpi and by 100 dpi at which most of the adult worms are cleared. Jirds harbor the adult worms for more than one year.

L. sigmodontis Mouse Model.

The L. sigmodontis mouse model allows the analysis of the activity of compounds on the adult worm or the development into adult worms.

L. sigmodontis Jird Model.

In order to assess the efficacy of drug candidates during chronic, patent infection the L. sigmodontis jird model was used. In general, treatment with drug candidates was initiated 12 weeks post infection and only microfilariae-positive jirds were included in the experiments. Necropsies were performed in general 8-16 weeks post treatment. This extended time between initiation of treatment and necropsy allowed to identify the macrofilaricidal (adult worm killing) efficacy of slow acting compounds. The jird model allowed the assessment of the in vivo impact of compounds on microfilariae over time. Compounds with strong microfilaricidal efficacy clear the microfilariae from peripheral blood within a short period of time. Compounds with an adult worm sterilizing or macrofilaricidal efficacy (lacking a microfilaricidal efficacy) lead to a delayed reduction of the microfilaremia that exceeds 4 weeks post treatment start. Additional analysis at the time of necropsy included the quantification of adult worms, ratios of female and male adult worms, and motility of adult worms at the time of necropsy. Remaining female adult worms were assessed for their embryogenesis and therefore sterilizing effects of compounds. Embryograms from female adult worms included the quantification of early developmental stages (egg/morulae) and later stages (pretzel stage & stretched microfilariae) according to (S. Ziewer et al., Immunization with *L. sigmodontis* Microfilariae Reduces Peripheral Microfilaraemia after Challenge Infection by Inhibition of Filarial Embryogenesis, *PLoS Negl Trop Dis* 6, e1558 (2012)). Lack of early and/or later developmental embryonic stages suggested a sterilizing effect of the compounds. Additional histological and TEM analysis was applied to analyze any tissue damages caused by the drug candidates that may be associated with permanent sterilization.

The *L. sigmodontis* jird model assessed the macrofilaricidal efficacy of compounds, their impact on microfilaremia, female worm embryogenesis and sterilization.

The Heterocyclic Compounds provided herein were tested and showed activity in both *L. sigmodontis* mouse and *L. sigmodontis* jird model assays performed as described herein, with some compounds showing macrofilaricidal activity, some compounds showing microfilaricidal activity, and some compounds showing macrofilaricidal selectivity.

In some embodiments, the compounds disclosed herein surprisingly presented distinct activity between parasitic nematodes in adult and juvenile stage. In some such embodiments, the compounds disclosed herein were found to be selectively effective against adult filarial nematodes (i.e., were macroselective). Therefore, the compounds disclosed herein have the potential to be potent anti-filarial drugs.

Heartworm Dog Studies.

Dogs with pre-existing heartworm infections, via surgical transplantation were used for these studies. To confirm that the dogs had circulating microfilariae, blood samples were taken from each dog and examined for microfilariae by using the modified Knott's method. All dog cohorts included in the studies exhibited average microfilariae counts of at least 15,000 MF/mL of the blood (pre-dose). On approximately Day −7, dogs were randomly allocated to treatments (three animals per treatment group) based on Day −7 MF counts. Dogs were fasted overnight prior to dosing and fed immediately following dosing of the test articles. Compounds were administered by point dosing in oral liquid-filled capsules on Day 0. Blood samples were collected to measure MF counts on Days 0 (pre-dose and 2 hours post-dose), 1, 2, 7, 21 and 28. Clinical observations were conducted by a suitably experienced veterinarian on days −7, 0 (immediately prior to treatment, 1-2 hours post-treatment), 1 and 2 whereby any abnormal clinical signs were documented using standard veterinary medical terminology. Additionally, general health observations were conducted throughout the study including (but not limited to) general physical appearance and behavior, abnormalities of food and water consumption, vomiting/regurgitation, appearance of urine and feces and any sign of MF anaphylaxis.

The Heterocyclic Compounds provided herein were tested and showed activity, or will be shown to have activity, on circulating microfilariae in vivo.

Activity Table

Each of the compounds in Table 1 was tested in at least one of the in vitro filarial motility assays and was found to have activity therein, with all of the Heterocyclic Compounds of formula (I), formula (Ia), formula (Ib), formula (Ic), formula (II) and formula (IIa) having an $IC_{50}$ below or 5 µM in one or more of the assays, with some compounds having an $IC_{50}$ or MED between 0.5 µM and 5 µM (activity level A), some having an $IC_{50}$ between 0.2 µM and 0.5 µM (activity level B), and some having an $IC_{50}$ below 0.2 µM (activity level C). Heterocyclic Compounds of formula (I), formula (Ia), formula (Ib), formula (Ic), formula (II) and formula (IIa) were tested in one or more of the assays and were shown to have activity therein, with some of the Heterocyclic Compounds of formula (I), formula (Ia), formula (Ib), formula (Ic), formula (II) or formula (IIa) having activity against microfilaria at compound concentrations below 1 µM (activity level D) with some compounds having activity against adult filaria at compound concentrations below 1 µM (activity level E).

TABLE 1

| Cmpd No. | Structure | Name | M + 1 | O. guttu-rosa | B. malayi | L. sigmo-dontis | B. paha-ngi | D. immit-is |
|---|---|---|---|---|---|---|---|---|
| 1 | 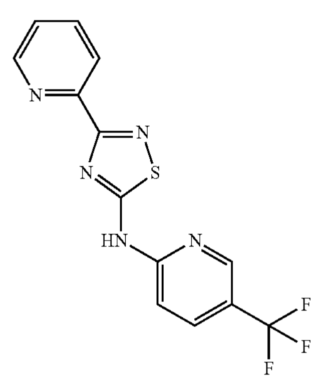 [SMILES: FC(F)(F)c1ccc(Nc2nc(-c3ccccn3)ns2)nc1] | 3-(pyridin-2-yl)-N-(5-trifluoromethyl)pyridin-2-yl)-1,2,4-thiadiazol-5-amine | 324.2 | C | D, E | | | C |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 2 | 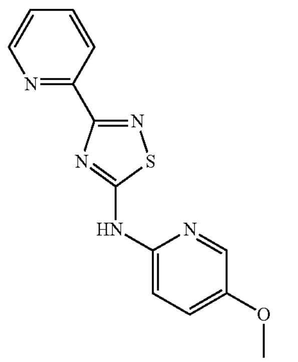 [SMILES: COc1ccc(Nc2nc(-c3ccccn3)ns2)nc1] | N-(5-methoxy-pyridin-2-yl)-3-(pyridin-2-yl)-1,2,4-thiadiazol-5-amine | 286.2 | A | D, E | E | | A |
| 3 | 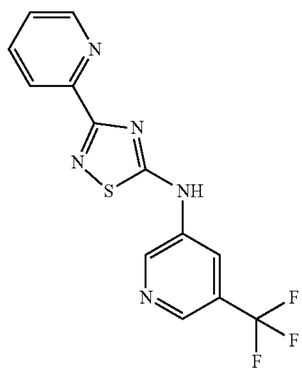 [SMILES: FC(F)(F)c1cncc(Nc2nc(-c3ccccn3)ns2)c1] | 3-(pyridin-2-yl)-N-(5-(trifluoromethyl)pyridin-3-yl)-1,2,4-thiadiazol-5-amine | 324.2 | A | D, E | | | A |
| 4 | 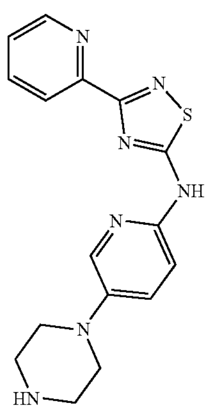 [SMILES: c1ccc(-c2nsc(Nc3ccc(N4CCNCC4)cn3)n2)nc1] | N-(5-(piperazin-1-yl)pyridin-2-yl)-3-(pyridin-2-yl)-1,2,4-thiadiazol-5-amine | 340.2 | A | E | | | |
| 5 | 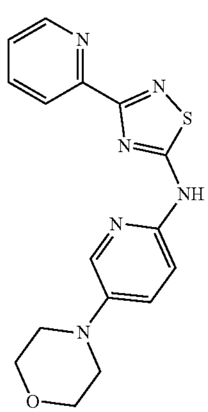 [SMILES: c1ccc(-c2nsc(Nc3ccc(N4CCOCC4)cn3)n2)nc1] | N-(5-morpholino-pyridin-2-yl)-3-(pyridin-2-yl)-1,2,4-thiadiazol-5-amine | 341.2 | A | D, E | | | |

TABLE 1-continued

| Cmpd No. | Structure | Name | M + 1 | *O. guttu- rosa* | *B. malayi* | *L. sigmo- dontis* | *B. paha- ngi* | *D. immit- is* |
|---|---|---|---|---|---|---|---|---|
| 6 | 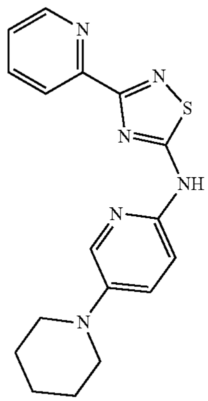 [SMILES: c1ccc(-c2nsc(Nc3ccc(N4CCCCC4)cn3)n2)nc1] | N-(5-(piperidin-1-yl)pyridin-2-yl)-3-(pyridin-2-yl)-1,2,4-thiadiazol-5-amine | 329.2 | C | D, E | | | A |
| 7 | 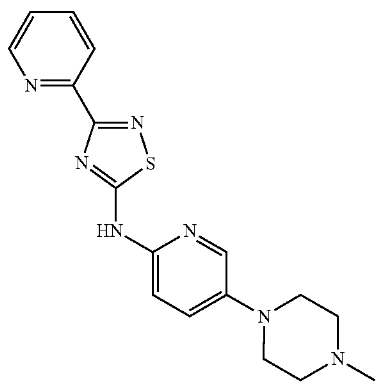 [SMILES: CN1CCN(c2ccc(Nc3nc(-c4ccccn4)ns3)nc2)CC1] | N-(5-(4-methyl-piperazin-1-yl)pyridin-2-yl)-3-(pyridin-2-yl)-1,2,4-thiadiazol-5-amine | 354.2 | | D, E | | | |
| 8 | 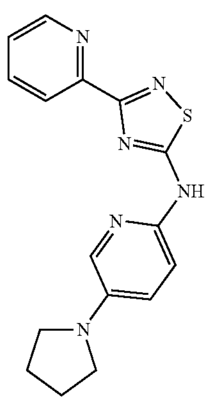 [SMILES: c1ccc(-c2nsc(Nc3ccc(N4CCCC4)cn3)n2)nc1] | 3-(pyridin-2-yl)-N-(5-(pyrrolidin-1-yl)pyridin-2-yl)-1,2,4-thiadiazol-5-amine | 325.2 | C | D, E | D, | E | A |
| 9 | 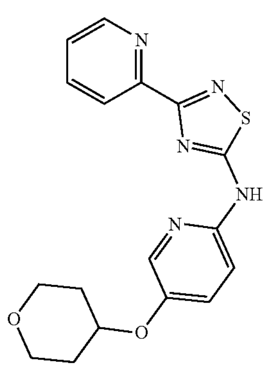 [SMILES: c1ccc(-c2nsc(Nc3ccc(OC4CCOCC4)cn3)n2)nc1] | 3-(pyridin-2-yl)-N-(5-(tetrahydro-2H-pyran-4-yloxy)pyridin-2-yl)-1,2,4-thiadiazol-5-amine | 356.2 | A | D | D, E | | A |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 10 | 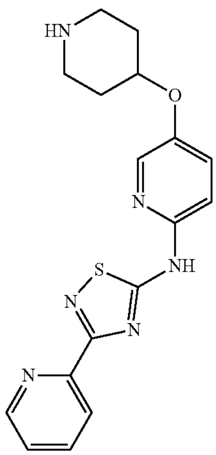 [SMILES: c1ccc(-c2nsc(Nc3ccc(OC4CCNCC4)cn3)n2)nc1] | N-(5-(piperidin-4-yloxy)pyridin-2-yl)-3-(pyridin-2-yl)-1,2,4-thiadiazol-5-amine | 355.2 | A | D | | | |
| 11 | 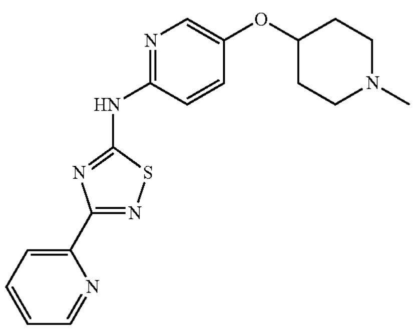 [SMILES: CN1CCC(Oc2ccc(Nc3nc(-c4ccccn4)ns3)nc2)CC1] | N-(5-(1-methyl-piperidin-4-yloxy)pyridin-2-yl)-3-(pyridin-2-yl)-1,2,4-thiadiazol-5-amine | 288.1 | A | D | | | |
| 12 | 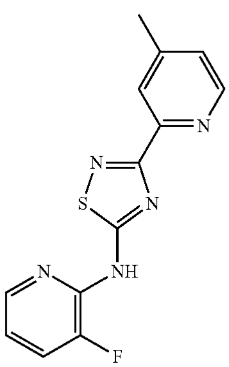 [SMILES: Cc1ccnc(-c2nsc(Nc3ncccc3F)n2)c1] | N-(3-fluoropyridin-2-yl)-3-(4-methylpyridin-2-yl)-1,2,4-thiadiazol-5-amine | 288 | C | D, E | D, E | | B |
| 13 | 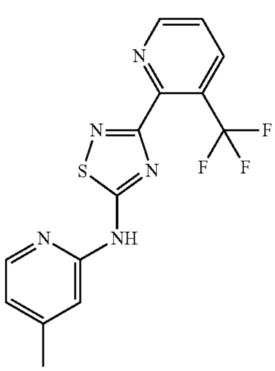 [SMILES: Cc1ccnc(Nc2nc(-c3ncccc3C(F)(F)F)ns2)c1] | N-(4-methyl-pyridin-2-yl)-3-(3-(trifluoro-methyl)pyridin-2-yl)-1,2,4-thiadiazol-5-amine | 338.1 | A | D, E | D, E | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 14 | 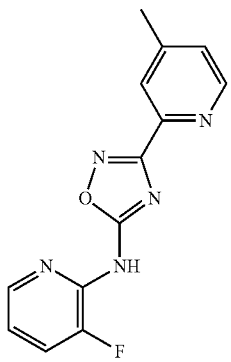 [SMILES: Cc1ccnc(-c2noc(Nc3ncccc3F)n2)c1] | N-(3-fluoro-pyridin-2-yl)-3-(4-methylpyridin-2-yl)-1,2,4-oxadiazol-5-amine | 272.1 | A | D, E | D, E | | A |
| 15 | 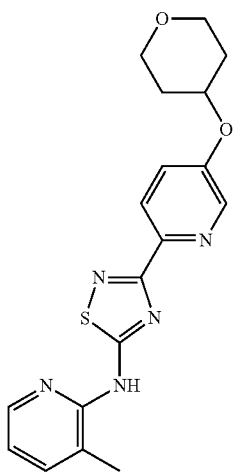 [SMILES: Cc1cccnc1Nc1nc(-c2ccc(OC3CCOCC3)cn2)ns1] | N-(3-methyl-pyridin-2-yl)-3-(5-(tetrahydro-2H-pyran-4-yloxy)pyridin-2-yl)-1,2,4-thiadiazol-5-amine | 370.2 | C | D, E | D, E | | A |
| 16 | 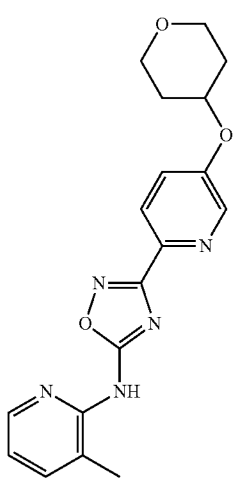 [SMILES: Cc1cccnc1Nc1nc(-c2ccc(OC3CCOCC3)cn2)no1] | N-(3-methyl-pyridin-2-yl)-3-(5-(tetrahydro-2H-pyran-4-yloxy)pyridin-2-yl)-1,2,4-oxadiazol-5-amine | 354.2 | C | D, E | D, E | | A |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 17 | 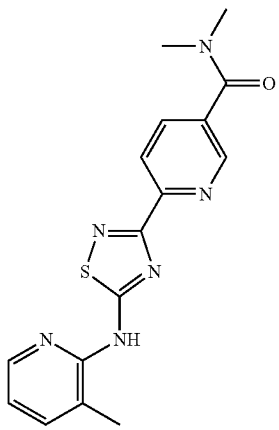 [SMILES: Cc1cccnc1Nc1nc(-c2ccc(C(=O)N(C)C)cn2)ns1] | N,N-dimethyl-6-(5-(3-methylpyridin-2-ylamino)-1,2,4-thiadiazol-3-yl)nicotinamide | 341.1 | C | D, E | D | | |
| 18 | 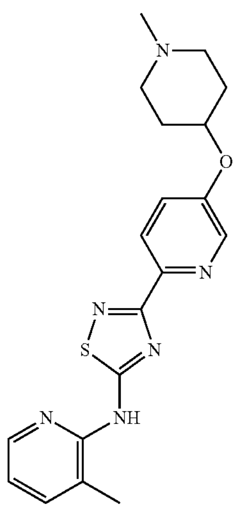 [SMILES: Cc1cccnc1Nc1nc(-c2ccc(OC3CCN(C)CC3)cn2)ns1] | 3-(5-(1-methyl-piperidin-4-yloxy)pyridin-2-yl)-N-(3-methylpyridin-2-yl)-1,2,4-thiadiazol-5-amine | 383.3 | B | D, E | D, E | E | |
| 19 | 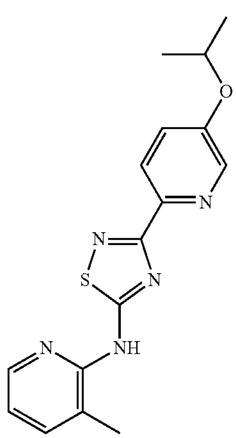 [SMILES: Cc1cccnc1Nc1nc(-c2ccc(OC(C)C)cn2)ns1] | 3-(5-isopropoxy-pyridin-2-yl)-N-(3-methyl-pyridin-2-yl)-1,2,4-thiadiazol-5-amine | 328.2 | C | D, E | D, E | E | C |

TABLE 1-continued

| Cmpd No. | Structure | Name | M + 1 | *O. guttu-rosa* | *B. malayi* | *L. sigmo-dontis* | *B. paha-ngi* | *D. immit-is* |
|---|---|---|---|---|---|---|---|---|
| 20 | 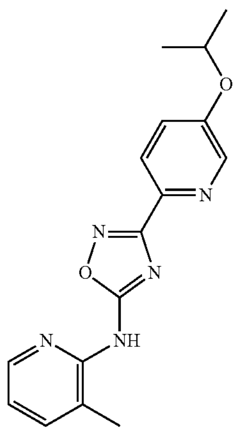 [SMILES: Cc1cccnc1Nc1nc(-c2ccc(OC(C)C)cn2)no1] | 3-(5-isopropoxy-pyridin-2-yl)-N-(3-methyl-pyridin-2-yl)-1,2,4-oxadiazol-5-amine | 312.1 | C | D, E | D | | A |
| 21 | 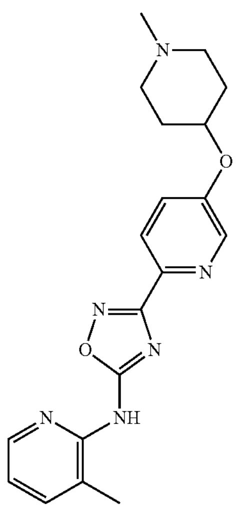 [SMILES: Cc1cccnc1Nc1nc(-c2ccc(OC3CCN(C)CC3)cn2)no1] | 3-(5-(1-methyl-piperidin-4-yloxy)pyridin-2-yl)-N-(3-methylpyridin-2-yl)-1,2,4-oxadiazol-5-amine | 367.2 | C | D, E | D | | |
| 22 | 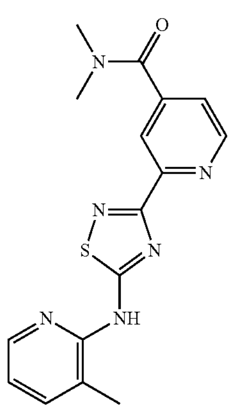 [SMILES: Cc1cccnc1Nc1nc(-c2cc(C(=O)N(C)C)ccn2)ns1] | N,N-dimethyl-2-(5-(3-methylpyridin-2-ylamino)-1,2,4-thiadiazol-3-yl)isonicotinamide | 341.3 | A | D, E | D | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 23 | 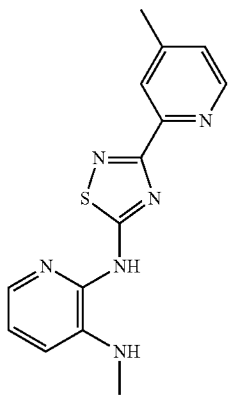 [SMILES: CNc1cccnc1Nc1nc(-c2cc(C)ccn2)ns1] | N3-methyl-N2-(3-(4-methylpyridin-2-yl)-1,2,4-thiadiazol-5-yl)pyridine-2,3-diamine | 299.3 | C | D, E | D, E | E | B |
| 24 | 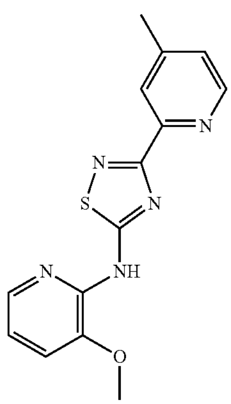 [SMILES: COc1cccnc1Nc1nc(-c2cc(C)ccn2)ns1] | N-(3-methoxy-pyridin-2-yl)-3-(4-methyl-pyridin-2-yl)-1,2,4-thiadiazol-5-amine | 300.1 | C | D, E | D | | |
| 25 | 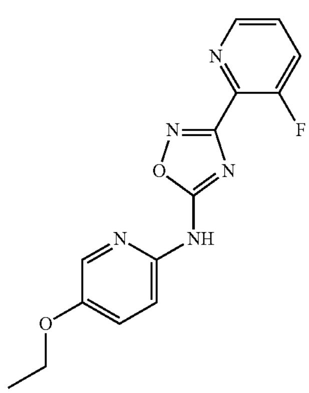 [SMILES: CCOc1ccc(Nc2nc(-c3ncccc3F)no2)nc1] | N-(5-ethoxy-pyridin-2-yl)-3-(3-fluoropyridin-2-yl)-1,2,4-oxadiazol-5-amine | 302.1 | C | | D | | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 26 | 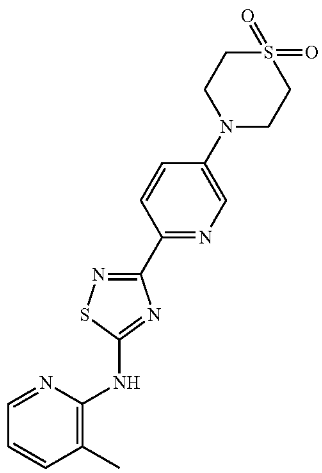 [SMILES: Cc1cccnc1Nc1nc(-c2ccc(N3CCS(=O)(=O)CC3)cn2)ns1] | 4-(6-(5-((3-methylpyridin-2-yl)amino)-1,2,4-thiadiazol-3-yl)pyridin-3-yl)thiomorpholine 1,1-dioxide | 403 | A | | D | | |
| 27 | 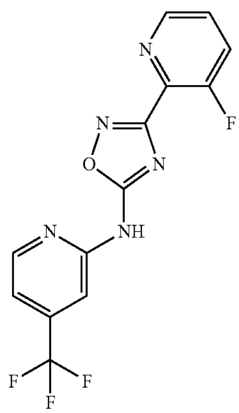 [SMILES: Fc1cccnc1-c1noc(Nc2cc(C(F)(F)F)ccn2)n1] | 3-(3-fluoropyridin-2-yl)-N-(4-(trifluoromethyl)pyridin-2-yl)-1,2,4-oxadiazol-5-amine | 326.1 | C | E | D | | |
| 28 | 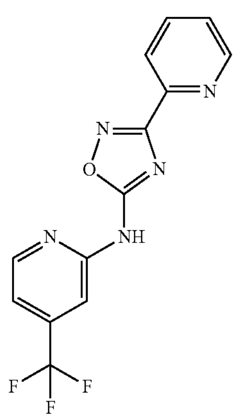 [SMILES: FC(F)(F)c1ccnc(Nc2nc(-c3ccccn3)no2)c1] | 3-(pyridin-2-yl)-N-(4-(trifluoromethyl)pyridin-2-yl)-1,2,4-oxadiazol-5-amine | 306.1 | C | D | D | E | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 29 | 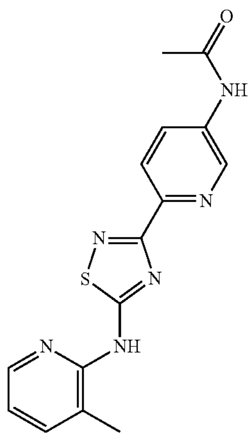 [SMILES: CC(=O)Nc1ccc(-c2nsc(Nc3ncccc3C)n2)nc1] | N-(6-(5-(3-methyl pyridin-2-ylamino)-1,2,4-thiadiazol-3-yl)pyridin-3-yl) acetamide | 327.1 | B | | D | E | |
| 30 | 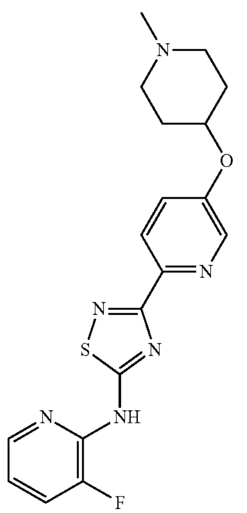 [SMILES: CN1CCC(Oc2ccc(-c3nsc(Nc4ncccc4F)n3)nc2)CC1] | N-(3-fluoro-pyridin-2-yl)-3-(5-(1-methyl-piperidin-4-yloxy)pyridin-2-yl)-1,2,4-thiadiazol-5-amine | 387.1 | C | | E | E | |
| 31 | 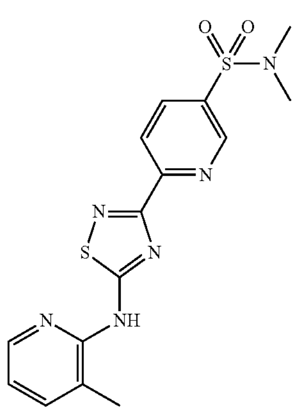 [SMILES: Cc1cccnc1Nc1nc(-c2ccc(S(=O)(=O)N(C)C)cn2)ns1] | N,N-dimethyl-6-(5-(3-methylpyridin-2-ylamino)-1,2,4-thiadiazol-3-yl)pyridine-3-sulfonamide | 337.1 | A | | D | E | |

TABLE 1-continued

| Cmpd No. | Structure | Name | M + 1 | *O. guttu- rosa* | *B. malayi* | *L. sigmo- dontis* | *B. paha- ngi* | *D. immit- is* |
|---|---|---|---|---|---|---|---|---|
| 32 | 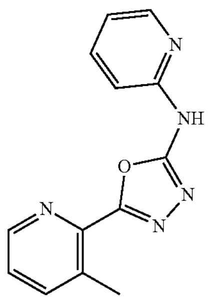 [SMILES: Cc1cccnc1-c1nnc(Nc2ccccn2)o1] | 5-(3-methyl-pyridin-2-yl)-N-(pyridin-2-yl)-1,3,4-oxadiazol-2-amine | 254.1 | A | | | E | |
| 33 | 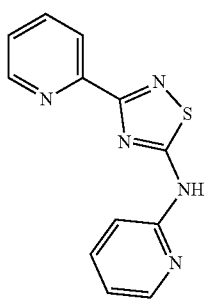 [SMILES: c1ccc(Nc2nc(-c3ccccn3)ns2)nc1] | N,3-di(pyridin-2-yl)-1,2,4-thiadiazol-5-amine | 256.1 | C | D, E | D | E | |
| 34 | 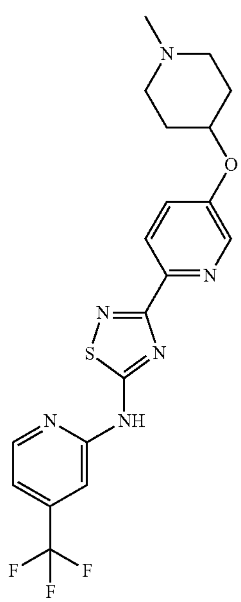 [SMILES: CN1CCC(Oc2ccc(-c3nsc(Nc4cc(C(F)(F)F)ccn4)n3)nc2)CC1] | 3-(5-(1-methyl-piperidin-4-yloxy)pyridin-2-yl)-N-(4-(trifluoro-methyl)pyridin-2-yl)-1,2,4-thiadiazol-5-amine | 437.1 | A | D, E | D | E | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 35 | 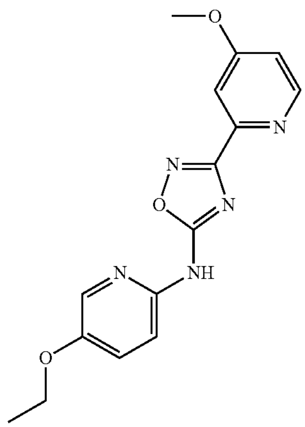 [SMILES: CCOc1ccc(Nc2nc(-c3cc(OC)ccn3)no2)nc1] | N-(5-ethoxy-pyridin-2-yl)-3-(4-methoxy-pyridin-2-yl)-1,2,4-oxadiazol-5-amine | 314.1 | C | D | D | E | |
| 36 | 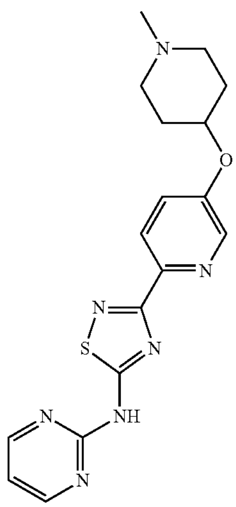 [SMILES: CN1CCC(Oc2ccc(-c3nsc(Nc4ncccn4)n3)nc2)CC1] | 3-(5-(1-methyl-piperidin-4-yloxy)pyridin-2-yl)-N-(pyrimidin-2-yl)-1,2,4-thiadiazol-5-amine | 370.2 | A | | D | E | |
| 37 | 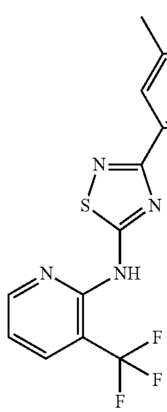 | 3-(4-methyl-pyridin-2-yl)-N-(3-(trifluoro-methyl)pyridin-2-yl)-1,2,4-thiadiazol-5-amine | 338.1 | C | D, E | D, E | E | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 38 | 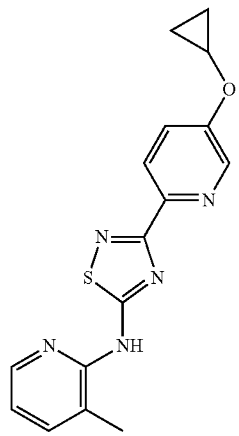 [SMILES: Cc1cccnc1Nc1nc(-c2ccc(OC3CC3)cn2)ns1] | 3-(5-cyclo-propoxypyridin-2-yl)-N-(3-methyl-pyridin-2-yl)-1,2,4-thiadiazol-5-amine | 326.1 | C | D, E | D, E | E | B |
| 39 | 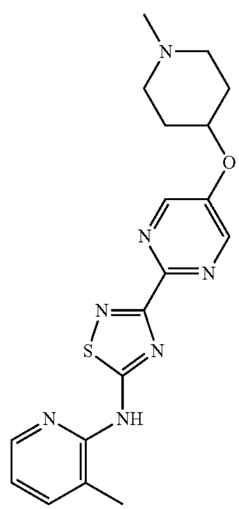 [SMILES: Cc1cccnc1Nc1nc(-c2ncc(OC3CCN(C)CC3)cn2)ns1] | 3-(5-(1-methyl-piperidin-4-yloxy)pyrimidin-2-yl)-N-(3-methylpyridin-2-yl)-1,2,4-thiadiazol-5-amine | 384.2 | | | E | E | |
| 40 | 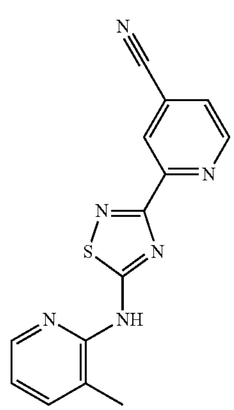 [SMILES: Cc1cccnc1Nc1nc(-c2cc(C#N)ccn2)ns1] | 2-(5-(3-methyl-pyridin-2-ylamino)-1,2,4-thiadiazol-3-yl)isonicotino-nitrile | 295.2 | A | D | D, E | E | A |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 41 | 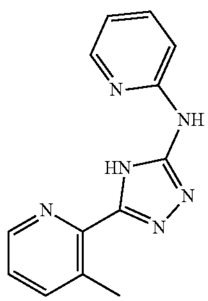 [SMILES: Cc1cccnc1-c1nnc(Nc2ccccn2)[nH]1] | N-(5-(3-methyl-pyridin-2-yl)-4H-1,2,4-triazol-3-yl)pyridin-2-amine | 253.2 | C | D, E | D, E | | |
| 42 | 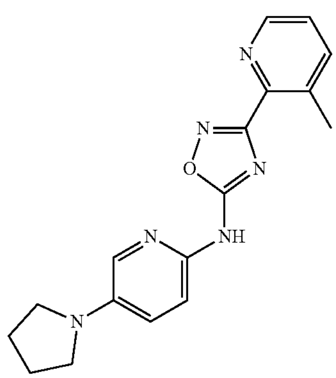 [SMILES: Cc1cccnc1-c1noc(Nc2ccc(N3CCCC3)cn2)n1] | 3-(3-methyl-pyridin-2-yl)-N-(5-(pyrrolidin-1-yl)pyridin-2-yl)-1,2,4-oxadiazol-5-amine | 323.3 | C | E | D | | A |
| 43 | 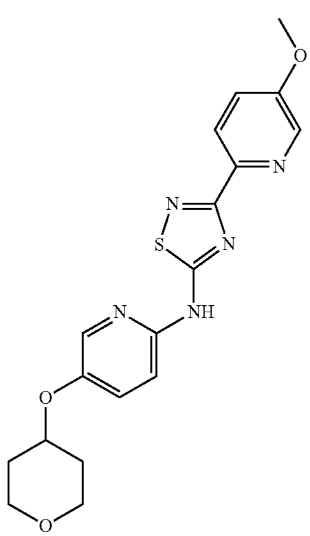 [SMILES: COc1ccc(-c2nsc(Nc3ccc(OC4CCOCC4)cn3)n2)nc1] | 3-(5-methoxy-pyridin-2-yl)-N-(5-(tetrahydro-2H-pyran-4-yloxy)pyridin-2-yl)-1,2,4-thiadiazol-5-amine | 386.1 | C | | D, E | E | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 44 | 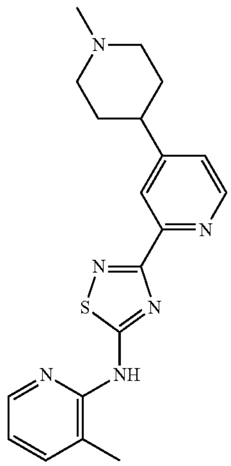 [SMILES: Cc1cccnc1Nc1nc(-c2cc(C3CCN(C)CC3)ccn2)ns1] | 3-(4-(1-methyl-piperidin-4-yl)pyridin-2-yl)-N-(3-methylpyridin-2-yl)-1,2,4-thiadiazol-5-amine | 367.1 | C | | E | E | |
| 45 | 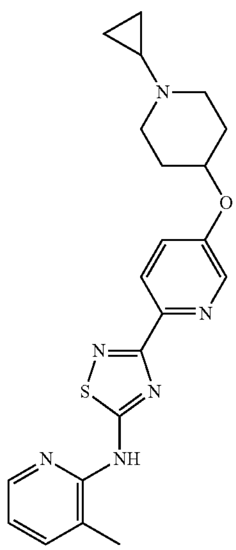 [SMILES: Cc1cccnc1Nc1nc(-c2ccc(OC3CCN(C4CC4)CC3)cn2)ns1] | 3-(5-(1-cyclo-propylpiperidin-4-yloxy)pyridin-2-yl)-N-(3-methylpyridin-2-yl)-1,2,4-thiadiazol-5-amine | 409.2 | C | E | D, E | E | A |
| 46 | 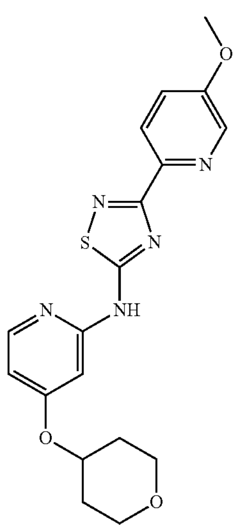 [SMILES: COc1ccc(-c2nsc(Nc3cc(OC4CCOCC4)ccn3)n2)nc1] | 3-(5-methoxy-pyridin-2-yl)-N-(4-(tetrahydro-2H-pyran-4-yloxy)pyridin-2-yl)-1,2,4-thiadiazol-5-amine | 386.1 | B | | D, E | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 47 | 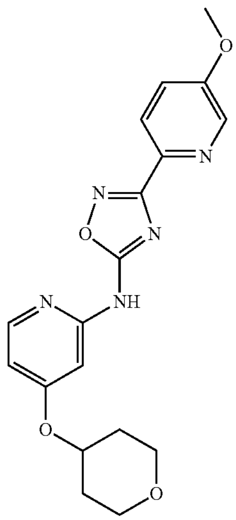 [SMILES: COc1ccc(-c2noc(Nc3cc(OC4CCOCC4)ccn3)n2)nc1] | 3-(5-methoxy- pyridin-2-yl)- N-(4-(tetrahydro- 2H-pyran-4- yloxy)pyridin-2- yl)-1,2,4- oxadiazol-5- amine | 370.2 | A | | D | | |
| 48 | 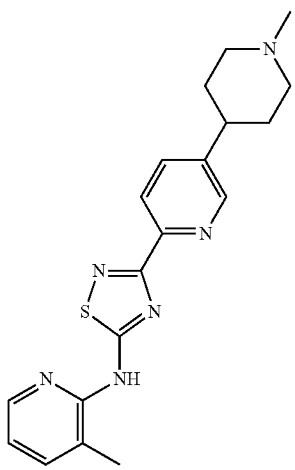 [SMILES: Cc1cccnc1Nc1nc(-c2ccc(C3CCN(C)CC3)cn2)ns1] | 3-(5-(1-methyl- piperidin-4- yl)pyridin-2-yl)- N-(3- methylpyridin- 2-yl)-1,2,4- thiadiazol-5- amine | 367.2 | A | | D, E | | |
| 49 | 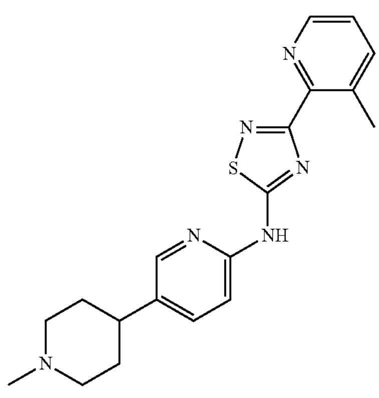 | N-(5-(1-methyl- piperidin-4- yl)pyridin-2- yl)-3-(3- methylpyridin- 2-yl)-1,2,4- thiadiazol-5- amine | 367.2 | A | | | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 50 | 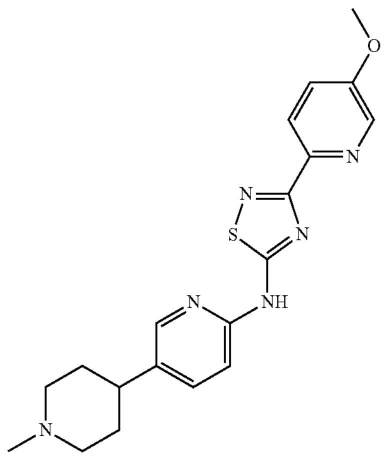 [SMILES: COc1ccc(-c2nsc(Nc3ccc(C4CCN(C)CC4)cn3)n2)nc1] | 3-(5-methoxy-pyridin-2-yl)-N-(5-(1-methyl-piperidin-4-yl)pyridin-2-yl)-1,2,4-thiadiazol-5-amine | 383.1 | A | | | | |
| 51 | 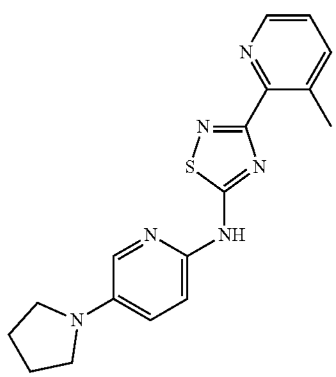 [SMILES: Cc1cccnc1-c1nsc(Nc2ccc(N3CCCC3)cn2)n1] | 3-(3-methyl-pyridin-2-yl)-N-(5-(pyrrolidin-1-yl)pyridin-2-yl)-1,2,4-thiadiazol-5-amine | 339.1 | C | D | D, E | E | A |
| 52 | 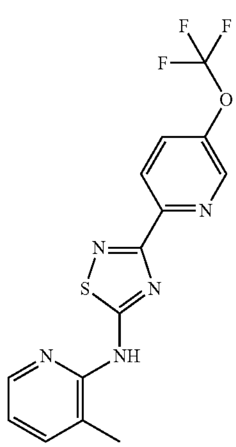 [SMILES: Cc1cccnc1Nc1nc(-c2ccc(OC(F)(F)F)cn2)ns1] | N-(3-methyl-pyridin-2-yl)-3-(5-(trifluoro-methoxy)pyridin-2-yl)-1,2,4-thiadiazol-5-amine | 354.1 | C | D | D | E | A |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 53 | 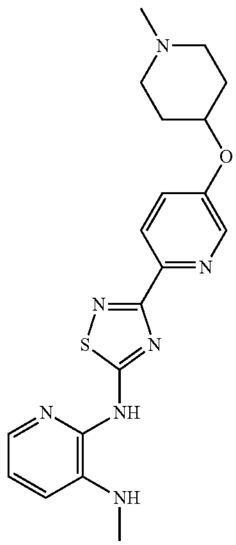 [SMILES: CNc1cccnc1Nc1nc(-c2ccc(OC3CCN(C)CC3)cn2)ns1] | N3-methyl-N2-(3-(5-(1-methyl-piperidin-4-yloxy)pyridin-2-yl)-1,2,4-thiadiazol-5-yl)pyridine-2,3-diamine | 398.3 | B | D | D | | |
| 54 | 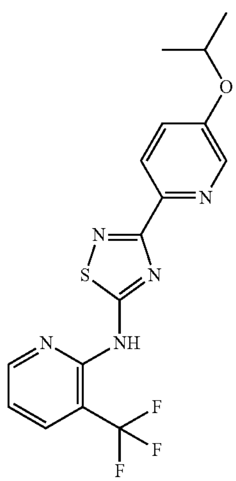 [SMILES: CC(C)Oc1ccc(-c2nsc(Nc3ncccc3C(F)(F)F)n2)nc1] | 3-(5-isopropoxy-pyridin-2-yl)-N-(3-(trifluoromethyl)pyridin-2-yl)-1,2,4-thiadiazol-5-amine | 382.2 | C | D, E | D, E | E | C |
| 55 | 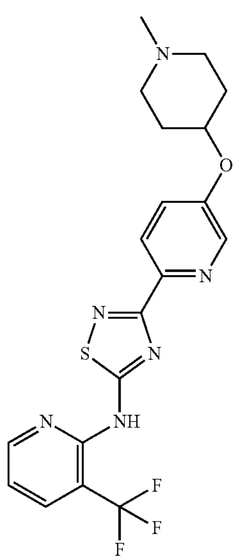 [SMILES: CN1CCC(Oc2ccc(-c3nsc(Nc4ncccc4C(F)(F)F)n3)nc2)CC1] | 3-(5-(1-methyl-piperidin-4-yloxy)pyridin-2-yl)-N-(3-(trifluoromethyl)pyridin-2-yl)-1,2,4-thiadiazol-5-amine | 437.1 | C | D | D, E | E | A |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 56 | 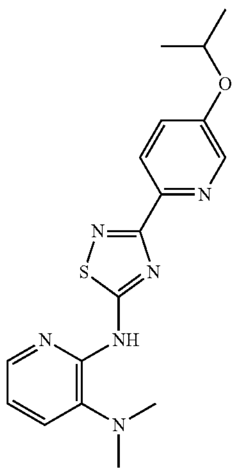 [SMILES: CC(C)Oc1ccc(-c2nsc(Nc3ncccc3N(C)C)n2)nc1] | N2-(3-(5-isoprop-oxypyridin-2-yl)-1,2,4-thiadiazol-5-yl)-N3,N3-dimethyl-pyridine-2,3-diamine | 357.1 | A | D, E | D, E | E | B |
| 57 | 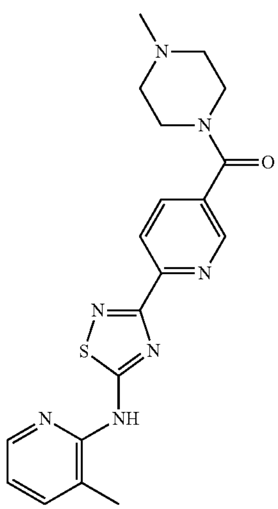 [SMILES: Cc1cccnc1Nc1nc(-c2ccc(C(=O)N3CCN(C)CC3)cn2)ns1] | (4-methyl-piperazin-1-yl)(6-(5-(3-methyl-pyridin-2-ylamino)-1,2,4-thiadiazol-3-yl)pyridin-3-yl)methanone | 396.1 | A | D | | E | |
| 58 | 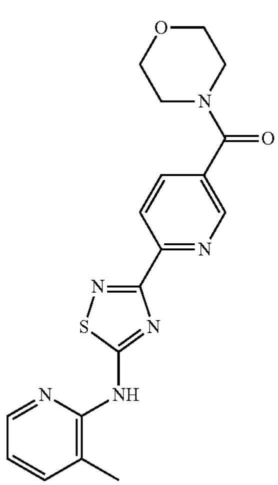 [SMILES: Cc1cccnc1Nc1nc(-c2ccc(C(=O)N3CCOCC3)cn2)ns1] | (6-(5-(3-methyl-pyridin-2-ylamino)-1,2,4-thiadiazol-3-yl)pyridin-3-yl)(morpholino)methanone | 383.1 | B | | | E | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 59 | 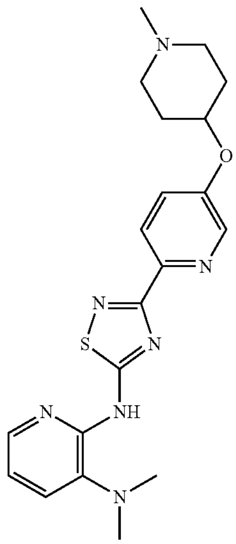 [SMILES: CN1CCC(Oc2ccc(-c3nsc(Nc4ncccc4N(C)C)n3)nc2)CC1] | N3,N3-dimethyl-N2-(3-(5-(1-methylpiperidin-4-yloxy)pyridin-2-yl)-1,2,4-thiadiazol-5-yl)pyridine-2,3-diamine | 412.2 | A | | | | |
| 60 | 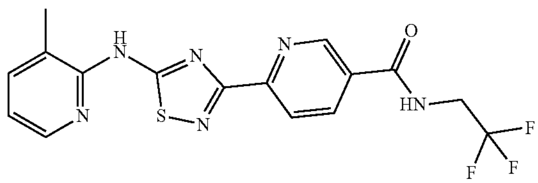 [SMILES: Cc1cccnc1Nc1nc(-c2ccc(C(=O)NCC(F)(F)F)cn2)ns1] | 6-(5-(3-methyl-pyridin-2-ylamino)-1,2,4-thiadiazol-3-yl)-N-(2,2,2-trifluoroethyl)nicotinamide | 395.1 | A | | D | E | |
| 61 | 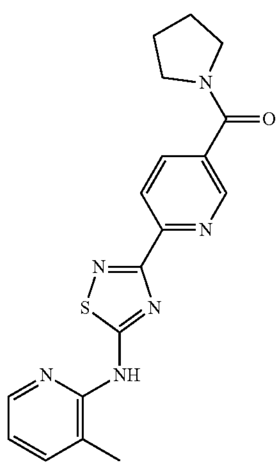 [SMILES: Cc1cccnc1Nc1nc(-c2ccc(C(=O)N3CCCC3)cn2)ns1] | (6-(5-(3-methyl-pyridin-2-ylamino)-1,2,4-thiadiazol-3-yl)pyridin-3-yl)(pyrrolidin-1-yl)methanone | 367.2 | B | | | | |
| 62 | 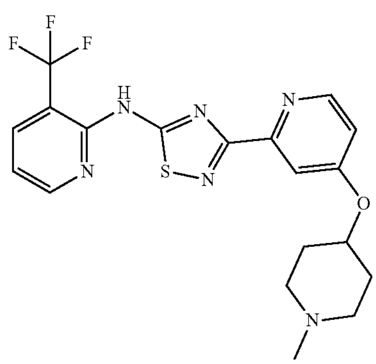 [SMILES: CN1CCC(Oc2ccnc(-c3nsc(Nc4ncccc4C(F)(F)F)n3)c2)CC1] | 3-(4-(1-methyl-piperidin-4-yloxy)pyridin-2-yl)-N-(3-(trifluoromethyl)pyridin-2-yl)-1,2,4-thiadiazol-5-amine | 437.1 | C | D | D | E | A |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 63 | 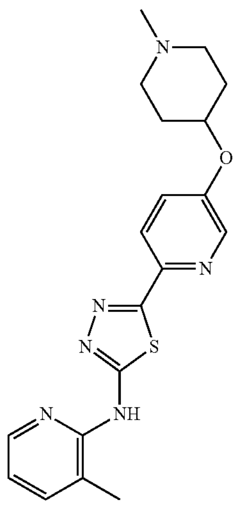 [SMILES: Cc1cccnc1Nc1nnc(-c2ccc(OC3CCN(C)CC3)cn2)s1] | 5-(5-(1-methyl-piperidin-4-yloxy)pyridin-2-yl)-N-(3-methylpyridin-2-yl)-1,3,4-thiadiazol-2-amine | 383.1 | A | | | E | |
| 64 | 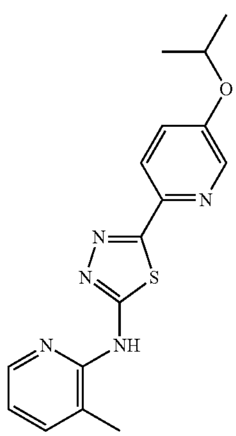 [SMILES: Cc1cccnc1Nc1nnc(-c2ccc(OC(C)C)cn2)s1] | 5-(5-isopropoxy-pyridin-2-yl)-N-(3-methyl-pyridin-2-yl)-1,3,4-thiadiazol-2-amine | 328.2 | A | | | E | |
| 65 | 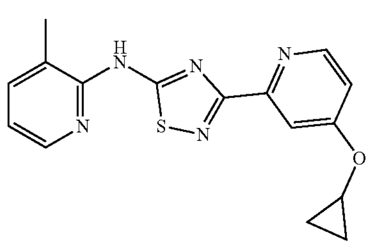 [SMILES: Cc1cccnc1Nc1nc(-c2cc(OC3CC3)ccn2)ns1] | 3-(4-cycloprop-oxypyridin-2-yl)-N-(3-methyl-pyridin-2-yl)-1,2,4-thiadiazol-5-amine | 326.1 | A | D, E | E | E | C |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 66 | 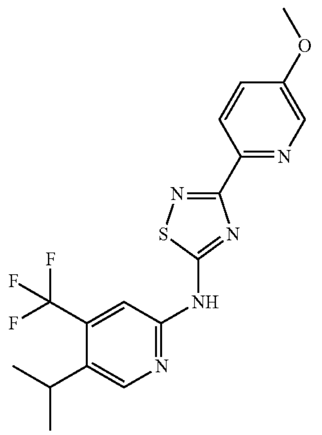 [SMILES: COc1ccc(-c2nsc(Nc3cc(C(F)(F)F)c(C(C)C)cn3)n2)nc1] | N-(5-isopropyl-4-(trifluoromethyl)pyridin-2-yl)-3-(5-methoxy-pyridin-2-yl)-1,2,4-thiadiazol-5-amine | 396.1 | B | D | E | E | |
| 67 | 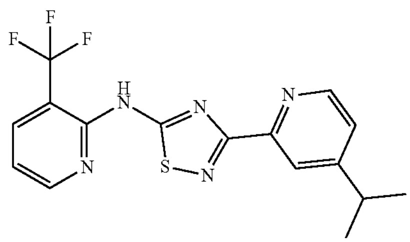 [SMILES: CC(C)c1ccnc(-c2nsc(Nc3ncccc3C(F)(F)F)n2)c1] | 3-(4-isopropyl-pyridin-2-yl)-N-(3-(trifluoromethyl)pyridin-2-yl)-1,2,4-thiadiazol-5-amine | 366.1 | C | D, E | E | E | C |
| 68 | 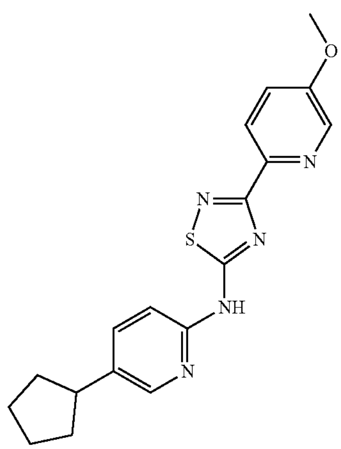 [SMILES: COc1ccc(-c2nsc(Nc3ccc(C4CCCC4)cn3)n2)nc1] | N-(5-cyclopentyl-pyridin-2-yl)-3-(5-methoxypyridin-2-yl)-1,2,4-thiadiazol-5-amine | 354.1 | B | D, E | E | E | A |
| 69 | 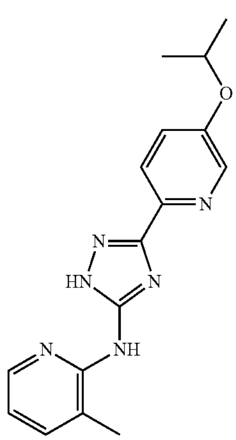 [SMILES: Cc1cccnc1Nc1nc(-c2ccc(OC(C)C)cn2)n[nH]1] | N-(3-(5-isopropoxy-pyridin-2-yl)-1H-1,2,4-triazol-5-yl)-3-methylpyridin-2-amine | 311.3 | B | D, E | | | |

TABLE 1-continued

| Cmpd No. | Structure | Name | M + 1 | *O. guttu- rosa* | *B. malayi* | *L. sigmo- dontis* | *B. paha- ngi* | *D. immit- is* |
|---|---|---|---|---|---|---|---|---|
| 70 | 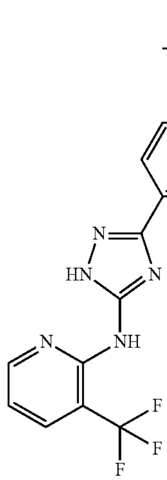 | N-(3-(5-isopropoxy-pyridin-2-yl)-1H-1,2,4-triazol-5-yl)-3-(trifluoromethyl)pyridin-2-amine | 365.1 | A | | | | A |
| 71 | 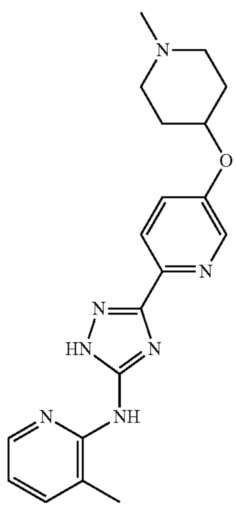 [SMILES: Cc1cccnc1Nc1nc(-c2ccc(OC3CCN(C)CC3)cn2)n[nH]1] | 3-methyl-N-(3-(5-(1-methyl-piperidin-4-yloxy)pyridin-2-yl)-1H-1,2,4-triazol-5-yl)pyridin-2-amine | 365.1 | A | | | | |
| 72 | 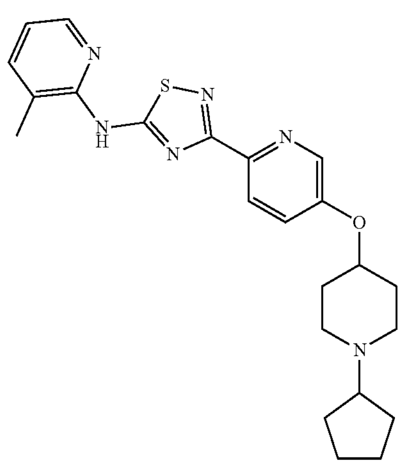 [SMILES: Cc1cccnc1Nc1nc(-c2ccc(OC3CCN(C4CCCC4)CC3)cn2)ns1] | 3-(5-(1-cyclo-pentylpiperidin-4-yloxy)pyridin-2-yl)-N-(3-methylpyridin-2-yl)-1,2,4-thiadiazol-5-amine | 365.1 | B | D | D | D | |

TABLE 1-continued

| Cmpd No. | Structure | Name | M + 1 | *O. guttu- rosa* | *B. malayi* | *L. sigmo- dontis* | *B. paha- ngi* | *D. immit- is* |
|---|---|---|---|---|---|---|---|---|
| 73 | 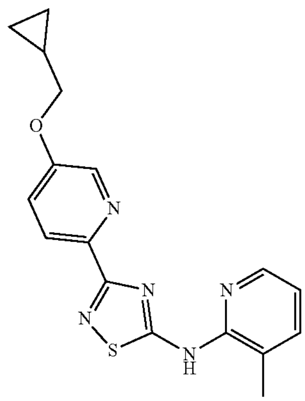 [SMILES: Cc1cccnc1Nc1nc(-c2ccc(OCC3CC3)cn2)ns1] | 3-(5-(cyclopropyl-methoxy)pyridin-2-yl)-N-(3-methylpyridin-2-yl)-1,2,4-thiadiazol-5-amine | 340.1 | C | D, E | D, E | D, E | B |
| 74 | 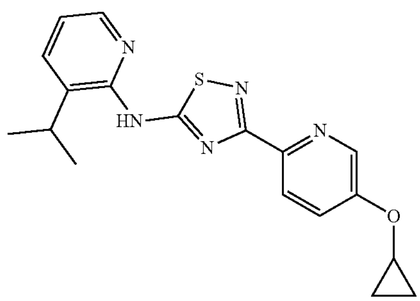 [SMILES: CC(C)c1cccnc1Nc1nc(-c2ccc(OC3CC3)cn2)ns1] | 3-(5-cyclopropoxy-pyridin-2-yl)-N-(3-isopropylpyridin-2-yl)-1,2,4-thiadiazol-5-amine | 354.2 | C | D, E | D, E | D, E | C |
| 75 | 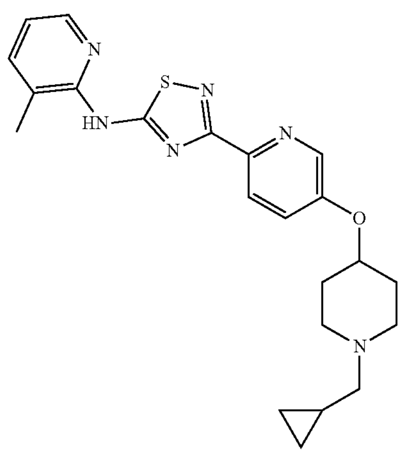 [SMILES: Cc1cccnc1Nc1nc(-c2ccc(OC3CCN(CC4CC4)CC3)cn2)ns1] | 3-(5-(1-(cyclopropyl-methyl)piperidin-4-yloxy)pyridin-2-yl)-N-(3-methylpyridin-2-yl)-1,2,4-thiadiazol-5-amine | 423.1 | B | D | D, E | D, E | |
| 76 | 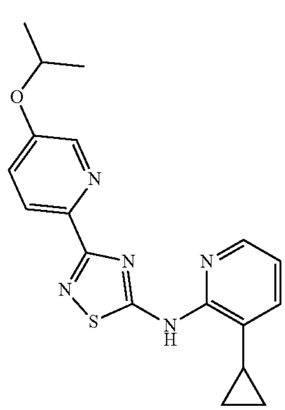 [SMILES: CC(C)Oc1ccc(-c2nsc(Nc3ncccc3C3CC3)n2)nc1] | N-(3-cyclopropyl-pyridin-2-yl)-3-(5-isopropoxy-pyridin-2-yl)-1,2,4-thiadiazol-5-amine | 354.1 | C | D, E | D, E | D, E | C |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 77 | 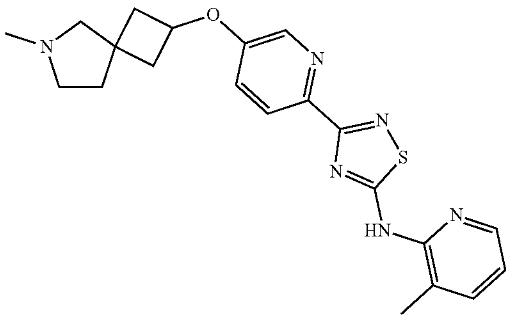 [SMILES: Cc1cccnc1Nc1nc(-c2ccc(OC3CC4(CCN(C)C4)C3)cn2)ns1] | 3-(5-(6-methyl-6-azaspiro[3.4]octan-2-yloxy)pyridin-2-yl)-N-(3-methylpyridin-2-yl)-1,2,4-thiadiazol-5-amine | 409.2 | A | D | D, E | D, E | |
| 78 | 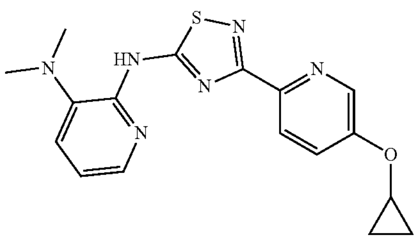 [SMILES: CN(C)c1cccnc1Nc1nc(-c2ccc(OC3CC3)cn2)ns1] | N2-(3-(5-cyclopropoxy-pyridin-2-yl)-1,2,4-thiadiazol-5-yl)-N3,N3-dimethyl-pyridine-2,3-diamine | 355.2 | A | D, E | D, E | D, E | A |
| 79 | 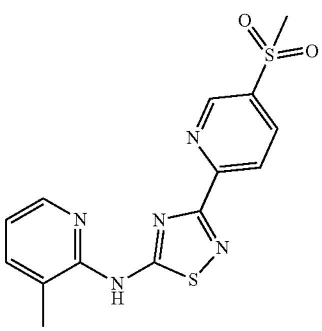 [SMILES: Cc1cccnc1Nc1nc(-c2ccc(S(C)(=O)=O)cn2)ns1] | N-(3-methyl-pyridin-2-yl)-3-(5-(methyl-sulfonyl)pyridin-2-yl)-1,2,4-thiadiazol-5-amine | 348.1 | A | D | | | |
| 80 | 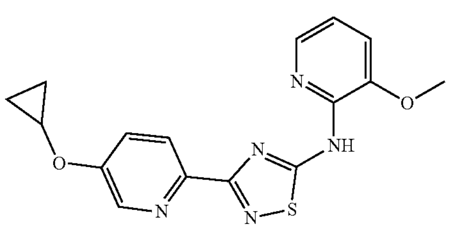 [SMILES: COc1cccnc1Nc1nc(-c2ccc(OC3CC3)cn2)ns1] | 3-(5-cycloprop-oxypyridin-2-yl)-N-(3-methoxypyridin-2-yl)-1,2,4-thiadiazol-5-amine | 342.1 | B | D, E | D | D, E | A |
| 81 | 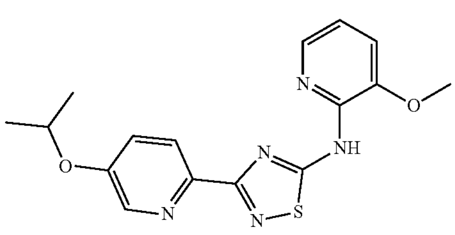 [SMILES: COc1cccnc1Nc1nc(-c2ccc(OC(C)C)cn2)ns1] | 3-(5-isopropoxy-pyridin-2-yl)-N-(3-methoxy-pyridin-2-yl)-1,2,4-thiadiazol-5-amine | 344.2 | C | D, E | D, E | D, E | |

TABLE 1-continued

| Cmpd No. | Structure | Name | M + 1 | *O. gutturosa* | *B. malayi* | *L. sigmodontis* | *B. pahangi* | *D. immitis* |
|---|---|---|---|---|---|---|---|---|
| 82 | 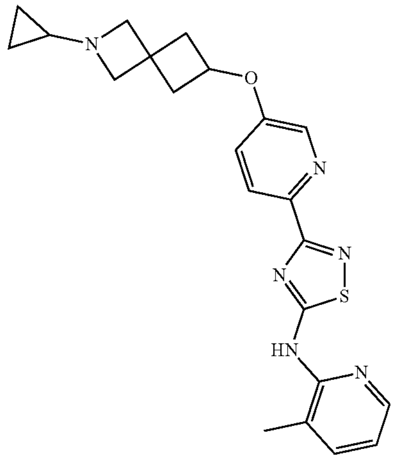 [SMILES: Cc1cccnc1Nc1nc(-c2ccc(OC3CC4(C3)CN(C3CC3)C4)cn2)ns1] | 3-(5-(2-cyclopropyl-2-azaspiro[3.3]heptan-6-yloxy)pyridin-2-yl)-N-(3-methylpyridin-2-yl)-1,2,4-thiadiazol-5-amine | 421.2 | B | | D, E | D, E | |
| 83 | 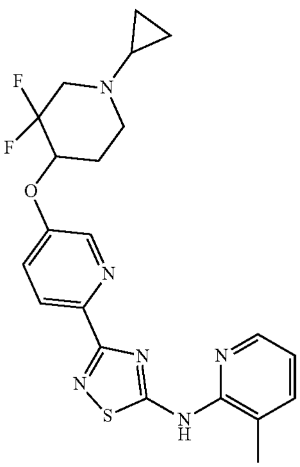 [SMILES: Cc1cccnc1Nc1nc(-c2ccc(OC3CCN(C4CC4)CC3(F)F)cn2)ns1] | 3-(5-(1-cyclopropyl-3,3-difluoro-piperidin-4-yloxy)pyridin-2-yl)-N-(3-methylpyridin-2-yl)-1,2,4-thiadiazol-5-amine | 445.2 | B | | D, E | D, E | B |
| 84 | 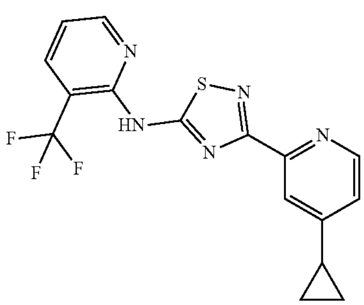 [SMILES: FC(F)(F)c1cccnc1Nc1nc(-c2cc(C3CC3)ccn2)ns1] | 3-(4-cyclopropyl-pyridin-2-yl)-N-(3-(trifluoromethyl)pyridin-2-yl)-1,2,4-thiadiazol-5-amine | 364 | C | | D, E | D, E | C |
| 85 | 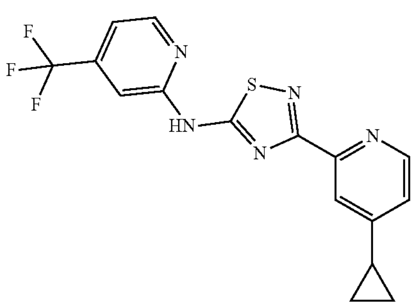 [SMILES: FC(F)(F)c1ccnc(Nc2nc(-c3cc(C4CC4)ccn3)ns2)c1] | 3-(4-cyclopropyl-pyridin-2-yl)-N-(4-(trifluoromethyl)pyridin-2-yl)-1,2,4-thiadiazol-5-amine | 364 | C | | D, E | D, E | C |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 86 | 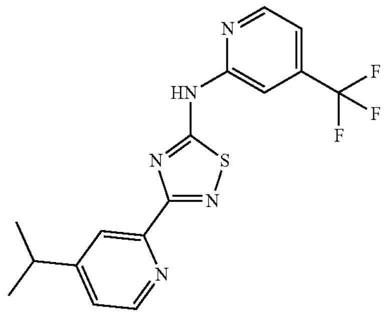 [SMILES: CC(C)c1ccnc(-c2nsc(Nc3cc(C(F)(F)F)ccn3)n2)c1] | 3-(4-isopropyl-pyridin-2-yl)-N-(4-(trifluoromethyl)pyridin-2-yl)-1,2,4-thiadiazol-5-amine | 366.1 | C | | D, E | D, E | C |
| 87 | 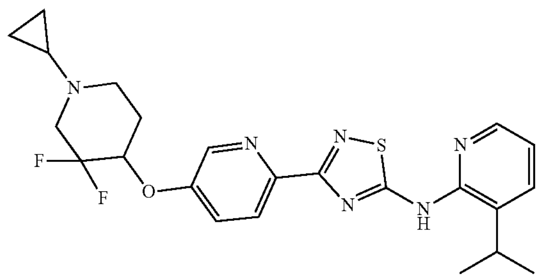 [SMILES: CC(C)c1cccnc1Nc1nc(-c2ccc(OC3CCN(C4CC4)CC3(F)F)cn2)ns1] | 3-(5-(1-cyclopropyl-3,3-difluoro-piperidin-4-yloxy)pyridin-2-yl)-N-(3-isopropylpyridin-2-yl)-1,2,4-thiadiazol-5-amine | 473.3 | C | | D, E | | B |
| 88 | 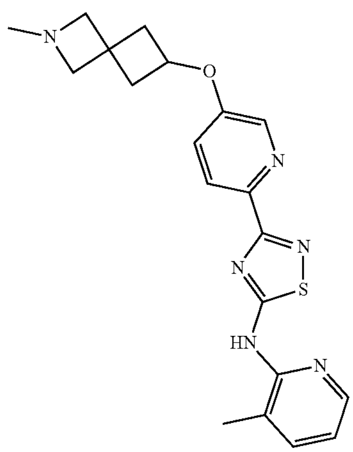 [SMILES: Cc1cccnc1Nc1nc(-c2ccc(OC3CC4(C3)CN(C)C4)cn2)ns1] | 3-(5-(2-methyl-2-azaspiro[3.3]heptan-6-yloxy)pyridin-2-yl)-N-(3-methylpyridin-2-yl)-1,2,4-thiadiazol-5-amine | 395.1 | A | | D | | |
| 89 | 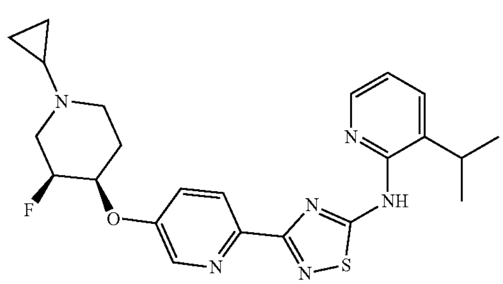 [SMILES: CC(C)c1cccnc1Nc1nc(-c2ccc(O[C@@H]3CCN(C4CC4)C[C@@H]3F)cn2)ns1] | 3-(5-((3S,4R)-1-cyclopropyl-3-fluoro-piperidin-4-yloxy)pyridin-2-yl)-N-(3-isopropylpyridin-2-yl)-1,2,4-thiadiazol-5-amine | 455.2 | C | E | D, E | | C |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 90 | 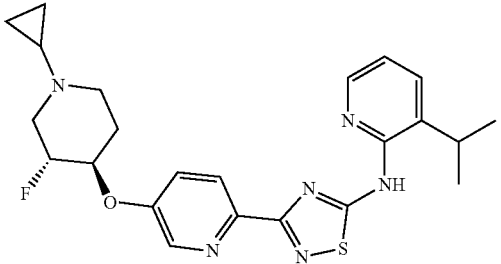 [SMILES: CC(C)c1cccnc1Nc1nc(-c2ccc(O[C@@H]3CCN(C4CC4)C[C@H]3F)cn2)ns1] | 3-(5-((3R,4R)-1-cyclopropyl-3-fluoro-piperidin-4-yloxy)pyridin-2-yl)-N-(3-isopropylpyridin-2-yl)-1,2,4-thiadiazol-5-amine | 455.1 | C | E | D, E | | |
| 91 | 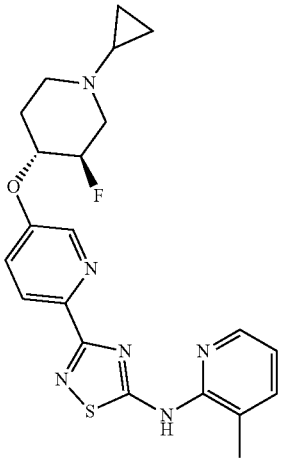 [SMILES: Cc1cccnc1Nc1nc(-c2ccc(O[C@@H]3CCN(C4CC4)C[C@H]3F)cn2)ns1] | 3-(5-((3R,4R)-1-cyclopropyl-3-fluoro-piperidin-4-yloxy)pyridin-2-yl)-N-(3-methylpyridin-2-yl)-1,2,4-thiadiazol-5-amine | 427.2 | C | E | D, E | | A |
| 92 | 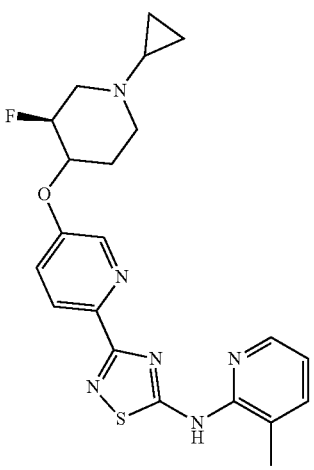 [SMILES: Cc1cccnc1Nc1nc(-c2ccc(OC3CCN(C4CC4)C[C@@H]3F)cn2)ns1] | 3-(5-((3S)-1-cyclopropyl-3-fluoro-piperidin-4-yloxy)pyridin-2-yl)-N-(3-methylpyridin-2-yl)-1,2,4-thiadiazol-5-amine | 427.2 | C | | D, E | | |
| 93 | 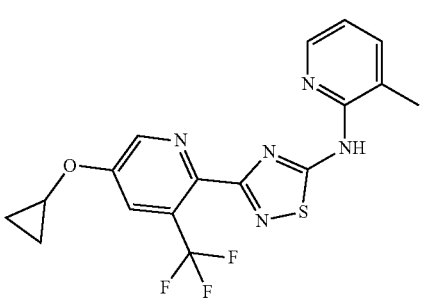 [SMILES: Cc1cccnc1Nc1nc(-c2ncc(OC3CC3)cc2C(F)(F)F)ns1] | 3-(5-cyclo-propoxy-3-(trifluoromethyl)pyridin-2-yl)-N-(3-methyl-pyridin-2-yl)-1,2,4-thiadiazol-5-amine | 394 | A | | D, E | | A |

TABLE 1-continued

| Cmpd No. | Structure | Name | M + 1 | *O. guttu-rosa* | *B. malayi* | *L. sigmo-dontis* | *B. paha-ngi* | *D. immit-is* |
|---|---|---|---|---|---|---|---|---|
| 94 | 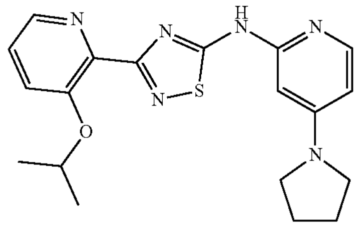 [SMILES: CC(C)Oc1cccnc1-c1nsc(Nc2cc(N3CCCC3)ccn2)n1] | 3-(3-isopropoxy-pyridin-2-yl)-N-(4-(pyrrolidin-1-yl)pyridin-2-yl)-1,2,4-thiadiazol-5-amine | 383.3 | C | | D, E | | A |
| 95 | 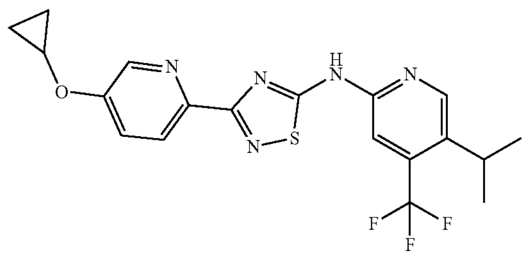 [SMILES: CC(C)c1cnc(Nc2nc(-c3ccc(OC4CC4)cn3)ns2)cc1C(F)(F)F] | 3-(5-cyclopropoxy-pyridin-2-yl)-N-(5-isopropyl-4-(trifluoromethyl)pyridin-2-yl)-1,2,4-thiadiazol-5-amine | 422.1 | C | D | D, E | | C |
| 96 | 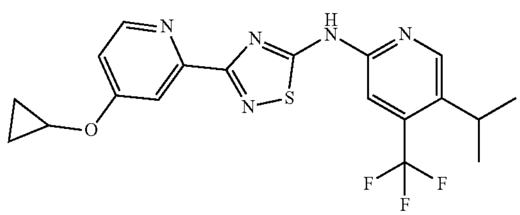 [SMILES: CC(C)c1cnc(Nc2nc(-c3cc(OC4CC4)ccn3)ns2)cc1C(F)(F)F] | 3-(4-cyclopropoxypyridin-2-yl)-N-(5-isopropyl-4-(trifluoromethyl)pyridin-2-yl)-1,2,4-thiadiazol-5-amine | 422.1 | C | D | D, E | | C |
| 97 | 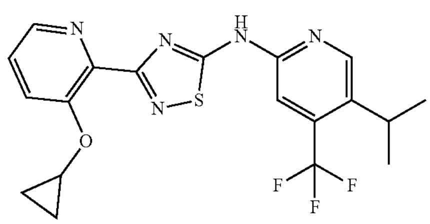 [SMILES: CC(C)c1cnc(Nc2nc(-c3ncccc3OC3CC3)ns2)cc1C(F)(F)F] | 3-(3-cyclopropoxypyridin-2-yl)-N-(5-isopropyl-4-(trifluoromethyl)pyridin-2-yl)-1,2,4-thiadiazol-5-amine | 422.1 | C | D | D, E | | C |
| 98 | 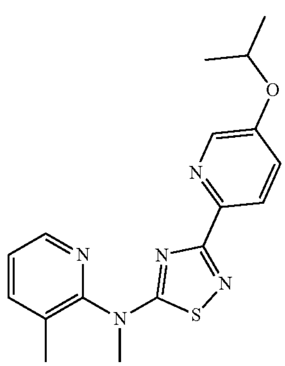 [SMILES: Cc1cccnc1N(C)c1nc(-c2ccc(OC(C)C)cn2)ns1] | 3-(5-isopropoxy-pyridin-2-yl)-N-methyl-N-(3-methylpyridin-2-yl)-1,2,4-thiadiazol-5-amine | 342.2 | B | | D | E | |
| 99 | 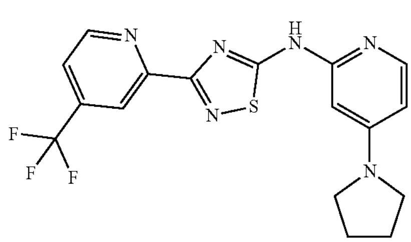 [SMILES: FC(F)(F)c1ccnc(-c2nsc(Nc3cc(N4CCCC4)ccn3)n2)c1] | N-(4-(pyrrolidin-1-yl)pyridin-2-yl)-3-(4-(trifluoromethyl)pyridin-2-yl)-1,2,4-thiadiazol-5-amine | 393.1 | A | D | E | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 100 | 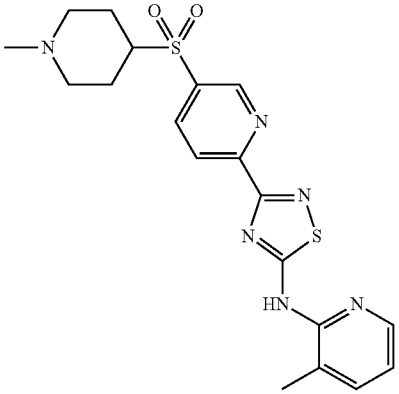 [SMILES: Cc1cccnc1Nc1nc(-c2ccc(S(=O)(=O)C3CCN(C)CC3)cn2)ns1] | 3-(5-(1-methylpiperidin-4-ylsulfonyl)pyridin-2-yl)-N-(3-methylpyridin-2-yl)-1,2,4-thiadiazol-5-amine | 431.1 | B | D | D | | |
| 101 | 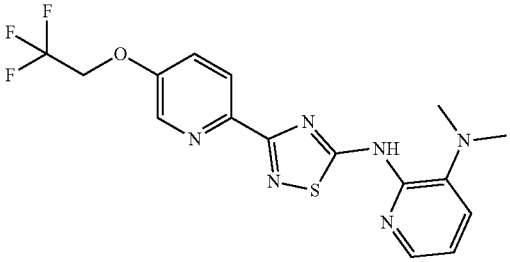 [SMILES: CN(C)c1cccnc1Nc1nc(-c2ccc(OCC(F)(F)F)cn2)ns1] | N3,N3-dimethyl-N2-(3-(5-(2,2,2-trifluoroethoxy)pyridin-2-yl)-1,2,4-thiadiazol-5-yl)pyridine-2,3-diamine | 397 | B | D | D, E | | |
| 102 | 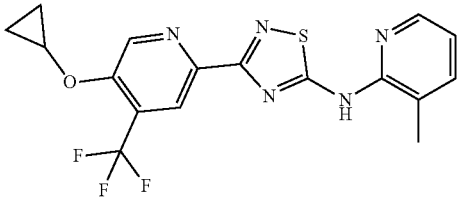 [SMILES: Cc1cccnc1Nc1nc(-c2cc(C(F)(F)F)c(OC3CC3)cn2)ns1] | 3-(5-cyclopropoxy-4-(trifluoromethyl)pyridin-2-yl)-N-(3-methyl-pyridin-2-yl)-1,2,4-thiadiazol-5-amine | 394 | A | D | E | E | B |
| 103 | 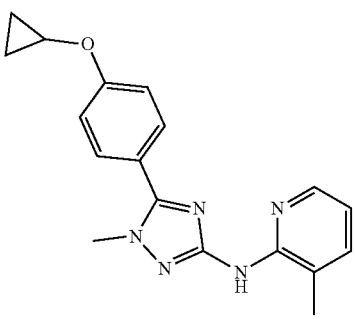 [SMILES: Cc1cccnc1Nc1nc(-c2ccc(OC3CC3)cc2)n(C)n1] | N-(5-(5-cyclopropoxy-pyridin-2-yl)-1-methyl-1H-1,2,4-triazol-3-yl)-3-methyl-pyridin-2-amine | 323.3 | C | | | | |
| 104 | 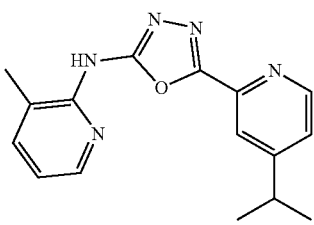 [SMILES: Cc1cccnc1Nc1nnc(-c2cc(C(C)C)ccn2)o1] | 5-(4-isopropyl-pyridin-2-yl)-N-(3-methyl-pyridin-2-yl)-1,3,4-oxadiazol-2-amine | 296.3 | C | | E | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 105 | 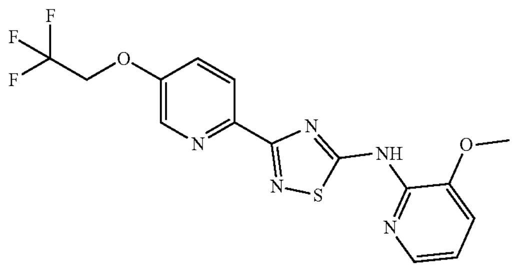 [SMILES: COc1cccnc1Nc1nc(-c2ccc(OCC(F)(F)F)cn2)ns1] | N-(3-methoxy-pyridin-2-yl)-3-(5-(2,2,2-trifluoroethoxy)pyridin-2-yl)-1,2,4-thiadiazol-5-amine | 384 | C | D | | E | |
| 106 | 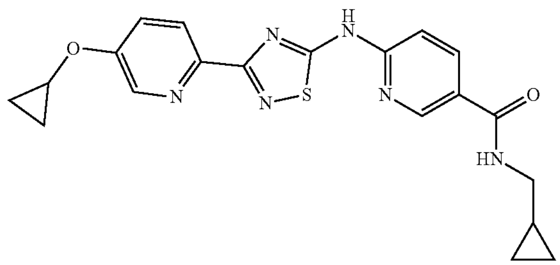 [SMILES: O=C(NCC1CC1)c1ccc(Nc2nc(-c3ccc(OC4CC4)cn3)ns2)nc1] | 6-(3-(5-cyclopropoxypyridin-2-yl)-1,2,4-thiadiazol-5-ylamino)-N-(cyclopropylmethyl)nicotinamide | 409.2 | A | D | E | E | |
| 107 | 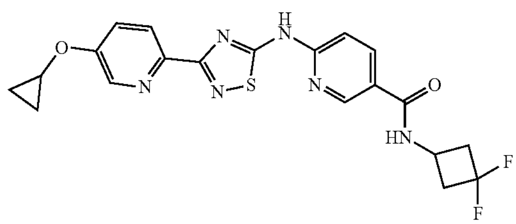 [SMILES: O=C(NC1CC(F)(F)C1)c1ccc(Nc2nc(-c3ccc(OC4CC4)cn3)ns2)nc1] | 6-(3-(5-cyclopropoxypyridin-2-yl)-1,2,4-thiadiazol-5-ylamino)-N-(3,3-difluorocyclobutyl)nicotinamide | 445.2 | A | D | E | | A |
| 108 | 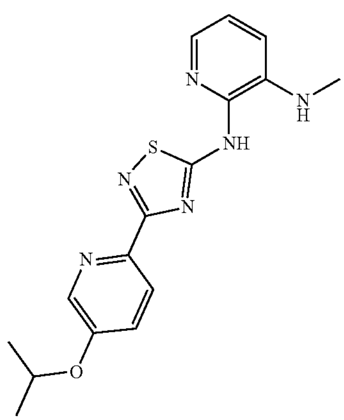 [SMILES: CNc1cccnc1Nc1nc(-c2ccc(OC(C)C)cn2)ns1] | N2-(3-(5-isopropoxypyridin-2-yl)-1,2,4-thiadiazol-5-yl)-N3-methyl-pyridine-2,3-diamine | 343.1 | B | D | E | E | B |
| 109 | 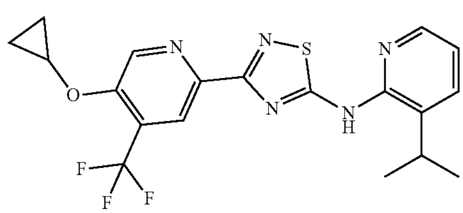 [SMILES: CC(C)c1cccnc1Nc1nc(-c2cc(C(F)(F)F)c(OC3CC3)cn2)ns1] | 3-(5-cyclopropoxy-4-(trifluoromethyl)pyridin-2-yl)-N-(3-isopropyl-pyridin-2-yl)-1,2,4-thiadiazol-5-amine | 422.1 | C | | D | E | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 110 | 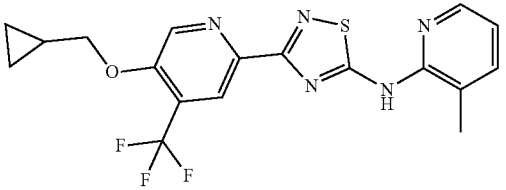 [SMILES: Cc1cccnc1Nc1nc(-c2cc(C(F)(F)F)c(OCC3CC3)cn2)ns1] | 3-(5-(cyclo-propylmethoxy)-4-(trifluoromethyl)pyridin-2-yl)-N-(3-methyl-pyridin-2-yl)-1,2,4-thiadiazol-5-amine | 408.1 | C | D | D, E | E | B |
| 111 | 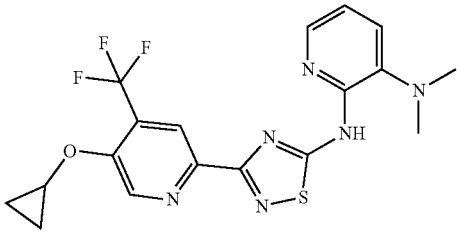 [SMILES: CN(C)c1cccnc1Nc1nc(-c2cc(C(F)(F)F)c(OC3CC3)cn2)ns1] | N2-(3-(5-cyclo-propoxy-4-(trifluoromethyl)pyridin-2-yl)-1,2,4-thiadiazol-5-yl)-N3,N3-dimethyl-pyridine-2,3-diamine | 423.1 | C | D | D, E | E | |
| 112 | 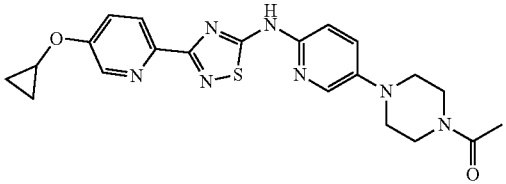 [SMILES: CC(=O)N1CCN(c2ccc(Nc3nc(-c4ccc(OC5CC5)cn4)ns3)nc2)CC1] | 1-(4-(6-(3-(5-cyclopropoxy-pyridin-2-yl)-1,2,4-thiadiazol-5-ylamino)pyridin-3-yl)piperazin-1-yl)ethanone | 438.1 | B | D | D | | |
| 113 | 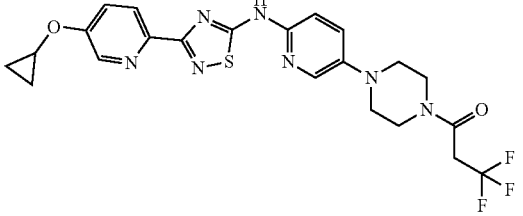 | 1-(4-(6-(3-(5-cycloprop-oxypyridin-2-yl)-1,2,4-thiadiazol-5-ylamino)pyridin-3-yl)piperazin-1-yl)-3,3,3-trifluoro-propan-1-one | 506.1 | A | D | D | | |
| 114 | 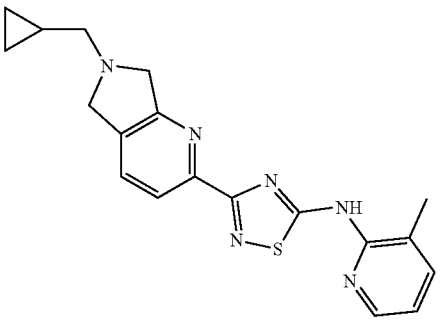 [SMILES: Cc1cccnc1Nc1nc(-c2ccc3c(n2)CN(CC2CC2)C3)ns1] | 3-(6-(cyclo-propylmethyl)-6,7-dihydro-5H-pyrrolo[3,4-b]pyridin-2-yl)-N-(3-methylpyridin-2-yl)-1,2,4-thiadiazol-5-amine | 365.2 | A | | | | |
| 115 | 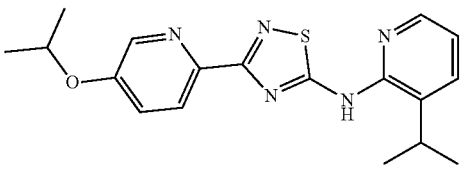 | 3-(5-isopropoxy-pyridin-2-yl)-N-(3-isopropyl-pyridin-2-yl)-1,2,4-thiadiazol-5-amine | 356.2 | C | D | D, E | | C |

TABLE 1-continued

| Cmpd No. | Structure | Name | M + 1 | *O. guttu-rosa* | *B. malayi* | *L. sigmo-dontis* | *B. paha-ngi* | *D. immit-is* |
|---|---|---|---|---|---|---|---|---|
| 116 | 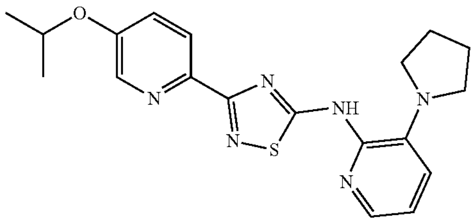 [SMILES: CC(C)Oc1ccc(-c2nsc(Nc3ncccc3N3CCCC3)n2)nc1] | 3-(5-isopropoxy-pyridin-2-yl)-N-(3-(pyrrolidin-1-yl)pyridin-2-yl)-1,2,4-thiadiazol-5-amine | 383.1 | C | D | D, E | | A |
| 117 | 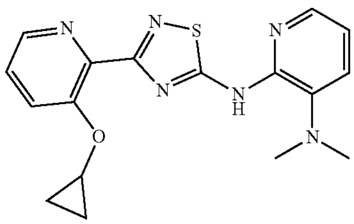 [SMILES: CN(C)c1cccnc1Nc1nc(-c2ncccc2OC2CC2)ns1] | N2-(3-(3-cycloprop-oxypyridin-2-yl)-1,2,4-thiadiazol-5-yl)-N3,N3-dimethyl-pyridine-2,3-diamine | 355 | B | D | D, E | | |
| 118 | 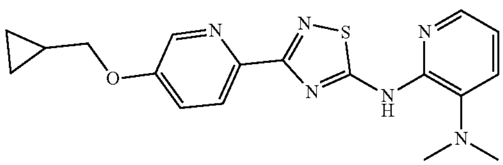 [SMILES: CN(C)c1cccnc1Nc1nc(-c2ccc(OCC3CC3)cn2)ns1] | N2-(3-(5-(cyclopropyl-methoxy)pyridin-2-yl)-1,2,4-thiadiazol-5-yl)-N3,N3-dimethyl-pyridine-2,3-diamine | 369.1 | C | D | D, E | | A |
| 119 | 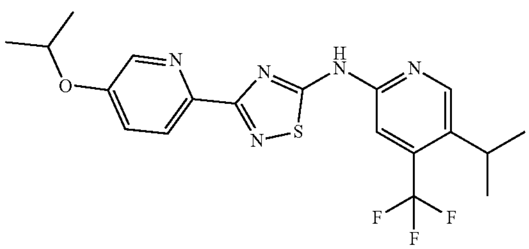 [SMILES: CC(C)Oc1ccc(-c2nsc(Nc3cc(C(F)(F)F)c(C(C)C)cn3)n2)nc1] | 3-(5-isopropoxy-pyridin-2-yl)-N-(5-isopropyl-4-(trifluoromethyl)pyridin-2-yl)-1,2,4-thiadiazol-5-amine | 424.1 | C | D, E | D, E | | |
| 120 | 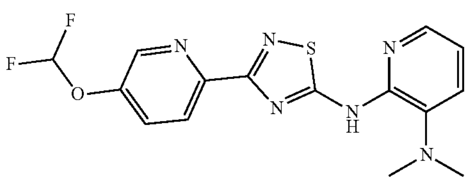 [SMILES: CN(C)c1cccnc1Nc1nc(-c2ccc(OC(F)F)cn2)ns1] | N2-(3-(5-(difluoromethoxy)pyridin-2-yl)-1,2,4-thiadiazol-5-yl)-N3,N3-dimethyl-pyridine-2,3-diamine | 365.1 | A | | | | A |
| 121 | 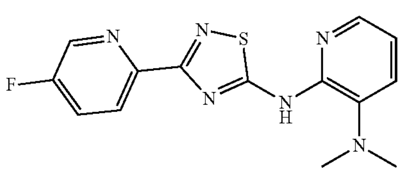 [SMILES: CN(C)c1cccnc1Nc1nc(-c2ccc(F)cn2)ns1] | N2-(3-(5-fluoro-pyridin-2-yl)-1,2,4-thiadiazol-5-yl)-N3,N3-dimethylpyridine-2,3-diamine | 317.1 | C | D, E | D, E | | A |
| 122 | 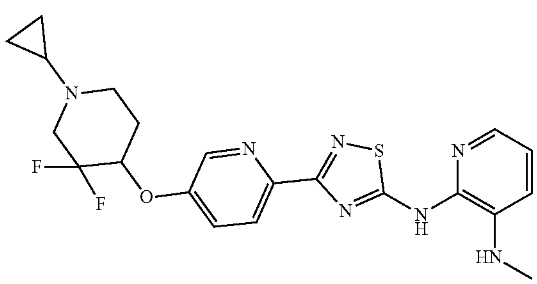 [SMILES: CNc1cccnc1Nc1nc(-c2ccc(OC3CCN(C4CC4)CC3(F)F)cn2)ns1] | N2-(3-(5-(1-cyclopropyl-3,3-difluoropiperidin-4-yloxy)pyridin-2-yl)-1,2,4-thiadiazol-5-yl)-N3-methyl-pyridine-2,3-diamine | 460.2 | B | D, E | D, E | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 123 | 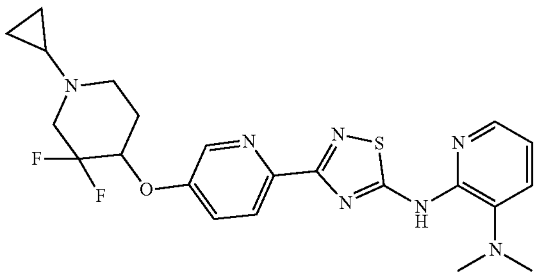 [SMILES: CN(C)c1cccnc1Nc1nc(-c2ccc(OC3CCN(C4CC4)CC3(F)F)cn2)ns1] | N2-(3-(5-(1-cyclopropyl-3,3-difluoro-piperidin-4-yloxy)pyridin-2-yl)-1,2,4-thiadiazol-5-yl)-N3,N3-dimethyl-pyridine-2,3-diamine | 474.2 | C | D, E | D, E | | |
| 124 | 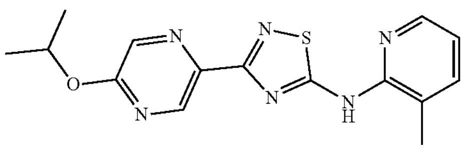 [SMILES: Cc1cccnc1Nc1nc(-c2cnc(OC(C)C)cn2)ns1] | 3-(5-isopropoxy-pyrazin-2-yl)-N-(3-methyl-pyridin-2-yl)-1,2,4-thiadiazol-5-amine | 329.1 | B | D | D | | A |
| 125 | 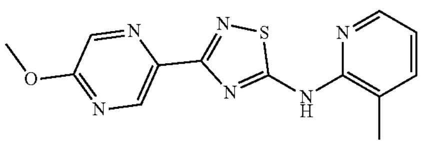 [SMILES: COc1cnc(-c2nsc(Nc3ncccc3C)n2)cn1] | 3-(5-methoxy-pyrazin-2-yl)-N-(3-methyl-pyridin-2-yl)-1,2,4-thiadiazol-5-amine | 301.1 | A | D | D | | |
| 126 | 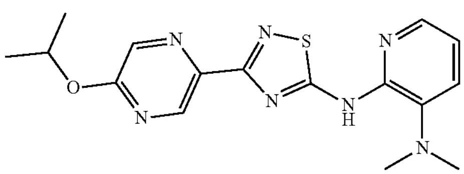 [SMILES: CC(C)Oc1cnc(-c2nsc(Nc3ncccc3N(C)C)n2)cn1] | N2-(3-(5-iso-propoxypyrazin-2-yl)-1,2,4-thiadiazol-5-yl)-N3,N3-dimethylpyridine-2,3-diamine | 358.2 | A | E | D, E | | |
| 127 | 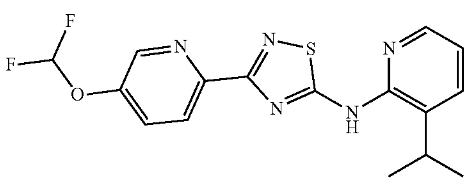 [SMILES: CC(C)c1cccnc1Nc1nc(-c2ccc(OC(F)F)cn2)ns1] | 3-(5-(difluoro-methoxy)pyridin-2-yl)-N-(3-isopropyl-pyridin-2-yl)-1,2,4-thiadiazol-5-amine | 364 | C | D, E | D | | A |
| 128 | 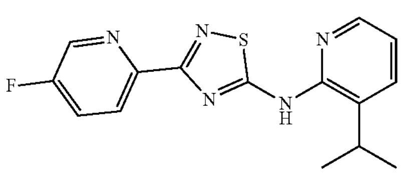 [SMILES: CC(C)c1cccnc1Nc1nc(-c2ccc(F)cn2)ns1] | 3-(5-fluoro-pyridin-2-yl)-N-(3-isopropyl-pyridin-2-yl)-1,2,4-thiadiazol-5-amine | 316 | A | D, E | D, E | | |
| 129 | 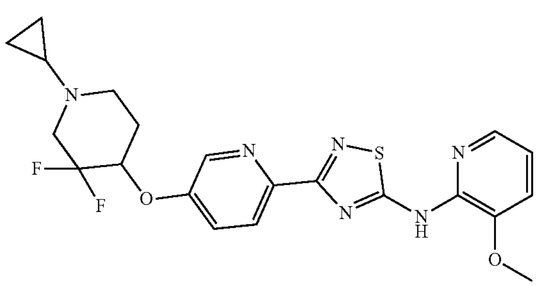 [SMILES: COc1cccnc1Nc1nc(-c2ccc(OC3CCN(C4CC4)CC3(F)F)cn2)ns1] | 3-(5-(1-cyclopropyl-3,3-difluoro-piperidin-4-yloxy)pyridin-2-yl)-N-(3-methoxypyridin-2-yl)-1,2,4-thiadiazol-5-amine | 461.1 | A | D | D | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 130 | 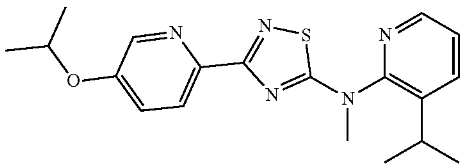 [SMILES: CC(C)Oc1ccc(-c2nsc(N(C)c3ncccc3C(C)C)n2)nc1] | 3-(5-isopropoxy-pyridin-2-yl)-N-(3-isopropylpyridin-2-yl)-N-methyl-1,2,4-thiadiazol-5-amine | 370.2 | A | D | D, E | | |
| 131 | 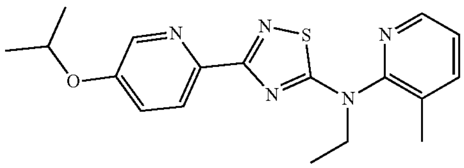 | N-ethyl-3-(5-isopropoxy-pyridin-2-yl)-N-(3-methylpyridin-2-yl)-1,2,4-thiadiazol-5-amine | 356.1 | C | D | | | |
| 132 | 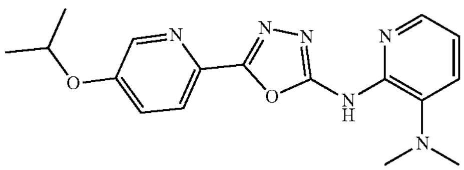 [SMILES: CC(C)Oc1ccc(-c2nnc(Nc3ncccc3N(C)C)o2)nc1] | N2-(5-(5-isopropoxy-pyridin-2-yl)-1,3,4-oxadiazol-2-yl)-N3,N3-dimethyl-pyridine-2,3-diamine | 341.1 | C | | D | | |
| 133 | 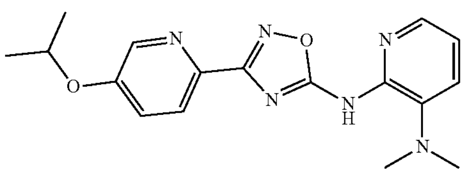 [SMILES: CC(C)Oc1ccc(-c2noc(Nc3ncccc3N(C)C)n2)nc1] | N2-(3-(5-isopropoxy-pyridin-2-yl)-1,2,4-oxadiazol-5-yl)-N3,N3-dimethyl-pyridine-2,3-diamine | 341.3 | A | | D | | |
| 134 | 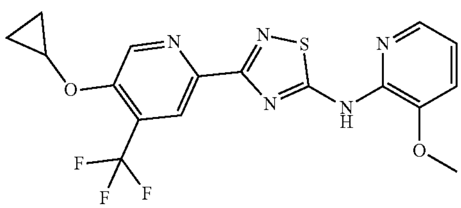 [SMILES: COc1cccnc1Nc1nc(-c2cc(C(F)(F)F)c(OC3CC3)cn2)ns1] | 3-(5-cyclopropoxy-4-(trifluoromethyl)pyridin-2-yl)-N-(3-methoxy-pyridin-2-yl)-1,2,4-thiadiazol-5-amine | 410.1 | A | D, E | D, E | | A |
| 135 | 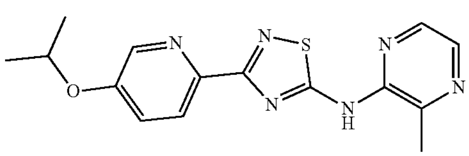 [SMILES: Cc1nccnc1Nc1nc(-c2ccc(OC(C)C)cn2)ns1] | 3-(5-isopropoxypyridin-2-yl)-N-(3-methyl-pyrazin-2-yl)-1,2,4-thiadiazol-5-amine | 329.1 | C | D, E | D | | B |
| 136 | 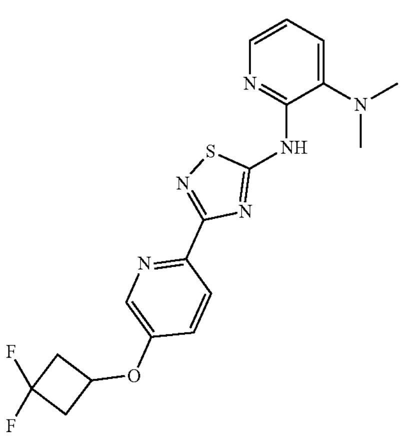 [SMILES: CN(C)c1cccnc1Nc1nc(-c2ccc(OC3CC(F)(F)C3)cn2)ns1] | N2-(3-(5-(3,3-difluorocyclobutoxy)pyridin-2-yl)-1,2,4-thiadiazol-5-yl)-N3,N3-dimethyl-pyridine-2,3-diamine | 405.1 | A | D, E | D, E | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 137 | 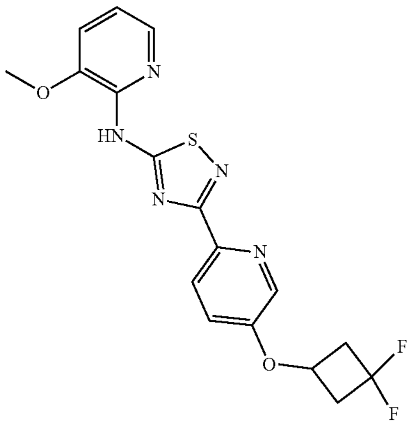 [SMILES: COc1cccnc1Nc1nc(-c2ccc(OC3CC(F)(F)C3)cn2)ns1] | 3-(5-(3,3-difluorocyclo-butoxy)pyridin-2-yl)-N-(3-methoxypyridin-2-yl)-1,2,4-thiadiazol-5-amine | 392.1 | A | D, E | D | | A |
| 138 | 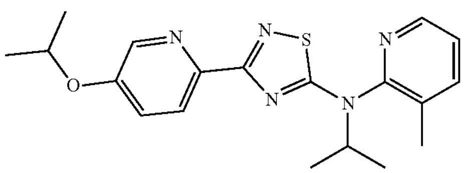 [SMILES: Cc1cccnc1N(c1nc(-c2ccc(OC(C)C)cn2)ns1)C(C)C] | 3-(5-isoprop-oxypyridin-2-yl)-N-isopropyl-N-(3-methylpyridin-2-yl)-1,2,4-thiadiazol-5-amine | 370.1 | A | | D | | |
| 139 | 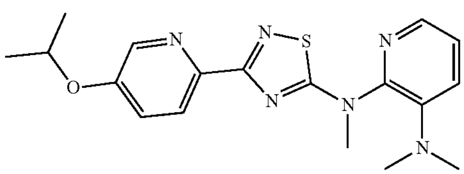 [SMILES: CC(C)Oc1ccc(-c2nsc(N(C)c3ncccc3N(C)C)n2)nc1] | N2-(3-(5-isoprop-oxypyridin-2-yl)-1,2,4-thiadiazol-5-yl)-N2,N3,N3-trimethylpyridine-2,3-diamine | 371.1 | A | D, E | D | | |
| 140 | 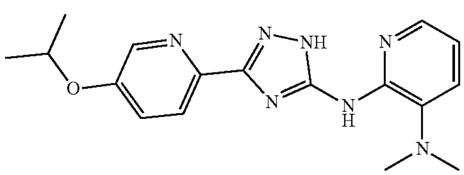 [SMILES: CC(C)Oc1ccc(-c2n[nH]c(Nc3ncccc3N(C)C)n2)nc1] | N2-(3-(5-isoprop-oxypyridin-2-yl)-1H-1,2,4-triazol-5-yl)-N3,N3-dimethyl-pyridine-2,3-diamine | 340.2 | A | D, E | D | | |
| 141 | 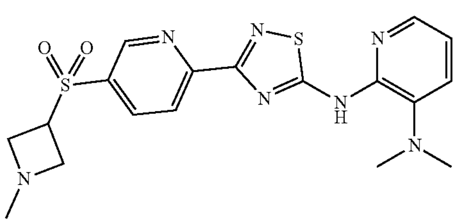 [SMILES: CN1CC(S(=O)(=O)c2ccc(-c3nsc(Nc4ncccc4N(C)C)n3)nc2)C1] | N3,N3-dimethyl-N2-(3-(5-(1-methylazetidin-3-ylsulfonyl)pyridin-2-yl)-1,2,4-thiadiazol-5-yl)pyridine-2,3-diamine | 432.1 | A | | D, E | | |
| 142 | 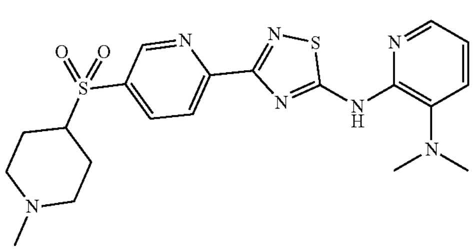 [SMILES: CN1CCC(S(=O)(=O)c2ccc(-c3nsc(Nc4ncccc4N(C)C)n3)nc2)CC1] | N3,N3-dimethyl-N2-(3-(5-(1-methylpiperidin-4-ylsulfonyl)pyridin-2-yl)-1,2,4-thiadiazol-5-yl)pyridine-2,3-diamine | 460.2 | A | | D | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 143 | 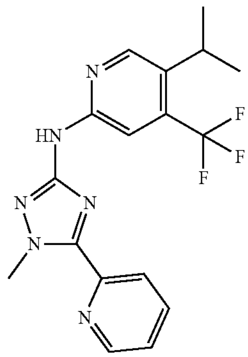 [SMILES: CC(C)c1cnc(Nc2nc(-c3ccccn3)n(C)n2)cc1C(F)(F)F] | 5-isopropyl-N-(1-methyl-5-(pyridin-2-yl)-1H-1,2,4-triazol-3-yl)-4-(trifluoromethyl)pyridin-2-amine | 363.1 | A | | D, E | | |
| 144 | 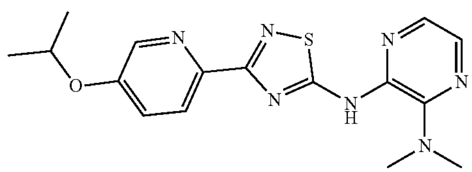 [SMILES: CC(C)Oc1ccc(-c2nsc(Nc3nccnc3N(C)C)n2)nc1] | N2-(3-(5-isoprop-oxypyridin-2-yl)-1,2,4-thiadiazol-5-yl)-N3,N3-dimethyl-pyrazine-2,3-diamine | 358 | B | | D, E | | B |
| 145 | 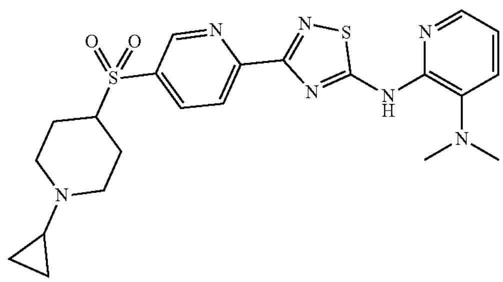 [SMILES: CN(C)c1cccnc1Nc1nc(-c2ccc(S(=O)(=O)C3CCN(C4CC4)CC3)cn2)ns1] | N2-(3-(5-(1-cyclopropyl-piperidin-4-ylsulfonyl)pyridin-2-yl)-1,2,4-thiadiazol-5-yl)-N3,N3-dimethyl-pyridine-2,3-diamine | 486.1 | A | | D, E | | |
| 146 | 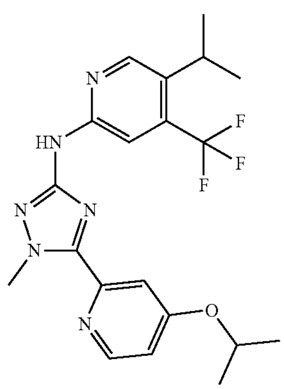 [SMILES: CC(C)Oc1ccnc(-c2nc(Nc3cc(C(F)(F)F)c(C(C)C)cn3)nn2C)c1] | N-(5-(4-isoprop-oxypyridin-2-yl)-1-methyl-1H-1,2,4-triazol-3-yl)-5-isopropyl-4-(trifluoro-methyl)pyridin-2-amine | 421.2 | A | | | | |
| 147 | 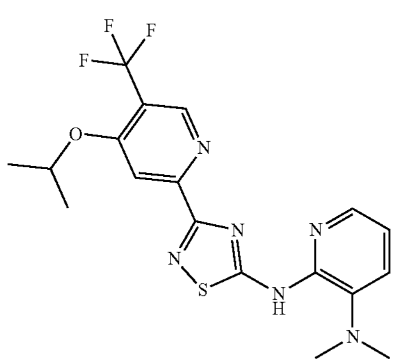 [SMILES: CC(C)Oc1cc(-c2nsc(Nc3ncccc3N(C)C)n2)ncc1C(F)(F)F] | N2-(3-(4-isoprop-oxy-5-(trifluoromethyl)pyridin-2-yl)-1,2,4-thiadiazol-5-yl)-N3,N3-dimethyl-pyridine-2,3-diamine | 425.1 | A | | D, E | | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 148 | 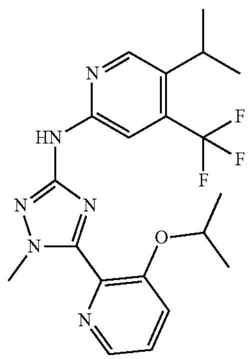 [SMILES: CC(C)Oc1cccnc1-c1nc(Nc2cc(C(F)(F)F)c(C(C)C)cn2)nn1C] | N-(5-(3-isoprop-oxypyridin-2-yl)-1-methyl-1H-1,2,4-triazol-3-yl)-5-isopropyl-4-(trifluoromethyl)pyridin-2-amine | 421.2 | A | | D | | |
| 149 | 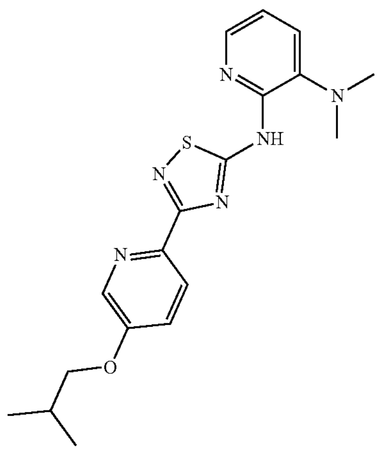 | N2-(3-(5-isobutoxy-pyridin-2-yl)-1,2,4-thiadiazol-5-yl)-N3,N3-dimethyl-pyridine-2,3-diamine | 371.1 | C | | D, E | | |
| 150 | 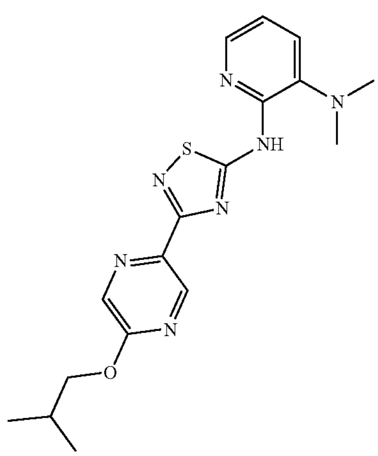 [SMILES: CC(C)COc1cnc(-c2nsc(Nc3ncccc3N(C)C)n2)cn1] | N2-(3-(5-isobutoxy-pyrazin-2-yl)-1,2,4-thiadiazol-5-yl)-N3,N3-dimethyl-pyridine-2,3-diamine | 372.1 | A | | D, E | | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 151 | 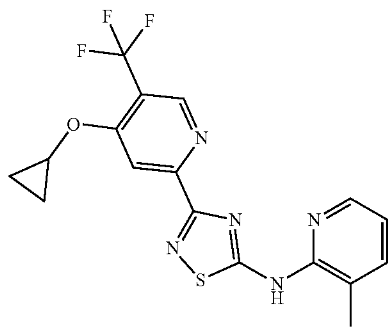 [SMILES: Cc1cccnc1Nc1nc(-c2cc(OC3CC3)c(C(F)(F)F)cn2)ns1] | 3-(4-cyclo-propoxy-5-(trifluoromethyl)pyridin-2-yl)-N-(3-methylpyridin-2-yl)-1,2,4-thiadiazol-5-amine | 394 | C | | E | | |
| 152 | 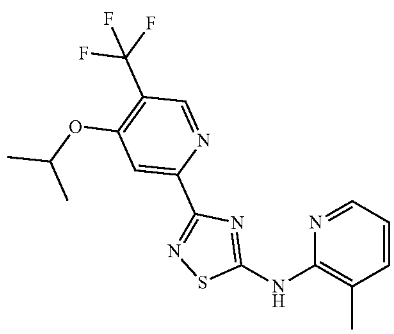 [SMILES: Cc1cccnc1Nc1nc(-c2cc(OC(C)C)c(C(F)(F)F)cn2)ns1] | 3-(4-isoprop-oxy-5-(trifluoromethyl)pyridin-2-yl)-N-(3-methylpyridin-2-yl)-1,2,4-thia-diazol-5-amine | 396.1 | B | | E | | B |
| 153 | 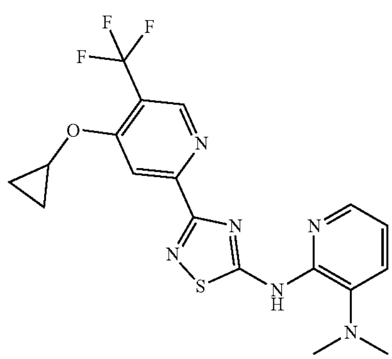 [SMILES: CN(C)c1cccnc1Nc1nc(-c2cc(OC3CC3)c(C(F)(F)F)cn2)ns1] | N2-(3-(4-cyclo-propoxy-5-(trifluoromethyl)pyridin-2-yl)-1,2,4-thiadiazol-5-yl)-N3,N3-dimethyl-pyridine-2,3-diamine | 423.1 | A | | E | | |
| 154 | 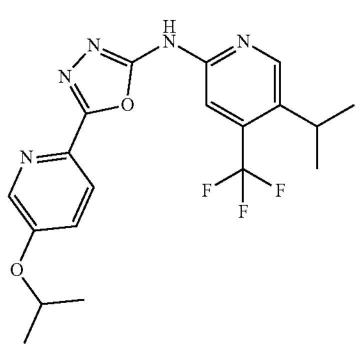 [SMILES: CC(C)Oc1ccc(-c2nnc(Nc3cc(C(F)(F)F)c(C(C)C)cn3)o2)nc1] | 5-(5-isoprop-oxypyridin-2-yl)-N-(5-isopropyl-4-(trifluoro-methyl)pyridin-2-yl)-1,3,4-oxadiazol-2-amine | 408.1 | B | | | | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 155 | 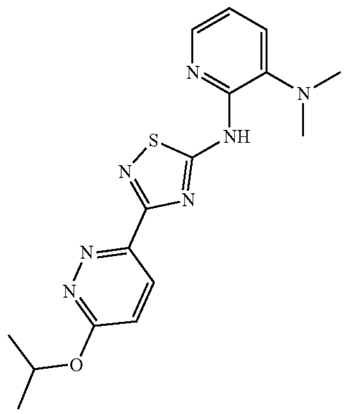 [SMILES: CC(C)Oc1ccc(-c2nsc(Nc3ncccc3N(C)C)n2)nn1] | N2-(3-(6-isopropoxy-pyridazin-3-yl)-1,2,4-thiadiazol-5-yl)-N3,N3-dimethyl-pyridine-2,3-diamine | 358.1 | A | D | D, E | E | A |
| 156 | 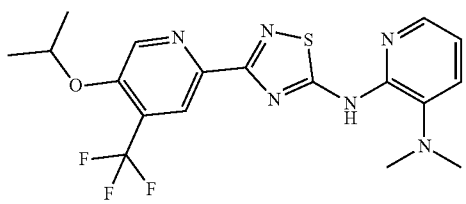 [SMILES: CC(C)Oc1cnc(-c2nsc(Nc3ncccc3N(C)C)n2)cc1C(F)(F)F] | N2-(3-(5-isopropoxy-4-(trifluoromethyl)pyridin-2-yl)-1,2,4-thiadiazol-5-yl)-N3,N3-dimethyl-pyridine-2,3-diamine | 425.1 | C | D | D, E | E | B |
| 157 | 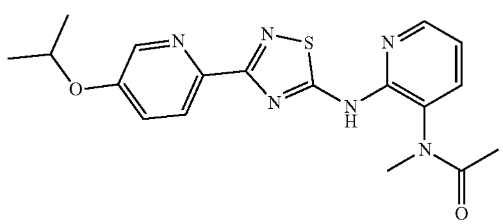 [SMILES: CC(=O)N(C)c1cccnc1Nc1nc(-c2ccc(OC(C)C)cn2)ns1] | N-(2-(3-(5-isopropoxy-pyridin-2-yl)-1,2,4-thiadiazol-5-ylamino)pyridin-3-yl)-N-methyl-acetamide | 385.2 | A | D, E | D, E | D, E | A |
| 158 | 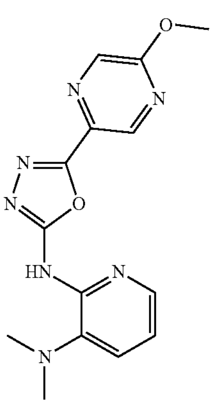 | N2-(5-(5-methoxy-pyrazin-2-yl)-1,3,4-oxadiazol-2-yl)-N3,N3-dimethyl-pyridine-2,3-diamine | 314.1 | A | | D, E | E | |
| 159 | 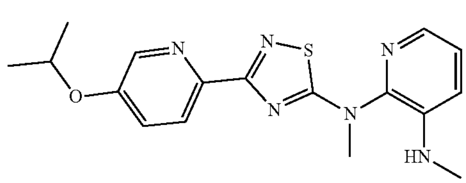 [SMILES: CNc1cccnc1N(C)c1nc(-c2ccc(OC(C)C)cn2)ns1] | N2-(3-(5-isopropoxy-pyridin-2-yl)-1,2,4-thiadiazol-5-yl)-N2,N3-dimethyl-pyridine-2,3-diamine | 357.3 | A | | D, E | E | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 160 | 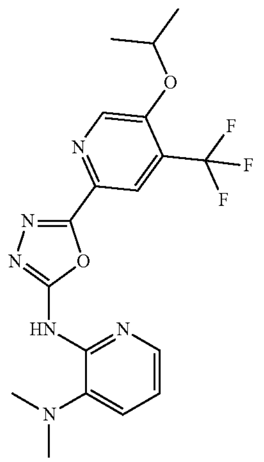 [SMILES: CC(C)Oc1cnc(-c2nnc(Nc3ncccc3N(C)C)o2)cc1C(F)(F)F] | N2-(5-(5-isopropoxy-4-(trifluoromethyl)pyridin-2-yl)-1,3,4-oxadiazol-2-yl)-N3,N3-dimethyl-pyridine-2,3-diamine | 409.3 | A | | D | E | |
| 161 | 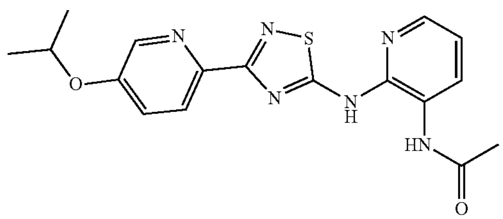 [SMILES: CC(=O)Nc1cccnc1Nc1nc(-c2ccc(OC(C)C)cn2)ns1] | N-(2-(3-(5-isopropoxy-pyridin-2-yl)-1,2,4-thiadiazol-5-ylamino)pyridin-3-yl)acetamide | 371.3 | A | D | D, E | E | A |
| 162 | 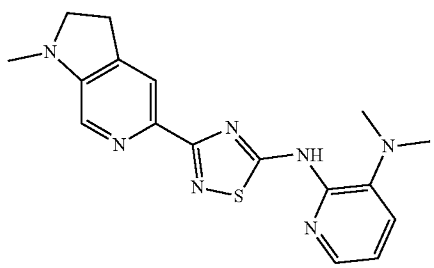 | N3,N3-dimethyl-N2-(3-(1-methyl-2,3-dihydro-1H-pyrrolo[2,3-c]pyridin-5-yl)-1,2,4-thiadiazol-5-yl)pyridine-2,3-diamine | 354.3 | C | D | D, E | E | |
| 163 | 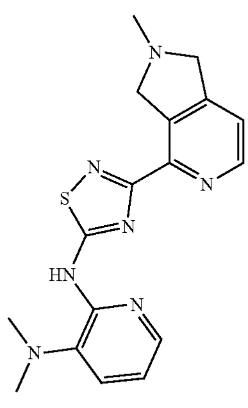 [SMILES: CN1Cc2ccnc(-c3nsc(Nc4ncccc4N(C)C)n3)c2C1] | N3,N3-dimethyl-N2-(3-(2-methyl-2,3-dihydro-1H-pyrrolo[3,4-c]pyridin-4-yl)-1,2,4-thiadiazol-5-yl)pyridine-2,3-diamine | 354.3 | C | D | D, E | E | |
| 164 | 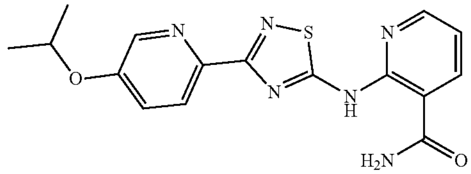 [SMILES: CC(C)Oc1ccc(-c2nsc(Nc3ncccc3C(N)=O)n2)nc1] | 2-(3-(5-isopropoxypyridin-2-yl)-1,2,4-thiadiazol-5-ylamino)nicotinamide | 357.3 | A | | D, E | E | |

TABLE 1-continued

| Cmpd No. | Structure | Name | M + 1 | *O. guttu-rosa* | *B. malayi* | *L. sigmo-dontis* | *B. paha-ngi* | *D. immit-is* |
|---|---|---|---|---|---|---|---|---|
| 165 | 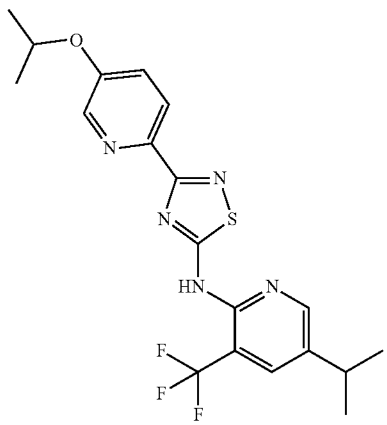 [SMILES: CC(C)Oc1ccc(-c2nsc(Nc3ncc(C(C)C)cc3C(F)(F)F)n2)nc1] | 3-(5-isopropoxy-pyridin-2-yl)-N-(5-isopropyl-3-(trifluoromethyl)pyridin-2-yl)-1,2,4-thiadiazol-5-amine | 424.2 | C | D | D, E | E | |
| 166 | 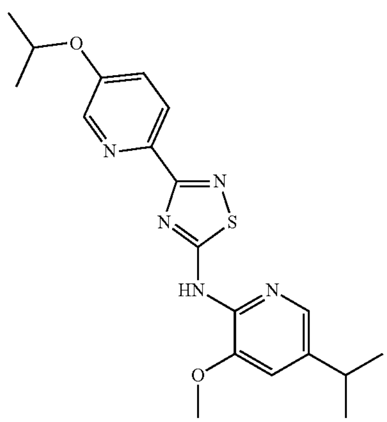 [SMILES: COc1cc(C(C)C)cnc1Nc1nc(-c2ccc(OC(C)C)cn2)ns1] | 3-(5-isopropoxy-pyridin-2-yl)-N-(5-isopropyl-3-methoxypyridin-2-yl)-1,2,4-thiadiazol-5-amine | 386.3 | C | D | D, E | E | A |
| 167 | 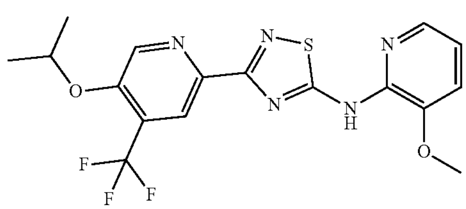 [SMILES: COc1cccnc1Nc1nc(-c2cc(C(F)(F)F)c(OC(C)C)cn2)ns1] | 3-(5-isopropoxy-4-(trifluoromethyl)pyridin-2-yl)-N-(3-methoxypyridin-2-yl)-1,2,4-thiadiazol-5-amine | 412.1 | B | D | D, E | E | A |
| 168 | 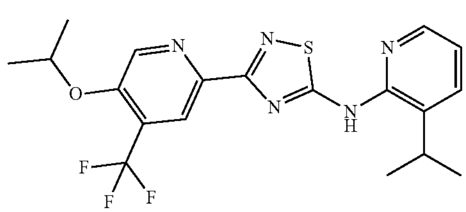 [SMILES: CC(C)Oc1cnc(-c2nsc(Nc3ncccc3C(C)C)n2)cc1C(F)(F)F] | 3-(5-isopropoxy-4-(trifluoromethyl)pyridin-2-yl)-N-(3-isopropyl-pyridin-2-yl)-1,2,4-thiadiazol-5-amine | 424.2 | C | D | D, E | E | B |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 169 | 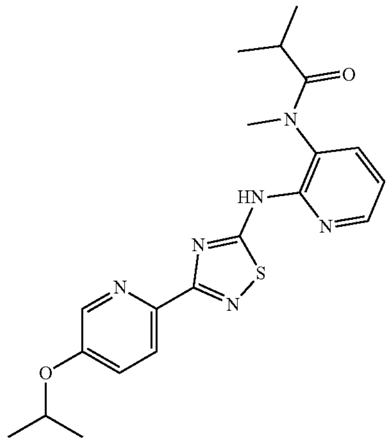 [SMILES: CC(C)Oc1ccc(-c2nsc(Nc3ncccc3N(C)C(=O)C(C)C)n2)nc1] | N-(2-(3-(5-isopropoxy-pyridin-2-yl)-1,2,4-thiadiazol-5-ylamino)pyridin-3-yl)-N-methylisobutyramide | 413.2 | B | D, E | D, E | E | |
| 170 | 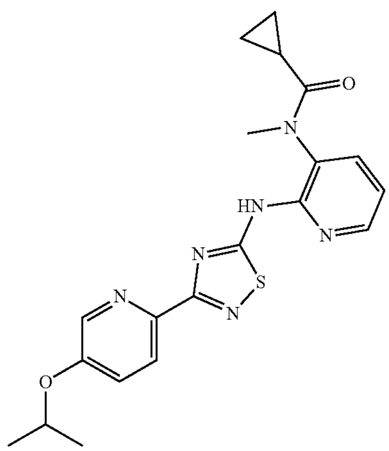 [SMILES: CC(C)Oc1ccc(-c2nsc(Nc3ncccc3N(C)C(=O)C3CC3)n2)nc1] | N-(2-(3-(5-isopropoxy-pyridin-2-yl)-1,2,4-thiadiazol-5-ylamino)pyridin-3-yl)-N-methylcyclopropanecarboxamide | 411.2 | B | D, E | D, E | D, E | A |
| 171 | 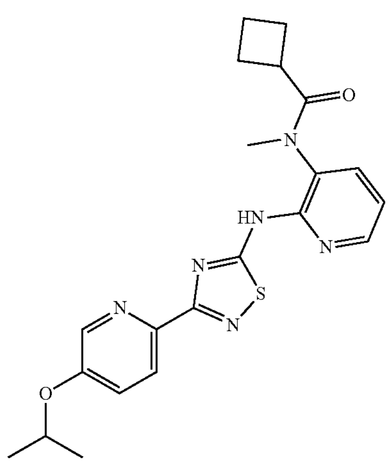 [SMILES: CC(C)Oc1ccc(-c2nsc(Nc3ncccc3N(C)C(=O)C3CCC3)n2)nc1] | N-(2-(3-(5-isopropoxy-pyridin-2-yl)-1,2,4-thiadiazol-5-ylamino)pyridin-3-yl)-N-methylcyclobutanecarboxamide | 425.2 | C | D | D | E | A |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 172 | 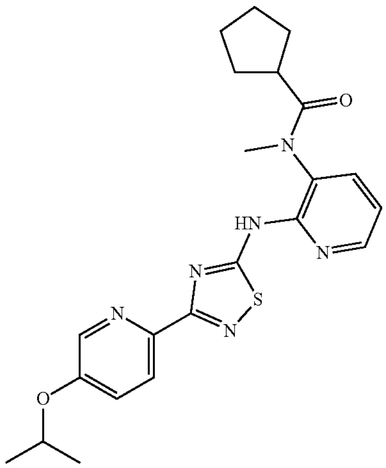 [SMILES: CC(C)Oc1ccc(-c2nsc(Nc3ncccc3N(C)C(=O)C3CCCC3)n2)nc1] | N-(2-(3-(5-isopropoxy-pyridin-2-yl)-1,2,4-thiadiazol-5-ylamino)pyridin-3-yl)-N-methylcyclo-pentane-carboxamide | 439.2 | C | D, E | D, E | E | B |
| 173 | 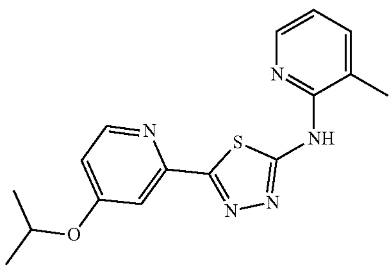 [SMILES: Cc1cccnc1Nc1nnc(-c2cc(OC(C)C)ccn2)s1] | 5-(4-isopropoxy-pyridin-2-yl)-N-(3-methyl-pyridin-2-yl)-1,3,4-thia-diazol-2-amine | 328.1 | A | E | E | | |
| 174 | 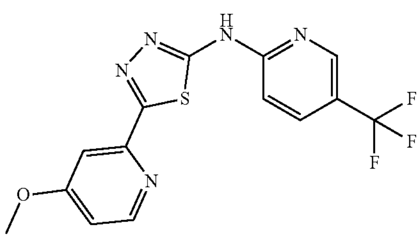 [SMILES: COc1ccnc(-c2nnc(Nc3ccc(C(F)(F)F)cn3)s2)c1] | 5-(4-methoxy-pyridin-2-yl)-N-(5-(trifluoromethyl)pyridin-2-yl)-1,3,4-thiadiazol-2-amine | 354 | B | | D | E | |
| 175 | 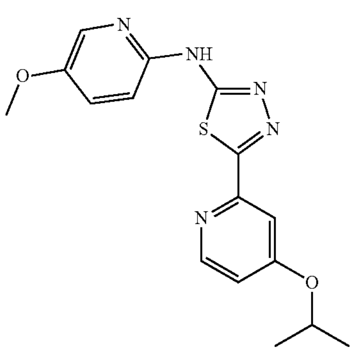 [SMILES: COc1ccc(Nc2nnc(-c3cc(OC(C)C)ccn3)s2)nc1] | 5-(4-isopropoxy-pyridin-2-yl)-N-(5-methoxy-pyridin-2-yl)-1,3,4-thiadiazol-2-amine | 344.1 | | | D | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 176 | 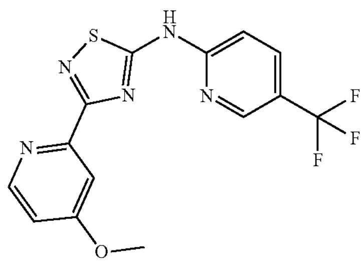 [SMILES: COc1ccnc(-c2nsc(Nc3ccc(C(F)(F)F)cn3)n2)c1] | 3-(4-methoxy-pyridin-2-yl)-N-(5-(trifluoromethyl)pyridin-2-yl)-1,2,4-thiadiazol-5-amine | 354 | C | D, E | D, E | E | C |
| 177 | 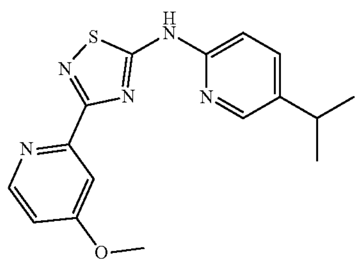 [SMILES: COc1ccnc(-c2nsc(Nc3ccc(C(C)C)cn3)n2)c1] | N-(5-isopropyl-pyridin-2-yl)-3-(4-methoxy-pyridin-2-yl)-1,2,4-thiadiazol-5-amine | 328 | C | D, E | D, E | | C |
| 178 | 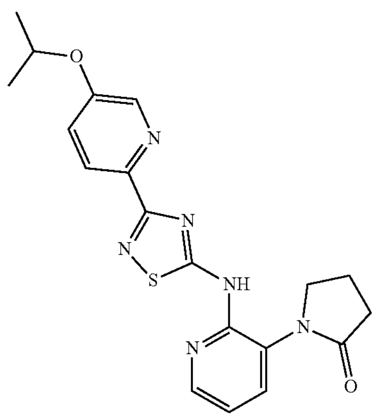 [SMILES: CC(C)Oc1ccc(-c2nsc(Nc3ncccc3N3CCCC3=O)n2)nc1] | 1-(2-(3-(5-isopropoxy-pyridin-2-yl)-1,2,4-thiadiazol-5-ylamino)pyridin-3-yl)pyrrolidin-2-one | 397.2 | A | D, E | D | E | A |
| 179 | 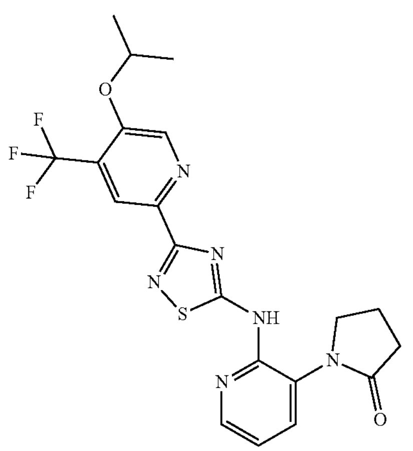 [SMILES: CC(C)Oc1cnc(-c2nsc(Nc3ncccc3N3CCCC3=O)n2)cc1C(F)(F)F] | 1-(2-(3-(5-isopropoxy-4-(trifluoromethyl)pyridin-2-yl)-1,2,4-thiadiazol-5-ylamino)pyridin-3-yl)pyrrolidin-2-one | 465.2 | A | D, E | D, E | E | A |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 180 | 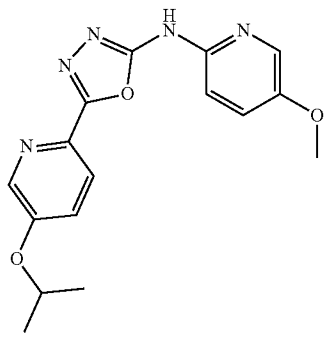 [SMILES: COc1ccc(Nc2nnc(-c3ccc(OC(C)C)cn3)o2)nc1] | 5-(5-isopropoxy- pyridin-2-yl)- N-(5-methoxy- pyridin-2-yl)- 1,3,4- oxadiazol-2- amine | 328.2 | A | | D | | |
| 181 | 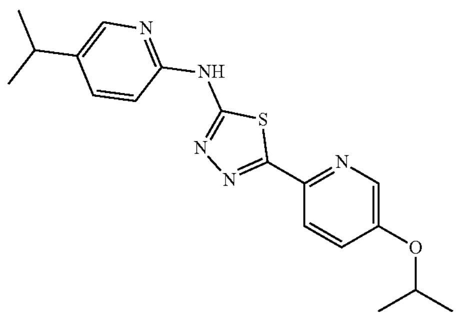 [SMILES: CC(C)Oc1ccc(-c2nnc(Nc3ccc(C(C)C)cn3)s2)nc1] | 5-(5-isopropoxy- pyridin-2-yl)- N-(5-isopropyl- pyridin-2-yl)- 1,3,4- thiadiazol-2- amine | 355.8 | A | | D | | |
| 182 | 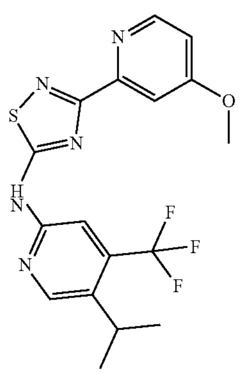 [SMILES: COc1ccnc(-c2nsc(Nc3cc(C(F)(F)F)c(C(C)C)cn3)n2)c1] | N-(5-iso- propyl-4- (trifluoro- methyl)pyridin-2- yl)-3-(4- methoxy- pyridin-2- yl)-1,2,4- thiadiazol-5- amine | 395.8 | B | D | D, E | D | C |
| 183 | 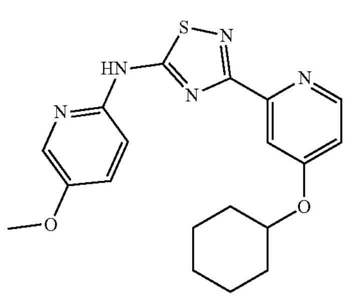 [SMILES: COc1ccc(Nc2nc(-c3cc(OC4CCCCC4)ccn3)ns2)nc1] | 3-(4-(cyclo- hexyloxy) pyridin- 2-yl)-N-(5- methoxypyridin- 2-yl)-1,2,4- thiadiazol-5- amine | 384.1 | B | D | D, E | D | C |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 184 | 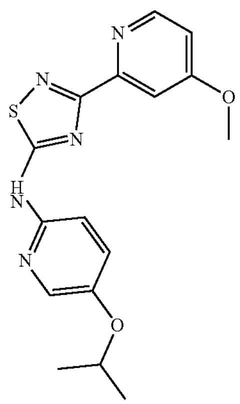 [SMILES: COc1ccnc(-c2nsc(Nc3ccc(OC(C)C)cn3)n2)c1] | N-(5-isoprop-oxypyridin-2-yl)-3-(4-methoxy-pyridin-2-yl)-1,2,4-thiadiazol-5-amine | 343.9 | C | D | D, E | D, E | |
| 185 | 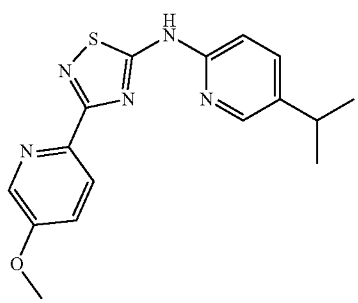 [SMILES: COc1ccc(-c2nsc(Nc3ccc(C(C)C)cn3)n2)nc1] | N-(5-isopropyl-pyridin-2-yl)-3-(5-methoxy-pyridin-2-yl)-1,2,4-thiadiazol-5-amine | 328 | B | D | D, E | D, E | |
| 186 | 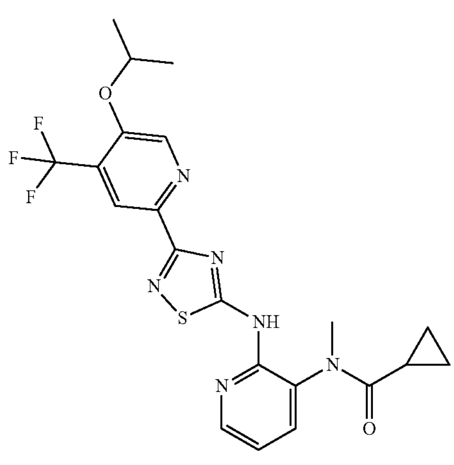 [SMILES: CC(C)Oc1cnc(-c2nsc(Nc3ncccc3N(C)C(=O)C3CC3)n2)cc1C(F)(F)F] | N-(2-(3-(5-isopropoxy-4-(trifluoro-methyl)pyridin-2-yl)-1,2,4-thiadiazol-5-ylamino)pyridin-3-yl)-N-methylcyclo-propanecarbox-amide | 479.1 | A | E | D, E | D, E | B |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 187 | 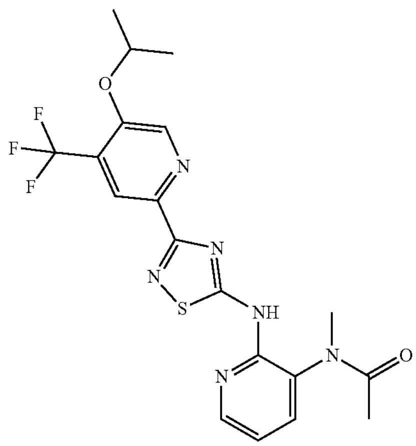 [SMILES: CC(=O)N(C)c1cccnc1Nc1nc(-c2cc(C(F)(F)F)c(OC(C)C)cn2)ns1] | N-(2-(3-(5-isopropoxy-4-(trifluoro-methyl)pyridin-2-yl)-1,2,4-thiadiazol-5-ylamino)pyridin-3-yl)-N-methylacetamide | 453.1 | A | D, E | D, E | D, E | B |
| 188 | 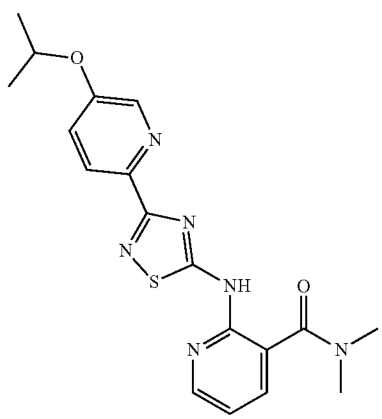 [SMILES: CC(C)Oc1ccc(-c2nsc(Nc3ncccc3C(=O)N(C)C)n2)nc1] | 2-(3-(5-isoprop-oxypyridin-2-yl)-1,2,4-thiadiazol-5-ylamino)-N,N-dimethyl nicotinamide | 385.2 | B | D | D, E | D | A |
| 189 | 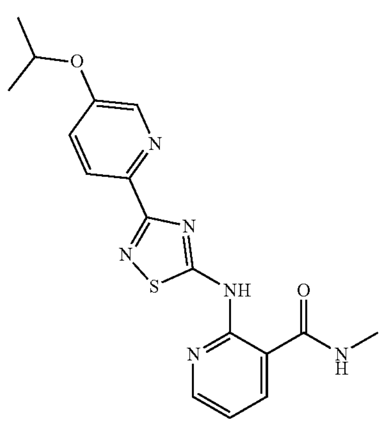 [SMILES: CNC(=O)c1cccnc1Nc1nc(-c2ccc(OC(C)C)cn2)ns1] | 2-(3-(5-isoprop-oxypyridin-2-yl)-1,2,4-thiadiazol-5-ylamino)-N-methyl-nicotinamide | 371.1 | A | | D, E | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 190 | 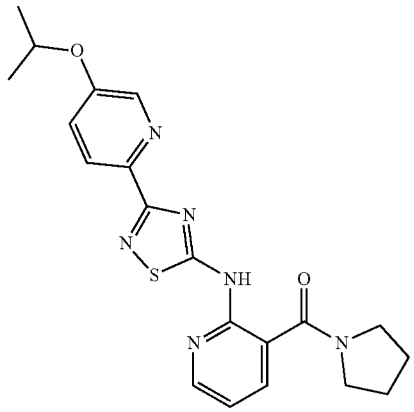 [SMILES: CC(C)Oc1ccc(-c2nsc(Nc3ncccc3C(=O)N3CCCC3)n2)nc1] | (2-(3-(5-isoprop- oxypyridin- 2-yl)-1,2,4- thiadiazol-5- ylamino) pyridin-3- yl) (pyrrolidin-1- yl) methanone | 411.3 | B | D | D, E | D, E | A |
| 191 | 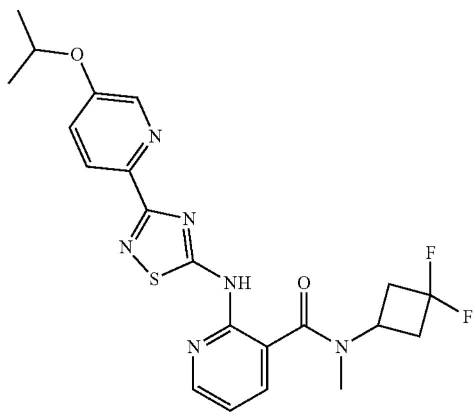 [SMILES: CC(C)Oc1ccc(-c2nsc(Nc3ncccc3C(=O)N(C)C3CC(F)(F)C3)n2)nc1] | N-(3,3-difluoro- cyclobutyl)-2- (3-(5-isoprop- oxypyridin-2- yl)-1,2,4- thiadiazol-5- ylamino)-N- methyl- nicotinamide | 461.3 | B | D | D, E | D, E | A |
| 192 | 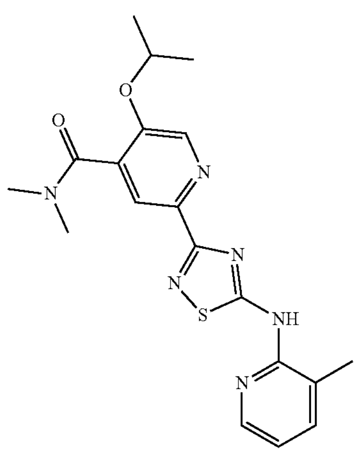 | 5-isopropoxy- N,N-dimethyl- 2-(5-(3- methylpyridin-2- ylamino)- 1,2,4- thiadiazol-3- yl)isonicotin- amide | 399.3 | A | | D | | |

TABLE 1-continued

| Cmpd No. | Structure | Name | M + 1 | *O. guttu-rosa* | *B. malayi* | *L. sigmo-dontis* | *B. paha-ngi* | *D. immit-is* |
|---|---|---|---|---|---|---|---|---|
| 193 | 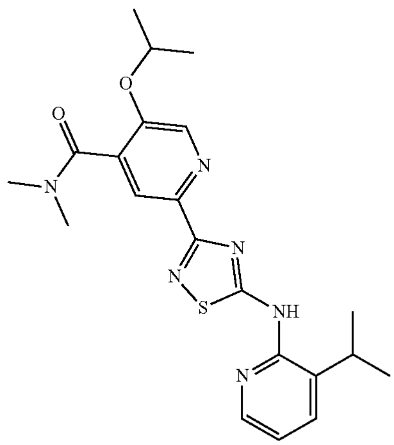 [SMILES: CC(C)Oc1cnc(-c2nsc(Nc3ncccc3C(C)C)n2)cc1C(=O)N(C)C] | 5-isopropoxy-2-(5-(3-isopropylpyridin-2-ylamino)-1,2,4-thiadiazol-3-yl)-N,N-dimethylisonicotinamide | 427.3 | B | D | D | D, E | |
| 194 | 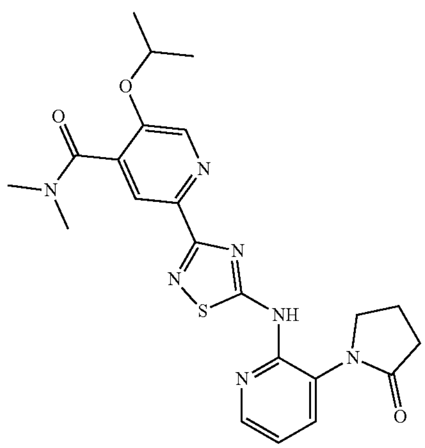 [SMILES: CC(C)Oc1cnc(-c2nsc(Nc3ncccc3N3CCCC3=O)n2)cc1C(=O)N(C)C] | 5-isopropoxy-N,N-dimethyl-2-(5-(3-(2-oxopyrrolidin-1-yl)pyridin-2-ylamino)-1,2,4-thiadiazol-3-yl)isonicotinamide | 468.3 | A | | D, E | E | |
| 195 | 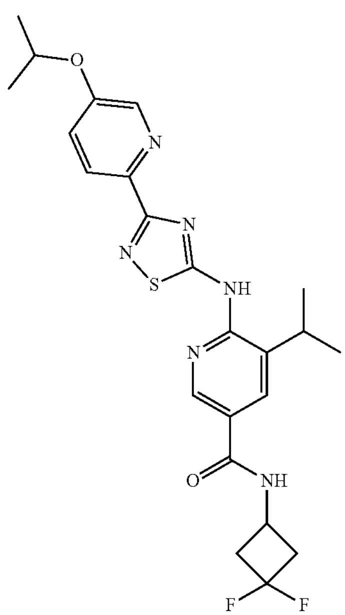 [SMILES: CC(C)Oc1ccc(-c2nsc(Nc3ncc(C(=O)NC4CC(F)(F)C4)cc3C(C)C)n2)nc1] | N-(3,3-difluorocyclobutyl)-6-(3-(5-isopropoxypyridin-2-yl)-1,2,4-thiadiazol-5-ylamino)-5-isopropylnicotinamide | 489.3 | C | D | D, E | D, E | A |

TABLE 1-continued

| Cmpd No. | Structure | Name | M + 1 | *O. guttu-rosa* | *B. malayi* | *L. sigmo-dontis* | *B. paha-ngi* | *D. immit-is* |
|---|---|---|---|---|---|---|---|---|
| 196 | 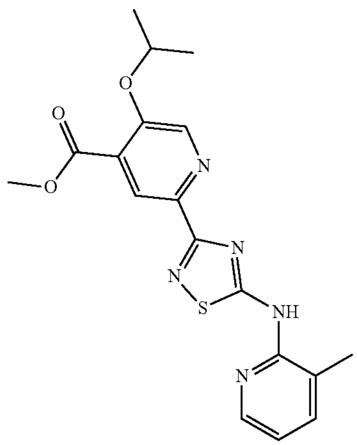 | methyl 5-isopropoxy-2-(5-(3-methylpyridin-2-ylamino)-1,2,4-thiadiazol-3-yl)isonicotinate | 386.3 | B | D, E | D, E | | B |
| 197 | 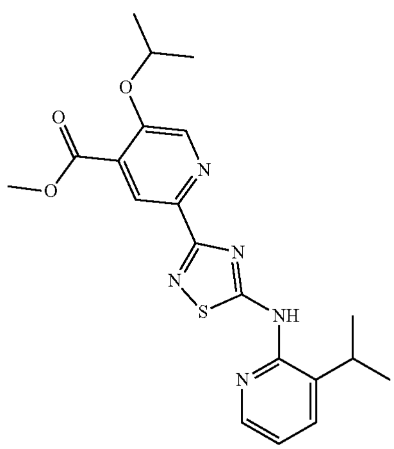 [SMILES: COC(=O)c1cc(-c2nsc(Nc3ncccc3C(C)C)n2)ncc1OC(C)C] | methyl 5-isopropoxy-2-(5-(3-isopropylpyridin-2-ylamino)-1,2,4-thiadiazol-3-yl)isonicotinate | 414.3 | C | D, E | E | E | C |
| 198 | 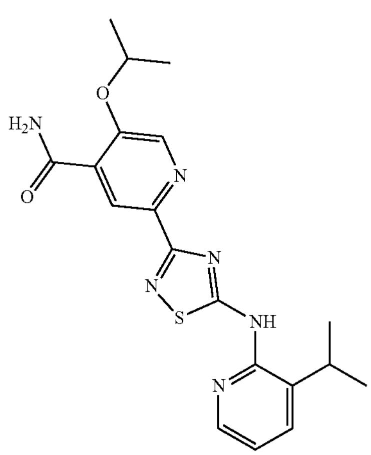 [SMILES: CC(C)Oc1cnc(-c2nsc(Nc3ncccc3C(C)C)n2)cc1C(N)=O] | 5-isopropoxy-2-(5-(3-isopropylpyridin-2-ylamino)-1,2,4-thiadiazol-3-yl)isonicotinamide | 399.3 | A | D, E | D, E | E | A |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 199 | 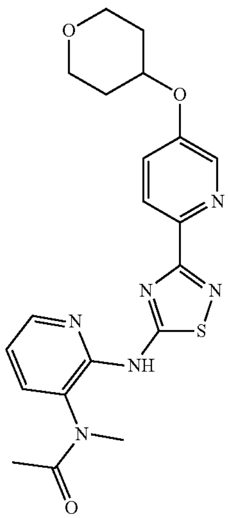 [SMILES: CC(=O)N(C)c1cccnc1Nc1nc(-c2ccc(OC3CCOCC3)cn2)ns1] | N-methyl-N-(2-(3-(5-(tetrahydro-2H-pyran-4-yloxy)pyridin-2-yl)-1,2,4-thiadiazol-5-ylamino)pyridin-3-yl)acetamide | 427.2 | A | E | | E | |
| 200 | 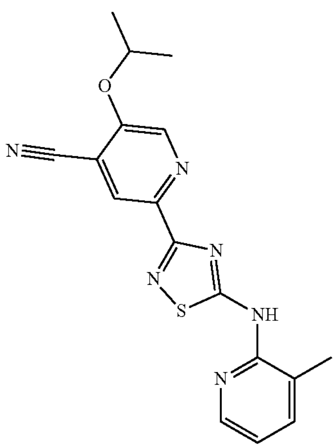 [SMILES: Cc1cccnc1Nc1nc(-c2cc(C#N)c(OC(C)C)cn2)ns1] | 5-isopropoxy-2-(5-(3-methylpyridin-2-ylamino)-1,2,4-thiadiazol-3-yl)isonicotinonitrile | 353.3 | A | D, E | E | E | B |
| 201 | 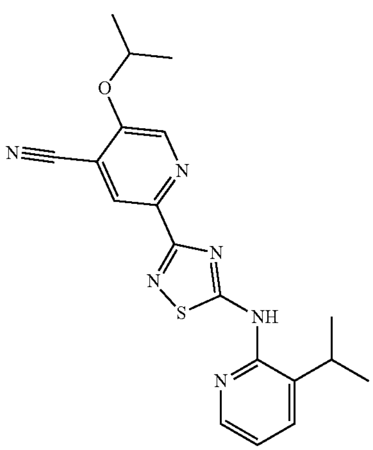 [SMILES: CC(C)Oc1cnc(-c2nsc(Nc3ncccc3C(C)C)n2)cc1C#N] | 5-isopropoxy-2-(5-(3-isopropyl-pyridin-2-ylamino)-1,2,4-thiadiazol-3-yl)isonicotinonitrile | 381.3 | A | D, E | E | E | C |

TABLE 1-continued

| Cmpd No. | Structure | Name | M + 1 | *O. guttu-rosa* | *B. malayi* | *L. sigmo-dontis* | *B. paha-ngi* | *D. immit-is* |
|---|---|---|---|---|---|---|---|---|
| 202 | 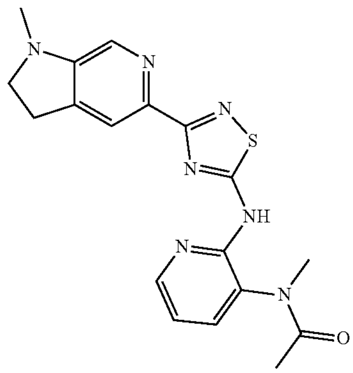 [SMILES: CC(=O)N(C)c1cccnc1Nc1nc(-c2cc3c(cn2)N(C)CC3)ns1] | N-methyl-N-(2-(3-(1-methyl-2,3-dihydro-1H-pyrrolo[2,3-c]pyridin-5-yl)-1,2,4-thiadiazol-5-ylamino)pyridin-3-yl)acetamide | 382.2 | B | D, E | D, E | E | A |
| 203 | 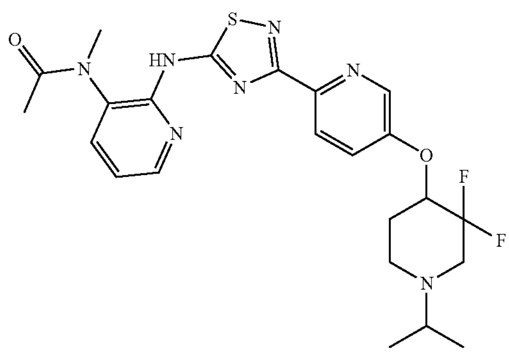 [SMILES: CC(=O)N(C)c1cccnc1Nc1nc(-c2ccc(OC3CCN(C(C)C)CC3(F)F)cn2)ns1] | N-(2-(3-(5-(3,3-difluoro-1-isopropyl-piperidin-4-yloxy)pyridin-2-yl)-1,2,4-thiadiazol-5-ylamino)pyridin-3-yl)-N-methylacetamide | 504.3 | A | D, E | E | E | A |
| 204 | 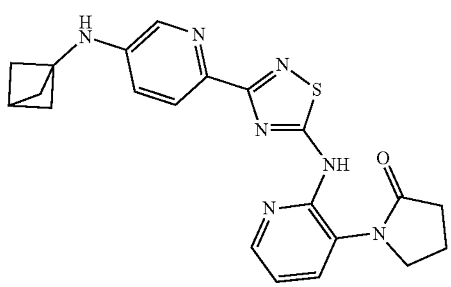 [SMILES: O=C1CCCN1c1cccnc1Nc1nc(-c2ccc(NC34CC(C3)C4)cn2)ns1] | 1-(2-(3-(5-(bicyclo[1.1.1]pentan-1-ylamino)pyridin-2-yl)-1,2,4-thiadiazol-5-ylamino)pyridin-3-yl)pyrrolidin-2-one | 420.3 | A | D, E | E | E | A |
| 205 | 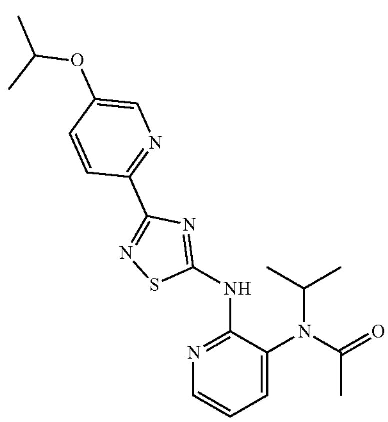 [SMILES: CC(=O)N(c1cccnc1Nc1nc(-c2ccc(OC(C)C)cn2)ns1)C(C)C] | N-(2-(3-(5-isopropoxy-pyridin-2-yl)-1,2,4-thiadiazol-5-ylamino)pyridin-3-yl)-N-isopropy-lacetamide | 413.3 | A | E | | E | A |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 206 | 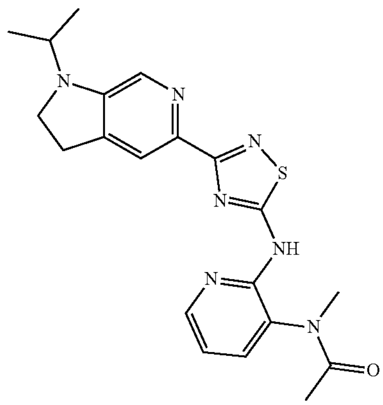 [SMILES: CC(=O)N(C)c1cccnc1Nc1nc(-c2cc3c(cn2)N(C(C)C)CC3)ns1] | N-(2-(3-(1-isopropyl-2,3-dihydro-1H-pyrrolo[2,3-c]pyridin-5-yl)-1,2,4-thiadiazol-5-ylamino)pyridin-3-yl)-N-methylacetamide | 410.3 | A | E | D, E | E | C |
| 207 | 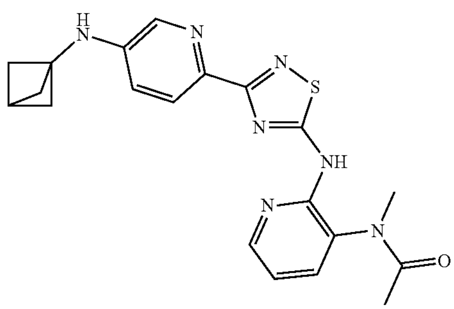 [SMILES: CC(=O)N(C)c1cccnc1Nc1nc(-c2ccc(NC34CC(C3)C4)cn2)ns1] | N-(2-(3-(5-(bicyclo[1.1.1]pentan-1-ylamino)pyridin-2-yl)-1,2,4-thiadiazol-5-ylamino)pyridin-3-yl)-N-methylacetamide | 408.3 | A | E | | E | A |
| 208 | 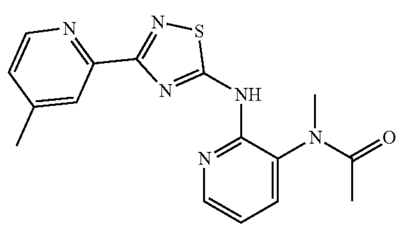 [SMILES: CC(=O)N(C)c1cccnc1Nc1nc(-c2cc(C)ccn2)ns1] | N-methyl-N-(2-(3-(4-methylpyridin-2-yl)-1,2,4-thiadiazol-5-ylamino)pyridin-3-yl)acetamide | 341.3 | A | | D, E | E | A |
| 209 | 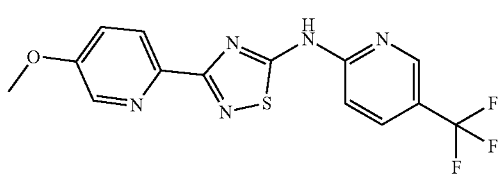 [SMILES: COc1ccc(-c2nsc(Nc3ccc(C(F)(F)F)cn3)n2)nc1] | 3-(5-methoxypyridin-2-yl)-N-(5-(trifluoromethyl)pyridin-2-yl)-1,2,4-thiadiazol-5-amine | 354.3 | C | | D, E | | A |
| 210 | 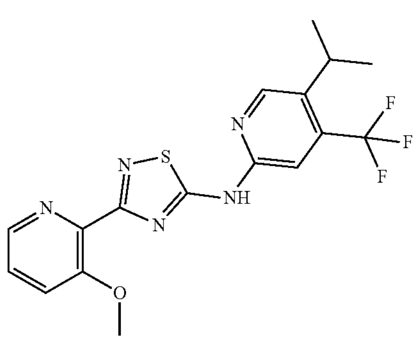 [SMILES: COc1cccnc1-c1nsc(Nc2cc(C(F)(F)F)c(C(C)C)cn2)n1] | N-(5-isopropyl-4-(trifluoromethyl)pyridin-2-yl)-3-(3-methoxypyridin-2-yl)-1,2,4-thiadiazol-5-amine | 396 | B | | D, E | | B |

TABLE 1-continued
| Cmpd No. | Structure | Name | M + 1 | O. guttu-rosa | B. malayi | L. sigmo-dontis | B. paha-ngi | D. immit-is |
|---|---|---|---|---|---|---|---|---|
| 211 | 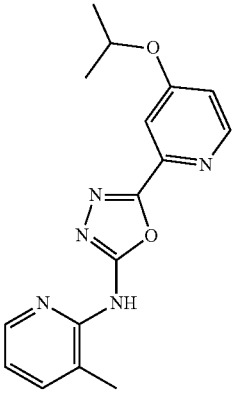 [SMILES: Cc1cccnc1Nc1nnc(-c2cc(OC(C)C)ccn2)o1] | 5-(4-isopropoxy-pyridin-2-yl)-N-(3-methyl-pyridin-2-yl)-1,3,4-oxadiazol-2-amine | 312.3 | A | | | | |
| 212 | 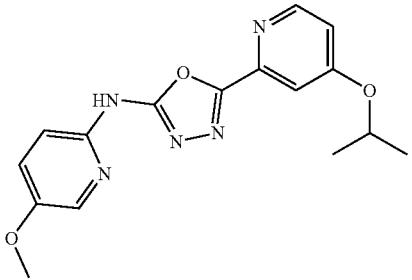 [SMILES: COc1ccc(Nc2nnc(-c3cc(OC(C)C)ccn3)o2)nc1] | 5-(4-isoprop-oxypyridin-2-yl)-N-(5-methoxy-pyridin-2-yl)-1,3,4-oxadiazol-2-amine | 328.1 | A | | | | |
| 213 | 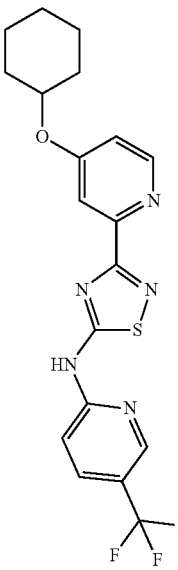 | 3-(4-(cyclo-hexyloxy)pyridin-2-yl)-N-(5-(trifluoromethyl)pyridin-2-yl)-1,2,4-thiadiazol-5-amine | 422.1 | C | | | | C |
| 214 | 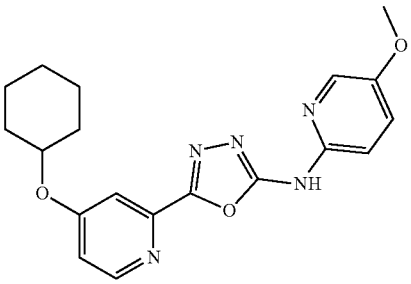 [SMILES: COc1ccc(Nc2nnc(-c3cc(OC4CCCCC4)ccn3)o2)nc1] | 5-(4-(cyclohexy-loxy)pyridin-2-yl)-N-(5-methoxypyridin-2-yl)-1,3,4-oxadiazol-2-amine | 368.2 | C | | | | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 215 | 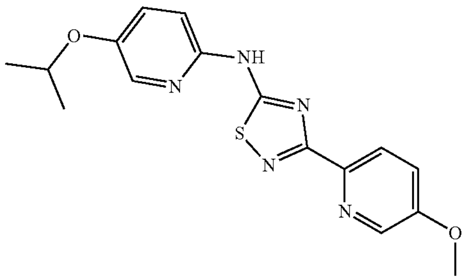 [SMILES: COc1ccc(-c2nsc(Nc3ccc(OC(C)C)cn3)n2)nc1] | N-(5-isoprop-oxypyridin-2-yl)-3-(5-methoxy-pyridin-2-yl)-1,2,4-thiadiazol-5-amine | 344.1 | A | | | | A |
| 216 | 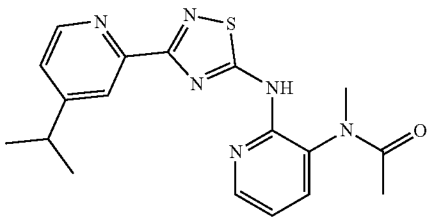 [SMILES: CC(=O)N(C)c1cccnc1Nc1nc(-c2cc(C(C)C)ccn2)ns1] | N-(2-(3-(4-iso-propylpyridin-2-yl)-1,2,4-thiadiazol-5-ylamino)pyridin-3-yl)-N-methyl-acetamide | 369.1 | B | E | E | D, E | B |
| 217 | 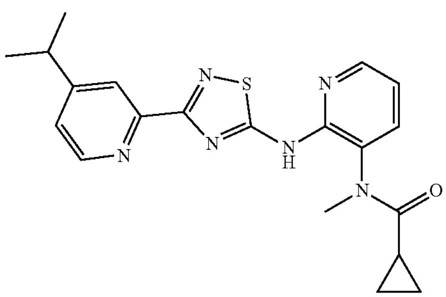 [SMILES: CC(C)c1ccnc(-c2nsc(Nc3ncccc3N(C)C(=O)C3CC3)n2)c1] | N-(2-(3-(4-isopropylpyridin-2-yl)-1,2,4-thiadiazol-5-ylamino)pyridin-3-yl)-N-methylcyclo-propanecarbox-amide | 395.3 | B | E | E | D, E | A |
| 218 | 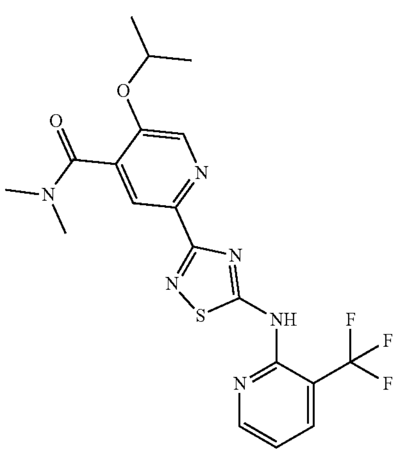 [SMILES: CC(C)Oc1cnc(-c2nsc(Nc3ncccc3C(F)(F)F)n2)cc1C(=O)N(C)C] | 5-isopropoxy-N,N-dimethyl-2-(5-(3-(trifluoromethyl)pyridin-2-ylamino)-1,2,4-thiadiazol-3-yl)isonico-tinamide | 453.1 | A | E | E | D, E | A |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 219 | 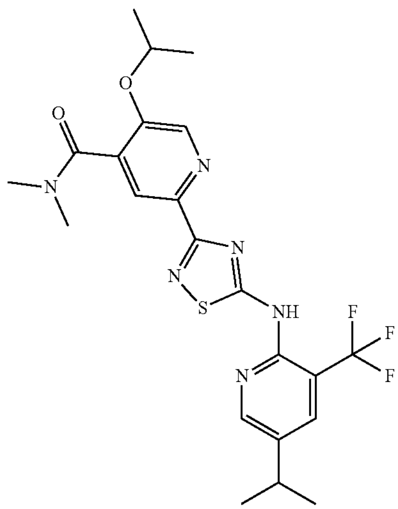 [SMILES: CC(C)Oc1cnc(-c2nsc(Nc3ncc(C(C)C)cc3C(F)(F)F)n2)cc1C(=O)N(C)C] | 5-isopropoxy-2-(5-(5-isopropyl-3-(trifluoromethyl)pyridin-2-ylamino)-1,2,4-thiadiazol-3-yl)-N,N-dimethylisonicotinamide | 495.3 | B | E | E | D, E | B |
| 220 | 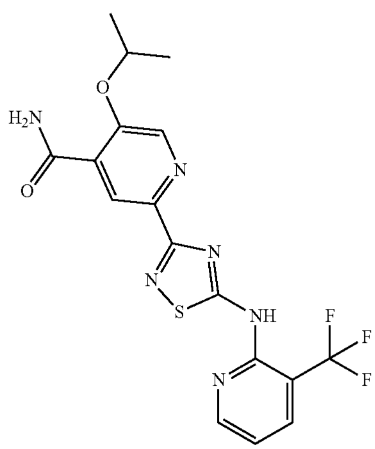 [SMILES: CC(C)Oc1cnc(-c2nsc(Nc3ncccc3C(F)(F)F)n2)cc1C(N)=O] | 5-isopropoxy-2-(5-(3-(trifluoromethyl)pyridin-2-ylamino)-1,2,4-thiadiazol-3-yl)isonicotinamide | 425.1 | B | E | E | E | A |
| 221 | 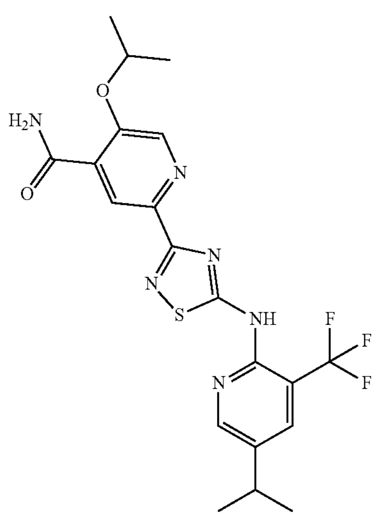 [SMILES: CC(C)Oc1cnc(-c2nsc(Nc3ncc(C(C)C)cc3C(F)(F)F)n2)cc1C(N)=O] | 5-isopropoxy-2-(5-(5-isopropyl-3-(trifluoromethyl)pyridin-2-ylamino)-1,2,4-thiadiazol-3-yl)isonicotinamide | 467.3 | B | E | E | E | B |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 222 | 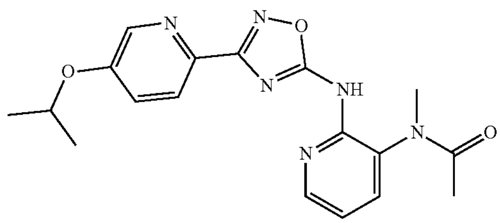 [SMILES: CC(=O)N(C)c1cccnc1Nc1nc(-c2ccc(OC(C)C)cn2)no1] | N-(2-(3-(5-isopropoxy-pyridin-2-yl)-1,2,4-oxadiazol-5-ylamino)pyridin-3-yl)-N-methyl-acetamide | 369.3 | A | | | | |
| 223 | 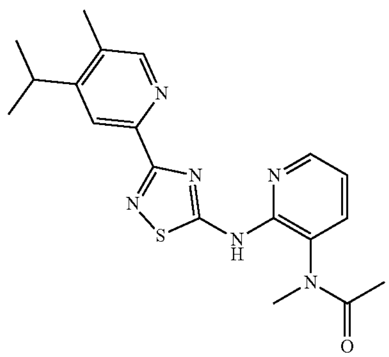 [SMILES: CC(=O)N(C)c1cccnc1Nc1nc(-c2cc(C(C)C)c(C)cn2)ns1] | N-(2-(3-(4-isopropyl-5-methylpyridin-2-yl)-1,2,4-thiadiazol-5-ylamino)pyridin-3-yl)-N-methyl-acetamide | 383.3 | B | E | E | D, E | B |
| 224 | 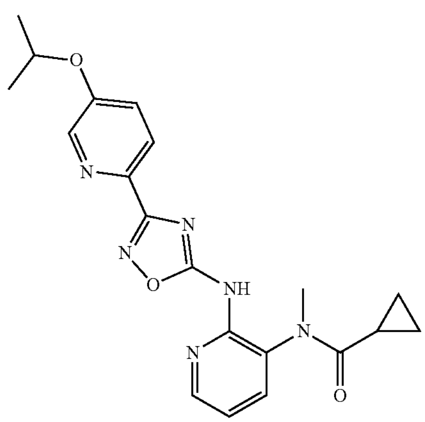 [SMILES: CC(C)Oc1ccc(-c2noc(Nc3ncccc3N(C)C(=O)C3CC3)n2)nc1] | N-(2-(3-(5-isopropoxy-pyridin-2-yl)-1,2,4-oxadiazol-5-ylamino)pyridin-3-yl)-N-methylcyclo-propanecarbox-amide | 395.3 | | | E | | |
| 225 | 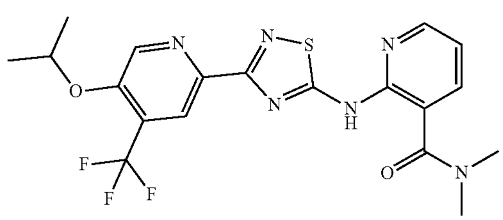 [SMILES: CC(C)Oc1cnc(-c2nsc(Nc3ncccc3C(=O)N(C)C)n2)cc1C(F)(F)F] | 2-(3-(5-isopropoxy-4-(trifluoromethyl)pyridin-2-yl)-1,2,4-thiadiazol-5-ylamino)-N,N-dimethyl-nicotinamide | 453.3 | A | E | D, E | D, E | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 226 | 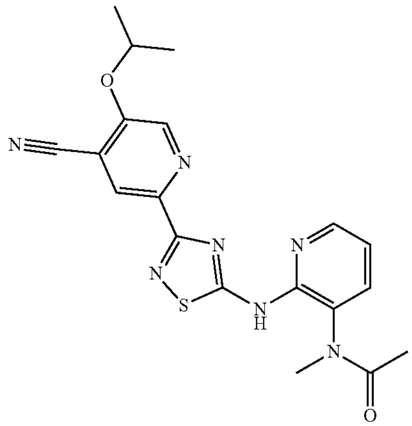 [SMILES: CC(=O)N(C)c1cccnc1Nc1nc(-c2cc(C#N)c(OC(C)C)cn2)ns1] | N-(2-(3-(4-cyano-5-isopropoxy-pyridin-2-yl)-1,2,4-thiadiazol-5-ylamino)pyridin-3-yl)-N-methyl-acetamide | 410.3 | A | E | | D, E | |
| 227 | 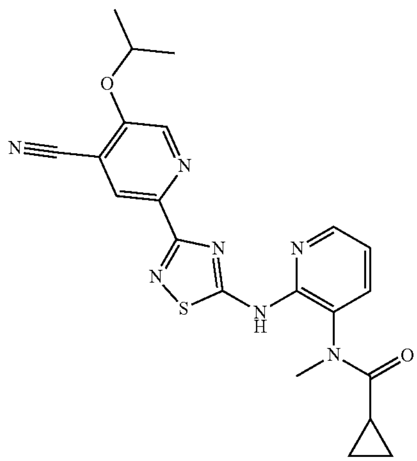 [SMILES: CC(C)Oc1cnc(-c2nsc(Nc3ncccc3N(C)C(=O)C3CC3)n2)cc1C#N] | N-(2-(3-(4-cyano-5-isopropoxy-pyridin-2-yl)-1,2,4-thiadiazol-5-ylamino)pyridin-3-yl)-N-methylcyclo-propanecarbox-amide | 436.2 | | E | | D | |
| 228 | 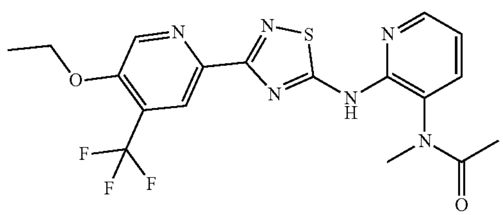 [SMILES: CCOc1cnc(-c2nsc(Nc3ncccc3N(C)C(C)=O)n2)cc1C(F)(F)F] | N-(2-(3-(5-ethoxy-4-(trifluoro-methyl)pyridin-2-yl)-1,2,4-thiadiazol-5-ylamino)pyridin-3-yl)-N-methyl-acetamide | 439.2 | | E | E | E | A |
| 229 | 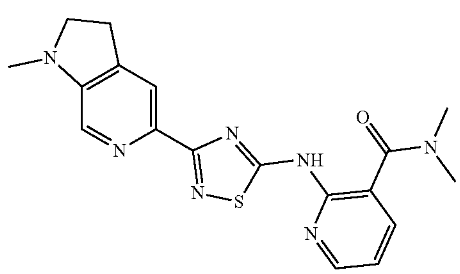 | N,N-dimethyl-2-(3-(1-methyl-2,3-dihydro-1H-pyrrolo[2,3-c]pyridin-5-yl)-1,2,4-thiadiazol-5-ylamino)nicotinamide | 382.2 | A | E | | D, E | |
| 230 | 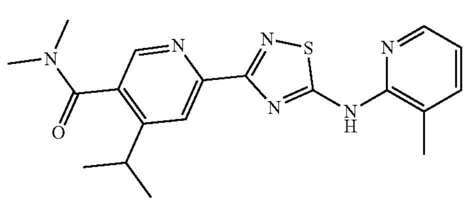 [SMILES: Cc1cccnc1Nc1nc(-c2cc(C(C)C)c(C(=O)N(C)C)cn2)ns1] | 4-isopropyl-N,N-dimethyl-6-(5-(3-methyl-pyridin-2-ylamino)-1,2,4-thiadiazol-3-yl)nicotinamide | 383.3 | A | | E | E | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 231 | 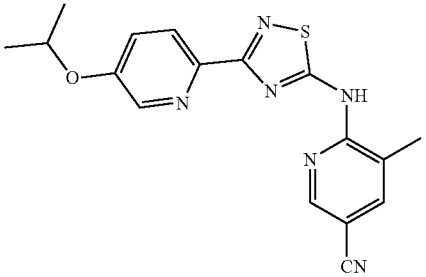 [SMILES: Cc1cc(C#N)cnc1Nc1nc(-c2ccc(OC(C)C)cn2)ns1] | 6-(3-(5-isoprop-oxypyridin-2-yl)-1,2,4-thiadiazol-5-ylamino)-5-methyl-nicotinonitrile | 353.3 | B | | E | E | B |
| 232 | 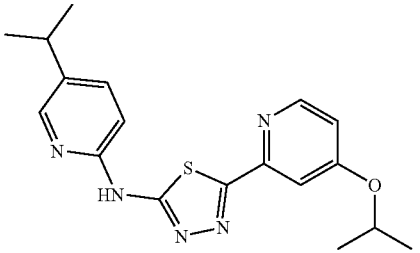 [SMILES: CC(C)Oc1ccnc(-c2nnc(Nc3ccc(C(C)C)cn3)s2)c1] | 5-(4-isopropoxy-pyridin-2-yl)-N-(5-isopropyl-pyridin-2-yl)-1,3,4-thiadiazol-2-amine | 356.1 | A | | | | |
| 233 | 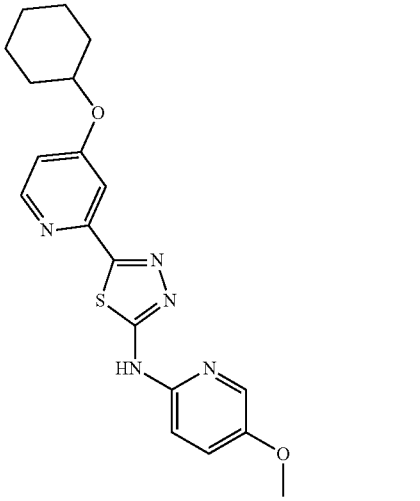 [SMILES: COc1ccc(Nc2nnc(-c3cc(OC4CCCCC4)ccn3)s2)nc1] | 5-(4-(cyclo-hexyloxy)pyridin-2-yl)-N-(5-methoxypyridin-2-yl)-1,3,4-thiadiazol-2-amine | 384.1 | C | | D | D, E | |
| 234 | 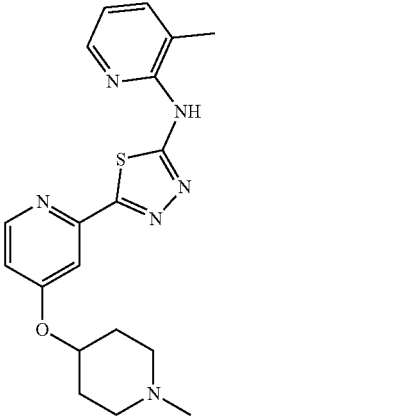 [SMILES: Cc1cccnc1Nc1nnc(-c2cc(OC3CCN(C)CC3)ccn2)s1] | 5-(4-(1-methyl-piperidin-4-yloxy)pyridin-2-yl)-N-(3-methylpyridin-2-yl)-1,3,4-thiadiazol-2-amine | 384.2 | | | D | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 235 | 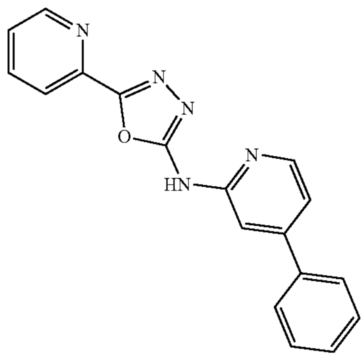 [SMILES: c1ccc(-c2ccnc(Nc3nnc(-c4ccccn4)o3)c2)cc1] | N-(4-phenyl-pyridin-2-yl)-5-(pyridin-2-yl)-1,3,4-oxadiazol-2-amine | 316.1 | A | | D | | |
| 236 | 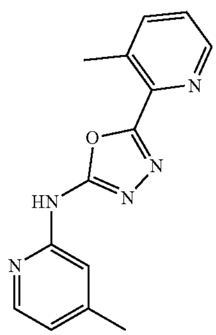 | 5-(3-methyl-pyridin-2-yl)-N-(4-methylpyridin-2-yl)-1,3,4-oxadiazol-2-amine | 268.1 | A | | D | | |
| 237 | 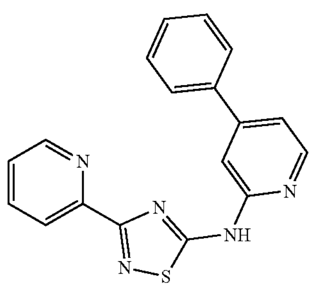 [SMILES: c1ccc(-c2ccnc(Nc3nc(-c4ccccn4)ns3)c2)cc1] | N-(4-phenyl-pyridin-2-yl)-3-(pyridin-2-yl)-1,2,4-thiadiazol-5-amine | 332.1 | A | | D, E | D | B |
| 238 | 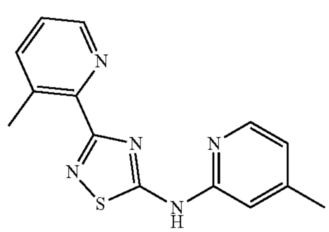 | 3-(3-methyl-pyridin-2-yl)-N-(4-methyl-pyridin-2-yl)-1,2,4-thiadiazol-5-amine | 283.9 | C | | D, E | D | B |
| 239 | 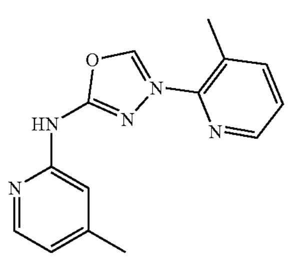 | 3-(3-methyl-pyridin-2-yl)-N-(4-methyl-pyridin-2-yl)-1,2,4-oxadiazol-5-amine | 268 | C | | D | D | A |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 240 | 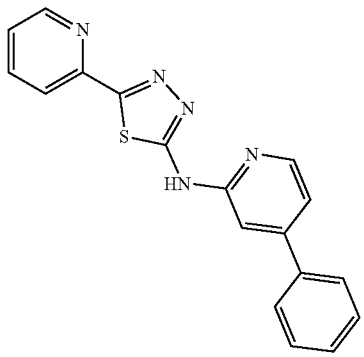 | N-(4-pheny-lpyridin-2-yl)-5-(pyridin-2-yl)-1,3,4-thiadiazol-2-amine | 332 | A | | D | | |
| 241 | 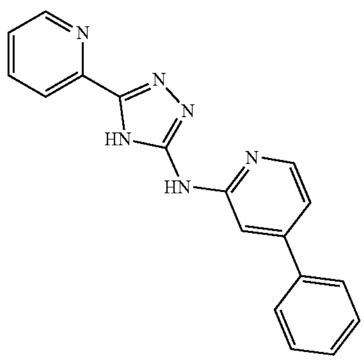 [SMILES: c1ccc(-c2ccnc(Nc3nnc(-c4ccccn4)[nH]3)c2)cc1] | 4-phenyl-N-(5-(pyridin-2-yl)-4H-1,2,4-triazol-3-yl)pyridin-2-amine | 315.2 | C | | D, E | D | B |
| 242 | 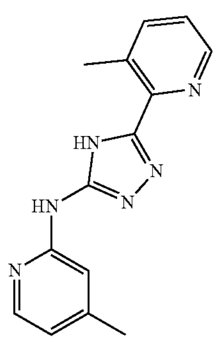 [SMILES: Cc1ccnc(Nc2nnc(-c3ncccc3C)[nH]2)c1] | 4-methyl-N-(5-(3-methyl-pyridin-2-yl)-4H-1,2,4-triazol-3-yl)pyridin-2-amine | 267.3 | A | | D | D | B |
| 243 | 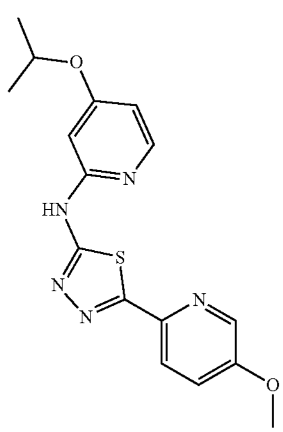 [SMILES: COc1ccc(-c2nnc(Nc3cc(OC(C)C)ccn3)s2)nc1] | N-(4-isoprop-oxypyridin-2-yl)-5-(5-methoxy-pyridin-2-yl)-1,3,4-thiadiazol-2-amine | 344.3 | A | | D | | |

TABLE 1-continued

| Cmpd No. | Structure | Name | M + 1 | *O. guttu-rosa* | *B. malayi* | *L. sigmo-dontis* | *B. paha-ngi* | *D. immit-is* |
|---|---|---|---|---|---|---|---|---|
| 244 | 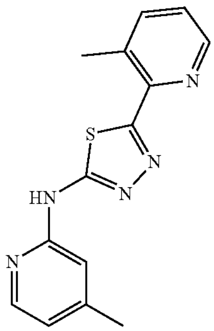 [SMILES: Cc1ccnc(Nc2nnc(-c3ncccc3C)s2)c1] | 5-(3-methyl-pyridin-2-yl)-N-(4-methyl-pyridin-2-yl)-1,3,4-thiadiazol-2-amine | 284.3 | A | | D | | |
| 245 | 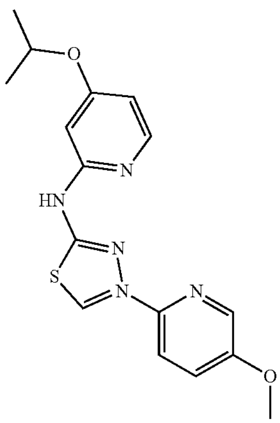 | N-(4-isoprop-oxypyridin-2-yl)-3-(5-methoxy-pyridin-2-yl)-1,2,4-thiadiazol-5-amine | 344.1 | A | | D, E | D | B |
| 246 | 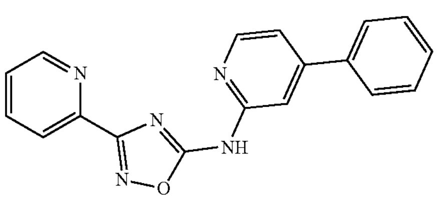 [SMILES: c1ccc(-c2ccnc(Nc3nc(-c4ccccn4)no3)c2)cc1] | N-(4-phenyl-pyridin-2-yl)-3-(pyridin-2-yl)-1,2,4-oxadiazol-5-amine | 316 | A | | | | A |
| 247 | 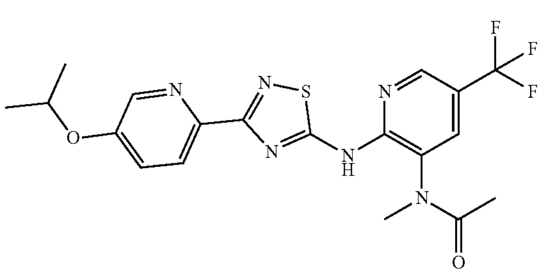 [SMILES: CC(=O)N(C)c1cc(C(F)(F)F)cnc1Nc1nc(-c2ccc(OC(C)C)cn2)ns1] | N-(2-(3-(5-isopropoxy-pyridin-2-yl)-1,2,4-thiadiazol-5-ylamino)-5-(trifluoro-methyl)pyridin-3-yl)-N-methylacetamide | 453.3 | C | E | D, E | D, E | C |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 248 | 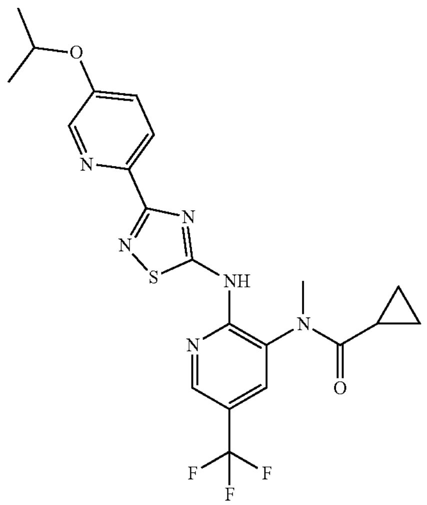 [SMILES: CC(C)Oc1ccc(-c2nsc(Nc3ncc(C(F)(F)F)cc3N(C)C(=O)C3CC3)n2)nc1] | N-(2-(3-(5-isopropoxy-pyridin-2-yl)-1,2,4-thiadiazol-5-ylamino)-5-(trifluoro-methyl)pyridin-3-yl)-N-methylcyclo-propanecarbox-amide | 479.2 | A | | E | E | C |
| 249 | 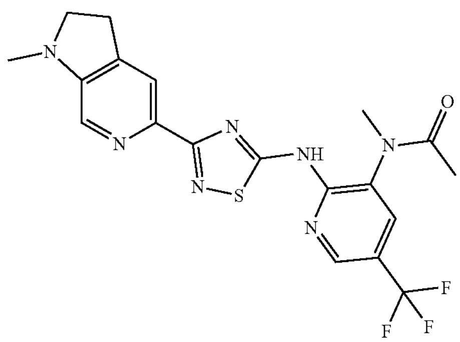 [SMILES: CC(=O)N(C)c1cc(C(F)(F)F)cnc1Nc1nc(-c2cc3c(cn2)N(C)CC3)ns1] | N-methyl-N-(2-(3-(1-methyl-2,3-dihydro-1H-pyrrolo[2,3-c]pyridin-5-yl)-1,2,4-thiadiazol-5-ylamino)-5-(trifluoromethyl)pyridin-3-yl)acetamide | 450.2 | B | E | D, E | D, E | C |
| 250 | 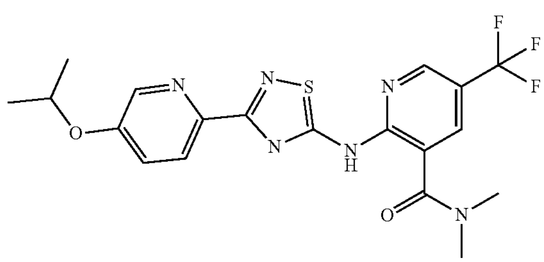 | 2-(3-(5-isoprop-oxypyridin-2-yl)-1,2,4-thiadiazol-5-ylamino)-N,N-dimethyl-5-(trifluoromethyl)nicotinamide | 453.1 | A | | D, E | E | C |
| 251 | 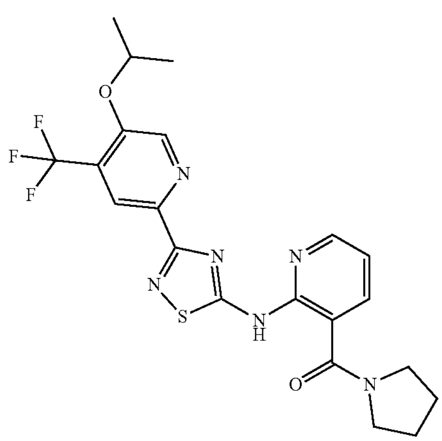 [SMILES: CC(C)Oc1cnc(-c2nsc(Nc3ncccc3C(=O)N3CCCC3)n2)cc1C(F)(F)F] | (2-(3-(5-isopropoxy-4-(trifluoromethyl)pyridin-2-yl)-1,2,4-thiadiazol-5-ylamino)pyridin-3-yl)(pyrrolidin-1-yl)methanone | 479.3 | A | | D, E | E | A |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 252 | 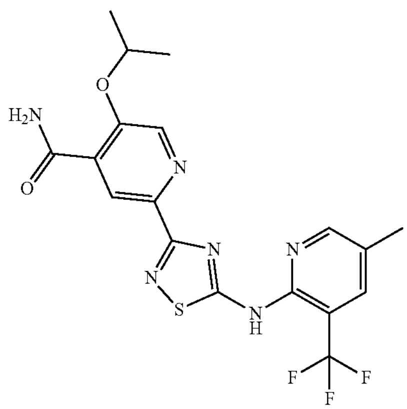 [SMILES: Cc1cnc(Nc2nc(-c3cc(C(N)=O)c(OC(C)C)cn3)ns2)c(C(F)(F)F)c1] | 5-isopropoxy-2-(5-(5-methyl-3-(trifluoromethyl)pyridin-2-ylamino)-1,2,4-thiadiazol-3-yl)isonicotinamide | 439.2 | A | | D, E | E | A |
| 253 | 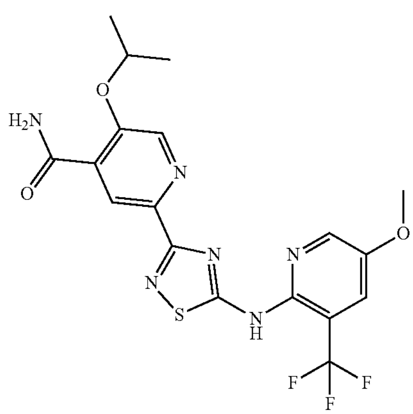 [SMILES: COc1cnc(Nc2nc(-c3cc(C(N)=O)c(OC(C)C)cn3)ns2)c(C(F)(F)F)c1] | 5-isopropoxy-2-(5-(5-methoxy-3-(trifluoromethyl)pyridin-2-ylamino)-1,2,4-thiadiazol-3-yl)isonicotinamide | 455.1 | A | | D, E | E | A |
| 254 | 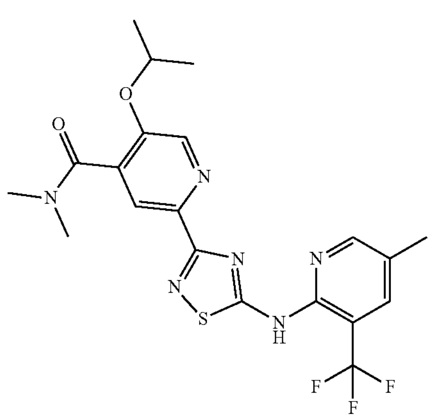 | 5-isopropoxy-N,N-dimethyl-2-(5-(5-methyl-3-(trifluoromethyl)pyridin-2-ylamino)-1,2,4-thiadiazol-3-yl)isonicotinamide | 467.3 | A | | D, E | E | A |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 255 | 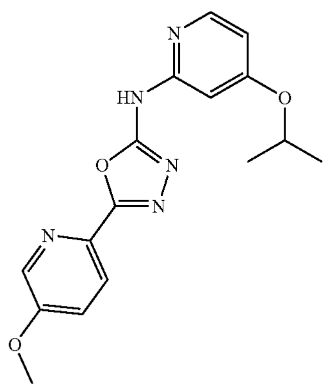 [SMILES: COc1ccc(-c2nnc(Nc3cc(OC(C)C)ccn3)o2)nc1] | N-(4-isoprop-oxypyridin-2-yl)-5-(5-methoxy-pyridin-2-yl)-1,3,4-oxadiazol-2-amine | 328 | A | | D | | |
| 256 | 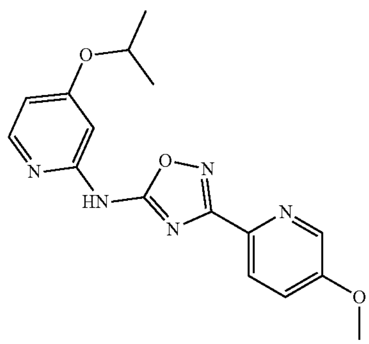 [SMILES: COc1ccc(-c2noc(Nc3cc(OC(C)C)ccn3)n2)nc1] | N-(4-isoprop-oxypyridin-2-yl)-3-(5-methoxy-pyridin-2-yl)-1,2,4-oxadiazol-5-amine | 328.1 | | | D | E | |
| 257 | 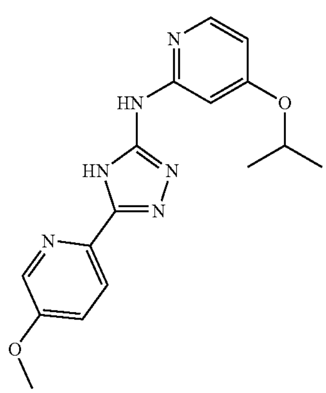 [SMILES: COc1ccc(-c2nnc(Nc3cc(OC(C)C)ccn3)[nH]2)nc1] | 4-isopropoxy-N-(5-(5-methoxy-pyridin-2-yl)-4H-1,2,4-triazol-3-yl)pyridin-2-amine | 327.3 | A | | D | D | A |
| 258 | 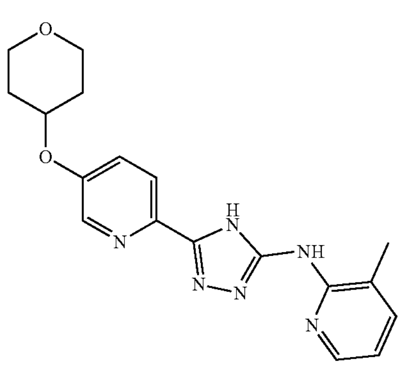 [SMILES: Cc1cccnc1Nc1nnc(-c2ccc(OC3CCOCC3)cn2)[nH]1] | 3-methyl-N-(5-(5-(tetrahydro-2H-pyran-4-yloxy)pyridin-2-yl)-4H-1,2,4-triazol-3-yl)pyridin-2-amine | 353.2 | C | | D | | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 259 | 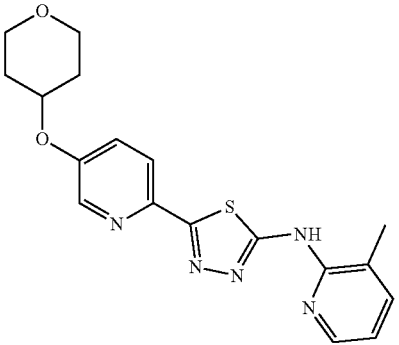 [SMILES: Cc1cccnc1Nc1nnc(-c2ccc(OC3CCOCC3)cn2)s1] | N-(3-methyl-pyridin-2-yl)-5-(5-(tetrahydro-2H-pyran-4-yloxy)pyridin-2-yl)-1,3,4-thiadiazol-2-amine | 370.2 | | | D | | |
| 260 | 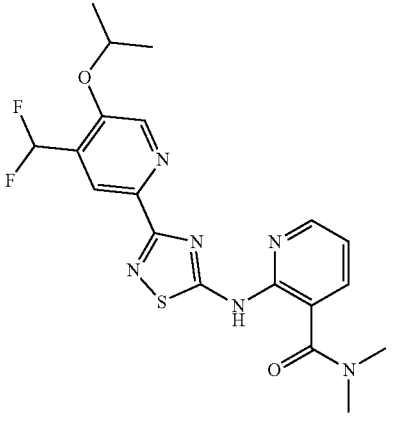 [SMILES: CC(C)Oc1cnc(-c2nsc(Nc3ncccc3C(=O)N(C)C)n2)cc1C(F)F] | 2-(3-(4-(difluoro-methyl)-5-isopropoxy-pyridin-2-yl)-1,2,4-thiadiazol-5-ylamino)-N,N-dimethyl-nicotinamide | 435.3 | A | | D | D, E | B |
| 261 | 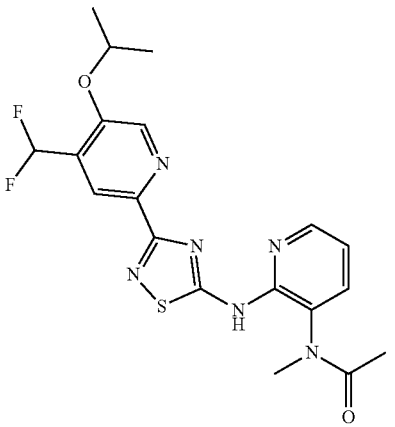 [SMILES: CC(=O)N(C)c1cccnc1Nc1nc(-c2cc(C(F)F)c(OC(C)C)cn2)ns1] | N-(2-(3-(4-(difluoromethyl)-5-isopropoxy-pyridin-2-yl)-1,2,4-thiadiazol-5-ylamino)pyridin-3-yl)-N-methylacetamide | 435.3 | A | E | D, E | D, E | B |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 262 | 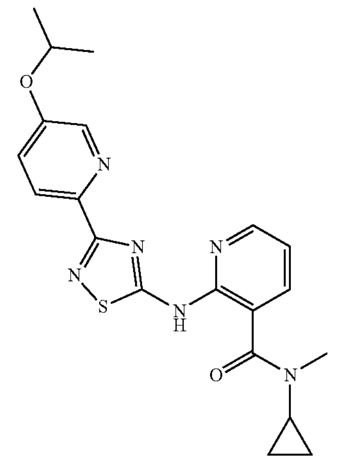 [SMILES: CC(C)Oc1ccc(-c2nsc(Nc3ncccc3C(=O)N(C)C3CC3)n2)nc1] | N-cyclo-propyl-2-(3-(5-isopropoxy-pyridin-2-yl)-1,2,4-thiadiazol-5-ylamino)-N-methyl-nicotinamide | 411.3 | A | D | D | D, E | B |
| 263 | 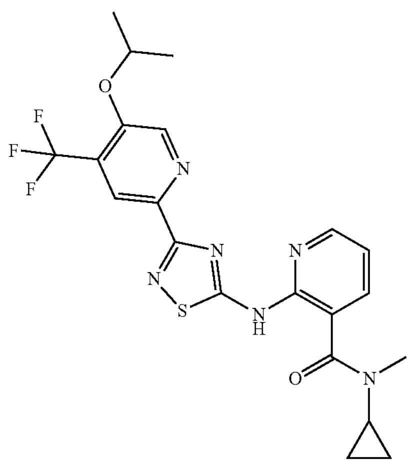 [SMILES: CC(C)Oc1cnc(-c2nsc(Nc3ncccc3C(=O)N(C)C3CC3)n2)cc1C(F)(F)F] | N-cyclo-propyl-2-(3-(5-isopropoxy-4-(trifluoro-methyl)pyridin-2-yl)-1,2,4-thiadiazol-5-ylamino)-N-methyl-nicotinamide | 479.3 | A | D | D, E | D, E | C |
| 264 | 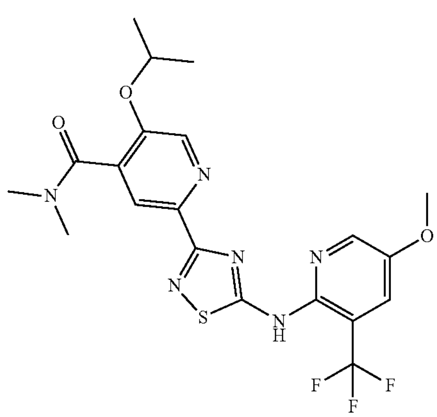 | 5-isopropoxy-2-(5-(5-methoxy-3-(trifluoro-methyl)pyridin-2-ylamino)-1,2,4-thiadiazol-3-yl)-N,N-dimethyliso-nicotinamide | 483.1 | A | D, E | D | D, E | B |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 265 | 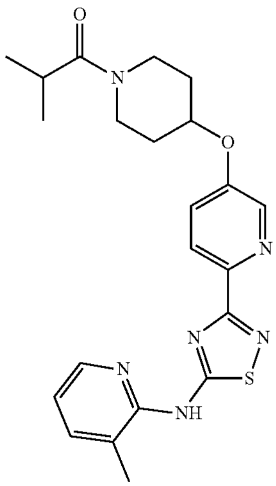 [SMILES: Cc1cccnc1Nc1nc(-c2ccc(OC3CCN(C(=O)C(C)C)CC3)cn2)ns1] | 2-methyl-1-(4-(6-(5-(3-methylpyridin-2-ylamino)-1,2,4-thiadiazol-3-yl)pyridin-3-yloxy)piperidin-1-yl)propan-1-one | 439.2 | A | D, E | D, E | D, E | A |
| 266 | 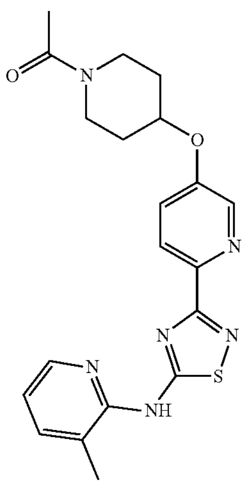 [SMILES: CC(=O)N1CCC(Oc2ccc(-c3nsc(Nc4ncccc4C)n3)nc2)CC1] | 1-(4-(6-(5-(3-methyl-pyridin-2-ylamino)-1,2,4-thiadiazol-3-yl)pyridin-3-yloxy)piperidin-1-yl)ethanone | 411.1 | A | | E | E | A |
| 267 | 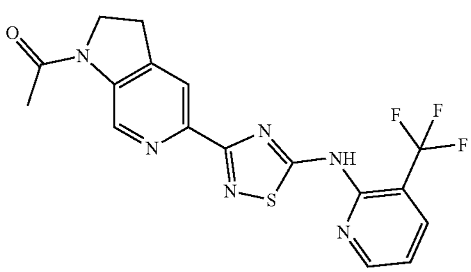 [SMILES: CC(=O)N1CCc2cc(-c3nsc(Nc4ncccc4C(F)(F)F)n3)ncc21] | 1-(5-(5-(3-(trifluoromethyl)pyridin-2-ylamino)-1,2,4-thiadiazol-3-yl)-2,3-dihydro-1H-pyrrolo[2,3-c]pyridin-1-yl)ethanone | 407.1 | A | E | E | D, E | B |
| 268 | 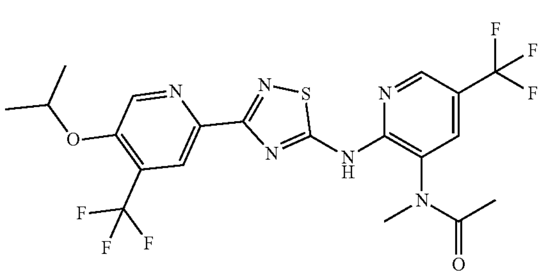 [SMILES: CC(=O)N(C)c1cc(C(F)(F)F)cnc1Nc1nc(-c2cc(C(F)(F)F)c(OC(C)C)cn2)ns1] | N-(2-(3-(5-isopropoxy-4-(trifluoromethyl)pyridin-2-yl)-1,2,4-thiadiazol-5-ylamino)-5-(trifluoromethyl)pyridin-3-yl)-N-methylacetamide | 521.2 | A | E | D, E | D, E | C |

TABLE 1-continued

| Cmpd No. | Structure | Name | O. guttu- rosa M + 1 | B. malayi | L. sigmo- dontis | B. paha- ngi | D. immit- is |
|---|---|---|---|---|---|---|---|
| 269 | 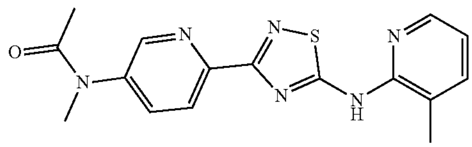 [SMILES: CC(=O)N(C)c1ccc(-c2nsc(Nc3ncccc3C)n2)nc1] | N-methyl-N-(6-(5-(3-methylpyridin-2-ylamino)-1,2,4-thiadiazol-3-yl)pyridin-3-yl)acetamide | 341.2 | D, E | D, E | E | A |
| 270 | 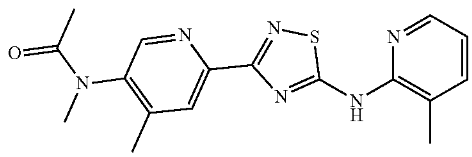 [SMILES: CC(=O)N(C)c1cnc(-c2nsc(Nc3ncccc3C)n2)cc1C] | N-methyl-N-(4-methyl-6-(5-(3-methylpyridin-2-ylamino)-1,2,4-thiadiazol-3-yl)pyridin-3-yl)acetamide | 355.2 A | D, E | D, E | E | |
| 271 | 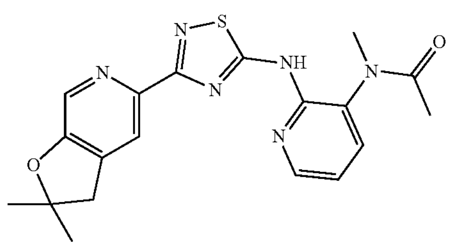 [SMILES: CC(=O)N(C)c1cccnc1Nc1nc(-c2cc3c(cn2)OC(C)(C)C3)ns1] | N-(2-(3-(2,2-dimethyl-2,3-dihydrofuro[2,3-c]pyridin-5-yl)-1,2,4-thiadiazol-5-ylamino)pyridin-3-yl)-N-methylacetamide | 397.2 A | D, E | D | D, E | A |
| 272 | 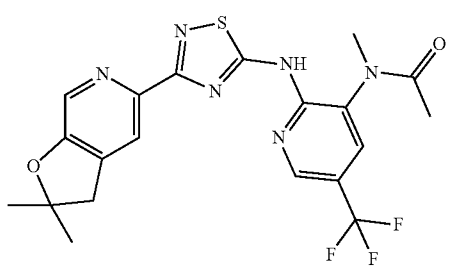 [SMILES: CC(=O)N(C)c1cc(C(F)(F)F)cnc1Nc1nc(-c2cc3c(cn2)OC(C)(C)C3)ns1] | N-(2-(3-(2,2-dimethyl-2,3-dihydrofuro[2,3-c]pyridin-5-yl)-1,2,4-thiadiazol-5-ylamino)-5-(trifluoromethyl)pyridin-3-yl)-N-methylacetamide | 465.1 B | D, E | D, E | D, E | C |
| 273 | 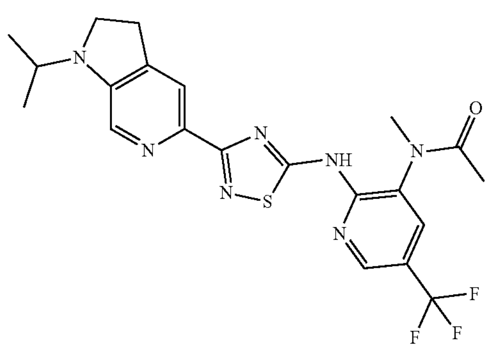 [SMILES: CC(=O)N(C)c1cc(C(F)(F)F)cnc1Nc1nc(-c2cc3c(cn2)N(C(C)C)CC3)ns1] | N-(2-(3-(1-isopropyl-2,3-dihydro-1H-pyrrolo[2,3-c]pyridin-5-yl)-1,2,4-thiadiazol-5-ylamino)-5-(trifluoromethyl)pyridin-3-yl)-N-methylacetamide | 478.2 B | D, E | D, E | D, E | C |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 274 | 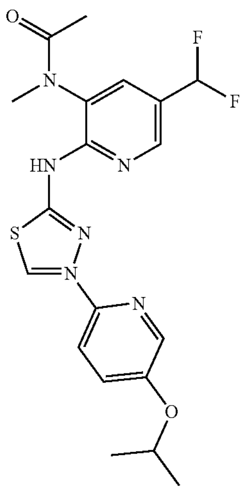 | N-(5-(difluoro-methyl)-2-(3-(5-isoprop-oxypyridin-2-yl)-1,2,4-thiadiazol-5-ylamino) pyridin-3-yl)-N-methylacetamide | 435.1 | A | D, E | D, E | E | A |
| 275 | 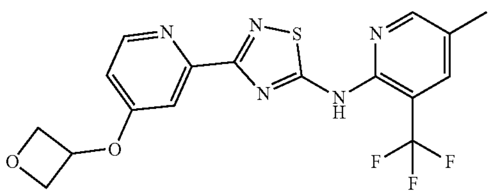 [SMILES: Cc1cnc(Nc2nc(-c3cc(OC4COC4)ccn3)ns2)c(C(F)(F)F)c1] | N-(5-methyl-3-(trifluoromethyl) pyridin-2-yl)-3-(4-(oxetan-3-yloxy)pyridin-2-yl)-1,2,4-thiadiazol-5-amine | 410 | A | D, E | D, E | D, E | C |
| 276 | 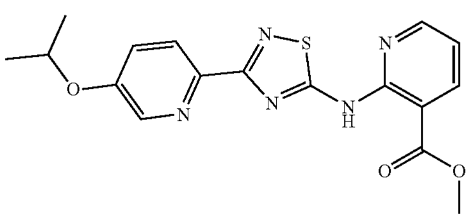 [SMILES: COC(=O)c1cccnc1Nc1nc(-c2ccc(OC(C)C)cn2)ns1] | methyl 2-(3-(5-isopropoxy-pyridin-2-yl)-1,2,4-thiadiazol-5-ylamino) nicotinate | 372.1 | A | D, E | D, E | D, E | A |
| 277 | 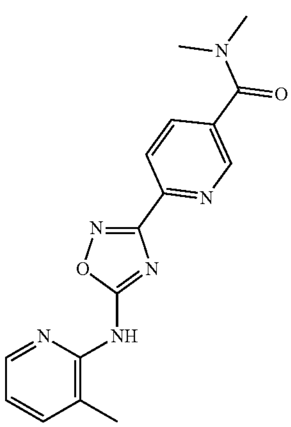 [SMILES: Cc1cccnc1Nc1nc(-c2ccc(C(=O)N(C)C)cn2)no1] | N,N-dimethyl-6-(5-(3-methylpyridin-2-ylamino)-1,2,4-oxadiazol-3-yl)nicotinamide | 325.2 | A | | | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 278 | 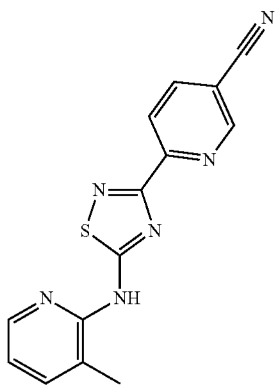 [SMILES: Cc1cccnc1Nc1nc(-c2ccc(C#N)cn2)ns1] | 6-(5-(3-methylpyridin-2-ylamino)-1,2,4-thiadiazol-3-yl)nicotinonitrile | 295.1 | A | | | | |
| 279 | 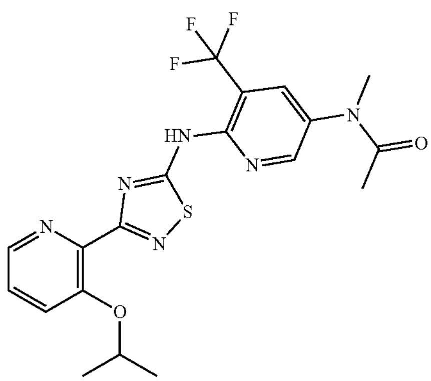 [SMILES: CC(=O)N(C)c1cnc(Nc2nc(-c3ncccc3OC(C)C)ns2)c(C(F)(F)F)c1] | N-(6-(3-(3-isopropoxy-pyridin-2-yl)-1,2,4-thiadiazol-5-ylamino)-5-(trifluoro-methyl)pyridin-3-yl)-N-methylacetamide | 453.1 | A | | D, E | | |
| 280 | 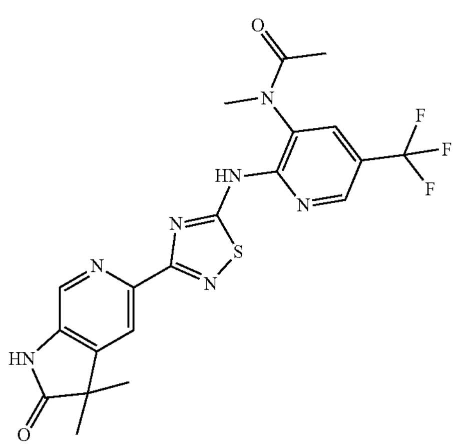 [SMILES: CC(=O)N(C)c1cc(C(F)(F)F)cnc1Nc1nc(-c2cc3c(cn2)NC(=O)C3(C)C)ns1] | N-(2-(3-(3,3-dimethyl-2-oxo-2,3-dihydro-1H-pyrrolo[2,3-c]pyridin-5-yl)-1,2,4-thiadiazol-5-ylamino)-5-(trifluoromethyl)pyridin-3-yl)-N-methylacetamide | 478.1 | A | | D | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 281 | 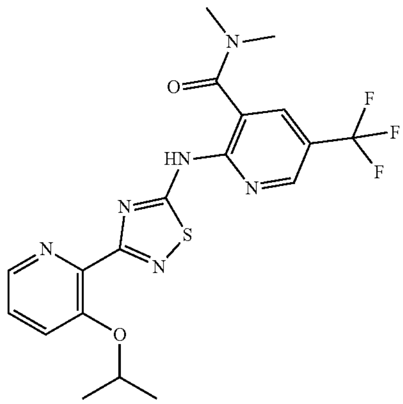 [SMILES: CC(C)Oc1cccnc1-c1nsc(Nc2ncc(C(F)(F)F)cc2C(=O)N(C)C)n1] | 2-(3-(3-isoprop- oxypyridin-2- yl)-1,2,4- thiadiazol-5- ylamino)- N,N-dimethyl-5- (trifluoromethyl) nicotinamide | 453.1 | A | D, E | | | |
| 282 | 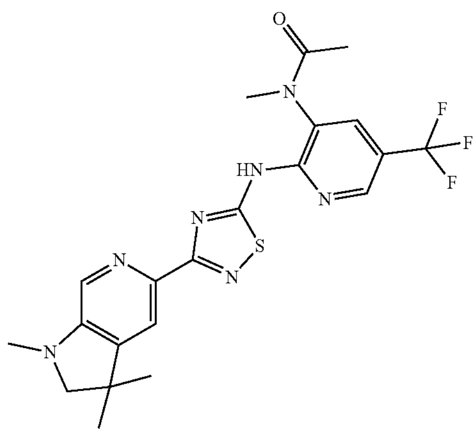 [SMILES: CC(=O)N(C)c1cc(C(F)(F)F)cnc1Nc1nc(-c2cc3c(cn2)N(C)CC3(C)C)ns1] | N-methyl-N-(5- (trifluoromethyl)- 2-(3-(1,3,3- trimethyl-2,3- dihydro-1H- pyrrolo[2,3-c] pyridin-5-yl)- 1,2,4-thiadiazol-5- ylamino)pyridin- 3-yl)acetamide | 478.2 | | D, E | | | |
| 283 | 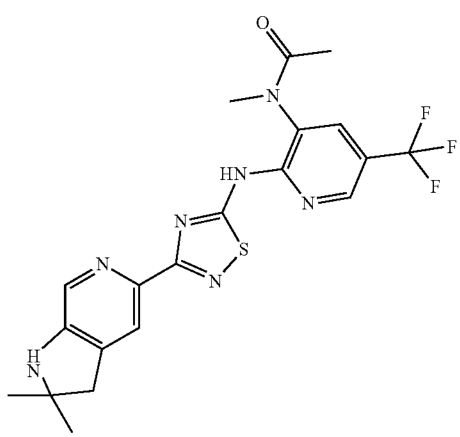 [SMILES: CC(=O)N(C)c1cc(C(F)(F)F)cnc1Nc1nc(-c2cc3c(cn2)NC(C)(C)C3)ns1] | N-(2-(3-(2,2- dimethyl-2,3- dihydro-1H- pyrrolo[2,3- c]pyridin-5-yl)- 1,2,4-thiadiazol- 5-ylamino)-5- (trifluoromethyl) pyridin-3-yl)- N-methylacetamide | 464.1 | | D, E | | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 284 | 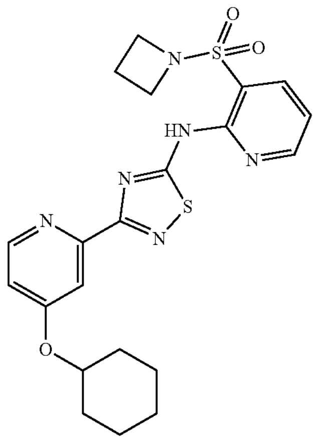 [SMILES: O=S(=O)(c1cccnc1Nc1nc(-c2cc(OC3CCCCC3)ccn2)ns1)N1CCC1] | N-(3-(azetidin-1-ylsulfonyl)pyridin-2-yl)-3-(4-(cyclohexyloxy)pyridin-2-yl)-1,2,4-thiadiazol-5-amine | 473.3 | | D, E | | | |
| 285 | 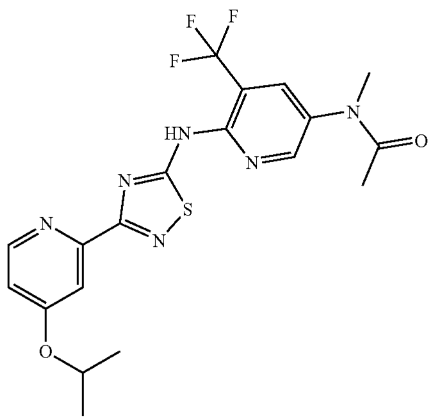 [SMILES: CC(=O)N(C)c1cnc(Nc2nc(-c3cc(OC(C)C)ccn3)ns2)c(C(F)(F)F)c1] | N-(6-(3-(4-isopropoxy-pyridin-2-yl)-1,2,4-thiadiazol-5-ylamino)-5-(trifluoromethyl)pyridin-3-yl)-N-methylacetamide | 453.1 | A | D, E | | | |
| 286 | 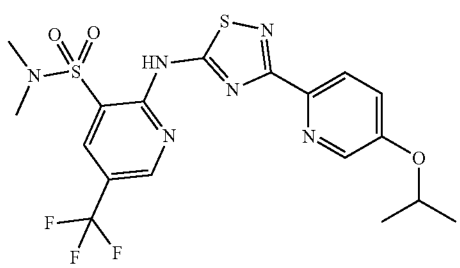 [SMILES: CC(C)Oc1ccc(-c2nsc(Nc3ncc(C(F)(F)F)cc3S(=O)(=O)N(C)C)n2)nc1] | 2-(3-(5-isopropoxy-pyridin-2-yl)-1,2,4-thiadiazol-5-ylamino)-N,N-dimethyl-5-(trifluoromethyl)pyridine-3-sulfonamide | 489.1 | A | D, E | | D, E | |
| 287 | 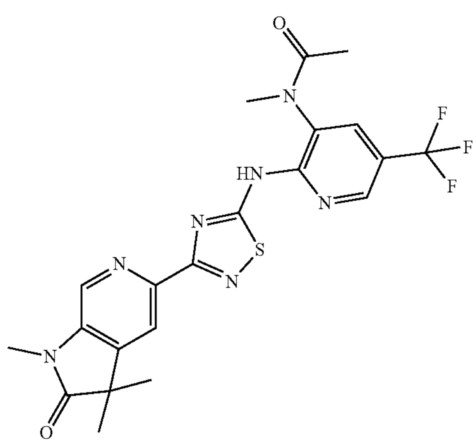 [SMILES: CC(=O)N(C)c1cc(C(F)(F)F)cnc1Nc1nc(-c2cc3c(cn2)N(C)C(=O)C3(C)C)ns1] | N-methyl-N-(5-(trifluoromethyl)-2-(3-(1,3,3-trimethyl-2-oxo-2,3-dihydro-1H-pyrrolo[2,3-c]pyridin-5-yl)-1,2,4-thiadiazol-5-ylamino)pyridin-3-yl)acetamide | 492.1 | A | D, E | | D, E | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 288 | 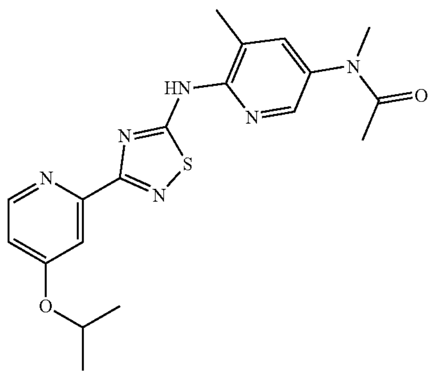 [SMILES: CC(=O)N(C)c1cnc(Nc2nc(-c3cc(OC(C)C)ccn3)ns2)c(C)c1] | N-(6-(3-(4-isopropoxypyridin-2-yl)-1,2,4-thiadiazol-5-ylamino)-5-methylpyridin-3-yl)-N-methylacetamide | 399.3 | A | D, E | | D, E | |
| 289 | 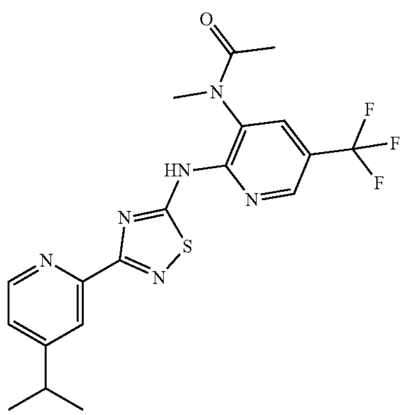 [SMILES: CC(=O)N(C)c1cc(C(F)(F)F)cnc1Nc1nc(-c2cc(C(C)C)ccn2)ns1] | 2-(3-(4-isopropylpyridin-2-yl)-1,2,4-thiadiazol-5-ylamino)-(trifluoromethyl)nicotinamide | 437.1 | | D, E | | D, E | |
| 290 | 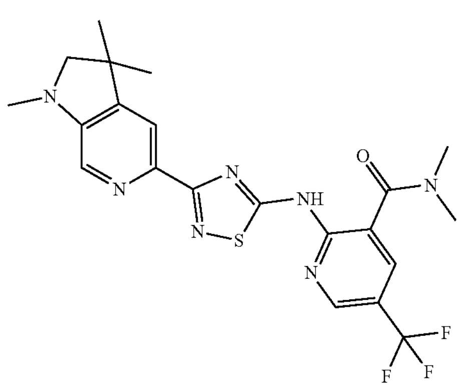 | N,N-dimethyl-5-(trifluoromethyl)-2-(3-(1,3,3-trimethyl-2,3-dihydro-1H-pyrrolo[2,3-c]pyridin-5-yl)-1,2,4-thiadiazol-5-ylamino)nicotinamide | 478.2 | | D, E | | D, E | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 291 | 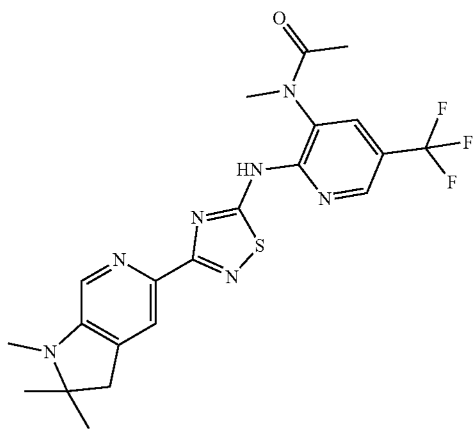 [SMILES: CC(=O)N(C)c1cc(C(F)(F)F)cnc1Nc1nc(-c2cc3c(cn2)N(C)C(C)(C)C3)ns1] | N-methyl-N-(5-(trifluoromethyl)-2-(3-(1,2,2-trimethyl-2,3-dihydro-1H-pyrrolo[2,3-c]pyridin-5-yl)-1,2,4-thiadiazol-5-ylamino)pyridin-3-yl)acetamide | 478.2 | C | D, E | | D, E | |
| 292 | 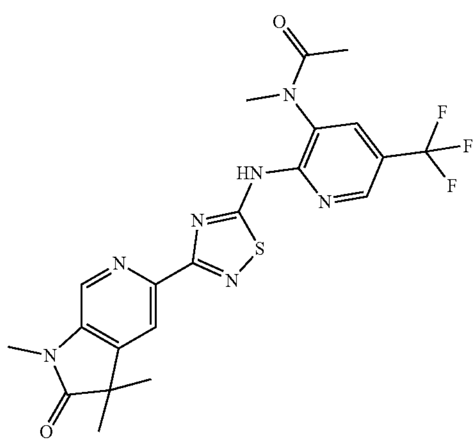 [SMILES: CC(=O)N(C)c1cc(C(F)(F)F)cnc1Nc1nc(-c2cc3c(cn2)N(C)C(=O)C3(C)C)ns1] | N,N-dimethyl-5-(trifluoromethyl)-2-(3-(1,3,3-trimethyl-2-oxo-2,3-dihydro-1H-pyrrolo[2,3-c]pyridin-5-yl)-1,2,4-thiadiazol-5-ylamino)nicotinamide | 492.2 | A | D, E | D, E | | |
| 293 | 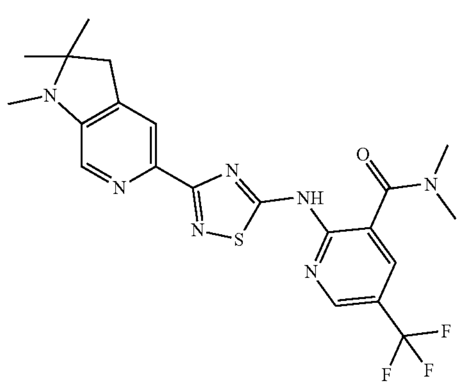 | N,N-dimethyl-5-(trifluoromethyl)-2-(3-(1,2,2-trimethyl-2,3-dihydro-1H-pyrrolo[2,3-c]pyridin-5-yl)-1,2,4-thiadiazol-5-ylamino)nicotinamide | 478.2 | C | D, E | | D, E | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 294 | 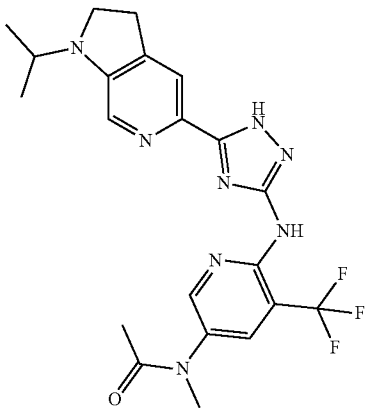 [SMILES: CC(=O)N(C)c1cnc(Nc2n[nH]c(-c3cc4c(cn3)N(C(C)C)CC4)n2)c(C(F)(F)F)c1] | N-(6-(5-(1-isopropyl-2,3-dihydro-1H-pyrrolo[2,3-c]pyridin-5-yl)-1H-1,2,4-triazol-3-ylamino)-5-(trifluoromethyl)pyridin-3-yl)-N-methylacetamide | 461.3 | A | D | | D, E | |
| 295 | 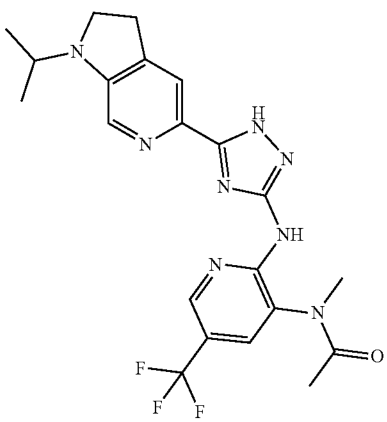 [SMILES: CC(=O)N(C)c1cc(C(F)(F)F)cnc1Nc1n[nH]c(-c2cc3c(cn2)N(C(C)C)CC3)n1] | N-(2-(5-(1-isopropyl-2,3-dihydro-1H-pyrrolo[2,3-c]pyridin-5-yl)-1H-1,2,4-triazol-3-ylamino)-5-(trifluoromethyl)pyridin-3-yl)-N-methylacetamide | 461.3 | A | D | | D, E | |
| 296 | 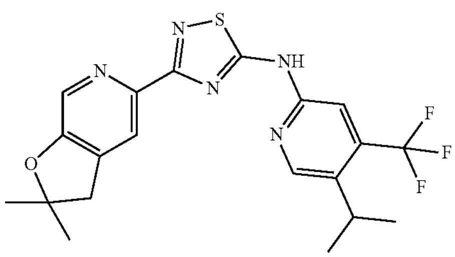 [SMILES: CC(C)c1cnc(Nc2nc(-c3cc4c(cn3)OC(C)(C)C4)ns2)cc1C(F)(F)F] | 3-(2,2-dimethyl-2,3-dihydrofuro[2,3-c]pyridin-5-yl)-N-(5-isopropyl-4-(trifluoromethyl)pyridin-2-yl)-1,2,4-thiadiazol-5-amine | 436.2 | C | D | D, E | D, E | |
| 297 | 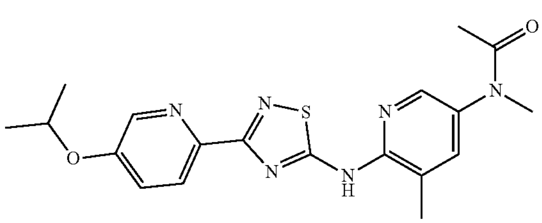 [SMILES: CC(=O)N(C)c1cnc(Nc2nc(-c3ccc(OC(C)C)cn3)ns2)c(C)c1] | N-(6-(3-(5-isopropoxypyridin-2-yl)-1,2,4-thiadiazol-5-ylamino)-5-methylpyridin-3-yl)-N-methylacetamide | 399.1 | B | | D | | |
| 298 | 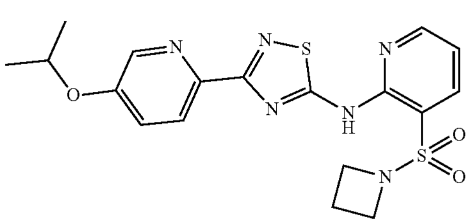 [SMILES: CC(C)Oc1ccc(-c2nsc(Nc3ncccc3S(=O)(=O)N3CCC3)n2)nc1] | N-(3-(azetidin-1-ylsulfonyl)pyridin-2-yl)-3-(5-isopropoxypyridin-2-yl)-1,2,4-thiadiazol-5-amine | 433.2 | B | | D | | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 299 | 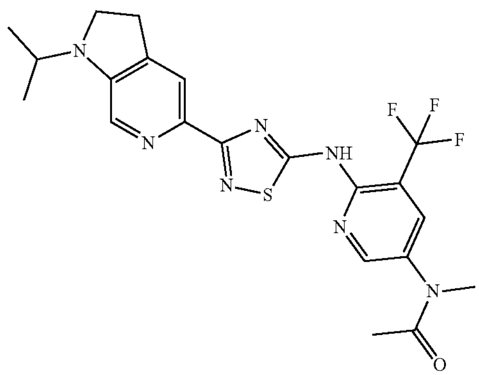 [SMILES: CC(=O)N(C)c1cnc(Nc2nc(-c3cc4c(cn3)N(C(C)C)CC4)ns2)c(C(F)(F)F)c1] | N-(6-(3-(1-isopropyl-2,3-dihydro-1H-pyrrolo[2,3-c]pyridin-5-yl)-1,2,4-thiadiazol-5-ylamino)-5-(trifluoromethyl)pyridin-3-yl)-N-methylacetamide | 478.2 | C | D | D, E | D, E | |
| 300 | 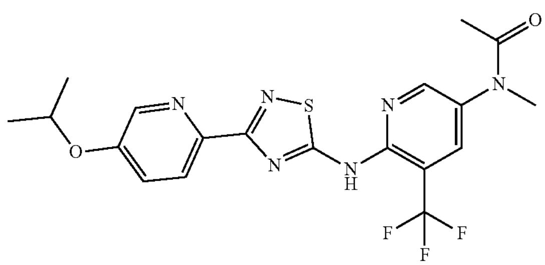 [SMILES: CC(=O)N(C)c1cnc(Nc2nc(-c3ccc(OC(C)C)cn3)ns2)c(C(F)(F)F)c1] | N-(6-(3-(5-isopropoxypyridin-2-yl)-1,2,4-thiadiazol-5-ylamino)-5-(trifluoromethyl)pyridin-3-yl)-N-methylacetamide | 453.2 | A | D | D | D, E | |
| 301 | 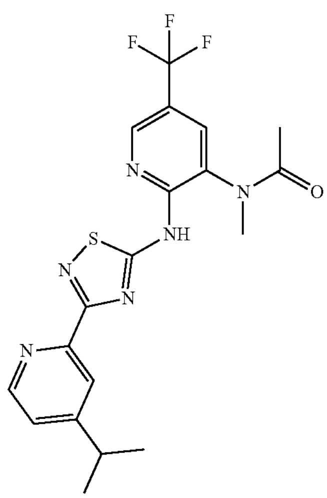 [SMILES: CC(=O)N(C)c1cc(C(F)(F)F)cnc1Nc1nc(-c2cc(C(C)C)ccn2)ns1] | N-(2-(3-(4-isopropylpyridin-2-yl)-1,2,4-thiadiazol-5-ylamino)-5-(trifluoromethyl)pyridin-3-yl)-N-methylacetamide | 437.3 | C | D | D, E | D, E | |
| 302 | 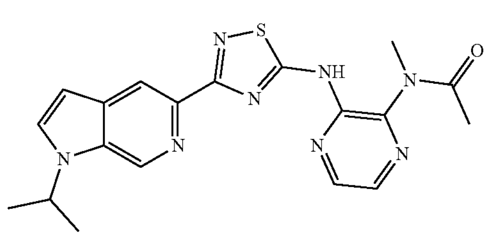 [SMILES: CC(=O)N(C)c1nccnc1Nc1nc(-c2cc3ccn(C(C)C)c3cn2)ns1] | N-(3-(3-(1-isopropyl-1H-pyrrolo[2,3-c]pyridin-5-yl)-1,2,4-thiadiazol-5-ylamino)pyrazin-2-yl)-N-methylacetamide | 409.2 | C | D | D, E | D, E | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 303 | 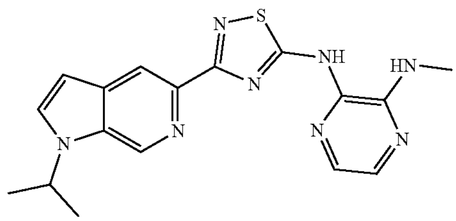 [SMILES: CNc1nccnc1Nc1nc(-c2cc3ccn(C(C)C)c3cn2)ns1] | N2-(3-(1-isopropyl-1H-pyrrolo[2,3-c]pyridin-5-yl)-1,2,4-thiadiazol-5-yl)-N3-methylpyrazine-2,3-diamine | 367.2 | C | | D, E | | |
| 304 | 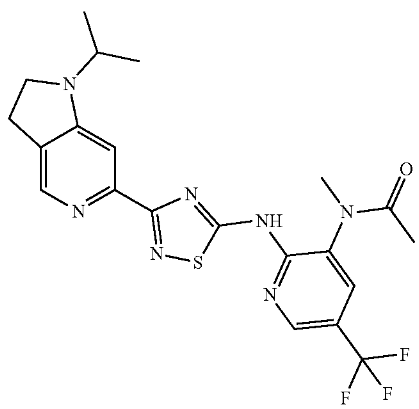 [SMILES: CC(=O)N(C)c1cc(C(F)(F)F)cnc1Nc1nc(-c2cc3c(cn2)CCN3C(C)C)ns1] | N-(2-(3-(1-isopropyl-2,3-dihydro-1H-pyrrolo[3,2-c]pyridin-6-yl)-1,2,4-thiadiazol-5-ylamino)-5-(trifluoromethyl)pyridin-3-yl)-N-methylacetamide | 478.2 | C | D | D, E | D, E | |
| 305 | 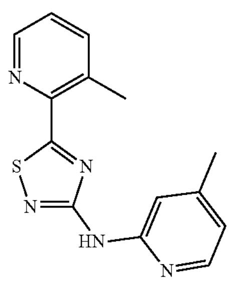 [SMILES: Cc1ccnc(Nc2nsc(-c3ncccc3C)n2)c1] | 5-(3-methyl-pyridin-2-yl)-N-(4-methylpyridin-2-yl)-1,2,4-thiadiazol-3-amine | 283.8 | C | | D | | |
| 306 | 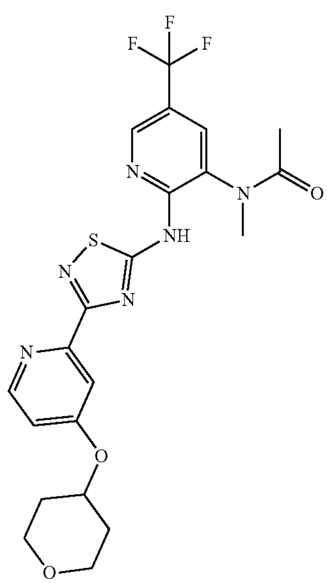 [SMILES: CC(=O)N(C)c1cc(C(F)(F)F)cnc1Nc1nc(-c2cc(OC3CCOCC3)ccn2)ns1] | N-methyl-N-(2-(3-(4-(tetrahydro-2H-pyran-4-yloxy)pyridin-2-yl)-1,2,4-thiadiazol-5-ylamino)-5-(trifluoromethyl)pyridin-3-yl)acetamide | 495.3 | C | D | | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 307 | 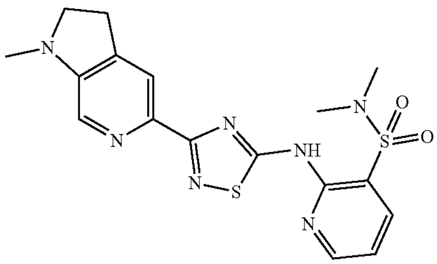 [SMILES: CN1CCc2cc(-c3nsc(Nc4ncccc4S(=O)(=O)N(C)C)n3)ncc21] | N,N-dimethyl-2-(3-(1-methyl-2,3-dihydro-1H-pyrrolo[2,3-c]pyridin-5-yl)-1,2,4-thiadiazol-5-ylamino)pyridine-3-sulfonamide | 418.2 | A | D, E | | | |
| 308 | 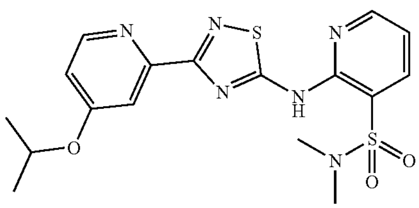 [SMILES: CC(C)Oc1ccnc(-c2nsc(Nc3ncccc3S(=O)(=O)N(C)C)n2)c1] | 2-(3-(4-isopropoxypyridin-2-yl)-1,2,4-thiadiazol-5-ylamino)-N,N-dimethyl-pyridine-3-sulfonamide | 421.2 | C | D, E | | | |
| 309 | 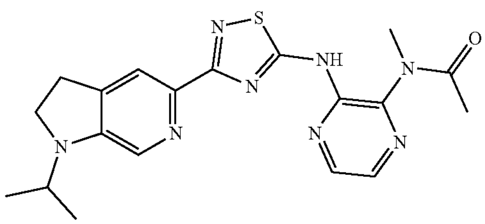 | N-(3-(3-(1-isopropyl-2,3-dihydro-1H-pyrrolo[2,3-c]pyridin-5-yl)-1,2,4-thiadiazol-5-ylamino)pyrazin-2-yl)-N-methylacetamide | 411.3 | C | D, E | | | |
| 310 | 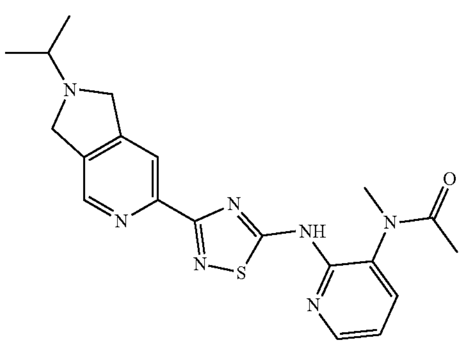 [SMILES: CC(=O)N(C)c1cccnc1Nc1nc(-c2cc3c(cn2)CN(C(C)C)C3)ns1] | N-(2-(3-(2-isopropyl-2,3-dihydro-1H-pyrrolo[3,4-c]pyridin-6-yl)-1,2,4-thiadiazol-5-ylamino)pyridin-3-yl)-N-methylacetamide | 410.3 | A | E | | | |
| 311 | 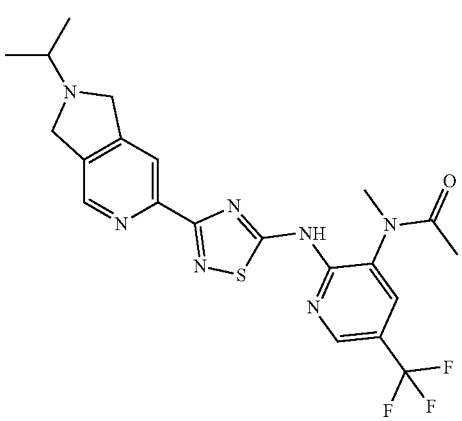 [SMILES: CC(=O)N(C)c1cc(C(F)(F)F)cnc1Nc1nc(-c2cc3c(cn2)CN(C(C)C)C3)ns1] | N-(2-(3-(2-isopropyl-2,3-dihydro-1H-pyrrolo[3,4-c]pyridin-6-yl)-1,2,4-thiadiazol-5-ylamino)-5-(trifluoromethyl)pyridin-3-yl)-N-methylacetamide | 478.2 | C | D, E | | | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 312 | 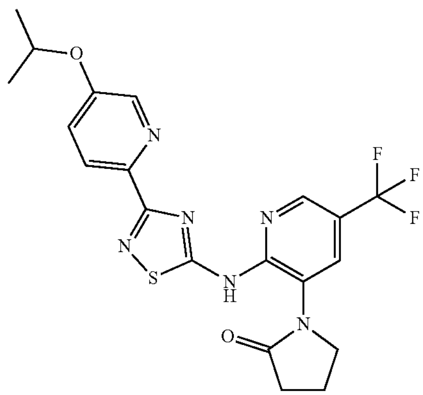 [SMILES: CC(C)Oc1ccc(-c2nsc(Nc3ncc(C(F)(F)F)cc3N3CCCC3=O)n2)nc1] | 1-(2-(3-(5-isopropoxypyridin-2-yl)-1,2,4-thiadiazol-5-ylamino)-5-(trifluoromethyl)pyridin-3-yl)pyrrolidin-2-one | 465.1 | A | D, E | | | |
| 313 | 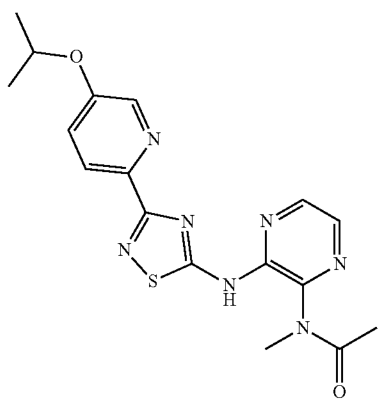 [SMILES: CC(=O)N(C)c1nccnc1Nc1nc(-c2ccc(OC(C)C)cn2)ns1] | N-(3-(3-(5-isopropoxypyridin-2-yl)-1,2,4-thiadiazol-5-ylamino)pyrazin-2-yl)-N-methylacetamide | 386.1 | A | D, E | | | |
| 314 | 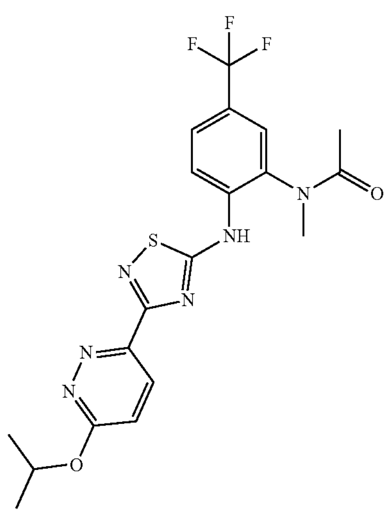 [SMILES: CC(=O)N(C)c1cc(C(F)(F)F)ccc1Nc1nc(-c2ccc(OC(C)C)nn2)ns1] | N-(2-(3-(6-isopropoxy-pyridazin-3-yl)-1,2,4-thiadiazol-5-ylamino)-5-(trifluoromethyl)pyridin-3-yl)-N-methylacetamide | 454.1 | A | D, E | | | |
| 315 | 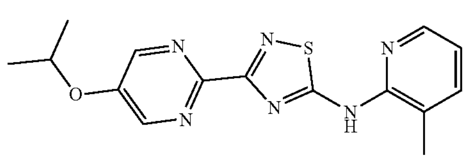 [SMILES: Cc1cccnc1Nc1nc(-c2ncc(OC(C)C)cn2)ns1] | 3-(5-isopropoxy-pyrimidin-2-yl)-N-(3-methylpyridin-2-yl)-1,2,4-thiadiazol-5-amine | 329.3 | A | E | | | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 316 | 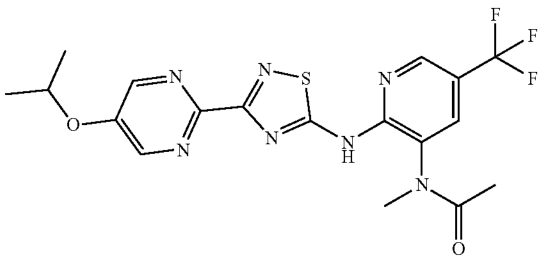 [SMILES: CC(=O)N(C)c1cc(C(F)(F)F)cnc1Nc1nc(-c2ncc(OC(C)C)cn2)ns1] | N-(2-(3-(5-isopropoxy-pyrimidin-2-yl)-1,2,4-thiadiazol-5-ylamino)-5-(trifluoromethyl) pyridin-3-yl)-N-methylacetamide | 454.2 | A | | | | |
| 317 | 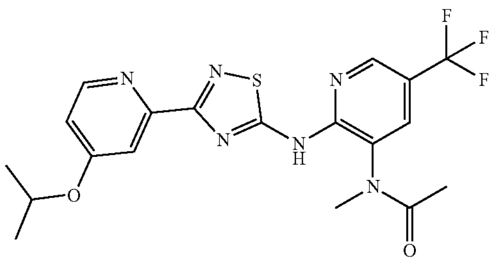 [SMILES: CC(=O)N(C)c1cc(C(F)(F)F)cnc1Nc1nc(-c2cc(OC(C)C)ccn2)ns1] | N-(2-(3-(4-isopropoxypyridin-2-yl)-1,2,4-thiadiazol-5-ylamino)-5-(trifluoromethyl) pyridin-3-yl)-N-methylacetamide | 453.3 | C | D, E | D, E | D, E | |
| 318 | 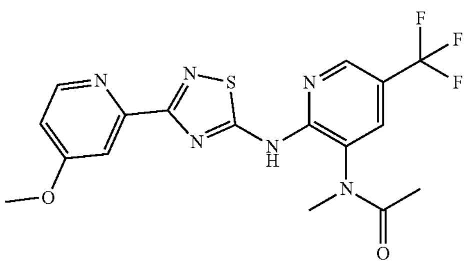 [SMILES: COc1ccnc(-c2nsc(Nc3ncc(C(F)(F)F)cc3N(C)C(C)=O)n2)c1] | N-(2-(3-(4-methoxypyridin-2-yl)-1,2,4-thiadiazol-5-ylamino)-5-(trifluoromethyl) pyridin-3-yl)-N-methylacetamide | 425.1 | C | D, E | D, E | D, E | |
| 319 | 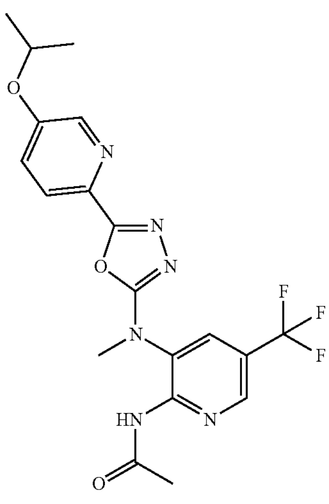 [SMILES: CC(=O)Nc1ncc(C(F)(F)F)cc1N(C)c1nnc(-c2ccc(OC(C)C)cn2)o1] | N-(3-((5-(5-isopropoxypyridin-2-yl)-1,3,4-oxadiazol-2-yl)(methyl) amino)-5-(trifluoromethyl) pyridin-2-yl)acetamide | 437.3 | A | D, E | | | |
| 320 | 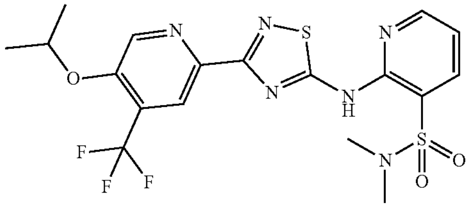 [SMILES: CC(C)Oc1cnc(-c2nsc(Nc3ncccc3S(=O)(=O)N(C)C)n2)cc1C(F)(F)F] | 2-(3-(5-isopropoxy-4-(trifluoromethyl) pyridin-2-yl)-1,2,4-thiadiazol-5-ylamino)-N,N-dimethyl-pyridine-3-sulfonamide | 489.1 | A | D, E | D, E | E | |

TABLE 1-continued

| Cmpd No. | Structure | Name | M + 1 | *O. guttu- rosa* | *B. malayi* | *L. sigmo- dontis* | *B. paha- ngi* | *D. immit- is* |
|---|---|---|---|---|---|---|---|---|
| 321 | 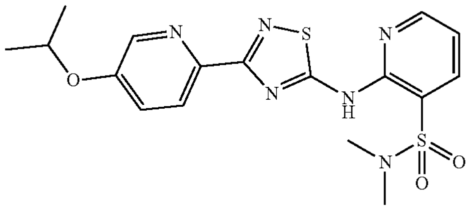 [SMILES: CC(C)Oc1ccc(-c2nsc(Nc3ncccc3S(=O)(=O)N(C)C)n2)nc1] | 2-(3-(5-isoprop- oxypyridin-2- yl)-1,2,4- thiadiazol-5- ylamino)- N,N-dimethyl- pyridine-3- sulfonamide | 421.2 | A | D, E | D | D, E | |
| 322 | 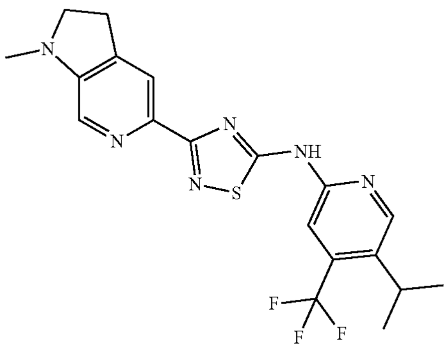 [SMILES: CC(C)c1cnc(Nc2nc(-c3cc4c(cn3)N(C)CC4)ns2)cc1C(F)(F)F] | N-(5-isopropyl-4- (trifluoromethyl) pyridin-2-yl)-3- (1-methyl-2,3- dihydro-1H- pyrrolo[2,3-c] pyridin-5-yl)- 1,2,4-thiadiazol- 5-amine | 421.2 | C | D, E | D, E | D, E | |
| 323 | 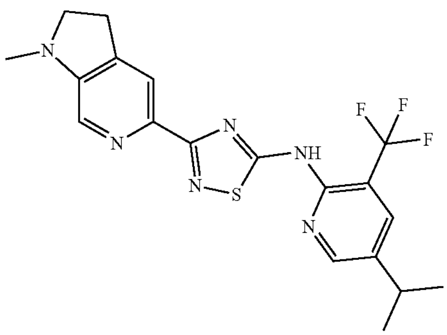 [SMILES: CC(C)c1cnc(Nc2nc(-c3cc4c(cn3)N(C)CC4)ns2)c(C(F)(F)F)c1] | N-(5-isopropyl-3- (trifluoromethyl) pyridin-2-yl)-3- (1-methyl-2,3- dihydro-1H- pyrrolo[2,3-c] pyridin-5-yl)- 1,2,4-thiadiazol- 5-amine | 421.2 | C | D, E | D, E | D, E | |
| 324 | 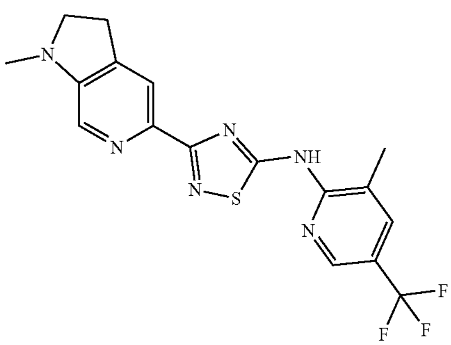 [SMILES: Cc1cc(C(F)(F)F)cnc1Nc1nc(-c2cc3c(cn2)N(C)CC3)ns1] | 3-(1-methyl-2,3- dihydro-1H- pyrrolo[2,3-c] pyridin-5-yl)-N- (3-methyl-5- (trifluoromethyl) pyridin-2-yl)- 1,2,4-thiadiazol- 5-amine | 393.1 | C | D | D, E | D, E | |
| 325 | 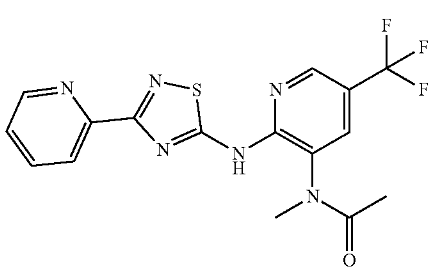 [SMILES: CC(=O)N(C)c1cc(C(F)(F)F)cnc1Nc1nc(-c2ccccn2)ns1] | N-methyl-N- (2-(3-(pyridin-2- yl)-1,2,4- thiadiazol-5- ylamino)- 5-(trifluoromethyl) pyridin-3- yl)acetamide | 395.2 | C | | D | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 326 | 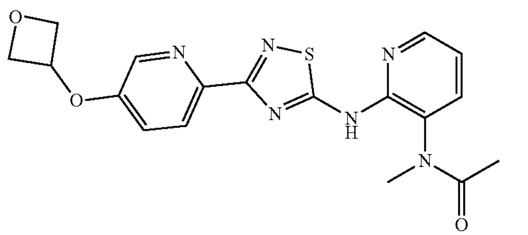 [SMILES: CC(=O)N(C)c1cccnc1Nc1nc(-c2ccc(OC3COC3)cn2)ns1] | N-methyl-N-(2-(3-(5-(oxetan-3-yloxy)pyridin-2-yl)-1,2,4-thiadiazol-5-ylamino)pyridin-3-yl)acetamide | 399.1 | A | | E | | |
| 327 | 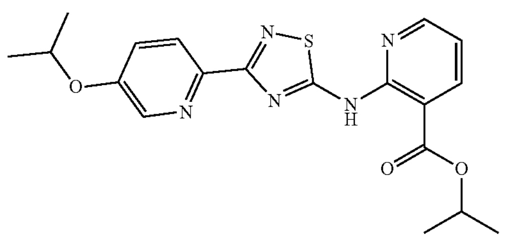 [SMILES: CC(C)OC(=O)c1cccnc1Nc1nc(-c2ccc(OC(C)C)cn2)ns1] | isopropyl 2-(3-(5-isopropoxypyridin-2-yl)-1,2,4-thiadiazol-5-ylamino)nicotinate | 400.2 | A | D | D | | |
| 328 | 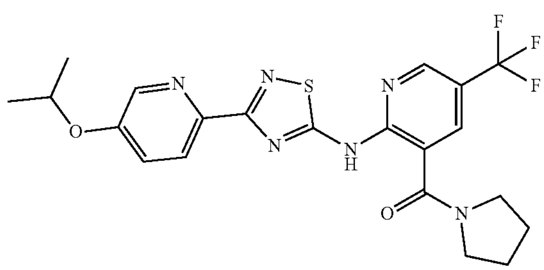 [SMILES: CC(C)Oc1ccc(-c2nsc(Nc3ncc(C(F)(F)F)cc3C(=O)N3CCCC3)n2)nc1] | (2-(3-(5-isopropoxypyridin-2-yl)-1,2,4-thiadiazol-5-ylamino)-5-(trifluoromethyl)pyridin-3-yl)(pyrrolidin-1-yl)methanone | 479.1 | A | D | D, E | | |
| 329 | 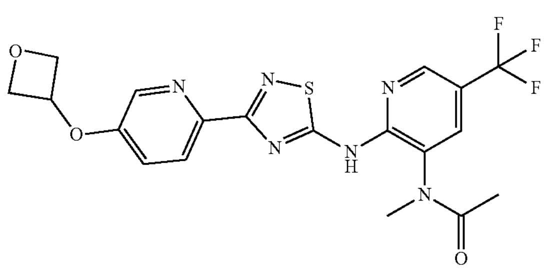 [SMILES: CC(=O)N(C)c1cc(C(F)(F)F)cnc1Nc1nc(-c2ccc(OC3COC3)cn2)ns1] | N-methyl-N-(2-(3-(5-(oxetan-3-yloxy)pyridin-2-yl)-1,2,4-thiadiazol-5-ylamino)-5-(trifluoromethyl)pyridin-3-yl)acetamide | 467.1 | A | D | D | | |
| 330 | 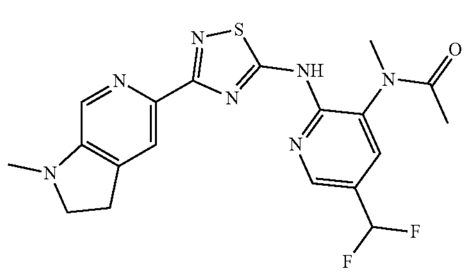 [SMILES: CC(=O)N(C)c1cc(C(F)F)cnc1Nc1nc(-c2cc3c(cn2)N(C)CC3)ns1] | N-(5-(difluoromethyl)-2-(3-(1-methyl-2,3-dihydro-1H-pyrrolo[2,3-c]pyridin-5-yl)-1,2,4-thiadiazol-5-ylamino)pyridin-3-yl)-N-methylacetamide | 432.2 | A | D | D | | |

TABLE 1-continued

| Cmpd No. | Structure | Name | M + 1 | O. guttu-rosa | B. malayi | L. sigmo-dontis | B. paha-ngi | D. immit-is |
|---|---|---|---|---|---|---|---|---|
| 331 | 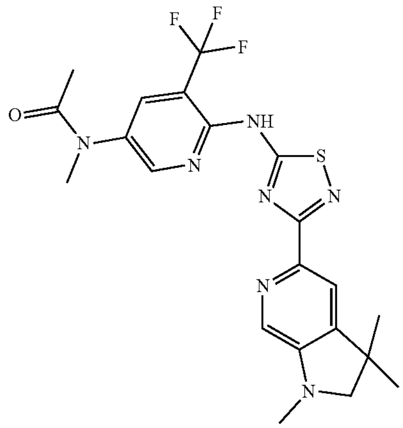 [SMILES: CC(=O)N(C)c1cnc(Nc2nc(-c3cc4c(cn3)N(C)CC4(C)C)ns2)c(C(F)(F)F)c1] | N-methyl-N-(5-(trifluoromethyl)-6-((3-(1,3,3-trimethyl-2,3-dihydro-1H-pyrrolo[2,3-c]pyridin-5-yl)-1,2,4-thiadiazol-5-yl)amino)-1l2-piperidin-3-yl)acetamide | 478.2 | | | | | |
| 332 | 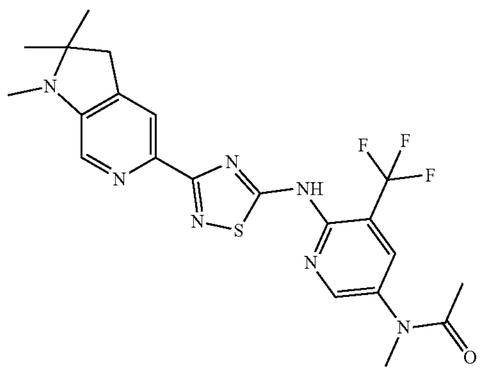 [SMILES: CC(=O)N(C)c1cnc(Nc2nc(-c3cc4c(cn3)N(C)C(C)(C)C4)ns2)c(C(F)(F)F)c1] | N-methyl-N-(5-(trifluoromethyl)-6-((3-(1,2,2-trimethyl-2,3-dihydro-1H-pyrrolo[2,3-c]pyridin-5-yl)-1,2,4-thiadiazol-5-yl)amino)pyridin-3-yl)acetamide | 478.2 | | | | | |
| 333 | 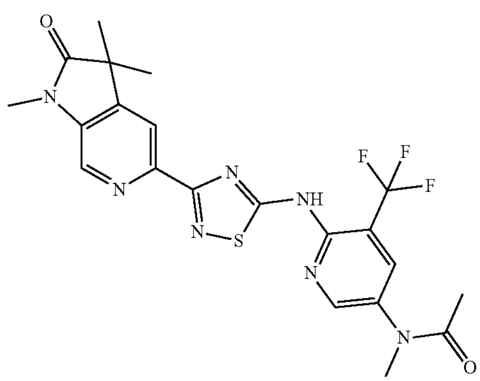 [SMILES: CC(=O)N(C)c1cnc(Nc2nc(-c3cc4c(cn3)N(C)C(=O)C4(C)C)ns2)c(C(F)(F)F)c1] | N-methyl-N-(5-(trifluoromethyl)-6-((3-(1,3,3-trimethyl-2-oxo-2,3-dihydro-1H-pyrrolo[2,3-c]pyridin-5-yl)-1,2,4-thiadiazol-5-yl)amino)pyridin-3-yl)acetamide | 492.1 | | | | | |
| 334 | 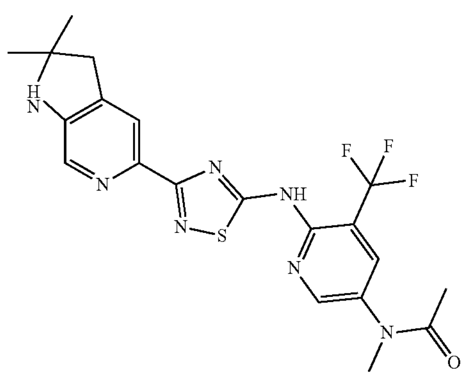 [SMILES: CC(=O)N(C)c1cnc(Nc2nc(-c3cc4c(cn3)NC(C)(C)C4)ns2)c(C(F)(F)F)c1] | N-(6-((3-(2,2-dimethyl-2,3-dihydro-1H-pyrrolo[2,3-c]pyridin-5-yl)-1,2,4-thiadiazol-5-yl)amino)-5-(trifluoromethyl)pyridin-3-yl)-N-methylacetamide | 464.1 | | | | | |

TABLE 1-continued

| Cmpd No. | Structure | Name | M + 1 | *O. guttu- rosa* | *B. malayi* | *L. sigmo- dontis* | *B. paha- ngi* | *D. immit- is* |
|---|---|---|---|---|---|---|---|---|
| 335 | 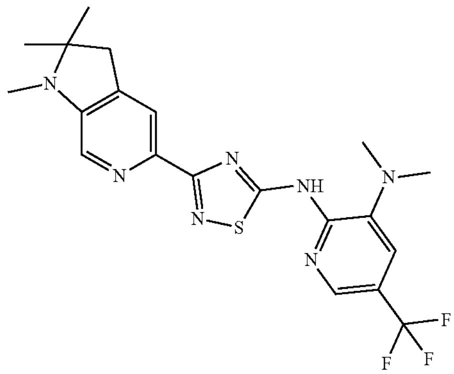 [SMILES: CN(C)c1cc(C(F)(F)F)cnc1Nc1nc(-c2cc3c(cn2)N(C)C(C)(C)C3)ns1] | N3,N3-dimethyl-5-(trifluoromethyl)-N2-(3-(1,2,2-trimethyl-2,3-dihydro-1H-pyrrolo[2,3-c]pyridin-5-yl)-3H-1,2l2,4-thiadiazol-5-yl)pyridine-2,3-diamine | | | | | | |
| 336 | 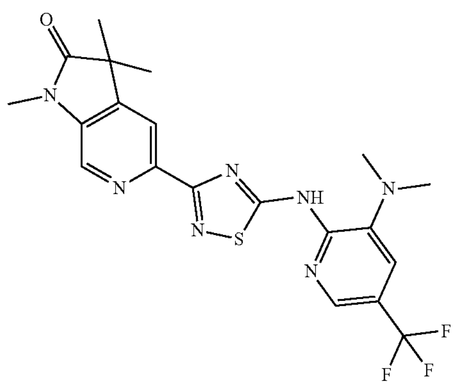 [SMILES: CN(C)c1cc(C(F)(F)F)cnc1Nc1nc(-c2cc3c(cn2)N(C)C(=O)C3(C)C)ns1] | 5-(5-((3-(dimethyl-amino)-5-(trifluoromethyl)pyridin-2-yl)amino)-1,2,4-thiadiazol-3-yl)-1,3,3-trimethyl-1,3-dihydro-2H-pyrrolo[2,3-c]pyridin-2-one | | | | | | |
| 337 | 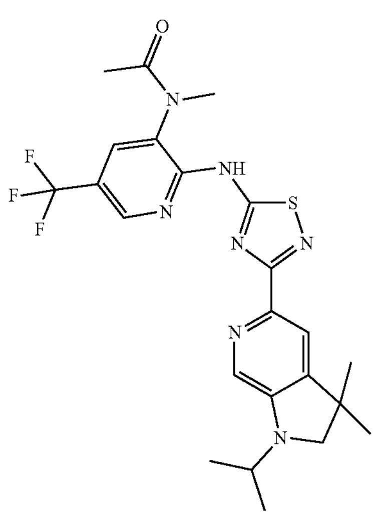 [SMILES: CC(=O)N(C)c1cc(C(F)(F)F)cnc1Nc1nc(-c2cc3c(cn2)N(C(C)C)CC3(C)C)ns1] | N-(2-((3-(1-isopropyl-3,3-dimethyl-2,3,3a,6-tetrahydro-1H-pyrrolo[2,3-c]pyridin-5-yl)-1,2,4l2-thiadiazol-5-yl)amino)-5-(trifluoro-methyl)pyridin-3-yl)-N-methylacetamide | | | | | | |

TABLE 1-continued

| Cmpd No. | Structure | Name | M + 1 | *O. guttu-rosa* | *B. malayi* | *L. sigmo-dontis* | *B. paha-ngi* | *D. immitis* |
|---|---|---|---|---|---|---|---|---|
| 338 | 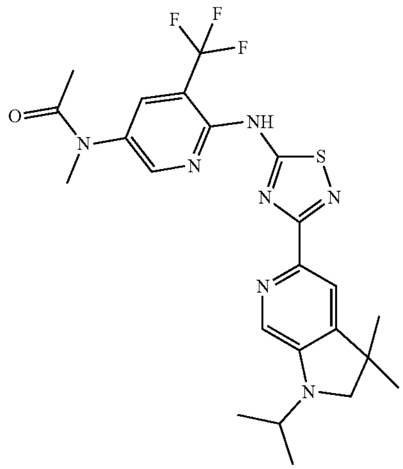 [SMILES: CC(=O)N(C)c1cnc(Nc2nc(-c3cc4c(cn3)N(C(C)C)CC4(C)C)ns2)c(C(F)(F)F)c1] | N-(6-((3-(1-isopropyl-3,3-dimethyl-2,3,3a,6-tetrahydro-1H-pyrrolo[2,3-c]pyridin-5-yl)-1,2,4-thiadiazol-5-yl)amino)-5-(trifluoromethyl)pyridin-3-yl)-N-methylacetamide | | | | | | |
| 339 | 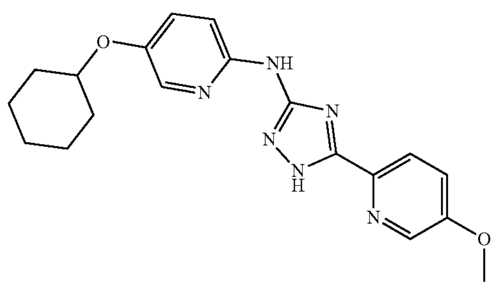 [SMILES: COc1ccc(-c2nc(Nc3ccc(OC4CCCCC4)cn3)n[nH]2)nc1] | 5-(cyclohexyl-oxy)-N-(5-(5-methoxypyridin-2-yl)-1H-1,2,4-triazol-3-yl)pyridin-2-amine | | | | | | |
| 340 | 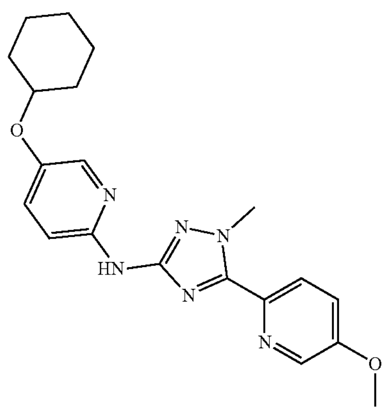 [SMILES: COc1ccc(-c2nc(Nc3ccc(OC4CCCCC4)cn3)nn2C)nc1] | 5-(cyclohexyl-oxy)-N-(5-(5-methoxypyridin-2-yl)-1-methyl-1H-1,2,4-triazol-3-yl)pyridin-2-amine | | | | | | |
| 341 | 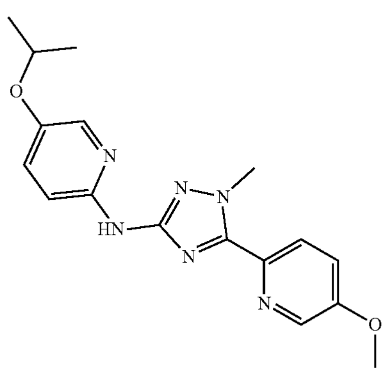 [SMILES: COc1ccc(-c2nc(Nc3ccc(OC(C)C)cn3)nn2C)nc1] | 5-isopropoxy-N-(5-(5-methoxypyridin-2-yl)-1-methyl-1H-1,2,4-triazol-3-yl)pyridin-2-amine | | | | | | |

TABLE 1-continued

| Cmpd No. | Structure | Name | M + 1 | O. guttu- rosa | B. malayi | L. sigmo- dontis | B. paha- ngi | D. immit- is |
|---|---|---|---|---|---|---|---|---|
| 342 | 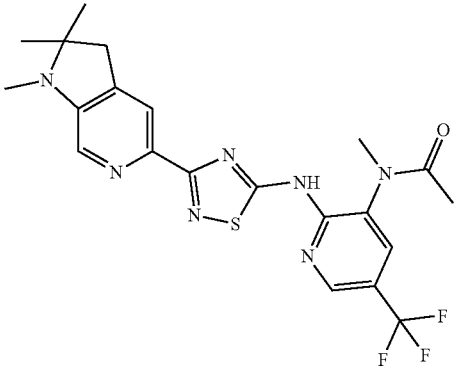 [SMILES: CC(=O)N(C)c1cc(C(F)(F)F)cnc1Nc1nc(-c2cc3c(cn2)N(C)C(C)(C)C3)ns1] | N-methyl-N-(5-(trifluoromethyl)-2-((3-(1,2,2-trimethyl-2,3-dihydro-1H-pyrrolo[2,3-c]pyridin-5-yl)-1,2,4-thiadiazol-5-yl)amino)pyridin-3-yl)acetamide | | | | | | |
| 343 | 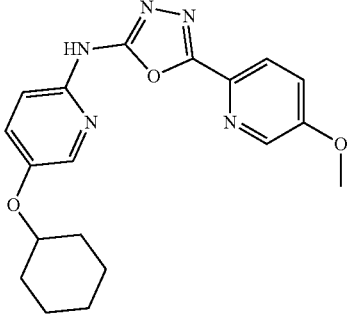 [SMILES: COc1ccc(-c2nnc(Nc3ccc(OC4CCCCC4)cn3)o2)nc1] | N-(5-(cyclohexyl-oxy)pyridin-2-yl)-5-(5-methoxypyridin-2-yl)-1,3,4-oxadiazol-2-amine | | | | | | |
| 344 | 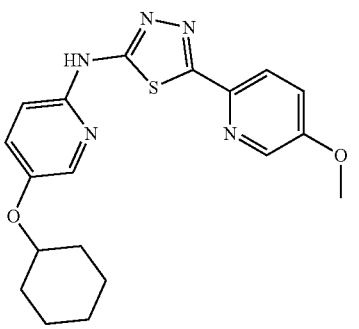 [SMILES: COc1ccc(-c2nnc(Nc3ccc(OC4CCCCC4)cn3)s2)nc1] | N-(5-(cyclohexyl-oxy)pyridin-2-yl)-5-(5-methoxypyridin-2-yl)-1,3,4-thiadiazol-2-amine | | | | | | |
| 345 | 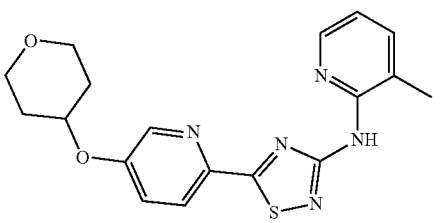 [SMILES: Cc1cccnc1Nc1nsc(-c2ccc(OC3CCOCC3)cn2)n1] | N-(3-methyl-pyridin-2-yl)-5-(5-((tetrahydro-2H-pyran-4-yl)oxy)pyridin-2-yl)-1,2,4-thiadiazol-3-amine | | | | | | |

TABLE 1-continued

| Cmpd No. | Structure | Name | O. guttu- rosa M + 1 | B. malayi | L. sigmo- dontis | B. paha- ngi | D. immit- is |
|---|---|---|---|---|---|---|---|
| 346 | 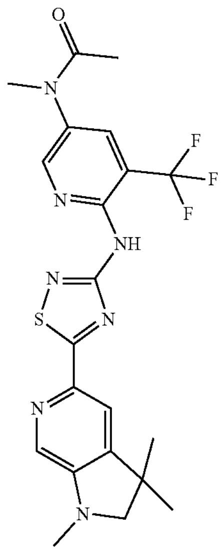 [SMILES: CC(=O)N(C)c1cnc(Nc2nsc(-c3cc4c(cn3)N(C)CC4(C)C)n2)c(C(F)(F)F)c1] | N-methyl-N-(5-(trifluoromethyl)-6-((5-(1,3,3-trimethyl-2,3,3a,6,7,7a-hexahydro-1H-pyrrolo[2,3-c]pyridin-5-yl)-1,2,4-thiadiazol-3-yl)amino)pyridin-3-yl)acetamide | | | | | |
| 347 | 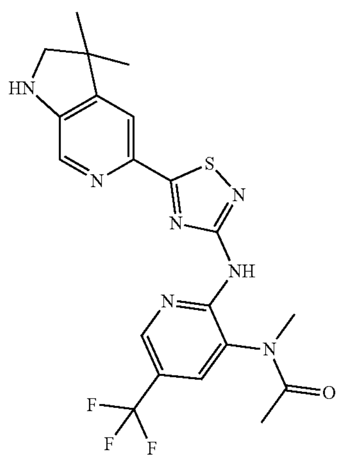 [SMILES: CC(=O)N(C)c1cc(C(F)(F)F)cnc1Nc1nsc(-c2cc3c(cn2)NCC3(C)C)n1] | N-(2-((5-(3,3-dimethyl-2,3-dihydro-1H-pyrrolo[2,3-c]pyridin-5-yl)-1,2,4-thiadiazol-3-yl)amino)-5-(trifluoromethyl)pyridin-3-yl)-N-methylacetamide | | | | | |
| 348 | 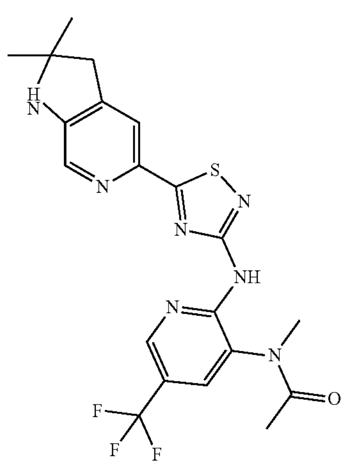 [SMILES: CC(=O)N(C)c1cc(C(F)(F)F)cnc1Nc1nsc(-c2cc3c(cn2)NC(C)(C)C3)n1] | N-(2-((5-(2,2-dimethyl-2,3-dihydro-1H-pyrrolo[2,3-c]pyridin-5-yl)-1,2,4-thiadiazol-3-yl)amino)-5-(trifluoromethyl)pyridin-3-yl)-N-methylacetamide | | | | | |

| Cmpd No. | Structure | Name | M + 1 | *O. guttu- rosa* | *B. malayi* | *L. sigmo- dontis* | *B. paha- ngi* | *D. immit- is* |
|---|---|---|---|---|---|---|---|---|
| 349 | 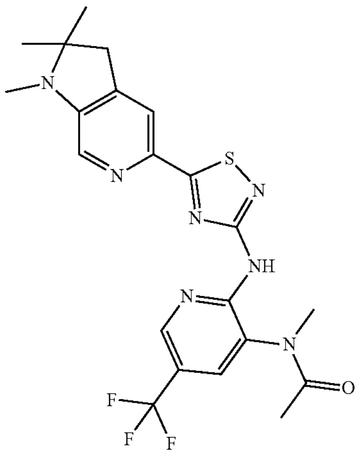 [SMILES: CC(=O)N(C)c1cc(C(F)(F)F)cnc1Nc1nsc(-c2cc3c(cn2)N(C)C(C)(C)C3)n1] | N-methyl-N-(5-(trifluoromethyl)-2-((5-(1,2,2-trimethyl-2,3-dihydro-1H-pyrrolo[2,3-c]pyridin-5-yl)-1,2,4-thiadiazol-3-yl)amino)pyridin-3-yl)acetamide | | | | | | |
| 350 | 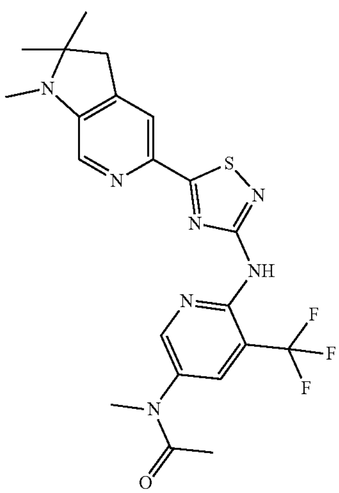 [SMILES: CC(=O)N(C)c1cnc(Nc2nsc(-c3cc4c(cn3)N(C)C(C)(C)C4)n2)c(C(F)(F)F)c1] | N-methyl-N-(5-(trifluoromethyl)-6-((5-(1,2,2-trimethyl-2,3-dihydro-1H-pyrrolo[2,3-c]pyridin-5-yl)-1,2,4-thiadiazol-3-yl)amino)pyridin-3-yl)acetamide | | | | | | |
| 351 | 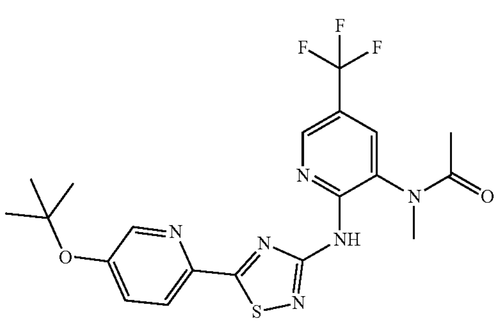 [SMILES: CC(=O)N(C)c1cc(C(F)(F)F)cnc1Nc1nsc(-c2ccc(OC(C)(C)C)cn2)n1] | N-(2-((5-(5-(tert-butoxy)-1,6-dihydropyridin-2-yl)-1,2,4-thiadiazol-3-yl)amino)-5-(trifluoromethyl)-2,3-dihydropyridin-3-yl)-N-methylacetamide | | | | | | |

A number of references have been cited, the disclosures of each of which are incorporated herein by reference in their entirety.

What is claimed is:

1. A compound of formula (II)

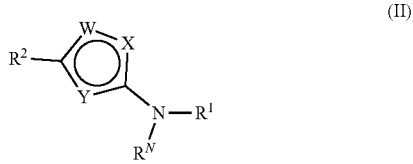

or pharmaceutically acceptable salts, tautomers, isotopologues, or stereoisomers thereof, wherein:

W is N, NR, or S;
X is N, NR, O, or S;
Y is N, NR, O, or S;
$R^1$ is 2-pyridyl, 3-pyridyl, pyrazinyl, or pyrimidyl, each unsubstituted or substituted with one or more substituents independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —$NR_2$, —COOR, —$OR^3$, —$SO_2NR_2$, —$SO_2$(substituted or unsubstituted heterocyclyl), —$N(R)CO(R^4)$, —$CON(R^5)_2$, and substituted or unsubstituted $C_{6-10}$ aryl;
$R^2$ is

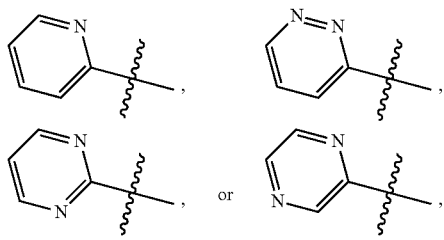

each unsubstituted or substituted with one or more substituents Z, wherein Z is independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —NR(substituted or unsubstituted $C_{3-7}$ cycloalkyl), —N(R)COR, —COOR, —$SO_2(C_{1-3}$ alkyl), —$SO_2NR_2$, —$SO_2$(substituted or unsubstituted heterocyclyl), —$OR^6$, and —$CON(R^7)_2$; or two Z together with the carbons to which they are attached form a substituted or unsubstituted 5-6 membered heterocyclyl or substituted or unsubstituted $C_{5-6}$ heteroaryl;

Each $R^3$ is independently selected from substituted or unsubstituted $C_{1-5}$ alkyl, or substituted or unsubstituted 3-6 membered heterocyclyl;

Each $R^4$ is independently selected from substituted or unsubstituted $C_{1-5}$ alkyl, or substituted or unsubstituted $C_{3-6}$ cycloalkyl;

Each $R^5$ is independently selected from H, substituted or unsubstituted $C_{1-5}$ alkyl, substituted or unsubstituted $C_{3-6}$ cycloalkyl, and substituted or unsubstituted $(C_{1-3}$ alkyl)($C_{3-6}$ cycloalkyl), or two $R^5$ and the nitrogen to which they are attached form a substituted or unsubstituted 3 to 6 membered heterocyclyl;

Each $R^6$ is independently selected from substituted or unsubstituted $C_{1-5}$ alkyl, substituted or unsubstituted $C_{3-6}$ cycloalkyl, —($C_{1-3}$ alkyl)(substituted or unsubstituted $C_{3-6}$ cycloalkyl), or substituted or unsubstituted 3-8 membered heterocyclyl;

Each $R^7$ is independently selected from H, and substituted or unsubstituted $C_{1-5}$ alkyl, or two $R^7$ and the nitrogen to which they are attached form a substituted or unsubstituted 3 to 6 membered heterocyclyl;

$R^N$ is H, or substituted or unsubstituted $C_{1-5}$ alkyl; and each R is independently selected from H and substituted or unsubstituted $C_{1-4}$ alkyl;

provided $R^1$ and $R^2$ are not both unsubstituted.

2. The compound of claim 1, wherein the compound is a compound of formula (IIa)

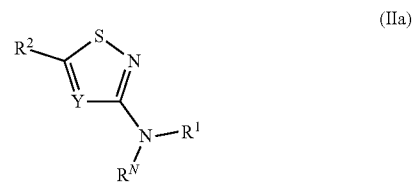

or pharmaceutically acceptable salts, tautomers, isotopologues, or stereoisomers thereof.

3. The compound of claim 2, wherein Y is N.

4. The compound of claim 1, wherein $R^1$ is substituted with one or more substituents independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, substituted or unsubstituted $C_{6-10}$ aryl, —$NR_2$, —COOR, —$OR^3$, —$SO_2NR_2$, —$SO_2$(substituted or unsubstituted heterocyclyl), —$N(R)CO(R^4)$, and —$CON(R^5)_2$.

5. The compound of claim 1, wherein $R^1$ is substituted with one or more substituents independently selected from Cl, F, Br, CN, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CH_2F$, —$CHF_2$, —$CF_3$; substituted or unsubstituted cycloalkyl selected from cyclopropyl, cyclobutyl, and cyclopentyl; substituted or unsubstituted heterocyclyl selected from pyrrolidyl, pyrrolidinonyl, piperidyl, piperazinyl, and morpholinyl; substituted or unsubstituted phenyl; —$NH_2$, —$NHCH_3$, —$N(CH_3)_2$, —COOH, —$COOCH_3$, —$OR^3$, —$SO_2N(CH_3)_2$; —$S_{O2}$(aziridinyl), —$NHCO(R^4)$, —$N(CH_3)CO(R^4)$, —$N(CH_2CH_3)CO(R^4)$, —$N(CH_2CH_2CH_3)CO(R^4)$, —$N(CH_2CH(CH_3)_2)CO(R^4)$, and —$CON(R^5)_2$.

6. The compound of claim 1, wherein $R^3$ is —$CH_3$, —$CH_2CH_3$, —$CH_2CH_2CH_3$, —$CH(CH_3)_2$, tetrahydrofuranyl, tetrahydropyranyl, piperidyl, or 1-($CH_3$)-piperidyl.

7. The compound of claim 1, wherein $R^4$ is selected from —$CH_3$, —$CH_2CH_3$, —$CH_2CH_2CH_3$, —$CH(CH_3)_2$; substituted or unsubstituted cycloalkyl selected from cyclopropyl, cyclobutyl, cyclopentyl and cyclohexyl.

8. The compound of claim 1, wherein each $R^5$ is independently selected from H, —$CH_3$, —$CH_2CH_3$, —$CH_2CH_2CH_3$, —$CH(CH_3)_2$; substituted or unsubstituted cycloalkyl selected from cyclopropyl, cyclobutyl, cyclopentyl and cyclohexyl; substituted or unsubstituted (alkyl)(cycloalkyl) selected from —$CH_2$-cyclopropyl, —$CH_2$-cyclobutyl, and —$CH_2$-cyclopentyl; or two $R^5$ and the nitrogen to which they are attached form a pyrrolidyl.

9. The compound of claim 1, wherein $R^1$ is 2-pyridyl, 3-pyridyl or pyrazinyl.

10. The compound of claim 1, wherein $R^2$ is substituted with one or more substituents Z, wherein Z is independently selected from halogen, CN, substituted or unsubstituted $C_{1-4}$ alkyl, substituted or unsubstituted $C_{3-7}$ cycloalkyl, substituted or unsubstituted 3-6 membered heterocyclyl, —NR (substituted or unsubstituted $C_{3-7}$ cycloalkyl), —N(R)COR, —COOR, —$SO_2$($C_{1-3}$ alkyl), —$SO_2NR_2$, —$SO_2$(substituted or unsubstituted heterocyclyl), —$OR^6$, and —CON$(R^7)_2$, or two Z together with the carbons to which they are attached form a substituted or unsubstituted 5-6 membered heterocyclyl or substituted or unsubstituted $C_{5-6}$ heteroaryl.

11. The compound of claim 1, wherein $R^2$ is substituted with one or more substituents independently selected from Cl, F, Br, CN, —$CH_3$, —$CH_2CH_3$, —$CH_2CH_2CH_3$, —CH$(CH_3)_2$, —$CH_2CH_2CH_2CH_3$, —CH$(CH_3)CH_2CH_3$, —C$(CH_3)_3$, —$CH_2F$, —$CHF_2$, —$CF_3$; substituted or unsubstituted cycloalkyl selected from cyclopropyl, cyclobutyl, and cyclopentyl; substituted or unsubstituted heterocyclyl selected from piperidyl, piperazinyl, morpholinyl and thiomorpholinyl; —NH(bicyclo[1.1.1]pentyl), —N($CH_3$)(bicyclo[1.1.1]pentyl); —NHCO($CH_3$), —N($CH_3$)CO($CH_3$), —NHCO($CH_2CH_3$), —N($CH_3$)CO($CH_2CH_3$); —COOH, —COO$CH_3$; —$SO_2CH_3$, —$SO_2CH_2CH_3$; —$SO_2NHCH_3$, —$SO_2N(CH_3)_2$; —$SO_2$(aziridinyl), —$SO_2$(piperidyl), —$SO_2$(1-methyl-aziridinyl), —$SO_2$(1-methyl-piperidyl), $SO_2$(1-cyclopropyl-piperidyl), —$OR^6$, and —CON$(R^7)_2$.

12. The compound of claim 1, wherein $R^6$ is selected from —$CH_3$, —$CH_2CH_3$, —$CH_2CH_2CH_3$, —CH($CH_3$)$CH_3$, —CH$(CH_3)_2$, —$CH_2CH_2CH_2CH_3$, —CH($CH_3$)$CH_2CH_3$, —C$(CH_3)_3$, —$CH_2F$, —$CHF_2$, —$CF_3$, —$CH_2CH_2F$, —$CH_2CHF_2$, —$CH_2CF_3$, cyclopropyl, cyclobutyl, cyclopentyl, cyclohexyl, difluorocyclobutyl, difluorocyclopentyl, —$CH_2$-cyclopropyl, —$CH_2$-cyclobutyl, oxetanyl, piperidyl, fluoropiperidyl, -(1-methyl-piperidyl), -(1-isopropyl-piperidyl), -(1-isopropyl-fluoropiperidyl), -(1-isopropyl-difluoropiperidyl), -(1-cyclopropyl-piperidyl), -(1-cyclobutyl-piperidyl), -(1-cyclopentyl-piperidyl), -(1-cyclopropyl-fluoropiperidyl), -(1-cyclopropyl-difluoropiperidyl), -(1-$CH_2$-cyclopropyl-piperidyl), -(1-acetyl-piperidyl), -(1-(COCH$(CH_3)_2$)-piperidyl), tetrahydrofuranyl, tetrahydropyranyl, -(2-methyl-2-azaspiro[3.3]heptyl), -(2-cyclopropyl-2-azaspiro[3.3]heptyl), and -(6-methyl-6-azaspiro[3.4]octyl).

13. The compound of claim 1, wherein each $R^7$ is independently selected from —H, —$CH_3$, —$CH_2CH_3$, —$CH_2F$, —$CHF_2$, —$CF_3$, —$CH_2CH_2F$, —$CH_2CHF_2$, and —$CH_2CF_3$, or two $R^7$ and the nitrogen to which they are attached form a heterocycle selected from unsubstituted or substituted pyrrolidyl, piperidyl, piperazinyl, or morpholinyl.

14. The compound of claim 1, wherein $R^2$ is 2-pyridyl substituted with two substituents Z, wherein the two Z together with the carbons to which they are attached form a substituted or unsubstituted 5-membered heterocyclyl.

15. The compound of claim 14, wherein the two Z together with the carbons to which they are attached form a substituted or unsubstituted dihydropyrrolyl or dihydrofuryl.

16. The compound of claim 15, wherein $R^2$ is a substituted or unsubstituted 6,7-dihydro-5H-pyrrolo[3,4-b]pyridyl; 2,3-dihydro-1H-pyrrolo[2,3-c]pyridyl; 2,3-dihydro-1H-pyrrolo[3,4-c]pyridyl; 2-oxo-2,3-dihydro-1H-pyrrolo[2,3-c]pyridyl; or 2,3-dihydrofuro[2,3-c]pyridyl.

17. The compound of claim 1, wherein the compound is selected from:

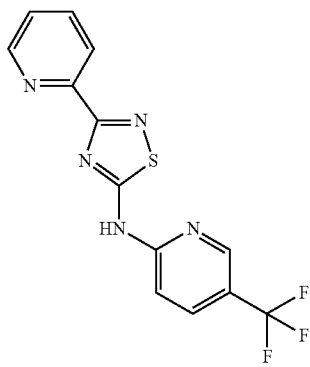 [SMILES: FC(F)(F)c1ccc(Nc2nc(-c3ccccn3)ns2)nc1]

3-(pyridin-2-yl)-N-(5-(trifluoromethyl)pyridin-2-yl)-1,2,4-thiadiazol-5-amine

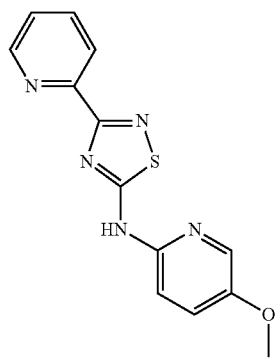 [SMILES: COc1ccc(Nc2nc(-c3ccccn3)ns2)nc1]

N-(5-methoxypyridin-2-yl)-3-(pyridin-2-yl)-1,2,4-thiadiazol-5-amine

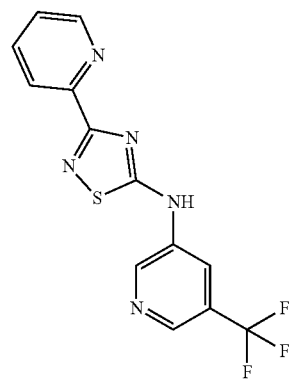 [SMILES: FC(F)(F)c1cncc(Nc2nc(-c3ccccn3)ns2)c1]
3-(pyridin-2-yl)-N-(5-(trifluoromethyl)pyridin-3-yl)-1,2,4-thiadiazol-5-amine
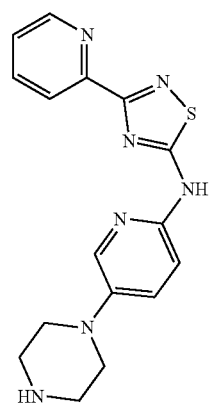
N-(5-(piperazin-1-yl)pyridin-2-yl)-3-(pyridin-2-yl)-1,2,4-thiadiazol-5-amine
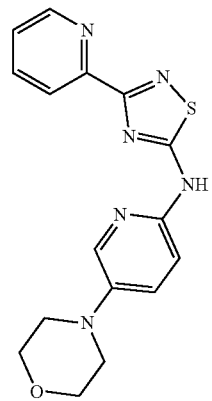
N-(5-morpholinopyridin-2-yl)-3-(pyridin-2-yl)-1,2,4-thiadiazol-5-amine
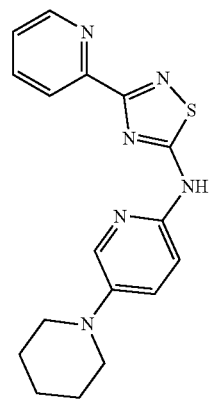
N-(5-(piperidin-1-yl)pyridin-2-yl)-3-(pyridin-2-yl)-1,2,4-thiadiazol-5-amine

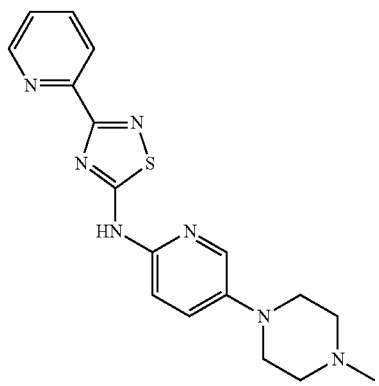 [SMILES: CN1CCN(c2ccc(Nc3nc(-c4ccccn4)ns3)nc2)CC1]
N-(5-(4-methylpiperazin-1-yl)pyridin-2-yl)-3-(pyridin-2-yl)-1,2,4-thiadiazol-5-amine
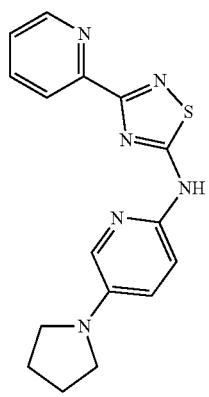 [SMILES: c1ccc(-c2nsc(Nc3ccc(N4CCCC4)cn3)n2)nc1]
3-(pyridin-2-yl)-N-(5-(pyrrolidin-1-yl)pyridin-2-yl)-1,2,4-thiadiazol-5-amine
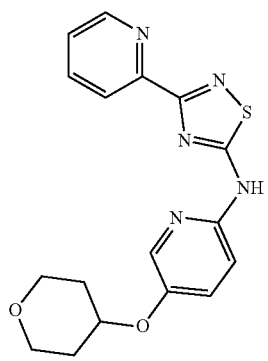 [SMILES: c1ccc(-c2nsc(Nc3ccc(OC4CCOCC4)cn3)n2)nc1]
3-(pyridin-2-yl)-N-(5-(tetrahydro-2H-pyran-4-yloxy)pyridin-2-yl)-1,2,4-thiadiazol-5-amine
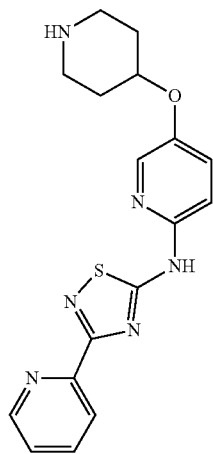 [SMILES: c1ccc(-c2nsc(Nc3ccc(OC4CCNCC4)cn3)n2)nc1]
N-(5-(piperidin-4-yloxy)pyridin-2-yl)-3-(pyridin-2-yl)-1,2,4-thiadiazol-5-amine

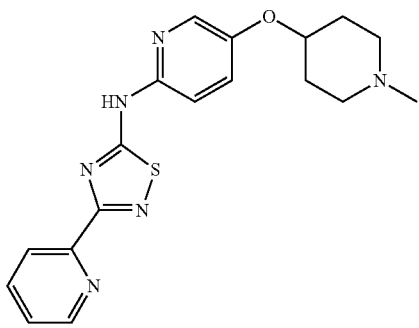 [SMILES: CN1CCC(Oc2ccc(Nc3nc(-c4ccccn4)ns3)nc2)CC1]
N-(5-(1-methylpiperidin-4-yloxy)pyridin-2-yl)-3-(pyridin-2-yl)-1,2,4-thiadiazol-5-amine
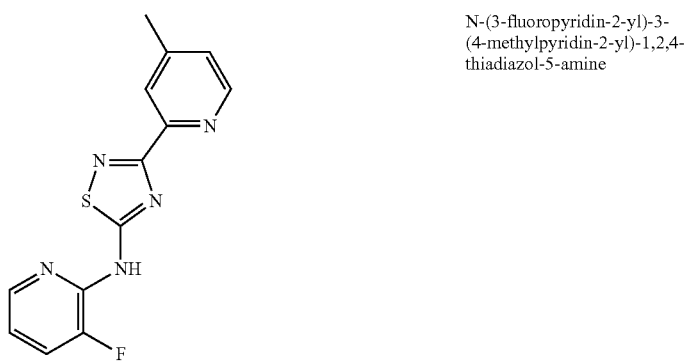
N-(3-fluoropyridin-2-yl)-3-(4-methylpyridin-2-yl)-1,2,4-thiadiazol-5-amine
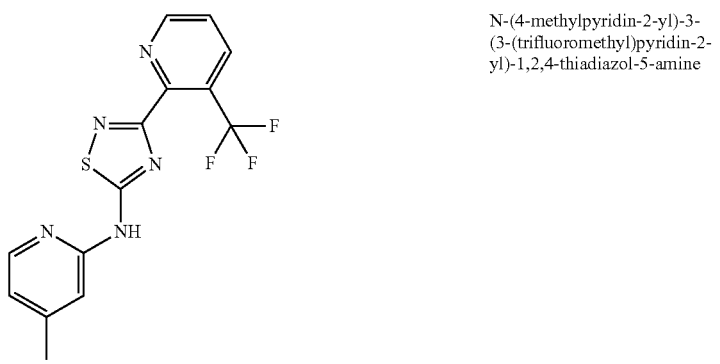
N-(4-methylpyridin-2-yl)-3-(3-(trifluoromethyl)pyridin-2-yl)-1,2,4-thiadiazol-5-amine
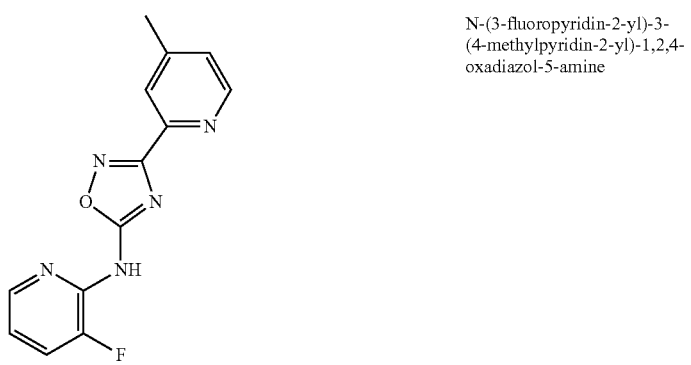
N-(3-fluoropyridin-2-yl)-3-(4-methylpyridin-2-yl)-1,2,4-oxadiazol-5-amine

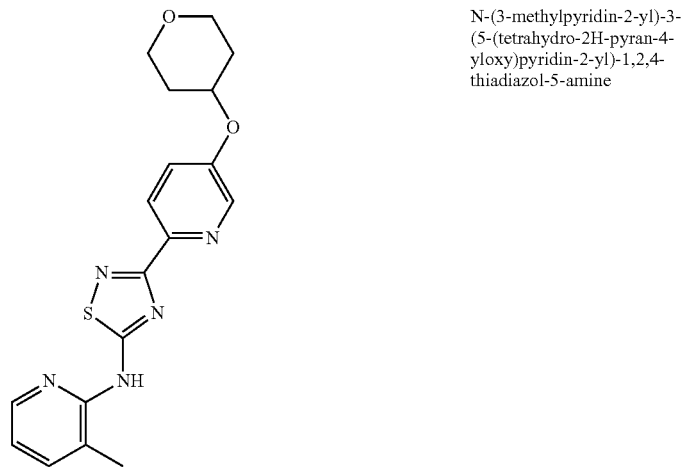
N-(3-methylpyridin-2-yl)-3-(5-(tetrahydro-2H-pyran-4-yloxy)pyridin-2-yl)-1,2,4-thiadiazol-5-amine
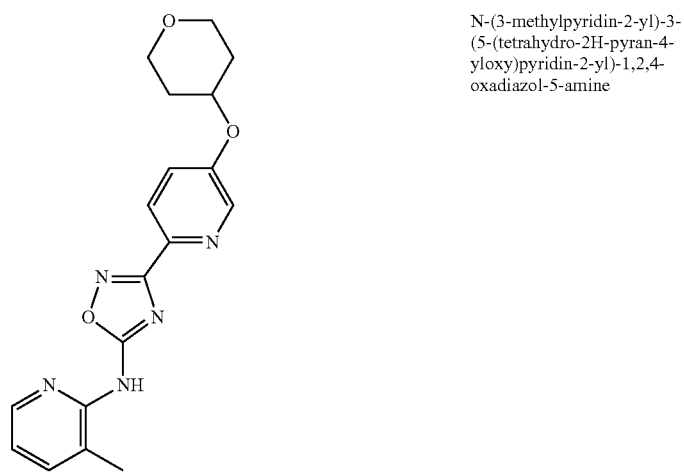
N-(3-methylpyridin-2-yl)-3-(5-(tetrahydro-2H-pyran-4-yloxy)pyridin-2-yl)-1,2,4-oxadiazol-5-amine
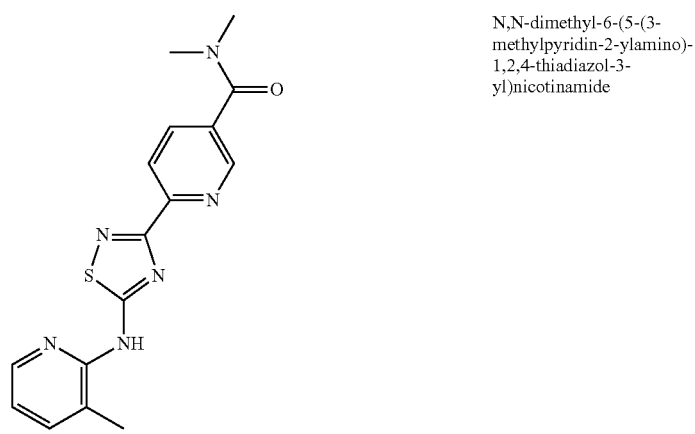
N,N-dimethyl-6-(5-(3-methylpyridin-2-ylamino)-1,2,4-thiadiazol-3-yl)nicotinamide

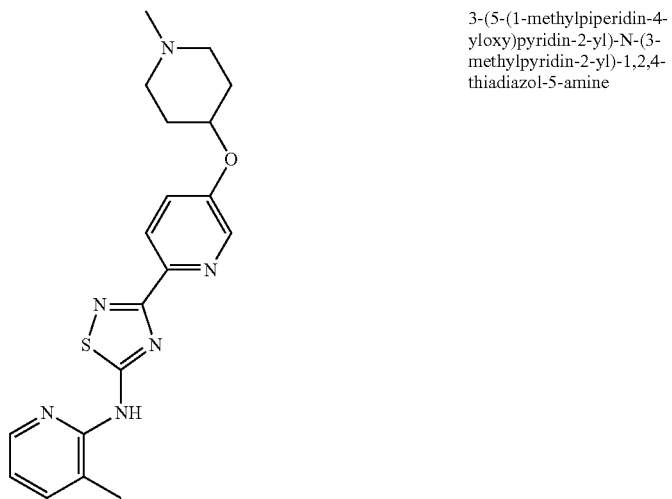
3-(5-(1-methylpiperidin-4-yloxy)pyridin-2-yl)-N-(3-methylpyridin-2-yl)-1,2,4-thiadiazol-5-amine
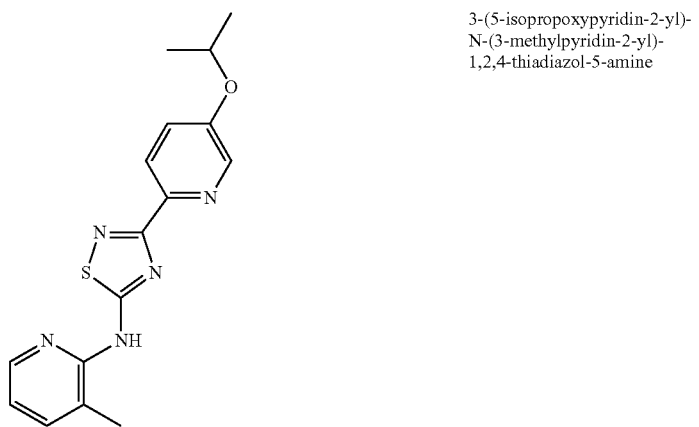
3-(5-isopropoxypyridin-2-yl)-N-(3-methylpyridin-2-yl)-1,2,4-thiadiazol-5-amine
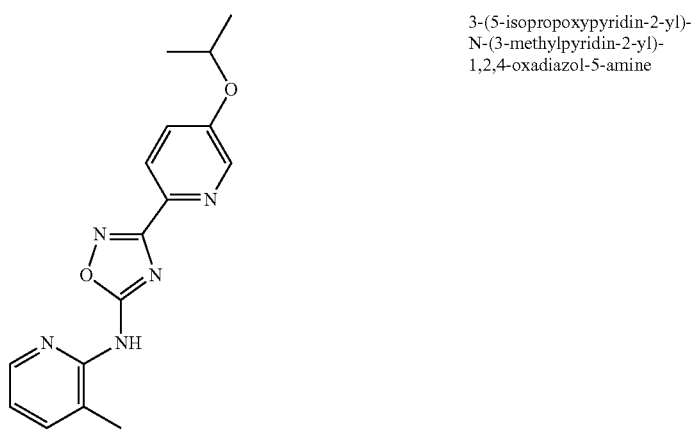
3-(5-isopropoxypyridin-2-yl)-N-(3-methylpyridin-2-yl)-1,2,4-oxadiazol-5-amine

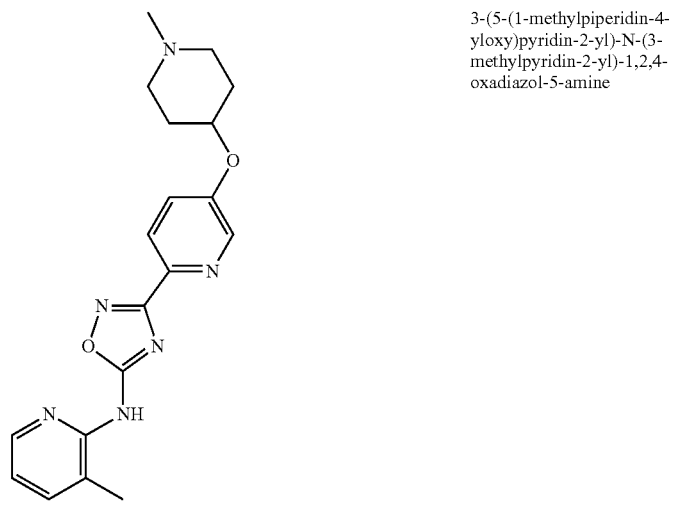
3-(5-(1-methylpiperidin-4-yloxy)pyridin-2-yl)-N-(3-methylpyridin-2-yl)-1,2,4-oxadiazol-5-amine
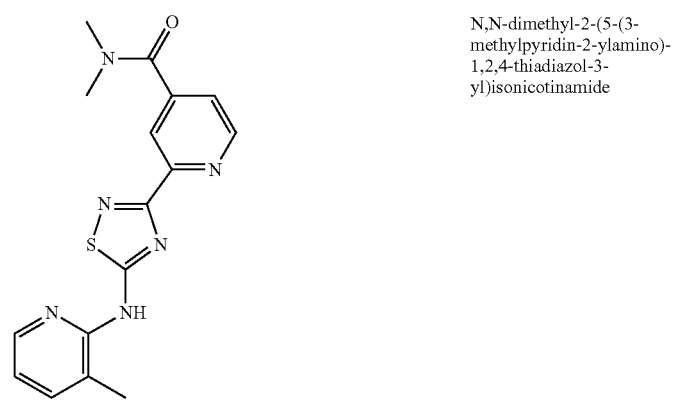
N,N-dimethyl-2-(5-(3-methylpyridin-2-ylamino)-1,2,4-thiadiazol-3-yl)isonicotinamide
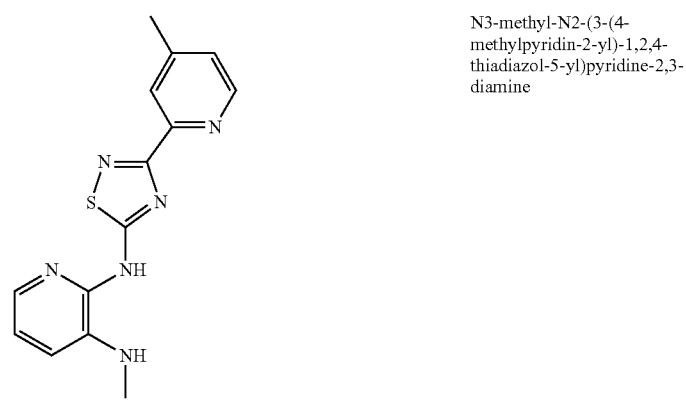
N3-methyl-N2-(3-(4-methylpyridin-2-yl)-1,2,4-thiadiazol-5-yl)pyridine-2,3-diamine

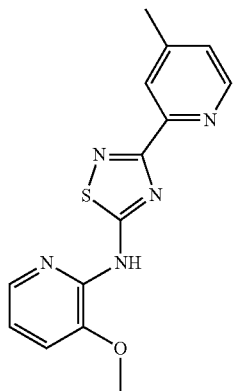 [SMILES: COc1cccnc1Nc1nc(-c2cc(C)ccn2)ns1] N-(3-methoxypyridin-2-yl)-3-(4-methylpyridin-2-yl)-1,2,4-thiadiazol-5-amine
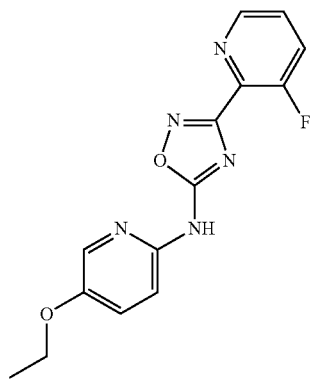 [SMILES: CCOc1ccc(Nc2nc(-c3ncccc3F)no2)nc1] N-(5-ethoxypyridin-2-yl)-3-(3-fluoropyridin-2-yl)-1,2,4-oxadiazol-5-amine
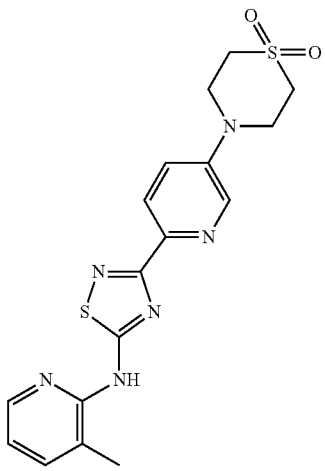 [SMILES: Cc1cccnc1Nc1nc(-c2ccc(N3CCS(=O)(=O)CC3)cn2)ns1] 4-(6-(5-((3-methylpyridin-2-yl)amino)-1,2,4-thiadiazol-3-yl)pyridin-3-yl)thiomorpholine 1,1-dioxide
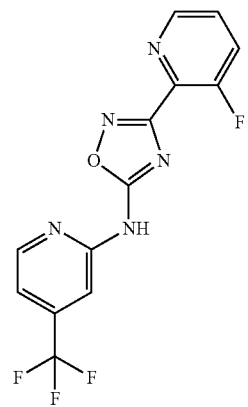 [SMILES: Fc1cccnc1-c1noc(Nc2cc(C(F)(F)F)ccn2)n1] 3-(3-fluoropyridin-2-yl)-N-(4-(trifluoromethyl)pyridin-2-yl)-1,2,4-oxadiazol-5-amine

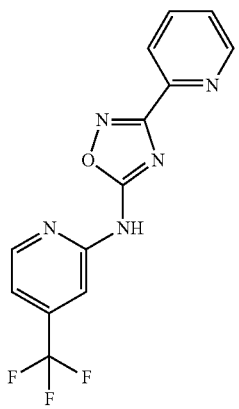 [SMILES: FC(F)(F)c1ccnc(Nc2nc(-c3ccccn3)no2)c1]
3-(pyridin-2-yl)-N-(4-(trifluoromethyl)pyridin-2-yl)-1,2,4-oxadiazol-5-amine
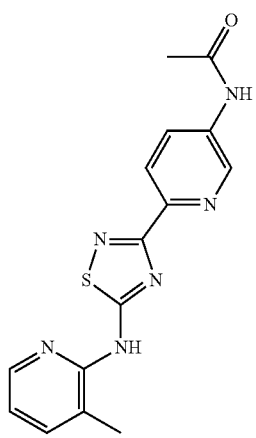 [SMILES: CC(=O)Nc1ccc(-c2nsc(Nc3ncccc3C)n2)nc1]
N-(6-(5-(3-methylpyridin-2-ylamino)-1,2,4-thiadiazol-3-yl)pyridin-3-yl)acetamide
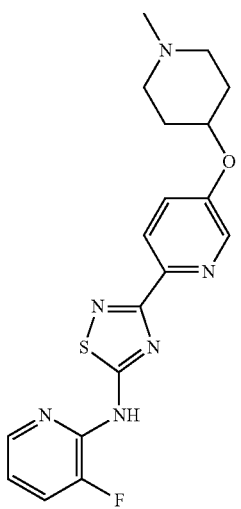 [SMILES: CN1CCC(Oc2ccc(-c3nsc(Nc4ncccc4F)n3)nc2)CC1]
N-(3-fluoropyridin-2-yl)-3-(5-(1-methylpiperidin-4-yloxy)pyridin-2-yl)-1,2,4-thiadiazol-5-amine

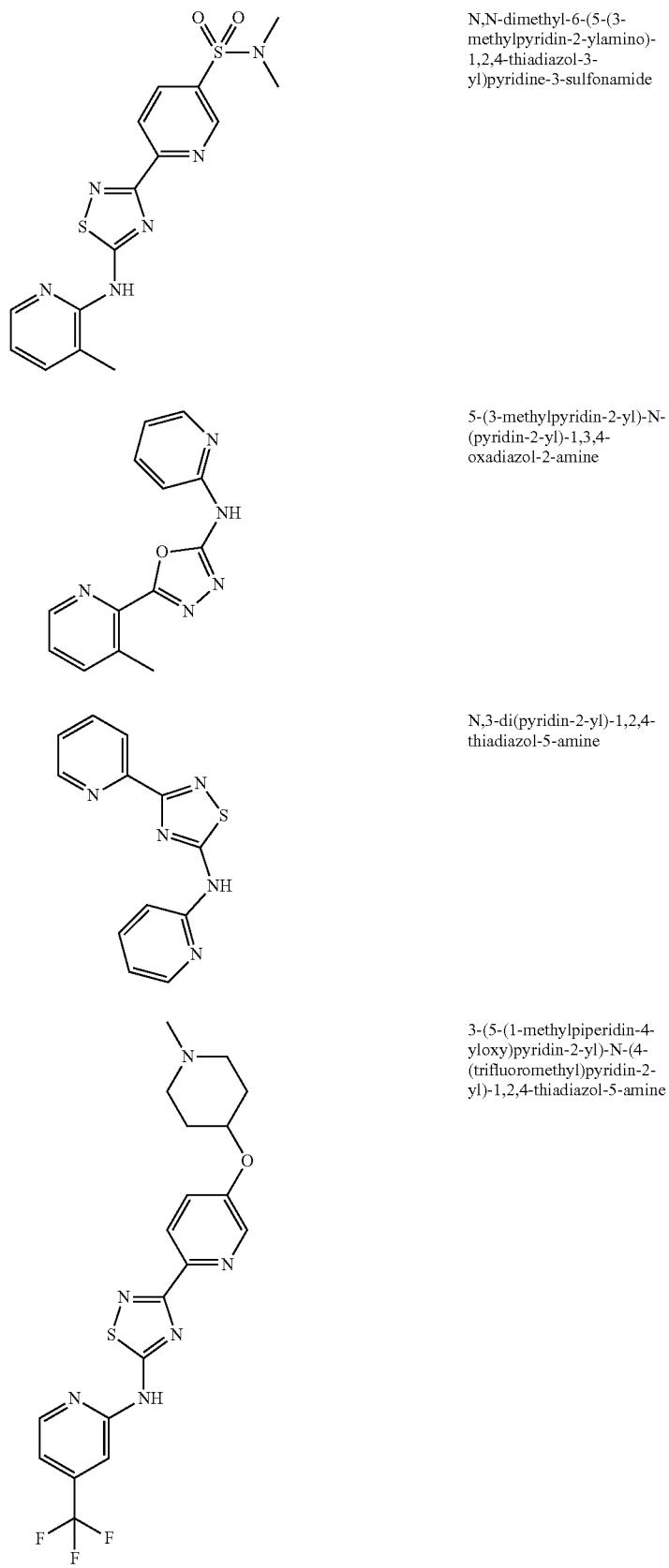
N,N-dimethyl-6-(5-(3-methylpyridin-2-ylamino)-1,2,4-thiadiazol-3-yl)pyridine-3-sulfonamide
5-(3-methylpyridin-2-yl)-N-(pyridin-2-yl)-1,3,4-oxadiazol-2-amine
N,3-di(pyridin-2-yl)-1,2,4-thiadiazol-5-amine
3-(5-(1-methylpiperidin-4-yloxy)pyridin-2-yl)-N-(4-(trifluoromethyl)pyridin-2-yl)-1,2,4-thiadiazol-5-amine

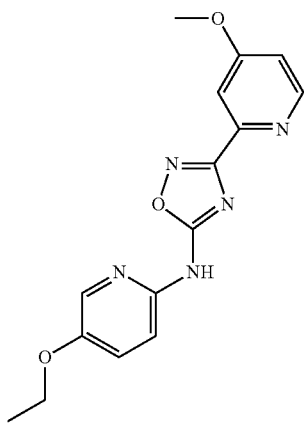 [SMILES: CCOc1ccc(Nc2nc(-c3cc(OC)ccn3)no2)nc1]
N-(5-ethoxypyridin-2-yl)-3-(4-methoxypyridin-2-yl)-1,2,4-oxadiazol-5-amine
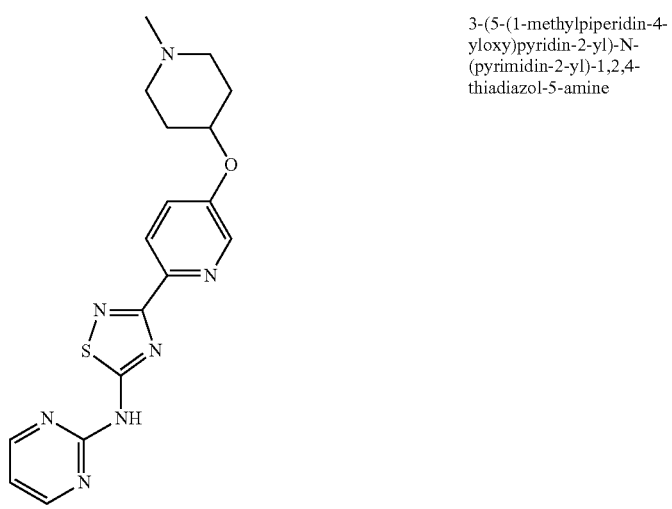
3-(5-(1-methylpiperidin-4-yloxy)pyridin-2-yl)-N-(pyrimidin-2-yl)-1,2,4-thiadiazol-5-amine
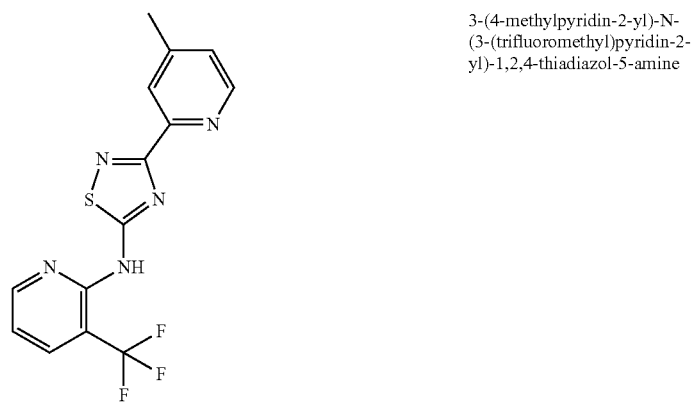
3-(4-methylpyridin-2-yl)-N-(3-(trifluoromethyl)pyridin-2-yl)-1,2,4-thiadiazol-5-amine

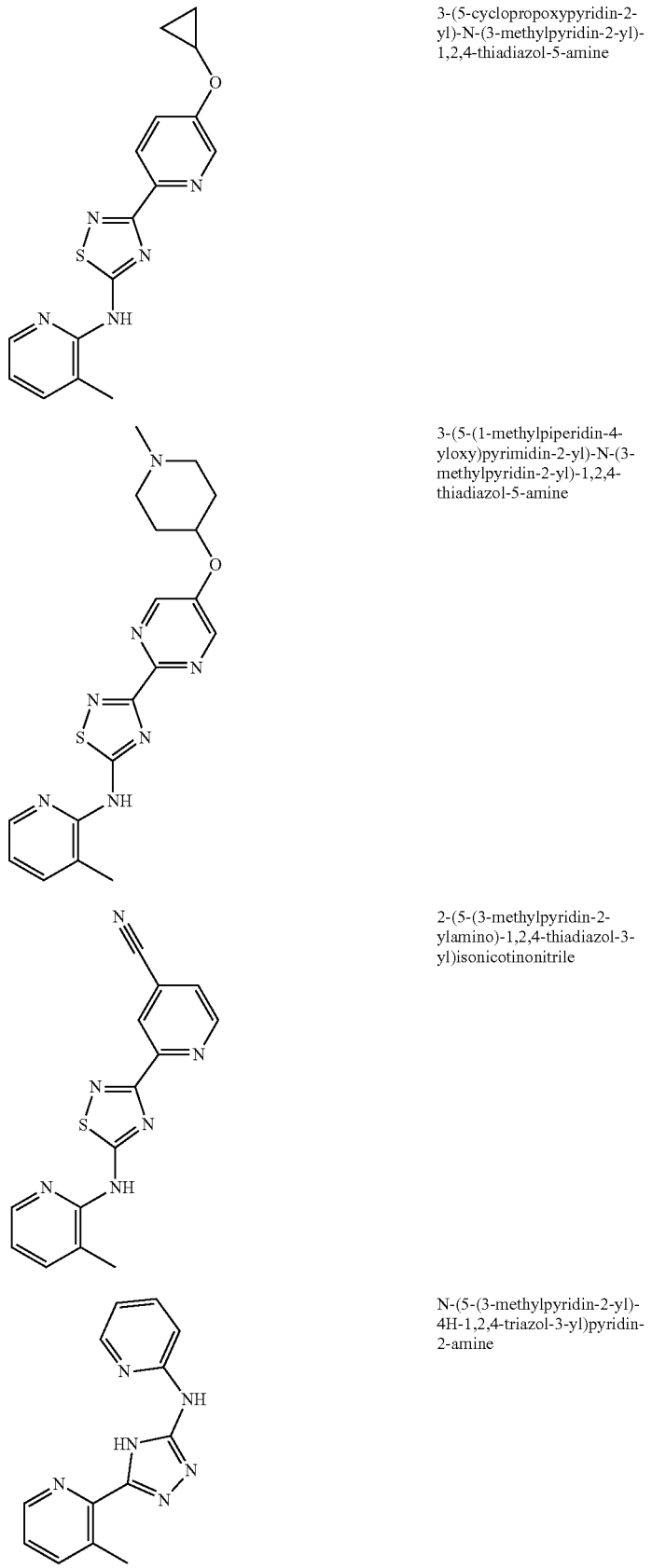
3-(5-cyclopropoxypyridin-2-yl)-N-(3-methylpyridin-2-yl)-1,2,4-thiadiazol-5-amine
3-(5-(1-methylpiperidin-4-yloxy)pyrimidin-2-yl)-N-(3-methylpyridin-2-yl)-1,2,4-thiadiazol-5-amine
2-(5-(3-methylpyridin-2-ylamino)-1,2,4-thiadiazol-3-yl)isonicotinonitrile
N-(5-(3-methylpyridin-2-yl)-4H-1,2,4-triazol-3-yl)pyridin-2-amine -continued
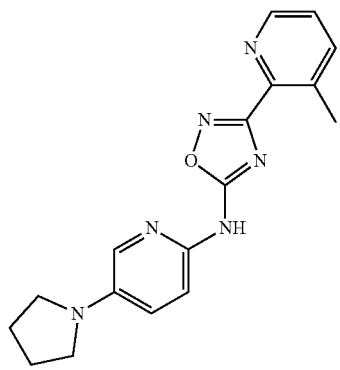 [SMILES: Cc1cccnc1-c1noc(Nc2ccc(N3CCCC3)cn2)n1]
3-(3-methylpyridin-2-yl)-N-(5-(pyrrolidin-1-yl)pyridin-2-yl)-1,2,4-oxadiazol-5-amine
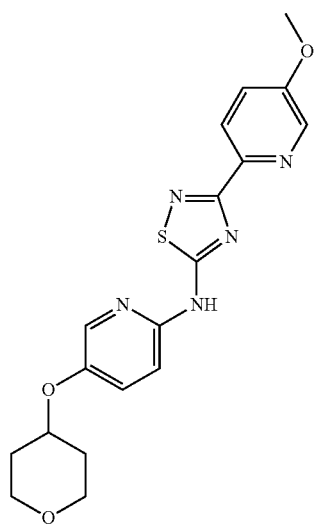 [SMILES: COc1ccc(-c2nsc(Nc3ccc(OC4CCOCC4)cn3)n2)nc1]
3-(5-methoxypyridin-2-yl)-N-(5-(tetrahydro-2H-pyran-4-yloxy)pyridin-2-yl)-1,2,4-thiadiazol-5-amine
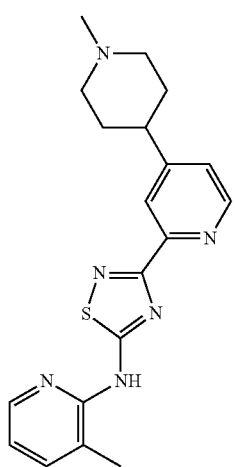 [SMILES: Cc1cccnc1Nc1nc(-c2cc(C3CCN(C)CC3)ccn2)ns1]
3-(4-(1-methylpiperidin-4-yl)pyridin-2-yl)-N-(3-methylpyridin-2-yl)-1,2,4-thiadiazol-5-amine

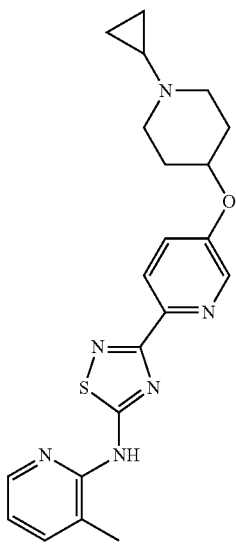 [SMILES: Cc1cccnc1Nc1nc(-c2ccc(OC3CCN(C4CC4)CC3)cn2)ns1]
3-(5-(1-cyclopropylpiperidin-4-yloxy)pyridin-2-yl)-N-(3-methylpyridin-2-yl)-1,2,4-thiadiazol-5-amine
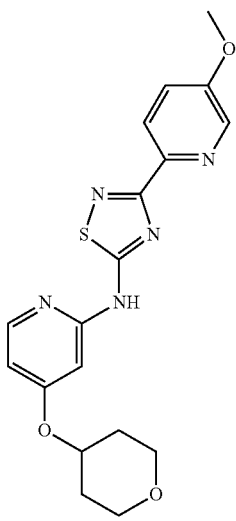 [SMILES: COc1ccc(-c2nsc(Nc3cc(OC4CCOCC4)ccn3)n2)nc1]
3-(5-methoxypyridin-2-yl)-N-(4-(tetrahydro-2H-pyran-4-yloxy)pyridin-2-yl)-1,2,4-thiadiazol-5-amine
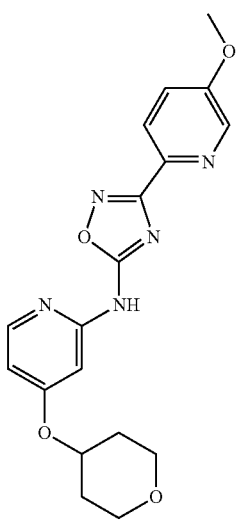 [SMILES: COc1ccc(-c2noc(Nc3cc(OC4CCOCC4)ccn3)n2)nc1]
3-(5-methoxypyridin-2-yl)-N-(4-(tetrahydro-2H-pyran-4-yloxy)pyridin-2-yl)-1,2,4-oxadiazol-5-amine

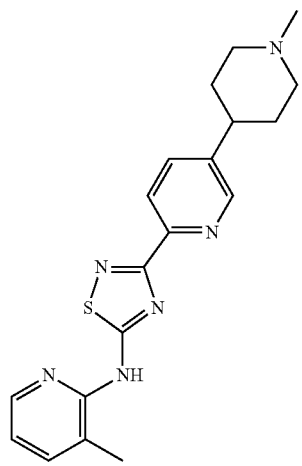 [SMILES: Cc1cccnc1Nc1nc(-c2ccc(C3CCN(C)CC3)cn2)ns1]
3-(5-(1-methylpiperidin-4-yl)pyridin-2-yl)-N-(3-methylpyridin-2-yl)-1,2,4-thiadiazol-5-amine
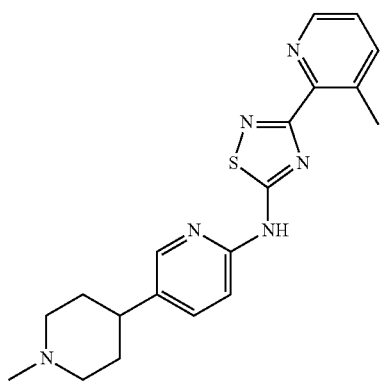
N-(5-(1-methylpiperidin-4-yl)pyridin-2-yl)-3-(3-methylpyridin-2-yl)-1,2,4-thiadiazol-5-amine
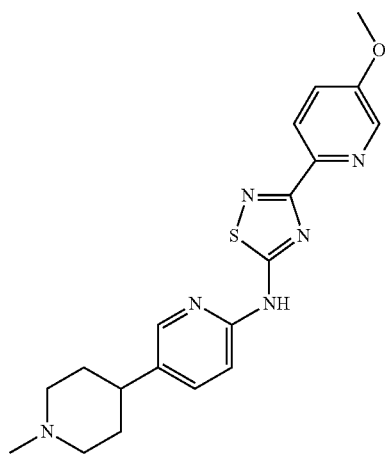 [SMILES: COc1ccc(-c2nsc(Nc3ccc(C4CCN(C)CC4)cn3)n2)nc1]
3-(5-methoxypyridin-2-yl)-N-(5-(1-methylpiperidin-4-yl)pyridin-2-yl)-1,2,4-thiadiazol-5-amine

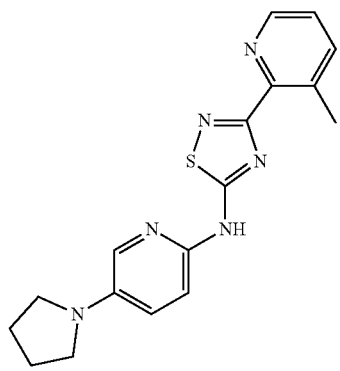
3-(3-methylpyridin-2-yl)-N-(5-(pyrrolidin-1-yl)pyridin-2-yl)-1,2,4-thiadiazol-5-amine
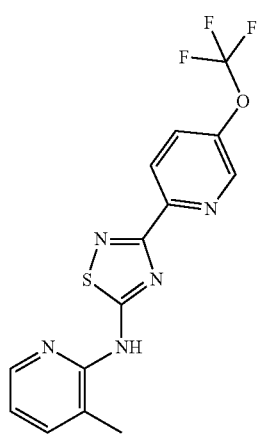 [SMILES: Cc1cccnc1Nc1nc(-c2ccc(OC(F)(F)F)cn2)ns1]
N-(3-methylpyridin-2-yl)-3-(5-(trifluoromethoxy)pyridin-2-yl)-1,2,4-thiadiazol-5-amine
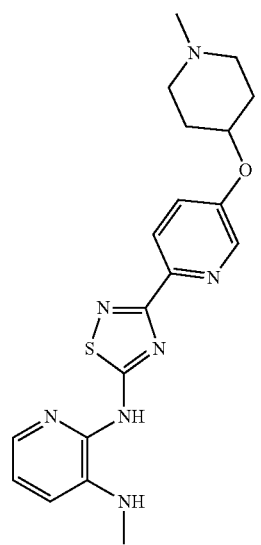 [SMILES: CNc1cccnc1Nc1nc(-c2ccc(OC3CCN(C)CC3)cn2)ns1]
N3-methyl-N2-(3-(5-(1-methylpiperidin-4-yloxy)pyridin-2-yl)-1,2,4-thiadiazol-5-yl)pyridine-2,3-diamine

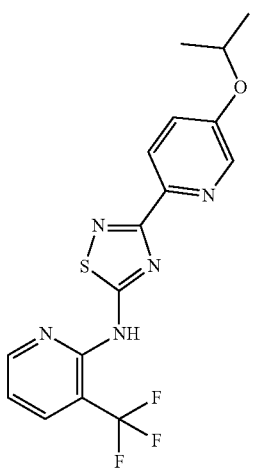 [SMILES: CC(C)Oc1ccc(-c2nsc(Nc3ncccc3C(F)(F)F)n2)nc1]
3-(5-isopropoxypyridin-2-yl)-N-(3-(trifluoromethyl)pyridin-2-yl)-1,2,4-thiadiazol-5-amine
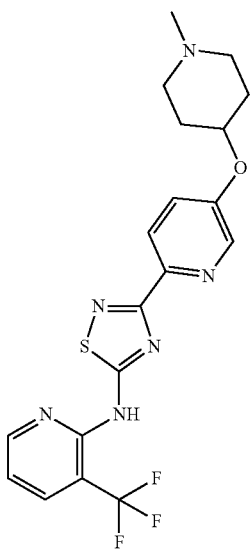 [SMILES: CN1CCC(Oc2ccc(-c3nsc(Nc4ncccc4C(F)(F)F)n3)nc2)CC1]
3-(5-(1-methylpiperidin-4-yloxy)pyridin-2-yl)-N-(3-(trifluoromethyl)pyridin-2-yl)-1,2,4-thiadiazol-5-amine
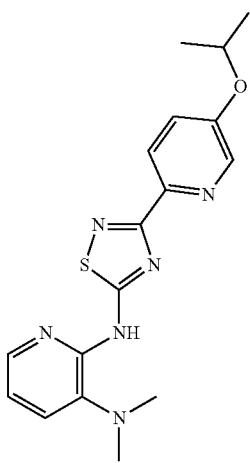 [SMILES: CC(C)Oc1ccc(-c2nsc(Nc3ncccc3N(C)C)n2)nc1]
N2-(3-(5-isopropoxypyridin-2-yl)-1,2,4-thiadiazol-5-yl)-N3,N3-dimethylpyridine-2,3-diamine

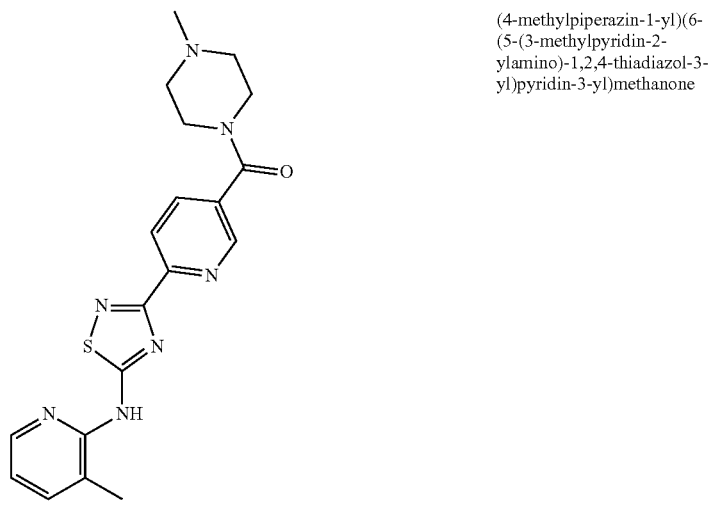
(4-methylpiperazin-1-yl)(6-(5-(3-methylpyridin-2-ylamino)-1,2,4-thiadiazol-3-yl)pyridin-3-yl)methanone
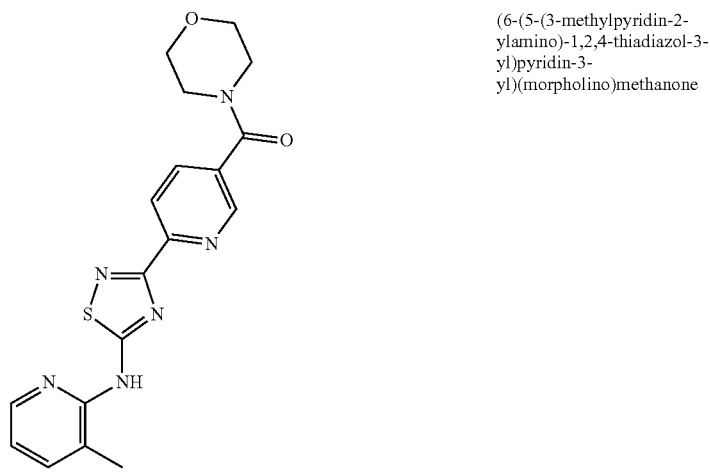
(6-(5-(3-methylpyridin-2-ylamino)-1,2,4-thiadiazol-3-yl)pyridin-3-yl)(morpholino)methanone
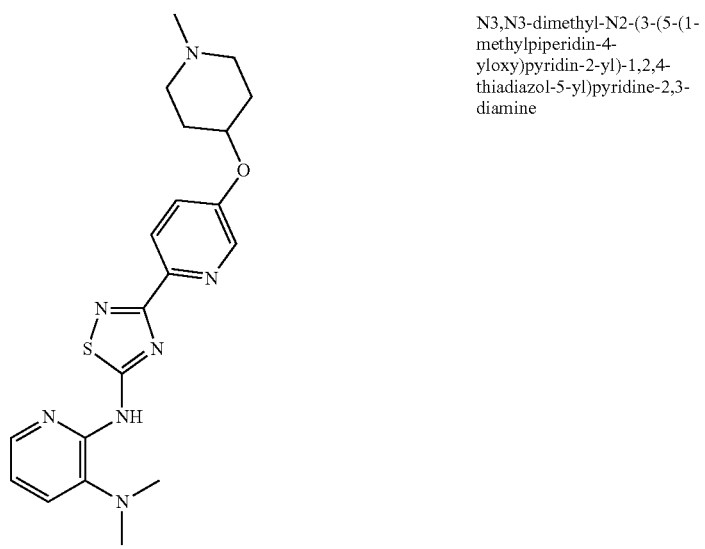
N3,N3-dimethyl-N2-(3-(5-(1-methylpiperidin-4-yloxy)pyridin-2-yl)-1,2,4-thiadiazol-5-yl)pyridine-2,3-diamine

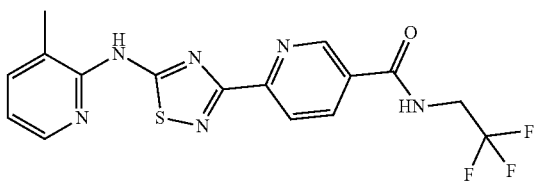 [SMILES: Cc1cccnc1Nc1nc(-c2ccc(C(=O)NCC(F)(F)F)cn2)ns1]
6-(5-(3-methylpyridin-2-ylamino)-1,2,4-thiadiazol-3-yl)-N-(2,2,2-trifluoroethyl)nicotinamide
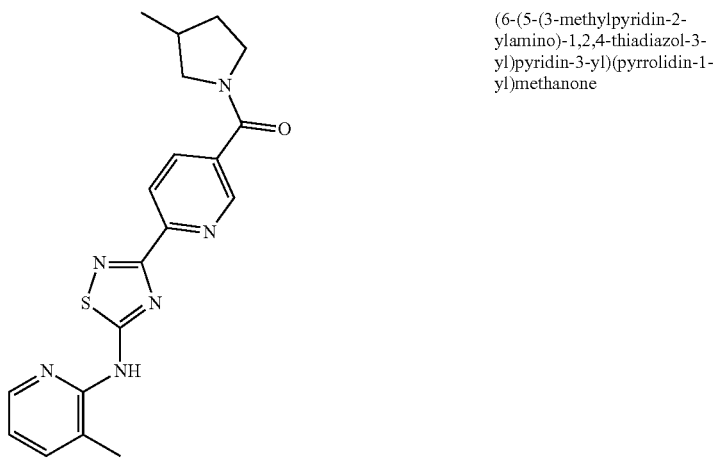
(6-(5-(3-methylpyridin-2-ylamino)-1,2,4-thiadiazol-3-yl)pyridin-3-yl)(pyrrolidin-1-yl)methanone
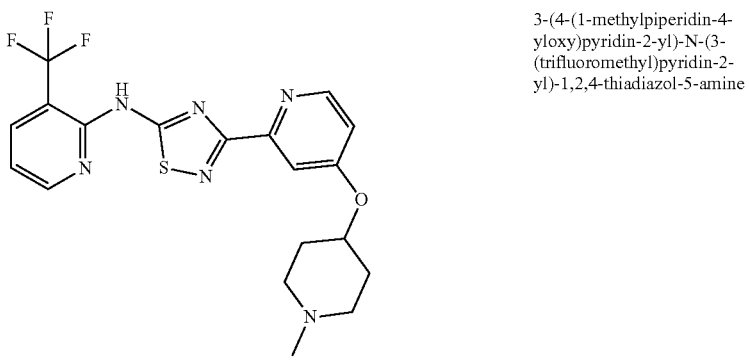
3-(4-(1-methylpiperidin-4-yloxy)pyridin-2-yl)-N-(3-(trifluoromethyl)pyridin-2-yl)-1,2,4-thiadiazol-5-amine
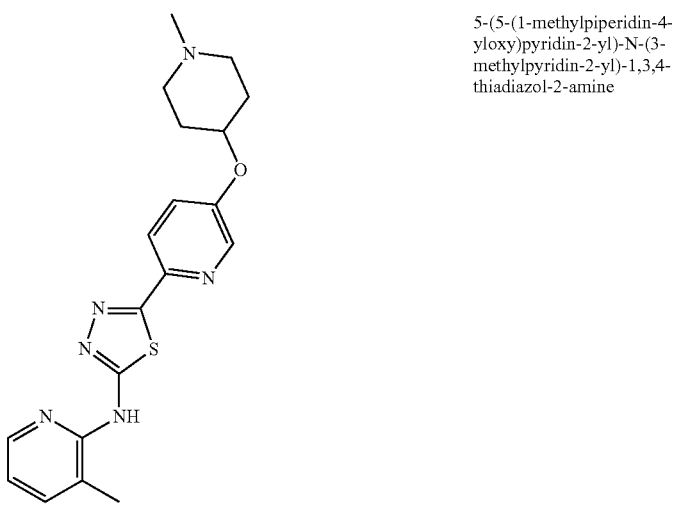
5-(5-(1-methylpiperidin-4-yloxy)pyridin-2-yl)-N-(3-methylpyridin-2-yl)-1,3,4-thiadiazol-2-amine

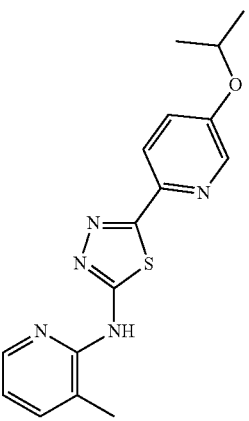 [SMILES: Cc1cccnc1Nc1nnc(-c2ccc(OC(C)C)cn2)s1]
5-(5-isopropoxypyridin-2-yl)-N-(3-methylpyridin-2-yl)-1,3,4-thiadiazol-2-amine
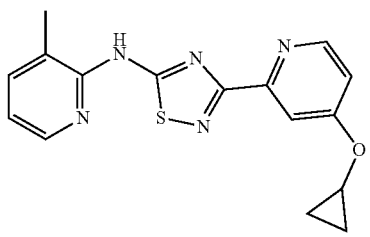 [SMILES: Cc1cccnc1Nc1nc(-c2cc(OC3CC3)ccn2)ns1]
3-(4-cyclopropoxypyridin-2-yl)-N-(3-methylpyridin-2-yl)-1,2,4-thiadiazol-5-amine
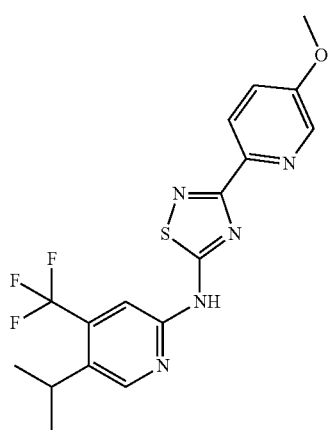 [SMILES: COc1ccc(-c2nsc(Nc3cc(C(F)(F)F)c(C(C)C)cn3)n2)nc1]
N-(5-isopropyl-4-(trifluoromethyl)pyridin-2-yl)-3-(5-methoxypyridin-2-yl)-1,2,4-thiadiazol-5-amine
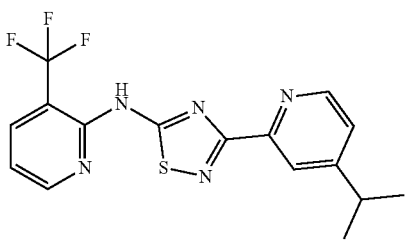 [SMILES: CC(C)c1ccnc(-c2nsc(Nc3ncccc3C(F)(F)F)n2)c1]
3-(4-isopropylpyridin-2-yl)-N-(3-(trifluoromethyl)pyridin-2-yl)-1,2,4-thiadiazol-5-amine

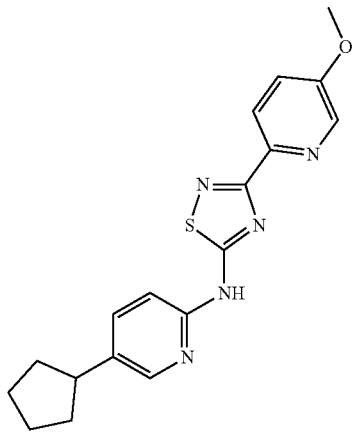 [SMILES: COc1ccc(-c2nsc(Nc3ccc(C4CCCC4)cn3)n2)nc1]
N-(5-cyclopentylpyridin-2-yl)-3-(5-methoxypyridin-2-yl)-1,2,4-thiadiazol-5-amine
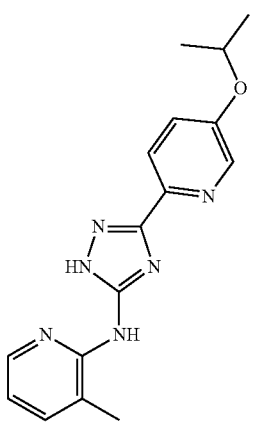 [SMILES: Cc1cccnc1Nc1nc(-c2ccc(OC(C)C)cn2)n[nH]1]
N-(3-(5-isopropoxypyridin-2-yl)-1H-1,2,4-triazol-5-yl)-3-methylpyridin-2-amine
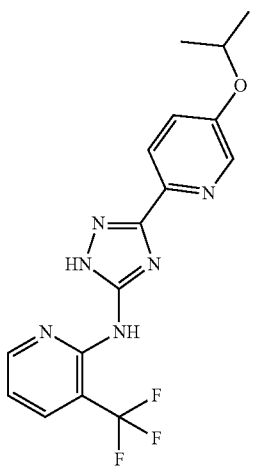 [SMILES: CC(C)Oc1ccc(-c2n[nH]c(Nc3ncccc3C(F)(F)F)n2)nc1]
N-(3-(5-isopropoxypyridin-2-yl)-1H-1,2,4-triazol-5-yl)-3-(trifluoromethyl)pyridin-2-amine

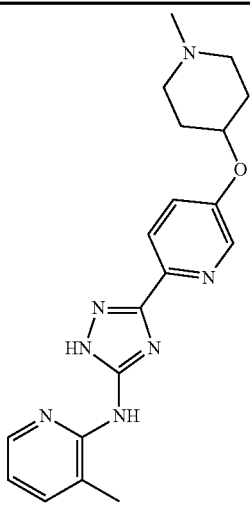
3-methyl-N-(3-(5-(1-methylpiperidin-4-yloxy)pyridin-2-yl)-1H-1,2,4-triazol-5-yl)pyridin-2-amine
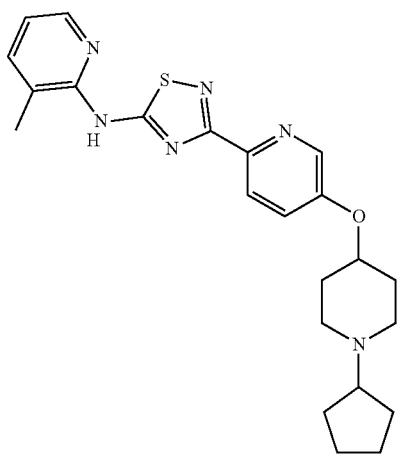
3-(5-(1-cyclopentylpiperidin-4-yloxy)pyridin-2-yl)-N-(3-methylpyridin-2-yl)-1,2,4-thiadiazol-5-amine
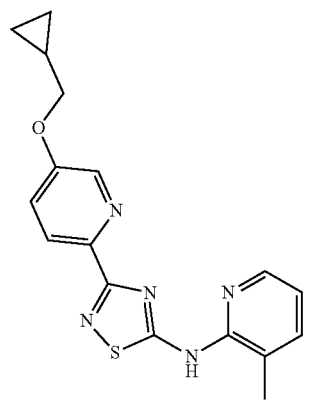 [SMILES: Cc1cccnc1Nc1nc(-c2ccc(OCC3CC3)cn2)ns1]
3-(5-(cyclopropylmethoxy)pyridin-2-yl)-N-(3-methylpyridin-2-yl)-1,2,4-thiadiazol-5-amine
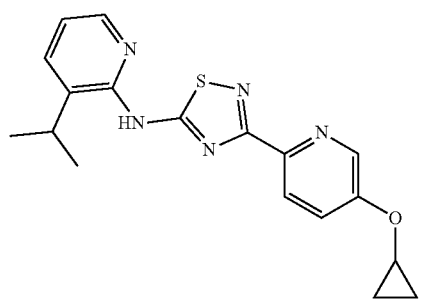 [SMILES: CC(C)c1cccnc1Nc1nc(-c2ccc(OC3CC3)cn2)ns1]
3-(5-cyclopropoxypyridin-2-yl)-N-(3-isopropylpyridin-2-yl)-1,2,4-thiadiazol-5-amine

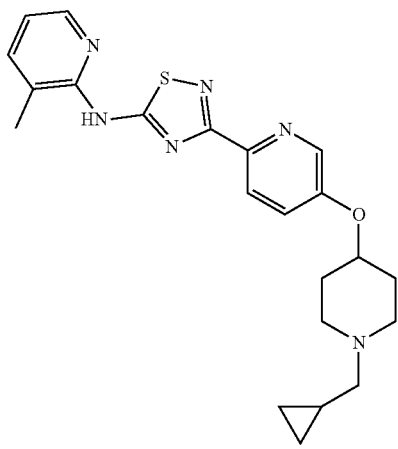 [SMILES: Cc1cccnc1Nc1nc(-c2ccc(OC3CCN(CC4CC4)CC3)cn2)ns1]
3-(5-(1-(cyclopropylmethyl)piperidin-4-yloxy)pyridin-2-yl)-N-(3-methylpyridin-2-yl)-1,2,4-thiadiazol-5-amine
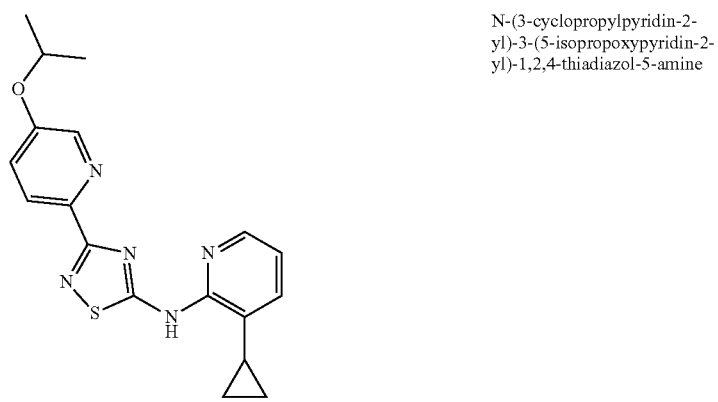
N-(3-cyclopropylpyridin-2-yl)-3-(5-isopropoxypyridin-2-yl)-1,2,4-thiadiazol-5-amine
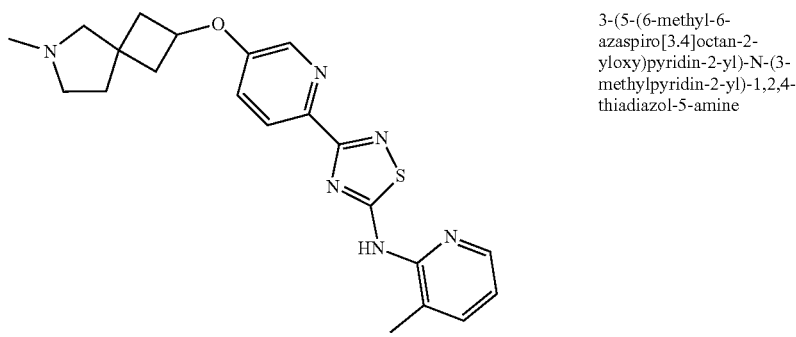
3-(5-(6-methyl-6-azaspiro[3.4]octan-2-yloxy)pyridin-2-yl)-N-(3-methylpyridin-2-yl)-1,2,4-thiadiazol-5-amine
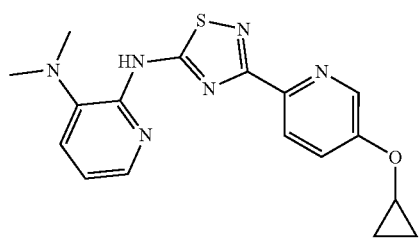 [SMILES: CN(C)c1cccnc1Nc1nc(-c2ccc(OC3CC3)cn2)ns1]
N2-(3-(5-cyclopropoxypyridin-2-yl)-1,2,4-thiadiazol-5-yl)-N3,N3-dimethylpyridine-2,3-diamine

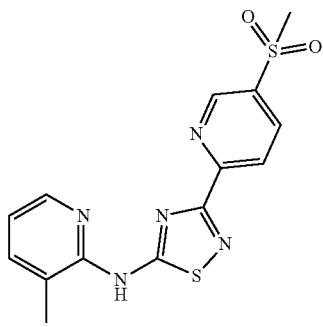 [SMILES: Cc1cccnc1Nc1nc(-c2ccc(S(C)(=O)=O)cn2)ns1]
N-(3-methylpyridin-2-yl)-3-(5-(methylsulfonyl)pyridin-2-yl)-1,2,4-thiadiazol-5-amine
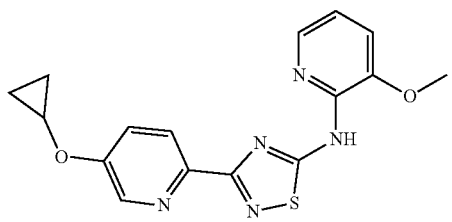 [SMILES: COc1cccnc1Nc1nc(-c2ccc(OC3CC3)cn2)ns1]
3-(5-cyclopropoxypyridin-2-yl)-N-(3-methoxypyridin-2-yl)-1,2,4-thiadiazol-5-amine
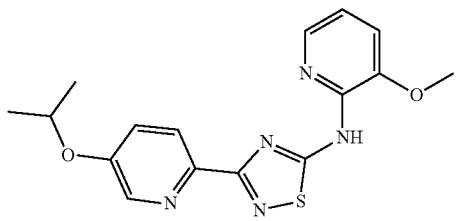 [SMILES: COc1cccnc1Nc1nc(-c2ccc(OC(C)C)cn2)ns1]
3-(5-isopropoxypyridin-2-yl)-N-(3-methoxypyridin-2-yl)-1,2,4-thiadiazol-5-amine
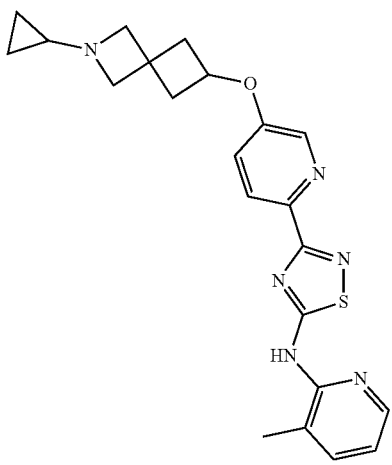 [SMILES: Cc1cccnc1Nc1nc(-c2ccc(OC3CC4(C3)CN(C3CC3)C4)cn2)ns1]
3-(5-(2-cyclopropyl-2-azaspiro[3.3]heptan-6-yloxy)pyridin-2-yl)-N-(3-methylpyridin-2-yl)-1,2,4-thiadiazol-5-amine

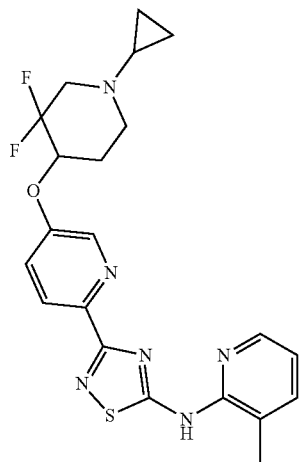 [SMILES: Cc1cccnc1Nc1nc(-c2ccc(OC3CCN(C4CC4)CC3(F)F)cn2)ns1]
3-(5-(1-cyclopropyl-3,3-difluoropiperidin-4-yloxy)pyridin-2-yl)-N-(3-methylpyridin-2-yl)-1,2,4-thiadiazol-5-amine
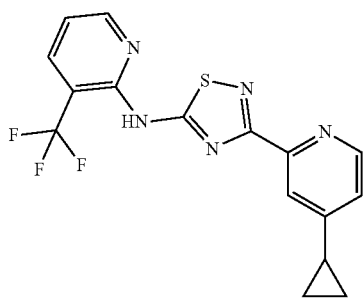 [SMILES: FC(F)(F)c1cccnc1Nc1nc(-c2cc(C3CC3)ccn2)ns1]
3-(4-cyclopropylpyridin-2-yl)-N-(3-(trifluoromethyl)pyridin-2-yl)-1,2,4-thiadiazol-5-amine
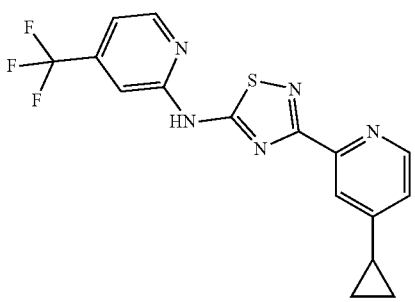 [SMILES: FC(F)(F)c1ccnc(Nc2nc(-c3cc(C4CC4)ccn3)ns2)c1]
3-(4-cyclopropylpyridin-2-yl)-N-(4-(trifluoromethyl)pyridin-2-yl)-1,2,4-thiadiazol-5-amine
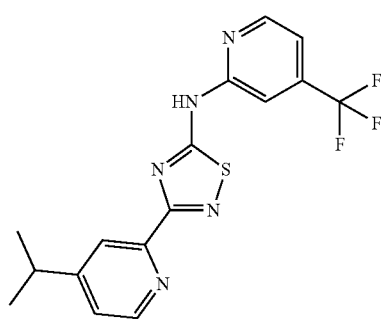 [SMILES: CC(C)c1ccnc(-c2nsc(Nc3cc(C(F)(F)F)ccn3)n2)c1]
3-(4-isopropylpyridin-2-yl)-N-(4-(trifluoromethyl)pyridin-2-yl)-1,2,4-thiadiazol-5-amine

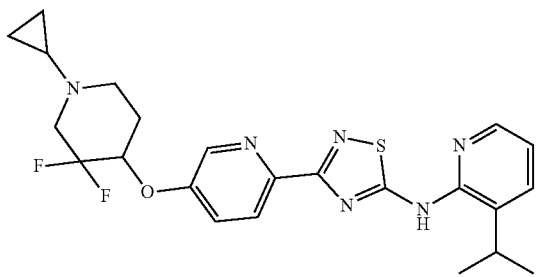 [SMILES: CC(C)c1cccnc1Nc1nc(-c2ccc(OC3CCN(C4CC4)CC3(F)F)cn2)ns1]
3-(5-(1-cyclopropyl-3,3-difluoropiperidin-4-yloxy)pyridin-2-yl)-N-(3-isopropylpyridin-2-yl)-1,2,4-thiadiazol-5-amine
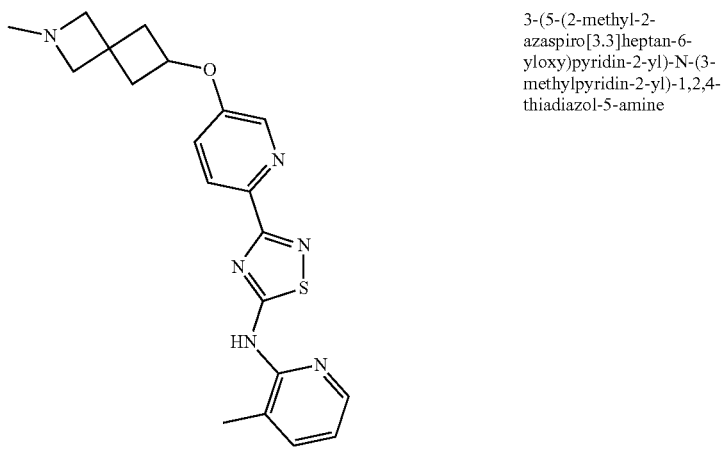
3-(5-(2-methyl-2-azaspiro[3.3]heptan-6-yloxy)pyridin-2-yl)-N-(3-methylpyridin-2-yl)-1,2,4-thiadiazol-5-amine
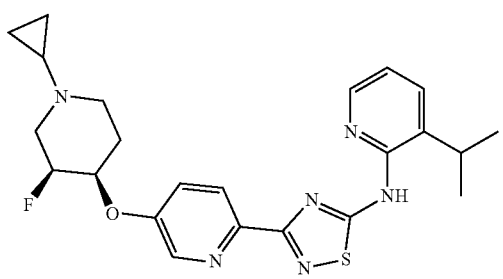 [SMILES: CC(C)c1cccnc1Nc1nc(-c2ccc(O[C@@H]3CCN(C4CC4)C[C@@H]3F)cn2)ns1]
3-(5-((3S,4R)-1-cyclopropyl-3-fluoropiperidin-4-yloxy)pyridin-2-yl)-N-(3-isopropylpyridin-2-yl)-1,2,4-thiadiazol-5-amine
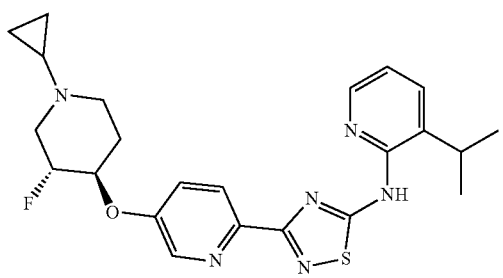 [SMILES: CC(C)c1cccnc1Nc1nc(-c2ccc(O[C@@H]3CCN(C4CC4)C[C@H]3F)cn2)ns1]
3-(5-((3R,4R)-1-cyclopropyl-3-fluoropiperidin-4-yloxy)pyridin-2-yl)-N-(3-isopropylpyridin-2-yl)-1,2,4-thiadiazol-5-amine

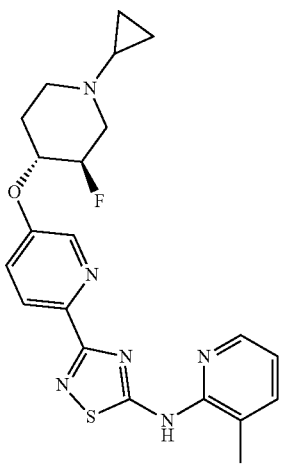 [SMILES: Cc1cccnc1Nc1nc(-c2ccc(O[C@@H]3CCN(C4CC4)C[C@H]3F)cn2)ns1]
3-(5-(((3R,4R)-1-cyclopropyl-3-fluoropiperidin-4-yloxy)pyridin-2-yl)-N-(3-methylpyridin-2-yl)-1,2,4-thiadiazol-5-amine
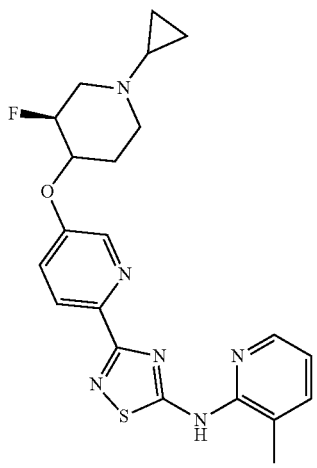 [SMILES: Cc1cccnc1Nc1nc(-c2ccc(OC3CCN(C4CC4)C[C@@H]3F)cn2)ns1]
3-(5-((3S)-1-cyclopropyl-3-fluoropiperidin-4-yloxy)pyridin-2-yl)-N-(3-methylpyridin-2-yl)-1,2,4-thiadiazol-5-amine
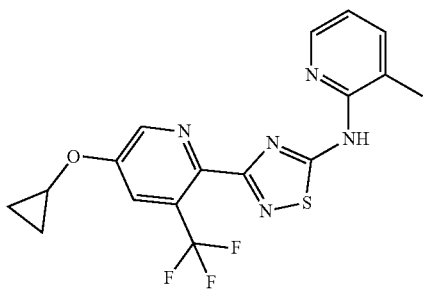 [SMILES: Cc1cccnc1Nc1nc(-c2ncc(OC3CC3)cc2C(F)(F)F)ns1]
3-(5-cyclopropoxy-3-(trifluoromethyl)pyridin-2-yl)-N-(3-methylpyridin-2-yl)-1,2,4-thiadiazol-5-amine
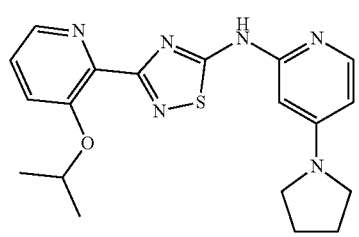 [SMILES: CC(C)Oc1cccnc1-c1nsc(Nc2cc(N3CCCC3)ccn2)n1]
3-(3-isopropoxypyridin-2-yl)-N-(4-(pyrrolidin-1-yl)pyridin-2-yl)-1,2,4-thiadiazol-5-amine

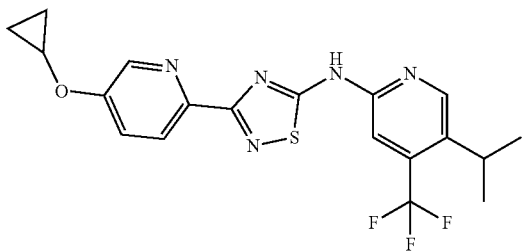 [SMILES: CC(C)c1cnc(Nc2nc(-c3ccc(OC4CC4)cn3)ns2)cc1C(F)(F)F]
3-(5-cyclopropoxypyridin-2-yl)-N-(5-isopropyl-4-(trifluoromethyl)pyridin-2-yl)-1,2,4-thiadiazol-5-amine

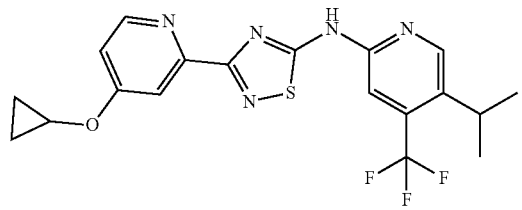 [SMILES: CC(C)c1cnc(Nc2nc(-c3cc(OC4CC4)ccn3)ns2)cc1C(F)(F)F]
3-(4-cyclopropoxypyridin-2-yl)-N-(5-isopropyl-4-(trifluoromethyl)pyridin-2-yl)-1,2,4-thiadiazol-5-amine

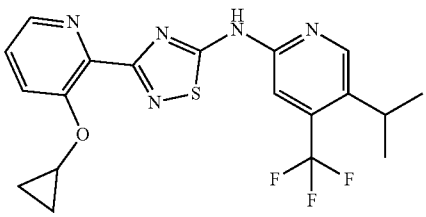 [SMILES: CC(C)c1cnc(Nc2nc(-c3ncccc3OC3CC3)ns2)cc1C(F)(F)F]
3-(3-cyclopropoxypyridin-2-yl)-N-(5-isopropyl-4-(trifluoromethyl)pyridin-2-yl)-1,2,4-thiadiazol-5-amine

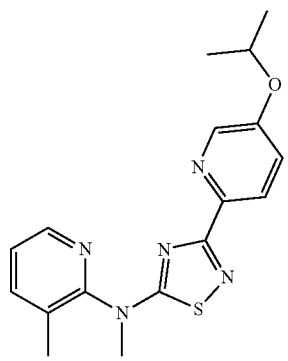 [SMILES: Cc1cccnc1N(C)c1nc(-c2ccc(OC(C)C)cn2)ns1]
3-(5-isopropoxypyridin-2-yl)-N-methyl-N-(3-methylpyridin-2-yl)-1,2,4-thiadiazol-5-amine

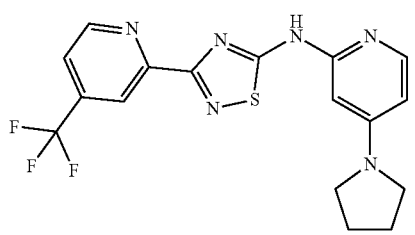 [SMILES: FC(F)(F)c1ccnc(-c2nsc(Nc3cc(N4CCCC4)ccn3)n2)c1]
N-(4-(pyrrolidin-1-yl)pyridin-2-yl)-3-(4-(trifluoromethyl)pyridin-2-yl)-1,2,4-thiadiazol-5-amine

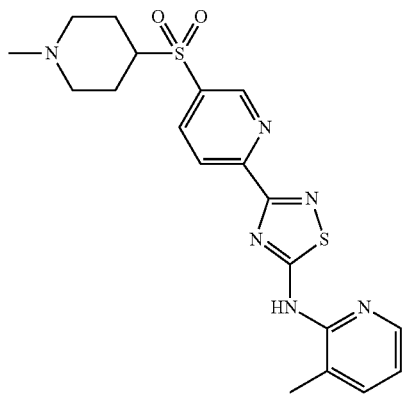 [SMILES: Cc1cccnc1Nc1nc(-c2ccc(S(=O)(=O)C3CCN(C)CC3)cn2)ns1]
3-(5-(1-methylpiperidin-4-ylsulfonyl)pyridin-2-yl)-N-(3-methylpyridin-2-yl)-1,2,4-thiadiazol-5-amine
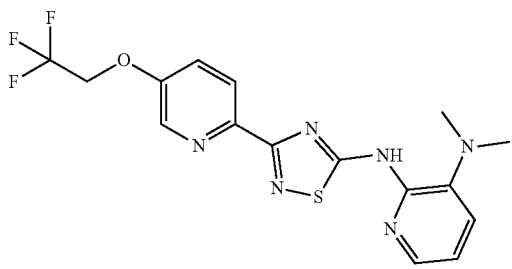 [SMILES: CN(C)c1cccnc1Nc1nc(-c2ccc(OCC(F)(F)F)cn2)ns1]
N3,N3-dimethyl-N2-(3-(5-(2,2,2-trifluoroethoxy)pyridin-2-yl)-1,2,4-thiadiazol-5-yl)pyridine-2,3-diamine
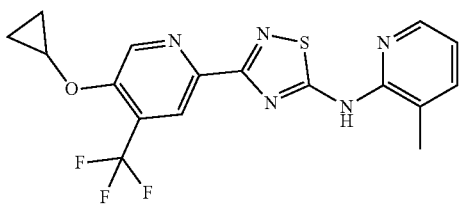 [SMILES: Cc1cccnc1Nc1nc(-c2cc(C(F)(F)F)c(OC3CC3)cn2)ns1]
3-(5-cyclopropoxy-4-(trifluoromethyl)pyridin-2-yl)-N-(3-methylpyridin-2-yl)-1,2,4-thiadiazol-5-amine
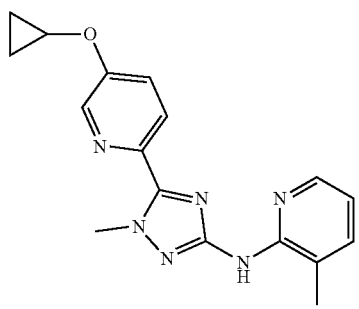 [SMILES: Cc1cccnc1Nc1nc(-c2ccc(OC3CC3)cn2)n(C)n1]
N-(5-(5-cyclopropoxypyridin-2-yl)-1-methyl-1H-1,2,4-triazol-3-yl)-3-methylpyridin-2-amine
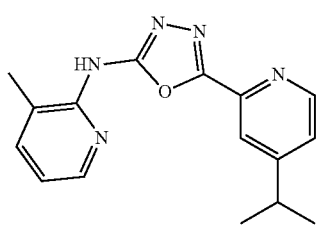 [SMILES: Cc1cccnc1Nc1nnc(-c2cc(C(C)C)ccn2)o1]
5-(4-isopropylpyridin-2-yl)-N-(3-methylpyridin-2-yl)-1,3,4-oxadiazol-2-amine -continued

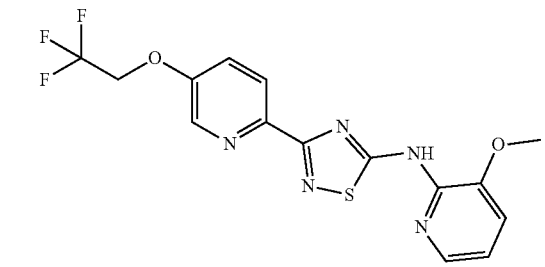 [SMILES: COc1cccnc1Nc1nc(-c2ccc(OCC(F)(F)F)cn2)ns1]

N-(3-methoxypyridin-2-yl)-
3-(5-(2,2,2-
trifluoroethoxy)pyridin-2-yl)-
1,2,4-thiadiazol-5-amine

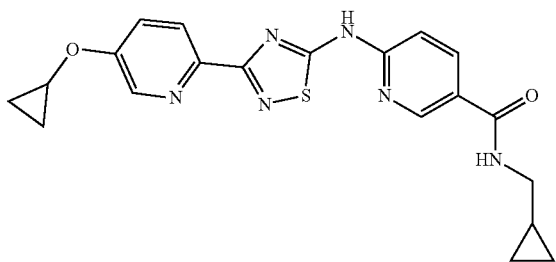 [SMILES: O=C(NCC1CC1)c1ccc(Nc2nc(-c3ccc(OC4CC4)cn3)ns2)nc1]

6-(3-(5-cyclopropoxypyridin-
2-yl)-1,2,4-thiadiazol-5-
ylamino)-N-
(cyclopropylmethyl)nicotinamide

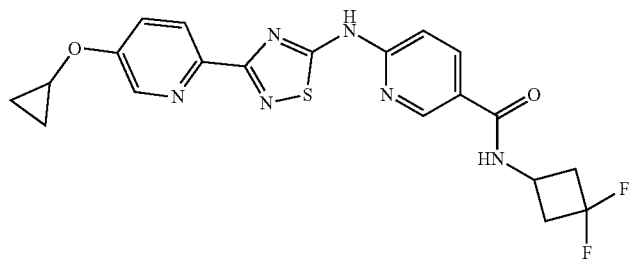 [SMILES: O=C(NC1CC(F)(F)C1)c1ccc(Nc2nc(-c3ccc(OC4CC4)cn3)ns2)nc1]

6-(3-(5-cyclopropoxypyridin-
2-yl)-1,2,4-thiadiazol-5-
ylamino)-N-(3,3-
difluorocyclobutyl)nicotinamide

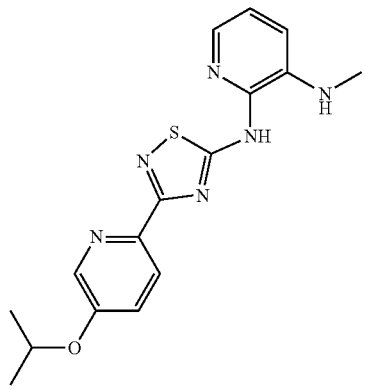 [SMILES: CNc1cccnc1Nc1nc(-c2ccc(OC(C)C)cn2)ns1]

N2-(3-(5-isopropoxypyridin-
2-yl)-1,2,4-thiadiazol-5-yl)-
N3-methylpyridine-2,3-
diamine

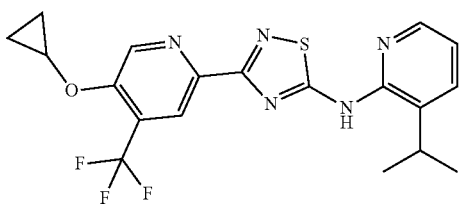

3-(5-cyclopropoxy-4-
(trifluoromethyl)pyridin-2-
yl)-N-(3-isopropylpyridin-2-
yl)-1,2,4-thiadiazol-5-amine

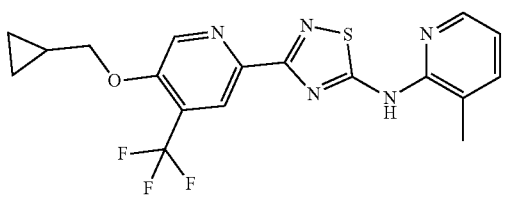 [SMILES: Cc1cccnc1Nc1nc(-c2cc(C(F)(F)F)c(OCC3CC3)cn2)ns1]

3-(5-(cyclopropylmethoxy)-
4-(trifluoromethyl)pyridin-2-
yl)-N-(3-methylpyridin-2-yl)-
1,2,4-thiadiazol-5-amine

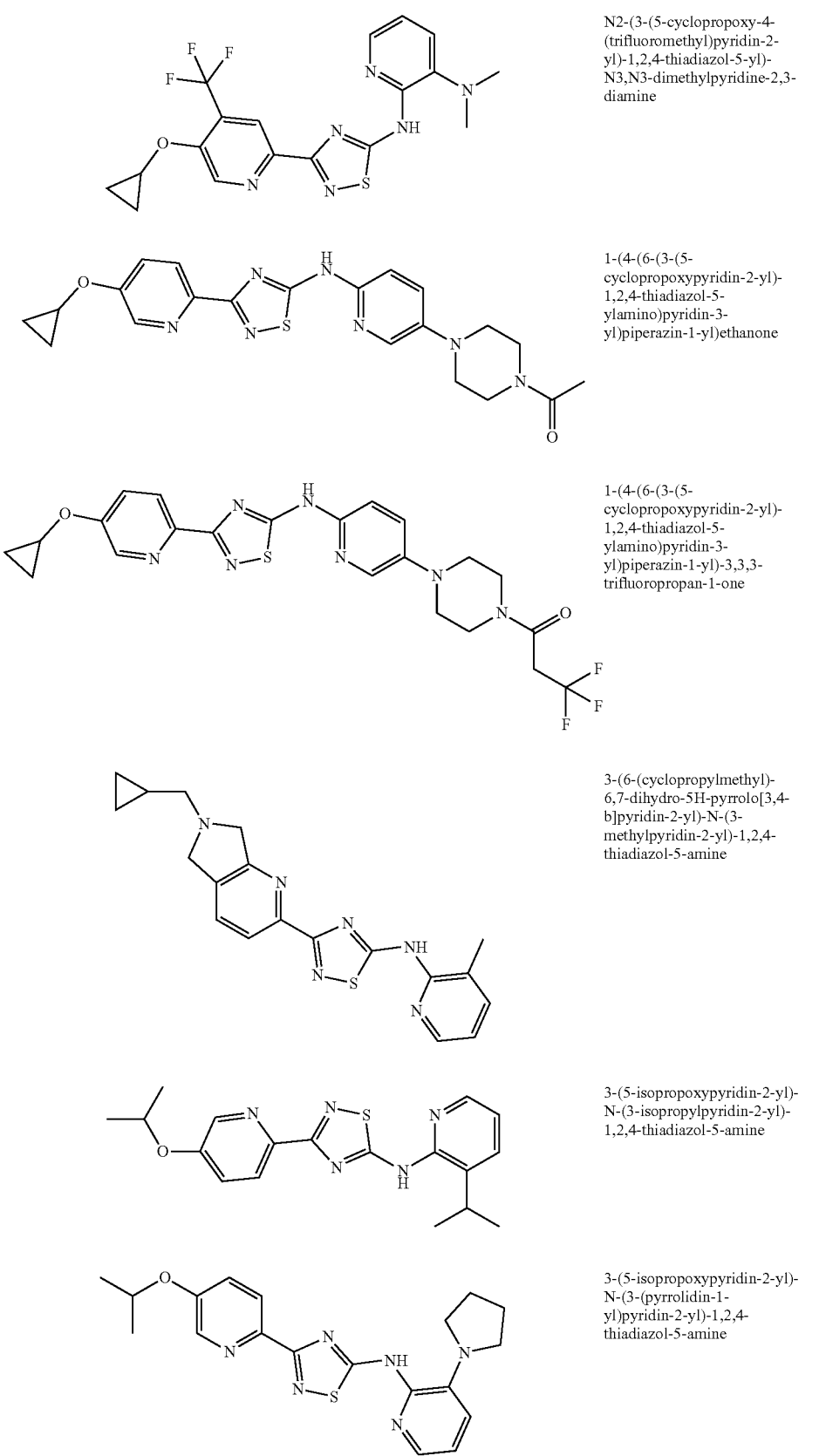

| | |
|---|---|
| | N2-(3-(5-cyclopropoxy-4-(trifluoromethyl)pyridin-2-yl)-1,2,4-thiadiazol-5-yl)-N3,N3-dimethylpyridine-2,3-diamine |
| | 1-(4-(6-(3-(5-cyclopropoxypyridin-2-yl)-1,2,4-thiadiazol-5-ylamino)pyridin-3-yl)piperazin-1-yl)ethanone |
| | 1-(4-(6-(3-(5-cyclopropoxypyridin-2-yl)-1,2,4-thiadiazol-5-ylamino)pyridin-3-yl)piperazin-1-yl)-3,3,3-trifluoropropan-1-one |
| | 3-(6-(cyclopropylmethyl)-6,7-dihydro-5H-pyrrolo[3,4-b]pyridin-2-yl)-N-(3-methylpyridin-2-yl)-1,2,4-thiadiazol-5-amine |
| | 3-(5-isopropoxypyridin-2-yl)-N-(3-isopropylpyridin-2-yl)-1,2,4-thiadiazol-5-amine |
| | 3-(5-isopropoxypyridin-2-yl)-N-(3-(pyrrolidin-1-yl)pyridin-2-yl)-1,2,4-thiadiazol-5-amine |

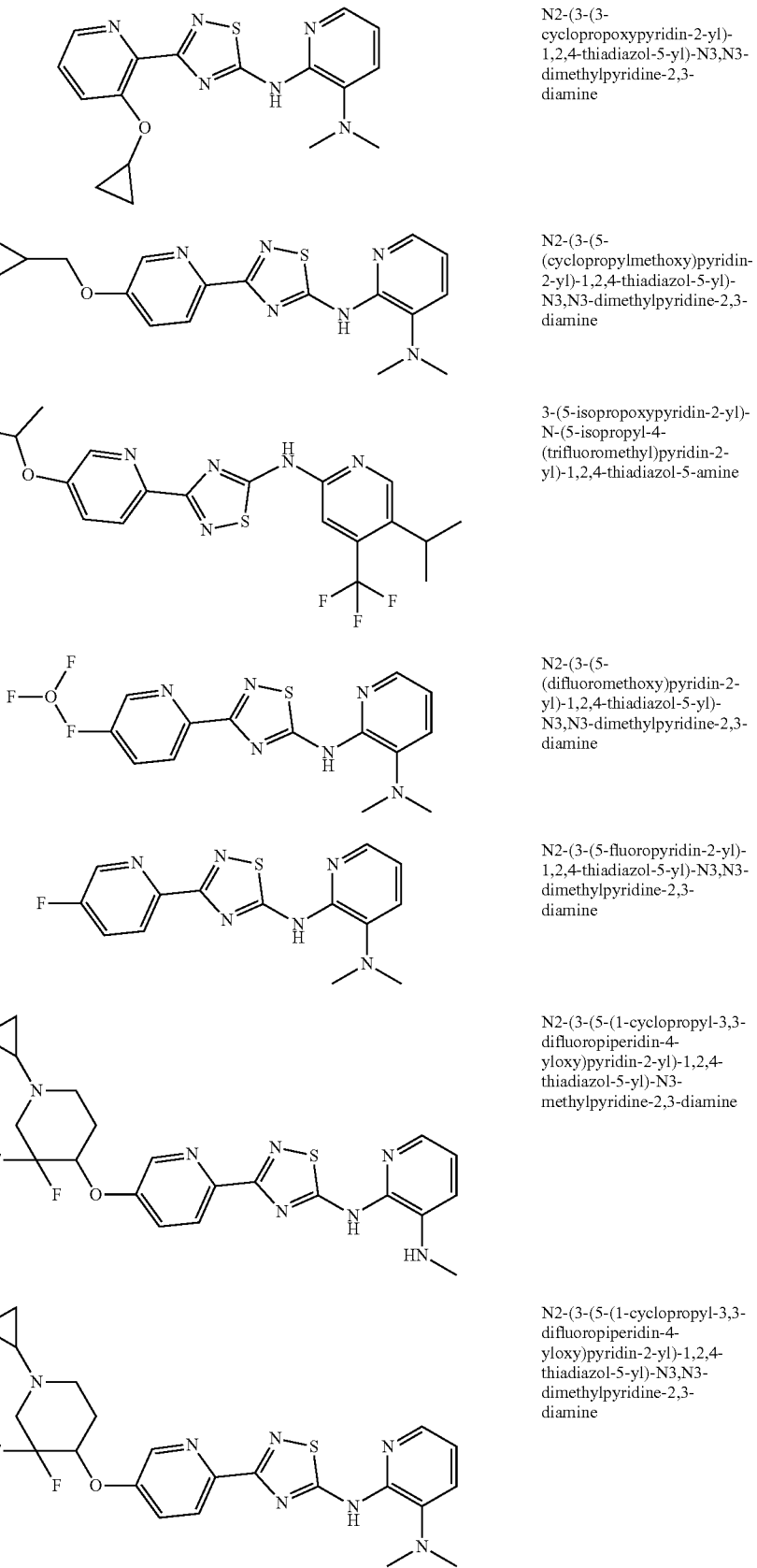

N2-(3-(3-cyclopropoxypyridin-2-yl)-1,2,4-thiadiazol-5-yl)-N3,N3-dimethylpyridine-2,3-diamine N2-(3-(5-(cyclopropylmethoxy)pyridin-2-yl)-1,2,4-thiadiazol-5-yl)-N3,N3-dimethylpyridine-2,3-diamine 3-(5-isopropoxypyridin-2-yl)-N-(5-isopropyl-4-(trifluoromethyl)pyridin-2-yl)-1,2,4-thiadiazol-5-amine N2-(3-(5-(difluoromethoxy)pyridin-2-yl)-1,2,4-thiadiazol-5-yl)-N3,N3-dimethylpyridine-2,3-diamine N2-(3-(5-fluoropyridin-2-yl)-1,2,4-thiadiazol-5-yl)-N3,N3-dimethylpyridine-2,3-diamine N2-(3-(5-(1-cyclopropyl-3,3-difluoropiperidin-4-yloxy)pyridin-2-yl)-1,2,4-thiadiazol-5-yl)-N3-methylpyridine-2,3-diamine N2-(3-(5-(1-cyclopropyl-3,3-difluoropiperidin-4-yloxy)pyridin-2-yl)-1,2,4-thiadiazol-5-yl)-N3,N3-dimethylpyridine-2,3-diamine -continued

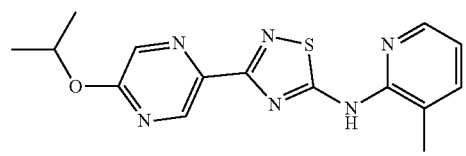 [SMILES: Cc1cccnc1Nc1nc(-c2cnc(OC(C)C)cn2)ns1]
3-(5-isopropoxypyrazin-2-yl)-N-(3-methylpyridin-2-yl)-1,2,4-thiadiazol-5-amine

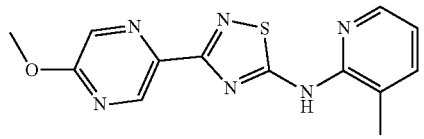 [SMILES: COc1cnc(-c2nsc(Nc3ncccc3C)n2)cn1]
3-(5-methoxypyrazin-2-yl)-N-(3-methylpyridin-2-yl)-1,2,4-thiadiazol-5-amine

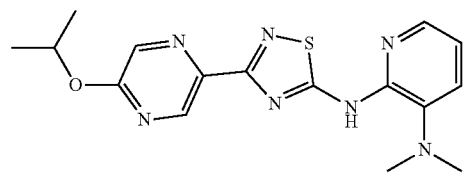 [SMILES: CC(C)Oc1cnc(-c2nsc(Nc3ncccc3N(C)C)n2)cn1]
N2-(3-(5-isopropoxypyrazin-2-yl)-1,2,4-thiadiazol-5-yl)-N3,N3-dimethylpyridine-2,3-diamine

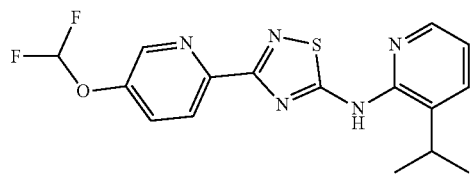 [SMILES: CC(C)c1cccnc1Nc1nc(-c2ccc(OC(F)F)cn2)ns1]
3-(5-(difluoromethoxy)pyridin-2-yl)-N-(3-isopropylpyridin-2-yl)-1,2,4-thiadiazol-5-amine

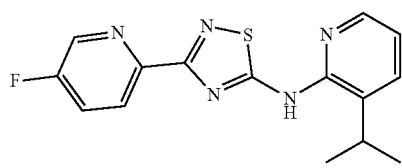 [SMILES: CC(C)c1cccnc1Nc1nc(-c2ccc(F)cn2)ns1]
3-(5-fluoropyridin-2-yl)-N-(3-isopropylpyridin-2-yl)-1,2,4-thiadiazol-5-amine

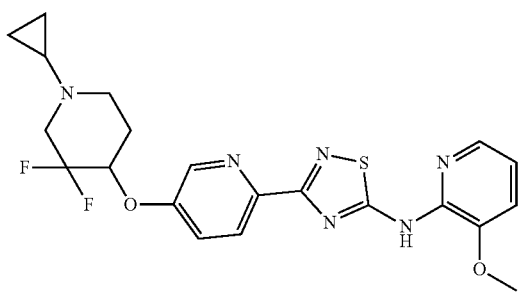 [SMILES: COc1cccnc1Nc1nc(-c2ccc(OC3CCN(C4CC4)CC3(F)F)cn2)ns1]
3-(5-(1-cyclopropyl-3,3-difluoropiperidin-4-yloxy)pyridin-2-yl)-N-(3-methoxypyridin-2-yl)-1,2,4-thiadiazol-5-amine

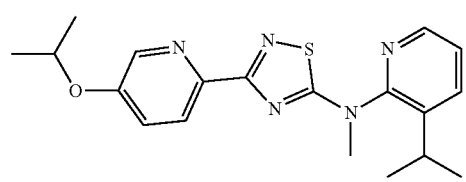 [SMILES: CC(C)Oc1ccc(-c2nsc(N(C)c3ncccc3C(C)C)n2)nc1]
3-(5-isopropoxypyridin-2-yl)-N-(3-isopropylpyridin-2-yl)-N-methyl-1,2,4-thiadiazol-5-amine

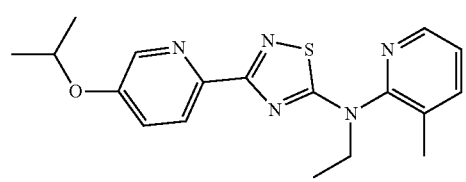 [SMILES: CCN(c1nc(-c2ccc(OC(C)C)cn2)ns1)c1ncccc1C]
N-ethyl-3-(5-isopropoxypyridin-2-yl)-N-(3-methylpyridin-2-yl)-1,2,4-thiadiazol-5-amine

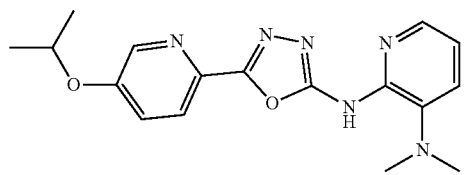 [SMILES: CC(C)Oc1ccc(-c2nnc(Nc3ncccc3N(C)C)o2)nc1]

N2-(5-(5-isopropoxypyridin-2-yl)-1,3,4-oxadiazol-2-yl)-N3,N3-dimethylpyridine-2,3-diamine

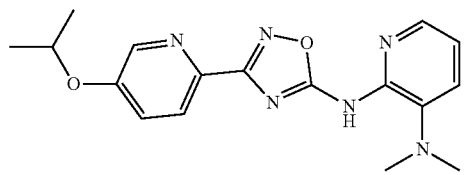 [SMILES: CC(C)Oc1ccc(-c2noc(Nc3ncccc3N(C)C)n2)nc1]

N2-(3-(5-isopropoxypyridin-2-yl)-1,2,4-oxadiazol-5-yl)-N3,N3-dimethylpyridine-2,3-diamine

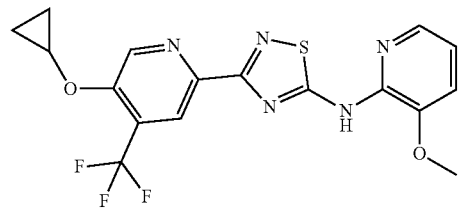 [SMILES: COc1cccnc1Nc1nc(-c2cc(C(F)(F)F)c(OC3CC3)cn2)ns1]

3-(5-cyclopropoxy-4-(trifluoromethyl)pyridin-2-yl)-N-(3-methoxypyridin-2-yl)-1,2,4-thiadiazol-5-amine

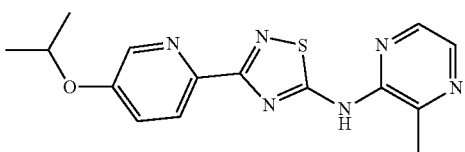 [SMILES: Cc1nccnc1Nc1nc(-c2ccc(OC(C)C)cn2)ns1]

3-(5-isopropoxypyridin-2-yl)-N-(3-methylpyrazin-2-yl)-1,2,4-thiadiazol-5-amine

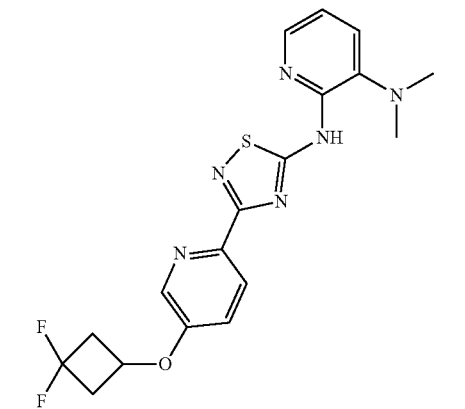 [SMILES: CN(C)c1cccnc1Nc1nc(-c2ccc(OC3CC(F)(F)C3)cn2)ns1]

N2-(3-(5-(3,3-difluorocyclobutoxy)pyridin-2-yl)-1,2,4-thiadiazol-5-yl)-N3,N3-dimethylpyridine-2,3-diamine

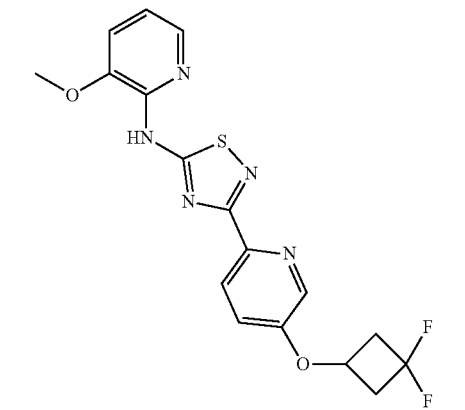 [SMILES: COc1cccnc1Nc1nc(-c2ccc(OC3CC(F)(F)C3)cn2)ns1]

3-(5-(3,3-difluorocyclobutoxy)pyridin-2-yl)-N-(3-methoxypyridin-2-yl)-1,2,4-thiadiazol-5-amine-

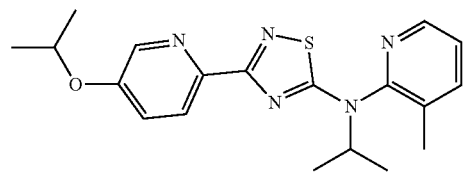 [SMILES: Cc1cccnc1N(c1nc(-c2ccc(OC(C)C)cn2)ns1)C(C)C]

3-(5-isopropoxypyridin-2-yl)-N-isopropyl-N-(3-methylpyridin-2-yl)-1,2,4-thiadiazol-5-amine

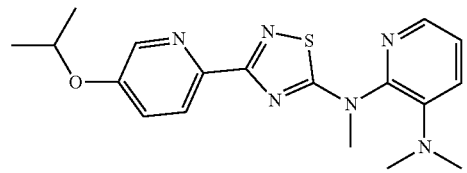 [SMILES: CC(C)Oc1ccc(-c2nsc(N(C)c3ncccc3N(C)C)n2)nc1]

N2-(3-(5-isopropoxypyridin-2-yl)-1,2,4-thiadiazol-5-yl)-N2,N3,N3-trimethylpyridine-2,3-diamine

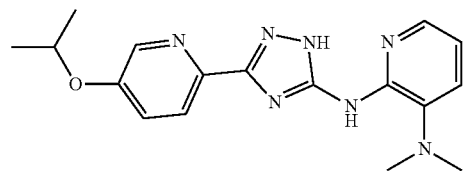

N2-(3-(5-isopropoxypyridin-2-yl)-1H-1,2,4-triazol-5-yl)-N3,N3-dimethylpyridine-2,3-diamine

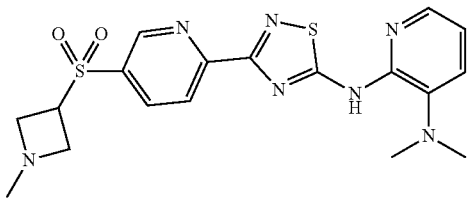

N3,N3-dimethyl-N2-(3-(5-(1-methylazetidin-3-ylsulfonyl)pyridin-2-yl)-1,2,4-thiadiazol-5-yl)pyridine-2,3-diamine

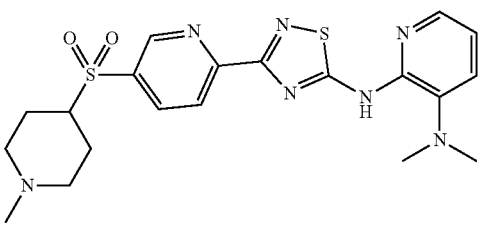 [SMILES: CN1CCC(S(=O)(=O)c2ccc(-c3nsc(Nc4ncccc4N(C)C)n3)nc2)CC1]

N3,N3-dimethyl-N2-(3-(5-(1-methylpiperidin-4-ylsulfonyl)pyridin-2-yl)-1,2,4-thiadiazol-5-yl)pyridine-2,3-diamine

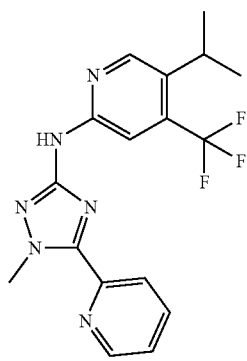 [SMILES: CC(C)c1cnc(Nc2nc(-c3ccccn3)n(C)n2)cc1C(F)(F)F]

5-isopropyl-N-(1-methyl-5-(pyridin-2-yl)-1H-1,2,4-triazol-3-yl)-4-(trifluoromethyl)pyridin-2-amine

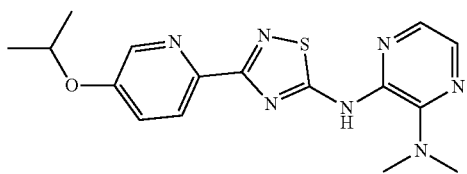 [SMILES: CC(C)Oc1ccc(-c2nsc(Nc3nccnc3N(C)C)n2)nc1]

N2-(3-(5-isopropoxypyridin-2-yl)-1,2,4-thiadiazol-5-yl)-N3,N3-dimethylpyrazine-2,3-diamine

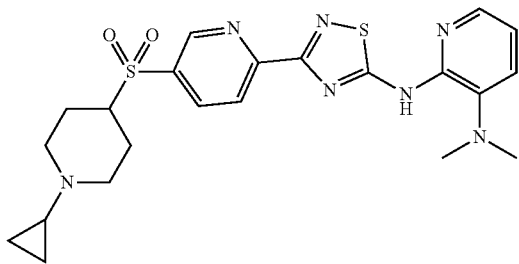 [SMILES: CN(C)c1cccnc1Nc1nc(-c2ccc(S(=O)(=O)C3CCN(C4CC4)CC3)cn2)ns1]
N2-(3-(5-(1-cyclopropylpiperidin-4-ylsulfonyl)pyridin-2-yl)-1,2,4-thiadiazol-5-yl)-N3,N3-dimethylpyridine-2,3-diamine
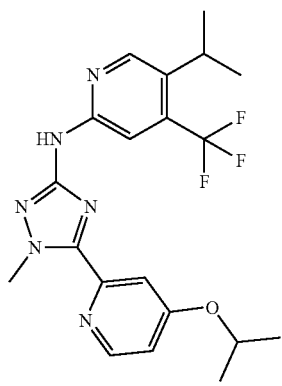 [SMILES: CC(C)Oc1ccnc(-c2nc(Nc3cc(C(F)(F)F)c(C(C)C)cn3)nn2C)c1]
N-(5-(4-isopropoxypyridin-2-yl)-1-methyl-1H-1,2,4-triazol-3-yl)-5-isopropyl-4-(trifluoromethyl)pyridin-2-amine
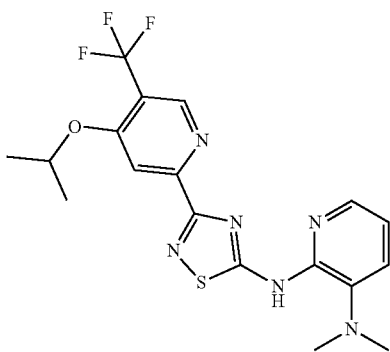 [SMILES: CC(C)Oc1cc(-c2nsc(Nc3ncccc3N(C)C)n2)ncc1C(F)(F)F]
N2-(3-(4-isopropoxy-5-(trifluoromethyl)pyridin-2-yl)-1,2,4-thiadiazol-5-yl)-N3,N3-dimethylpyridine-2,3-diamine
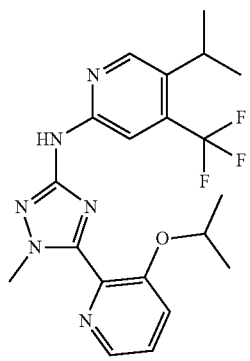 [SMILES: CC(C)Oc1cccnc1-c1nc(Nc2cc(C(F)(F)F)c(C(C)C)cn2)nn1C]
N-(5-(3-isopropoxypyridin-2-yl)-1-methyl-1H-1,2,4-triazol-3-yl)-5-isopropyl-4-(trifluoromethyl)pyridin-2-amine

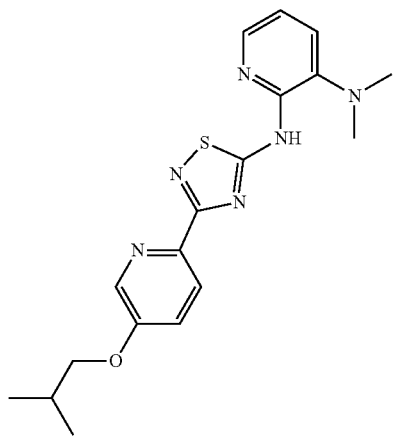
N2-(3-(5-isobutoxypyridin-2-yl)-1,2,4-thiadiazol-5-yl)-N3,N3-dimethylpyridine-2,3-diamine
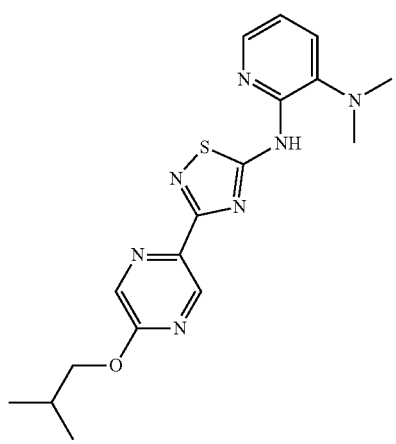 [SMILES: CC(C)COc1cnc(-c2nsc(Nc3ncccc3N(C)C)n2)cn1]
N2-(3-(5-isobutoxypyrazin-2-yl)-1,2,4-thiadiazol-5-yl)-N3,N3-dimethylpyridine-2,3-diamine
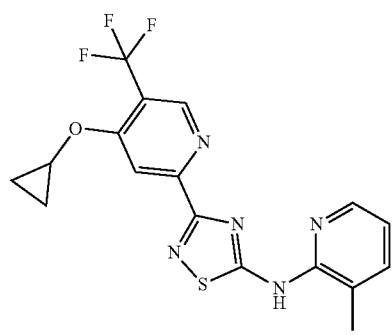 [SMILES: Cc1cccnc1Nc1nc(-c2cc(OC3CC3)c(C(F)(F)F)cn2)ns1]
3-(4-cyclopropoxy-5-(trifluoromethyl)pyridin-2-yl)-N-(3-methylpyridin-2-yl)-1,2,4-thiadiazol-5-amine
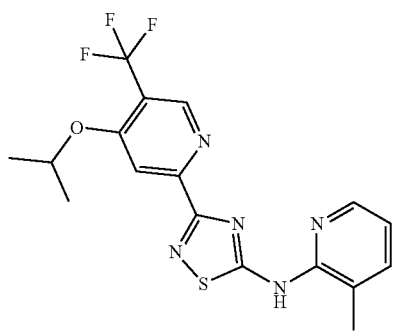 [SMILES: Cc1cccnc1Nc1nc(-c2cc(OC(C)C)c(C(F)(F)F)cn2)ns1]
3-(4-isopropoxy-5-(trifluoromethyl)pyridin-2-yl)-N-(3-methylpyridin-2-yl)-1,2,4-thiadiazol-5-amine

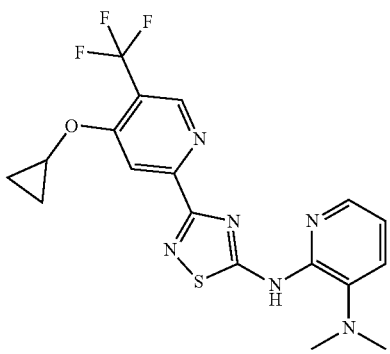 [SMILES: CN(C)c1cccnc1Nc1nc(-c2cc(OC3CC3)c(C(F)(F)F)cn2)ns1]

N2-(3-(4-cyclopropoxy-5-(trifluoromethyl)pyridin-2-yl)-1,2,4-thiadiazol-5-yl)-N3,N3-dimethylpyridine-2,3-diamine

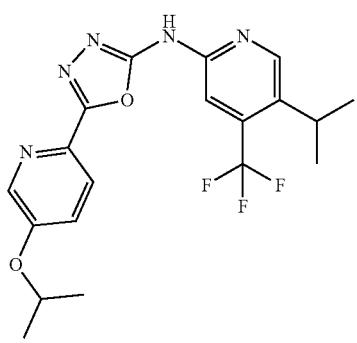 [SMILES: CC(C)Oc1ccc(-c2nnc(Nc3cc(C(F)(F)F)c(C(C)C)cn3)o2)nc1]

5-(5-isopropoxypyridin-2-yl)-N-(5-isopropyl-4-(trifluoromethyl)pyridin-2-yl)-1,3,4-oxadiazol-2-amine

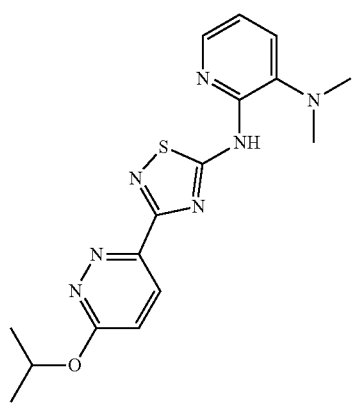 [SMILES: CC(C)Oc1ccc(-c2nsc(Nc3ncccc3N(C)C)n2)nn1]

N2-(3-(6-isopropoxypyridazin-3-yl)-1,2,4-thiadiazol-5-yl)-N3,N3-dimethylpyridine-2,3-diamine

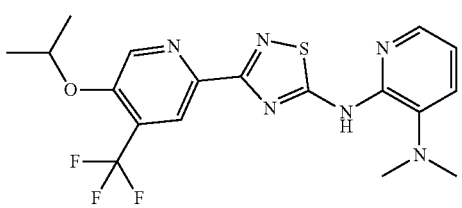

N2-(3-(5-isopropoxy-4-(trifluoromethyl)pyridin-2-yl)-1,2,4-thiadiazol-5-yl)-N3,N3-dimethylpyridine-2,3-diamine

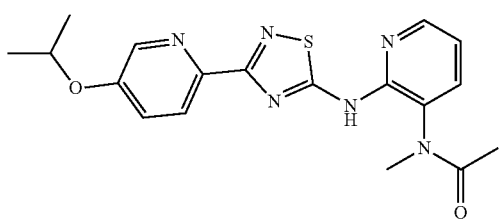 [SMILES: CC(=O)N(C)c1cccnc1Nc1nc(-c2ccc(OC(C)C)cn2)ns1]

N-(2-(3-(5-isopropoxypyridin-2-yl)-1,2,4-thiadiazol-5-ylamino)pyridin-3-yl)-N-methylacetamide -continued

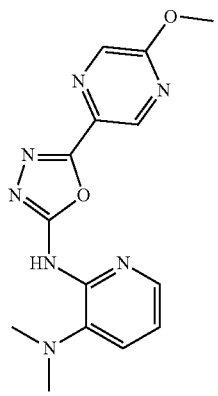

N2-(5-(5-methoxypyrazin-2-yl)-1,3,4-oxadiazol-2-yl)-N3,N3-dimethylpyridine-2,3-diamine

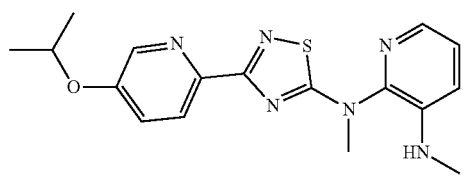 [SMILES: CNc1cccnc1N(C)c1nc(-c2ccc(OC(C)C)cn2)ns1]

N2-(3-(5-isopropoxypyridin-2-yl)-1,2,4-thiadiazol-5-yl)-N2,N3-dimethylpyridine-2,3-diamine

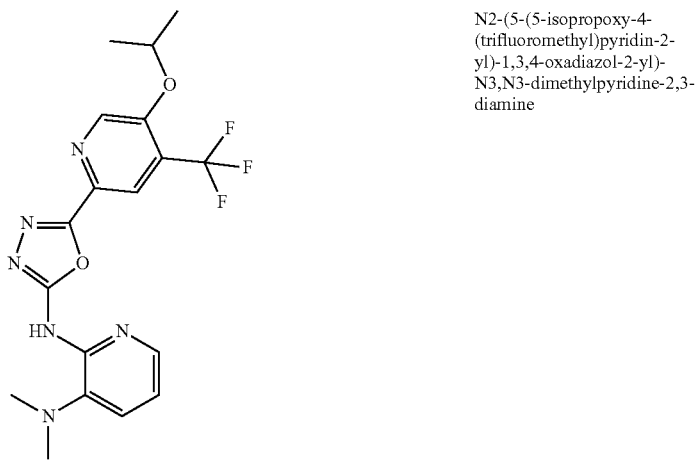

N2-(5-(5-isopropoxy-4-(trifluoromethyl)pyridin-2-yl)-1,3,4-oxadiazol-2-yl)-N3,N3-dimethylpyridine-2,3-diamine

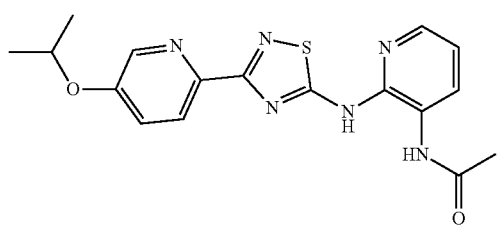 [SMILES: CC(=O)Nc1cccnc1Nc1nc(-c2ccc(OC(C)C)cn2)ns1]

N-(2-(3-(5-isopropoxypyridin-2-yl)-1,2,4-thiadiazol-5-ylamino)pyridin-3-yl)acetamide

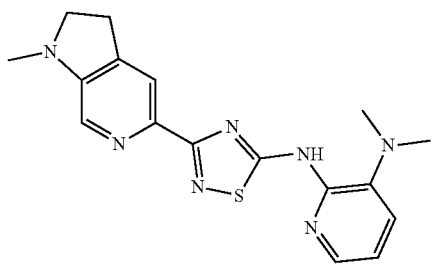

N3,N3-dimethyl-N2-(3-(1-methyl-2,3-dihydro-1H-pyrrolo[2,3-c]pyridin-5-yl)-1,2,4-thiadiazol-5-yl)pyridine-2,3-diamine

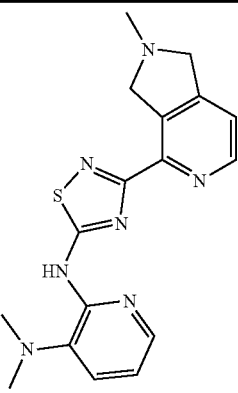

N3,N3-dimethyl-N2-(3-(2-methyl-2,3-dihydro-1H-pyrrolo[3,4-c]pyridin-4-yl)-1,2,4-thiadiazol-5-yl)pyridine-2,3-diamine

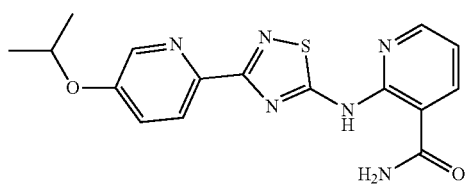 [SMILES: CC(C)Oc1ccc(-c2nsc(Nc3ncccc3C(N)=O)n2)nc1]

2-(3-(5-isopropoxypyridin-2-yl)-1,2,4-thiadiazol-5-ylamino)nicotinamide

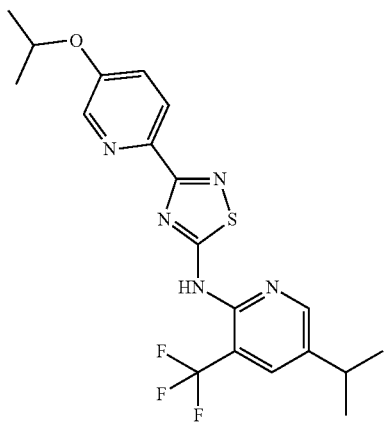 [SMILES: CC(C)Oc1ccc(-c2nsc(Nc3ncc(C(C)C)cc3C(F)(F)F)n2)nc1]

3-(5-isopropoxypyridin-2-yl)-N-(5-isopropyl-3-(trifluoromethyl)pyridin-2-yl)-1,2,4-thiadiazol-5-amine

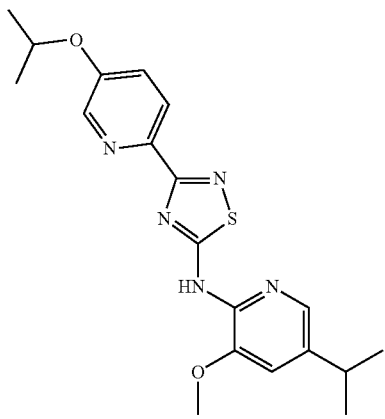 [SMILES: COc1cc(C(C)C)cnc1Nc1nc(-c2ccc(OC(C)C)cn2)ns1]

3-(5-isopropoxypyridin-2-yl)-N-(5-isopropyl-3-methoxypyridin-2-yl)-1,2,4-thiadiazol-5-amine

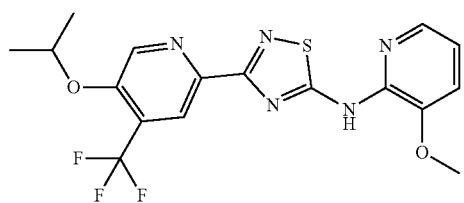 [SMILES: COc1cccnc1Nc1nc(-c2cc(C(F)(F)F)c(OC(C)C)cn2)ns1]

3-(5-isopropoxy-4-(trifluoromethyl)pyridin-2-yl)-N-(3-methoxypyridin-2-yl)-1,2,4-thiadiazol-5-amine

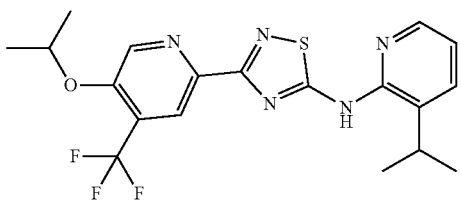
3-(5-isopropoxy-4-(trifluoromethyl)pyridin-2-yl)-N-(3-isopropylpyridin-2-yl)-1,2,4-thiadiazol-5-amine
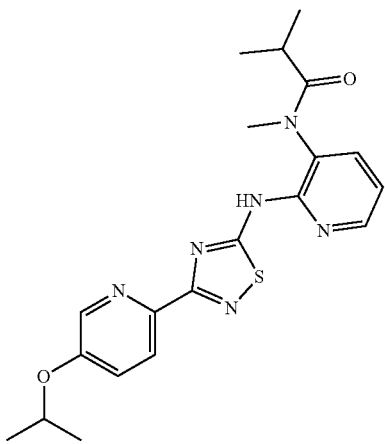 [SMILES: CC(C)Oc1ccc(-c2nsc(Nc3ncccc3N(C)C(=O)C(C)C)n2)nc1]
N-(2-(3-(5-isopropoxypyridin-2-yl)-1,2,4-thiadiazol-5-ylamino)pyridin-3-yl)-N-methylisobutyramide
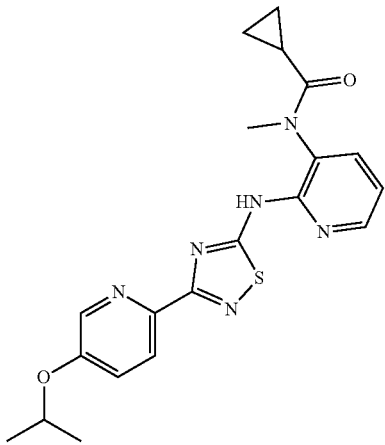 [SMILES: CC(C)Oc1ccc(-c2nsc(Nc3ncccc3N(C)C(=O)C3CC3)n2)nc1]
N-(2-(3-(5-isopropoxypyridin-2-yl)-1,2,4-thiadiazol-5-ylamino)pyridin-3-yl)-N-methylcyclopropanecarboxamide
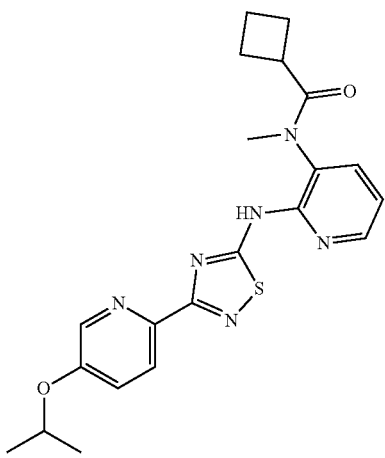 [SMILES: CC(C)Oc1ccc(-c2nsc(Nc3ncccc3N(C)C(=O)C3CCC3)n2)nc1]
N-(2-(3-(5-isopropoxypyridin-2-yl)-1,2,4-thiadiazol-5-ylamino)pyridin-3-yl)-N-methylcyclobutanecarboxamide

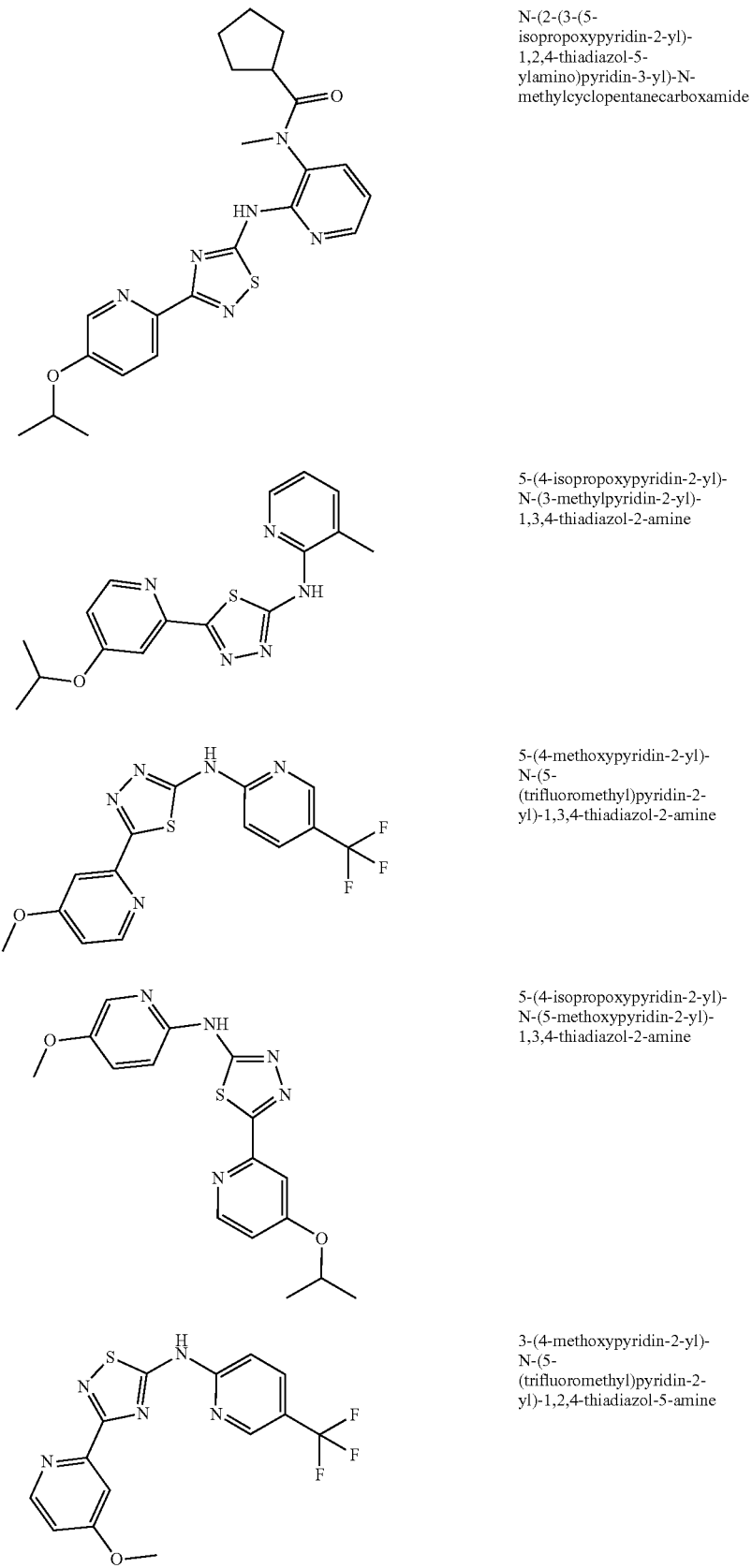
| | |
|---|---|
| | N-(2-(3-(5-isopropoxypyridin-2-yl)-1,2,4-thiadiazol-5-ylamino)pyridin-3-yl)-N-methylcyclopentanecarboxamide |
| | 5-(4-isopropoxypyridin-2-yl)-N-(3-methylpyridin-2-yl)-1,3,4-thiadiazol-2-amine |
| | 5-(4-methoxypyridin-2-yl)-N-(5-(trifluoromethyl)pyridin-2-yl)-1,3,4-thiadiazol-2-amine |
| | 5-(4-isopropoxypyridin-2-yl)-N-(5-methoxypyridin-2-yl)-1,3,4-thiadiazol-2-amine |
| | 3-(4-methoxypyridin-2-yl)-N-(5-(trifluoromethyl)pyridin-2-yl)-1,2,4-thiadiazol-5-amine |

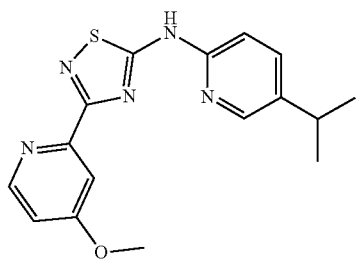 [SMILES: COc1ccnc(-c2nsc(Nc3ccc(C(C)C)cn3)n2)c1]
N-(5-isopropylpyridin-2-yl)-3-(4-methoxypyridin-2-yl)-1,2,4-thiadiazol-5-amine
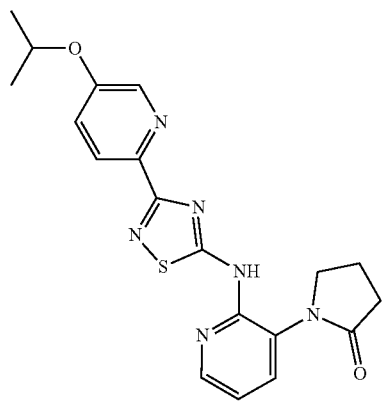 [SMILES: CC(C)Oc1ccc(-c2nsc(Nc3ncccc3N3CCCC3=O)n2)nc1]
1-(2-(3-(5-isopropoxypyridin-2-yl)-1,2,4-thiadiazol-5-ylamino)pyridin-3-yl)pyrrolidin-2-one
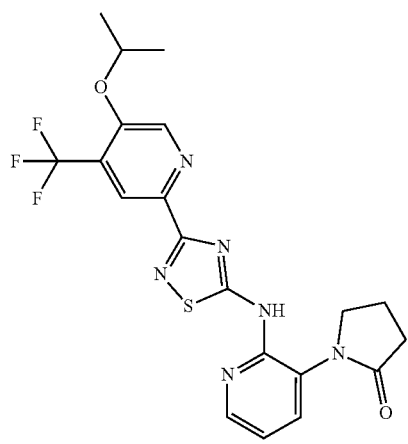 [SMILES: CC(C)Oc1cnc(-c2nsc(Nc3ncccc3N3CCCC3=O)n2)cc1C(F)(F)F]
1-(2-(3-(5-isopropoxy-4-(trifluoromethyl)pyridin-2-yl)-1,2,4-thiadiazol-5-ylamino)pyridin-3-yl)pyrrolidin-2-one
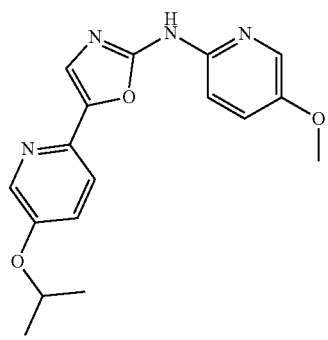 [SMILES: COc1ccc(Nc2ncc(-c3ccc(OC(C)C)cn3)o2)nc1]
5-(5-isopropoxypyridin-2-yl)-N-(5-methoxypyridin-2-yl)-1,3,4-oxadiazol-2-amine

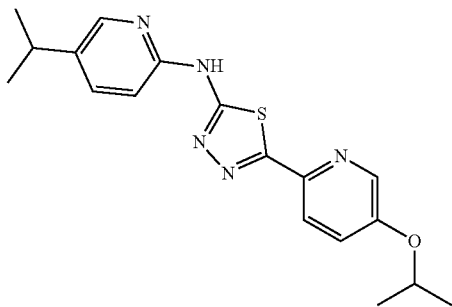 [SMILES: CC(C)Oc1ccc(-c2nnc(Nc3ccc(C(C)C)cn3)s2)nc1]
5-(5-isopropoxypyridin-2-yl)-N-(5-isopropylpyridin-2-yl)-1,3,4-thiadiazol-2-amine
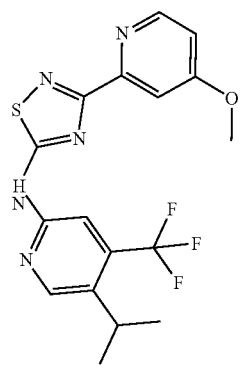
N-(5-isopropyl-4-(trifluoromethyl)pyridin-2-yl)-3-(4-methoxypyridin-2-yl)-1,2,4-thiadiazol-5-amine
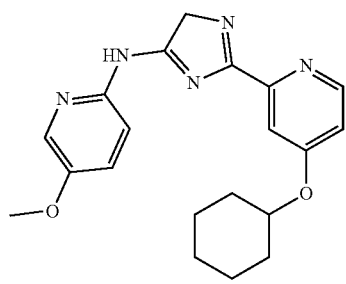 [SMILES: COc1ccc(NC2=NC(c3cc(OC4CCCCC4)ccn3)=NC2)nc1]
3-(4-(cyclohexyloxy)pyridin-2-yl)-N-(5-methoxypyridin-2-yl)-1,2,4-thiadiazol-5-amine
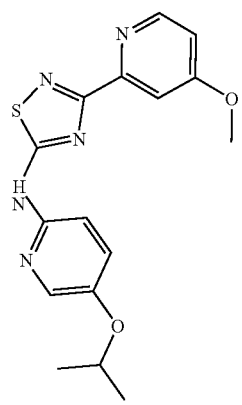
N-(5-isopropoxypyridin-2-yl)-3-(4-methoxypyridin-2-yl)-1,2,4-thiadiazol-5-amine

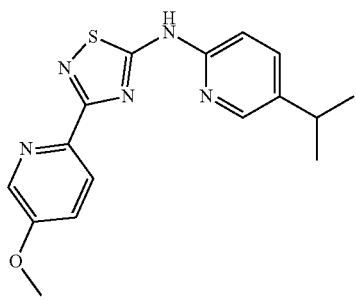 [SMILES: COc1ccc(-c2nsc(Nc3ccc(C(C)C)cn3)n2)nc1]
N-(5-isopropylpyridin-2-yl)-3-(5-methoxypyridin-2-yl)-1,2,4-thiadiazol-5-amine
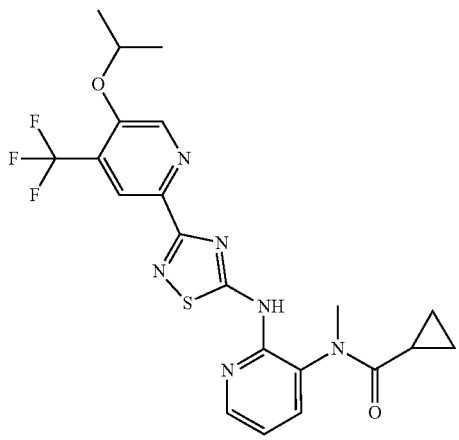 [SMILES: CC(C)Oc1cnc(-c2nsc(Nc3ncccc3N(C)C(=O)C3CC3)n2)cc1C(F)(F)F]
N-(2-(3-(5-isopropoxy-4-(trifluoromethyl)pyridin-2-yl)-1,2,4-thiadiazol-5-ylamino)pyridin-3-yl)-N-methylcyclopropanecarboxamide
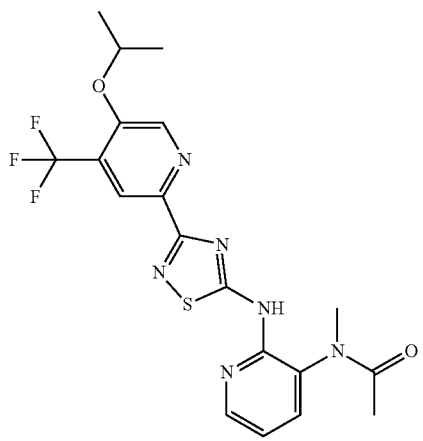 [SMILES: CC(=O)N(C)c1cccnc1Nc1nc(-c2cc(C(F)(F)F)c(OC(C)C)cn2)ns1]
N-(2-(3-(5-isopropoxy-4-(trifluoromethyl)pyridin-2-yl)-1,2,4-thiadiazol-5-ylamino)pyridin-3-yl)-N-methylacetamide
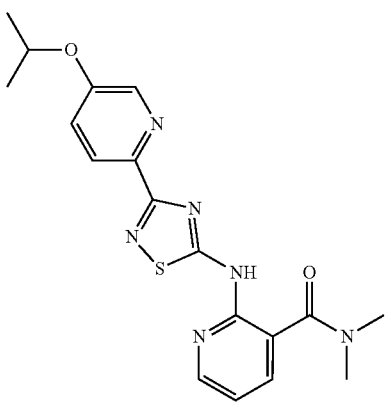 [SMILES: CC(C)Oc1ccc(-c2nsc(Nc3ncccc3C(=O)N(C)C)n2)nc1]
2-(3-(5-isopropoxypyridin-2-yl)-1,2,4-thiadiazol-5-ylamino)-N,N-dimethylnicotinamide

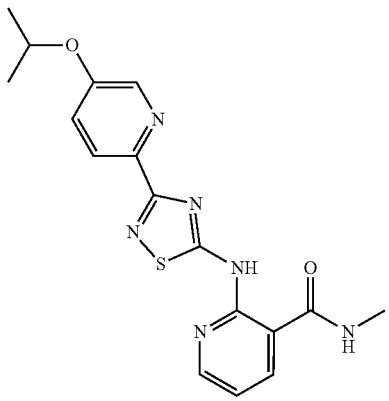 [SMILES: CNC(=O)c1cccnc1Nc1nc(-c2ccc(OC(C)C)cn2)ns1]
2-(3-(5-isopropoxypyridin-2-yl)-1,2,4-thiadiazol-5-ylamino)-N-methylnicotinamide
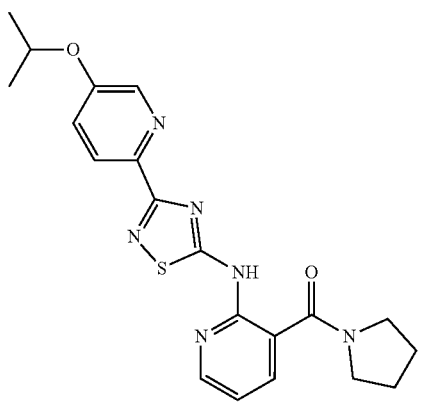 [SMILES: CC(C)Oc1ccc(-c2nsc(Nc3ncccc3C(=O)N3CCCC3)n2)nc1]
(2-(3-(5-isopropoxypyridin-2-yl)-1,2,4-thiadiazol-5-ylamino)pyridin-3-yl)(pyrrolidin-1-yl)methanone
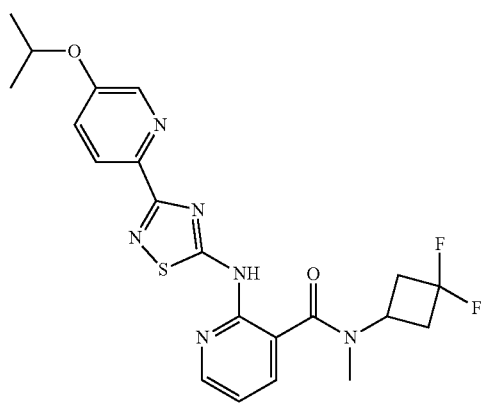 [SMILES: CC(C)Oc1ccc(-c2nsc(Nc3ncccc3C(=O)N(C)C3CC(F)(F)C3)n2)nc1]
N-(3,3-difluorocyclobutyl)-2-(3-(5-isopropoxypyridin-2-yl)-1,2,4-thiadiazol-5-ylamino)-N-methylnicotinamide
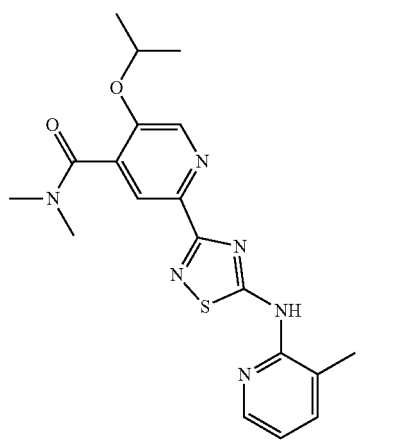
5-isopropoxy-N,N-dimethyl-2-(5-(3-methylpyridin-2-ylamino)-1,2,4-thiadiazol-3-yl)isonicotinamide -continued
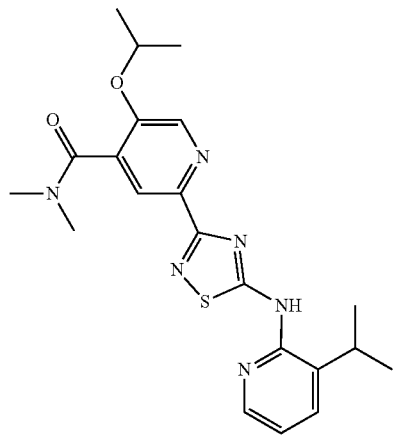 [SMILES: CC(C)Oc1cnc(-c2nsc(Nc3ncccc3C(C)C)n2)cc1C(=O)N(C)C]
5-isopropoxy-2-(5-(3-isopropylpyridin-2-ylamino)-1,2,4-thiadiazol-3-yl)-N,N-dimethylisonicotinamide
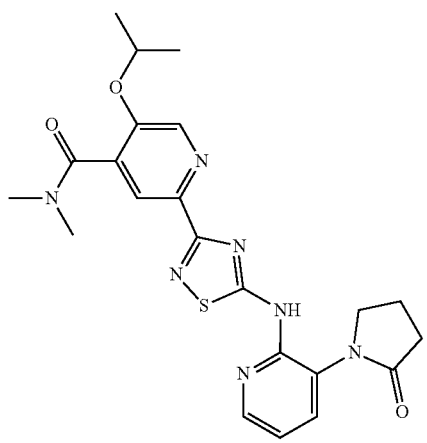 [SMILES: CC(C)Oc1cnc(-c2nsc(Nc3ncccc3N3CCCC3=O)n2)cc1C(=O)N(C)C]
5-isopropoxy-N,N-dimethyl-2-(5-(3-(2-oxopyrrolidin-1-yl)pyridin-2-ylamino)-1,2,4-thiadiazol-3-yl)isonicotinamide
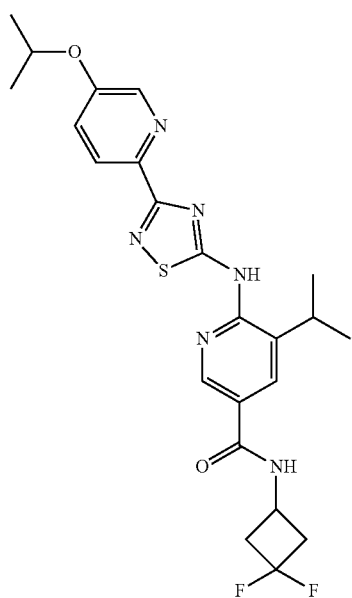 [SMILES: CC(C)Oc1ccc(-c2nsc(Nc3ncc(C(=O)NC4CC(F)(F)C4)cc3C(C)C)n2)nc1]
N-(3,3-difluorocyclobutyl)-6-(3-(5-isopropoxypyridin-2-yl)-1,2,4-thiadiazol-5-ylamino)-5-isopropylnicotinamide

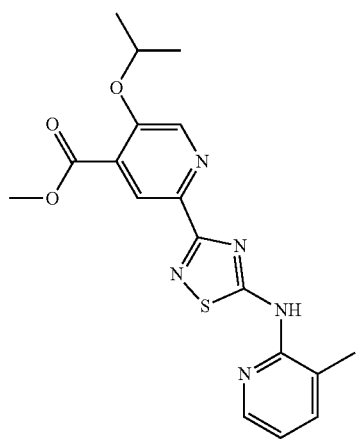
methyl 5-isopropoxy-2-(5-(3-methylpyridin-2-ylamino)-1,2,4-thiadiazol-3-yl)isonicotinate
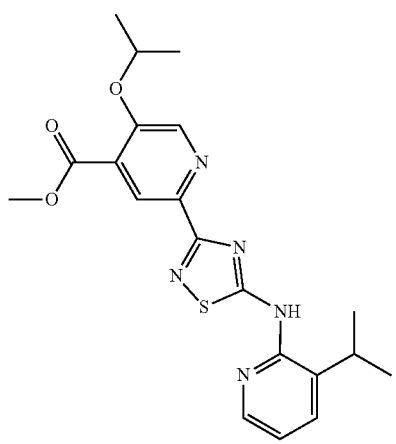 [SMILES: COC(=O)c1cc(-c2nsc(Nc3ncccc3C(C)C)n2)ncc1OC(C)C]
methyl 5-isopropoxy-2-(5-(3-isopropylpyridin-2-ylamino)-1,2,4-thiadiazol-3-yl)isonicotinate
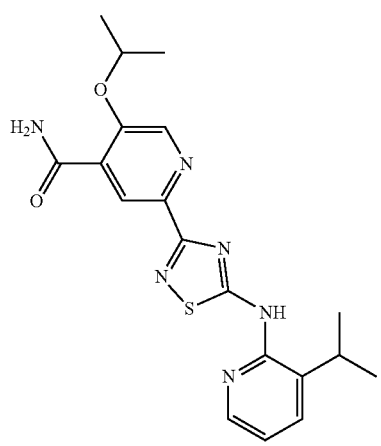 [SMILES: CC(C)Oc1cnc(-c2nsc(Nc3ncccc3C(C)C)n2)cc1C(N)=O]
5-isopropoxy-2-(5-(3-isopropylpyridin-2-ylamino)-1,2,4-thiadiazol-3-yl)isonicotinamide

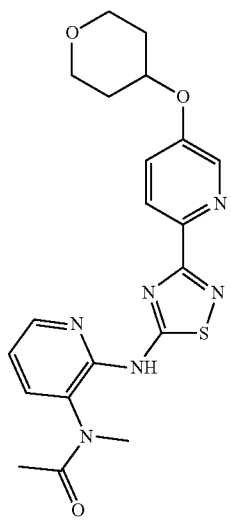 [SMILES: CC(=O)N(C)c1cccnc1Nc1nc(-c2ccc(OC3CCOCC3)cn2)ns1]
N-methyl-N-(2-(3-(5-(tetrahydro-2H-pyran-4-yloxy)pyridin-2-yl)-1,2,4-thiadiazol-5-ylamino)pyridin-3-yl)acetamide
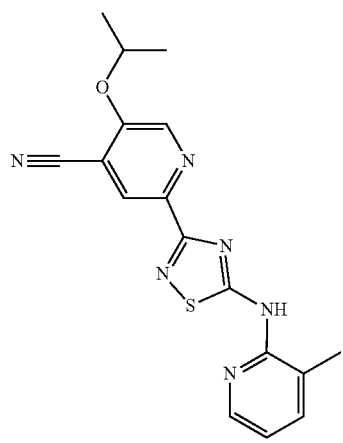 [SMILES: Cc1cccnc1Nc1nc(-c2cc(C#N)c(OC(C)C)cn2)ns1]
5-isopropoxy-2-(5-(3-methylpyridin-2-ylamino)-1,2,4-thiadiazol-3-yl)isonicotinonitrile
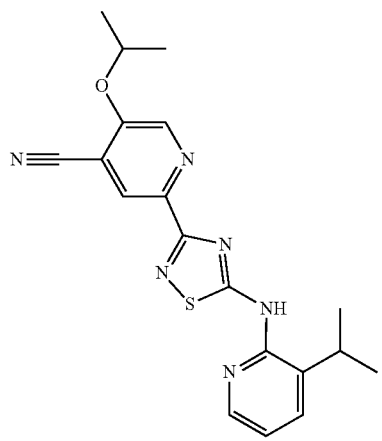 [SMILES: CC(C)Oc1cnc(-c2nsc(Nc3ncccc3C(C)C)n2)cc1C#N]
5-isopropoxy-2-(5-(3-isopropylpyridin-2-ylamino)-1,2,4-thiadiazol-3-yl)isonicotinonitrile

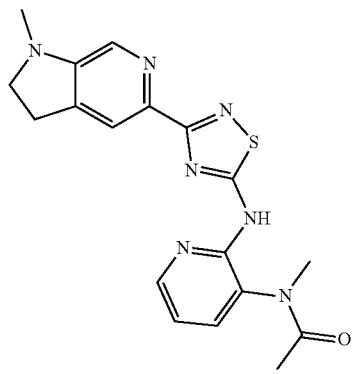 [SMILES: CC(=O)N(C)c1cccnc1Nc1nc(-c2cc3c(cn2)N(C)CC3)ns1]
N-methyl-N-(2-(3-(1-methyl-2,3-dihydro-1H-pyrrolo[2,3-c]pyridin-5-yl)-1,2,4-thiadiazol-5-ylamino)pyridin-3-yl)acetamide
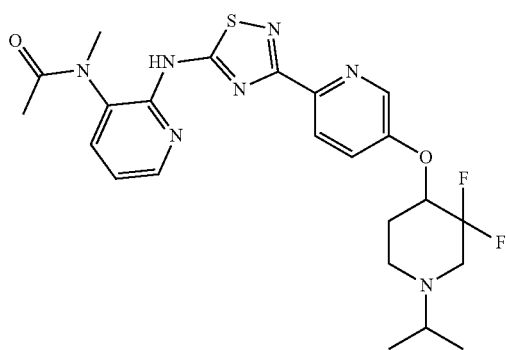 [SMILES: CC(=O)N(C)c1cccnc1Nc1nc(-c2ccc(OC3CCN(C(C)C)CC3(F)F)cn2)ns1]
N-(2-(3-(5-(3,3-difluoro-1-isopropylpiperidin-4-yloxy)pyridin-2-yl)-1,2,4-thiadiazol-5-ylamino)pyridin-3-yl)-N-methylacetamide
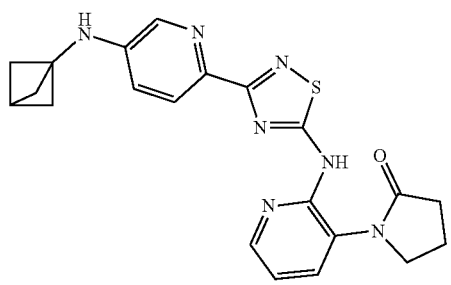 [SMILES: O=C1CCCN1c1cccnc1Nc1nc(-c2ccc(NC34CC(C3)C4)cn2)ns1]
1-(2-(3-(5-(bicyclo[1.1.1]pentan-1-ylamino)pyridin-2-yl)-1,2,4-thiadiazol-5-ylamino)pyridin-3-yl)pyrrolidin-2-one
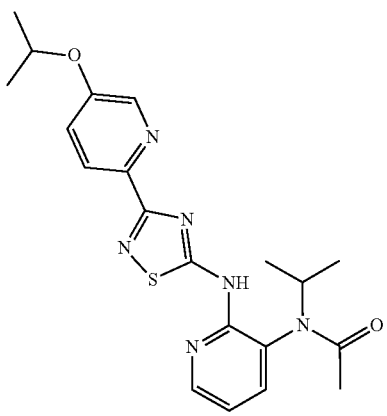 [SMILES: CC(=O)N(c1cccnc1Nc1nc(-c2ccc(OC(C)C)cn2)ns1)C(C)C]
N-(2-(3-(5-isopropoxypyridin-2-yl)-1,2,4-thiadiazol-5-ylamino)pyridin-3-yl)-N-isopropylacetamide

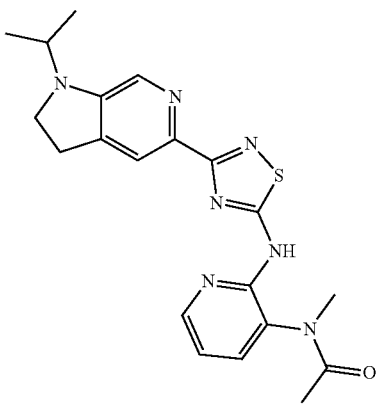 [SMILES: CC(=O)N(C)c1cccnc1Nc1nc(-c2cc3c(cn2)N(C(C)C)CC3)ns1]

N-(2-(3-(1-isopropyl-2,3-dihydro-1H-pyrrolo[2,3-c]pyridin-5-yl)-1,2,4-thiadiazol-5-ylamino)pyridin-3-yl)-N-methylacetamide

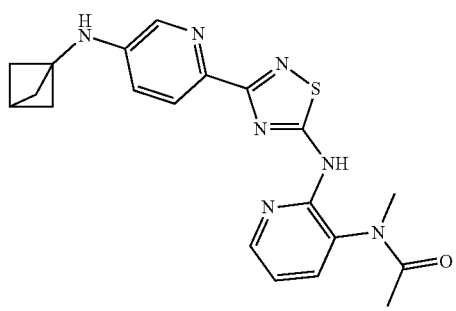 [SMILES: CC(=O)N(C)c1cccnc1Nc1nc(-c2ccc(NC34CC(C3)C4)cn2)ns1]

N-(2-(3-(5-(bicyclo[1.1.1]pentan-1-ylamino)pyridin-2-yl)-1,2,4-thiadiazol-5-ylamino)pyridin-3-yl)-N-methylacetamide

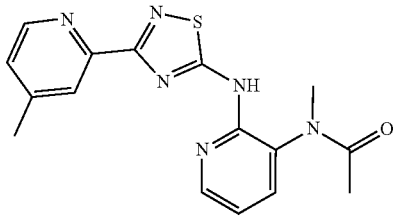 [SMILES: CC(=O)N(C)c1cccnc1Nc1nc(-c2cc(C)ccn2)ns1]

N-methyl-N-(2-(3-(4-methylpyridin-2-yl)-1,2,4-thiadiazol-5-ylamino)pyridin-3-yl)acetamide

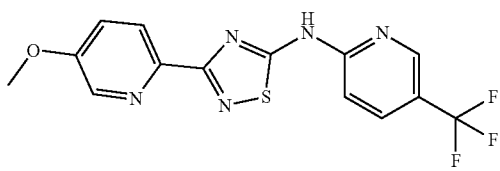 [SMILES: COc1ccc(-c2nsc(Nc3ccc(C(F)(F)F)cn3)n2)nc1]

3-(5-methoxypyridin-2-yl)-N-(5-(trifluoromethyl)pyridin-2-yl)-1,2,4-thiadiazol-5-amine

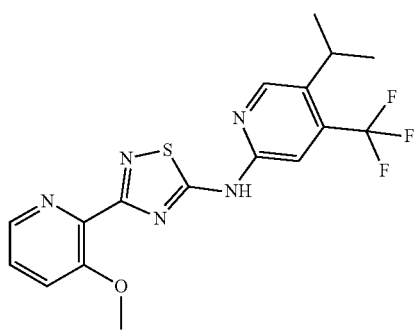 [SMILES: COc1cccnc1-c1nsc(Nc2cc(C(F)(F)F)c(C(C)C)cn2)n1]

N-(5-isopropyl-4-(trifluoromethyl)pyridin-2-yl)-3-(3-methoxypyridin-2-yl)-1,2,4-thiadiazol-5-amine

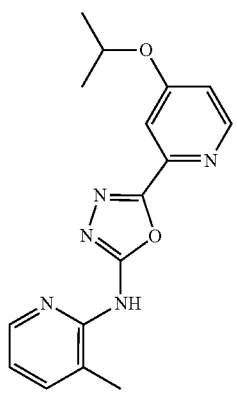 [SMILES: Cc1cccnc1Nc1nnc(-c2cc(OC(C)C)ccn2)o1]
5-(4-isopropoxypyridin-2-yl)-N-(3-methylpyridin-2-yl)-1,3,4-oxadiazol-2-amine
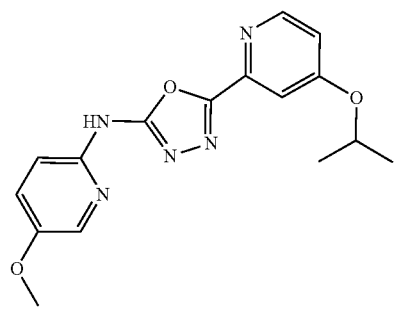 [SMILES: COc1ccc(Nc2nnc(-c3cc(OC(C)C)ccn3)o2)nc1]
5-(4-isopropoxypyridin-2-yl)-N-(5-methoxypyridin-2-yl)-1,3,4-oxadiazol-2-amine
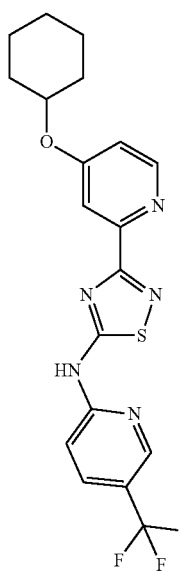
3-(4-(cyclohexyloxy)pyridin-2-yl)-N-(5-(trifluoromethyl)pyridin-2-yl)-1,2,4-thiadiazol-5-amine
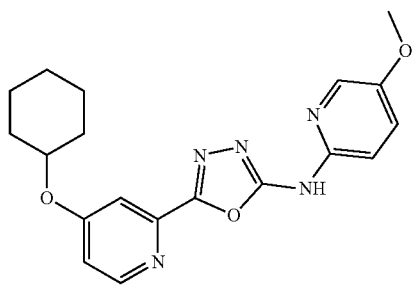 [SMILES: COc1ccc(Nc2nnc(-c3cc(OC4CCCCC4)ccn3)o2)nc1]
5-(4-(cyclohexyloxy)pyridin-2-yl)-N-(5-methoxypyridin-2-yl)-1,3,4-oxadiazol-2-amine

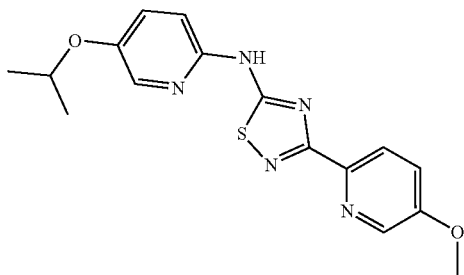 [SMILES: COc1ccc(-c2nsc(Nc3ccc(OC(C)C)cn3)n2)nc1]
N-(5-isopropoxypyridin-2-yl)-3-(5-methoxypyridin-2-yl)-1,2,4-thiadiazol-5-amine
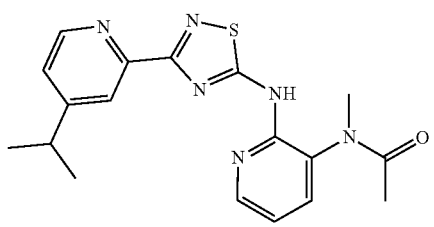 [SMILES: CC(=O)N(C)c1cccnc1Nc1nc(-c2cc(C(C)C)ccn2)ns1]
N-(2-(3-(4-isopropylpyridin-2-yl)-1,2,4-thiadiazol-5-ylamino)pyridin-3-yl)-N-methylacetamide
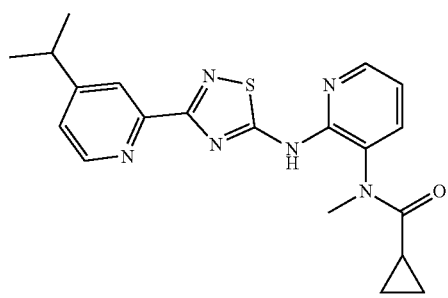 [SMILES: CC(C)c1ccnc(-c2nsc(Nc3ncccc3N(C)C(=O)C3CC3)n2)c1]
N-(2-(3-(4-isopropylpyridin-2-yl)-1,2,4-thiadiazol-5-ylamino)pyridin-3-yl)-N-methylcyclopropanecarboxamide
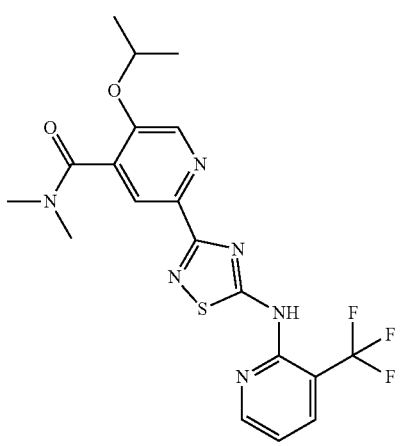 [SMILES: CC(C)Oc1cnc(-c2nsc(Nc3ncccc3C(F)(F)F)n2)cc1C(=O)N(C)C]
5-isopropoxy-N,N-dimethyl-2-(5-(3-(trifluoromethyl)pyridin-2-ylamino)-1,2,4-thiadiazol-3-yl)isonicotinamide

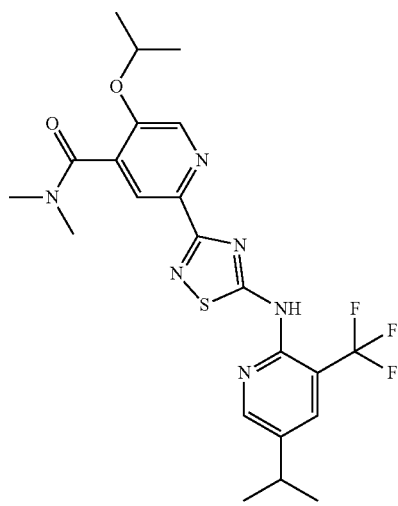 [SMILES: CC(C)Oc1cnc(-c2nsc(Nc3ncc(C(C)C)cc3C(F)(F)F)n2)cc1C(=O)N(C)C]
5-isopropoxy-2-(5-(5-isopropyl-3-(trifluoromethyl)pyridin-2-ylamino)-1,2,4-thiadiazol-3-yl)-N,N-dimethylisonicotinamide
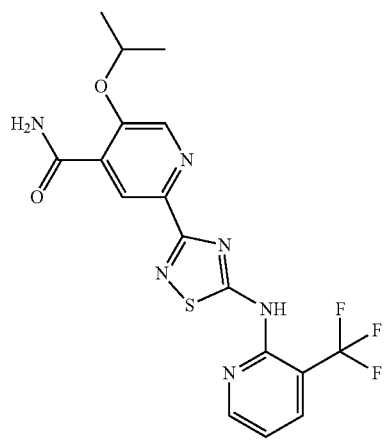 [SMILES: CC(C)Oc1cnc(-c2nsc(Nc3ncccc3C(F)(F)F)n2)cc1C(N)=O]
5-isopropoxy-2-(5-(3-(trifluoromethyl)pyridin-2-ylamino)-1,2,4-thiadiazol-3-yl)isonicotinamide
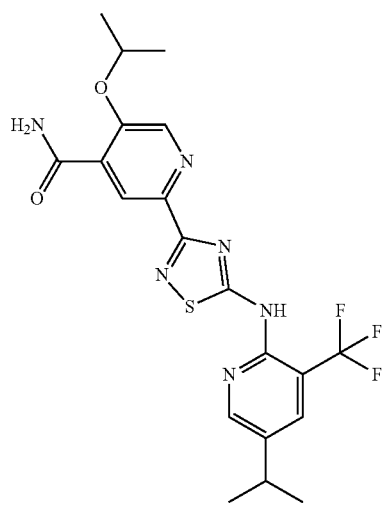 [SMILES: CC(C)Oc1cnc(-c2nsc(Nc3ncc(C(C)C)cc3C(F)(F)F)n2)cc1C(N)=O]
5-isopropoxy-2-(5-(5-isopropyl-3-(trifluoromethyl)pyridin-2-ylamino)-1,2,4-thiadiazol-3-yl)isonicotinamide

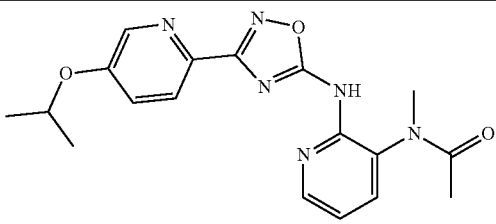 N-(2-(3-(5-isopropoxypyridin-2-yl)-1,2,4-oxadiazol-5-ylamino)pyridin-3-yl)-N-methylacetamide

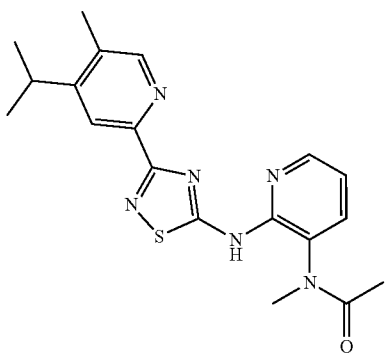 [SMILES: CC(=O)N(C)c1cccnc1Nc1nc(-c2cc(C(C)C)c(C)cn2)ns1] N-(2-(3-(4-isopropyl-5-methylpyridin-2-yl)-1,2,4-thiadiazol-5-ylamino)pyridin-3-yl)-N-methylacetamide

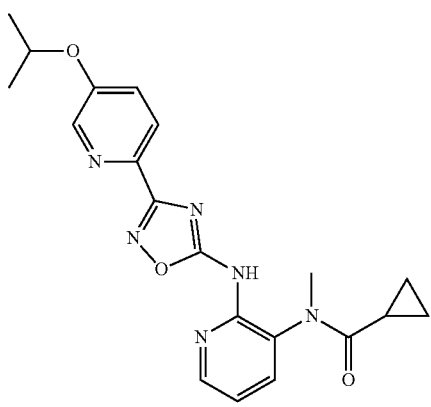 [SMILES: CC(C)Oc1ccc(-c2noc(Nc3ncccc3N(C)C(=O)C3CC3)n2)nc1] N-(2-(3-(5-isopropoxypyridin-2-yl)-1,2,4-oxadiazol-5-ylamino)pyridin-3-yl)-N-methylcyclopropanecarboxamide

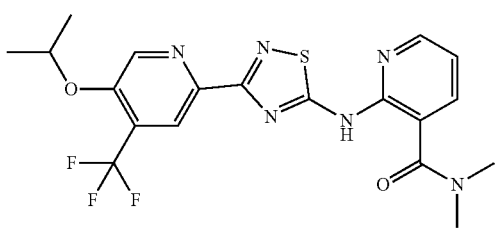 [SMILES: CC(C)Oc1cnc(-c2nsc(Nc3ncccc3C(=O)N(C)C)n2)cc1C(F)(F)F] 2-(3-(5-isopropoxy-4-(trifluoromethyl)pyridin-2-yl)-1,2,4-thiadiazol-5-ylamino)-N,N-dimethylnicotinamide

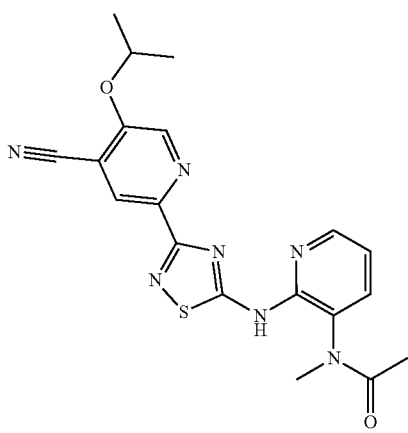 [SMILES: CC(=O)N(C)c1cccnc1Nc1nc(-c2cc(C#N)c(OC(C)C)cn2)ns1] N-(2-(3-(4-cyano-5-isopropoxypyridin-2-yl)-1,2,4-thiadiazol-5-ylamino)pyridin-3-yl)-N-methylacetamide

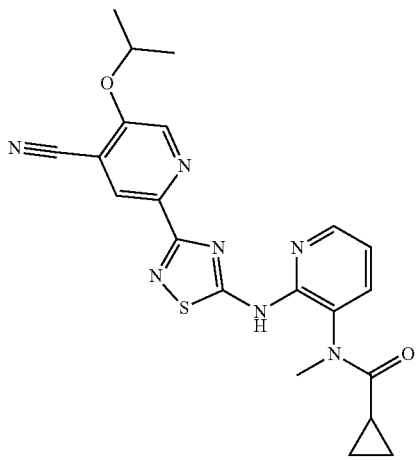 [SMILES: CC(C)Oc1cnc(-c2nsc(Nc3ncccc3N(C)C(=O)C3CC3)n2)cc1C#N]

N-(2-(3-(4-cyano-5-isopropoxypyridin-2-yl)-1,2,4-thiadiazol-5-ylamino)pyridin-3-yl)-N-methylcyclopropanecarboxamide

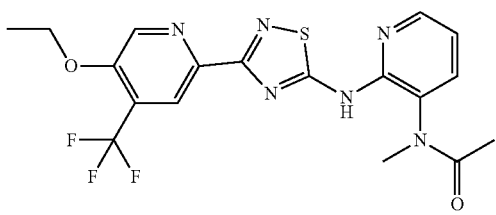 [SMILES: CCOc1cnc(-c2nsc(Nc3ncccc3N(C)C(C)=O)n2)cc1C(F)(F)F]

N-(2-(3-(5-ethoxy-4-(trifluoromethyl)pyridin-2-yl)-1,2,4-thiadiazol-5-ylamino)pyridin-3-yl)-N-methylacetamide

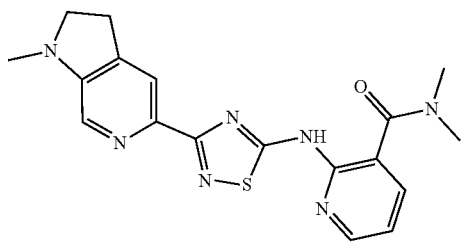

N,N-dimethyl-2-(3-(1-methyl-2,3-dihydro-1H-pyrrolo[2,3-c]pyridin-5-yl)-1,2,4-thiadiazol-5-ylamino)nicotinamide

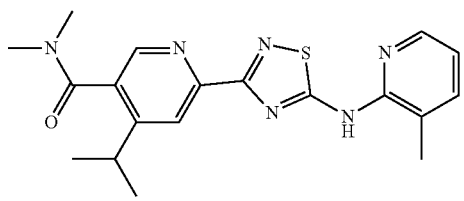 [SMILES: Cc1cccnc1Nc1nc(-c2cc(C(C)C)c(C(=O)N(C)C)cn2)ns1]

4-isopropyl-N,N-dimethyl-6-(5-(3-methylpyridin-2-ylamino)-1,2,4-thiadiazol-3-yl)nicotinamide

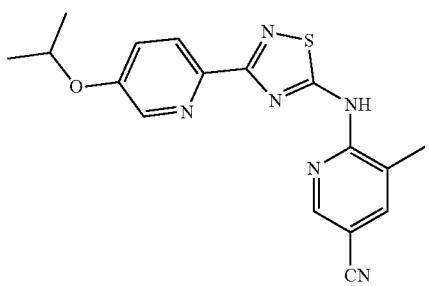 [SMILES: Cc1cc(C#N)cnc1Nc1nc(-c2ccc(OC(C)C)cn2)ns1]

6-(3-(5-isopropoxypyridin-2-yl)-1,2,4-thiadiazol-5-ylamino)-5-methylnicotinonitrile

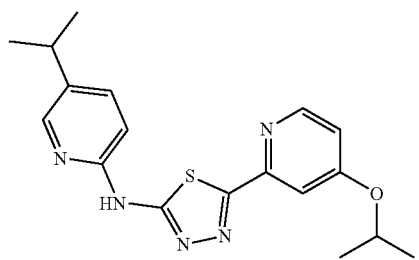 [SMILES: CC(C)Oc1ccnc(-c2nnc(Nc3ccc(C(C)C)cn3)s2)c1]
5-(4-isopropoxypyridin-2-yl)-N-(5-isopropylpyridin-2-yl)-1,3,4-thiadiazol-2-amine
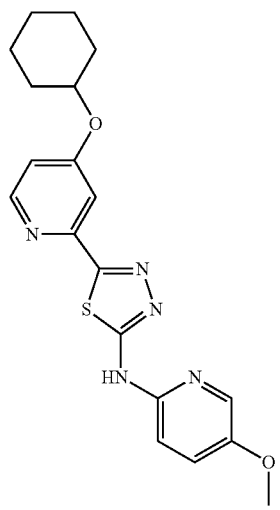 [SMILES: COc1ccc(Nc2nnc(-c3cc(OC4CCCCC4)ccn3)s2)nc1]
5-(4-(cyclohexyloxy)pyridin-2-yl)-N-(5-methoxypyridin-2-yl)-1,3,4-thiadiazol-2-amine
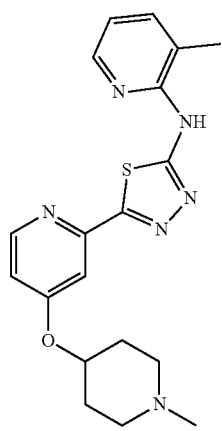 [SMILES: Cc1cccnc1Nc1nnc(-c2cc(OC3CCN(C)CC3)ccn2)s1]
5-(4-(1-methylpiperidin-4-yloxy)pyridin-2-yl)-N-(3-methylpyridin-2-yl)-1,3,4-thiadiazol-2-amine
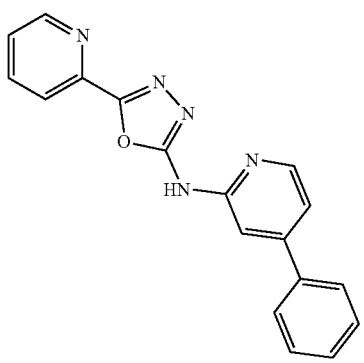
N-(4-phenylpyridin-2-yl)-5-(pyridin-2-yl)-1,3,4-oxadiazol-2-amine -continued
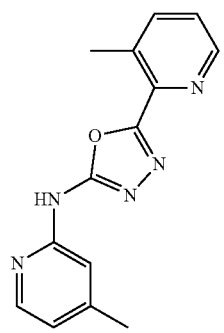 [SMILES: Cc1ccnc(Nc2nnc(-c3ncccc3C)o2)c1]
5-(3-methylpyridin-2-yl)-N-(4-methylpyridin-2-yl)-1,3,4-oxadiazol-2-amine
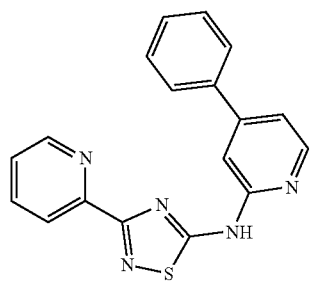 [SMILES: c1ccc(-c2ccnc(Nc3nc(-c4ccccn4)ns3)c2)cc1]
N-(4-phenylpyridin-2-yl)-3-(pyridin-2-yl)-1,2,4-thiadiazol-5-amine
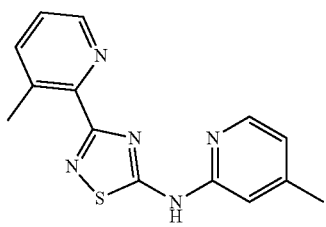
3-(3-methylpyridin-2-yl)-N-(4-methylpyridin-2-yl)-1,2,4-thiadiazol-5-amine
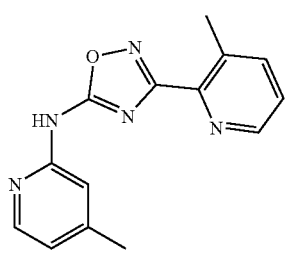 [SMILES: Cc1ccnc(Nc2nc(-c3ncccc3C)no2)c1]
3-(3-methylpyridin-2-yl)-N-(4-methylpyridin-2-yl)-1,2,4-oxadiazol-5-amine
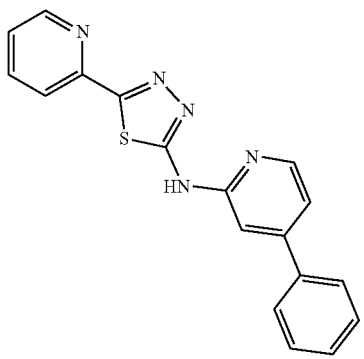 [SMILES: c1ccc(-c2ccnc(Nc3nnc(-c4ccccn4)s3)c2)cc1]
N-(4-phenylpyridin-2-yl)-5-(pyridin-2-yl)-1,3,4-thiadiazol-2-amine

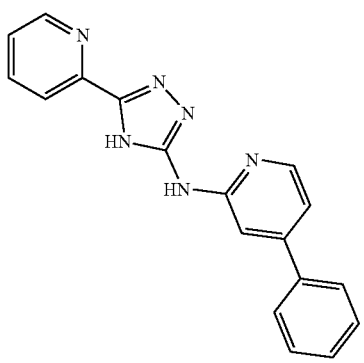
4-phenyl-N-(5-(pyridin-2-yl)-4H-1,2,4-triazol-3-yl)pyridin-2-amine
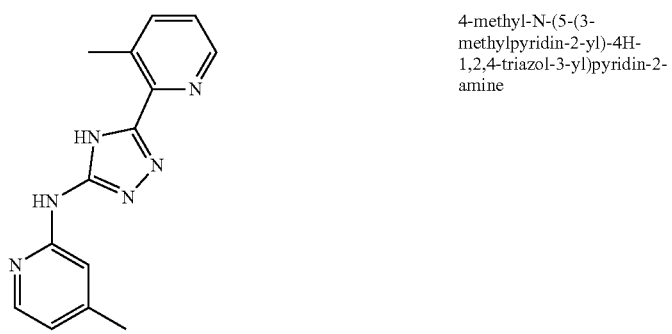
4-methyl-N-(5-(3-methylpyridin-2-yl)-4H-1,2,4-triazol-3-yl)pyridin-2-amine
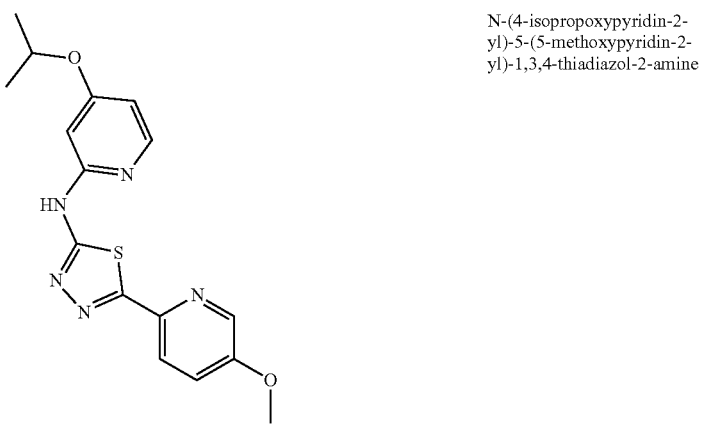
N-(4-isopropoxypyridin-2-yl)-5-(5-methoxypyridin-2-yl)-1,3,4-thiadiazol-2-amine
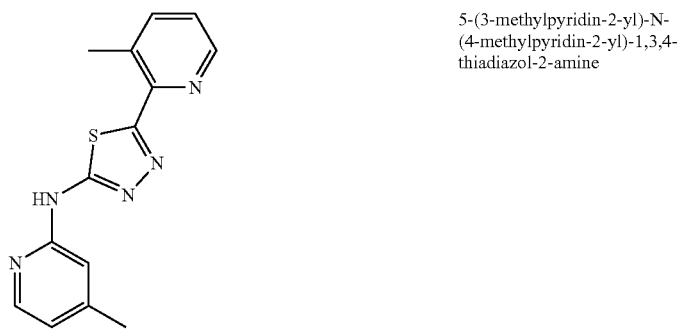
5-(3-methylpyridin-2-yl)-N-(4-methylpyridin-2-yl)-1,3,4-thiadiazol-2-amine

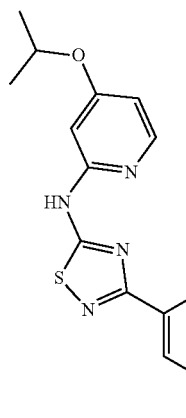
N-(4-isopropoxypyridin-2-yl)-3-(5-methoxypyridin-2-yl)-1,2,4-thiadiazol-5-amine
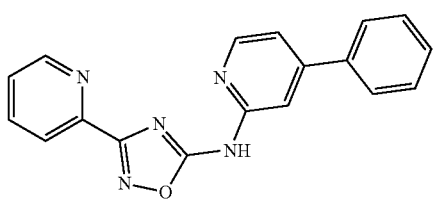 [SMILES: c1ccc(-c2ccnc(Nc3nc(-c4ccccn4)no3)c2)cc1]
N-(4-phenylpyridin-2-yl)-3-(pyridin-2-yl)-1,2,4-oxadiazol-5-amine
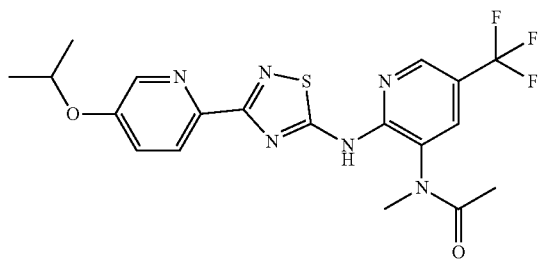 [SMILES: CC(=O)N(C)c1cc(C(F)(F)F)cnc1Nc1nc(-c2ccc(OC(C)C)cn2)ns1]
N-(2-(3-(5-isopropoxypyridin-2-yl)-1,2,4-thiadiazol-5-ylamino)-5-(trifluoromethyl)pyridin-3-yl)-N-methylacetamide
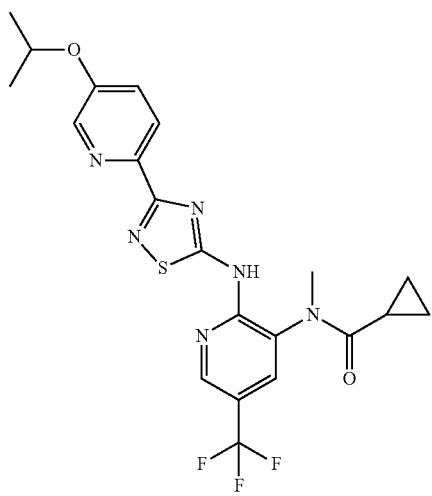 [SMILES: CC(C)Oc1ccc(-c2nsc(Nc3ncc(C(F)(F)F)cc3N(C)C(=O)C3CC3)n2)nc1]
N-(2-(3-(5-isopropoxypyridin-2-yl)-1,2,4-thiadiazol-5-ylamino)-5-(trifluoromethyl)pyridin-3-yl)-N-methylcyclopropanecarboxamide

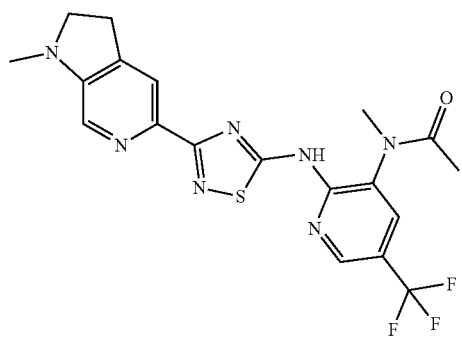 [SMILES: CC(=O)N(C)c1cc(C(F)(F)F)cnc1Nc1nc(-c2cc3c(cn2)N(C)CC3)ns1]

N-methyl-N-(2-(3-(1-methyl-2,3-dihydro-1H-pyrrolo[2,3-c]pyridin-5-yl)-1,2,4-thiadiazol-5-ylamino)-5-(trifluoromethyl)pyridin-3-yl)acetamide

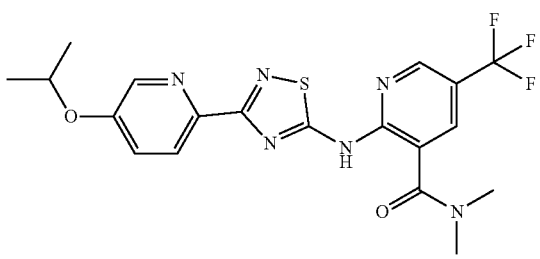 [SMILES: CC(C)Oc1ccc(-c2nsc(Nc3ncc(C(F)(F)F)cc3C(=O)N(C)C)n2)nc1]

2-(3-(5-isopropoxypyridin-2-yl)-1,2,4-thiadiazol-5-ylamino)-N,N-dimethyl-5-(trifluoromethyl)nicotinamide

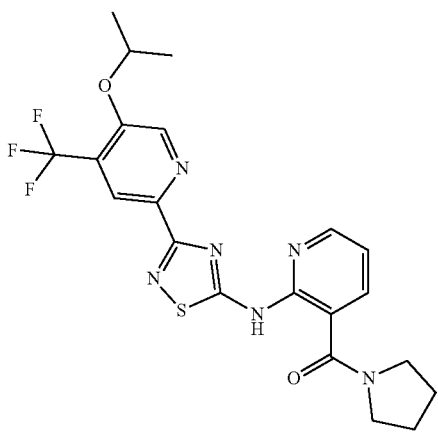 [SMILES: CC(C)Oc1cnc(-c2nsc(Nc3ncccc3C(=O)N3CCCC3)n2)cc1C(F)(F)F]

(2-(3-(5-isopropoxy-4-(trifluoromethyl)pyridin-2-yl)-1,2,4-thiadiazol-5-ylamino)pyridin-3-yl)(pyrrolidin-1-yl)methanone

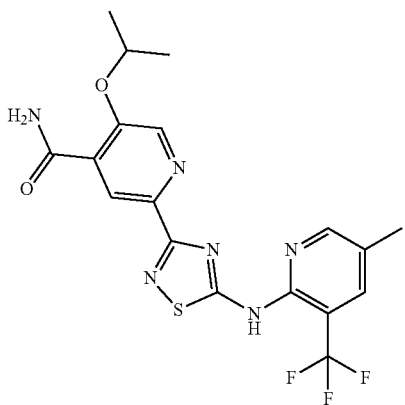 [SMILES: Cc1cnc(Nc2nc(-c3cc(C(N)=O)c(OC(C)C)cn3)ns2)c(C(F)(F)F)c1]

5-isopropoxy-2-(5-(5-methyl-3-(trifluoromethyl)pyridin-2-ylamino)-1,2,4-thiadiazol-3-yl)isonicotinamide

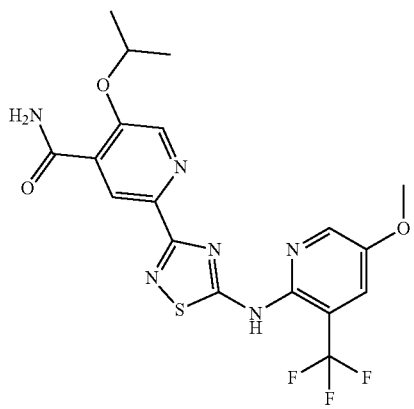
5-isopropoxy-2-(5-(5-methoxy-3-(trifluoromethyl)pyridin-2-ylamino)-1,2,4-thiadiazol-3-yl)isonicotinamide
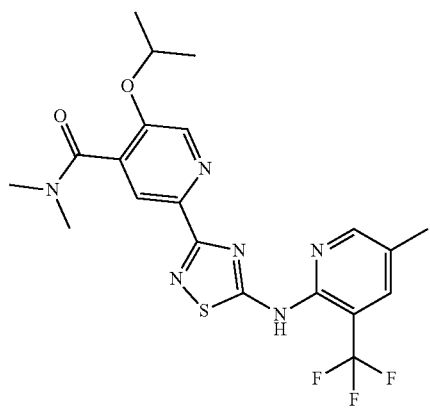
5-isopropoxy-N,N-dimethyl-2-(5-(5-methyl-3-(trifluoromethyl)pyridin-2-ylamino)-1,2,4-thiadiazol-3-yl)isonicotinamide
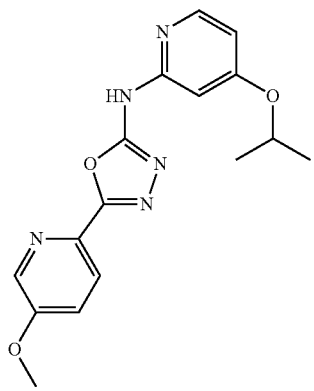 [SMILES: COc1ccc(-c2nnc(Nc3cc(OC(C)C)ccn3)o2)nc1]
N-(4-isopropoxypyridin-2-yl)-5-(5-methoxypyridin-2-yl)-1,3,4-oxadiazol-2-amine
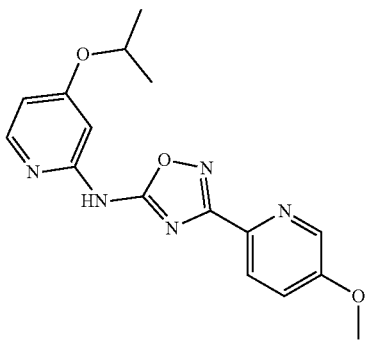 [SMILES: COc1ccc(-c2noc(Nc3cc(OC(C)C)ccn3)n2)nc1]
N-(4-isopropoxypyridin-2-yl)-3-(5-methoxypyridin-2-yl)-1,2,4-oxadiazol-5-amine

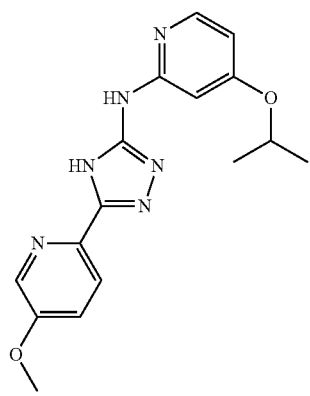 [SMILES: COc1ccc(-c2nnc(Nc3cc(OC(C)C)ccn3)[nH]2)nc1]
4-isopropoxy-N-(5-(5-methoxypyridin-2-yl)-4H-1,2,4-triazol-3-yl)pyridin-2-amine
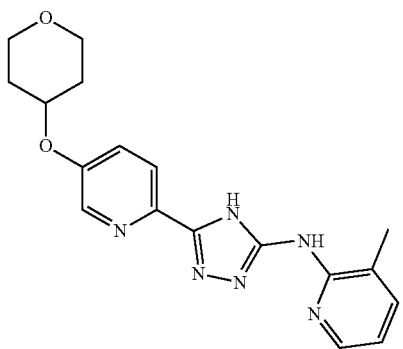 [SMILES: Cc1cccnc1Nc1nnc(-c2ccc(OC3CCOCC3)cn2)[nH]1]
3-methyl-N-(5-(5-(tetrahydro-2H-pyran-4-yloxy)pyridin-2-yl)-4H-1,2,4-triazol-3-yl)pyridin-2-amine
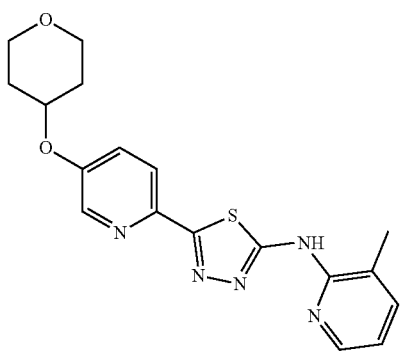 [SMILES: Cc1cccnc1Nc1nnc(-c2ccc(OC3CCOCC3)cn2)s1]
N-(3-methylpyridin-2-yl)-5-(5-(tetrahydro-2H-pyran-4-yloxy)pyridin-2-yl)-1,3,4-thiadiazol-2-amine
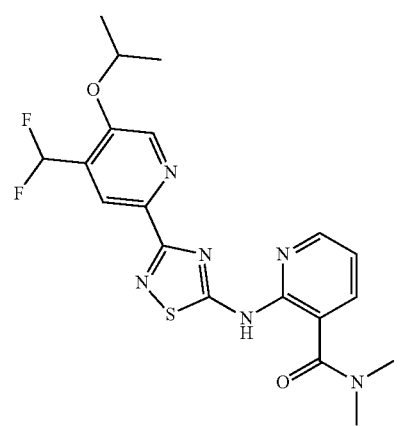 [SMILES: CC(C)Oc1cnc(-c2nsc(Nc3ncccc3C(=O)N(C)C)n2)cc1C(F)F]
2-(3-(4-(difluoromethyl)-5-isopropoxypyridin-2-yl)-1,2,4-thiadiazol-5-ylamino)-N,N-dimethylnicotinamide

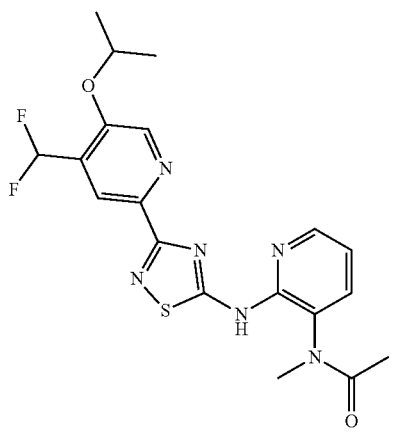 [SMILES: CC(=O)N(C)c1cccnc1Nc1nc(-c2cc(C(F)F)c(OC(C)C)cn2)ns1]
N-(2-(3-(4-(difluoromethyl)-5-isopropoxypyridin-2-yl)-1,2,4-thiadiazol-5-ylamino)pyridin-3-yl)-N-methylacetamide
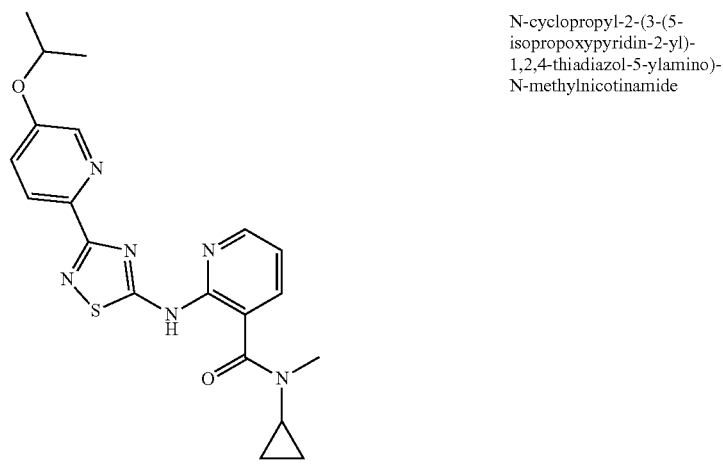
N-cyclopropyl-2-(3-(5-isopropoxypyridin-2-yl)-1,2,4-thiadiazol-5-ylamino)-N-methylnicotinamide
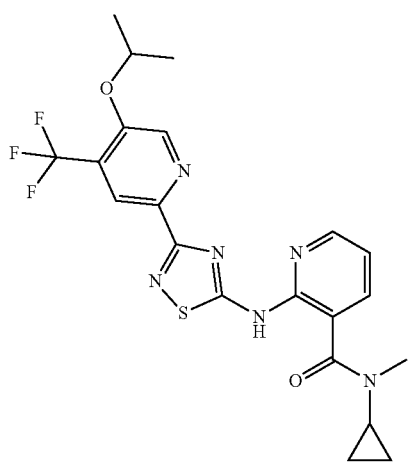 [SMILES: CC(C)Oc1cnc(-c2nsc(Nc3ncccc3C(=O)N(C)C3CC3)n2)cc1C(F)(F)F]
N-cyclopropyl-2-(3-(5-isopropoxy-4-(trifluoromethyl)pyridin-2-yl)-1,2,4-thiadiazol-5-ylamino)-N-methylnicotinamide

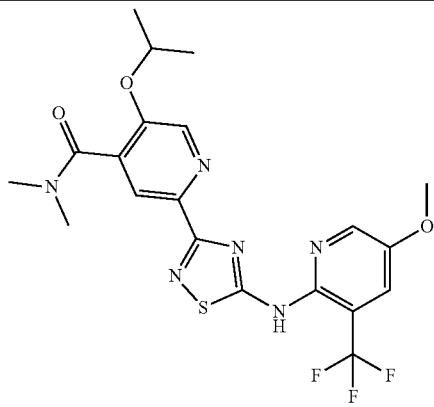
5-isopropoxy-2-(5-(5-methoxy-3-(trifluoromethyl)pyridin-2-ylamino)-1,2,4-thiadiazol-3-yl)-N,N-dimethylisonicotinamide
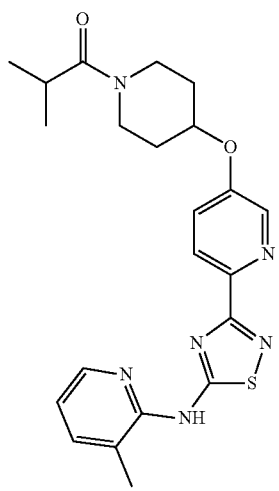 [SMILES: Cc1cccnc1Nc1nc(-c2ccc(OC3CCN(C(=O)C(C)C)CC3)cn2)ns1]
2-methyl-1-(4-(6-(5-(3-methylpyridin-2-ylamino)-1,2,4-thiadiazol-3-yl)pyridin-3-yloxy)piperidin-1-yl)propan-1-one
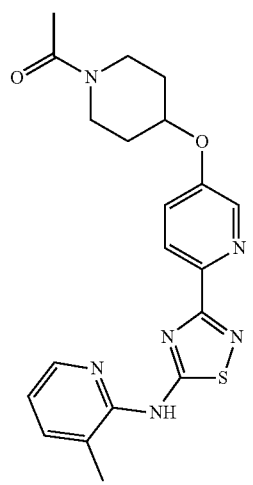 [SMILES: CC(=O)N1CCC(Oc2ccc(-c3nsc(Nc4ncccc4C)n3)nc2)CC1]
1-(4-(6-(5-(3-methylpyridin-2-ylamino)-1,2,4-thiadiazol-3-yl)pyridin-3-yloxy)piperidin-1-yl)ethanone
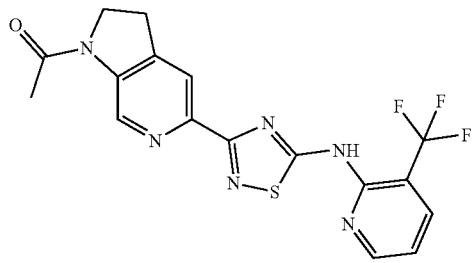 [SMILES: CC(=O)N1CCc2cc(-c3nsc(Nc4ncccc4C(F)(F)F)n3)ncc21]
1-(5-(5-(3-(trifluoromethyl)pyridin-2-ylamino)-1,2,4-thiadiazol-3-yl)-2,3-dihydro-1H-pyrrolo[2,3-c]pyridin-1-yl)ethanone -continued

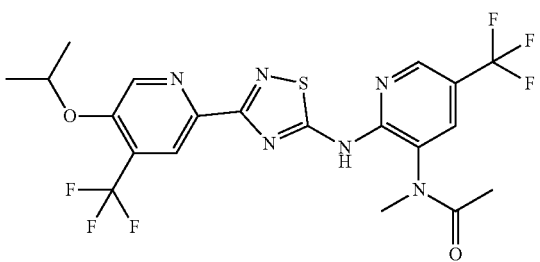 [SMILES: CC(=O)N(C)c1cc(C(F)(F)F)cnc1Nc1nc(-c2cc(C(F)(F)F)c(OC(C)C)cn2)ns1]

N-(2-(3-(5-isopropoxy-4-(trifluoromethyl)pyridin-2-yl)-1,2,4-thiadiazol-5-ylamino)-5-(trifluoromethyl)pyridin-3-yl)-N-methylacetamide

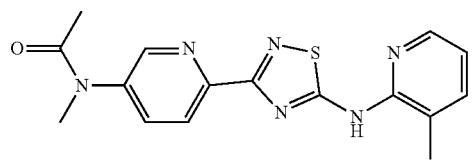 [SMILES: CC(=O)N(C)c1ccc(-c2nsc(Nc3ncccc3C)n2)nc1]

N-methyl-N-(6-(5-(3-methylpyridin-2-ylamino)-1,2,4-thiadiazol-3-yl)pyridin-3-yl)acetamide

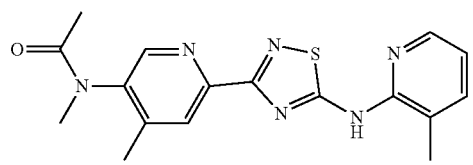 [SMILES: CC(=O)N(C)c1cnc(-c2nsc(Nc3ncccc3C)n2)cc1C]

N-methyl-N-(4-methyl-6-(5-(3-methylpyridin-2-ylamino)-1,2,4-thiadiazol-3-yl)pyridin-3-yl)acetamide

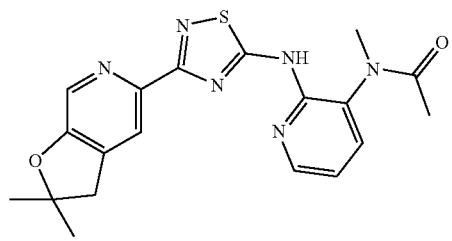 [SMILES: CC(=O)N(C)c1cccnc1Nc1nc(-c2cc3c(cn2)OC(C)(C)C3)ns1]

N-(2-(3-(2,2-dimethyl-2,3-dihydrofuro[2,3-c]pyridin-5-yl)-1,2,4-thiadiazol-5-ylamino)pyridin-3-yl)-N-methylacetamide

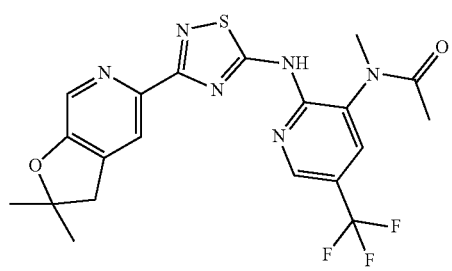 [SMILES: CC(=O)N(C)c1cc(C(F)(F)F)cnc1Nc1nc(-c2cc3c(cn2)OC(C)(C)C3)ns1]

N-(2-(3-(2,2-dimethyl-2,3-dihydrofuro[2,3-c]pyridin-5-yl)-1,2,4-thiadiazol-5-ylamino)-5-(trifluoromethyl)pyridin-3-yl)-N-methylacetamide

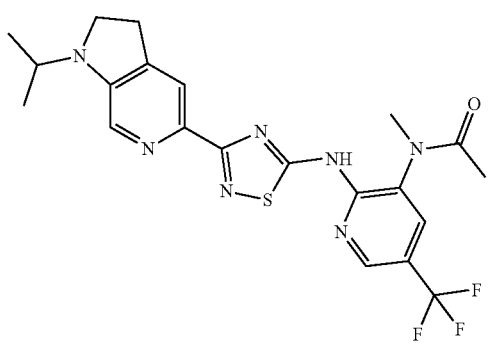 [SMILES: CC(=O)N(C)c1cc(C(F)(F)F)cnc1Nc1nc(-c2cc3c(cn2)N(C(C)C)CC3)ns1]

N-(2-(3-(1-isopropyl-2,3-dihydro-1H-pyrrolo[2,3-c]pyridin-5-yl)-1,2,4-thiadiazol-5-ylamino)-5-(trifluoromethyl)pyridin-3-yl)-N-methylacetamide

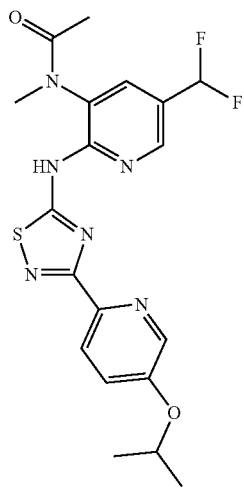 [SMILES: CC(=O)N(C)c1cc(C(F)F)cnc1Nc1nc(-c2ccc(OC(C)C)cn2)ns1] N-(5-(difluoromethyl)-2-(3-(5-isopropoxypyridin-2-yl)-1,2,4-thiadiazol-5-ylamino)pyridin-3-yl)-N-methylacetamide
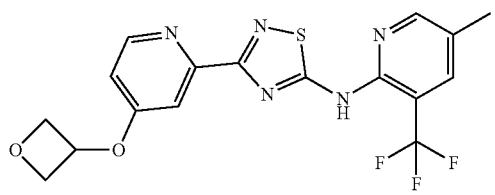 [SMILES: Cc1cnc(Nc2nc(-c3cc(OC4COC4)ccn3)ns2)c(C(F)(F)F)c1] N-(5-methyl-3-(trifluoromethyl)pyridin-2-yl)-3-(4-(oxetan-3-yloxy)pyridin-2-yl)-1,2,4-thiadiazol-5-amine
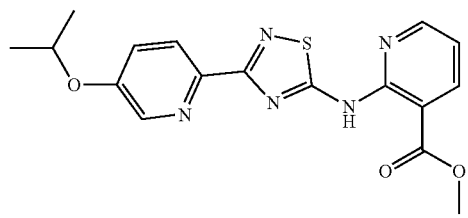 [SMILES: COC(=O)c1cccnc1Nc1nc(-c2ccc(OC(C)C)cn2)ns1] methyl 2-(3-(5-isopropoxypyridin-2-yl)-1,2,4-thiadiazol-5-ylamino)nicotinate
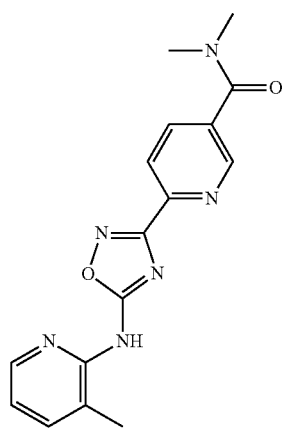 N,N-dimethyl-6-(5-(3-methylpyridin-2-ylamino)-1,2,4-oxadiazol-3-yl)nicotinamide

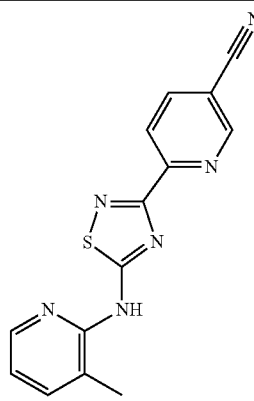
6-(5-(3-methylpyridin-2-ylamino)-1,2,4-thiadiazol-3-yl)nicotinonitrile
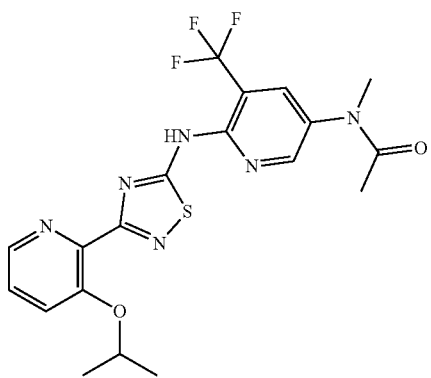 [SMILES: CC(=O)N(C)c1cnc(Nc2nc(-c3ncccc3OC(C)C)ns2)c(C(F)(F)F)c1]
N-(6-(3-(3-isopropoxypyridin-2-yl)-1,2,4-thiadiazol-5-ylamino)-5-(trifluoromethyl)pyridin-3-yl)-N-methylacetamide
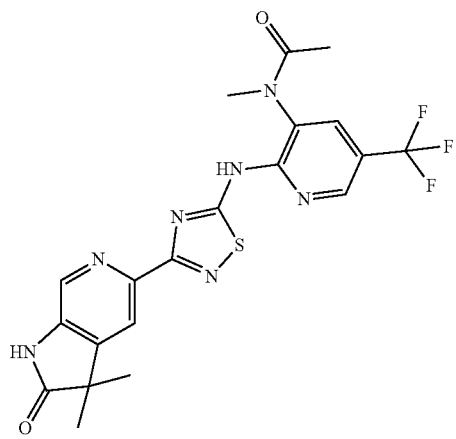 [SMILES: CC(=O)N(C)c1cc(C(F)(F)F)cnc1Nc1nc(-c2cc3c(cn2)NC(=O)C3(C)C)ns1]
N-(2-(3-(3,3-dimethyl-2-oxo-2,3-dihydro-1H-pyrrolo[2,3-c]pyridin-5-yl)-1,2,4-thiadiazol-5-ylamino)-5-(trifluoromethyl)pyridin-3-yl)-N-methylacetamide
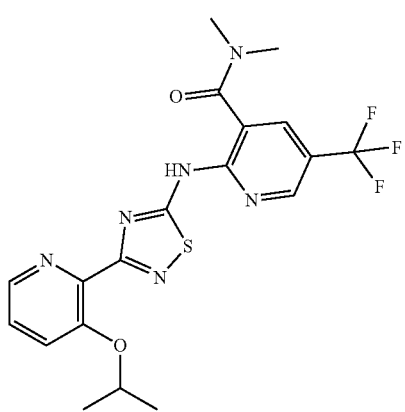 [SMILES: CC(C)Oc1cccnc1-c1nsc(Nc2ncc(C(F)(F)F)cc2C(=O)N(C)C)n1]
2-(3-(3-isopropoxypyridin-2-yl)-1,2,4-thiadiazol-5-ylamino)-N,N-dimethyl-5-(trifluoromethyl)nicotinamide

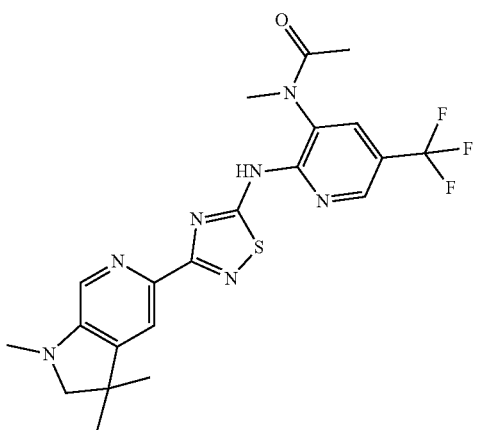 [SMILES: CC(=O)N(C)c1cc(C(F)(F)F)cnc1Nc1nc(-c2cc3c(cn2)N(C)CC3(C)C)ns1]
N-methyl-N-(5-(trifluoromethyl)-2-(3-(1,3,3-trimethyl-2,3-dihydro-1H-pyrrolo[2,3-c]pyridin-5-yl)-1,2,4-thiadiazol-5-ylamino)pyridin-3-yl)acetamide
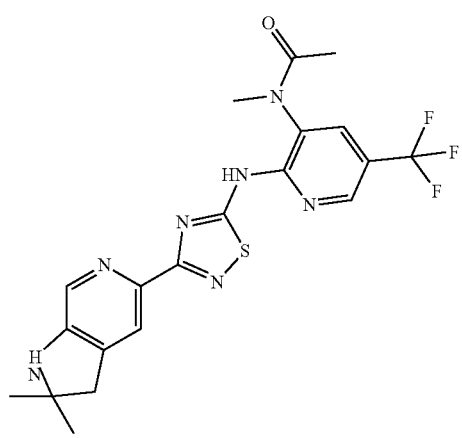
N-(2-(3-(2,2-dimethyl-2,3-dihydro-1H-pyrrolo[2,3-c]pyridin-5-yl)-1,2,4-thiadiazol-5-ylamino)-5-(trifluoromethyl)pyridin-3-yl)-N-methylacetamide
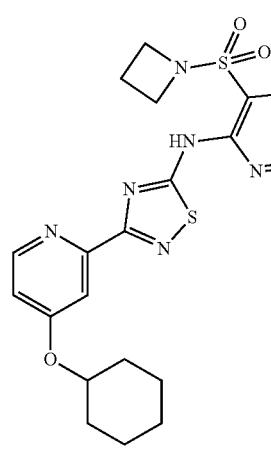
N-(3-(azetidin-1-ylsulfonyl)pyridin-2-yl)-3-(4-(cyclohexyloxy)pyridin-2-yl)-1,2,4-thiadiazol-5-amine -continued

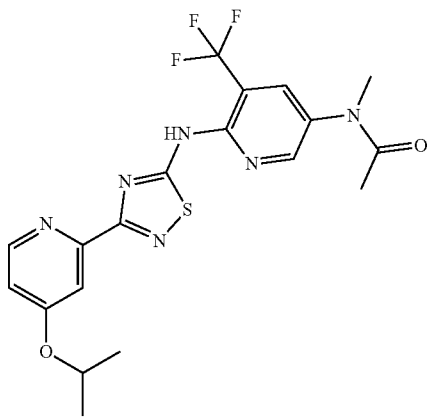 [SMILES: CC(=O)N(C)c1cnc(Nc2nc(-c3cc(OC(C)C)ccn3)ns2)c(C(F)(F)F)c1]

N-(6-(3-(4-isopropoxypyridin-2-yl)-1,2,4-thiadiazol-5-ylamino)-5-(trifluoromethyl)pyridin-3-yl)-N-methylacetamide

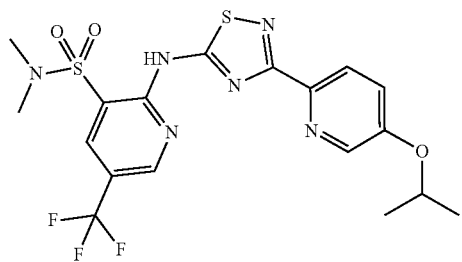 [SMILES: CC(C)Oc1ccc(-c2nsc(Nc3ncc(C(F)(F)F)cc3S(=O)(=O)N(C)C)n2)nc1]

2-(3-(5-isopropoxypyridin-2-yl)-1,2,4-thiadiazol-5-ylamino)-N,N-dimethyl-5-(trifluoromethyl)pyridine-3-sulfonamide

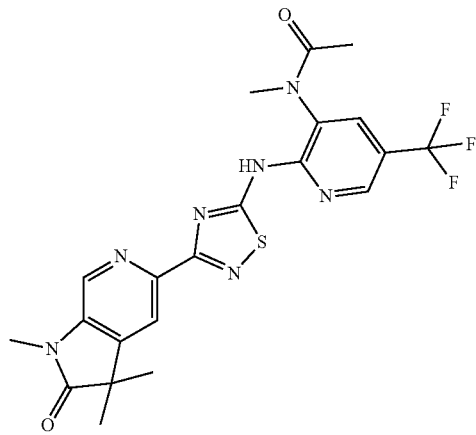 [SMILES: CC(=O)N(C)c1cc(C(F)(F)F)cnc1Nc1nc(-c2cc3c(cn2)N(C)C(=O)C3(C)C)ns1]

N-methyl-N-(5-(trifluoromethyl)-2-(3-(1,3,3-trimethyl-2-oxo-2,3-dihydro-1H-pyrrolo[2,3-c]pyridin-5-yl)-1,2,4-thiadiazol-5-ylamino)pyridin-3-yl)acetamide

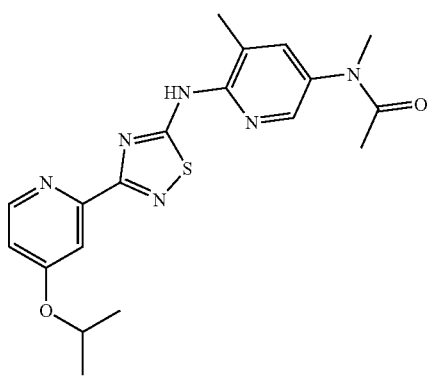 [SMILES: CC(=O)N(C)c1cnc(Nc2nc(-c3cc(OC(C)C)ccn3)ns2)c(C)c1]

N-(6-(3-(4-isopropoxypyridin-2-yl)-1,2,4-thiadiazol-5-ylamino)-5-methylpyridin-3-yl)-N-methylacetamide

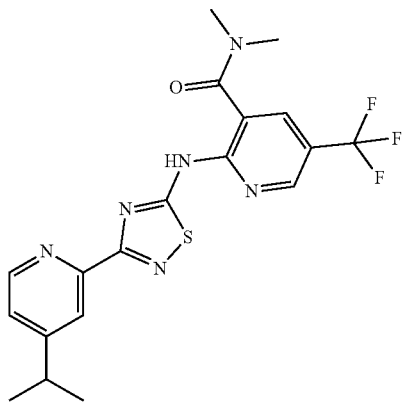 [SMILES: CC(C)c1ccnc(-c2nsc(Nc3ncc(C(F)(F)F)cc3C(=O)N(C)C)n2)c1]

2-(3-(4-isopropylpyridin-2-yl)-1,2,4-thiadiazol-5-ylamino)-N,N-dimethyl-5-(trifluoromethyl)nicotinamide

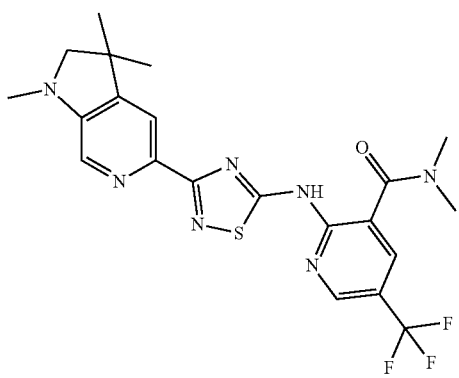

N,N-dimethyl-5-(trifluoromethyl)-2-(3-(1,3,3-trimethyl-2,3-dihydro-1H-pyrrolo[2,3-c]pyridin-5-yl)-1,2,4-thiadiazol-5-ylamino)nicotinamide

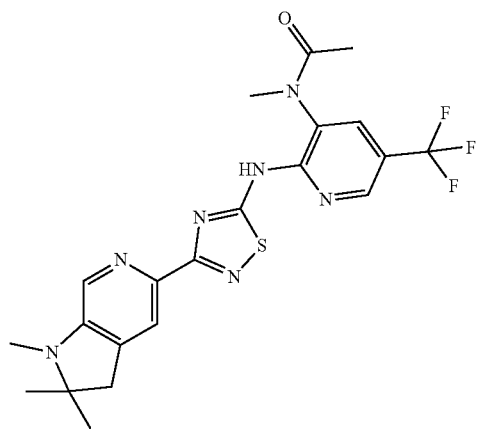 [SMILES: CC(=O)N(C)c1cc(C(F)(F)F)cnc1Nc1nc(-c2cc3c(cn2)N(C)C(C)(C)C3)ns1]

N-methyl-N-(5-(trifluoromethyl)-2-(3-(1,2,2-trimethyl-2,3-dihydro-1H-pyrrolo[2,3-c]pyridin-5-yl)-1,2,4-thiadiazol-5-ylamino)pyridin-3-yl)acetamide

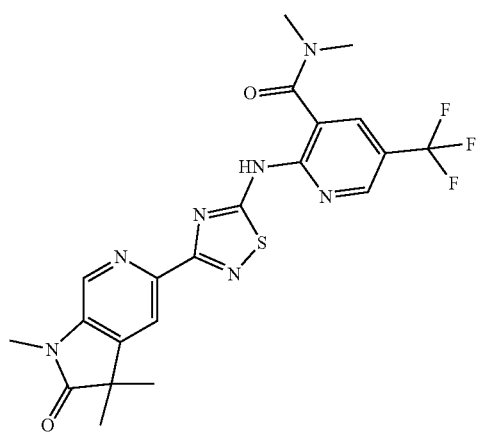 [SMILES: CN(C)C(=O)c1cc(C(F)(F)F)cnc1Nc1nc(-c2cc3c(cn2)N(C)C(=O)C3(C)C)ns1]

N,N-dimethyl-5-(trifluoromethyl)-2-(3-(1,3,3-trimethyl-2-oxo-2,3-dihydro-1H-pyrrolo[2,3-c]pyridin-5-yl)-1,2,4-thiadiazol-5-ylamino)nicotinamide

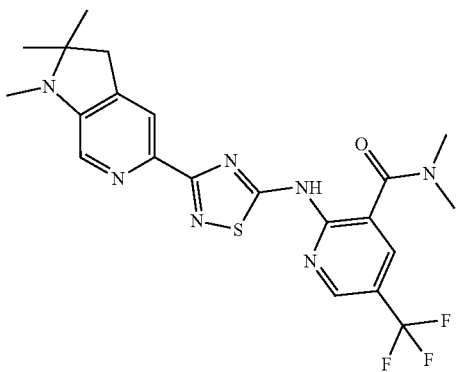

N,N-dimethyl-5-(trifluoromethyl)-2-(3-(1,2,2-trimethyl-2,3-dihydro-1H-pyrrolo[2,3-c]pyridin-5-yl)-1,2,4-thiadiazol-5-ylamino)nicotinamide

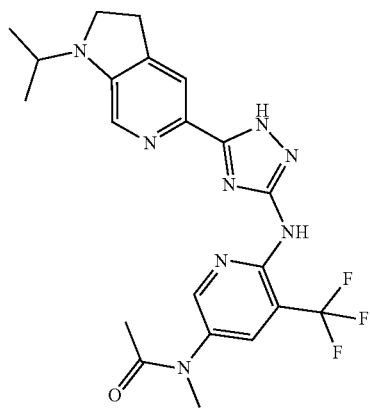 [SMILES: CC(=O)N(C)c1cnc(Nc2n[nH]c(-c3cc4c(cn3)N(C(C)C)CC4)n2)c(C(F)(F)F)c1]

N-(6-(5-(1-isopropyl-2,3-dihydro-1H-pyrrolo[2,3-c]pyridin-5-yl)-1H-1,2,4-triazol-3-ylamino)-5-(trifluoromethyl)pyridin-3-yl)-N-methylacetamide

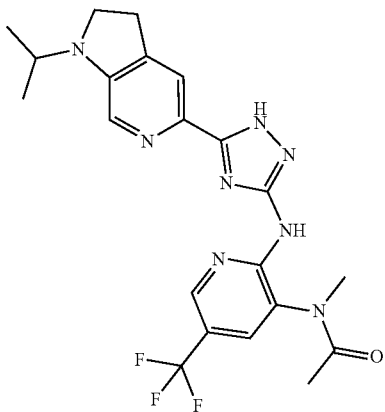 [SMILES: CC(=O)N(C)c1cc(C(F)(F)F)cnc1Nc1n[nH]c(-c2cc3c(cn2)N(C(C)C)CC3)n1]

N-(2-(5-(1-isopropyl-2,3-dihydro-1H-pyrrolo[2,3-c]pyridin-5-yl)-1H-1,2,4-triazol-3-ylamino)-5-(trifluoromethyl)pyridin-3-yl)-N-methylacetamide

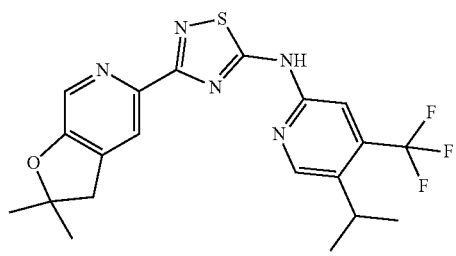 [SMILES: CC(C)c1cnc(Nc2nc(-c3cc4c(cn3)OC(C)(C)C4)ns2)cc1C(F)(F)F]

3-(2,2-dimethyl-2,3-dihydrofuro[2,3-c]pyridin-5-yl)-N-(5-isopropyl-4-(trifluoromethyl)pyridin-2-yl)-1,2,4-thiadiazol-5-amine

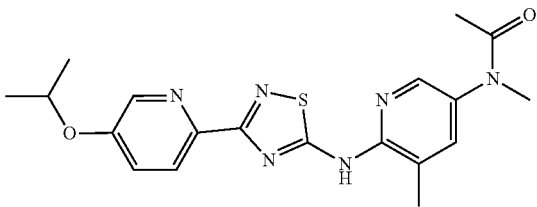 [SMILES: CC(=O)N(C)c1cnc(Nc2nc(-c3ccc(OC(C)C)cn3)ns2)c(C)c1] N-(6-(3-(5-isopropoxypyridin-2-yl)-1,2,4-thiadiazol-5-ylamino)-5-methylpyridin-3-yl)-N-methylacetamide

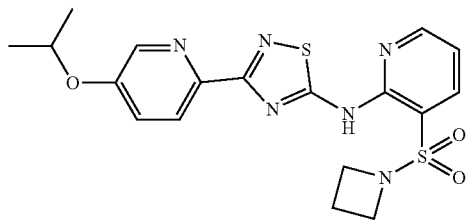 [SMILES: CC(C)Oc1ccc(-c2nsc(Nc3ncccc3S(=O)(=O)N3CCC3)n2)nc1] N-(3-(azetidin-1-ylsulfonyl)pyridin-2-yl)-3-(5-isopropoxypyridin-2-yl)-1,2,4-thiadiazol-5-amine

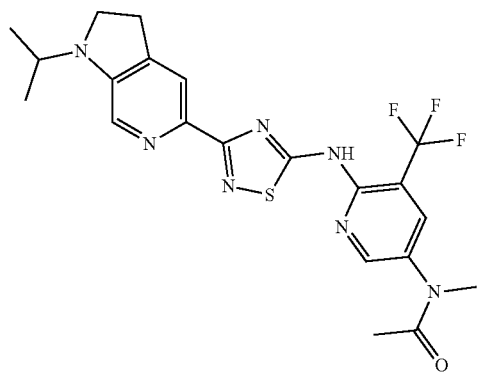 [SMILES: CC(=O)N(C)c1cnc(Nc2nc(-c3cc4c(cn3)N(C(C)C)CC4)ns2)c(C(F)(F)F)c1] N-(6-(3-(1-isopropyl-2,3-dihydro-1H-pyrrolo[2,3-c]pyridin-5-yl)-1,2,4-thiadiazol-5-ylamino)-5-(trifluoromethyl)pyridin-3-yl)-N-methylacetamide

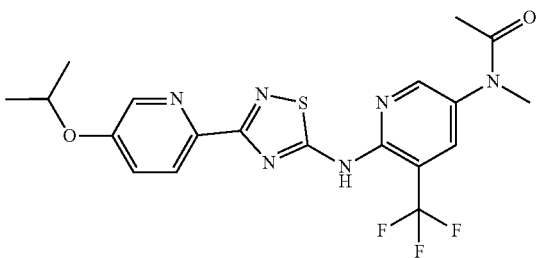 [SMILES: CC(=O)N(C)c1cnc(Nc2nc(-c3ccc(OC(C)C)cn3)ns2)c(C(F)(F)F)c1] N-(6-(3-(5-isopropoxypyridin-2-yl)-1,2,4-thiadiazol-5-ylamino)-5-(trifluoromethyl)pyridin-3-yl)-N-methylacetamide

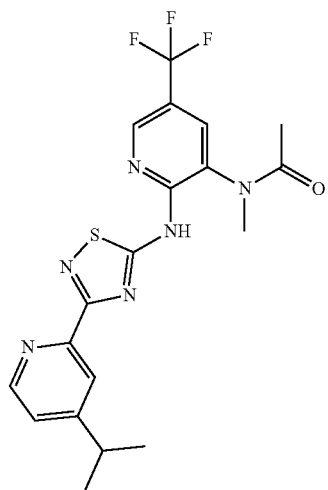 [SMILES: CC(=O)N(C)c1cc(C(F)(F)F)cnc1Nc1nc(-c2cc(C(C)C)ccn2)ns1] N-(2-(3-(4-isopropylpyridin-2-yl)-1,2,4-thiadiazol-5-ylamino)-5-(trifluoromethyl)pyridin-3-yl)-N-methylacetamide

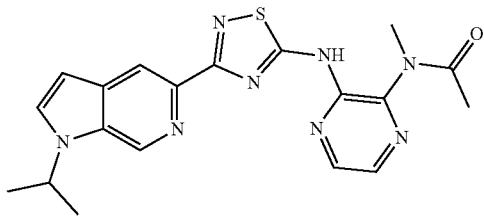 [SMILES: CC(=O)N(C)c1nccnc1Nc1nc(-c2cc3ccn(C(C)C)c3cn2)ns1]
N-(3-(3-(1-isopropyl-1H-pyrrolo[2,3-c]pyridin-5-yl)-1,2,4-thiadiazol-5-ylamino)pyrazin-2-yl)-N-methylacetamide
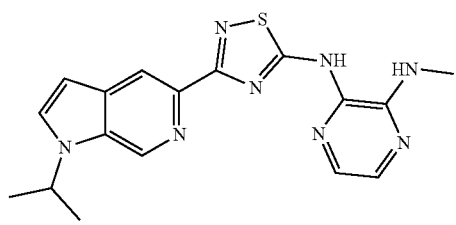 [SMILES: CNc1nccnc1Nc1nc(-c2cc3ccn(C(C)C)c3cn2)ns1]
N2-(3-(1-isopropyl-1H-pyrrolo[2,3-c]pyridin-5-yl)-1,2,4-thiadiazol-5-yl)-N3-methylpyrazine-2,3-diamine
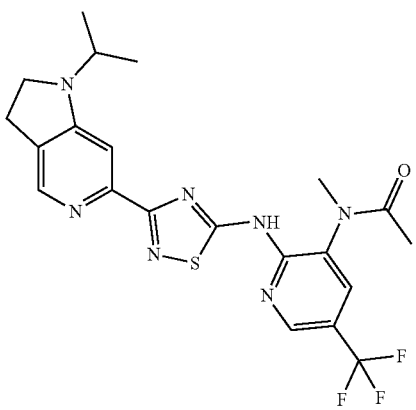 [SMILES: CC(=O)N(C)c1cc(C(F)(F)F)cnc1Nc1nc(-c2cc3c(cn2)CCN3C(C)C)ns1]
N-(2-(3-(1-isopropyl-2,3-dihydro-1H-pyrrolo[3,2-c]pyridin-6-yl)-1,2,4-thiadiazol-5-ylamino)-5-(trifluoromethyl)pyridin-3-yl)-N-methylacetamide
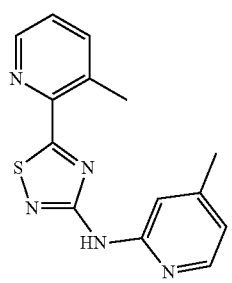 [SMILES: Cc1ccnc(Nc2nsc(-c3ncccc3C)n2)c1]
5-(3-methylpyridin-2-yl)-N-(4-methylpyridin-2-yl)-1,2,4-thiadiazol-3-amine

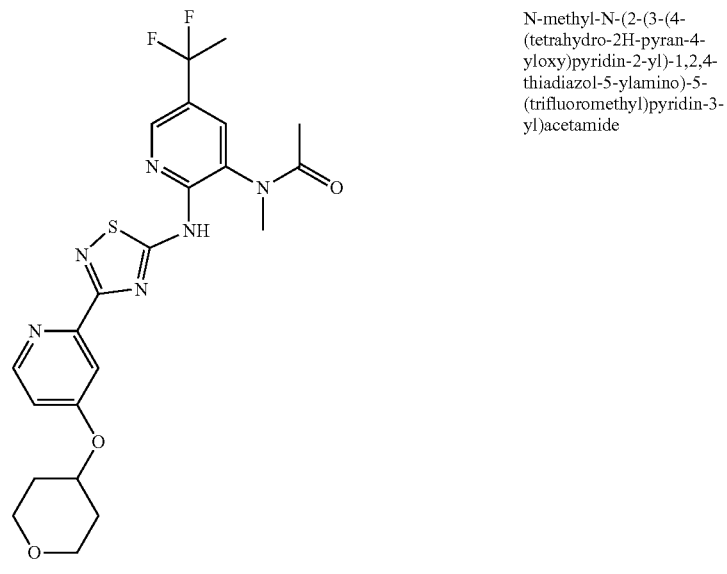

N-methyl-N-(2-(3-(4-(tetrahydro-2H-pyran-4-yloxy)pyridin-2-yl)-1,2,4-thiadiazol-5-ylamino)-5-(trifluoromethyl)pyridin-3-yl)acetamide

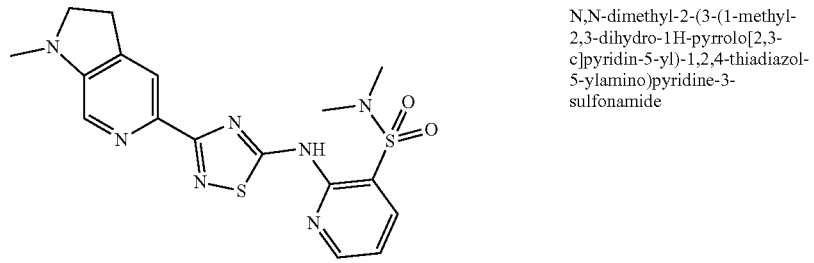

N,N-dimethyl-2-(3-(1-methyl-2,3-dihydro-1H-pyrrolo[2,3-c]pyridin-5-yl)-1,2,4-thiadiazol-5-ylamino)pyridine-3-sulfonamide

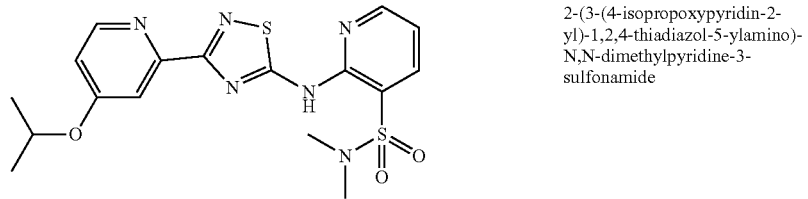

2-(3-(4-isopropoxypyridin-2-yl)-1,2,4-thiadiazol-5-ylamino)-N,N-dimethylpyridine-3-sulfonamide

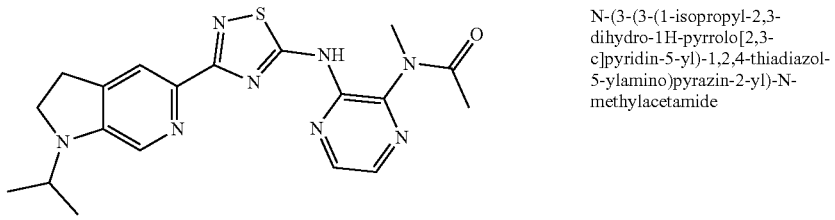

N-(3-(3-(1-isopropyl-2,3-dihydro-1H-pyrrolo[2,3-c]pyridin-5-yl)-1,2,4-thiadiazol-5-ylamino)pyrazin-2-yl)-N-methylacetamide

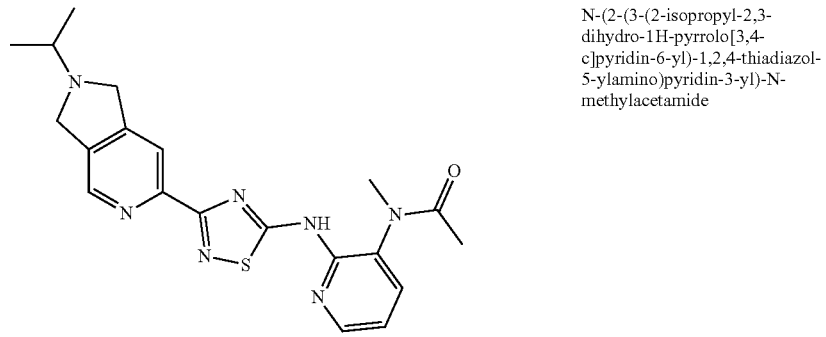

N-(2-(3-(2-isopropyl-2,3-dihydro-1H-pyrrolo[3,4-c]pyridin-6-yl)-1,2,4-thiadiazol-5-ylamino)pyridin-3-yl)-N-methylacetamide -continued
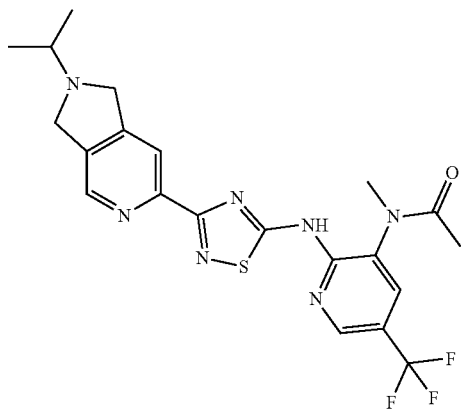 [SMILES: CC(=O)N(C)c1cc(C(F)(F)F)cnc1Nc1nc(-c2cc3c(cn2)CN(C(C)C)C3)ns1]
N-(2-(3-(2-isopropyl-2,3-dihydro-1H-pyrrolo[3,4-c]pyridin-6-yl)-1,2,4-thiadiazol-5-ylamino)-5-(trifluoromethyl)pyridin-3-yl)-N-methylacetamide
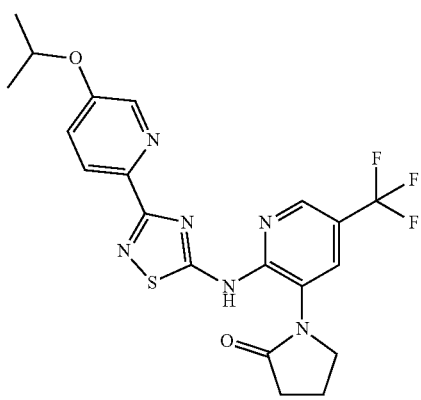 [SMILES: CC(C)Oc1ccc(-c2nsc(Nc3ncc(C(F)(F)F)cc3N3CCCC3=O)n2)nc1]
1-(2-(3-(5-isopropoxypyridin-2-yl)-1,2,4-thiadiazol-5-ylamino)-5-(trifluoromethyl)pyridin-3-yl)pyrrolidin-2-one
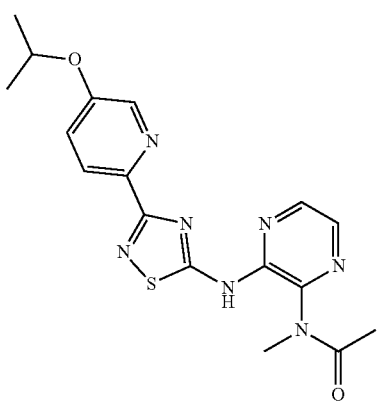 [SMILES: CC(=O)N(C)c1nccnc1Nc1nc(-c2ccc(OC(C)C)cn2)ns1]
N-(3-(3-(5-isopropoxypyridin-2-yl)-1,2,4-thiadiazol-5-ylamino)pyrazin-2-yl)-N-methylacetamide

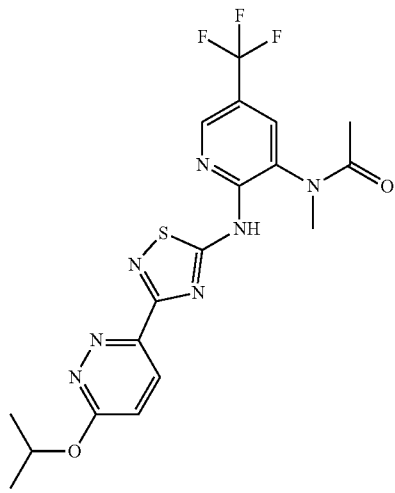 [SMILES: CC(=O)N(C)c1cc(C(F)(F)F)cnc1Nc1nc(-c2ccc(OC(C)C)nn2)ns1]

N-(2-(3-(6-isopropoxypyridazin-3-yl)-1,2,4-thiadiazol-5-ylamino)-5-(trifluoromethyl)pyridin-3-yl)-N-methylacetamide

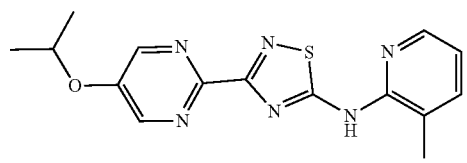 [SMILES: Cc1cccnc1Nc1nc(-c2ncc(OC(C)C)cn2)ns1]

3-(5-isopropoxypyrimidin-2-yl)-N-(3-methylpyridin-2-yl)-1,2,4-thiadiazol-5-amine

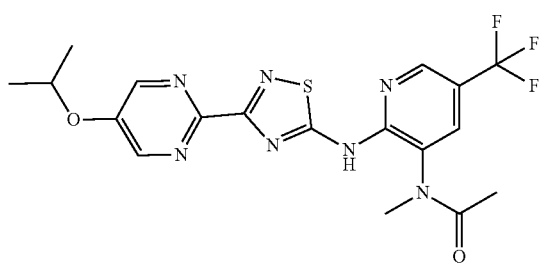 [SMILES: CC(=O)N(C)c1cc(C(F)(F)F)cnc1Nc1nc(-c2ncc(OC(C)C)cn2)ns1]

N-(2-(3-(5-isopropoxypyrimidin-2-yl)-1,2,4-thiadiazol-5-ylamino)-5-(trifluoromethyl)pyridin-3-yl)-N-methylacetamide

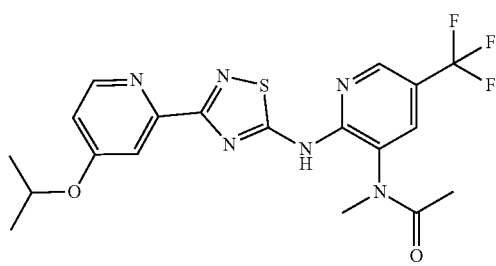 [SMILES: CC(=O)N(C)c1cc(C(F)(F)F)cnc1Nc1nc(-c2cc(OC(C)C)ccn2)ns1]

N-(2-(3-(4-isopropoxypyridin-2-yl)-1,2,4-thiadiazol-5-ylamino)-5-(trifluoromethyl)pyridin-3-yl)-N-methylacetamide

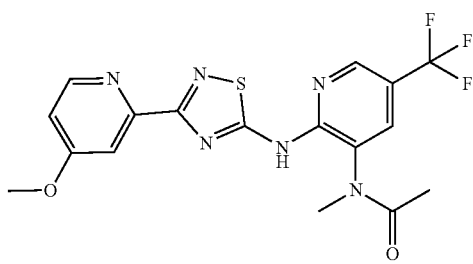 [SMILES: COc1ccnc(-c2nsc(Nc3ncc(C(F)(F)F)cc3N(C)C(C)=O)n2)c1]

N-(2-(3-(4-methoxypyridin-2-yl)-1,2,4-thiadiazol-5-ylamino)-5-(trifluoromethyl)pyridin-3-yl)-N-methylacetamide

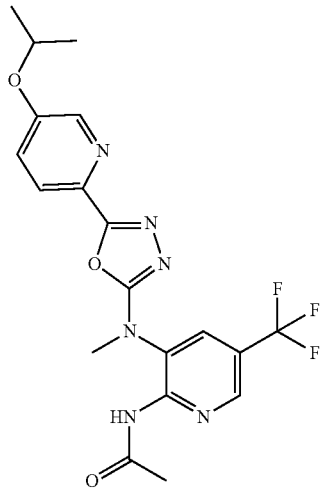 [SMILES: CC(=O)Nc1ncc(C(F)(F)F)cc1N(C)c1nnc(-c2ccc(OC(C)C)cn2)o1]

N-(3-((5-(5-isopropoxypyridin-2-yl)-1,3,4-oxadiazol-2-yl)(methyl)amino)-5-(trifluoromethyl)pyridin-2-yl)acetamide

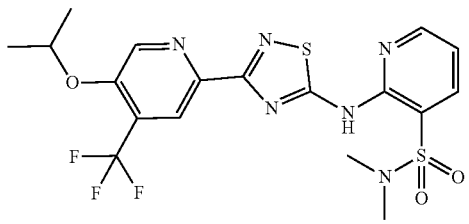 [SMILES: CC(C)Oc1cnc(-c2nsc(Nc3ncccc3S(=O)(=O)N(C)C)n2)cc1C(F)(F)F]

2-(3-(5-isopropoxy-4-(trifluoromethyl)pyridin-2-yl)-1,2,4-thiadiazol-5-ylamino)-N,N-dimethylpyridine-3-sulfonamide

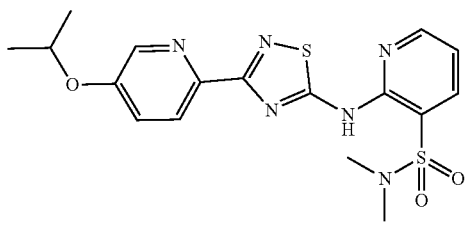 [SMILES: CC(C)Oc1ccc(-c2nsc(Nc3ncccc3S(=O)(=O)N(C)C)n2)nc1]

2-(3-(5-isopropoxypyridin-2-yl)-1,2,4-thiadiazol-5-ylamino)-N,N-dimethylpyridine-3-sulfonamide

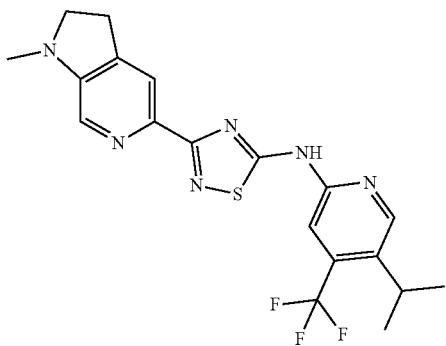 [SMILES: CC(C)c1cnc(Nc2nc(-c3cc4c(cn3)N(C)CC4)ns2)cc1C(F)(F)F]

N-(5-isopropyl-4-(trifluoromethyl)pyridin-2-yl)-3-(1-methyl-2,3-dihydro-1H-pyrrolo[2,3-c]pyridin-5-yl)-1,2,4-thiadiazol-5-amine

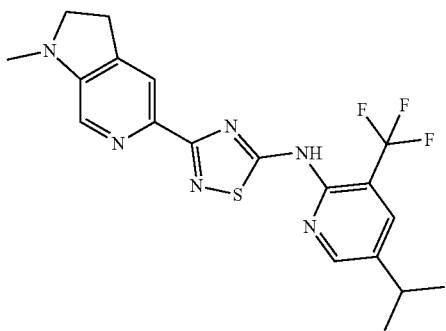 [SMILES: CC(C)c1cnc(Nc2nc(-c3cc4c(cn3)N(C)CC4)ns2)c(C(F)(F)F)c1]

N-(5-isopropyl-3-(trifluoromethyl)pyridin-2-yl)-3-(1-methyl-2,3-dihydro-1H-pyrrolo[2,3-c]pyridin-5-yl)-1,2,4-thiadiazol-5-amine

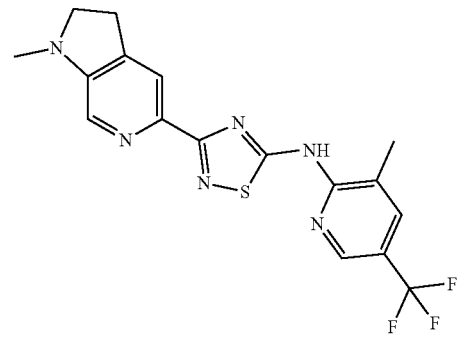 [SMILES: Cc1cc(C(F)(F)F)cnc1Nc1nc(-c2cc3c(cn2)N(C)CC3)ns1]

3-(1-methyl-2,3-dihydro-1H-pyrrolo[2,3-c]pyridin-5-yl)-N-(3-methyl-5-(trifluoromethyl)pyridin-2-yl)-1,2,4-thiadiazol-5-amine

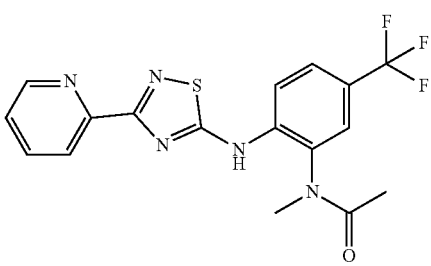 [SMILES: CC(=O)N(C)c1cc(C(F)(F)F)ccc1Nc1nc(-c2ccccn2)ns1]

N-methyl-N-(2-(3-(pyridin-2-yl)-1,2,4-thiadiazol-5-ylamino)-5-(trifluoromethyl)pyridin-3-yl)acetamide

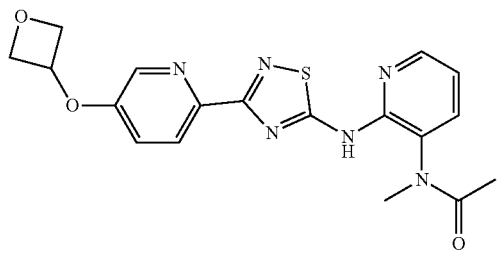 [SMILES: CC(=O)N(C)c1cccnc1Nc1nc(-c2ccc(OC3COC3)cn2)ns1]

N-methyl-N-(2-(3-(5-(oxetan-3-yloxy)pyridin-2-yl)-1,2,4-thiadiazol-5-ylamino)pyridin-3-yl)acetamide

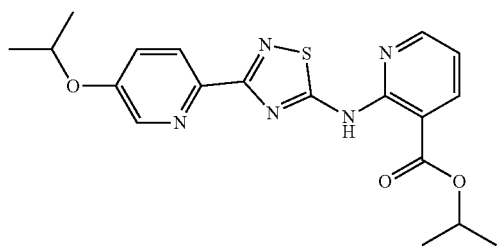 [SMILES: CC(C)OC(=O)c1cccnc1Nc1nc(-c2ccc(OC(C)C)cn2)ns1]

isopropyl 2-(3-(5-isopropoxypyridin-2-yl)-1,2,4-thiadiazol-5-ylamino)nicotinate

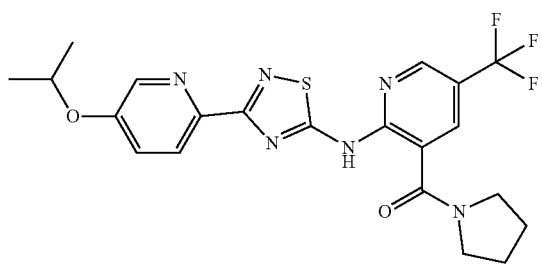 [SMILES: CC(C)Oc1ccc(-c2nsc(Nc3ncc(C(F)(F)F)cc3C(=O)N3CCCC3)n2)nc1]

(2-(3-(5-isopropoxypyridin-2-yl)-1,2,4-thiadiazol-5-ylamino)-5-(trifluoromethyl)pyridin-3-yl)(pyrrolidin-1-yl)methanone

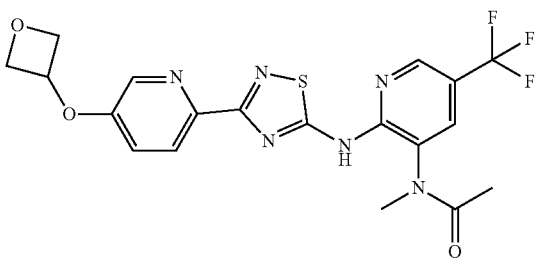 [SMILES: CC(=O)N(C)c1cc(C(F)(F)F)cnc1Nc1nc(-c2ccc(OC3COC3)cn2)ns1]

N-methyl-N-(2-(3-(5-(oxetan-3-yloxy)pyridin-2-yl)-1,2,4-thiadiazol-5-ylamino)-5-(trifluoromethyl)pyridin-3-yl)acetamide

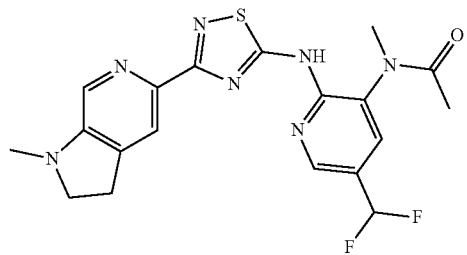 [SMILES: CC(=O)N(C)c1cc(C(F)F)cnc1Nc1nc(-c2cc3c(cn2)N(C)CC3)ns1]

N-(5-(difluoromethyl)-2-(3-(1-methyl-2,3-dihydro-1H-pyrrolo[2,3-c]pyridin-5-yl)-1,2,4-thiadiazol-5-ylamino)pyridin-3-yl)-N-methylacetamide

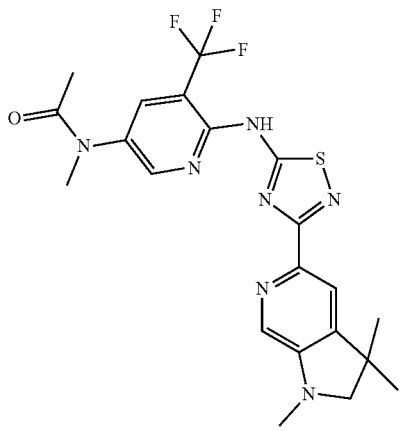 [SMILES: CC(=O)N(C)c1cnc(Nc2nc(-c3cc4c(cn3)N(C)CC4(C)C)ns2)c(C(F)(F)F)c1]

N-methyl-N-(5-(trifluoromethyl)-6-((3-(1,3,3-trimethyl-2,3-dihydro-1H-pyrrolo[2,3-c]pyridin-5-yl)-1,2,4-thiadiazol-5-yl)amino)-1l2-piperidin-3-yl)acetamide

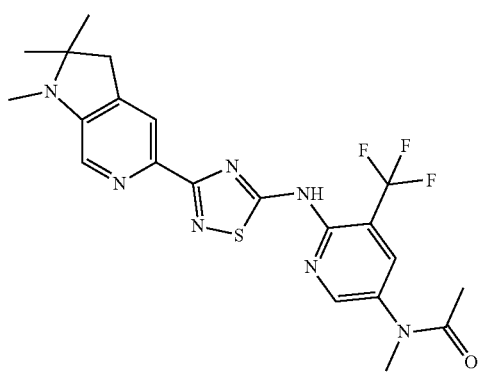 [SMILES: CC(=O)N(C)c1cnc(Nc2nc(-c3cc4c(cn3)N(C)C(C)(C)C4)ns2)c(C(F)(F)F)c1]

N-methyl-N-(5-(trifluoromethyl)-6-((3-(1,2,2-trimethyl-2,3-dihydro-1H-pyrrolo[2,3-c]pyridin-5-yl)-1,2,4-thiadiazol-5-yl)amino)pyridin-3-yl)acetamide

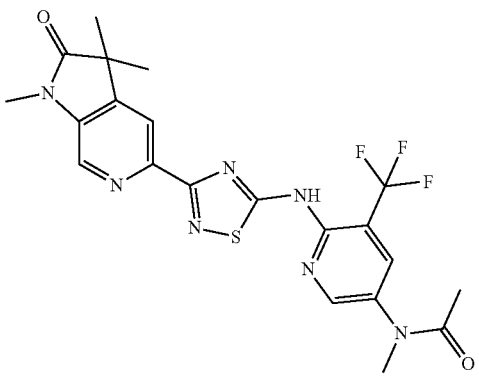 [SMILES: CC(=O)N(C)c1cnc(Nc2nc(-c3cc4c(cn3)N(C)C(=O)C4(C)C)ns2)c(C(F)(F)F)c1]

N-methyl-N-(5-(trifluoromethyl)-6-((3-(1,3,3-trimethyl-2-oxo-2,3-dihydro-1H-pyrrolo[2,3-c]pyridin-5-yl)-1,2,4-thiadiazol-5-yl)amino)pyridin-3-yl)acetamide

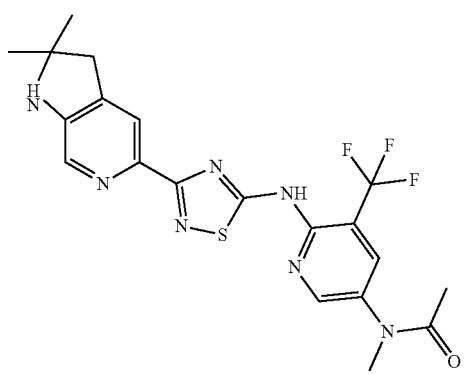 [SMILES: CC(=O)N(C)c1cnc(Nc2nc(-c3cc4c(cn3)NC(C)(C)C4)ns2)c(C(F)(F)F)c1]

N-(6-((3-(2,2-dimethyl-2,3-dihydro-1H-pyrrolo[2,3-c]pyridin-5-yl)-1,2,4-thiadiazol-5-yl)amino)-5-(trifluoromethyl)pyridin-3-yl)-N-methylacetamide

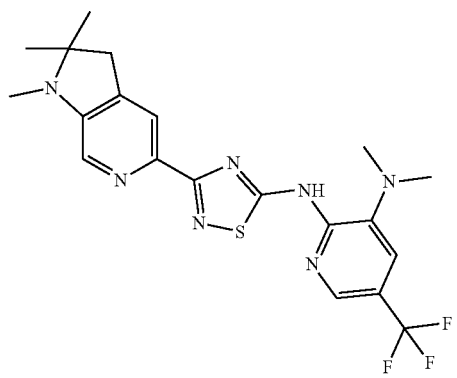 [SMILES: CN(C)c1cc(C(F)(F)F)cnc1Nc1nc(-c2cc3c(cn2)N(C)C(C)(C)C3)ns1]

N3,N3-dimethyl-5-(trifluoromethyl)-N2-(3-(1,2,2-trimethyl-2,3-dihydro-1H-pyrrolo[2,3-c]pyridin-5-yl)-3H-1,2l2,4-thiadiazol-5-yl)pyridine-2,3-diamine

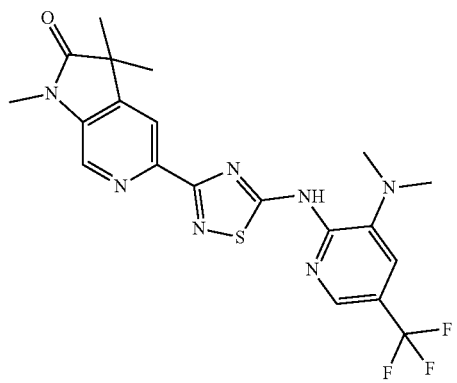 [SMILES: CN(C)c1cc(C(F)(F)F)cnc1Nc1nc(-c2cc3c(cn2)N(C)C(=O)C3(C)C)ns1]

5-(5-((3-(dimethylamino)-5-(trifluoromethyl)pyridin-2-yl)amino)-1,2,4-thiadiazol-3-yl)-1,3,3-trimethyl-1,3-dihydro-2H-pyrrolo[2,3-c]pyridin-2-one

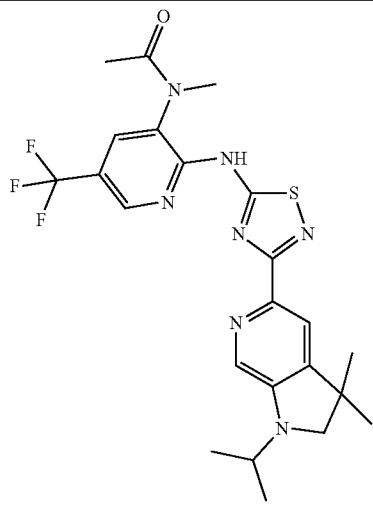

N-(2-((3-(1-isopropyl-3,3-dimethyl-2,3,3a,6-tetrahydro-1H-pyrrolo[2,3-c]pyridin-5-yl)-1,2,4l2-thiadiazol-5-yl)amino)-5-(trifluoromethyl)pyridin-3-yl)-N-methylacetamide

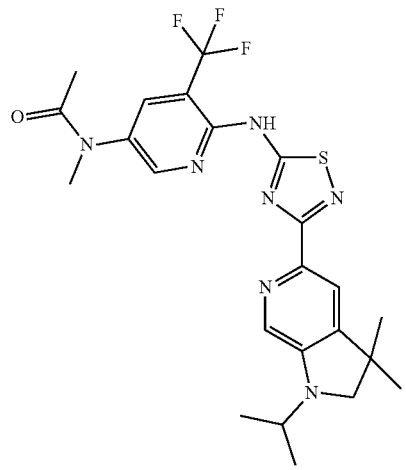 [SMILES: CC(=O)N(C)c1cnc(Nc2nc(-c3cc4c(cn3)N(C(C)C)CC4(C)C)ns2)c(C(F)(F)F)c1]

N-(6-((3-(1-isopropyl-3,3-dimethyl-2,3,3a,6-tetrahydro-1H-pyrrolo[2,3-c]pyridin-5-yl)-1,2,4-thiadiazol-5-yl)amino)-5-(trifluoromethyl)pyridin-3-yl)-N-methylacetamide

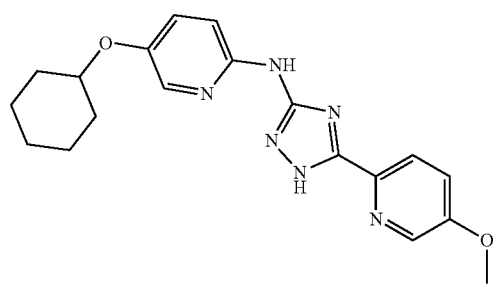 [SMILES: COc1ccc(-c2nc(Nc3ccc(OC4CCCCC4)cn3)n[nH]2)nc1]

5-(cyclohexyloxy)-N-(5-(5-methoxypyridin-2-yl)-1H-1,2,4-triazol-3-yl)pyridin-2-amine

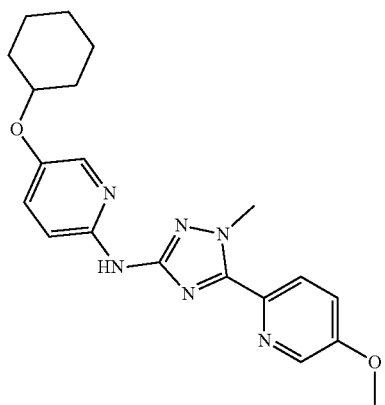 [SMILES: COc1ccc(-c2nc(Nc3ccc(OC4CCCCC4)cn3)nn2C)nc1]

5-(cyclohexyloxy)-N-(5-(5-methoxypyridin-2-yl)-1-methyl-1H-1,2,4-triazol-3-yl)pyridin-2-amine -continued

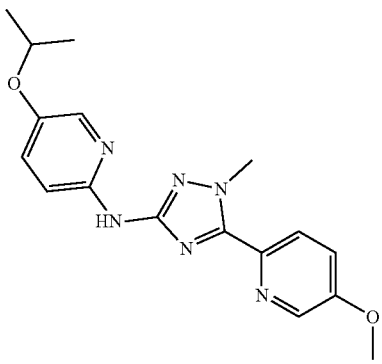 [SMILES: COc1ccc(-c2nc(Nc3ccc(OC(C)C)cn3)nn2C)nc1]

5-isopropoxy-N-(5-(5-methoxypyridin-2-yl)-1-methyl-1H-1,2,4-triazol-3-yl)pyridin-2-amine

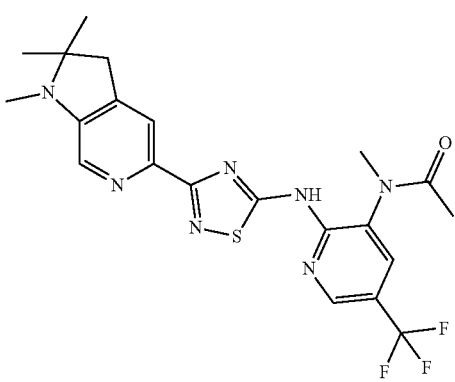 [SMILES: CC(=O)N(C)c1cc(C(F)(F)F)cnc1Nc1nc(-c2cc3c(cn2)N(C)C(C)(C)C3)ns1]

N-methyl-N-(5-(trifluoromethyl)-2-((3-(1,2,2-trimethyl-2,3-dihydro-1H-pyrrolo[2,3-c]pyridin-5-yl)-1,2,4-thiadiazol-5-yl)amino)pyridin-3-yl)acetamide

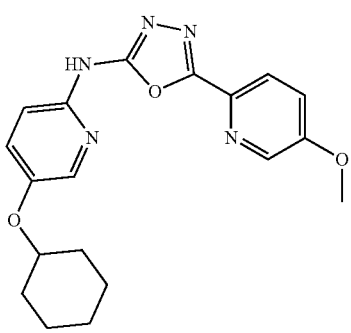 [SMILES: COc1ccc(-c2nnc(Nc3ccc(OC4CCCCC4)cn3)o2)nc1]

N-(5-(cyclohexyloxy)pyridin-2-yl)-5-(5-methoxypyridin-2-yl)-1,3,4-oxadiazol-2-amine

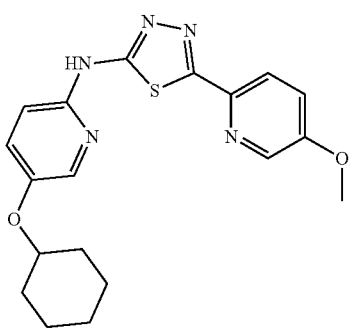 [SMILES: COc1ccc(-c2nnc(Nc3ccc(OC4CCCCC4)cn3)s2)nc1]

N-(5-(cyclohexyloxy)pyridin-2-yl)-5-(5-methoxypyridin-2-yl)-1,3,4-thiadiazol-2-amine

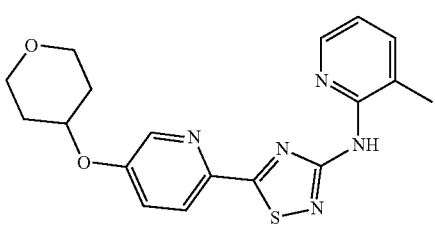 [SMILES: Cc1cccnc1Nc1nsc(-c2ccc(OC3CCOCC3)cn2)n1]

N-(3-methylpyridin-2-yl)-5-(5-((tetrahydro-2H-pyran-4-yl)oxy)pyridin-2-yl)-1,2,4-thiadiazol-3-amine

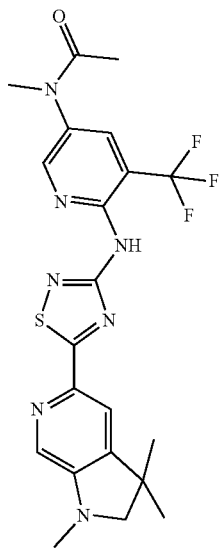 [SMILES: CC(=O)N(C)c1cnc(Nc2nsc(-c3cc4c(cn3)N(C)CC4(C)C)n2)c(C(F)(F)F)c1]
N-methyl-N-(5-(trifluoromethyl)-6-((5-(1,3,3-trimethyl-2,3,3a,6,7,7a-hexahydro-1H-pyrrolo[2,3-c]pyridin-5-yl)-1,2,4-thiadiazol-3-yl)amino)pyridin-3-yl)acetamide
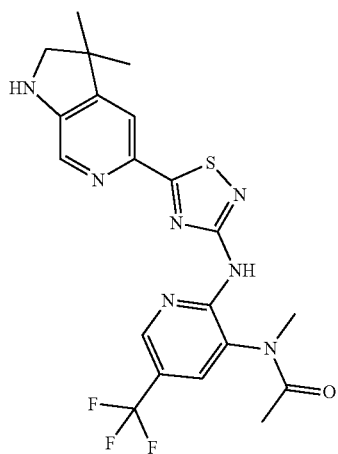 [SMILES: CC(=O)N(C)c1cc(C(F)(F)F)cnc1Nc1nsc(-c2cc3c(cn2)NCC3(C)C)n1]
N-(2-((5-(3,3-dimethyl-2,3-dihydro-1H-pyrrolo[2,3-c]pyridin-5-yl)-1,2,4-thiadiazol-3-yl)amino)-5-(trifluoromethyl)pyridin-3-yl)-N-methylacetamide
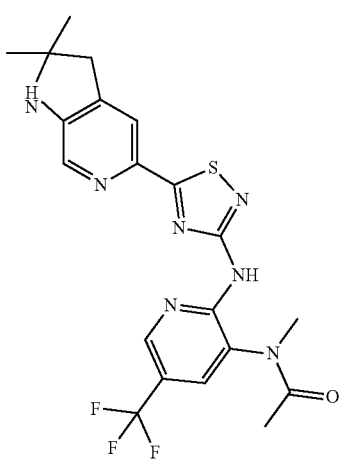 [SMILES: CC(=O)N(C)c1cc(C(F)(F)F)cnc1Nc1nsc(-c2cc3c(cn2)NC(C)(C)C3)n1]
N-(2-((5-(2,2-dimethyl-2,3-dihydro-1H-pyrrolo[2,3-c]pyridin-5-yl)-1,2,4-thiadiazol-3-yl)amino)-5-(trifluoromethyl)pyridin-3-yl)-N-methylacetamide

| | |
|---|---|
| 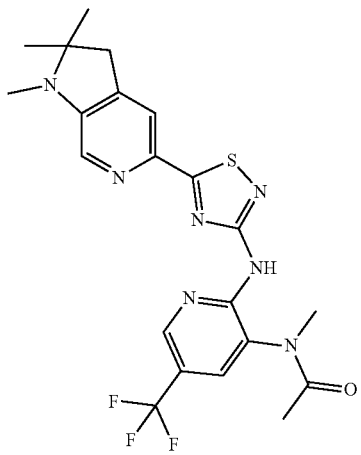 [SMILES: CC(=O)N(C)c1cc(C(F)(F)F)cnc1Nc1nsc(-c2cc3c(cn2)N(C)C(C)(C)C3)n1] | N-methyl-N-(5-(trifluoromethyl)-2-((5-(1,2,2-trimethyl-2,3-dihydro-1H-pyrrolo[2,3-c]pyridin-5-yl)-1,2,4-thiadiazol-3-yl)amino)pyridin-3-yl)acetamide |
| 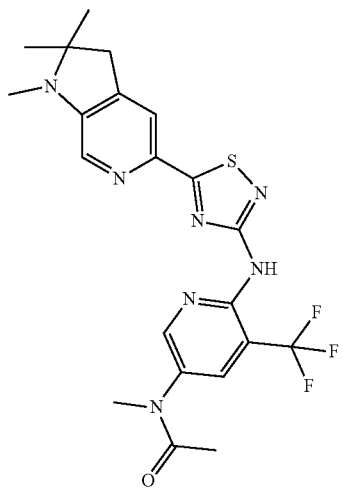 [SMILES: CC(=O)N(C)c1cnc(Nc2nsc(-c3cc4c(cn3)N(C)C(C)(C)C4)n2)c(C(F)(F)F)c1] | N-methyl-N-(5-(trifluoromethyl)-6-((5-(1,2,2-trimethyl-2,3-dihydro-1H-pyrrolo[2,3-c]pyridin-5-yl)-1,2,4-thiadiazol-3-yl)amino)pyridin-3-yl)acetamide |
| 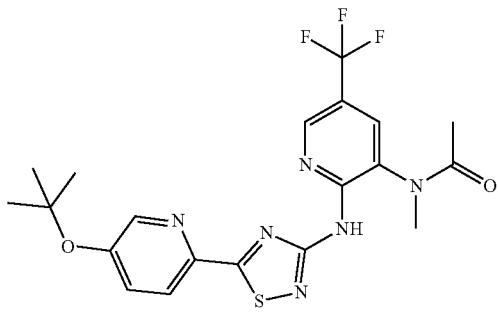 [SMILES: CC(=O)N(C)c1cc(C(F)(F)F)cnc1Nc1nsc(-c2ccc(OC(C)(C)C)cn2)n1] | N-(2-((5-(5-(tert-butoxy)-1,6-dihydropyridin-2-yl)-1,2,4-thiadiazol-3-yl)amino)-5-(trifluoromethyl)-2,3-dihydropyridin-3-yl)-N-methylacetamide. |

18. A pharmaceutical composition comprising an effective amount of a compound of claim 1 or a pharmaceutically acceptable salt, tautomer, isotopologue, or stereoisomer thereof, and a pharmaceutically acceptable carrier, excipient or vehicle.

19. A method of killing a filarial worm, comprising contacting the filarial worm with a compound of claim 1, or a pharmaceutical composition of claim 18, or a pharmaceutically acceptable salt, tautomer, isotopologue, or stereoisomer thereof, in an amount effective to kill the filarial worm.

20. A method of inhibiting growth or molt of a filarial worm, comprising contacting the filarial worm with a compound of claim 1, or a pharmaceutical composition of claim 18, or a pharmaceutically acceptable salt, tautomer, isotopologue, or stereoisomer thereof, in an amount effective to inhibit growth or molt of the filarial worm.

21. A method of inhibiting motility of a filarial worm, comprising contacting the filarial worm with a compound of claim 1, or a pharmaceutical composition of claim 18, or a pharmaceutically acceptable salt, tautomer, isotopologue, or stereoisomer thereof, in an amount effective to inhibit motility of the filarial worm.

22. A method for the treatment or prevention of helminthic infections and diseases, the methods comprising administering to a subject an effective amount of a compound of claim 1, or a pharmaceutical composition of claim 18, or a pharmaceutically acceptable salt, tautomer, isotopologue, or stereoisomer thereof.

23. A method for the treatment or prevention of helminthic infections and diseases, the methods comprising administering to a subject an effective amount of a compound of claim 1, or a pharmaceutical composition of claim 18, or a pharmaceutically acceptable salt, tautomer, isotopologue, or stereoisomer thereof in combination with another anti-parasitic agent.

\* \* \* \* \*